US011248027B2

(12) United States Patent
Schief et al.

(10) Patent No.: US 11,248,027 B2
(45) Date of Patent: Feb. 15, 2022

(54) ENGINEERED OUTER DOMAIN (EOD) OF HIV GP120, MUTANTS AND USE THEREOF

(71) Applicants: International AIDS Vaccine Initiative, New York, NY (US); The Scripps Research Institute, La Jolla, CA (US)

(72) Inventors: William Schief, La Jolla, CA (US); Sergey Menis, New York, NY (US); Daniel Kulp, New York, NY (US); Joseph Jardine, La Jolla, CA (US)

(73) Assignees: INTERNATIONAL AIDS VACCINE INITIATIVE, New York, NY (US); THE SCRIPPS RESEARCH INSTITUTE, La Jolla, CA (US)

( * ) Notice: Subject to any disclaimer, the term of this patent is extended or adjusted under 35 U.S.C. 154(b) by 550 days.

(21) Appl. No.: 15/844,753

(22) Filed: Dec. 18, 2017

(65) Prior Publication Data

US 2018/0194809 A1 Jul. 12, 2018

Related U.S. Application Data

(63) Continuation-in-part of application No. PCT/US2016/038162, filed on Jun. 17, 2016.

(60) Provisional application No. 62/181,147, filed on Jun. 17, 2015.

(51) Int. Cl.

| | |
|---|---|
| ***C07K 16/28*** | (2006.01) |
| ***A61K 39/00*** | (2006.01) |
| ***C07K 16/00*** | (2006.01) |
| ***A61K 38/00*** | (2006.01) |
| ***A61K 39/395*** | (2006.01) |
| ***C07K 14/005*** | (2006.01) |
| ***A01K 67/027*** | (2006.01) |
| ***A61K 39/12*** | (2006.01) |
| ***A61K 39/21*** | (2006.01) |
| ***A61K 49/00*** | (2006.01) |
| ***C12N 7/00*** | (2006.01) |
| ***C12N 9/10*** | (2006.01) |

(52) U.S. Cl.

CPC ........ *C07K 14/005* (2013.01); *A01K 67/0278* (2013.01); *A61K 39/12* (2013.01); *A61K 39/21* (2013.01); *A61K 49/0008* (2013.01); *C12N 7/00* (2013.01); *C12N 9/1085* (2013.01); *C12Y 205/01078* (2013.01); *A01K 2207/15* (2013.01); *A01K 2217/072* (2013.01); *A01K 2227/105* (2013.01); *A01K 2267/03* (2013.01); *C07K 2319/00* (2013.01); *C07K 2319/21* (2013.01); *C12N 2740/16122* (2013.01); *C12N 2740/16134* (2013.01); *C12N 2740/16171* (2013.01)

(58) Field of Classification Search

CPC .......... A61P 35/00; A61P 43/00; A61P 25/00; C07K 2317/92; A61K 2300/00

See application file for complete search history.

(56) References Cited

U.S. PATENT DOCUMENTS

| | | | | |
|---|---|---|---|---|
| 2011/0217338 A1 | 9/2011 | Phogat et al. | | |
| 2012/0282264 A1 | 11/2012 | Mascola et al. | | |
| 2014/0302081 A1 | 10/2014 | Wilson et al. | | |
| 2014/0322269 A1* | 10/2014 | Huang ................ | C07K 14/005 424/208.1 | |

FOREIGN PATENT DOCUMENTS

| | | | |
|---|---|---|---|
| WO | 2013056122 A1 | | 4/2013 |
| WO | 2013056122 A8 | | 4/2013 |
| WO | WO2013056122 | * | 4/2013 |

OTHER PUBLICATIONS

J. Jardine, et al., Supplementary Materials for Rational HIV Immunogen Design to Target Specific Germline B Cell Receptors, published Mar. 28, 2013 on Science Express DOI: 10.1126/science. 1234150.

International Search Report and Written Opinion of the International Searching Authority dated Feb. 3, 2017, which issued during prosecution of International Application No. PCT/US16/38162.

Jardine, et al. "HIV-1 broadly neutralizing antibody precursor B cells revealed by germline-targeting immunogen" Science, Mar. 2016, 351(6280):1458-1463.

Azoitei, et al. "Computational design of protein antigens that interact with the CDR H3 loop of HIV broadly neutralizing antibody 2F5" Proteins, Oct. 2014, 82(10):2770-2782.

International Preliminary Report on Patentability and Written Opinion of the International Searching Authority dated Dec. 19, 2017, which issued during prosecution of International Application No. PCT/US16/038162.

Bryan Briney, et al., Tailored Immunogens Direct Affinity Maturation Toward HIV Neutralizing Antibodies, Cell (Sep. 8, 2016) 166:1459-1470.

(Continued)

*Primary Examiner* — Barry A Chestnut

(74) *Attorney, Agent, or Firm* — Duane Morris LLP; Thomas J. Kowalski; Deborah L. Lu

(57) ABSTRACT

The present invention relates to engineered outer domain (eOD) immunogens of HIV gp120 and mutants thereof and methods of making and using the same. The present invention also includes fusions of eOD to various protein multimers to enhance immunogenicity. The mutant eODs bind to neutralizing antibody precursors. The mutant eODs can activate germline precursors on the pathway to eliciting a broadly neutralizing antibody (bnAb) response. The invention also relates to immunized knock-in mice expressing germline-reverted heavy chains. Induced antibodies showed characteristics of bnAbs and mutations that favored binding to near-native HIV-1 gp120 constructs. In contrast, native-like immunogens failed to activate precursors. The invention also relates to rational epitope design that can prime rare B cell precursors for affinity maturation to desired targets.

5 Claims, 144 Drawing Sheets
(108 of 144 Drawing Sheet(s) Filed in Color)
Specification includes a Sequence Listing.

(56) References Cited

OTHER PUBLICATIONS

Pia Dosenovic, et el., Immunization for HIV-1 Broadly Neutralizing Antibodies in Human Ig Knockin Mice, Cell (Jun. 15, 2015) 161:1505-1515.

Joseph Jardine, et al., Rotational HIV Immunogen Design to Target Specific Germline B Cell Receptors, Science (May 10, 2013) vol. 340 p. 711-176.

Joseph G. Jardine, et al., Priming a Broadly Neutralizing Antibody Response to HIV-1 Using a Germline-Targeting Immunogen, Science Jul. 10, 2015) vol. 349, Issue 6244, p. 156-161.

Joseph G. Jardine, et al., Supplementary Materials for Priming a Broadly Neutralizing Antibody Response to HIV-1 Using a Germline-Targeting Immunogen, Science Jul. 10, 2015) vol. 349, Issue 6244, p. 156-161.

Partial EP Search Report dated Feb. 12, 2019 in EP Application No. 16812553.2.

* cited by examiner

D

Experimental overview

| Immunogen | Multimerization | Adjuvant | VRC01 gH mice (n) | WT mice (n) |
|---|---|---|---|---|
| eOD-GT8 60mer | Nanoparticle | Alum | 11 | 5 |
| eOD-GT8 60mer | Nanoparticle | Iscomatrix | 5 | 5 |
| eOD-GT8 60mer | Nanoparticle | Ribi | 12 | 5 |
| eOD-GT8 3mer | Trimer | Alum | 5 | 5 |
| eOD-GT8 3mer | Trimer | Ribi | 5 | 5 |
| eOD-17 60mer | Nanoparticle | Alum | 5 | 5 |
| BG505 SOSIP | Trimer | Iscomatrix | 5 | 0 |
| BG505 SOSIP | Trimer | Ribi | 5 | 0 |

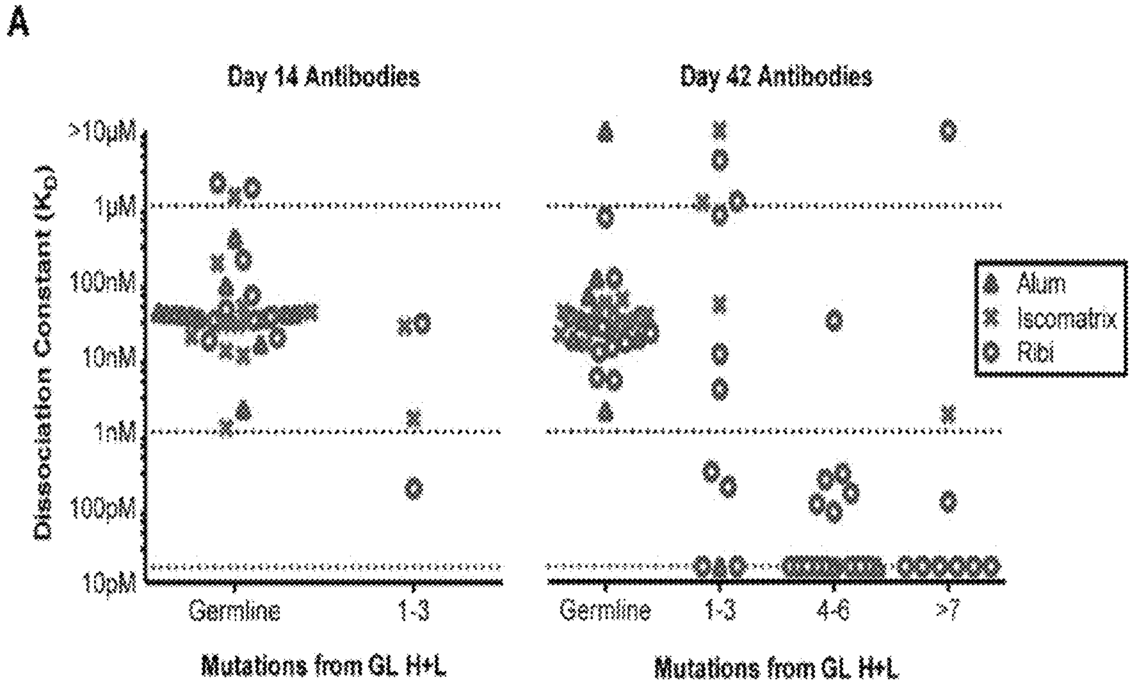
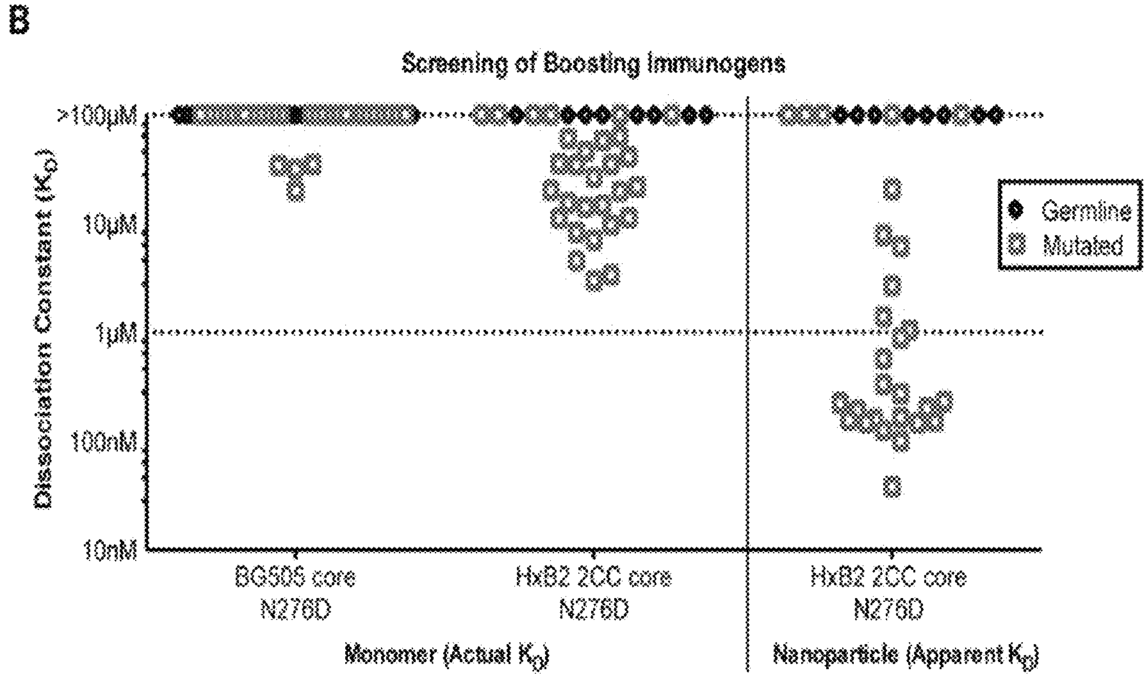
Fig. 5

A.
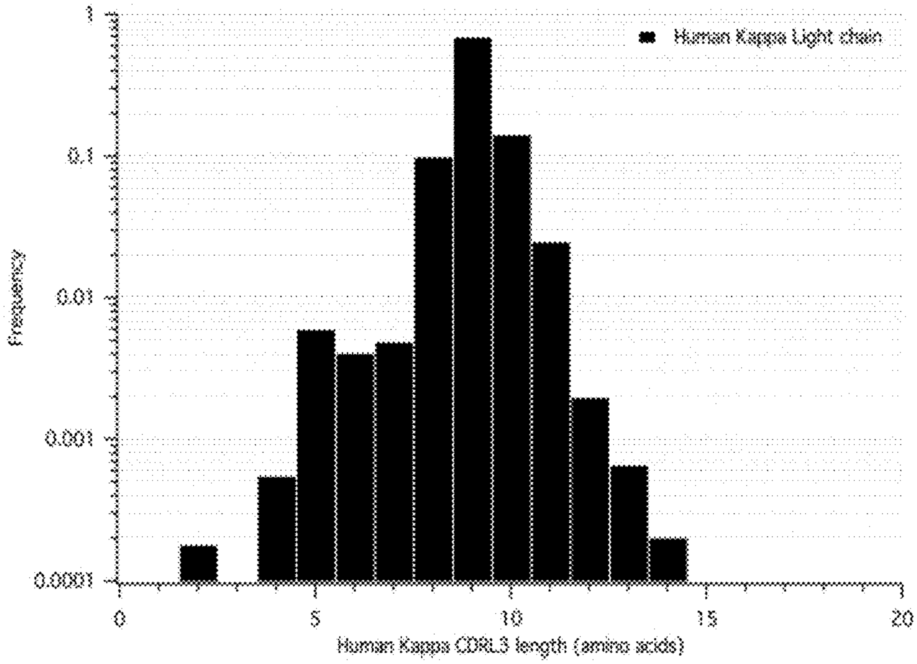
B.
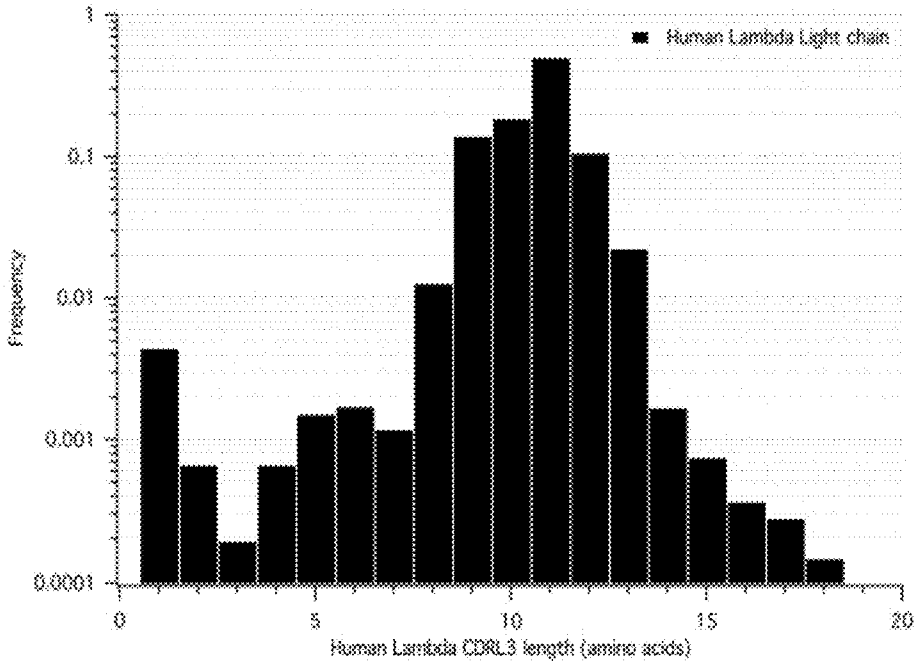
Fig. 6

A.
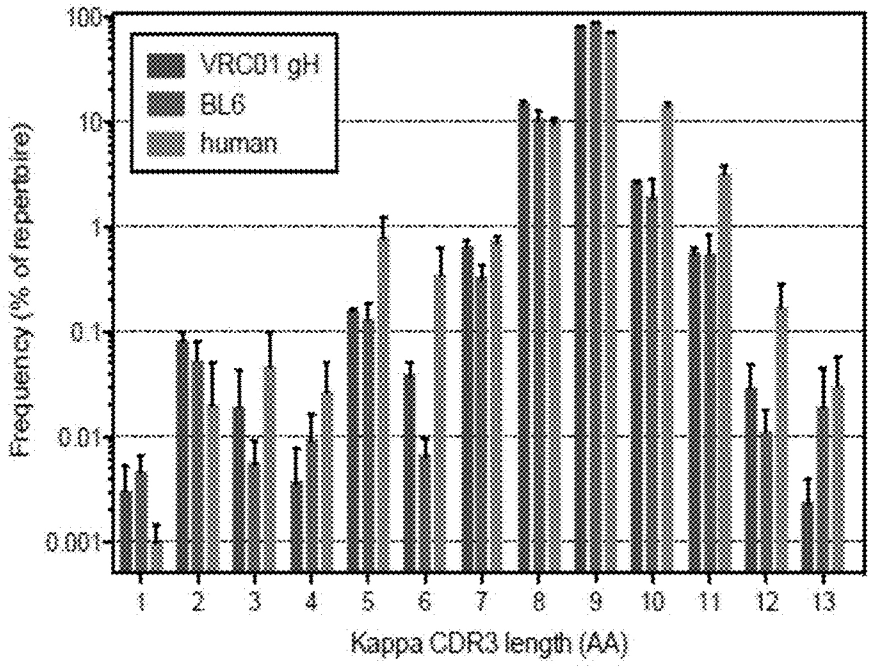
B.
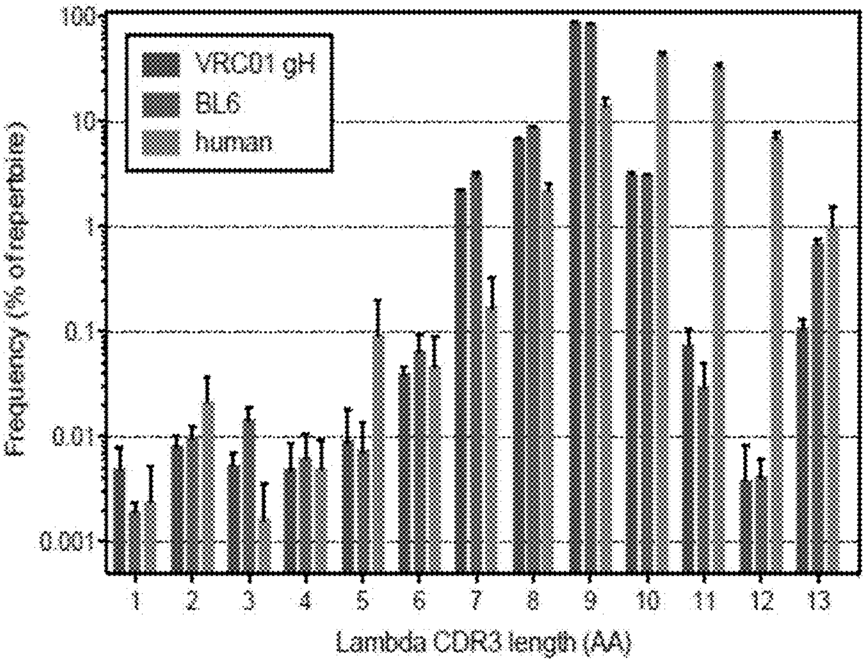
Fig. 7

A.

VH Gene Alignment

```
VRC01 AA        Q   V   Q   L   V   Q   S   G   G       Q   M   K   K   P   G   E   S
VRC01 NT       CAG GTG CAG CTG GTG CAG TCT GGG GGT --- CAG ATG AAG AAG CCT GGC GAG TCG
IGHV1-02*02    ... ... ... ... ... ... ... ... .C. --- G.. G.. ... ... ... ..G .CC ..A

VRC01 AA        M   R   I   S   C   R   A   S   G   Y   E   F   I   D   C   T
VRC01 NT       ATG AGA ATT TCT TGT CGG GCT TCT GGA TAT GAA TTT ATT GAT TGT ACG --- ---
IGHV1-02*02    G.. .AG G.C ..C ..C AA. ... ... ... ..C ACC ..C .CC .GC .AC TAT --- ---

VRC01 AA        L   N   W   I   R   L   A   P   G   K   R   P   E   W   M   G
VRC01 NT       --- --- CTA AAT TGG ATT CGT CTG GCC CCC GGA AAA AGG CCT GAG TGG ATG GGA
IGHV1-02*02    --- --- A.G C.C ... G.G ..A .A. ... ..T ... C.. G.. .T. ... ... ... ...

VRC01 AA        W   L   K   P   R   G   G   A   V           N   Y   A   R   P   L   Q
VRC01 NT       TGG CTG AAG CCT CGG GGG GGG GCC GTC --- --- AAC TAC GCA CGT CCA CTT CAG
IGHV1-02*02    ... A.C ..C ... AAC A.T ..T .G. ACA --- --- ... ..T ... .AG AAG T.. ...

VRC01 AA        G   R   V   T   M   T   R   D   V   Y   S   D   T   A   F   L   E
VRC01 NT       --- GGC AGA GTG ACC ATG ACT CGA GAC GTT TAT TCC GAC ACA GCC TTT TTG GAG
IGHV1-02*02    --- ... ..G ..C ... ... ..C A.G ... ACG .CC AT. AG. ... ... .AC A.. ...

VRC01 AA        L   R   S   L   T   V   D   D   T   A   V   Y   F   C   T   R   G
VRC01 NT       CTG CGC TCG TTG ACA GTA GAC GAC ACG GCC GTC TAC TTT TGT ACT AGG GG
IGHV1-02*02    ... A.. AG. C.. .G. TCT ... ... ... ... ..G ..T .AC ... G.G ..A .A
```

DH Gene Alignment

```
VRC01 AA          T   R   G   K   N   C   D   Y   N   W   D   F   E   H   W   G   R   G   T
VRC01 NT         ACT AGG GGA AAA AAC TGT GAT TAC AAT TGG GAC TTC GAA CAC TGG GGC CGG GGC ACC
IGHD3-16*02                      G T.T .A. ... ... GT. ... .GG AGT T.T .GT .AT AC.
IGHD3-16*01                      G T.T .A. ... ... GT. ... .GG AGT T.T GCT .AT AC.
IGHD2/OR15-2B  GG CAT A.. ..G T.G .AC T.. ... ... ATT CT
IGHD5-24*01                     GT .GA GA. .GC ... ... .AC
IGHD1-01*01                                 GG ... ..C ... A.. GA.
```

JH Gene Alignment

```
VRC01 AA     C   D   Y   N   W   D   F   E   H   W   G   R   G   T   P   V   I   V   S   S
VRC01 NT    TGT GAT TAC AAT TGG GAC TTC GAA CAC TGG GGC CGG GGC ACC CCG GTC ATC GTC TCA TCA
IGHJ1*01                GC. GAA T.. ... C.G ... ... ... .A. ... ... .T. ... .C. ... ..C ...
IGHJ2*01              . T.C ... T.. ... ..T .T. ... ... ..T ... ... .T. ... .CT ... ..C ...
IGHJ5*02                 .C AAC TGG ... ..C .C. ... ... .A. ..A ... .T. ... .C. ... ..C ...
IGHJ4*02                    AC T.. ..T ..C T.. ... ... .A. ..A ... .T. ... .C. ... ..C ...
IGHJ4*03                    .C T.. ..T ..C T.. ... ... .AA ..G ... .T. ... .C. ... ..C ...
```

B.

```
VRC01        QVQLVQSGGQMKKPGESMRISCRASGYEFIDCTLNWIRLAPGKRPEWMGWLKPRGGAVNYARPLQGRV
IGHV1-2*02   ........AEV....A.VKV..K....T.TGYYMH.V.Q...QGL.....IN.NS.GT...QKF....
VRC01 gH     ........AEV....A.VKV..K....T.TGYYMH.V.Q...QGL.....IN.NS.GT...QKF....

VRC01        TMTRDVYSDTAFLELRSLTVDDTAVYFCTRGKNCDYNWDFEHWGRGTPVIVSS
IGHV1-2*02   .....TSIS..YM..SR.RS......Y.A.
IGHJ1*01                                            .Q...Q..L.T...
VRC01 gH     .....TSIS..YM..SR.RS......Y.A...S.....Q...Q..L.T...
```

Fig. 8

```
                            Somatic          VJ
                            Mutation      Junction
                               ↓             |
Nem_0014    TGTCAGCAATATGATAGCTTCGGTGCTGGGACC
             C  Q  Q  Y  D  S  F  G  A  G  T
IGKV8-30     C  Q  Q  Y  Y  S  ...ATCC.C.
             ........T........ 
IGKJ5                    GCTC.CG...
                               F  G  A  G  T
```

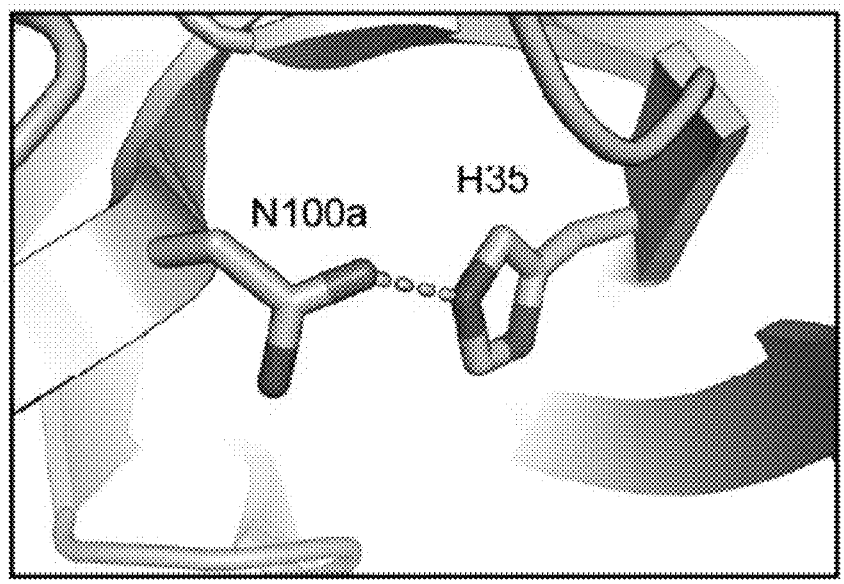
GL-VRC01 HC (PDBID:4jpk)
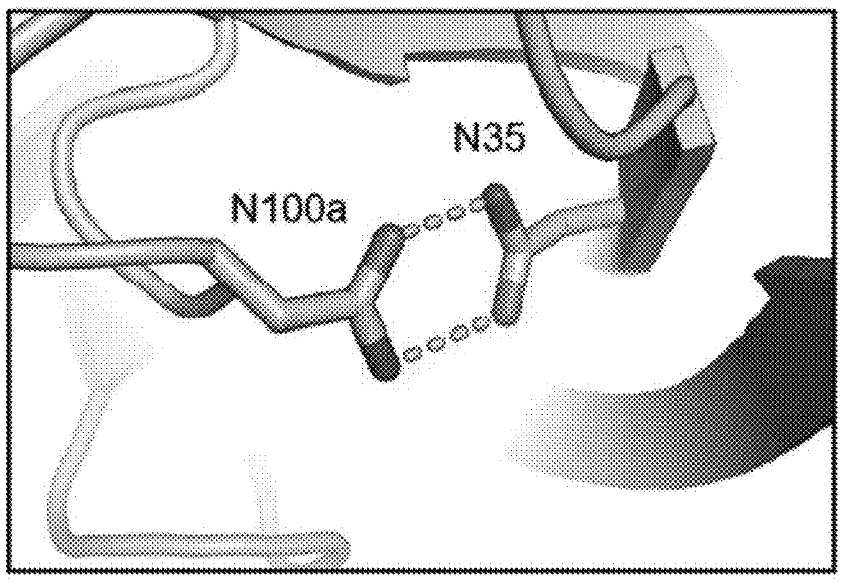
VRC01 HC (PDBID:3ngb)
Fig. 20

| Neutralization $IC_{50}$ (μg/mL) | | | | | | | | | |
|---|---|---|---|---|---|---|---|---|---|
| | Nem 0072 | Nem 0098 | Nem 0103 | Nem 0110 | Nem 0164 | Nem 0109 | Nem 0071 | Nem 0080 | VRC01 |
| BG505 | > 50 | > 50 | > 50 | > 50 | > 50 | > 50 | > 50 | > 50 | 0.039 |
| HXB2 | > 50 | > 50 | > 50 | > 50 | > 50 | > 50 | > 50 | > 50 | 0.100 |
| BG505 N276A | > 50 | > 50 | > 50 | > 50 | > 50 | > 50 | > 50 | > 50 | 0.007 |
| HXB2 N276A | > 50 | > 50 | > 50 | > 50 | > 50 | > 50 | > 50 | > 50 | 0.004 |

Fig. 22

| Donor | B cells screened | VRC01 class naive B cells |
|---|---|---|
| 1 | $1.6x10^6$ | 2 |
| 2 | $2.1x10^6$ | 1 |
| 3 | $0.9x10^6$ | 0 |
| 4 | $5.4x10^6$ | 2 |
| 5 | $0.6x10^6$ | 0 |
| 6 | $0.5x10^6$ | 0 |
| 7 | $1.8x10^6$ | 0 |
| 8 | $14.4x10^6$ | 4 |
| 9 | $7.8x10^6$ | 6 |
| 10 | $4.5x10^6$ | 2 |
| 11 | $7.0x10^6$ | 1 |
| 12 | $5.9x10^6$ | 1 |
| Total | $54.0x10^6$ | 19 |
| Frequency | 1 in $2.8x10^6$ | |

Fig. 24 eOD-GT8-60mer (wild-type) and eOD-GT8-d4-60mer were incubated at pH 3 for 90 minutes and analyzed by SEC-MALS

Conclusion: Only eOD-GT8-60mer has a pentamer peak after 90 min @ pH 3.

Observed MW for pH 4-treated samples

| | Primary Peak Mw (kDa) | Secondary Peak Mw (kDa) | Sample Composition |
|---|---|---|---|
| eOD-GT8_60mer -Untreated | 2204.1 | | 60mers |
| eOD-GT8_60mer - 90min @ pH 4 | 2122.8 | 214.2 | 60mers and 5mers |
| eOD-GT8_d4_60mer - Untreated | 2404 | | 60mers |
| eOD-GT8_d4_60mer - 90min @ pH 4 | 2196.6 | | 60mers |
| eOD-GT8_d41_60mer - 90min @ pH 4 | 2100.5 | | 60mers |
| eOD-GT8_m3_d41_60mer - Untreated | 2093.5 | | 60mers |
| eOD-GT8_m3_d41_60mer - 90min @ pH 4 | 2040.2 | | 60mers |

Fig. 27

J
| Donor | B cells Screened (millions) | VRC01-class naive B cells |
|---|---|---|
| 1 | 1.6 | 1 |
| 2 | 2.1 | 1 |
| 3 | 0.9 | 0 |
| 4 | 5.4 | 2 |
| 5 | 0.6 | 0 |
| 6 | 0.5 | 0 |
| 7 | 1.8 | 0 |
| 8 | 14.4 | 4 |
| 9 | 7.8 | 6 |
| 10 | 4.5 | 2 |
| 11 | 7.0 | 1 |
| 12 | 5.9 | 1 |
| 13 | 1.1 | 2 |
| 14 | 6.7 | 5 |
| 15 | 1.3 | 1 |
| Total | 61.6 | 26 |
Frequency: 1 in 2.4 million
Fig. 29J
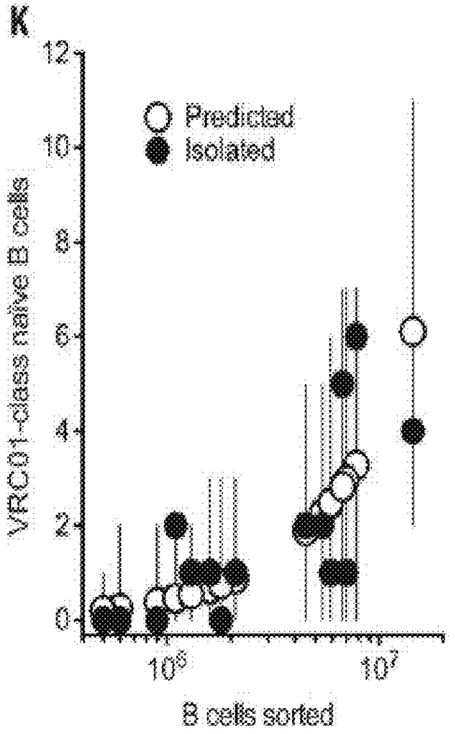
Fig. 29K
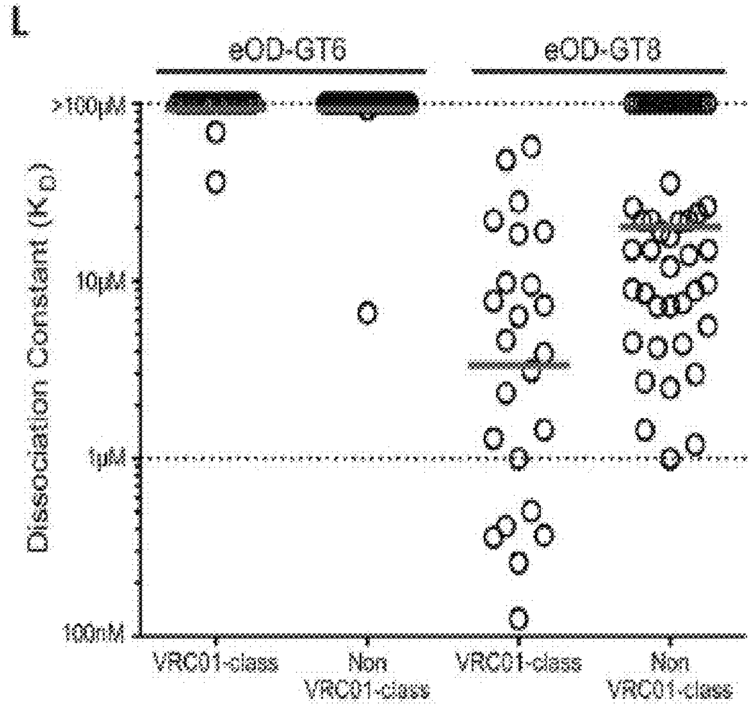
Fig. 29L

G

| Name | V-GENE | J-GENE | D-GENE | CDR3 Length | AA JUNCTION | Affinity by SPR (equilibrium KD) |
|---|---|---|---|---|---|---|
| Non-VRC01c | V3-66*01 | J3*02 | D3-10*01 | 13 | CARELQQTEDAFDIW | 120 µM |
| HuGL1 | KV1-9*01 | KJ2*01 | | 9 | CQQLNSYPYTF | |
| Non-VRC01c | V4-4*02 | J6*02 | D5-18*01 | 22 | CARGGTMVRGENLTYYYYYGMDVW | 49 µM |
| HuGL2 | KV1-6*01 | KJ2*01 | | 9 | CLQDYNYPYTF | |
| Non-VRC01c | V4-39*01 | J5*02 | D6-13*01 | 14 | CARESSSWRYNWFDPW | 86 µM |
| HuGL3 | KV3-20*01 | KJ2*01 | | 9 | CQQYGSSSYTF | |

Fig. 31G

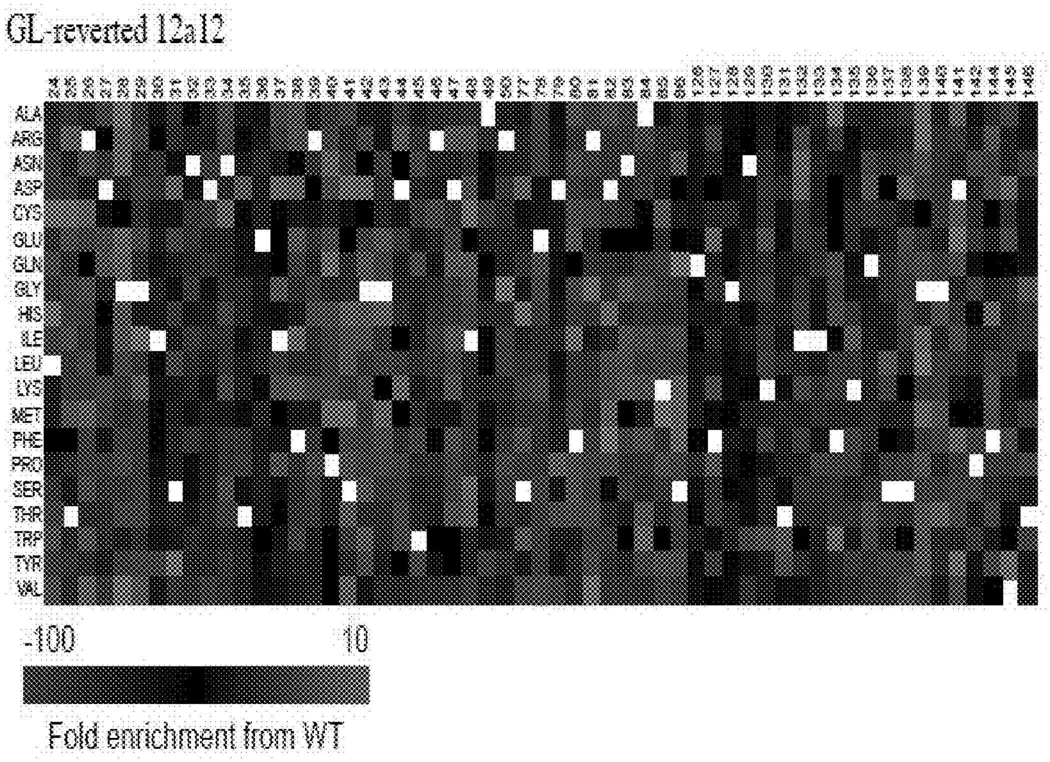
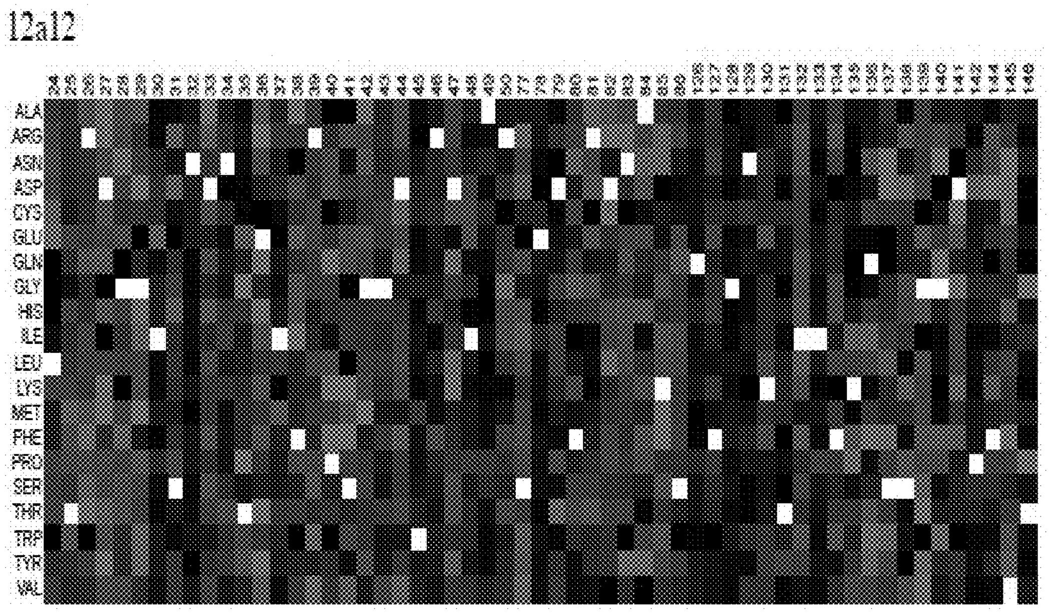
Fig. 32A

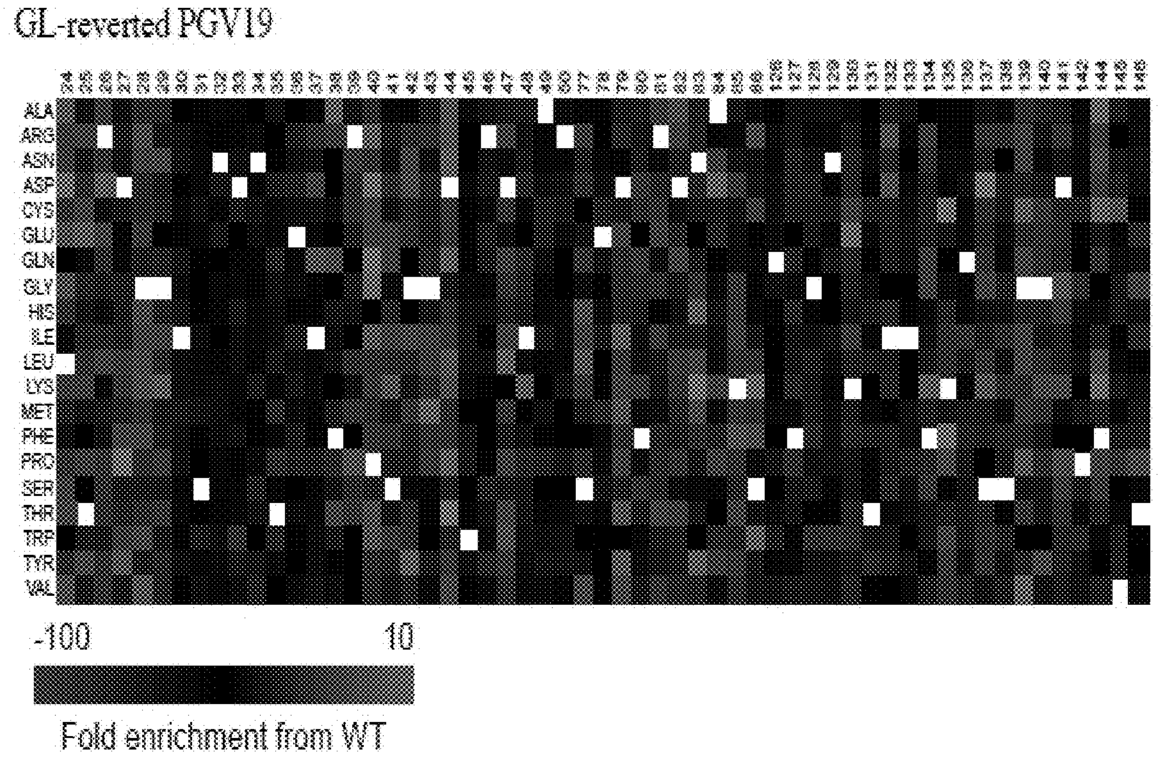
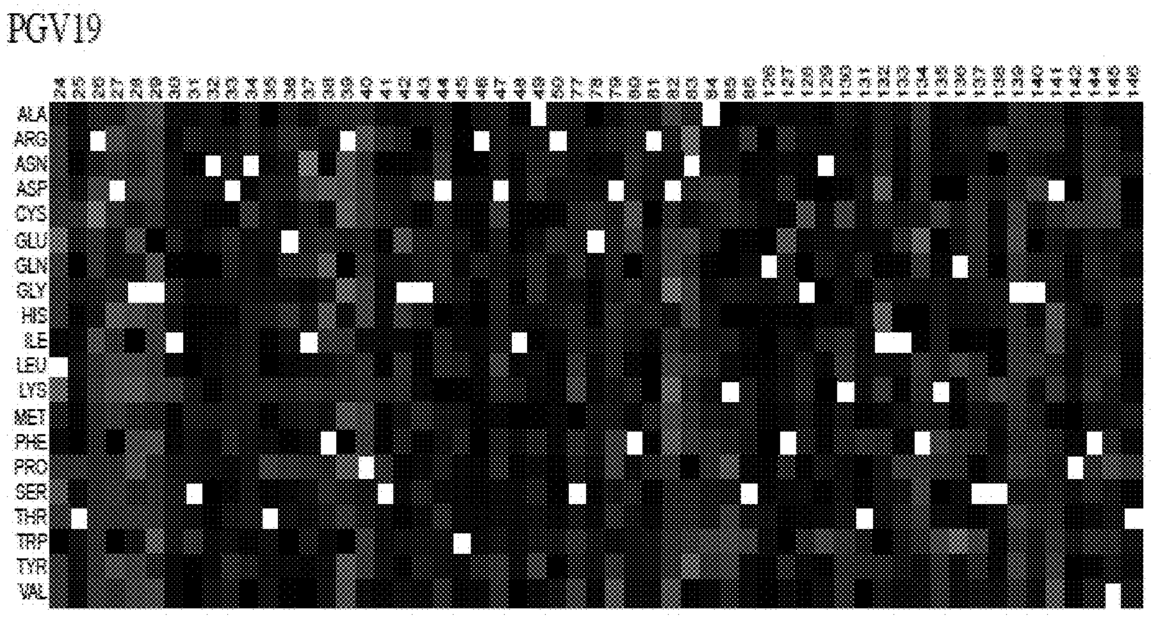
Fig. 32E

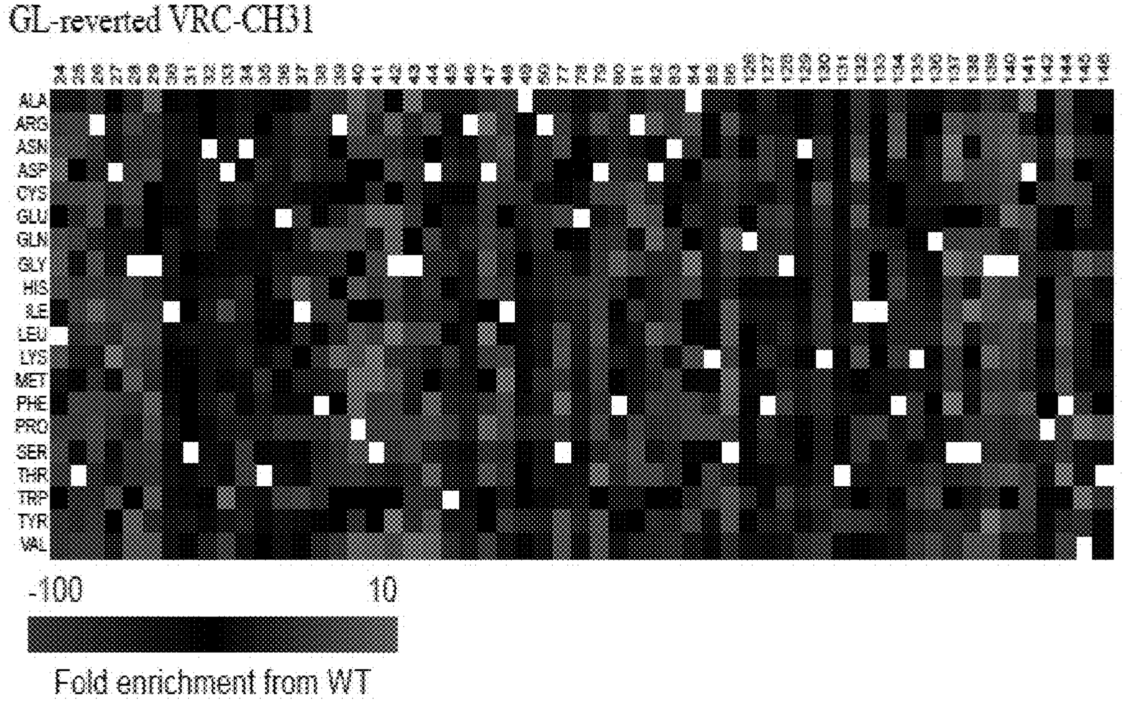
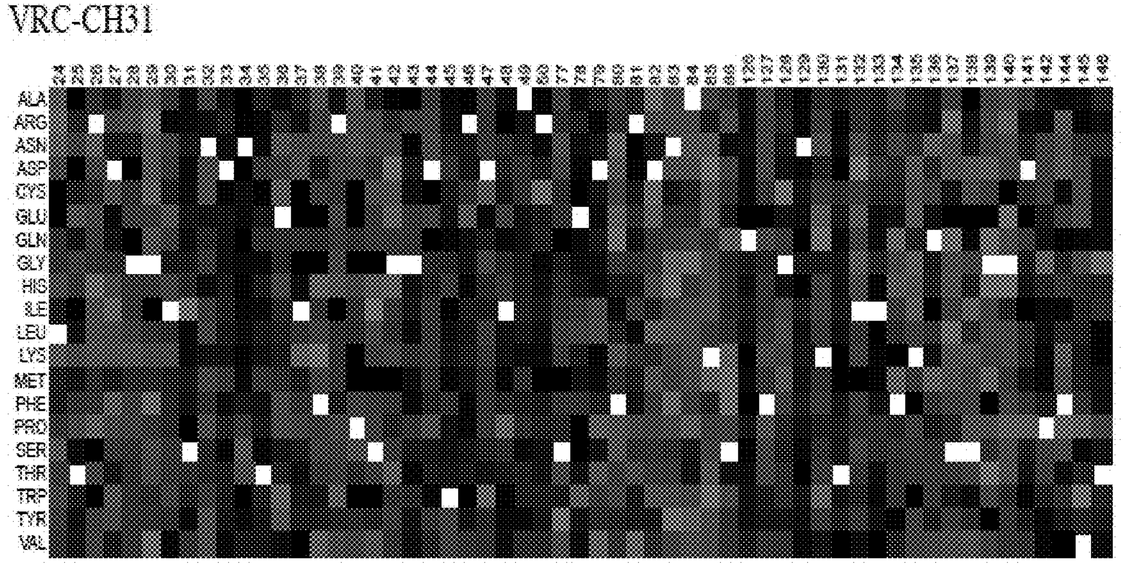
Fig. 32H

| | |
|---|---|
| eOD-GT6 | D T I T L P C R P A P P P H C S S N I T G L I L T R D G G |
| eOD-GT7 | D T I T L P C R P A P P P H C S S N I T G L I L T R D G G |
| eOD-GT8 | D T I T L P C R P A P P P H C S S N I T G L I L T R Q G G |
| eOD-GT6 | V S N D E T E I F R P S G G D M R D I A R C Q I A G T V V |
| eOD-GT7 | I S N D N T E I F R P S G G D W R D I A R C Q I A G T V V |
| eOD-GT8 | Y S N D N T V I F R P S G G D W R D I A R C Q I A G T V V |
| eOD-GT6 | S T Q L F L N G S L A E E E V V I R S V D F R D N A K S I |
| eOD-GT7 | S T Q L F L N G S L A E E E V V I R S E D F R D N A K S I |
| eOD-GT8 | S T Q L F L N G S L A E E E V V I R S E W F R D N A K S I |
| eOD-GT6 | C V Q L N T S V E I N C T G A G H C N I S R A K W N N T L |
| eOD-GT7 | C V Q L N T S V E I N C T G A G H C N I S R A K W N N T L |
| eOD-GT8 | C V Q L N T S V E I N C T G A G H C N I S R A K W N N T L |
| eOD-GT6 | K Q I A S K L R E Q F G N R T I I F K Q S S G G D P E F V |
| eOD-GT7 | K Q I A S K L R E Q F G K R T I I F K Q S S G G D P E F V |
| eOD-GT8 | K Q I A S K L R E Q Y G K R T I I F P Q S S G G D P E F V |
| eOD-GT6 | T H S F N C G G E F F Y C D S T Q L F N S T W F N S T |
| eOD-GT7 | T H S F N C G G E F F Y C D S T Q L F N S T W F N S T |
| eOD-GT8 | N H S F N C G G E F F Y C D S T Q L F N S T W F N S T |

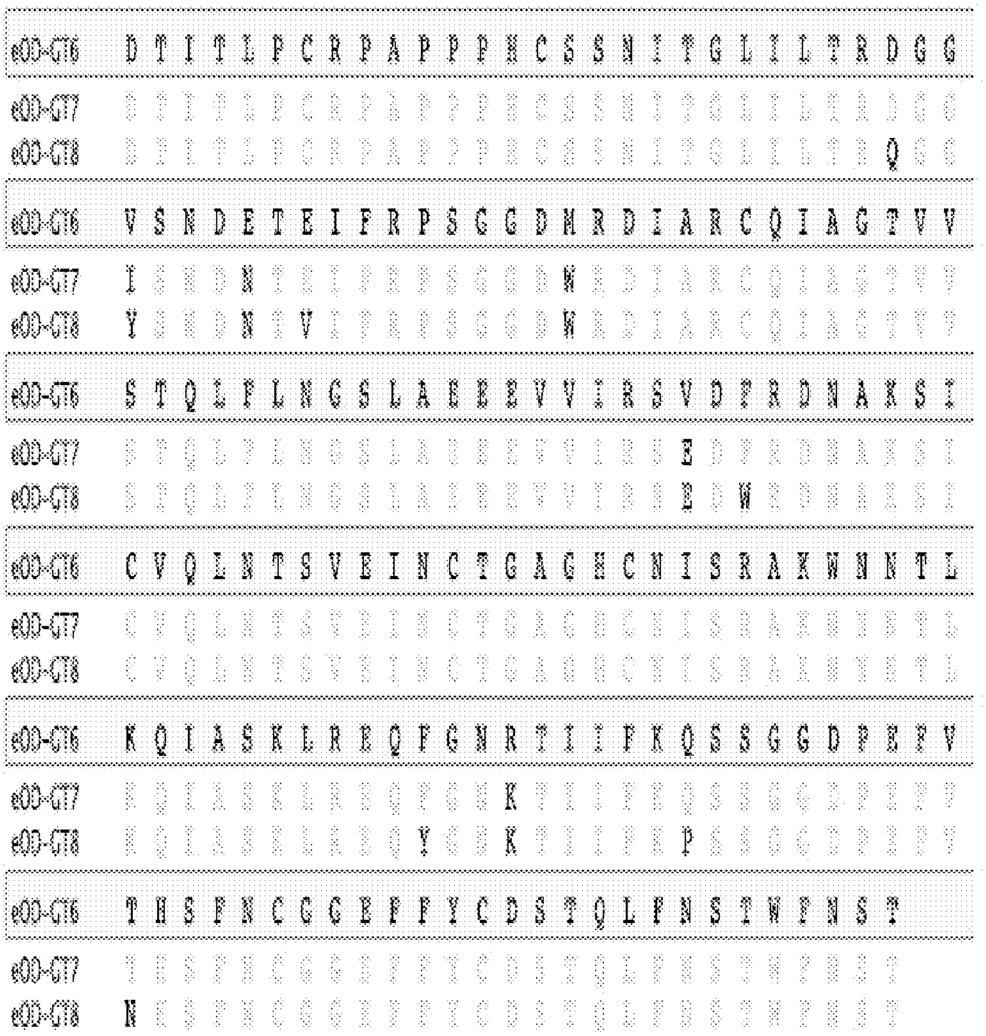

Fig. 34

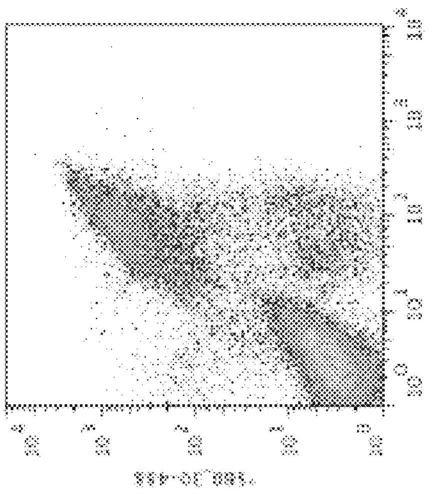
1 nM 3BNC60
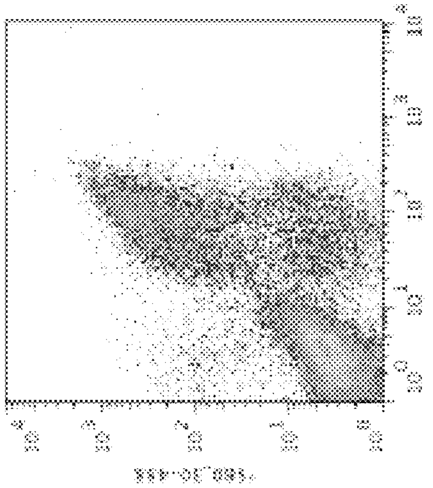
1 nM 12a12
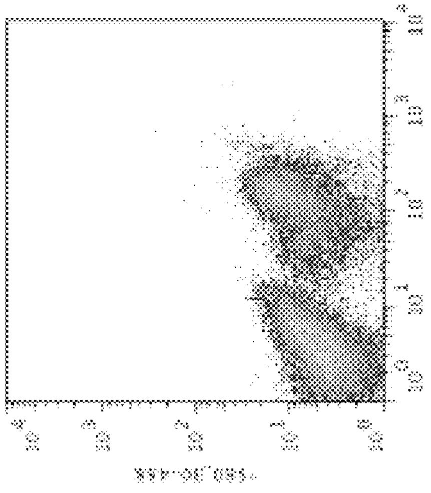
Display only
Fig. 44A 1 nM PGV19

1 nM PGV04

1 nM NIH45-46

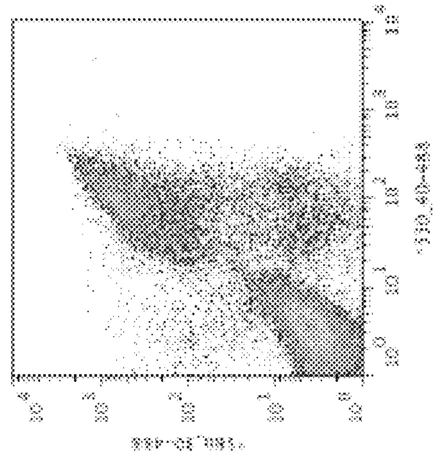
1 nM VRC03
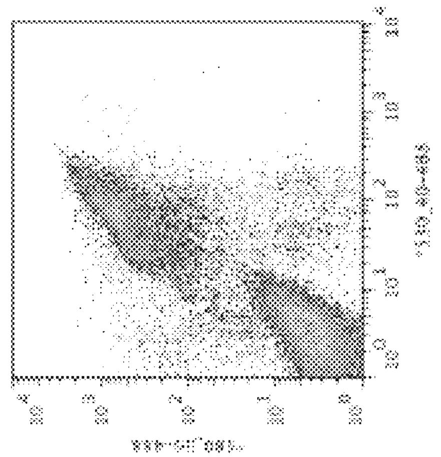
1 nM VRC01
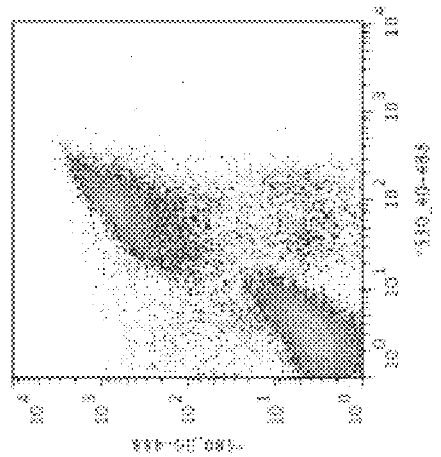
1 nM PGV20
Fig. 44C 1 nM VRC-CH31

100 nM VRC23

1 nM VRC06

100 nM GL 12a12

1 μM GL 3BNC60.v1

1 μM GL 3BNC60.v2

100 nM GL NIH45-46_H
GL NIH45-46_L 100 nM GL NIH45-46_H
GL VRC01_L 100 nM GL PGV04 v1_H
GL PGV04_L

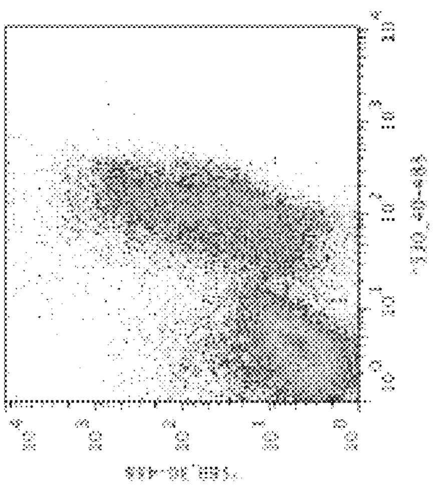
1 μM nM GL PGV04.v2_H
GL VRC01_L
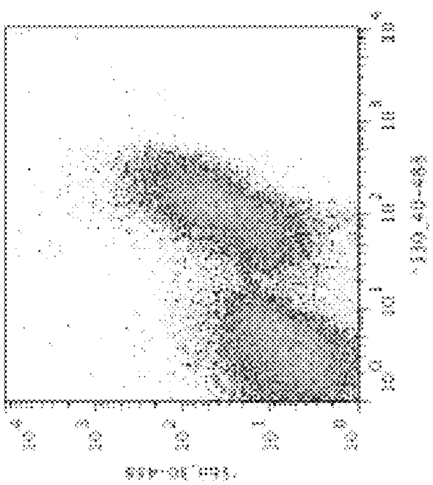
100 nM GL PGV04.v2_H
GL PGV04_L
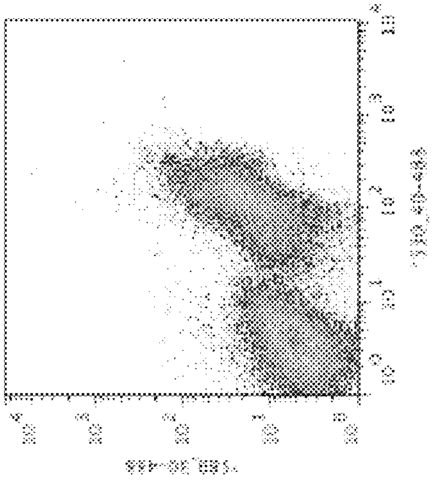
1 μM nM GL PGV04.v1_H
GL VRC01_L
Fig. 44G 1 nM GL PGV19

1 μM GL PGV04.v3_H
GL VRC01_L

1 μM GL PGV04.v3_H
GL PGV04_L

1 μM GL VRC03

10 nM GL VRC01

1 nM GL PGV20

1 μM GL VRC23

1 μM GL VRC-CH31

1 μM GL VRC-H5
GL PGV04

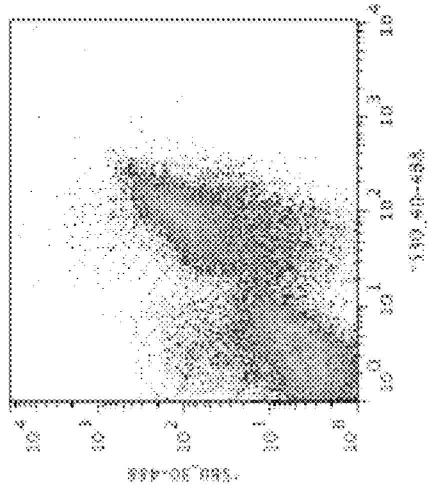
1 μM GL VRC-H5
GL VRC01
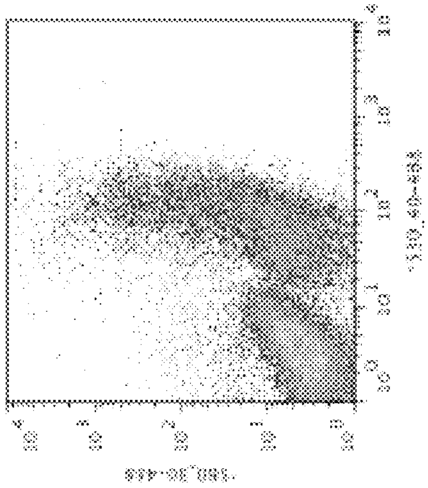
1 μM GL VRC-H15
GL PGV04
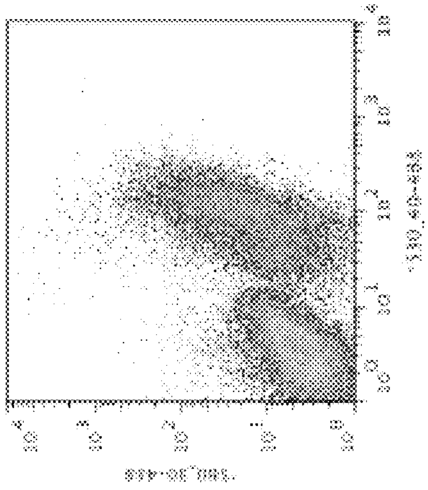
1 μM GL VRC-H15
GL VRC01
Fig. 44K A
| Experiment | Immunogen | Amount (μg) | Adjuvant/ route | Number of mice HK | HL | HKL | Timeline d0 | d14 | d28 | d42 |
|---|---|---|---|---|---|---|---|---|---|---|
| 1 | eOD-GT8 60mer | 20 | Isco/SC | 5 | 5 | 0 | - immunize - bleed | - cull 2/gp - bleed | bleed all | cull 3/gp |
| | eOD-GT8 60mer | 4 | Isco/SC | 5 | 5 | 0 | | | | |
| | eOD-GT8 60mer | 20 | Ribi/IP | 5 | 5 | 0 | | | | |
| | eOD-GT8 60mer | 4 | Ribi/IP | 5 | 5 | 0 | | | | |
| | eOD-17 60mer | 20 | Isco/SC | 5 | 5 | 0 | | | | |
| 2 | eOD-GT8 60mer | 20 | Isco/SC | 10 | 0 | 10 | - immunize - bleed | --- | --- | cull all |
| | eOD-17 60mer | 20 | Isco/SC | 5 | 0 | 5 | | | | |
| | BG505 SOSIP | 20 | Isco/SC | 5 | 0 | 5 | | | | |
B
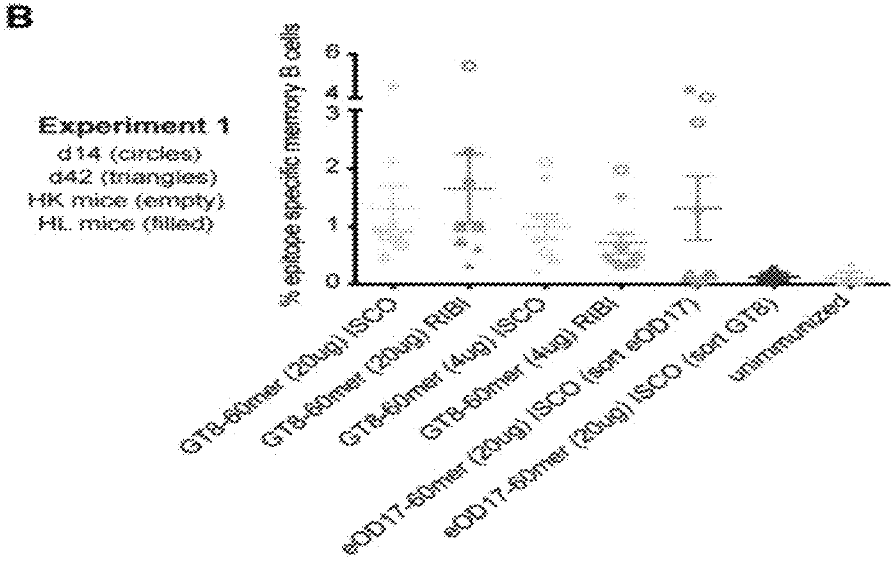
C
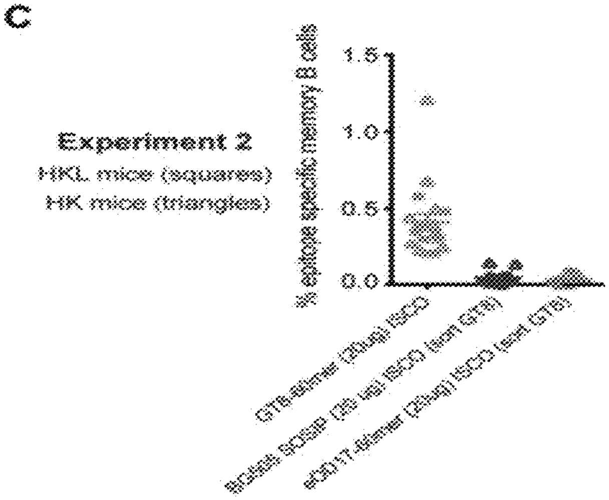
Fig. 46

A

| | HCs | LCs | Pairs | $V_H$1-2 HCs | 5 aa L-CDR3 LCs | $V_H$1-2 pairs | 5 aa L-CDR3 pairs | VRC01-class pairs |
|---|---|---|---|---|---|---|---|---|
| eOD-GT8 60mer | 5327 | 5059 | 2618 | 214 | 70 | | | 33 |
| BG505 SOSIP | 197 | 372 | 124 | 2 | 0 | | | 0 |
| eOD-17 60mer | 1136 | 1228 | 424 | 20 | 0 | | | 0 |
| unimmunized | 184 | 146 | 60 | 8 | 0 | | | 0 |
| TOTAL | 6844 | 6805 | 3226 | 244 | 70 | | | 33 |

Fig. 51I
VRC01
GT8
GT8x3
GT8
GT3
GT8
GT3
SOSIP

Removal of N276 glycan does not make viruses susceptible to non-neutralizing a antiobdies wild-type virus

| | 94UG103 | 92RW020 | JR-CSF | JR-FL | IAVI C22 | 92TH021 |
|---|---|---|---|---|---|---|
| Clade | A | A | B | B | C | AE |
| Tier | 2 | 2 | 2 | 2 | 2 | 2 |
| VRC01 | 0.164 | 0.205 | 0.225 | 0.021 | 0.651 | 0.370 |
| CD4 IgG2 | 0.044 | 0.434 | 1.11 | 0.045 | 5.16 | 0.325 |
| b12 | 2.02 | > 50 | 0.590 | 0.019 | 8.55 | 1.14 |
| b6 | > 50 | > 50 | > 50 | > 50 | > 50 | > 50 |
| F105 | > 50 | > 50 | > 50 | > 50 | > 50 | > 50 |

N276A virus

| | | | | | | |
|---|---|---|---|---|---|---|
| Clade | A | A | B | B | C | AE |
| Tier | 2 | 2 | 2 | 2 | 2 | 2 |
| VRC01 | 0.026 | 0.040 | 0.063 | 0.026 | 0.069 | 0.149 |
| CD4 IgG2 | 0.166 | 0.815 | 5.20 | 0.050 | 19.3 | 0.675 |
| b12 | 8.00 | > 50 | 0.738 | 0.016 | 11.3 | 3.75 |
| b6 | > 50 | > 50 | > 50 | > 50 | > 50 | > 50 |
| F105 | > 50 | > 50 | > 50 | > 50 | > 50 | > 50 |

| Conc (ug/ml) | 50 | 10 | 1 | 0.1 | 0.01 |
|---|---|---|---|---|---|

Fig. 54

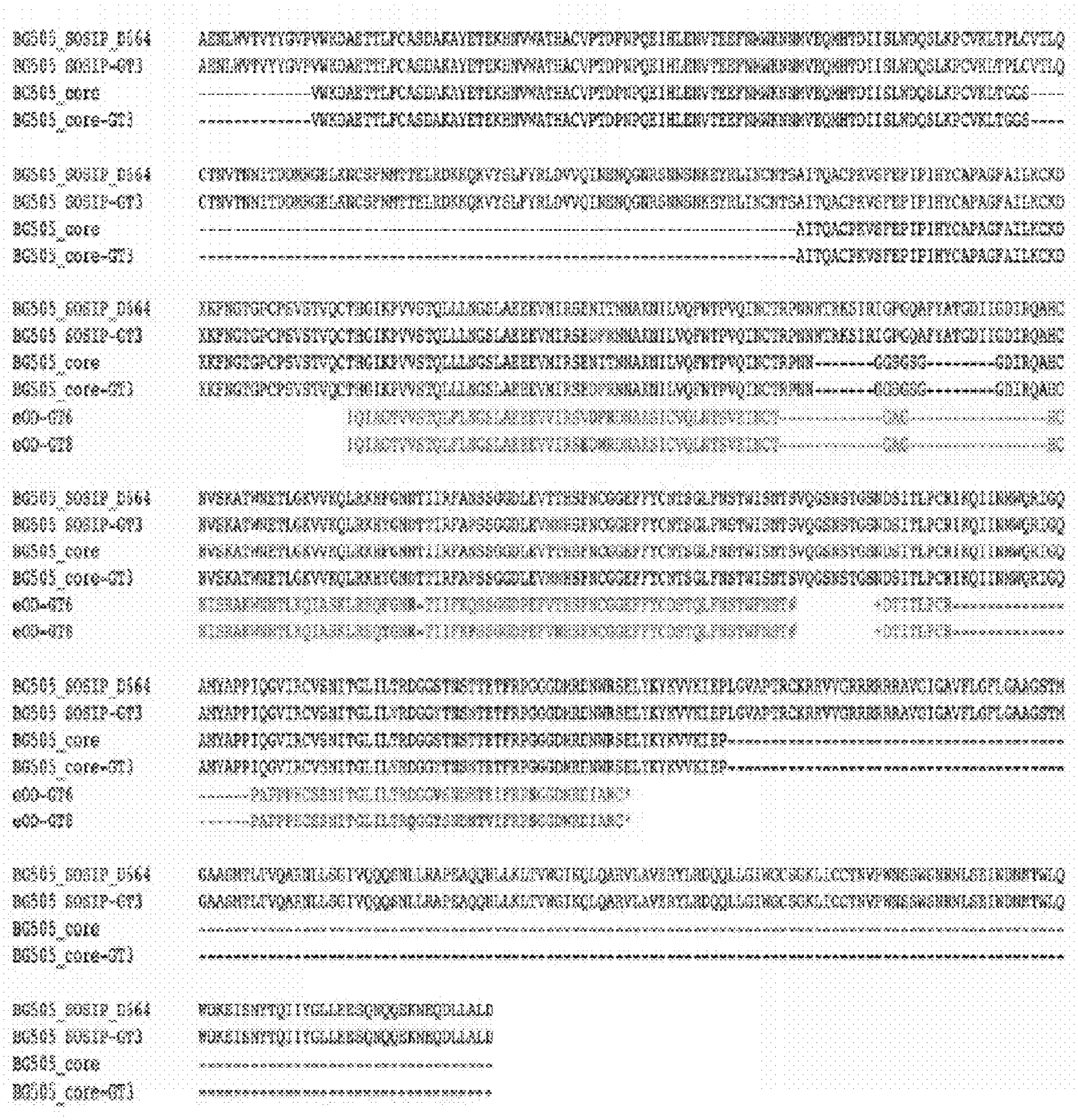

+, N-terminus of eOD-GT6 and eOD-GT8

*, end of outer domain exit helix at outer domain C-terminus

!, start of loop connection outer domain exit helix to outer domain N-terminus

#, C-terminus of eOD-GT6 and eOD-GT8 blue: N-terminal segment of eOD-GT6 and eOD-GT8 (with bold indicating mutations relative to eOD base from 3XB2)

red: C-terminal segment of eOD-GT6 and eOD-GT8 (with bold indicating mutations relative to eOD base from 3XB2)

magenta: GT3 mutations relative to BG505

BG505 core-GT3 60mer

MQIYEGKLTAEGLRFGIVASRFNHALVDRLVEGAIDAIVRHGGREEDITLVRVPGSWEIPVAAGELARKEDIDAVIAIGVLIRGATPHFDYIASEVSK
GLADLSLELRKPITFGVITADTLEQAIERAGTKHGNKGWEAALSAIEMANLFKSLRGGSGGSGGSGGSGGSGGSGGVWKDAETTLFCASDAKAYETE
KHNVWATHACVPTDPNPQEIHLENVTEEFNMWKNNMVEQMHTDIISLWDQSLKPCVKLTGGSAITQACPKVSFEPIPIHYCAPAGFAILKCKDKKFNG
TGPCPSVSTVQCTHGIKPVVSTQLLLNGSLAEEEVMIRSEDFRNNAKNILVQFNTPVQINCTRPNNGGSGSGGDIRQAHCNVSKATWNETLGKVVKQL
RKHYGNDTTIRPAPSSGGDLEVMNHSFNCGGEFFYCNTSGLFNSTWISNTSVQGSNSTGSNDSITLPCRIKQIINMWQRIGQAMYAPPIQGVIRCVSN
ITGLILVRDGGYTNSNTETFRPGGGDMRDNWRSELYKYKVVKIEP

LumSyn_1hgk_naked

MQIYEGKLTAEGLRFGIVASRFNHALVDRLVEGAIDAIVRHGGREEDITLVRVPGSWEIPVAAGELARKEDIDAVIAIGVLIRGATPHFDYIASEVSK
GLADLSLELRKPITFGVITADTLEQAIERAGTKHGNKGWEAALSAIEMANLFKSLR

B

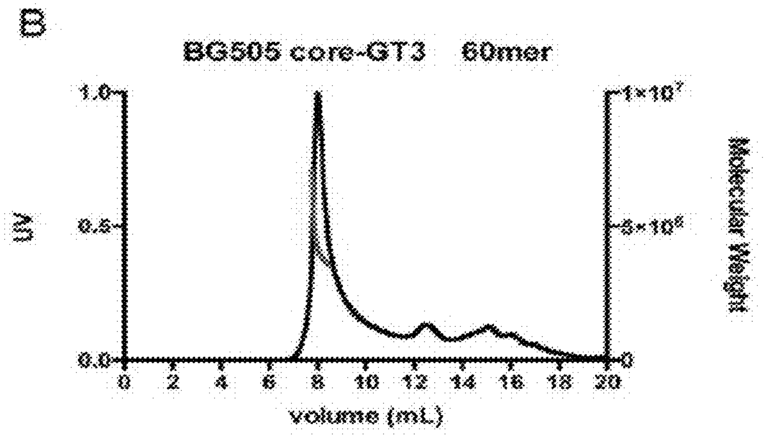

C

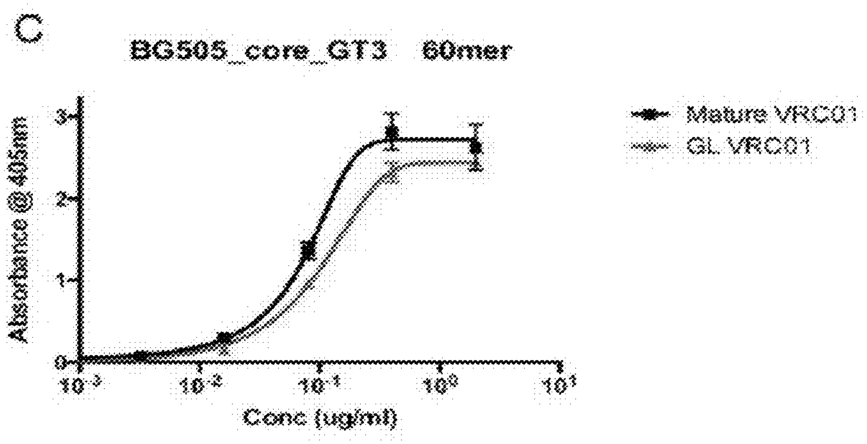

A

| | |
|---|---|
| gp120core-e-2CC_8x82 | [illegible] |
| r1-core | [illegible] |
| gp120core-e-2CC_8x82 | [illegible] |
| r1-core | [illegible] |
| gp120core-e-2CC_8x82 | [illegible] |
| r1-core | [illegible] |
| gp120core-e-2CC_8x82 | [illegible] |
| r1-core | [illegible] |

B

Kd values (nM)

| | VRC01 | PGV04 | 3BNC60 | 12A12 | CHA31 | 4546 | PGV19 | PGV20 | VRC03 | VRC06 | VRC23 |
|---|---|---|---|---|---|---|---|---|---|---|---|
| RSC3 | 3.8 | 7.1 | 263 | 64 | 53 | NA | 263 | NA | 21 | 103 | 1900 |
| gp120core-e-2CC_8x82_r1 | 2.9 | 8.7 | 105 | 3.9 | 55 | 27 | 3.3 | 9.7 | 5.2 | 16 | 43 |
| core-e-2CC_8x82 | 1.0 | NA | NA | NA | NA | NA | NA | NA | NA | NA | NA |

Table 1

Summary of IgG B cells

| Mouse | IgG cells isolated | IgG cells isolated with 5aa CDRL3 | Different Vks with 5 aa CDRL3 | Adjuvant | Day post priming | Mutations per cell | | |
|---|---|---|---|---|---|---|---|---|
| ***Single cell cloning*** | | | | | | **H** | **L** | **Average** |
| 363 | 1 | 1 | 1 | Alum | 14 | 0 | 2 | 2 |
| 457 | 13 | 13 | 3 | | | 0 | 0 | 0 |
| 339 | 10 | 10 | 3 | | 42 | 20 | 10 | 3 |
| 340 | 3 | 3 | 2 | | | 7 | 15 | 5 |
| 341 | 1 | 1 | 1 | | | 2 | 1 | 3 |
| Bulk sorted | 6 | 4 | 2 | | | 0 | 2 | 0.5 |
| 521 | 19 | 17 | 3 | Isco | 14 | 9 | 6 | 0.88 |
| 526 | 13 | 13 | 5 | | | 3 | 2 | 0.385 |
| 552 | 5 | 5 | 1 | | 42 | 0 | 0 | 0 |
| 553 | 2 | 1 | 1 | | | 3 | 3 | 6 |
| Bulk sorted | 21 | 11 | 3 | | | 7 | 9 | 1.45 |
| 331 | 2 | 2 | 2 | Ribi | 14 | 1 | 1 | 1 |
| 353 | 10 | 10 | 6 | | | 2 | 2 | 0.4 |
| 355 | 23 | 21 | 3 | | 42 | 72 | 88 | 7.62 |
| 360 | 8 | 6 | 2 | | | 6 | 8 | 2.33 |
| 361 | 21 | 19 | 3 | | | 59 | 62 | 6.37 |
| Bulk sorted | 19 | 17 | 4 | | | 33 | 36 | 4.06 |
| ***Hybridomas*** | | | | | | | | |
| 463 | 1 | 1 | 1 | Alum | 5 | 0 | 0 | 0 |
| 512 | 1 | 0 | 0 | Alum | 10 | 1 | 0 | 1 |
| 443 | 1 | 1 | 1 | Ribi | 10 | 0 | 2 | 2 |
| 513 | 1 | 1 | 1 | Ribi | 10 | 2 | 7 | 9 |
| 401 | 1 | 1 | 1 | Ribi | 31 | 5 | 2 | 7 |
| 406 | 1 | 1 | 1 | Ribi | 31 | 3 | 2 | 5 |
| 407 | 1 | 1 | 1 | Ribi | 31 | 4 | 10 | 14 |
| **Total** | | | | | | | | |
| **31*** | **184** | **160** | **51** | | | **239** | **270** | |

* Mice marked "bulk" were pools of three d42 lymph nodes; other samples were from spleens of individual mice.

Fig. 60A

Table 2

Antigen-sorted IgG Sequences

| Name | VDJ sequence | Vk | Jk | CDRL3 |
|---|---|---|---|---|
| VRC01 | ---------GQM----E-MRI--R----E-IDCTLN-I-L---KRP-----LK-RG-AV---RPL---------VYSD--FL--RS-TV------F-T----C------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYLT |
| Mouse 363 Day 14 Alum | ------------------------------------------------------------------------------------------------------------------------ | 3-30 | 1 | QQYYS |
| Mouse 457 Day 14 Alum | ------------------------------------------------------------------------------------------------------------------------ | 4-50 | 1 | QQFTT |
| | ------------------------------------------------------------------------------------------------------------------------ | 6-15 | 4 | QQYNS |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 1 | QQYWT |
| | ------------------------------------------------------------------------------------------------------------------------ | 3-30 | 2 | QQYYT |
| | ------------------------------------------------------------------------------------------------------------------------ | 3-30 | 4 | QQYYT |
| | ------------------------------------------------------------------------------------------------------------------------ | 3-30 | 4 | QQYFT |
| | ------------------------------------------------------------------------------------------------------------------------ | 3-30 | 5 | QQYAT |
| Mouse 339 Day 42 Alum | ---------------------------------D--N----------------L------------------------------------------V----------------------- | 4-61 | 5 | QQYHT |
| | -------------------------------------N---------------M------------------------------------------------------------------ | 6-15 | 2 | QQYNT |
| | ------------------------------------------------------------------------------------------------------------------------ | 6-15 | 2 | QQYNT |
| | -----------------------------N--------N--------------------------------------------------------------------------------- | 6-15 | 5 | QQYNS |
| | ------------------------------------------------------------------------------------------------------------------------ | 6-15 | 5 | QQYNS |
| | ------------------------------------------------------------------------------------------------------------------------ | 3-30 | 1 | QQYWT |
| | -------------N-----------------------N---------------------------------------------F------------------------------------ | 3-30 | 2 | QQYDT |
| | ----------------------------------N--N---------------M-L---------------------------------------------------------------- | 3-30 | 4 | QQYDS |
| | ------------------------------------------------------------------------------------------------------------------------ | 3-30 | 4 | QQYST |
| | ------------------------------------------------------------------------------------------------------------------------ | 3-30 | 5 | QQYFT |

Fig. 60B

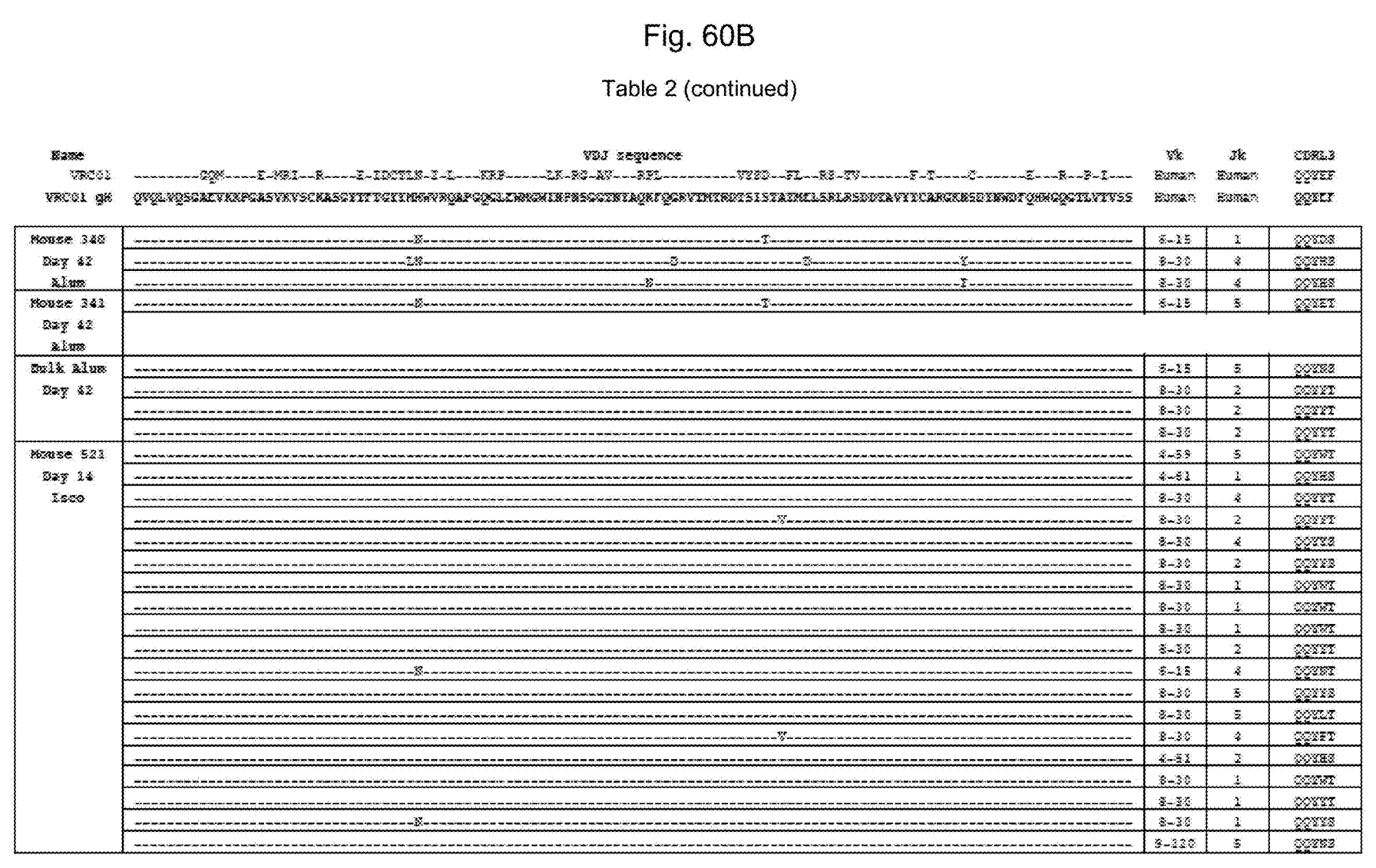

Table 2 (continued)

| Name | VDJ sequence | Vk | Jk | CDRL3 |
|---|---|---|---|---|
| VRC01 | ---------QQM----E-MRI--R----E-IDCTLR-I-L---KRP-----LK-RG-AV---RPL----------VYSD--FL--RS-TV------F-T----C------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYLF |
| Mouse 340 Day 42 Alum | ------------------------------------N-------------------------------------------T------------------------------------------------ | 6-15 | 1 | QQYDS |
| | ------------------------------------LR------------------------------D-----------------S-------------------Y-------------------- | 8-30 | 4 | QQYHS |
| | -------------------------------------------------------------------R-------------------------------------Y-------------------- | 8-30 | 4 | QQYHS |
| Mouse 341 Day 42 Alum | ------------------------------------N-------------------------------------------T------------------------------------------------ | 6-15 | 5 | QQYET |
| | | | | |
| Bulk Alum Day 42 | ------------------------------------------------------------------------------------------------------------------------------- | 6-15 | 5 | QQYHS |
| | ------------------------------------------------------------------------------------------------------------------------------- | 8-30 | 2 | QQYYT |
| | ------------------------------------------------------------------------------------------------------------------------------- | 8-30 | 2 | QQYYT |
| | ------------------------------------------------------------------------------------------------------------------------------- | 8-30 | 2 | QQYYT |
| Mouse 521 Day 14 Isco | ------------------------------------------------------------------------------------------------------------------------------- | 4-59 | 5 | QQSWT |
| | ------------------------------------------------------------------------------------------------------------------------------- | 4-61 | 1 | QQYHS |
| | ------------------------------------------------------------------------------------------------------------------------------- | 8-30 | 4 | QQYYT |
| | ---------------------------------------------------------------------------------V--------------------------------------------- | 8-30 | 2 | QQYYT |
| | ------------------------------------------------------------------------------------------------------------------------------- | 8-30 | 4 | QQYYS |
| | ------------------------------------------------------------------------------------------------------------------------------- | 8-30 | 2 | QQYYS |
| | ------------------------------------------------------------------------------------------------------------------------------- | 8-30 | 1 | QQSWT |
| | ------------------------------------------------------------------------------------------------------------------------------- | 8-30 | 1 | QQSWT |
| | ------------------------------------------------------------------------------------------------------------------------------- | 8-30 | 1 | QQSWT |
| | ------------------------------------------------------------------------------------------------------------------------------- | 8-30 | 2 | QQYYT |
| | ------------------------------------N------------------------------------------------------------------------------------------ | 6-15 | 4 | QQSWT |
| | ------------------------------------------------------------------------------------------------------------------------------- | 8-30 | 5 | QQYYS |
| | ------------------------------------------------------------------------------------------------------------------------------- | 8-30 | 5 | QQYLT |
| | ---------------------------------------------------------------------------------V--------------------------------------------- | 8-30 | 4 | QQYFT |
| | ------------------------------------------------------------------------------------------------------------------------------- | 4-61 | 2 | QQYHS |
| | ------------------------------------------------------------------------------------------------------------------------------- | 8-30 | 1 | QQSWT |
| | ------------------------------------------------------------------------------------------------------------------------------- | 8-30 | 1 | QQYYT |
| | ------------------------------------N------------------------------------------------------------------------------------------ | 8-30 | 1 | QQYYS |
| | ------------------------------------------------------------------------------------------------------------------------------- | 9-120 | 5 | QQYHS |

Fig. 60C

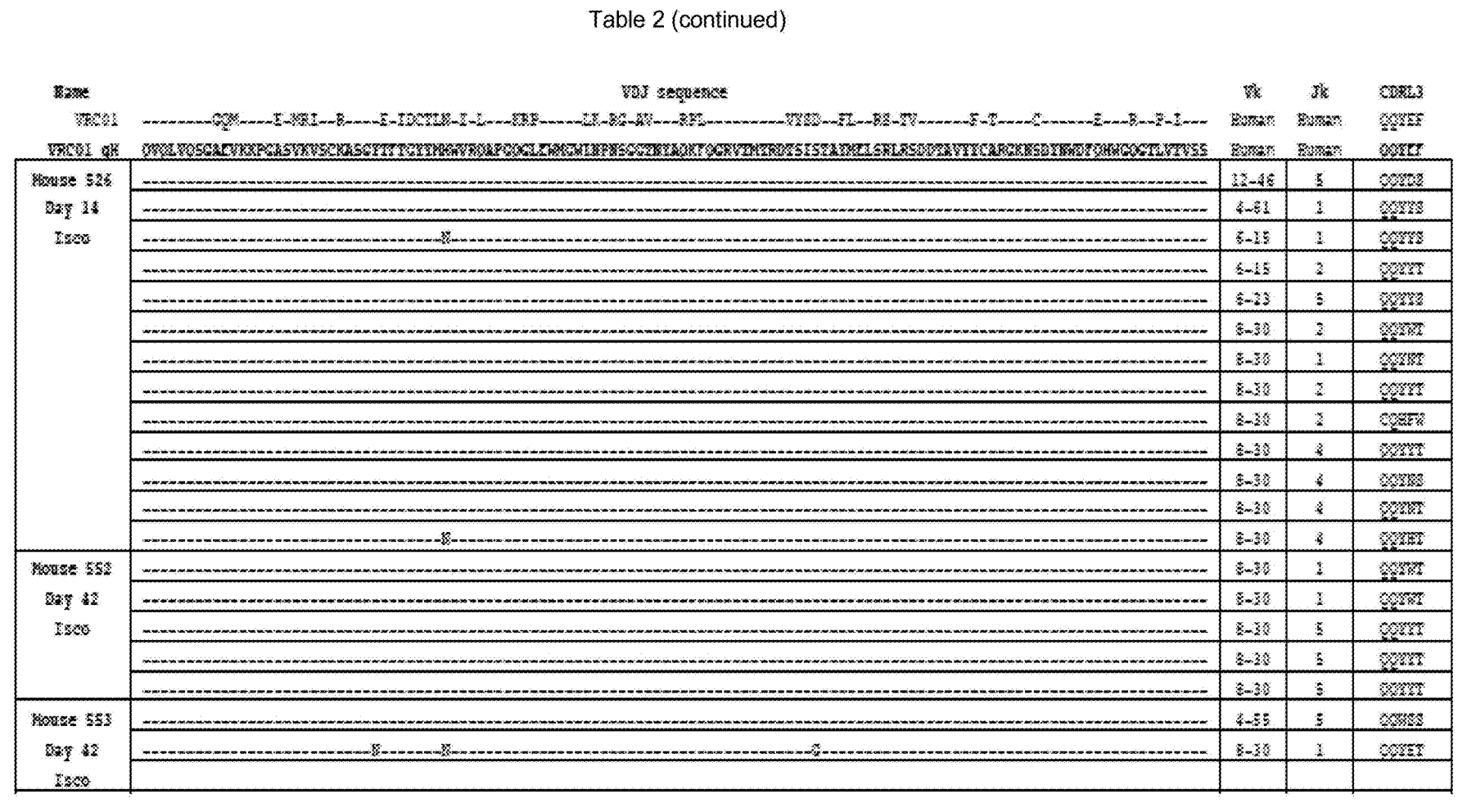

Table 2 (continued)

| Name | VDJ sequence | Vk | Jk | CDRL3 |
|---|---|---|---|---|
| VRC01 | --------GQM----I-MRI--R----E-IDCTLN-I-L---SRP-----LK-RS-AV---RPL----------VYSD--FL--RS-TV------F-T----C------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYLF |
| Mouse 526 Day 14 Isco | ------------------------------------------------------------------------------------------------------------------------- | 12-46 | 5 | QQYDN |
| | ------------------------------------------------------------------------------------------------------------------------- | 4-61 | 1 | QQYYS |
| | ----------------------------------N-------------------------------------------------------------------------------------- | 6-15 | 1 | QQYYS |
| | ------------------------------------------------------------------------------------------------------------------------- | 6-15 | 2 | QQYYT |
| | ------------------------------------------------------------------------------------------------------------------------- | 6-23 | 5 | QQYYS |
| | ------------------------------------------------------------------------------------------------------------------------- | 8-30 | 2 | QQYNT |
| | ------------------------------------------------------------------------------------------------------------------------- | 8-30 | 1 | QQYNT |
| | ------------------------------------------------------------------------------------------------------------------------- | 8-30 | 2 | QQYYT |
| | ------------------------------------------------------------------------------------------------------------------------- | 8-30 | 2 | CQHFW |
| | ------------------------------------------------------------------------------------------------------------------------- | 8-30 | 4 | QQYYT |
| | ------------------------------------------------------------------------------------------------------------------------- | 8-30 | 4 | QQYNS |
| | ------------------------------------------------------------------------------------------------------------------------- | 8-30 | 4 | QQYNT |
| | ----------------------------------N-------------------------------------------------------------------------------------- | 8-30 | 4 | QQYET |
| Mouse 552 Day 42 Isco | ------------------------------------------------------------------------------------------------------------------------- | 8-30 | 1 | QQYNT |
| | ------------------------------------------------------------------------------------------------------------------------- | 8-30 | 1 | QQYNT |
| | ------------------------------------------------------------------------------------------------------------------------- | 8-30 | 5 | QQYYT |
| | ------------------------------------------------------------------------------------------------------------------------- | 8-30 | 5 | QQYYT |
| | ------------------------------------------------------------------------------------------------------------------------- | 8-30 | 5 | QQYYT |
| Mouse 553 Day 42 Isco | ------------------------------------------------------------------------------------------------------------------------- | 4-55 | 5 | QQWSS |
| | -------------------------K--------N----------------------------------------G--------------------------------------------- | 8-30 | 1 | QQYET |
| | | | | |

Fig. 60D

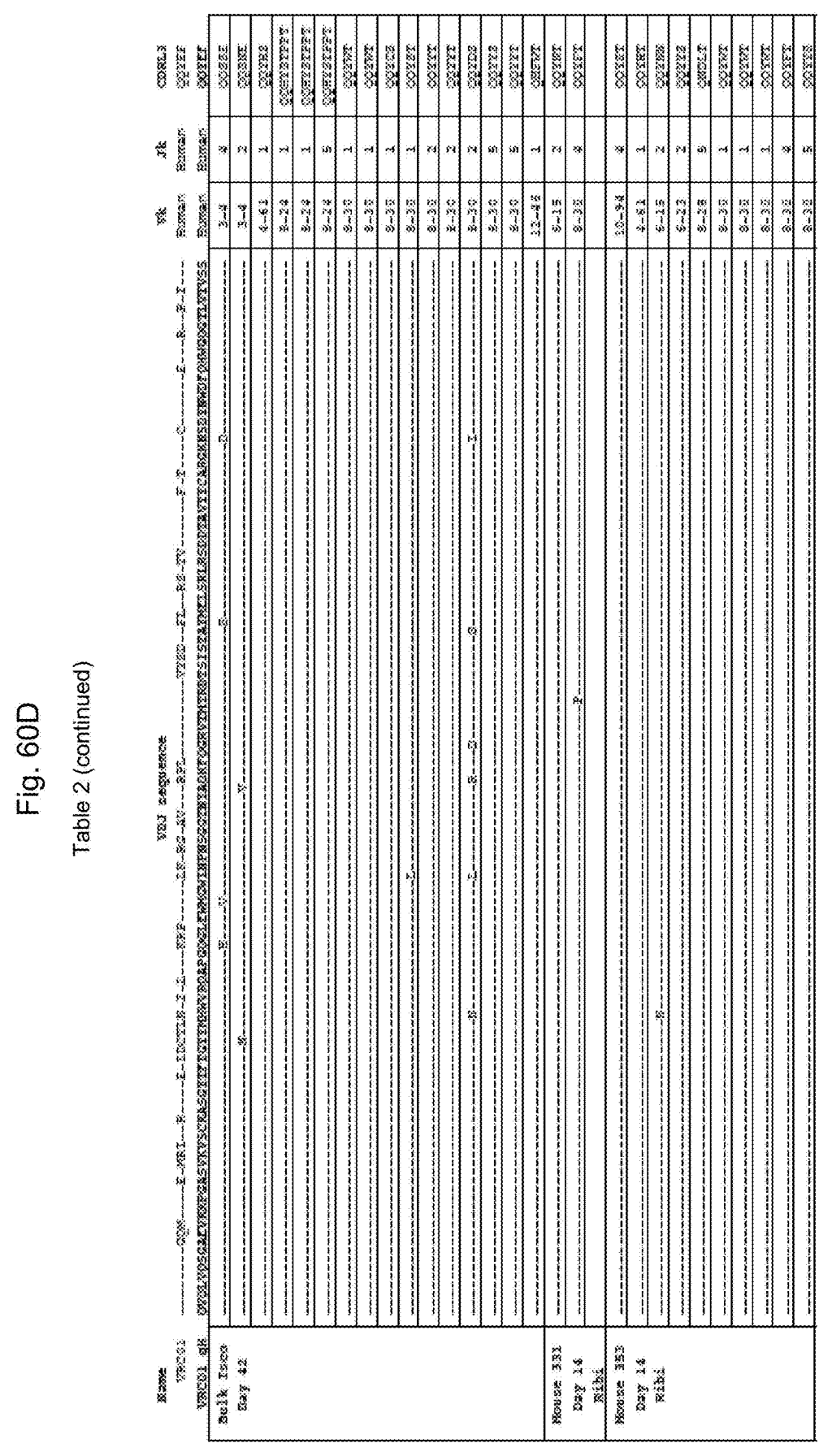

Table 2 (continued)

| Name | VDJ sequence | Vk | Jk | CDRL3 |
|---|---|---|---|---|
| VRC01 | ---------QQM-----E-MRI--R-----E-IDCTLN-I-L---KRP-----LK-RG-AV---RPL----------VYSD--FL--RS-TV-------F-T----C-------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYEF |
| Bulk Isco Day 42 | ------------------------------------------Y----V-------------------------------S--------------------D-------------------- | 3-4 | 4 | QQSSE |
| | -------------------------------N----------------------------Y------------------------------------------------------------ | 3-4 | 2 | QQSNE |
| | ------------------------------------------------------------------------------------------------------------------------- | 4-61 | 1 | QQYHS |
| | ------------------------------------------------------------------------------------------------------------------------- | 8-24 | 1 | QQHYSTPPT |
| | ------------------------------------------------------------------------------------------------------------------------- | 8-24 | 1 | QQHYSTPPT |
| | ------------------------------------------------------------------------------------------------------------------------- | 8-24 | 5 | QQHYSTPPT |
| | ------------------------------------------------------------------------------------------------------------------------- | 8-30 | 1 | QQYWT |
| | ------------------------------------------------------------------------------------------------------------------------- | 8-30 | 1 | QQYWT |
| | ------------------------------------------------------------------------------------------------------------------------- | 8-30 | 1 | QQYES |
| | --------------------------------------------------L---------------------------------------------------------------------- | 8-30 | 1 | QQYET |
| | ------------------------------------------------------------------------------------------------------------------------- | 8-30 | 2 | QQYYT |
| | ------------------------------------------------------------------------------------------------------------------------- | 8-30 | 2 | QQYYT |
| | ----------------------------------N---------------L----------R---D------------S---------------------I-------------------- | 8-30 | 2 | QQYDS |
| | ------------------------------------------------------------------------------------------------------------------------- | 8-30 | 5 | QQYYS |
| | ------------------------------------------------------------------------------------------------------------------------- | 8-30 | 5 | QQYYT |
| | ------------------------------------------------------------------------------------------------------------------------- | 12-44 | 1 | QHFWT |
| Mouse 331 Day 14 Ribi | ------------------------------------------------------------------------------------------------------------------------- | 6-15 | 2 | QQYNT |
| | ----------------------------------------------------------------------P-------------------------------------------------- | 8-30 | 4 | QQYFT |
| | | | | |
| Mouse 353 Day 14 Ribi | ------------------------------------------------------------------------------------------------------------------------- | 10-94 | 4 | QQYST |
| | ------------------------------------------------------------------------------------------------------------------------- | 4-61 | 1 | QQYNT |
| | ----------------------------------N-------------------------------------------------------------------------------------- | 6-15 | 2 | QQYNN |
| | ------------------------------------------------------------------------------------------------------------------------- | 6-23 | 2 | QQYYS |
| | ------------------------------------------------------------------------------------------------------------------------- | 8-28 | 5 | QNDLT |
| | ------------------------------------------------------------------------------------------------------------------------- | 8-30 | 1 | QQYWT |
| | ------------------------------------------------------------------------------------------------------------------------- | 8-30 | 1 | QQYWT |
| | ------------------------------------------------------------------------------------------------------------------------- | 8-30 | 1 | QQYNT |
| | ------------------------------------------------------------------------------------------------------------------------- | 8-30 | 4 | QQYFT |
| | ------------------------------------------------------------------------------------------------------------------------- | 8-30 | 5 | QQYYS |

Fig. 60E

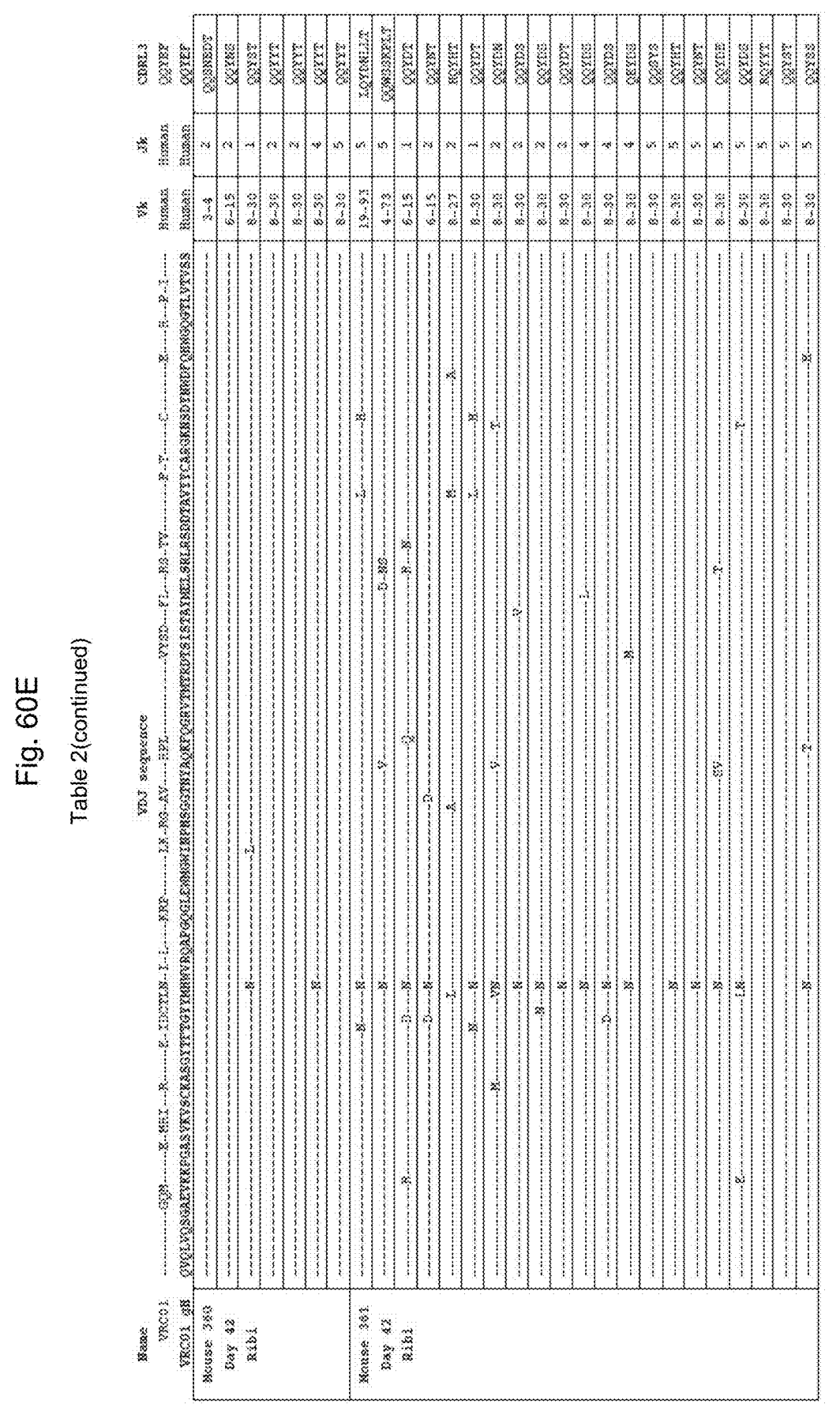

Table 2(continued)

| Name | VDJ sequence | Vk | Jk | CDRL3 |
|---|---|---|---|---|
| VRC01 | ----------GQN------K-MRI---R------E-IDCTLN-I-L----RRP-------LK-RG-AV----RPL------------VYSD---FL---RS-TV---------F-T-----C--------E----R---P-I----- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYEF |
| Mouse 360 | ------------------------------------------------------------------------------------------------------------------------- | 3-4 | 2 | QQSNEDT |
| Day 42 | ------------------------------------------------------------------------------------------------------------------------- | 6-15 | 2 | QQYNS |
| Ribi | ----------------------------------N---------------L---------------------------------------------------------------------- | 8-30 | 1 | QQYST |
| | ------------------------------------------------------------------------------------------------------------------------- | 8-30 | 2 | QQYYT |
| | ------------------------------------------------------------------------------------------------------------------------- | 8-30 | 2 | QQYYT |
| | ----------------------------------N-------------------------------------------------------------------------------------- | 8-30 | 4 | QQYYT |
| | ------------------------------------------------------------------------------------------------------------------------- | 8-30 | 5 | QQYYT |
| Mouse 361 | -----------------------------N----N---------------------------------------------------------L--------N------------------- | 19-93 | 5 | LQYDNLLT |
| Day 42 | ----------------------------------N-------------------------V--------------------D-NS------------------------------------ | 4-73 | 5 | QQWSSKPLT |
| Ribi | -----------N------------------D---N----------------------------Q-------------------N--N---------------------------------- | 6-15 | 1 | QQYDT |
| | ------------------------------D---N---------------------D---------------------------------------------------------------- | 6-15 | 2 | QQYNT |
| | ---------------------------------L---------------------A------------------------------------N-------------A-------------- | 8-27 | 2 | HQYHT |
| | -----------------------------N----N---------------------------------------------------------L--------N------------------- | 8-30 | 1 | QQYDT |
| | ----------------------M----------VN-------------------------V---------------------------------------T-------------------- | 8-30 | 2 | QQYDN |
| | ----------------------------------N-------------------------------------------V------------------------------------------ | 8-30 | 3 | QQYDS |
| | -------------------------------N--N-------------------------------------------------------------------------------------- | 8-30 | 2 | QQYDS |
| | ----------------------------------N-------------------------------------------------------------------------------------- | 8-30 | 3 | QQYDT |
| | ----------------------------------N---------------------------------------------L---------------------------------------- | 8-30 | 4 | QQYDS |
| | ------------------------------D---N-------------------------------------------------------------------------------------- | 8-30 | 4 | QQYDS |
| | ----------------------------------N--------------------------------------N----------------------------------------------- | 8-30 | 4 | QEYDS |
| | ------------------------------------------------------------------------------------------------------------------------- | 8-30 | 5 | QQSYS |
| | ----------------------------------N-------------------------------------------------------------------------------------- | 8-30 | 5 | QQYHT |
| | ----------------------------------N-------------------------------------------------------------------------------------- | 8-30 | 5 | QQYNT |
| | ----------------------------------N------------------------SV----------------------T------------------------------------- | 8-30 | 5 | QQYDE |
| | -----------E---------------------LN-----------------------------------------------------------------T-------------------- | 8-30 | 5 | QQYDS |
| | ------------------------------------------------------------------------------------------------------------------------- | 8-30 | 5 | RQYYT |
| | ------------------------------------------------------------------------------------------------------------------------- | 8-30 | 5 | QQYST |
| | ----------------------------------N---------------------------T---------------------------------------------K------------ | 8-30 | 5 | QQYSS |

Fig. 60F

Table 2 (continued)

| Name | VDJ sequence | Vk | Jk | CDRL3 |
|---|---|---|---|---|
| VRC01 | ---------GQM----E-MRI--R----E-IDCTLN-I-L---KRP------LK-RG-AV---RPL----------VYSD--FL--RS-TV------P-T----C------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYEF |
| Mouse 355 | ------------------------------------------------------------------------------------------------------------------------- | 4-55 | 5 | QQWSSYPT |
| Day 42 | -----------------------------------N---------------------------------------P----------I--------------D------------------- | 4-61 | 1 | QQYET |
| Ribi | ---------------------------------LN------------------S-----------D------------------------------T------------------------ | 4-61 | 1 | QQYET |
| | -----------------------------------N------------------------------------------------------------------------------------- | 6-15 | 5 | QQYNN |
| | ------------------------------------------------------------------------------------------------------------------------- | 8-30 | 1 | QQYYR |
| | ---------------------------------V---------------------------------------------------G-------P----------T---------------- | 8-30 | 1 | QQYEA |
| | ---------------------------N-------N----------------------------------------------D-------------------------------------- | 8-30 | 1 | QQYWT |
| | -----------------------------------N----------------------D---------------------P---------------------------------------- | 8-30 | 2 | QQYSS |
| | -----------------------------------N--------------V---------------------------------------------------------------------- | 8-30 | 2 | QQYST |
| | -------------------------------D---N----------------------V------D-----------T------------------------------------------- | 8-30 | 2 | QQYYS |
| | -----------------------------------N------------------------------------------------------------------------------------- | 8-30 | 4 | QQYFT |
| | -----------------------------------N------------------------------------------------------------------------------------- | 8-30 | 4 | QQYFT |
| | ------------------------------------------------------------------------------------------------------------------------- | 8-30 | 4 | QQYYS |
| | -----------------------------------N-----------------------------D------------------W------------------------------------ | 8-30 | 4 | QQYFT |
| | ---------------------------------I--------------------------------------------------------------------------------------- | 8-30 | 5 | QQYFS |
| | -----------------------------------N--------------------------N---------------------R------------------------------------ | 8-30 | 5 | QQYDT |
| | -----------------------------------N----V------------------------D------------------N--T--------------------------------- | 8-30 | 5 | QQYHS |
| | -----------------------------------N-----------------L--------------------------N----W----------------------------------- | 8-30 | 5 | QQYWT |
| | ------------------------------------------------------------------------------------------------------------------------- | 8-30 | 5 | QQYLT |
| | -----------------------------------N-----------------------------D------------------N--T--------------------------------- | 8-30 | 5 | QQYHS |
| | -----------------------------------N--------------L-------------------------F--------N-----G---------T-------R----------- | 8-30 | 5 | QQYDS |
| | -------------------------------D-----------------------------------------------------------A----------------------------- | 8-30 | 5 | QQYSS |
| | ------------------------------------------------------------------------------------------------------------------------- | 9-120 | 1 | LQYASSPWT |

Table 60G

Table 2 (continued)

| Name | VDJ sequence | Vk | Jk | CDRL3 |
|---|---|---|---|---|
| VRC01 | --------GQM----E-MRI--R----E-IDCTLN-I-L---KRP-----LK-RG-AV---RPL---------VYSD--FL--RS-TV------F-T----C------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYEF |
| Bulk Ribi Day 42 Ribi | ------------------------------------------------------------------------------------------------------------------------- | 12-46 | 1 | QHFWT |
| | ----------------------------------N----G----------------------Q-----------------------T-------------D-------N------------ | 4-61 | 5 | QQYDN |
| | ------------------R---E----------IN---------------L-----------Q---------------------------------------------------------- | 6-15 | 2 | QQYDT |
| | ------------------------------------------------------------------------------------------------------------------------- | 6-15 | 2 | QQYNT |
| | ------------------------------------------------------------------------------------------------------------------------- | 6-15 | 5 | QQYNT |
| | ------------------------------------------------------------------------------------------------------------------------- | 8-30 | 1 | QQYYS |
| | ------------------------------------------------------------------------------------------------------------------------- | 8-30 | 1 | QQLYT |
| | ----------------------------------F------------------------------D---------------------------F--------------------------- | 8-30 | 1 | QQYWT |
| | ------------------------------------------------------------------------------------------------------------------------- | 8-30 | 2 | QQYWT |
| | ------------------------------------------------------------------------------------------------------------------------- | 8-30 | 2 | QQYWT |
| | --------T----------------A--------N----------------------------------------------------------------R--------------------- | 8-30 | 2 | QQYDS |
| | ------------------------------------------------------------------------------------------------------------------------- | 8-30 | 2 | QQYYT |
| | ----------------------------------N-------------------------------------------------------------------------------------- | 8-30 | 5 | EQYDS |
| | ------------------------------------------------------------------------------------------------------------------------- | 8-30 | 5 | QQYST |
| | ------------------------------------------------------------------------------------------------------------------------- | 8-30 | 5 | QQYYK |
| | ------------------------------------------------------------------------------------------------------------------------- | 8-30 | 5 | QQYYS |
| | ---------------------------------LN-----------------------------------------N----------------R--------------------------- | 8-30 | 5 | QQYST |

Fig. 61

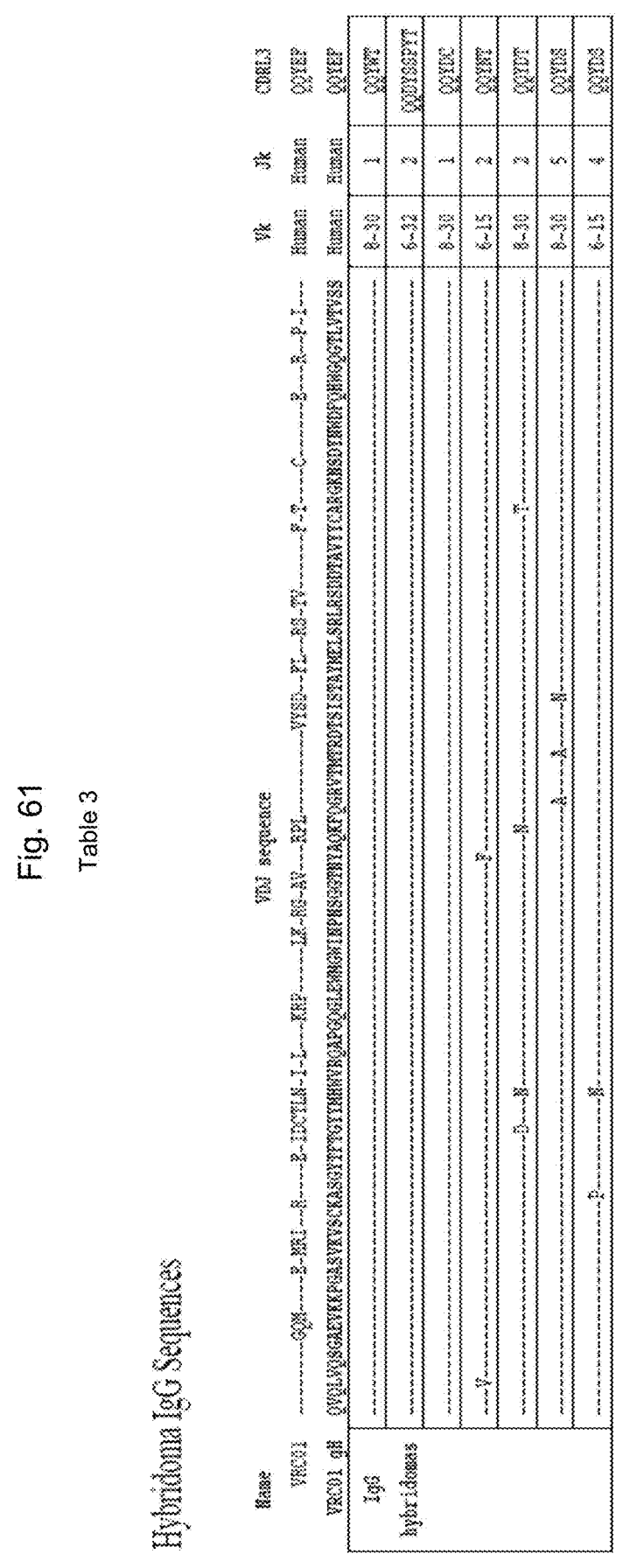

Table 3

Hybridoma IgG Sequences

| Name | VDJ sequence | Vk | Jk | CDRL3 |
|---|---|---|---|---|
| VRC01 | ---------GQM----E-MRI--N----E-IDCTLN-I-L---KNP-----LK-RG-AV---RPL----------VYSD--FL--RS-TV-------F-T----C-------E---R--P-I--- | Human | Human | QQYEF |
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS | Human | Human | QQYEF |
| IgG hybridomas | ------------------------------------------------------------------------------------------------------------------------- | 8-30 | 1 | QQYWT |
| | ------------------------------------------------------------------------------------------------------------------------- | 6-32 | 2 | QQDYSSPYT |
| | ------------------------------------------------------------------------------------------------------------------------- | 8-30 | 1 | QQYDC |
| | ---V-------------------------------------------------------F------------------------------------------------------------- | 6-15 | 2 | QQYNT |
| | ------------------------------D---N---------------------------N---------------------------------T------------------------ | 8-30 | 3 | QQYDT |
| | -----------------------------------------------------------------A----A-----N-------------------------------------------- | 8-30 | 5 | QQYDS |
| | -----------------------P----------N-------------------------------------------------------------------------------------- | 6-15 | 4 | QQYDS |

Fig. 62

Table 4

Properties of VRC01 gH hybridomas raised by eOD-GT8 60mer.

| Mouse # | Adjuvant | Day of response | Hybrids tested | ELISA binding | Sequenced | Class | | | | | Cells with 5 aa CDRL3 | | | Mutations H chain | | | Mutations L chain | | |
|---|---|---|---|---|---|---|---|---|---|---|---|---|---|---|---|---|---|---|---|
| | | | | | | k | l | IgM | IgG | IgA | IgM | IgG | IgA | IgM | IgG | IgA | IgM | IgG | IgA |
| 482 | Alum | 5 | 400 | 33 | 32 | 23 | 10 | 33 | 0 | nd | | | | 0 | | | 2 | | |
| 483 | Alum | 5 | 158 | 12 | 11 | 10 | 1 | 11 | 1 | nd | 1 | 1 | | 0 | 0 | | 0 | 0 | |
| 511 | Alum | 10 | 12 | 3 | 2 | 1 | 1 | 2 | 0 | nd | | | | 0 | | | 0 | | |
| 512 | Alum | 10 | 44 | 9 | 9 | 9 | 0 | 8 | 1 | nd | | | | 0 | 1 | | 15 | 0 | |
| 514 | Alum | 10 | 31 | 3 | 2 | 2 | 0 | 2 | 0 | nd | | | | 0 | | | 0 | | |
| 443 | Ribi | 10 | 96 | 8 | 8 | 6 | 3 | 8 | 1 | nd | | 1 | | 0 | 0 | | 2 | 4 | |
| 513 | Ribi | 10 | 143 | 12 | 12 | 9 | 4 | 12 | 1 | nd | | 1 | | 0 | 2 | | 8 | 9 | |
| 480 | Alum | d46 (2nd boost) | 200 | 35 | 32 | 23 | 12 | 34 | 0 | 1 | | | 1 | 0 | | 1 | 0 | | 0 |
| Hybridomas from fusions only screened for IgG binding. | | | | | | | | | | | | | | | | | | | |
| 396 | Ribi | 31 | 192 | 0 | | | | | | | | | | | | | | | |
| 401 | Ribi | 31 | 165 | 1 | 1 | 1 | 0 | nd | 1 | nd | | 1 | | | 5 | | | 2 | |
| 402 | Ribi | 31 | 243 | 0 | | | | | | | | | | | | | | | |
| 406 | Ribi | 31 | 282 | 4 | 1 | 1 | 0 | nd | 1 | nd | | 1 | | | 3 | | | 2 | |
| 407 | Ribi | 31 | 242 | 1 | 1 | 1 | 0 | nd | 1 | nd | | 1 | | | 4 | | | 10 | |
| Totals: | | | | | | | | | | | 1/88 | 6/7 | | 0/88 | 15/7 | 1/1 | 27/88 | 27/7 | 0/1 |
| | | | | | | | | | Frequency: | | 0.01 | 0.86 | | 0 | 2.14 | | 0.31 | 3.86 | 0 |
| VRC01 gH hybridomas obtained in vitro after stimulation with LPS: | | | | | | | | | | | | | | | | | | | |
| 1 | LPS | 3 | ~500 | 2 | 2 | 2 | | 2 | | | | | | 0 | | | 0 | | |

Fig. 63

Table 5

Sequences and sequence analysis of VRC01 gH IgG hybridomas raised by eOD-GT8 60mer

| Name | day | adj | isotypes | Kd | L- chain Vk | Jk | CDRL3 | L-chain mutations total | R | S | H-chain | H-chain mutations total | R | S |
|---|---|---|---|---|---|---|---|---|---|---|---|---|---|---|
| 483-40 | d5 | alum | IgG3,k | 2.88E-10 | Vk8-30 | Jk1 | CQQYWT | 0 | | | VRC01 gH | 0 | | |
| 512-9 | d10 | alum | IgG2c,k | not detected | Vk6-32 | Jk2 | CQQDYSSPYT | 0 | | | VRC01 gH | 1 | | 1 |
| 443-19 | d10 | Ribi | IgG2b,k | 2.88E-10 | Vk8-30 | Jk1 | CQQYDC | 2 | 2 | 0 | VRC01 gH | 0 | | |
| 513-28 | d10 | Ribi | IgG3,k | 9.60E-07 | Vk6-15 | Jk2 | CQQYNT | 0 | | | VRC01 gH | 2 | 2 | 0 |
| 401-87 | d31 | Ribi | IgG2c,k | 1.30E-10 | Vk8-30 | Jk2 | CQQYDT | 2 | 2 | 0 | VRC01 gH | 5 | 4 | 1 |
| 406-143 | d31 | Ribi | IgG2b,k | 1.20E-09 | Vk8-30 | Jk5 | CQQYDS | 2 | 1 | 1 | VRC01 gH | 3 | 3 | 0 |
| 407-77 | d31 | Ribi | IgG2b,k | not done | Vk6-15 | Jk4 | CQQYDS | 10 | 8 | 2 | VRC01 gH | 4 | 2 | 2 |

| Name | H-chain protein sequence |
|---|---|
| VRC01 gH | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGKNSDYNWDFQHWGQGTLVTVSS |
| VRC01 | ---------GQM-----E-MRI--R-----E-IDCTLN-I-L---KRP------LK-RF-AV---RPL----------VYSD--FL--RS-TV-------F-T-----C-------E---R--P-I--- |
| 483-40 | --------------------------------------------------------------------------------------------------------------------------- |
| 512-9 | --------------------------------------------------------------------------------------------------------------------------- |
| 443-19 | --------------------------------------------------------------------------------------------------------------------------- |
| 513-28 | ---V--------------------------------------------------------F-------------------------------------------------------------- |
| 401-87 | -------------------------------D---N---------------------------N----------------------------------Y------------------------ |
| 406-143 | -------------------------------------------------------------------A----A-----N-------------------------------------------- |
| 407-77 | ------------------------P----------N--------------------------------------------------------------------------------------- |

| Name | Jk | L-chain protein sequence |
|---|---|---|
| Vk8-30 | | DIVMSQSPSSLAVSVGEKVTMSCKSSQSLLYSSNQKNYLAWYQQKPGQSPKLLIYWASTRESGVPDRFTGSGSGTDFTLTISSVKAEDLAVYYCQQYYSYP |
| 483-40 | Jk1 | ---------------------------------------------------------------------------------------------CQQYWT/FGGGTKLEIK |
| 443-19 | Jk1 | -----------------R--------------T------------------------------------------------------------CQQYDC/FGGGTKLEIK |
| 406-143 | Jk5 | ------------------------------------K--------------------------------------------------------CQQYDS/FGAGTKLELK |
| 401-87 | Jk2 | ------------------------------N-I------------------------------------------------------------CQQYDT/FGGGTKLEIK |
| Vk6-15 | | DIVMTQSQKFMSTSVGDRVSVTCKASQNVGTNVAWYQQKPGQSPKALIYSASYRYSGVPDRFTGSGSGTDFTLTISNVQSEDLAEYFCQQYNSYP |
| 513-28 | Jk5 | ---------------------------------------------------------------------------------------CQQYNT/FGAGTKLELK |
| 407-77 | Jk4 | --------------I----------------------N------------T---F---------G----------T--------K--CQQYDT/FGSGTKLEIK |
| Vk6-32 | | SIVMTQTPKFLLVSAGDRVTITCKASQSVSNDVAWYQQKPGQSPKLLIYYASNRYTGVPDRFTGSGYGTDFTFTISTVQAEDLAVYFCQQDYSSP |
| 512-9 | Jk2 | ---------------------------------------------------------------------------------------CQQDYSSPYT/FGGGTKLEIK |

Fig. 64A

Table 6

L-chain sequence analysis of IgM hybridomas positive for binding to GT8-60mer. All hybridomas carried a VRC01 gH chain.

| Hybridoma number | VL/JL | CDRL3 | Length |
|---|---|---|---|
| **Lps hybridomas** | | | |
| LPS-1D9 | Vk12-46/Jk1 | CQHFWGTPWT | 9 |
| LPS-2D10 | Vk12-44/Jk5 | CHQHYGTPT | 8 |
| **Day 10 Alum eOD-GT8 60mers** | | | |
| 511-3 | Vk6-20/Jk5 | CGQSYSYPLT | 9 |
| 511-6 | Vl2/Jl2 | CALWYSTHFV | 9 |
| 512-5 | Vk4-91/Jk5 | CQQGSSIPT | 8 |
| 512-15 | Vk12-41/Jk1 | CQHFWSTPWT | 9 |
| 512-18 | Vk9-120/Jk1 | CLQYXSSPPT | 9 |
| 512-25 | Vk3-4/Jk2 | CQQSNEDPYT | 9 |
| 512-26 | Vk12-41/Jk1 | CQHFWSTPRA | 9 |
| 512-28 | Vk12-41/Jk1 | CQHFWSTPRA | 9 |
| 512-32 | Vk1-110/Jk2 | CSQSTHVPYT | 9 |
| 512-35 | Vk1-110/Jk2 | CSQSTHVPYT | 9 |
| 514-17 | Vk6-23/Jk4 | CHQYSYPLT | 9 |
| 514-L9 | Vk12-44/Jk2 | CQHHYGTPYT | 9 |
| **Day 5 Ribi eOD-GT8 60mers** | | | |
| 482-B | Vk12-46/Jk2 | CQHFWGTPYT | 9 |
| 482-C | Vk12-46/Jk2 | CQHFWGTPYT | 9 |
| 482-D | Vk8-27/Jk2 | CHQYLSYT | 7 |
| 483-E | Vk8-28/Jk5 | CQNDHSYPLT | 9 |
| 482-I | Vk8-28/Jk5 | CQNDHSYPLT | 9 |
| 482-L | Vk8-28/Jk5 | CQNDHSYPLT | 9 |
| 482-N | Vk8-28/Jk5 | CQNDHSYPLT | 9 |
| 482-AA | Vk8-28/Jk5 | CQNDHSYPLT | 9 |
| 482-BB | Vk8-28/Jk5 | CQNDHSYPLT | 9 |
| 482-DD | Vk8-28/Jk5 | CQNDHSYPLT | 9 |
| 482-X | Vk8-28/Jk5 | CQNDHSYPLT | 9 |
| 482-P | Vk8-28/Jk5 | CQNDHSYPLT | 9 |
| 482-U | Vk3-4/Jk2<br>Vk8-28/Jk2 | CQQSNEDPYT<br>CQKNHKYPFT | 9;9 |
| 482-H | Vk8-30/Jk4 | CQQYYSYPFT | 8 |
| 482-M | Vk8-21/Jk2 | CKQSYNLYT | 8 |
| 482-S | Vk1-117/Jk1 | CLQGSHVPWT | 9 |
| 482-W | Vk1-117/Jk2 | CFQGSHVPYT | 9 |
| 482-A | Vl1/Jl1 | CALWYSNHWV | 9 |
| 482-O | Vl1/Jl1 | CALWYSNLWV | 9 |
| 482-T | Vl1/Jl1 | CALWYSNHLV | 9 |
| 482-CC | Vl1/Jl1 | CALWYSNHLV | 9 |
| 482-F | Vl2/Jl2 | CALWYSTHYV | 9 |
| 482-R | Vl2/Jl2 | CALWYSTHYV | 9 |
| 482-V | Vl2/Jl2 | CALWYSTHYV | 9 |
| 482-FF | Vl2/Jl2 | CALWYSTHYV | 9 |

Table 64B

Table 6 (continued)

| | | | |
|---|---|---|---|
| 482-J | Vl2/Jl2 | CALWYSTHYV | 9 |
| 482-II | Vl2/Jl2 | CALWYSTHYV | 9 |
| 483-23 | Vk8-21/Jk2 | CKQSYNLYT | 8 |
| 483-63 | Vk8-21/Jk2 | CKQSYNLYT | 8 |
| 483-69 | Vk6-15/Jk2 | CQQYNRFGSGT | 10 |
| 483-77 | Vk1-117/Jk4 | CFQGSHVPFT | 9 |
| 483-132 | Vk4-61/Jk1 | CQQYHT | 5 |
| 483-135 | Vk6-23/Jk5 | CQQYSSYPT | 8 |
| 483-149 | Vk12-38/Jk4 | CKQAYDVPPT | 9 |
| 483-154 | Vk3-5/Jk4 | CQQSNEDPFT | 9 |
| 483-6 | Vl1/Jl1 | CALWYSNHLV | 9 |
| **Day 10 Ribi eOD-GT8 60mers** | | | |
| 443-3 | Vk4-59/Jk5 | CQQWSSNPIT | 9 |
| 443-19M | Vl1/Jl1 | CALWYSNHTFWV | 10 |
| 443-21 | Vk6-15/Jk2 | CQQYNSYPYT | 9 |
| 443-36 | Vl/Jl2 | CALWYSTHYV | 9 |
| 443-40 | Vk3-10/Jk5 | CQQNNEDLT | 8 |
| 443-82 | Vl1/Jl1 | CALWYSNTHYV | 9 |
| 443-88 | Vk4-55/Jk2 | CQQWSSYPPT | 8 |
| 513-16 | Vl1/Jl1 | CALWYSNHWV | 9 |
| 513-28M | Vl1/Jl1 | CALWYSNHWV | 9 |
| 513-29 | Vk5-39/ | CQXGHXFXFT | 9 |
| 513-41 | Vk6-14/Jk1 | CLQHWNYPWT | 9 |
| 513-52 | Vk1-110/Jk2 | CSQSTHVPYT | 9 |
| 513-58 | Vk19-93/Jk2 | CLQYECVFT | 9 |
| 513-63 | Vk3-2/Jk2 | CQQSKEVPYT | 9 |
| 513-69 | Vl2/Jl2 | CALWYSTHYV | 9 |
| 513-79 | Vk4-91/Jk2 | CQQNSIIPRT | 9 |
| 513-91 | Vk8-28/Jk5 | CQNDHSYPLT | 9 |
| 513-93 | Vk6-15/Jk5 | CQQYNSYPLT | 9 |
| 513-124 | Vl1/Jl1 | CALWYSNHWV | 9 |
| **Day 49 Alum x eOD-GT8 60mer** | | | |
| 480-13 | Vk3-4/Jk5 | CQQSNEDPLT | 9 |
| 480-62 | Vk3-4/Jk5 | CQQSNEDPLT | 9 |
| 480-42 | Vk8-21/Jk4 | CKQSYNLPT | 8 |
| 480-50 | Vk8-28/Jk5 | CQNDHSYPLT | 9;9 |
| | Vk12-44/Jk1 | CQHHYGTPPT | |
| 480-76 | Vk8-24/Jk5 | CQQHYSTPLT | 9 |
| 480-98 | Vk8-24/Jk5 | CQQHYSTPLT | 9 |
| 480-87 | Vk6-23/Jk5 | CQQYSSYPT | 8 |
| 480-90 | Vk8-21/Jk1 | CKQSYNLWT | 8 |
| 480-94 | Vk4-72/Jk5 | CQQWSSNPFMGT | 11 |
| 480-118 | Vk4-57/Jk5 | CQQRSSYPLT | 9 |
| 480-146 | Vk19-93/Jk2 | CLQYDNLYT | 8 |
| 480-183 | Vk12-46/Jk2 | CQHFWGTPYT | 9 |
| 480-199 | Vk19-93/Jk5 | CLQYDNLLT | 8;9 |
| | Vk10-96/Jk2 | CQQGNTLPYT | |
| 480-160 | Vk3-4/Jk2 | CQQSNEDPYT | 9 |
| 480-25 | Vl1/Jl1 | CALWYSNHLV | 9 |
| 480-73 | Vl1/Jl1 | CALWYSNHLV | 9 |
| 480-80 | Vl1/Jl1 | CALWYSNHLV | 9 |
| 480-144 | Vl1/Jl1 | CALWYSNHLV | 9 |
| 480-44 | Vl1/Jl1 | CALWYSNHWV | 9 |
| 480-207 | Vl1/Jl1 | CALWYSNHWV | 9 |

Fig. 65

Table 7

Summary of the numbers of complete H/L paired antibody sequences recovered by B cell sorting from VRC01 gH mice immunized with eOD-GT8 60-mers.

All antibodies

| | VRC01 gH | | | |
|---|---|---|---|---|
| | Paired with 5 aa CDR-L3 | Paired with non 5 aa CDR-L3 | Mouse HCs | Total |
| Day 14 | 56 | 2 | 0 | 58 |
| Day 42 | 98 | 11 | 10 | 119 |
| Total | 154 | 13 | 10 | 177 |

VRC01-class antibodies (using VRC01 gH and 5aa CDRL3)

| | Unmutated VRC01 gH | Mutated VRC01 gH | Total |
|---|---|---|---|
| Day 14 | 48 | 8 | 56 |
| Day 42 | 45 | 53 | 98 |
| Total | 93 | 61 | 154 |

VRC01-class antibodies (using VRC01 gH and 5aa CDRL3) that were successfully expressed and tested by SPR

| | No mutations in VRC01 gH or mouse L-chain | At least one mutation in either VRC01 gH or mouse L-chain | Total |
|---|---|---|---|
| Day 14 | 38 | 4 | 42 |
| Day 42 | 34 | 39 | 73 |
| Total | 72 | 43 | 115 |

Fig. 66A

Table 8

Summary of SPR results for eOD-GT8 analyte binding to eOD-GT8 60mer-induced Abs isolated by cell sorting.

| Ab Name | Rmax | Kon | Koff | Kd |
|---|---|---|---|---|
| Nem_0016 | Pass | 1.10E+05 | 1.90E-02 | 1.72E-07 |
| Nem_0018 | Pass | 2.20E+05 | 5.90E-03 | 2.66E-08 |
| Nem_0021 | Pass | 1.90E+05 | 5.80E-03 | 3.05E-08 |
| Nem_0024 | Pass | 2.00E+05 | 3.00E-04 | 1.49E-09 |
| Nem_0025 | Pass | 1.50E+05 | 5.80E-03 | 3.84E-08 |
| Nem_0026 | Pass | 1.00E+05 | 1.40E-01 | 1.33E-06 |
| Nem_0027 | Pass | 2.50E+05 | 6.60E-03 | 2.70E-08 |
| Nem_0028 | Pass | 1.60E+05 | 3.00E-03 | 1.86E-08 |
| Nem_0030 | Pass | 4.40E+05 | 1.80E-02 | 3.94E-08 |
| Nem_0031 | Pass | 2.40E+05 | 5.90E-03 | 2.45E-08 |
| Nem_0032 | Pass | 2.40E+05 | 6.80E-03 | 2.85E-08 |
| Nem_0033 | Pass | 2.20E+05 | 1.20E-02 | 5.74E-08 |
| Nem_0037 | Pass | 2.00E+05 | 6.70E-03 | 3.27E-08 |
| Nem_0038 | Pass | 2.00E+05 | 7.00E-03 | 3.53E-08 |
| Nem_0039 | Pass | 1.00E+05 | 8.80E-03 | 8.78E-08 |
| Nem_0040 | Pass | 2.00E+05 | 7.50E-03 | 3.73E-08 |
| Nem_0041 | Pass | 1.80E+05 | 7.20E-03 | 3.93E-08 |
| Nem_0042 | Pass | 2.10E+05 | 7.40E-03 | 3.58E-08 |
| Nem_0043 | Pass | 2.00E+05 | 7.40E-03 | 3.71E-08 |
| Nem_0044 | Pass | 2.00E+05 | 6.40E-03 | 3.25E-08 |
| Nem_0045 | Pass | 2.10E+05 | 6.90E-03 | 3.27E-08 |
| Nem_0046 | Pass | 2.40E+05 | 4.80E-04 | 2.00E-09 |
| Nem_0048 | Pass | 2.00E+05 | 7.40E-03 | 3.71E-08 |
| Nem_0049 | Pass | 7.30E+04 | 2.70E-02 | 3.73E-07 |
| Nem_0050 | Pass | 2.10E+05 | 7.70E-03 | 3.63E-08 |
| Nem_0052 | Pass | 2.00E+05 | 7.10E-03 | 3.51E-08 |
| Nem_0054 | Pass | 1.90E+05 | 5.60E-03 | 2.93E-08 |
| Nem_0055 | Pass | 6.40E+05 | <5.0E-05 | <1.6e-11 |
| Nem_0057 | Pass | 1.00E+05 | 1.10E-02 | 1.10E-07 |
| Nem_0058 | Pass | 1.90E+05 | 3.30E-03 | 1.74E-08 |
| Nem_0061 | Pass | 1.20E+06 | <5.0E-05 | <1.6e-11 |
| Nem_0062 | Pass | 1.10E+05 | 7.20E-03 | 6.39E-08 |
| Nem_0063 | Pass | 2.80E+05 | 5.40E-04 | 1.89E-09 |
| Nem_0066 | Pass | 8.30E+05 | 2.50E-02 | 3.01E-08 |

Fig. 66B

Table 8(continued)

| | | | | |
|---|---|---|---|---|
| Nem_0067 | Pass | 1.40E+06 | <5.0E-05 | <1.6e-11 |
| Nem_0068 | Pass | 1.80E+05 | 4.60E-03 | 2.59E-08 |
| Nem_0069 | Pass | 6.60E+05 | 5.60E-05 | 8.49E-11 |
| Nem_0070 | Pass | 1.60E+05 | 1.70E-03 | 1.08E-08 |
| Nem_0071 | Pass | 9.90E+05 | <5.0E-05 | <1.6e-11 |
| Nem_0072 | Pass | 1.20E+06 | <5.0E-05 | <1.6e-11 |
| Nem_0074 | Pass | 6.90E+05 | 1.00E-04 | 1.51E-10 |
| Nem_0077 | Pass | 1.60E+05 | 1.80E-03 | 1.15E-08 |
| Nem_0078 | Pass | 5.20E+05 | 6.00E-05 | 1.16E-10 |
| Nem_0079 | Pass | 7.10E+05 | <5.0E-05 | <1.6e-11 |
| Nem_0080 | Pass | 1.20E+06 | <5.0E-05 | <1.6e-11 |
| Nem_0081 | Pass | 2.10E+05 | 3.30E-03 | 1.54E-08 |
| Nem_0083 | Pass | 1.00E+06 | <5.0E-05 | <1.6e-11 |
| Nem_0086 | Pass | 8.90E+05 | 9.60E-05 | 1.08E-10 |
| Nem_0087 | Pass | 1.10E+06 | 3.10E-04 | 2.94E-10 |
| Nem_0088 | Fail | 3.30E+04 | 1.10E-01 | >1.0E-05 |
| Nem_0089 | Pass | 2.10E+05 | 2.50E-01 | 1.16E-06 |
| Nem_0096 | Pass | 4.60E+05 | <5.0E-05 | <1.6e-11 |
| Nem_0097 | Pass | 6.40E+05 | <5.0E-05 | <1.6e-11 |
| Nem_0098 | Pass | 5.10E+05 | <5.0E-05 | <1.6e-11 |
| Nem_0101 | Pass | 3.80E+05 | <5.0E-05 | <1.6e-11 |
| Nem_0103 | Pass | 4.20E+05 | <5.0E-05 | <1.6e-11 |
| Nem_0104 | Pass | 7.90E+05 | <5.0E-05 | <1.6e-11 |
| Nem_0105 | Pass | 9.40E+04 | 3.80E-01 | 4.08E-06 |
| Nem_0106 | Pass | 1.60E+05 | 7.80E-04 | 4.80E-09 |
| Nem_0108 | Pass | 3.30E+05 | 9.20E-05 | 2.75E-10 |
| Nem_0109 | Pass | 4.80E+05 | <5.0E-05 | <1.6e-11 |
| Nem_0110 | Pass | 6.20E+05 | <5.0E-05 | <1.6e-11 |
| Nem_0112 | Pass | 1.10E+05 | 7.10E-03 | 6.46E-08 |
| Nem_0113 | Pass | 1.90E+05 | 5.30E-03 | 2.77E-08 |
| Nem_0114 | Pass | 1.90E+05 | 5.80E-03 | 3.03E-08 |
| Nem_0115 | Pass | 2.10E+05 | 7.20E-03 | 3.37E-08 |
| Nem_0116 | Pass | 8.60E+04 | 1.70E-01 | 1.98E-06 |
| Nem_0117 | Pass | 2.00E+05 | 5.90E-03 | 2.99E-08 |
| Nem_0118 | Pass | 5.60E+05 | 9.90E-05 | 1.76E-10 |
| Nem_0119 | Pass | 2.00E+05 | 3.60E-03 | 1.78E-08 |
| Nem_0120 | Pass | 2.10E+05 | 3.50E-03 | 1.64E-08 |
| Nem_0121 | Pass | 1.30E+05 | 2.50E-02 | 1.93E-07 |
| Nem_0122 | Pass | 1.50E+05 | 2.60E-01 | 1.72E-06 |
| Nem_0123 | Pass | 3.90E+05 | 1.60E-02 | 4.19E-08 |
| Nem_0124 | Pass | 1.40E+05 | 3.50E-03 | 2.56E-08 |
| Nem_0126 | Pass | 2.30E+05 | 5.30E-03 | 2.31E-08 |
| Nem_0128 | Pass | 2.10E+05 | 6.90E-03 | 3.37E-08 |

Fig. 66C

Table 8(continued)

| | | | | |
|---|---|---|---|---|
| Nem_0129 | Pass | 5.90E+05 | 1.10E-04 | 1.85E-10 |
| Nem_0130 | Fail | 2.40E+04 | 1.50E-01 | >1.0E-05 |
| Nem_0132 | Fail | 1.20E+06 | >6.0E-01 | >1.0E-05 |
| Nem_0135 | Fail | 6.70E+05 | >6.0E-01 | >1.0E-05 |
| Nem_0138 | Pass | 5.20E+05 | 1.80E-01 | 3.50E-07 |
| Nem_0139 | Pass | 1.50E+05 | 6.30E-03 | 4.16E-08 |
| Nem_0141 | Pass | 3.70E+05 | <5.0E-05 | <1.6e-11 |
| Nem_0143 | Fail | 5.70E+05 | >6.0E-01 | >1.0E-05 |
| Nem_0144 | Pass | 2.00E+05 | 6.40E-03 | 3.10E-08 |
| Nem_0145 | Pass | 3.00E+05 | 1.30E-02 | 4.34E-08 |
| Nem_0146 | Pass | >3.0E06 | >6.0E-01 | >1.0E-05 |
| Nem_0147 | Fail | 1.50E+05 | 6.00E-03 | >1.0E-05 |
| Nem_0149 | Pass | 7.60E+04 | >6.0E-01 | >1.0E-05 |
| Nem_0150 | Pass | 1.30E+05 | 6.20E-03 | 4.92E-08 |
| Nem_0151 | Pass | 9.30E+04 | >6.0E-01 | >1.0E-05 |
| Nem_0152 | Pass | 1.20E+05 | 2.40E-03 | 1.96E-08 |
| Nem_0153 | Fail | 1.30E+05 | 3.80E-01 | >1.0E-05 |
| Nem_0155 | Pass | 1.70E+05 | 2.90E-04 | 1.69E-09 |
| Nem_0156 | Pass | 2.60E+06 | 2.80E-02 | 1.09E-08 |
| Nem_0159 | Pass | 1.80E+05 | 2.60E-03 | 1.45E-08 |
| Nem_0160 | Fail | 7.50E+04 | 1.90E-03 | >1.0E-05 |
| Nem_0161 | Pass | 1.40E+05 | 7.10E-03 | 5.09E-08 |
| Nem_0162 | Pass | 8.70E+04 | 9.80E-02 | 1.12E-06 |
| Nem_0164 | Pass | 6.10E+05 | <5.0E-05 | <1.6e-11 |
| Nem_0169 | Pass | 2.30E+05 | 3.40E-03 | 1.48E-08 |
| Nem_0175 | Pass | 1.20E+05 | 8.60E-02 | 7.02E-07 |
| Nem_0176 | Pass | 2.20E+05 | 2.90E-03 | 1.33E-08 |
| Nem_0177 | Pass | 2.00E+05 | 1.50E-01 | 7.54E-07 |
| Nem_0178 | Pass | 3.60E+05 | 8.30E-05 | 2.28E-10 |
| Nem_0179 | Pass | 2.20E+05 | 5.20E-03 | 2.44E-08 |
| Nem_0181 | Pass | 4.30E+05 | <5.0E-05 | <1.6e-11 |
| Nem_0182 | Pass | 2.10E+05 | 5.70E-03 | 2.67E-08 |
| Nem_0186 | Pass | 2.10E+05 | 7.80E-04 | 3.63E-09 |
| Nem_0187 | Pass | 1.80E+05 | 3.80E-03 | 2.04E-08 |
| Nem_0188 | Pass | 9.50E+05 | <5.0E-05 | <1.6e-11 |
| Nem_0190 | Pass | 2.20E+05 | 7.50E-03 | 3.37E-08 |
| Nem_0191 | Pass | 2.90E+05 | 1.50E-03 | 5.20E-09 |
| Nem_0195 | Pass | 1.10E+05 | 1.20E-02 | 1.09E-07 |
| Nem_0201 | Pass | 2.20E+05 | 3.60E-03 | 1.68E-08 |
| Nem_0203 | Fail | 1.50E+06 | 1.90E-04 | >1.0E-05 |
| Nem_0204 | Fail | 8.00E+05 | 2.00E-02 | >1.0E-05 |
| Nem_0205 | Pass | 4.10E+05 | 1.50E-02 | 3.57E-08 |
| Nem_0206 | Pass | 2.10E+05 | 5.30E-03 | 2.54E-08 |

Fig. 66D

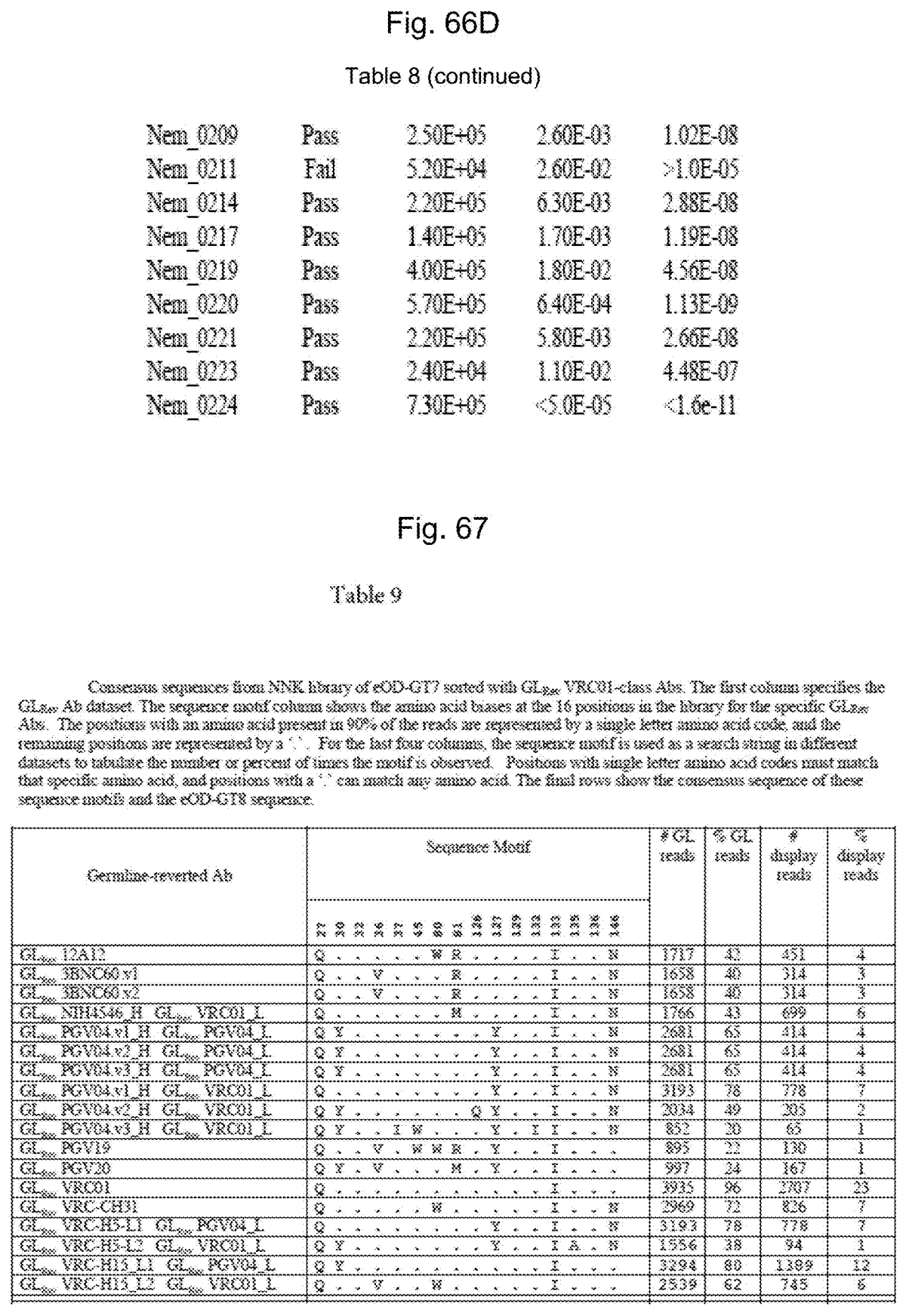

Table 8 (continued)

| | | | | |
|---|---|---|---|---|
| Nem_0209 | Pass | 2.50E+05 | 2.60E-03 | 1.02E-08 |
| Nem_0211 | Fail | 5.20E+04 | 2.60E-02 | >1.0E-05 |
| Nem_0214 | Pass | 2.20E+05 | 6.30E-03 | 2.88E-08 |
| Nem_0217 | Pass | 1.40E+05 | 1.70E-03 | 1.19E-08 |
| Nem_0219 | Pass | 4.00E+05 | 1.80E-02 | 4.56E-08 |
| Nem_0220 | Pass | 5.70E+05 | 6.40E-04 | 1.13E-09 |
| Nem_0221 | Pass | 2.20E+05 | 5.80E-03 | 2.66E-08 |
| Nem_0223 | Pass | 2.40E+04 | 1.10E-02 | 4.48E-07 |
| Nem_0224 | Pass | 7.30E+05 | <5.0E-05 | <1.6e-11 |

Fig. 67

Table 9

Consensus sequences from NNK library of eOD-GT7 sorted with $GL_{rev}$ VRC01-class Abs. The first column specifies the $GL_{rev}$ Ab dataset. The sequence motif column shows the amino acid biases at the 16 positions in the library for the specific $GL_{rev}$ Abs. The positions with an amino acid present in 90% of the reads are represented by a single letter amino acid code, and the remaining positions are represented by a '.'. For the last four columns, the sequence motif is used as a search string in different datasets to tabulate the number or percent of times the motif is observed. Positions with single letter amino acid codes must match that specific amino acid, and positions with a '.' can match any amino acid. The final rows show the consensus sequence of these sequence motifs and the eOD-GT8 sequence.

| Germline-reverted Ab | Sequence Motif | # GL reads | % GL reads | # display reads | % display reads |
|---|---|---|---|---|---|
| | [illegible] | | | | |
| $GL_{rev}$ 12A12 | Q . . . . . W R . . . . I . . N | 1717 | 42 | 451 | 4 |
| $GL_{rev}$ 3BNC60 v1 | Q . . V . . . R . . . . I . . N | 1658 | 40 | 314 | 3 |
| $GL_{rev}$ 3BNC60 v2 | Q . . V . . . R . . . . I . . N | 1658 | 40 | 314 | 3 |
| $GL_{rev}$ NIH4546_H $GL_{rev}$ VRC01_L | Q . . . . . . M . . . . I . . N | 1766 | 43 | 699 | 6 |
| $GL_{rev}$ PGV04.v1_H $GL_{rev}$ PGV04_L | Q Y . . . . . . . Y . . I . . N | 2681 | 65 | 414 | 4 |
| $GL_{rev}$ PGV04.v2_H $GL_{rev}$ PGV04_L | Q Y . . . . . . . Y . . I . . N | 2681 | 65 | 414 | 4 |
| $GL_{rev}$ PGV04.v3_H $GL_{rev}$ PGV04_L | Q Y . . . . . . . Y . . I . . N | 2681 | 65 | 414 | 4 |
| $GL_{rev}$ PGV04.v1_H $GL_{rev}$ VRC01_L | Q . . . . . . . . Y . . I . . N | 3193 | 78 | 778 | 7 |
| $GL_{rev}$ PGV04.v2_H $GL_{rev}$ VRC01_L | Q Y . . . . . . Q Y . . I . . N | 2034 | 49 | 205 | 2 |
| $GL_{rev}$ PGV04.v3_H $GL_{rev}$ VRC01_L | Q Y . . I W . . . Y . I I . . N | 852 | 20 | 65 | 1 |
| $GL_{rev}$ PGV19 | Q . . V . W W R . Y . . I . . . | 895 | 22 | 130 | 1 |
| $GL_{rev}$ PGV20 | Q Y . V . . . M . Y . . I . . . | 997 | 24 | 167 | 1 |
| $GL_{rev}$ VRC01 | Q . . . . . . . . . . . I . . . | 3935 | 96 | 2707 | 23 |
| $GL_{rev}$ VRC-CH31 | Q . . . . . W . . . . . I . . N | 2969 | 72 | 826 | 7 |
| $GL_{rev}$ VRC-H5-L1 $GL_{rev}$ PGV04_L | Q . . . . . . . . Y . . I . . N | 3193 | 78 | 778 | 7 |
| $GL_{rev}$ VRC-H5-L2 $GL_{rev}$ VRC01_L | Q Y . . . . . . . Y . . I A . N | 1556 | 38 | 94 | 1 |
| $GL_{rev}$ VRC-H13_L1 $GL_{rev}$ PGV04_L | Q Y . . . . . . . . . . I . . . | 3294 | 80 | 1389 | 12 |
| $GL_{rev}$ VRC-H13_L2 $GL_{rev}$ VRC01_L | Q . . V . . W . . . . . I . . . | 2539 | 62 | 745 | 6 |

Fig. 68A

Table 10

SPR binding to germline-reverted and VRC01-class bnAbs.

| Ligand | Rmax | Analyte | Kon | Koff | KD |
|---|---|---|---|---|---|
| 12a12 | Pass | eOD-GT6 | 5.80E+04 | 1.80E-02 | 3.09E-07 |
| 12a21 | Fail | eOD-GT6 | <3.00E+03 | 1.40E-02 | >1.0E-04 |
| 3BNC117 | Pass | eOD-GT6 | 1.50E+05 | 2.90E-02 | 1.97E-07 |
| 3BNC60 | Pass | eOD-GT6 | 1.80E+05 | 2.10E-02 | 1.18E-07 |
| NIH45-46 | Pass | eOD-GT6 | 1.30E+05 | 1.70E-04 | 1.31E-09 |
| PGV04 | Pass | eOD-GT6 | 1.40E+05 | 1.10E-03 | 8.09E-09 |
| PGV19 | Pass | eOD-GT6 | 1.20E+05 | 8.60E-03 | 7.24E-08 |
| PGV20 | Pass | eOD-GT6 | 1.90E+05 | 6.90E-04 | 3.61E-09 |
| VRC-CH31 | Pass | eOD-GT6 | 4.20E+04 | >6.0E-01 | >1.0E-04 |
| VRC-H12 | Pass | eOD-GT6 | 1.80E+05 | 3.30E-03 | 1.83E-08 |
| VRC-H15 | Pass | eOD-GT6 | 2.10E+05 | 4.30E-03 | 2.08E-08 |
| VRC01 | Pass | eOD-GT6 | 1.90E+05 | 5.30E-05 | 2.76E-10 |
| VRC03 | Pass | eOD-GT6 | 1.79E+05 | 1.60E-01 | 8.94E-07 |
| VRC07 | Pass | eOD-GT6 | 2.60E+05 | <5.0E-05 | <1.6e-11 |
| $GL_{Rev}$ 12a12 | Pass | eOD-GT6 | 2.00E+04 | 2.20E-02 | 1.09E-06 |
| $GL_{Rev}$ 12a21 | Fail | eOD-GT6 | 6.40E+05 | >6.0E-01 | >1.0E-04 |
| $GL_{Rev}$ 3BNC117 | Fail | eOD-GT6 | 4.10E+03 | 1.60E-02 | >1.0E-04 |
| $GL_{Rev}$ 3BNC60 | Pass | eOD-GT6 | 4.20E+04 | 2.70E-01 | 6.38E-06 |
| $GL_{Rev}$ NIH45-46 | Pass | eOD-GT6 | 6.70E+03 | 1.80E-03 | 2.76E-07 |
| $GL_{Rev}$ PGV04 | Fail | eOD-GT6 | 5.00E+04 | 1.30E-03 | >1.0E-04 |
| $GL_{Rev}$ PGV19 | Pass | eOD-GT6 | 6.90E+04 | 8.40E-04 | 1.22E-08 |
| $GL_{Rev}$ PGV20 | Pass | eOD-GT6 | 1.30E+05 | 7.70E-05 | 6.11E-10 |
| $GL_{Rev}$ VRC-CH31 | Pass | eOD-GT6 | 2.20E+04 | 2.60E-01 | 1.19E-05 |
| $GL_{Rev}$ VRC-H12 | Fail | eOD-GT6 | <3.00E+03 | 5.10E-03 | >1.0E-04 |
| $GL_{Rev}$ VRC-H15 | Fail | eOD-GT6 | 5.20E+03 | 1.30E-01 | >1.0E-04 |
| $GL_{Rev}$ VRC01 | Pass | eOD-GT6 | 1.80E+04 | 5.60E-04 | 3.13E-08 |
| $GL_{Rev}$ VRC03 | Pass | eOD-GT6 | 1.60E+04 | >6.0E-01 | >1.0E-04 |
| $GL_{Rev}$ VRC07 | Pass | eOD-GT6 | 7.40E+04 | 1.40E-04 | 1.86E-09 |
| | | | | | |
| 12a12 | Pass | eOD-GT7 | 8.80E+04 | 4.30E-02 | 4.88E-07 |
| 12a21 | Pass | eOD-GT7 | 1.30E+05 | >6.0E-01 | >1.0E-04 |
| 3BNC117 | Pass | eOD-GT7 | 2.10E+05 | 1.40E-02 | 6.60E-08 |
| 3BNC60 | Pass | eOD-GT7 | 2.50E+05 | 1.30E-02 | 5.39E-08 |

Fig. 68B

Table 10 (continued)

| | | | | | |
|---|---|---|---|---|---|
| NIH45-46 | Pass | eOD-GT7 | 2.40E+05 | <5.0E-05 | <1.6e-11 |
| PGV04 | Pass | eOD-GT7 | 3.50E+05 | 2.30E-04 | 6.38E-10 |
| PGV19 | Pass | eOD-GT7 | 2.20E+05 | 2.30E-03 | 1.03E-08 |
| PGV20 | Pass | eOD-GT7 | 2.60E+05 | 9.40E-04 | 3.65E-09 |
| VRC-CH31 | Pass | eOD-GT7 | 4.40E+04 | 4.30E-01 | 9.95E-06 |
| VRC-H12 | Pass | eOD-GT7 | 3.40E+05 | 7.60E-04 | 2.27E-09 |
| VRC-H15 | Pass | eOD-GT7 | 3.40E+05 | 6.10E-03 | 1.80E-08 |
| VRC01 | Pass | eOD-GT7 | 3.30E+05 | <5.0E-05 | <1.6e-11 |
| VRC03 | Pass | eOD-GT7 | 2.10E+05 | 1.90E-02 | 9.03E-08 |
| VRC07 | Pass | eOD-GT7 | 3.00E+05 | <5.0E-05 | <1.6e-11 |
| $GL_{Rev}$ 12a12 | Pass | eOD-GT7 | 1.10E+04 | 7.30E-02 | 6.60E-06 |
| $GL_{Rev}$ 12a21 | Fail | eOD-GT7 | <3.00E+03 | >6.0E-01 | >1.0E-04 |
| $GL_{Rev}$ 3BNC117 | Fail | eOD-GT7 | <3.00E+03 | 4.80E-02 | >1.0E-04 |
| $GL_{Rev}$ 3BNC60 | Pass | eOD-GT7 | 4.90E+04 | 1.60E-01 | 3.31E-06 |
| $GL_{Rev}$ NIH45-46 | Pass | eOD-GT7 | 8.00E+03 | 5.80E-03 | 7.25E-07 |
| $GL_{Rev}$ PGV04 | Fail | eOD-GT7 | 2.20E+05 | 1.60E-02 | >1.0E-04 |
| $GL_{Rev}$ PGV19 | Pass | eOD-GT7 | 1.20E+05 | 6.50E-04 | 5.21E-09 |
| $GL_{Rev}$ PGV20 | Pass | eOD-GT7 | 1.50E+05 | 7.10E-05 | 4.84E-10 |
| $GL_{Rev}$ VRC-CH31 | Pass | eOD-GT7 | 4.70E+04 | 3.00E-01 | 6.41E-06 |
| $GL_{Rev}$ VRC-H12 | Fail | eOD-GT7 | >3.00E+06 | 5.00E-02 | >1.0E-04 |
| $GL_{Rev}$ VRC-H15 | Fail | eOD-GT7 | >3.00E+06 | >6.0E-01 | >1.0E-04 |
| $GL_{Rev}$ VRC01 | Pass | eOD-GT7 | 2.50E+04 | 2.60E-04 | 1.03E-08 |
| $GL_{Rev}$ VRC03 | Fail | eOD-GT7 | 2.20E+05 | >6.0E-01 | >1.0E-04 |
| $GL_{Rev}$ VRC07 | Pass | eOD-GT7 | 4.10E+04 | 4.20E-04 | 1.03E-08 |
| 12a12 | Pass | eOD-GT8 | 7.90E+04 | 9.40E-02 | 1.19E-06 |
| 12a21 | Fail | eOD-GT8 | <3.00E+03 | 2.20E-03 | >1.0E-04 |
| 3BNC117 | Pass | eOD-GT8 | 2.90E+05 | 1.20E-03 | 4.06E-09 |
| 3BNC60 | Pass | eOD-GT8 | 2.90E+05 | 7.00E-04 | 2.43E-09 |
| NIH45-46 | Pass | eOD-GT8 | 7.90E+05 | <5.0E-05 | <1.6e-11 |
| PGV04 | Pass | eOD-GT8 | 2.30E+05 | 2.10E-02 | 8.83E-08 |
| PGV19 | Pass | eOD-GT8 | 1.40E+05 | 5.90E-04 | 4.20E-09 |
| PGV20 | Pass | eOD-GT8 | 1.80E+05 | 7.30E-04 | 4.05E-09 |
| VRC-CH31 | Pass | eOD-GT8 | 1.30E+05 | 9.60E-02 | 7.48E-07 |
| VRC-H12 | Pass | eOD-GT8 | 2.50E+05 | 1.30E-02 | 5.38E-08 |
| VRC-H15 | Pass | eOD-GT8 | 3.00E+05 | 2.20E-01 | 7.30E-07 |
| VRC01 | Pass | eOD-GT8 | 1.00E+06 | <5.0E-05 | <1.6e-11 |
| VRC03 | Pass | eOD-GT8 | 1.20E+05 | 4.80E-02 | 4.07E-07 |

Fig. 68C

Table 10 (continued)

| | | | | | |
|---|---|---|---|---|---|
| VRC07 | Pass | eOD-GT8 | 2.70E+05 | <5.0E-05 | <1.6e-11 |
| $GL_{Rev}$ 12a12 | Pass | eOD-GT8 | 1.20E+05 | 2.10E-03 | 1.77E-08 |
| $GL_{Rev}$ 12a21 | Pass | eOD-GT8 | 1.30E+04 | 5.70E-01 | 4.49E-05 |
| $GL_{Rev}$ 3BNC117 | Pass | eOD-GT8 | 4.40E+04 | 3.20E-02 | 7.25E-07 |
| $GL_{Rev}$ 3BNC60 | Pass | eOD-GT8 | 3.60E+05 | 5.10E-04 | 1.41E-09 |
| $GL_{Rev}$ NIH45-46 | Pass | eOD-GT8 | 2.30E+04 | 1.20E-04 | 5.35E-09 |
| $GL_{Rev}$ PGV04 | Pass | eOD-GT8 | 5.60E+04 | 6.30E-02 | 1.12E-06 |
| $GL_{Rev}$ PGV19 | Pass | eOD-GT8 | 9.50E+05 | <5.0E-05 | <1.6e-11 |
| $GL_{Rev}$ PGV20 | Pass | eOD-GT8 | 8.70E+05 | <5.0E-05 | <1.6e-11 |
| $GL_{Rev}$ VRC-CH31 | Pass | eOD-GT8 | 2.00E+05 | 1.40E-03 | 7.22E-09 |
| $GL_{Rev}$ VRC-H12 | Pass | eOD-GT8 | 6.10E+04 | 7.30E-02 | 1.21E-06 |
| $GL_{Rev}$ VRC-H15 | Pass | eOD-GT8 | 7.10E+04 | 1.80E-02 | 2.51E-07 |
| $GL_{Rev}$ VRC01 | Pass | eOD-GT8 | 1.10E+05 | <5.0E-05 | <1.6e-11 |
| $GL_{Rev}$ VRC03 | Pass | eOD-GT8 | 2.00E+05 | 2.60E-02 | 1.35E-07 |
| $GL_{Rev}$ VRC07 | Pass | eOD-GT8 | 1.30E+05 | <5.0E-05 | <1.6e-11 |

Fig. 69A

Table 11

Summary of isolated VRC01-class germline Abs.

| Ab Name | Donor | V-GENE and allele | J-GENE and allele | D-GENE and allele | CDR3 |
|---|---|---|---|---|---|
| VRC01c-HuGL1 | Pooled Cells | IGHV1-2*02 | IGHJ5*02 | IGHD5-12*01 | CARIYSGYDLWWFDPW |
| | | IGKV3-20*01 | IGKJ1*01 | | CHQFGTF |
| VRC01c-HuGL2 | B046-D5 | IGHV1-2*02 | IGHJ4*02 | IGHD1-26*01 | CAKISGSYSFDYW |
| | | IGKV4-1*01 | IGKJ4*01 | | CQQYYSF |
| VRC01c-HuGL3 | B047-B3 | IGHV1-2*02 | IGHJ5*02 | IGHD1-20*01 | CARMYNWNDVWFDPW |
| | | IGKV3-20*01 | IGKJ5*01 | | CQQYSTF |
| VRC01c-HuGL4 | B048-J06 | IGHV1-2*02 | IGHJ1*01 | IGHD1-26*01 | CARASRLGGYFQHW |
| | | IGKV4-1*01 | IGKJ1*01 | | CQHQETF |
| VRC01c-HuGL5 | B048-I9 | IGHV1-2*02 | IGHJ5*02 | IGHD3-16*01 | CAKHHIRGWFDPW |
| | | IGKV1-5*03 | IGKJ5*01 | | CQHYNTF |
| VRC01c-HuGL6 | B053-p1-w6 | IGHV1-2*02 | IGHJ2*01 | IGHD4-17*01 | CARVDYGDYYGSWYFDLW |
| | | IGKV3-20*01 | IGKJ3*01 | | CQQYGSF |
| VRC01c-HuGL7 | B053-p2-A2 | IGHV1-2*02 | IGHJ2*01 | IGHD5-24*01 ORF | CARSDGYNLGWYFDLW |
| | | IGKV1-27*01 | IGKJ1*01 | | CQKFETF |
| VRC01c-HuGL8 | B053-p2-B3 | IGHV1-2*02 | IGHJ4*02 | IGHD3-22*01 | CALSPYYDSSGYFDW |
| | | IGKV3-20*01 | IGKJ4*01 | | CQQYALF |
| VRC01c-HuGL9 | B053-p2-F1 | IGHV1-2*02 | IGHJ5*02 | IGHD1-1*01 | CARDSNWWFDPW |
| | | IGKV3-20*01 | IGKJ1*01 | | CQQYGTF |
| VRC01c-HuGL10 | B053-p3-A4 | IGHV1-2*02 | IGHJ5*02 | IGHD2-15*01 | CARRQYCSGGSCLYLFDPW |
| | | IGKV1-NL1*01 | IGKJ2*01 | | CQQYYSF |
| VRC01c-HuGL11 | B053-p3-E8 | IGHV1-2*02 | IGHJ3*02 | IGHD6-13*01 | CASKVAAAGTLAKDAFDIW |
| | | IGKV3-15*01 | IGKJ4*01 | | CQQYITF |
| VRC01c-HuGL12 | B053-p3-F11 | IGHV1-2*02 | IGHJ5*02 | IGHD6-13*01 | CARAAIAAAYFRDPW |
| | | IGKV3-15*01 | IGKJ2*01 | | CQIEYTF |
| | | IGHV1-2*02 | IGHJ4*02 | IGHD6-19*01 | CARDKAVAGTNFDYW |

Fig. 69B

Table 11(continued)

| | | | | | |
|---|---|---|---|---|---|
| VRC01c-HuGL14 | B053-p3-G1 | IGHV1-2*02 | IGHJ6*02 | IGHD5-12*01 | CARRGLLGRGYSGYDRMGYYYYYGMDVW |
| | | IGKV2-29*02 | IGKJ2*01 | | CMQGDTF |
| VRC01c-HuGL15 | B053-p3-G2 | IGHV1-2*02 | IGHJ5*02 | IGHD6-13*01 | CARPTEYSSSWYWFDPW |
| | | IGKV1-5*03 | IGKJ3*01 | | CQQYNSF |
| VRC01c-HuGL16 | B056-78-p1-D2 | IGHV1-2*02 | IGHJ4*02 | IGHD6-13*01 | CARDHQGHSSSWSKRFDYW |
| | | IGKV1-33*01 | IGKJ4*01 | | CQQYDLF |
| VRC01c-HuGL17 | B056-96-p1-B2 | IGHV1-2*02 | IGHJ4*02 | IGHD6-13*01 | CARVERSSSSWRYDYW |
| | | IGKV1-5*03 | IGKJ1*01 | | CQQYETF |
| VRC01c-HuGL18 | B057-87-A10 | IGHV1-2*02 | IGHJ4*02 | IGHD6-13*01 | CARVRYGSWTGYYFDYW |
| | | IGKV3-20*01 | IGKJ1*01 | | CQQYETF |
| VRC01c-HuGL19 | B57-87-E4 | IGHV1-2*02 | IGHJ4*02 | IGHD3-3*01 | CARVPYDFWSGYYVLSHFDYW |
| | | IGKV3-15*01 | IGKJ1*01 | | CQQYETF |
| VRC01c-HuGL20 | B059-55-p3-G6 | IGHV1-2*02 | IGHJ4*02 | IGHD1-26*01 | CARLVGATGTSEDYW |
| | | IGKV1-5*03 | IGKJ1*01 | | CQQWGTF |
| VRC01c-HuGL21 | B059-55-p4-H3 | IGHV1-2*02 | IGHJ4*02 | IGHD2-8*02 | CAREGRGYSTGAYFDYW |
| | | IGKV1-9*01 | IGKJ4*01 | | CQQLNSF |
| VRC01c-HuGL22 | B059-55-p5-A10 | IGHV1-2*02 | IGHJ5*02 | IGHD6-19*01 | CARPRGPAVAGRYNWWFDPW |
| | | IGKV3-15*01 | IGKJ2*02 | | CQQYGTF |
| VRC01c-HuGL23 | B059-55-p5-E3 | IGHV1-2*02 | IGHJ4*02 | IGHD2-21*02 | CARGSRATWIQLHW |
| | | IGKV3D-15*01 | IGKJ3*01 | | CQQYNTF |
| VRC01c-HuGL24 | B54-p1-H7 | IGHV1-2*02 | IGHJ3*02 | IGHD6-6*01 | CARVGEQLVLNDAFDIW |
| | | IGKV3-15*01 | IGKJ1*01 | | CQQYNKF |
| VRC01c-HuGL25 | B54-p1-A4 | IGHV1-2*02 | IGHJ1*01 | IGHD4-17*01 | CARDLTEVTTPPPW |
| | | IGKV3-20*01 | IGKJ2*01 | | CQQYNTF |
| VRC01c-HuGL26 | B057-84-D1 | IGHV1-2*04 | IGHJ2*01 | Unknown | incomplete sequence |
| | | IGKV3-20*01 | IGKJ3*01 | | CQQLSTF |
| VRC01c-HuGL27 | B059-55-p2-E11 | IGHV1-2*02 | IGHJ3*01 | Unknown | incomplete sequence |
| | | IGKV3-20*01 | IGKJ5*01 | | CQQYGSF |

Fig. 70

Table 12

SPR binding to isolated human GL Abs.

| Ab Name | Equlibrium KD eOD-GT6 | eOD-GT8 |
|---|---|---|
| VRC01c-HuGL1 | >1E-04 | 2.20E-05 |
| VRC01c-HuGL2 | >1E-04 | 3.68E-07 |
| VRC01c-HuGL3 | >1E-04 | 7.29E-06 |
| VRC01c-HuGL4 | >1E-04 | 1.91E-05 |
| VRC01c-HuGL6 | >1E-04 | 4.62E-06 |
| VRC01c-HuGL7 | 3.60E-05 | 4.78E-07 |
| VRC01c-HuGL8 | >1E-04 | 3.12E-06 |
| VRC01c-HuGL9 | >1E-04 | 9.79E-06 |
| VRC01c-HuGL10 | >1E-04 | 2.35E-06 |
| VRC01c-HuGL11 | >1E-04 | 3.61E-07 |
| VRC01c-HuGL12 | >1E-04 | 6.32E-06 |
| VRC01c-HuGL13 | >1E-04 | 1.45E-06 |
| VRC01c-HuGL14 | >1E-04 | 4.80E-05 |
| VRC01c-HuGL15 | >1E-04 | 3.94E-07 |
| VRC01c-HuGL16 | >1E-04 | 1.85E-05 |
| VRC01c-HuGL17 | >1E-04 | 1.30E-06 |
| VRC01c-HuGL18 | >1E-04 | 1.20E-07 |
| VRC01c-HuGL19 | 6.90E-05 | 2.60E-07 |
| VRC01c-HuGL20 | >1E-04 | 2.80E-05 |
| VRC01c-HuGL21 | >1E-04 | 5.70E-05 |
| VRC01c-HuGL22 | NA | 7.70E-06 |
| VRC01c-HuGL23 | NA | 9.50E-06 |
| VRC01c-HuGL24 | NA | 1.00E-05 |
| VRC01c-HuGL25 | NA | 3.90E-06 |

Fig. 71

Table 13

X-ray data collection and refinement statistics.

| | eOD-GT8minglyc | VRC01c-HuGL2 Fab | VRC01c-HuGL2+eOD-GT8minglyc | VRC01c-HuGL2+eOD-GT8minglyc |
|---|---|---|---|---|
| **Data collection** | | | | |
| Beamline | SSRL 11-1 | SSRL 12-2 | SSRL 12-2 | SSRL 12-2 |
| Detector | Dectris Pilatus 6M | Dectris Pilatus 6M | Dectris Pilatus 6M | Dectris Pilatus 6M |
| Wavelength (Å) | 0.97945 | 0.9795 | 0.9795 | 0.9795 |
| Space group | $P2_12_12_1$ | $P2_12_12$ | C2 | I222 |
| Unit cell (a, b, and c; Å) | 34.33, 53.06, 77.99 | 79.06, 124.20, 47.95 | 174.19, 147.58, 103.89 | 102.55, 138.60, 147.89 |
| (α, β and γ; °) | 90.0, 90.0, 90.0 | 90.0, 90.0, 90.0 | 90.0, 125.6, 90.0 | 90.0, 90.0, 90.0 |
| Resolution range* (Å) | 31.42 – 2.90 (3.00 – 2.90) | 48.84 – 1.82 (1.86 -1.82) | 44.45 – 2.44 (2.48 – 2.44) | 46.45 – 2.16 (2.23 – 2.16) |
| No. of total reflections | 21,244 (1,228) | 193,379 (7,695) | 203,723 (9,118) | 206,686 (8,866) |
| No. of unique reflections | 3,333 (243) | 40,894 (1,973) | 73,979 (3,647) | 52,709 (2,535) |
| Redundancy* | 5.8 (5.0) | 4.7 (3.9) | 2.8 (2.5) | 3.9 (3.5) |
| Completeness* (%) | 96.6 (77.8) | 97.8 (96.3) | 99.2 (94.2) | 92.5 (89.6) |
| $R_{merge}$*[a] | 12.0 (36.0) | 16.3 (69.7) | 10.2 (77.8) | 6.7 (66.5) |
| $R_{pim}$*[b] | 5.0 (15.0) | 7.8 (35.6) | 7.2 (56.5) | 3.7 (40.1) |
| <I>/<σ> * | 10.2 (3.6) | 9.5 (2.3) | 9.2 (1.1) | 16.2 (1.9) |
| CC1/2 * | 99.4 | 87.2 | 84.9 | 90.2 |
| Solvent content (%) | 38.7 | 49.9 | 70.4 | 69.4 |
| **Refinement** | | | | |
| Reflections used for refinement* ($R_{work}$) | 3,332 (334) | 40,834 (2,043) | 73,945 (3,692) | 52,699 (2,619) |
| $R_{work}$[c] (%) | 25.3 | 20.6 | 19.7 | 19.1 |
| $R_{free}$[d] (%) | 28.7 | 23.9 | 23.8 | 21.9 |
| **Model components (asymmetric unit)** | | | | |
| Fabs | N/A | 1 | 2 | 1 |
| eOD-GT8 minglyc | 1 | N/A | 2 | 1 |
| Waters | - | 203 | 76 | 183 |
| $PO_4$ ions | - | N/A | 1 | N/A |
| $SO_4$ ions | - | 4 | N/A | N/A |
| PEG | - | 6 | - | - |
| Glycerol | - | 6 | - | 4 |
| Glycan | 2 | - | 4 | 2 |
| **B-values (Å2)** | | | | |
| Wilson B | 62.7 | 34.4 | 47.6 | 48.7 |
| Overall | 53.3 | 42.7 | 57.9 | 57.7 |
| Protein | 53.2 | 41.7 | 57.8 | 57.5 |
| Glycan | 58.8 | N/A | 78.2 | 71.3 |
| Solvent | N/A | 53.5 | 61.4 | 60.5 |
| **Root mean square deviation from ideal values** | | | | |
| Bond lengths (Å) | 0.002 | 0.003 | 0.003 | 0.006 |
| Bond angles (°) | 0.5 | 1.3 | 0.9 | 0.9 |
| **Ramachandran** | | | | |
| Most favored (%) | 95.5 | 95.8 | 94.6 | 95.9 |
| Additional allowed (%) | 4.5 | 3.5 | 5.1 | 4.1 |
| Disallowed (%) | 0 | 0.7 | 0.3 | 0 |

* Values in parentheses correspond to the highest resolution shells.

[a] $R_{merge} = \Sigma_{hkl} \Sigma_{i=1,N} |I_{hkl,i} - \langle I_{hkl} \rangle| / \Sigma_{hkl} \Sigma_{i=1,N} I_{hkl,i}$, where the outer sum (hkl) is taken over the unique reflections.

[b] $R_{pim} = \Sigma_{hkl} [1/(N-1)]^{1/2} \Sigma_{i=1,N} |I_{hkl,i} - \langle I_{hkl} \rangle| / \Sigma_{hkl} \Sigma_{i=1,N} I_{hkl,i}$

[c] $R_{work} = \Sigma_{hkl} |F_{obs,hkl} - kF_{calc,hkl}| / \Sigma_{hkl} |F_{obs,hkl}|$, where $|F_{obs,hkl}|$ and $|F_{calc,hkl}|$ are the observed and calculated structure factor amplitudes, respectively.

[d] $R_{free}$, as for $R_{work}$, but for a set of reflections (5% of total) omitted from refinement.

Fig. 72

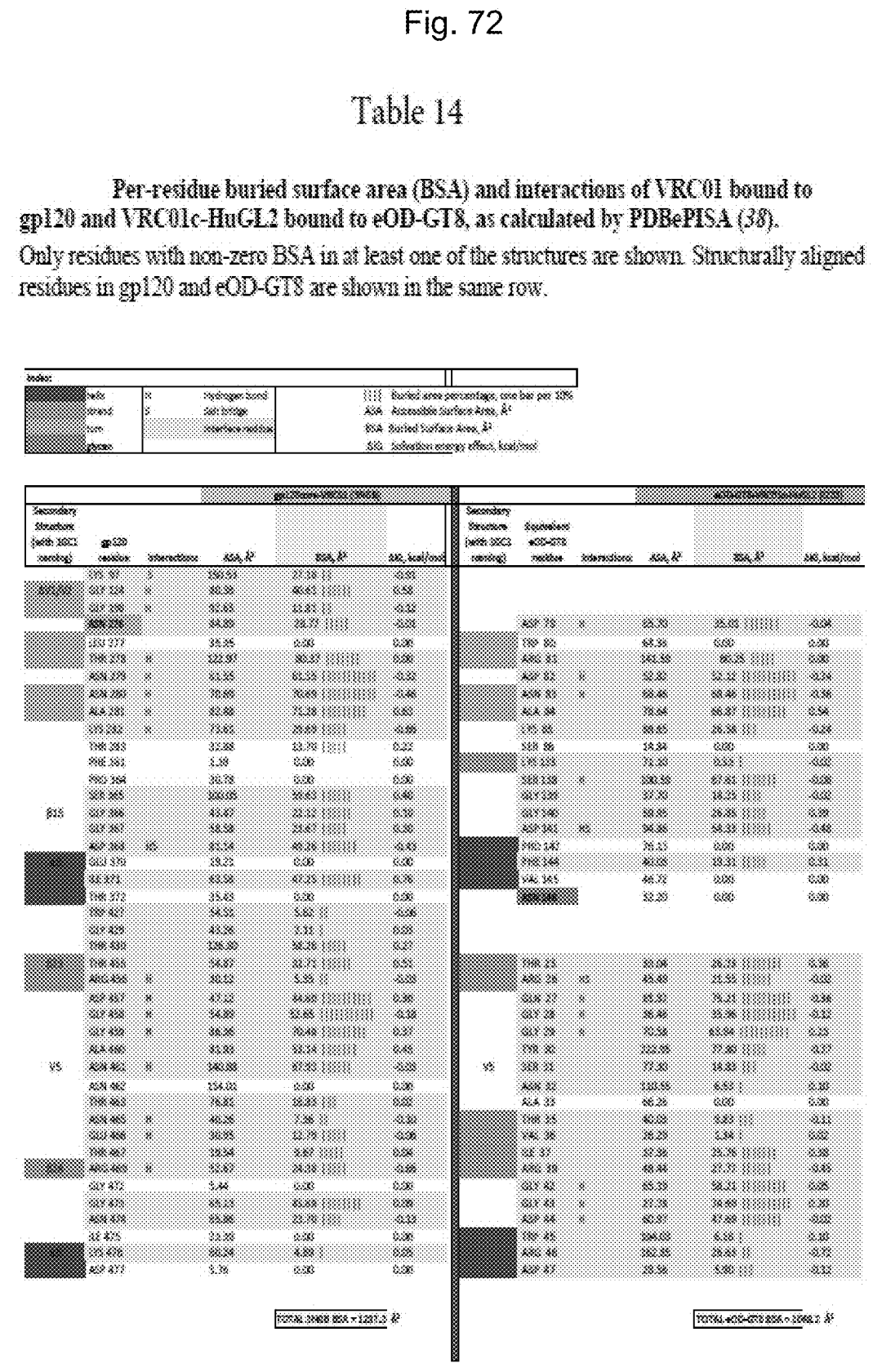

Table 14

**Per-residue buried surface area (BSA) and interactions of VRC01 bound to gp120 and VRC01c-HuGL2 bound to eOD-GT8, as calculated by PDBePISA (*38*).**

Only residues with non-zero BSA in at least one of the structures are shown. Structurally aligned residues in gp120 and eOD-GT8 are shown in the same row.

| Index: | | | | | |
|---|---|---|---|---|---|
| helix | H | Hydrogen bond | | \|\|\|\| | Buried area percentage, one bar per 10% |
| strand | S | Salt bridge | | ASA | Accessible Surface Area, Å² |
| turn | | Interface residue | | BSA | Buried Surface Area, Å² |
| gap | | | | ΔG | Solvation energy effect, kcal/mol |

| gp120 core-VRC01 (3NGB) | | | | | | eOD-GT8-VRC01c-HuGL2 | | | | | |
|---|---|---|---|---|---|---|---|---|---|---|---|
| Secondary Structure (with 3NGB naming) | gp120 residue | Interactions | ASA, Å² | BSA, Å² | ΔG, kcal/mol | Secondary Structure (with 3NGB naming) | Equivalent eOD-GT8 residue | Interactions | ASA, Å² | BSA, Å² | ΔG, kcal/mol |
| | TYR 97 | S | 150.93 | 27.18 \|\| | -0.01 | | | | | | |
| [illegible] | GLY 124 | H | 80.30 | 40.41 \|\|\|\|\| | 0.58 | | | | | | |
| | GLY 198 | H | 92.63 | 12.81 \|\| | -0.32 | | | | | | |
| | ASN 276 | | 84.80 | 28.77 \|\|\|\| | 0.01 | | ASP 79 | H | 66.70 | 36.05 \|\|\|\|\|\| | -0.04 |
| | LEU 277 | | 35.25 | 0.00 | 0.00 | | TRP 80 | | 65.58 | 0.00 | 0.00 |
| | THR 278 | H | 122.97 | 30.37 \|\|\|\|\| | 0.00 | | ARG 81 | | 161.59 | 66.25 \|\|\|\| | 0.00 |
| | ASN 279 | H | 61.25 | 61.25 \|\|\|\|\|\|\|\|\| | -0.33 | | ASP 82 | H | 52.30 | 52.32 \|\|\|\|\|\|\|\|\| | -0.24 |
| | ASN 280 | H | 70.60 | 70.69 \|\|\|\|\|\|\|\|\| | -0.46 | | ASN 83 | H | 68.46 | 68.46 \|\|\|\|\|\|\|\|\| | -0.36 |
| | ALA 281 | H | 82.80 | 71.28 \|\|\|\|\|\|\|\| | 0.63 | | ALA 84 | | 78.04 | 66.87 \|\|\|\|\|\|\|\| | 0.54 |
| | LYS 282 | H | 73.61 | 29.69 \|\|\|\| | -0.88 | | LYS 85 | | 88.65 | 26.36 \|\|\| | -0.24 |
| | THR 283 | | 37.88 | 13.70 \|\|\|\| | 0.22 | | SER 86 | | 14.84 | 0.00 | 0.00 |
| | PHE 353 | | 1.39 | 0.00 | 0.00 | | LYS 135 | | 71.30 | 3.53 \| | -0.02 |
| | PRO 364 | | 30.78 | 0.00 | 0.00 | | SER 138 | H | 100.59 | 67.81 \|\|\|\|\|\| | -0.08 |
| | SER 365 | | 100.05 | 50.63 \|\|\|\|\| | 0.48 | | GLY 139 | | 37.30 | 18.23 \|\|\| | -0.02 |
| β15 | GLY 366 | | 43.47 | 22.12 \|\|\|\|\| | 0.10 | | GLY 140 | | 58.86 | 26.86 \|\|\|\| | 0.08 |
| | GLY 367 | | 58.58 | 28.47 \|\|\|\| | 0.30 | | ASP 141 | HS | 96.86 | 56.33 \|\|\|\|\| | -0.48 |
| | ASP 368 | HS | 81.54 | 49.26 \|\|\|\|\|\| | -0.43 | | PRO 142 | | 76.13 | 0.00 | 0.00 |
| | GLU 370 | | 19.23 | 0.00 | 0.00 | | PHE 144 | | 40.08 | 15.31 \|\|\|\| | 0.31 |
| | ILE 371 | | 63.58 | 47.25 \|\|\|\|\|\|\| | 0.76 | | VAL 145 | | 66.72 | 0.00 | 0.00 |
| | THR 372 | | 35.43 | 0.00 | 0.00 | | [illegible] | | 32.25 | 0.00 | 0.00 |
| | TRP 427 | | 54.51 | 5.62 \|\| | -0.06 | | | | | | |
| | GLY 429 | | 43.26 | 3.31 \| | 0.01 | | | | | | |
| | THR 430 | | 108.30 | 58.26 \|\|\|\| | 0.27 | | | | | | |
| [illegible] | THR 455 | | 54.87 | 32.71 \|\|\|\|\| | 0.51 | | THR 25 | | 33.06 | 26.25 \|\|\|\|\|\| | 0.36 |
| | ARG 456 | H | 30.12 | 5.35 \|\| | -0.03 | | ARG 26 | HS | 43.48 | 21.55 \|\|\|\| | -0.02 |
| | ASP 457 | H | 47.12 | 44.60 \|\|\|\|\|\|\|\|\| | 0.30 | | GLN 27 | H | 85.30 | 79.21 \|\|\|\|\|\|\|\|\| | -0.38 |
| | GLY 458 | H | 54.80 | 53.85 \|\|\|\|\|\|\|\|\|\| | -0.18 | | GLY 28 | H | 38.48 | 35.96 \|\|\|\|\|\|\|\|\| | -0.12 |
| | GLY 459 | H | 88.30 | 70.48 \|\|\|\|\|\|\|\| | 0.37 | | GLY 29 | H | 70.58 | 63.04 \|\|\|\|\|\|\|\| | 0.23 |
| | ALA 460 | | 83.90 | 53.14 \|\|\|\|\|\| | 0.45 | | THR 30 | | 112.05 | 77.80 \|\|\|\| | -0.37 |
| V5 | ASN 461 | H | 140.88 | 87.93 \|\|\|\|\|\| | -0.03 | V5 | SER 31 | | 77.30 | 16.83 \|\|\| | -0.02 |
| | ASN 462 | | 154.01 | 0.00 | 0.00 | | ASN 32 | | 110.55 | 6.57 \| | 0.10 |
| | THR 463 | | 78.81 | 18.83 \|\|\| | 0.02 | | ALA 33 | | 66.26 | 0.00 | 0.00 |
| | ASN 465 | H | 40.26 | 7.26 \|\| | -0.10 | | THR 35 | | 40.08 | 8.83 \|\|\| | -0.11 |
| | GLU 466 | H | 30.95 | 12.79 \|\|\|\| | -0.06 | | VAL 36 | | 26.25 | 1.34 \| | 0.02 |
| | THR 467 | | 19.54 | 9.97 \|\|\|\| | 0.04 | | ILE 37 | | 37.36 | 25.76 \|\|\|\|\|\| | 0.38 |
| [illegible] | ARG 469 | H | 52.67 | 24.18 \|\|\|\| | -0.46 | | ARG 38 | | 48.44 | 27.71 \|\|\|\| | -0.45 |
| | GLY 472 | | 5.44 | 0.00 | 0.00 | | GLY 42 | H | 65.39 | 58.21 \|\|\|\|\|\|\|\| | 0.08 |
| | GLY 473 | | 69.13 | 46.69 \|\|\|\|\|\|\| | 0.00 | | GLY 43 | H | 37.38 | 34.69 \|\|\|\|\|\|\|\| | 0.20 |
| | ASN 474 | | 83.08 | 22.70 \|\|\| | -0.13 | | ASP 44 | H | 60.97 | 47.80 \|\|\|\|\|\| | -0.03 |
| | ILE 475 | | 13.30 | 0.00 | 0.00 | | TRP 45 | | 104.03 | 6.16 \| | 0.10 |
| | LYS 476 | | 88.24 | 4.89 \| | 0.05 | | ARG 46 | | 102.35 | 28.63 \|\| | -0.72 |
| | ASP 477 | | 5.76 | 0.00 | 0.00 | | ASP 47 | | 28.56 | 5.80 \|\|\| | -0.12 |

TOTAL 3NGB BSA = 1237.2 Å²

TOTAL eOD-GT8 BSA = 1048.2 Å²

Fig. 73

Table 15

List of VRC01-class bnAbs and $GL_{Rev}$ Abs.

VRC01-class bnAbs

| Heavy Chain | Light Chain | Reference Heavy/ | Light |
|---|---|---|---|
| 12a12 | 12a12 | *(7)* | *(7)* |
| 3BNC60 | 3BNC60 | *(7)* | *(7)* |
| NIH45-46 | NIH45-46 | *(7)* | *(7)* |
| PGV04 | PGV04 | *(23)* | *(23)* |
| PGV19 | PGV19 | *(17)* | *(17)* |
| PGV20 | PGV20 | *(17)* | *(17)* |
| VRC01 | VRC01 | *(39)* | *(39)* |
| VRC03 | VRC03 | *(39)* | *(39)* |
| VRC06 | VRC06 | *(40)* | *(40)* |
| VRC23 | VRC23 | *(41)* | *(41)* |
| VRC-CHA31 | VRC-CHA31 | *(23)* | *(23)* |

Germline-reverted Antibodies

| Heavy Chain | Light Chain | Reference Heavy/ | Light |
|---|---|---|---|
| $GL_{Rev}$ 12a12 | $GL_{Rev}$ 12a12 | *(7)* | *(7)* |
| $GL_{Rev}$ 3BNC60v1 | $GL_{Rev}$ 3BNC60 | *(7)* | *(7)* |
| $GL_{Rev}$ 3BNC60v2 | $GL_{Rev}$ 3BNC60 | *(7)* | *(7)* |
| $GL_{Rev}$ NIH45-46 | $GL_{Rev}$ NIH45-46 | *(7)* | *(7)* |
| $GL_{Rev}$ NIH45-46 | $GL_{Rev}$ VRC01 | *(7)* | *(39)* |
| $GL_{Rev}$ PGV04v1 | $GL_{Rev}$ PGV04 | *(23)* | *(23)* |
| $GL_{Rev}$ PGV04v2 | $GL_{Rev}$ PGV04 | *(23)* | *(23)* |
| $GL_{Rev}$ PGV04v3 | $GL_{Rev}$ PGV04 | *(23)* | *(23)* |
| $GL_{Rev}$ PGV04v1 | $GL_{Rev}$ VRC01 | *(23)* | *(39)* |
| $GL_{Rev}$ PGV04v2 | $GL_{Rev}$ VRC01 | *(23)* | *(39)* |
| $GL_{Rev}$ PGV04v3 | $GL_{Rev}$ VRC01 | *(23)* | *(39)* |
| $GL_{Rev}$ PGV19 | $GL_{Rev}$ PGV19 | *(17)* | *(17)* |
| $GL_{Rev}$ PGV20 | $GL_{Rev}$ PGV20 | *(17)* | *(17)* |
| $GL_{Rev}$ VRC01 | $GL_{Rev}$ VRC01 | *(39)* | *(39)* |
| $GL_{Rev}$ VRC03 | $GL_{Rev}$ VRC03 | *(39)* | *(39)* |
| $GL_{Rev}$ VRC23 | $GL_{Rev}$ VRC23 | *(41)* | *(41)* |
| $GL_{Rev}$ VRC-CH31 | $GL_{Rev}$ VRC-CH31 | *(23)* | *(23)* |
| $GL_{Rev}$ VRC-H5 | $GL_{Rev}$ PGV04 | *(14)* | *(23)* |
| $GL_{Rev}$ VRC-H5 | $GL_{Rev}$ VRC01 | *(14)* | *(39)* |
| $GL_{Rev}$ VRC-H15 | $GL_{Rev}$ PGV04 | *(14)* | *(23)* |
| $GL_{Rev}$ VRC-H15 | $GL_{Rev}$ VRC01 | *(14)* | *(39)* |

```
eOD-GT8 60mer           1 MQIYEGKLTAEGLRFGIVASRFNHALVDRLVEGAIDAIVRHGGREEDITLVRVPGSWEIP  60
                          MQIYEGKLTAEGLRFGIVASR NHALVDRLVEGAIDAIVRHGGREEDITLVRV GSWEIP
eOD-GT8 d41m3-60mer     1 MQIYEGKLTAEGLRFGIVASRANHALVDRLVEGAIDAIVRHGGREEDITLVRVCGSWEIP  60

eOD-GT8 60mer          61 VAAGELARKEDIDAVIAIGVLIRGATPHFDYIASEVSKGLADLSLELRKPITFGVITADT 120
                          VAAGELARKEDIDAVIAIGVL RGATP FDYIASEVSKGLADLSLELRKPITFGVITADT
eOD-GT8 d41m3-60mer    61 VAAGELARKEDIDAVIAIGVLCRGATPSFDYIASEVSKGLADLSLELRKPITFGVITADT 120

eOD-GT8 60mer         121 LEQAIERAGTKHGNKGWEAALSAIEMANLFKSLRGGSGGSGGSGGSGGGDTITLPCRPAP 180
                          LEQAIE AGT HGNKGWEAAL AIEMANLFKSLRGGSGGSGGSGGSGGGDTITLPCRPAP
eOD-GT8 d41m3-60mer   121 LEQAIEAAGTCHGNKGWEAALCAIEMANLFKSLRGGSGGSGGSGGSGGGDTITLPCRPAP 180

eOD-GT8 60mer         181 PPHCSSNITGLILTRQGGYSNDNTVIFRPSGGDWRDIARCQIAGTVVSTQLFLNGSLAEE 240
                          PPHCSSNITGLILTRQGGYSNDNTVIFRPSGGDWRDIARCQIAGTVVSTQLFLNGSLAEE
eOD-GT8 d41m3-60mer   181 PPHCSSNITGLILTRQGGYSNDNTVIFRPSGGDWRDIARCQIAGTVVSTQLFLNGSLAEE 240

eOD-GT8 60mer         241 EVVIRSEDWRDNAKSICVQLNTSVEINCTGAGHCNISRAKWNNTLKQIASKLREQYGNKT 300
                          EVVIRSEDWRDNAKSICVQLNTSVEINCTGAGHCNISRAKWNNTLKQIASKLREQYGNKT
eOD-GT8 d41m3-60mer   241 EVVIRSEDWRDNAKSICVQLNTSVEINCTGAGHCNISRAKWNNTLKQIASKLREQYGNKT 300

eOD-GT8 60mer         301 IIFKPSSGGDPEFVNHSFNCGGEFFYCDSTQLFNSTWFNST** 343
                          IIFKPSSGGDPEFVNHSFNCGGEFFYCDSTQLFNSTWFNST**
eOD-GT8 d41m3-60mer   301 IIFKPSSGGDPEFVNHSFNCGGEFFYCDSTQLFNSTWFNST** 343
```

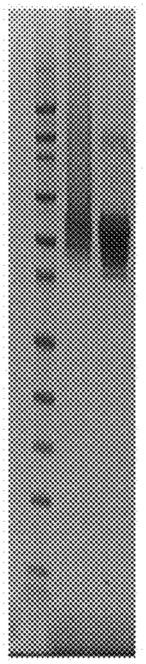

Fig. 78

<u>Two shots:</u>
eOD-GT8 60mer
+ HXB2-core-N276D 60mer boost

| N276A | 1 | 2 | 3 | 5 | 6 | 7 | 9 | 10 | 11 | 13 | 14 | 15 | 17 | 19 | 23 | 24 | 26 |
|---|---|---|---|---|---|---|---|---|---|---|---|---|---|---|---|---|---|
| SC422661.8 | | 42 | | | | 1101 | 5123 | 2067 | | | | | | | 2900 | | 530 |
| 1012_11_TC21_3257 | | 1898 | | | | 8287 | 5321 | 7307 | | | | | | | 5110 | | 4051 |
| ZM249M.PL1 | | | | | | 20 | | | | | | | | | | | 6 |
| HIV-001428-2.42 | | | | | | | | 100 | | | | | | | | | 7551 |
| 0815.v3.c3 | | | | | | | | | | | | | | | | | |
| 191084 B7-19 | 43 | 5078 | | 173 | 1280 | 4429 | 41088 | 9683 | | | | | 106 | 1124 | 9546 | | 3725 |
| BG505 T332N | | | | | | | | | | | | | | | | | |

Fig. 79
| | Immunogens | Primary Objectives | Neutralization Readout |
|---|---|---|---|
| **Prime** | 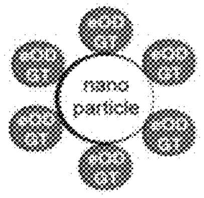  | Activate VRC01-class precursors and Select H-CDR1/2 mutations to bind N276(-) Env | None against tier 2 |
| **Boost 1** | 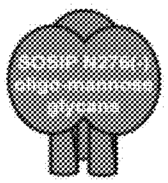 | Select H-CDR1/2 and H-FW3 mutations | Neutralize tier 2 N276A |
| **Boost 2** | 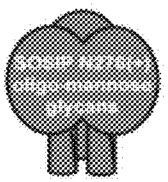 | Select L-CDR1 mutations | Neutralize tier 2 GnTi(-) with Man5-9 oligomannose |
| **Boost 3** | 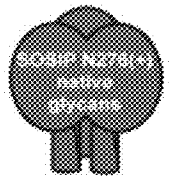 | Select L-FW3 mutations | Neutralize tier 2 |

SEQUENCE LISTING

```
<160> NUMBER OF SEQ ID NOS: 753

<210> SEQ ID NO 1
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Thr Ile Thr Leu Pro Cys Arg Pro Ala Pro Pro Pro His Cys Ser
1               5                   10                  15
```

```
Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175


<210> SEQ ID NO 2
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Thr Ile Thr Leu Pro Cys Arg Pro Ala Pro Pro Pro His Cys Ser
1               5                   10                  15

Ser Asn Ile Thr Gly Leu Ile Leu Thr Arg Asp Gly Gly Val Ser Asn
            20                  25                  30

Asp Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170


<210> SEQ ID NO 3
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Gly Gly Ser Gly Gly Ser Gly Gly
1               5


<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Gly Gly Ser Gly Gly Ser Gly Gly Ser Gly Gly Gly
1               5                   10                  15


<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Tyr Ile Lys Ala Asn Ser Lys Phe Ile Gly Ile Thr Glu Leu
1               5                   10                  15


<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Gln Tyr Ile Lys Ala Asn Ser Lys Phe Ile Gly Ile Thr Glu
1               5                   10                  15

Leu Ser Gly


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His His His His His His
1               5


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 8

His His His His His His Gly Ser Gly
1 5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gly Thr Lys His His His His His His
1 5

<210> SEQ ID NO 10
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Asp Thr Ile Thr Leu Pro Cys Arg Pro Ala Pro Pro Pro His Cys Ser
1               5                   10                  15

Ser Asn Ile Thr Gly Leu Ile Leu Thr Arg Gln Gly Gly Tyr Ser Asn
            20                  25                  30

Asp Asn Thr Val Ile Phe Arg Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Glu Asp Trp
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Tyr Gly
        115                 120                 125

Asn Lys Thr Ile Ile Phe Lys Pro Ser Ser Gly Gly Asp Pro Glu Phe
    130                 135                 140

Val Asn His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 11
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Asp Thr Ile Thr Leu Pro Cys Arg Pro Ala Pro Pro Pro His Cys Ser
1               5                   10                  15
```

Ser Asn Ile Thr Gly Leu Ile Leu Thr Arg Gln Gly Gly Trp Ser Asn
20 25 30

Asp Asn Thr Val Ile Phe Arg Pro Ser Ala Gly Asp Trp Arg Asp Ile
35 40 45

Ala Arg Cys Gln Ile Ala Gly Thr Val Val Ser Thr Gln Leu Phe Leu
50 55 60

Asn Gly Ser Leu Ala Glu Glu Glu Val Val Ile Arg Ser Arg Asp Trp
65 70 75 80

Arg Asp Asn Ala Lys Ser Ile Cys Val Gln Leu Asn Thr Ser Val Glu
85 90 95

Ile Asn Cys Thr Gly Ala Gly His Cys Asn Ile Ser Arg Ala Lys Trp
100 105 110

Asn Asn Thr Leu Lys Gln Ile Ala Ser Lys Leu Arg Glu Gln Tyr Gly
115 120 125

Asn Lys Thr Val Ile Phe Ala Pro Ser Ser Gly Gly Asp Pro Glu Phe
130 135 140

Val Asn His Ser Phe Asn Cys Gly Gly Glu Phe Phe Tyr Cys Asp Ser
145 150 155 160

Thr Gln Leu Phe Asn Ser Thr Trp Phe Asn Ser Thr
165 170

<210> SEQ ID NO 12
<211> LENGTH: 229
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

Asp Thr Ile Thr Leu Pro Cys Arg Pro Ala Pro Pro Pro His Cys Ser
1 5 10 15

Ser Asn Ile Thr Gly Leu Ile Leu Thr Arg Gln Gly Gly Tyr Ser Asn
20 25 30

Asp Asn Thr Val Ile Phe Arg Pro Ser Gly Gly Asp Trp Arg Asp Ile
35 40 45

Ala Arg Cys Gln Ile Ala Gly Thr Val Val Ser Thr Gln Leu Phe Leu
50 55 60

Asn Gly Ser Leu Ala Glu Glu Glu Val Val Ile Arg Ser Glu Asp Trp
65 70 75 80

Arg Asp Asn Ala Lys Ser Ile Cys Val Gln Leu Asn Thr Ser Val Glu
85 90 95

Ile Asn Cys Thr Gly Ala Gly His Cys Asn Ile Ser Arg Ala Lys Trp
100 105 110

Asn Asn Thr Leu Lys Gln Ile Ala Ser Lys Leu Arg Glu Gln Tyr Gly
115 120 125

Asn Lys Thr Ile Ile Phe Lys Pro Ser Ser Gly Gly Asp Pro Glu Phe
130 135 140

Val Asn His Ser Phe Asn Cys Gly Gly Glu Phe Phe Tyr Cys Asp Ser
145 150 155 160

Thr Gln Leu Phe Asn Ser Thr Trp Phe Asn Ser Thr Gly Ser Gly Gly
165 170 175

Ser Gly Gly Ser Gly Gly Ser Gly Gly Ser Gly Arg Met Lys Gln Ile
180 185 190

```
Glu Asp Lys Ile Glu Glu Ile Leu Ser Lys Ile Tyr His Ile Glu Asn
        195                 200                 205

Glu Ile Ala Arg Ile Lys Lys Leu Ile Gly Glu Arg Gly Thr Lys His
    210                 215                 220

His His His His His
225


<210> SEQ ID NO 13
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300
```

```
Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 14
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300
```

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 15
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Met Gln Ile Tyr Cys Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Cys Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Tyr Ser Asn Asp Asn Thr Val Ile Phe Arg
195 200 205

Pro Ser Gly Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Glu Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Ile Ile Phe Lys
290 295 300

```
Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 16
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300
```

```
Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 17
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300
```

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 18
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Tyr Ser Asn Asp Asn Thr Val Ile Phe Arg
195 200 205

Pro Ser Gly Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Glu Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Ile Ile Phe Lys
290 295 300

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 19
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Cys Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Ala Ala
115 120 125

Gly Thr Cys His Gly Asn Lys Gly Trp Glu Ala Ala Leu Cys Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Tyr Ser Asn Asp Asn Thr Val Ile Phe Arg
195 200 205

Pro Ser Gly Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Glu Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Ile Ile Phe Lys
290 295 300

-continued

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 20
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Cys Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro Ser Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Ala Ala
115 120 125

Gly Thr Cys His Gly Asn Lys Gly Trp Glu Ala Ala Leu Cys Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Tyr Ser Asn Asp Asn Thr Val Ile Phe Arg
195 200 205

Pro Ser Gly Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Glu Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Ile Ile Phe Lys
290 295 300

Pro Ser Ser Gly Gly Asp Pro Glu Phe Val Asn His Ser Phe Asn Cys
305 310 315 320

```
Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 21
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gln Ile Tyr Glu Gly Lys Leu Thr Ala Glu Gly Leu Arg Phe Gly
1               5                   10                  15

Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335
```

Trp Phe Asn Ser Thr
340

<210> SEQ ID NO 22
<211> LENGTH: 229
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Asp Thr Ile Thr Leu Pro Cys Arg Pro Ala Pro Pro Pro His Cys Ser
1 5 10 15

Ser Asn Ile Thr Gly Leu Ile Leu Thr Arg Gln Gly Gly Trp Ser Asn
20 25 30

Asp Asn Thr Val Ile Phe Arg Pro Ser Ala Gly Asp Trp Arg Asp Ile
35 40 45

Ala Arg Cys Gln Ile Ala Gly Thr Val Val Ser Thr Gln Leu Phe Leu
50 55 60

Asn Gly Ser Leu Ala Glu Glu Glu Val Val Ile Arg Ser Arg Asp Trp
65 70 75 80

Arg Asp Asn Ala Lys Ser Ile Cys Val Gln Leu Asn Thr Ser Val Glu
85 90 95

Ile Asn Cys Thr Gly Ala Gly His Cys Asn Ile Ser Arg Ala Lys Trp
100 105 110

Asn Asn Thr Leu Lys Gln Ile Ala Ser Lys Leu Arg Glu Gln Tyr Gly
115 120 125

Asn Lys Thr Val Ile Phe Ala Pro Ser Ser Gly Gly Asp Pro Glu Phe
130 135 140

Val Asn His Ser Phe Asn Cys Gly Gly Glu Phe Phe Tyr Cys Asp Ser
145 150 155 160

Thr Gln Leu Phe Asn Ser Thr Trp Phe Asn Ser Thr Gly Ser Gly Gly
165 170 175

Ser Gly Gly Ser Gly Gly Ser Gly Gly Ser Gly Arg Met Lys Gln Ile
180 185 190

Glu Asp Lys Ile Glu Glu Ile Leu Ser Lys Ile Tyr His Ile Glu Asn
195 200 205

Glu Ile Ala Arg Ile Lys Lys Leu Ile Gly Glu Arg Gly Thr Lys His
210 215 220

His His His His His
225

<210> SEQ ID NO 23
<211> LENGTH: 341
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

-continued

```
Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 24
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45
```

Thr Leu Val Arg Val Cys Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Cys Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Trp Ser Asn Asp Asn Thr Val Ile Phe Arg
195 200 205

Pro Ser Ala Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Arg Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Val Ile Phe Ala
290 295 300

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 25
<211> LENGTH: 341
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Met Gln Ile Tyr Cys Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Cys Val Pro Gly Ser Trp Glu Ile Pro Val Ala Ala Gly
50 55 60

```
Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 26
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80
```

```
Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 27
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80
```

```
Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340
```

```
<210> SEQ ID NO 28
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95
```

```
Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 29
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110
```

Phe Gly Val Ile Thr Ala Asp Thr Leu Glu Gln Ala Ile Glu Ala Ala
115 120 125

Gly Thr Cys His Gly Asn Lys Gly Trp Glu Ala Ala Leu Cys Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Gln Gly Gly Tyr Ser Asn Asp Asn Thr Val Ile Phe Arg
195 200 205

Pro Ser Gly Gly Asp Trp Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Glu Asp Trp Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Tyr Gly Asn Lys Thr Ile Ile Phe Lys
290 295 300

Pro Ser Ser Gly Gly Asp Pro Glu Phe Val Asn His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 30
<211> LENGTH: 341
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Cys Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro Ser Phe Asp Tyr Ile Ala Ser Glu Val
85 90 95

Ser Lys Gly Leu Ala Asp Leu Ser Leu Glu Leu Arg Lys Pro Ile Thr
100 105 110

```
Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340
```

<210> SEQ ID NO 31
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Gln Ile Tyr Glu Gly Lys Leu Thr Ala Glu Gly Leu Arg Phe Gly
1               5                   10                  15

Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125
```

-continued

```
Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Trp Ser Asn Asp Asn Thr Val Ile Phe Arg
        195                 200                 205

Pro Ser Ala Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Arg Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Val Ile Phe Ala
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340
```

<210> SEQ ID NO 32
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Cys His Gly Asn Lys Gly Trp Glu Ala Ala Leu Ser Ala Ile
    130                 135                 140
```

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Asp Gly Gly Val Ser Asn Asp Glu Thr Glu Ile Phe Arg
195 200 205

Pro Ser Gly Gly Asp Met Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Val Asp Phe Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Phe Gly Asn Arg Thr Ile Ile Phe Lys
290 295 300

Gln Ser Ser Gly Gly Asp Pro Glu Phe Val Thr His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 33
<211> LENGTH: 341
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Cys Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Cys Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Asp Gly Gly Val Ser Asn Asp Glu Thr Glu Ile Phe Arg
195 200 205

Pro Ser Gly Gly Asp Met Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Val Asp Phe Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Phe Gly Asn Arg Thr Ile Ile Phe Lys
290 295 300

Gln Ser Ser Gly Gly Asp Pro Glu Phe Val Thr His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 34
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Met Gln Ile Tyr Cys Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Cys Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Asp Gly Gly Val Ser Asn Asp Glu Thr Glu Ile Phe Arg
195 200 205

Pro Ser Gly Gly Asp Met Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Val Asp Phe Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Phe Gly Asn Arg Thr Ile Ile Phe Lys
290 295 300

Gln Ser Ser Gly Gly Asp Pro Glu Phe Val Thr His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 35
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Asp Gly Gly Val Ser Asn Asp Glu Thr Glu Ile Phe Arg
195 200 205

Pro Ser Gly Gly Asp Met Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Val Asp Phe Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Phe Gly Asn Arg Thr Ile Ile Phe Lys
290 295 300

Gln Ser Ser Gly Gly Asp Pro Glu Phe Val Thr His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 36
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

Leu Thr Arg Asp Gly Gly Val Ser Asn Asp Glu Thr Glu Ile Phe Arg
195 200 205

Pro Ser Gly Gly Asp Met Arg Asp Ile Ala Arg Cys Gln Ile Ala Gly
210 215 220

Thr Val Val Ser Thr Gln Leu Phe Leu Asn Gly Ser Leu Ala Glu Glu
225 230 235 240

Glu Val Val Ile Arg Ser Val Asp Phe Arg Asp Asn Ala Lys Ser Ile
245 250 255

Cys Val Gln Leu Asn Thr Ser Val Glu Ile Asn Cys Thr Gly Ala Gly
260 265 270

His Cys Asn Ile Ser Arg Ala Lys Trp Asn Asn Thr Leu Lys Gln Ile
275 280 285

Ala Ser Lys Leu Arg Glu Gln Phe Gly Asn Arg Thr Ile Ile Phe Lys
290 295 300

Gln Ser Ser Gly Gly Asp Pro Glu Phe Val Thr His Ser Phe Asn Cys
305 310 315 320

Gly Gly Glu Phe Phe Tyr Cys Asp Ser Thr Gln Leu Phe Asn Ser Thr
325 330 335

Trp Phe Asn Ser Thr
340

<210> SEQ ID NO 37
<211> LENGTH: 341
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Cys Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Cys His Gly Asn Lys Gly Trp Glu Ala Ala Leu Ser Ala Ile
130 135 140

Glu Met Ala Asn Leu Phe Lys Ser Leu Arg Gly Gly Ser Gly Gly Ser
145 150 155 160

Gly Gly Ser Gly Gly Ser Gly Gly Gly Asp Thr Ile Thr Leu Pro Cys
165 170 175

Arg Pro Ala Pro Pro Pro His Cys Ser Ser Asn Ile Thr Gly Leu Ile
180 185 190

-continued

```
Leu Thr Arg Asp Gly Gly Val Ser Asn Asp Glu Thr Glu Ile Phe Arg
        195                 200                 205

Pro Ser Gly Gly Asp Met Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Val Asp Phe Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Arg Thr Ile Ile Phe Lys
    290                 295                 300

Gln Ser Ser Gly Gly Asp Pro Glu Phe Val Thr His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 38
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Asp Gly Gly Val Ser Asn Asp Glu Thr Glu Ile Phe Arg
        195                 200                 205
```

```
Pro Ser Gly Gly Asp Met Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Val Asp Phe Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Arg Thr Ile Ile Phe Lys
    290                 295                 300

Gln Ser Ser Gly Gly Asp Pro Glu Phe Val Thr His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 39
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Asp Gly Gly Val Ser Asn Asp Glu Thr Glu Ile Phe Arg
        195                 200                 205
```

```
Pro Ser Gly Gly Asp Met Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Val Asp Phe Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Arg Thr Ile Ile Phe Lys
    290                 295                 300

Gln Ser Ser Gly Gly Asp Pro Glu Phe Val Thr His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 40
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gln Ile Tyr Glu Gly Lys Leu Thr Ala Glu Gly Leu Arg Phe Gly
1               5                   10                  15

Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Asp Gly Gly Val Ser Asn Asp Glu Thr Glu Ile Phe Arg
        195                 200                 205

Pro Ser Gly Gly Asp Met Arg Asp Ile Ala Arg Cys Gln Ile Ala Gly
    210                 215                 220
```

```
Thr Val Val Ser Thr Gln Leu Phe Leu Asn Gly Ser Leu Ala Glu Glu
225                 230                 235                 240

Glu Val Val Ile Arg Ser Val Asp Phe Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Arg Thr Ile Ile Phe Lys
    290                 295                 300

Gln Ser Ser Gly Gly Asp Pro Glu Phe Val Thr His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 41
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Asp Ala Glu Thr Thr Leu Phe Cys Ala Ser Asp Ala Lys Ala
            180                 185                 190

Tyr Glu Thr Glu Lys His Asn Val Trp Ala Thr His Ala Cys Val Pro
        195                 200                 205

Thr Asp Pro Asn Pro Gln Glu Ile His Leu Glu Asn Val Thr Glu Glu
    210                 215                 220

Phe Asn Met Trp Lys Asn Asn Met Val Glu Gln Met His Thr Asp Ile
225                 230                 235                 240
```

```
Ile Ser Leu Trp Asp Gln Ser Leu Lys Pro Cys Val Lys Leu Thr Gly
                245                 250                 255

Gly Ser Ala Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Lys
        275                 280                 285

Asp Lys Lys Phe Asn Gly Thr Gly Pro Cys Pro Ser Val Ser Thr Val
    290                 295                 300

Gln Cys Thr His Gly Ile Lys Pro Val Val Ser Thr Gln Leu Leu Leu
305                 310                 315                 320

Asn Gly Ser Leu Ala Glu Glu Glu Val Met Ile Arg Ser Glu Asp Phe
                325                 330                 335

Arg Asn Asn Ala Lys Asn Ile Leu Val Gln Phe Asn Thr Pro Val Gln
            340                 345                 350

Ile Asn Cys Thr Arg Pro Asn Asn Gly Gly Ser Gly Ser Gly Gly Asp
        355                 360                 365

Ile Arg Gln Ala His Cys Asn Val Ser Lys Ala Thr Trp Asn Glu Thr
    370                 375                 380

Leu Gly Lys Val Val Lys Gln Leu Arg Lys His Tyr Gly Asn Asp Thr
385                 390                 395                 400

Thr Ile Arg Phe Ala Pro Ser Ser Gly Gly Asp Leu Glu Val Met Asn
                405                 410                 415

His Ser Phe Asn Cys Gly Gly Glu Phe Phe Tyr Cys Asn Thr Ser Gly
            420                 425                 430

Leu Phe Asn Ser Thr Trp Ile Ser Asn Thr Ser Val Gln Gly Ser Asn
        435                 440                 445

Ser Thr Gly Ser Asn Asp Ser Ile Thr Leu Pro Cys Arg Ile Lys Gln
    450                 455                 460

Ile Ile Asn Met Trp Gln Arg Ile Gly Gln Ala Met Tyr Ala Pro Pro
465                 470                 475                 480

Ile Gln Gly Val Ile Arg Cys Val Ser Asn Ile Thr Gly Leu Ile Leu
                485                 490                 495

Val Arg Asp Gly Gly Tyr Thr Asn Ser Asn Thr Glu Thr Phe Arg Pro
            500                 505                 510

Gly Gly Gly Asp Met Arg Asp Asn Trp Arg Ser Glu Leu Tyr Lys Tyr
        515                 520                 525

Lys Val Val Lys Ile Glu Pro
    530                 535
```

<210> SEQ ID NO 42
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45
```

Thr Leu Val Arg Val Pro Gly Ser Trp Glu Ile Pro Val Ala Ala Gly
50 55 60

Glu Leu Ala Arg Lys Glu Asp Ile Asp Ala Val Ile Ala Ile Gly Val
65 70 75 80

Leu Ile Arg Gly Ala Thr Pro His Phe Asp Tyr Ile Ala Ser Glu Val
85 90 95

Ser Lys Gly Leu Ala Asp Leu Ser Leu Glu Leu Arg Lys Pro Ile Thr
100 105 110

Phe Gly Val Ile Thr Ala Asp Thr Leu Glu Gln Ala Ile Glu Arg Ala
115 120 125

Gly Thr Lys His Gly Asn Lys Gly Trp Glu Ala Ala Leu Ser Ala Ile
130 135 140

Glu Met Ala Asn Leu Phe Lys Ser Leu Arg
145 150

<210> SEQ ID NO 43
<211> LENGTH: 360
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Val Trp Lys Glu Ala Thr Thr Thr Leu Phe Cys Ala Ser Asp Ala Lys
1 5 10 15

Ala Tyr Asp Thr Glu Val His Asn Val Trp Ala Thr His Ala Cys Val
20 25 30

Pro Thr Asp Pro Asn Pro Gln Glu Val Val Leu Val Asn Val Thr Glu
35 40 45

Asn Phe Asn Trp Cys Lys Asn Asp Met Val Glu Gln Met His Glu Asp
50 55 60

Ile Cys Ser Leu Trp Asp Gln Ser Leu Lys Pro Cys Val Lys Leu Thr
65 70 75 80

Gly Gly Ser Val Ile Thr Gln Ala Cys Pro Lys Val Ser Phe Glu Pro
85 90 95

Ile Pro Ile His Tyr Cys Ala Pro Ala Gly Phe Ala Ile Leu Lys Cys
100 105 110

Asn Asn Lys Thr Phe Asn Gly Thr Gly Pro Cys Thr Asn Val Ser Thr
115 120 125

Val Gln Cys Thr His Gly Ile Arg Pro Val Val Ser Ser Gln Leu Leu
130 135 140

Leu Asn Gly Ser Leu Ala Glu Glu Glu Val Val Ile Arg Ser Cys Asn
145 150 155 160

Phe Thr Asp Asn Ala Lys Thr Ile Ile Val Gln Leu Asn Thr Ser Val
165 170 175

Glu Ile Asn Cys Thr Arg Pro Asn Asn Gly Gly Ser Gly Ser Gly Gly
180 185 190

Asn Met Arg Gln Ala His Cys Asn Ile Ser Arg Ala Lys Trp Asn Asn
195 200 205

Thr Leu Lys Gln Ile Ala Ser Lys Leu Arg Glu Gln Phe Gly Asn Asn
210 215 220

Lys Thr Ile Ile Phe Lys Gln Ser Ser Gly Gly Asp Pro Glu Ile Val
225 230 235 240

Thr His Trp Phe Asn Cys Gly Gly Glu Phe Phe Tyr Cys Asn Ser Thr
245 250 255

-continued

```
Gln Leu Phe Asn Ser Thr Trp Phe Asn Ser Thr Trp Ser Thr Glu Gly
            260                 265                 270

Ser Asn Asn Thr Glu Gly Ser Asp Thr Ile Thr Leu Pro Cys Arg Ile
        275                 280                 285

Lys Gln Ile Ile Asn Met Trp Cys Lys Val Gly Lys Met Met Tyr Ala
    290                 295                 300

Pro Pro Ile Ser Gly Gln Ile Arg Cys Ser Ser Asn Ile Thr Gly Leu
305                 310                 315                 320

Leu Leu Thr Arg Asp Gly Gly Asn Ser Asn Asn Glu Ser Glu Ile Phe
                325                 330                 335

Arg Pro Gly Gly Gly Asp Met Arg Asp Asn Trp Arg Ser Glu Leu Tyr
            340                 345                 350

Lys Tyr Lys Val Val Lys Ile Glu
        355                 360
```

<210> SEQ ID NO 44
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Glu Ala Thr Thr Thr Leu Phe Cys Ala Ser Asp Ala Lys Ala
            180                 185                 190

Tyr Asp Thr Glu Val His Asn Val Trp Ala Thr His Ala Cys Val Pro
        195                 200                 205

Thr Asp Pro Asn Pro Gln Glu Val Val Leu Val Asn Val Thr Glu Asn
    210                 215                 220

Phe Asn Trp Cys Lys Asn Asp Met Val Glu Gln Met His Glu Asp Ile
225                 230                 235                 240

Cys Ser Leu Trp Asp Gln Ser Leu Lys Pro Cys Val Lys Leu Thr Gly
                245                 250                 255
```

-continued

```
Gly Ser Val Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Asn
        275                 280                 285

Asn Lys Thr Phe Asn Gly Thr Gly Pro Cys Thr Asn Val Ser Thr Val
    290                 295                 300

Gln Cys Thr His Gly Ile Arg Pro Val Val Ser Ser Gln Leu Leu Leu
305                 310                 315                 320

Asn Gly Ser Leu Ala Glu Glu Glu Val Val Ile Arg Ser Cys Asp Phe
                325                 330                 335

Thr Asp Asn Ala Lys Thr Ile Ile Val Gln Leu Asn Thr Ser Val Glu
            340                 345                 350

Ile Asn Cys Thr Arg Pro Asn Asn Gly Gly Ser Gly Ser Gly Gly Asn
        355                 360                 365

Met Arg Gln Ala His Cys Asn Ile Ser Arg Ala Lys Trp Asn Asn Thr
    370                 375                 380

Leu Lys Gln Ile Ala Ser Lys Leu Arg Glu Gln Phe Gly Asn Asn Lys
385                 390                 395                 400

Thr Ile Ile Phe Lys Gln Ser Ser Gly Gly Asp Pro Glu Ile Val Thr
                405                 410                 415

His Trp Phe Asn Cys Gly Gly Glu Phe Phe Tyr Cys Asn Ser Thr Gln
            420                 425                 430

Leu Phe Asn Ser Thr Trp Phe Asn Ser Thr Trp Ser Thr Glu Gly Ser
        435                 440                 445

Asn Asn Thr Glu Gly Ser Asp Thr Ile Thr Leu Pro Cys Arg Ile Lys
    450                 455                 460

Gln Ile Ile Asn Met Trp Cys Lys Val Gly Lys Met Met Tyr Ala Pro
465                 470                 475                 480

Pro Ile Ser Gly Gln Ile Arg Cys Ser Ser Asn Ile Thr Gly Leu Leu
                485                 490                 495

Leu Thr Arg Asp Gly Gly Asn Ser Asn Asn Glu Ser Glu Ile Phe Arg
            500                 505                 510

Pro Gly Gly Gly Asp Met Arg Asp Asn Trp Arg Ser Glu Leu Tyr Lys
        515                 520                 525

Tyr Lys Val Val Lys Ile Glu
    530                 535
```

<210> SEQ ID NO 45
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Met Gln Ile Tyr Glu Gly Lys Leu Thr Ala Glu Gly Leu Arg Phe Gly
1               5                   10                  15

Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60
```

```
Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Glu Ala Thr Thr Thr Leu Phe Cys Ala Ser Asp Ala Lys Ala
            180                 185                 190

Tyr Asp Thr Glu Val His Asn Val Trp Ala Thr His Ala Cys Val Pro
        195                 200                 205

Thr Asp Pro Asn Pro Gln Glu Val Val Leu Val Asn Val Thr Glu Asn
    210                 215                 220

Phe Asn Trp Cys Lys Asn Asp Met Val Glu Gln Met His Glu Asp Ile
225                 230                 235                 240

Cys Ser Leu Trp Asp Gln Ser Leu Lys Pro Cys Val Lys Leu Thr Gly
                245                 250                 255

Gly Ser Val Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Asn
        275                 280                 285

Asn Lys Thr Phe Asn Gly Thr Gly Pro Cys Thr Asn Val Ser Thr Val
    290                 295                 300

Gln Cys Thr His Gly Ile Arg Pro Val Val Ser Ser Gln Leu Leu Leu
305                 310                 315                 320

Asn Gly Ser Leu Ala Glu Glu Glu Val Val Ile Arg Ser Cys Asp Phe
                325                 330                 335

Thr Asp Asn Ala Lys Thr Ile Ile Val Gln Leu Asn Thr Ser Val Glu
            340                 345                 350

Ile Asn Cys Thr Arg Pro Asn Asn Gly Gly Ser Gly Ser Gly Gly Asn
        355                 360                 365

Met Arg Gln Ala His Cys Asn Ile Ser Arg Ala Lys Trp Asn Asn Thr
    370                 375                 380

Leu Lys Gln Ile Ala Ser Lys Leu Arg Glu Gln Phe Gly Asn Asn Lys
385                 390                 395                 400

Thr Ile Ile Phe Lys Gln Ser Ser Gly Gly Asp Pro Glu Ile Val Thr
                405                 410                 415

His Trp Phe Asn Cys Gly Gly Glu Phe Phe Tyr Cys Asn Ser Thr Gln
            420                 425                 430

Leu Phe Asn Ser Thr Trp Phe Asn Ser Thr Trp Ser Thr Glu Gly Ser
        435                 440                 445

Asn Asn Thr Glu Gly Ser Asp Thr Ile Thr Leu Pro Cys Arg Ile Lys
    450                 455                 460

Gln Ile Ile Asn Met Trp Cys Lys Val Gly Lys Met Met Tyr Ala Pro
465                 470                 475                 480
```

Pro Ile Ser Gly Gln Ile Arg Cys Ser Ser Asn Ile Thr Gly Leu Leu
485 490 495

Leu Thr Arg Asp Gly Gly Asn Ser Asn Asn Glu Ser Glu Ile Phe Arg
500 505 510

Pro Gly Gly Gly Asp Met Arg Asp Asn Trp Arg Ser Glu Leu Tyr Lys
515 520 525

Tyr Lys Val Val Lys Ile Glu
530 535

<210> SEQ ID NO 46
<211> LENGTH: 634
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Ala Glu Asn Leu Trp Val Thr Val Tyr Tyr Gly Val Pro Val Trp Lys
1 5 10 15

Asp Ala Glu Thr Thr Leu Phe Cys Ala Ser Asp Ala Lys Ala Tyr Glu
20 25 30

Thr Glu Lys His Asn Val Trp Ala Thr His Ala Cys Val Pro Thr Asp
35 40 45

Pro Asn Pro Gln Glu Ile His Leu Glu Asn Val Thr Glu Glu Phe Asn
50 55 60

Met Trp Lys Asn Asn Met Val Glu Gln Met His Thr Asp Ile Ile Ser
65 70 75 80

Leu Trp Asp Gln Ser Leu Lys Pro Cys Val Lys Leu Thr Pro Leu Cys
85 90 95

Val Thr Leu Gln Cys Thr Asn Val Thr Asn Asn Ile Thr Asp Asp Met
100 105 110

Arg Gly Glu Leu Lys Asn Cys Ser Phe Asn Met Thr Thr Glu Leu Arg
115 120 125

Asp Lys Lys Gln Lys Val Tyr Ser Leu Phe Tyr Arg Leu Asp Val Val
130 135 140

Gln Ile Asn Glu Asn Gln Gly Asn Arg Ser Asn Asn Ser Asn Lys Glu
145 150 155 160

Tyr Arg Leu Ile Asn Cys Asn Thr Ser Ala Ile Thr Gln Ala Cys Pro
165 170 175

Lys Val Ser Phe Glu Pro Ile Pro Ile His Tyr Cys Ala Pro Ala Gly
180 185 190

Phe Ala Ile Leu Lys Cys Lys Asp Lys Lys Phe Asn Gly Thr Gly Pro
195 200 205

Cys Pro Ser Val Ser Thr Val Gln Cys Thr His Gly Ile Lys Pro Val
210 215 220

Val Ser Thr Gln Leu Leu Leu Asn Gly Ser Leu Ala Glu Glu Glu Val
225 230 235 240

Met Ile Arg Ser Glu Asp Ile Thr Asn Asn Ala Lys Asn Ile Leu Val
245 250 255

Gln Phe Asn Thr Pro Val Gln Ile Asn Cys Thr Arg Pro Asn Asn Asn
260 265 270

Thr Arg Lys Ser Ile Arg Ile Gly Pro Gly Gln Ala Phe Tyr Ala Thr
275 280 285

```
Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 47
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Val Trp Lys Asp Ala Glu Thr Thr Leu Phe Cys Ala Ser Asp Ala Lys
1               5                   10                  15
```

```
Ala Tyr Glu Thr Glu Lys His Asn Val Trp Ala Thr His Ala Cys Val
            20                  25                  30

Pro Thr Asp Pro Asn Pro Gln Glu Ile His Leu Glu Asn Val Thr Glu
        35                  40                  45

Glu Phe Asn Met Trp Lys Asn Asn Met Val Glu Gln Met His Thr Asp
    50                  55                  60

Ile Ile Ser Leu Trp Asp Gln Ser Leu Lys Pro Cys Val Lys Leu Thr
65                  70                  75                  80

Gly Gly Ser Ala Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Thr Gly Pro Cys Pro Ser Val Ser Thr
        115                 120                 125

Val Gln Cys Thr His Gly Ile Lys Pro Val Val Ser Thr Gln Leu Leu
    130                 135                 140

Leu Asn Gly Ser Leu Ala Glu Glu Glu Val Met Ile Arg Ser Glu Asp
145                 150                 155                 160

Phe Arg Asn Asn Ala Lys Asn Ile Leu Val Gln Phe Asn Thr Pro Val
                165                 170                 175

Gln Ile Asn Cys Thr Arg Pro Asn Asn Gly Gly Ser Gly Ser Gly Gly
            180                 185                 190

Asp Ile Arg Gln Ala His Cys Asn Val Ser Lys Ala Thr Trp Asn Glu
        195                 200                 205

Thr Leu Gly Lys Val Val Lys Gln Leu Arg Lys His Tyr Gly Asn Asp
    210                 215                 220

Thr Thr Ile Arg Phe Ala Pro Ser Ser Gly Gly Asp Leu Glu Val Met
225                 230                 235                 240

Asn His Ser Phe Asn Cys Gly Gly Glu Phe Phe Tyr Cys Asn Thr Ser
                245                 250                 255

Gly Leu Phe Asn Ser Thr Trp Ile Ser Asn Thr Ser Val Gln Gly Ser
            260                 265                 270

Asn Ser Thr Gly Ser Asn Asp Ser Ile Thr Leu Pro Cys Arg Ile Lys
        275                 280                 285

Gln Ile Ile Asn Met Trp Gln Arg Ile Gly Gln Ala Met Tyr Ala Pro
    290                 295                 300

Pro Ile Gln Gly Val Ile Arg Cys Val Ser Asn Ile Thr Gly Leu Ile
305                 310                 315                 320

Leu Val Arg Asp Gly Gly Tyr Thr Asn Ser Asn Thr Glu Thr Phe Arg
                325                 330                 335

Pro Gly Gly Gly Asp Met Arg Asp Asn Trp Arg Ser Glu Leu Tyr Lys
            340                 345                 350

Tyr Lys Val Val Lys Ile Glu Pro
        355                 360
```

<210> SEQ ID NO 48
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Met Gln Ile Tyr Glu Gly Lys Leu Thr Ala Glu Gly Leu Arg Phe Gly
1               5                   10                  15
```

-continued

```
Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Asp Ala Glu Thr Thr Leu Phe Cys Ala Ser Asp Ala Lys Ala
            180                 185                 190

Tyr Glu Thr Glu Lys His Asn Val Trp Ala Thr His Ala Cys Val Pro
        195                 200                 205

Thr Asp Pro Asn Pro Gln Glu Ile His Leu Glu Asn Val Thr Glu Glu
    210                 215                 220

Phe Asn Met Trp Lys Asn Asn Met Val Glu Gln Met His Thr Asp Ile
225                 230                 235                 240

Ile Ser Leu Trp Asp Gln Ser Leu Lys Pro Cys Val Lys Leu Thr Gly
                245                 250                 255

Gly Ser Ala Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Lys
        275                 280                 285

Asp Lys Lys Phe Asn Gly Thr Gly Pro Cys Pro Ser Val Ser Thr Val
    290                 295                 300

Gln Cys Thr His Gly Ile Lys Pro Val Val Ser Thr Gln Leu Leu Leu
305                 310                 315                 320

Asn Gly Ser Leu Ala Glu Glu Glu Val Met Ile Arg Ser Glu Asp Phe
                325                 330                 335

Arg Asn Asn Ala Lys Asn Ile Leu Val Gln Phe Asn Thr Pro Val Gln
            340                 345                 350

Ile Asn Cys Thr Arg Pro Asn Asn Gly Gly Ser Gly Ser Gly Gly Asp
        355                 360                 365

Ile Arg Gln Ala His Cys Asn Val Ser Lys Ala Thr Trp Asn Glu Thr
    370                 375                 380

Leu Gly Lys Val Val Lys Gln Leu Arg Lys His Tyr Gly Asn Asp Thr
385                 390                 395                 400

Thr Ile Arg Phe Ala Pro Ser Ser Gly Gly Asp Leu Glu Val Met Asn
                405                 410                 415

His Ser Phe Asn Cys Gly Gly Glu Phe Phe Tyr Cys Asn Thr Ser Gly
            420                 425                 430
```

```
Leu Phe Asn Ser Thr Trp Ile Ser Asn Thr Ser Val Gln Gly Ser Asn
        435                 440                 445

Ser Thr Gly Ser Asn Asp Ser Ile Thr Leu Pro Cys Arg Ile Lys Gln
    450                 455                 460

Ile Ile Asn Met Trp Gln Arg Ile Gly Gln Ala Met Tyr Ala Pro Pro
465                 470                 475                 480

Ile Gln Gly Val Ile Arg Cys Val Ser Asn Ile Thr Gly Leu Ile Leu
                485                 490                 495

Val Arg Asp Gly Gly Tyr Thr Asn Ser Asn Thr Glu Thr Phe Arg Pro
            500                 505                 510

Gly Gly Gly Asp Met Arg Asp Asn Trp Arg Ser Glu Leu Tyr Lys Tyr
        515                 520                 525

Lys Val Val Lys Ile Glu Pro
    530                 535


<210> SEQ ID NO 49
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asp Phe Arg Asn Asn Ala Lys Asn Ile Leu Val
                245                 250                 255
```

```
Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Tyr Gly Asn Asp Thr Thr Ile Arg Phe Ala Pro Ser Ser Gly Gly
                325                 330                 335

Asp Leu Glu Val Met Asn His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Val Arg Asp Gly Gly Tyr Thr Asn Ser Asn
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 50
<211> LENGTH: 658
<212> TYPE: PRT
<213> ORGANISM: Artificial Sequence
<220> FEATURE:

-continued

<223> OTHER INFORMATION: Description of Artificial Sequence: Synthetic
polypeptide

<400> SEQUENCE: 50

Ala Glu Asn Leu Trp Val Thr Val Tyr Tyr Gly Val Pro Val Trp Lys
1 5 10 15

Asp Ala Glu Thr Thr Leu Phe Cys Ala Ser Asp Ala Lys Ala Tyr Glu
20 25 30

Thr Glu Lys His Asn Val Trp Ala Thr His Ala Cys Val Pro Thr Asp
35 40 45

Pro Asn Pro Gln Glu Ile His Leu Glu Asn Val Thr Glu Glu Phe Asn
50 55 60

Met Trp Lys Asn Asn Met Val Glu Gln Met His Thr Asp Ile Ile Ser
65 70 75 80

Leu Trp Asp Gln Ser Leu Lys Pro Cys Val Lys Leu Thr Pro Leu Cys
85 90 95

Val Thr Leu Gln Cys Thr Asn Val Thr Asn Asn Ile Thr Asp Asp Met
100 105 110

Arg Gly Glu Leu Lys Asn Cys Ser Phe Asn Met Thr Thr Glu Leu Arg
115 120 125

Asp Lys Lys Gln Lys Val Tyr Ser Leu Phe Tyr Arg Leu Asp Val Val
130 135 140

Gln Ile Asn Glu Asn Gln Gly Asn Arg Ser Asn Asn Ser Asn Lys Glu
145 150 155 160

Tyr Arg Leu Ile Asn Cys Asn Thr Ser Ala Ile Thr Gln Ala Cys Pro
165 170 175

Lys Val Ser Phe Glu Pro Ile Pro Ile His Tyr Cys Ala Pro Ala Gly
180 185 190

Phe Ala Ile Leu Lys Cys Lys Asp Lys Lys Phe Asn Gly Thr Gly Pro
195 200 205

Cys Pro Ser Val Ser Thr Val Gln Cys Thr His Gly Ile Lys Pro Val
210 215 220

Val Ser Thr Gln Leu Leu Leu Asn Gly Ser Leu Ala Glu Glu Glu Val
225 230 235 240

Met Ile Arg Ser Glu Asp Phe Arg Asn Asn Ala Lys Asn Ile Leu Val
245 250 255

Gln Phe Asn Thr Pro Val Gln Ile Asn Cys Thr Arg Pro Asn Asn Asn
260 265 270

Thr Arg Lys Ser Ile Arg Ile Gly Pro Gly Gln Ala Phe Tyr Ala Thr
275 280 285

Gly Asp Ile Ile Gly Asp Ile Arg Gln Ala His Cys Asn Val Ser Lys
290 295 300

Ala Thr Trp Asn Glu Thr Leu Gly Lys Val Val Lys Gln Leu Arg Lys
305 310 315 320

His Tyr Gly Asn Asp Thr Thr Ile Arg Phe Ala Pro Ser Ser Gly Gly
325 330 335

Asp Leu Glu Val Met Asn His Ser Phe Asn Cys Gly Gly Glu Phe Phe
340 345 350

Tyr Cys Asn Thr Ser Gly Leu Phe Asn Ser Thr Trp Ile Ser Asn Thr
355 360 365

Ser Val Gln Gly Ser Asn Ser Thr Gly Ser Asn Asp Ser Ile Thr Leu
370 375 380

Pro Cys Arg Ile Lys Gln Ile Ile Asn Met Trp Gln Arg Ile Gly Gln
385 390 395 400

Ala Met Tyr Ala Pro Pro Ile Gln Gly Val Ile Arg Cys Val Ser Asn
405 410 415

Ile Thr Gly Leu Ile Leu Val Arg Asp Gly Gly Tyr Thr Asn Ser Asn
420 425 430

Thr Glu Thr Phe Arg Pro Gly Gly Gly Asp Met Arg Asp Asn Trp Arg
435 440 445

Ser Glu Leu Tyr Lys Tyr Lys Val Val Lys Ile Glu Pro Leu Gly Val
450 455 460

Ala Pro Thr Arg Cys Lys Arg Arg Val Val Gly Arg Arg Arg Arg Arg
465 470 475 480

Arg Ala Val Gly Ile Gly Ala Val Phe Leu Gly Phe Leu Gly Ala Ala
485 490 495

Gly Ser Thr Met Gly Ala Ala Ser Met Thr Leu Thr Val Gln Ala Arg
500 505 510

Asn Leu Leu Ser Gly Ile Val Gln Gln Gln Ser Asn Leu Leu Arg Ala
515 520 525

Pro Glu Ala Gln Gln His Leu Leu Lys Leu Thr Val Trp Gly Ile Lys
530 535 540

Gln Leu Gln Ala Arg Val Leu Ala Val Glu Arg Tyr Leu Arg Asp Gln
545 550 555 560

Gln Leu Leu Gly Ile Trp Gly Cys Ser Gly Lys Leu Ile Cys Cys Thr
565 570 575

Asn Val Pro Trp Asn Ser Ser Trp Ser Asn Arg Asn Leu Ser Glu Ile
580 585 590

Trp Asp Asn Met Thr Trp Leu Gln Trp Asp Lys Glu Ile Ser Asn Tyr
595 600 605

Thr Gln Ile Ile Tyr Gly Leu Leu Glu Glu Ser Gln Asn Gln Gln Glu
610 615 620

Lys Asn Glu Gln Asp Leu Leu Ala Leu Asp Gly Thr Lys His His His
625 630 635 640

His His His Gly Ser Ala Phe Lys Val Ala Ala Trp Thr Leu Lys Ala
645 650 655

Ala Ala

<210> SEQ ID NO 51
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Val Trp Lys Asp Ala Glu Thr Thr Leu Phe Cys Ala Ser Asp Ala Lys
1 5 10 15

Ala Tyr Glu Thr Glu Lys His Asn Val Trp Ala Thr His Ala Cys Val
20 25 30

Pro Thr Asp Pro Asn Pro Gln Glu Ile His Leu Glu Asn Val Thr Glu
35 40 45

Glu Phe Asn Met Trp Lys Asn Asn Met Val Glu Gln Met His Thr Asp
50 55 60

Ile Ile Ser Leu Trp Asp Gln Ser Leu Lys Pro Cys Val Lys Leu Thr
65 70 75 80

Gly Gly Ser Ala Ile Thr Gln Ala Cys Pro Lys Val Ser Phe Glu Pro
85 90 95

```
Ile Pro Ile His Tyr Cys Ala Pro Ala Gly Phe Ala Ile Leu Lys Cys
            100                 105                 110

Lys Asp Lys Lys Phe Asn Gly Thr Gly Pro Cys Pro Ser Val Ser Thr
        115                 120                 125

Val Gln Cys Thr His Gly Ile Lys Pro Val Val Ser Thr Gln Leu Leu
    130                 135                 140

Leu Asn Gly Ser Leu Ala Glu Glu Glu Val Met Ile Arg Ser Glu Asp
145                 150                 155                 160

Phe Arg Asn Asn Ala Lys Asn Ile Leu Val Gln Phe Asn Thr Pro Val
                165                 170                 175

Gln Ile Asn Cys Thr Arg Pro Asn Asn Gly Gly Ser Gly Ser Gly Gly
            180                 185                 190

Asp Ile Arg Gln Ala His Cys Asn Val Ser Lys Ala Thr Trp Asn Glu
        195                 200                 205

Thr Leu Gly Lys Val Val Lys Gln Leu Arg Lys His Tyr Gly Asp Asp
    210                 215                 220

Thr Thr Ile Arg Phe Ala Pro Ser Ser Gly Gly Asp Leu Glu Val Ala
225                 230                 235                 240

Thr His Ser Phe Asn Cys Gly Gly Glu Phe Phe Tyr Cys Asn Thr Ser
                245                 250                 255

Gly Leu Phe Asn Ser Thr Trp Ile Ser Asn Thr Ser Val Gln Gly Ser
            260                 265                 270

Asn Ser Thr Gly Ser Asn Asp Ser Ile Thr Leu Pro Cys Arg Ile Lys
        275                 280                 285

Gln Ile Ile Asn Met Trp Gln Arg Ile Gly Gln Ala Met Tyr Ala Pro
    290                 295                 300

Pro Ile Gln Gly Val Ile Arg Cys Val Ser Asn Ile Thr Gly Leu Ile
305                 310                 315                 320

Leu Val Arg Asp Gly Gly Tyr Thr Asn Ser Asn Thr Glu Thr Phe Arg
                325                 330                 335

Pro Gly Gly Gly Asp Met Arg Asp Asn Trp Arg Ser Glu Leu Tyr Lys
            340                 345                 350

Tyr Lys Val Val Lys Ile Glu Pro
        355                 360
```

<210> SEQ ID NO 52
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80
```

```
Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Asp Ala Glu Thr Thr Leu Phe Cys Ala Ser Asp Ala Lys Ala
            180                 185                 190

Tyr Glu Thr Glu Lys His Asn Val Trp Ala Thr His Ala Cys Val Pro
        195                 200                 205

Thr Asp Pro Asn Pro Gln Glu Ile His Leu Glu Asn Val Thr Glu Glu
    210                 215                 220

Phe Asn Met Trp Lys Asn Asn Met Val Glu Gln Met His Thr Asp Ile
225                 230                 235                 240

Ile Ser Leu Trp Asp Gln Ser Leu Lys Pro Cys Val Lys Leu Thr Gly
                245                 250                 255

Gly Ser Ala Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Lys
        275                 280                 285

Asp Lys Lys Phe Asn Gly Thr Gly Pro Cys Pro Ser Val Ser Thr Val
    290                 295                 300

Gln Cys Thr His Gly Ile Lys Pro Val Val Ser Thr Gln Leu Leu Leu
305                 310                 315                 320

Asn Gly Ser Leu Ala Glu Glu Glu Val Met Ile Arg Ser Glu Asp Phe
                325                 330                 335

Arg Asn Asn Ala Lys Asn Ile Leu Val Gln Phe Asn Thr Pro Val Gln
            340                 345                 350

Ile Asn Cys Thr Arg Pro Asn Asn Gly Gly Ser Gly Ser Gly Gly Asp
        355                 360                 365

Ile Arg Gln Ala His Cys Asn Val Ser Lys Ala Thr Trp Asn Glu Thr
    370                 375                 380

Leu Gly Lys Val Val Lys Gln Leu Arg Lys His Tyr Gly Asn Asp Thr
385                 390                 395                 400

Thr Ile Arg Phe Ala Pro Ser Ser Gly Gly Asp Leu Glu Val Ala Thr
                405                 410                 415

His Ser Phe Asn Cys Gly Gly Glu Phe Phe Tyr Cys Asn Thr Ser Gly
            420                 425                 430

Leu Phe Asn Ser Thr Trp Ile Ser Asn Thr Ser Val Gln Gly Ser Asn
        435                 440                 445

Ser Thr Gly Ser Asn Asp Ser Ile Thr Leu Pro Cys Arg Ile Lys Gln
    450                 455                 460

Ile Ile Asn Met Trp Gln Arg Ile Gly Gln Ala Met Tyr Ala Pro Pro
465                 470                 475                 480

Ile Gln Gly Val Ile Arg Cys Val Ser Asn Ile Thr Gly Leu Ile Leu
                485                 490                 495
```

```
Val Arg Asp Gly Gly Tyr Thr Asn Ser Asn Thr Glu Thr Phe Arg Pro
            500                 505                 510

Gly Gly Gly Asp Met Arg Asp Asn Trp Arg Ser Glu Leu Tyr Lys Tyr
        515                 520                 525

Lys Val Val Lys Ile Glu Pro
    530                 535


<210> SEQ ID NO 53
<211> LENGTH: 658
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asp Phe Arg Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300
```

```
Ala Thr Trp Asn Glu Thr Leu Gly Lys Val Val Lys Gln Leu Arg Lys
305                 310                 315                 320

His Tyr Gly Asn Asp Thr Thr Ile Arg Phe Ala Pro Ser Ser Gly Gly
                325                 330                 335

Asp Leu Glu Val Ala Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Val Arg Asp Gly Gly Tyr Thr Asn Ser Asn
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp Gly Thr Lys His His His
625                 630                 635                 640

His His His Gly Ser Ala Phe Lys Val Ala Ala Trp Thr Leu Lys Ala
                645                 650                 655

Ala Ala


<210> SEQ ID NO 54
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 54

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

-continued

```
Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gtgcagtctg gggctgaggt gaag 24

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
agcactcaga gaagcccacc catct 25

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Cys Asp Tyr Asn Trp Asp Phe Gln His Trp Gly
            100                 105                 110

Gln Gly Thr Leu Val Thr Val Ser Ser
        115                 120
```

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
caggtgcagc tggtgcagtc tgg 23

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 59
aagcagtggt atcaacgcag agtagacgtg tgctcttccg atctggggg 49

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
cccattgctc ttccaacatt 20

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
caatagaaaa actcaccacc aca 23

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Cys Gln Gln Tyr Glu Phe Phe
1 5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gln Gln Tyr Glu Phe
1 5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Any amino acid

<400> SEQUENCE: 64

Gln Gln Tyr Glu Xaa
1 5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Cys Gln Gln Tyr
1

<210> SEQ ID NO 66
<211> LENGTH: 99
<212> TYPE: PRT
<213> ORGANISM: Mus sp.

<400> SEQUENCE: 66

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

-continued

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly

<210> SEQ ID NO 67
<211> LENGTH: 296
<212> TYPE: DNA
<213> ORGANISM: Mus sp.

<400> SEQUENCE: 67
caggtgcagc tggtgcagtc tgggggtcag atgaagaagc ctggcgagtc gatgagaatt      60
tcttgtcggg cttctggata tgaatttatt gattgtacgc taaattggat tcgtctggcc     120
cccggaaaaa ggcctgagtg gatgggatgg ctgaagcctc gggggggggc cgtcaactac     180
gcacgtccac ttcagggcag agtgaccatg actcgagacg tttattccga cacagccttt     240
ttggagctgc gctcgttgac agtagacgac acggccgtct acttttgtac tagggg         296

<210> SEQ ID NO 68
<211> LENGTH: 296
<212> TYPE: DNA
<213> ORGANISM: Homo sapiens

<400> SEQUENCE: 68
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaacccta acagtggtgg cacaaactat     180
gcacagaagt ttcagggcag ggtcaccatg accagggaca cgtccatcag cacagcctac     240
atggagctga gcaggctgag atctgacgac acggccgtgt attactgtgc gagaga         296

<210> SEQ ID NO 69
<211> LENGTH: 19
<212> TYPE: PRT
<213> ORGANISM: Mus sp.

<400> SEQUENCE: 69

Thr Arg Gly Lys Asn Cys Asp Tyr Asn Trp Asp Phe Glu His Trp Gly
1               5                   10                  15

Arg Gly Thr

<210> SEQ ID NO 70
<211> LENGTH: 57
<212> TYPE: DNA
<213> ORGANISM: Mus sp.

<400> SEQUENCE: 70
actaggggaa aaaactgtga ttacaattgg gacttcgaac actggggccg gggcacc          57

<210> SEQ ID NO 71
<211> LENGTH: 37
<212> TYPE: DNA
<213> ORGANISM: Homo sapiens

```
<400> SEQUENCE: 71

gtattatgat tacgtttggg ggagttatcg ttatacc                                37

<210> SEQ ID NO 72
<211> LENGTH: 37
<212> TYPE: DNA
<213> ORGANISM: Homo sapiens

<400> SEQUENCE: 72

gtattatgat tacgtttggg ggagttatgc ttatacc                                37

<210> SEQ ID NO 73
<211> LENGTH: 31
<212> TYPE: DNA
<213> ORGANISM: Homo sapiens

<400> SEQUENCE: 73

ggcatagaaa gtagtactat tacaatattc t                                      31

<210> SEQ ID NO 74
<211> LENGTH: 20
<212> TYPE: DNA
<213> ORGANISM: Homo sapiens

<400> SEQUENCE: 74

gtagagatgg ctacaattac                                                   20

<210> SEQ ID NO 75
<211> LENGTH: 17
<212> TYPE: DNA
<213> ORGANISM: Homo sapiens

<400> SEQUENCE: 75

ggtacaactg gaacgac                                                      17

<210> SEQ ID NO 76
<211> LENGTH: 20
<212> TYPE: PRT
<213> ORGANISM: Mus sp.

<400> SEQUENCE: 76

Cys Asp Tyr Asn Trp Asp Phe Glu His Trp Gly Arg Gly Thr Pro Val
1               5                   10                  15

Ile Val Ser Ser
            20

<210> SEQ ID NO 77
<211> LENGTH: 60
<212> TYPE: DNA
<213> ORGANISM: Mus sp.

<400> SEQUENCE: 77

tgtgattaca attgggactt cgaacactgg ggccggggca ccccggtcat cgtctcatca       60

<210> SEQ ID NO 78
<211> LENGTH: 51
<212> TYPE: DNA
<213> ORGANISM: Homo sapiens

<400> SEQUENCE: 78

gctgaatact tccagcactg gggccagggc accctggtca ccgtctcctc a                51
```

-continued

<210> SEQ ID NO 79
<211> LENGTH: 52
<212> TYPE: DNA
<213> ORGANISM: Homo sapiens

<400> SEQUENCE: 79
ctactggtac ttcgatctct ggggccgtgg caccctggtc actgtctcct ca 52

<210> SEQ ID NO 80
<211> LENGTH: 50
<212> TYPE: DNA
<213> ORGANISM: Homo sapiens

<400> SEQUENCE: 80
acaactggtt cgacccctgg ggccagggaa ccctggtcac cgtctcctca 50

<210> SEQ ID NO 81
<211> LENGTH: 47
<212> TYPE: DNA
<213> ORGANISM: Homo sapiens

<400> SEQUENCE: 81
actactttga ctactggggc cagggaaccc tggtcaccgt ctcctca 47

<210> SEQ ID NO 82
<211> LENGTH: 47
<212> TYPE: DNA
<213> ORGANISM: Homo sapiens

<400> SEQUENCE: 82
gctactttga ctactggggc caagggaccc tggtcaccgt ctcctca 47

<210> SEQ ID NO 83
<211> LENGTH: 121
<212> TYPE: PRT
<213> ORGANISM: Mus sp.

<400> SEQUENCE: 83

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

Arg Gly Thr Pro Val Ile Val Ser Ser
115 120

<210> SEQ ID NO 84
<211> LENGTH: 98
<212> TYPE: PRT
<213> ORGANISM: Homo sapiens

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg
```

<210> SEQ ID NO 85
<211> LENGTH: 121
<212> TYPE: PRT
<213> ORGANISM: Mus sp.

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
tgtcagcaat atgatagctt cggtgctggg acc 33

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Cys Gln Gln Tyr Asp Ser Phe Gly Ala Gly Thr
1 5 10

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
tgtcagcaat attatagcta tcctcc 26

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Cys Gln Gln Tyr Tyr Ser
1 5

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
gctcacgttc ggtgctggga cc 22

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Phe Gly Ala Gly Thr
1 5

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Cys Ala Arg Glu Leu Gln Gln Thr Glu Asp Ala Phe Asp Ile Trp
1 5 10 15

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Cys Gln Gln Leu Asn Ser Tyr Pro Tyr Thr Phe
1 5 10

<210> SEQ ID NO 94
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Cys Ala Arg Gly Gly Thr Met Val Arg Gly Glu Asn Leu Thr Tyr Tyr
1 5 10 15

Tyr Tyr Tyr Gly Met Asp Val Trp
20

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Cys Leu Gln Asp Tyr Asn Tyr Pro Tyr Thr Phe
1 5 10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Cys Ala Arg Glu Ser Ser Ser Trp Arg Tyr Asn Trp Phe Asp Pro Trp
1 5 10 15

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Cys Gln Gln Tyr Gly Ser Ser Ser Tyr Thr Phe
1 5 10

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Asp Thr Ile Thr Leu Pro Cys Arg Pro Ala Pro Pro Pro His Cys Ser
1 5 10 15

Ser Asn Ile Thr Gly Leu Ile Leu Thr Arg Asp Gly Gly
20 25

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Asp Thr Ile Thr Leu Pro Cys Arg Pro Ala Pro Pro Pro His Cys Ser
1 5 10 15

Ser Asn Ile Thr Gly Leu Ile Leu Thr Arg Asp Gly Gly
20 25

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Asp Thr Ile Thr Leu Pro Cys Arg Pro Ala Pro Pro Pro His Cys Ser
1 5 10 15

Ser Asn Ile Thr Gly Leu Ile Leu Thr Arg Gln Gly Gly
20 25

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Val Ser Asn Asp Glu Thr Glu Ile Phe Arg Pro Ser Gly Gly Asp Met
1 5 10 15

Arg Asp Ile Ala Arg Cys Gln Ile Ala Gly Thr Val Val
20 25

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Ile Ser Asn Asp Asn Thr Glu Ile Phe Arg Pro Ser Gly Gly Asp Trp
1 5 10 15

Arg Asp Ile Ala Arg Cys Gln Ile Ala Gly Thr Val Val
20 25

<210> SEQ ID NO 103
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Tyr Ser Asn Asp Asn Thr Val Ile Phe Arg Pro Ser Gly Gly Asp Trp
1               5                   10                  15

Arg Asp Ile Ala Arg Cys Gln Ile Ala Gly Thr Val Val
            20                  25
```

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Ser Thr Gln Leu Phe Leu Asn Gly Ser Leu Ala Glu Glu Glu Val Val
1               5                   10                  15

Ile Arg Ser Val Asp Phe Arg Asp Asn Ala Lys Ser Ile
            20                  25
```

<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Ser Thr Gln Leu Phe Leu Asn Gly Ser Leu Ala Glu Glu Glu Val Val
1               5                   10                  15

Ile Arg Ser Glu Asp Phe Arg Asp Asn Ala Lys Ser Ile
            20                  25
```

<210> SEQ ID NO 106
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Ser Thr Gln Leu Phe Leu Asn Gly Ser Leu Ala Glu Glu Glu Val Val
1               5                   10                  15

Ile Arg Ser Glu Asp Trp Arg Asp Asn Ala Lys Ser Ile
            20                  25
```

<210> SEQ ID NO 107
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Cys Val Gln Leu Asn Thr Ser Val Glu Ile Asn Cys Thr Gly Ala Gly
1               5                   10                  15

His Cys Asn Ile Ser Arg Ala Lys Trp Asn Asn Thr Leu
            20                  25
```

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

```
Cys Val Gln Leu Asn Thr Ser Val Glu Ile Asn Cys Thr Gly Ala Gly
1               5                   10                  15

His Cys Asn Ile Ser Arg Ala Lys Trp Asn Asn Thr Leu
            20                  25
```

<210> SEQ ID NO 109
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

```
Cys Val Gln Leu Asn Thr Ser Val Glu Ile Asn Cys Thr Gly Ala Gly
1               5                   10                  15

His Cys Asn Ile Ser Arg Ala Lys Trp Asn Asn Thr Leu
            20                  25
```

<210> SEQ ID NO 110
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

```
Lys Gln Ile Ala Ser Lys Leu Arg Glu Gln Phe Gly Asn Arg Thr Ile
1               5                   10                  15

Ile Phe Lys Gln Ser Ser Gly Gly Asp Pro Glu Phe Val
            20                  25
```

<210> SEQ ID NO 111
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

```
Lys Gln Ile Ala Ser Lys Leu Arg Glu Gln Phe Gly Asn Lys Thr Ile
1               5                   10                  15

Ile Phe Lys Gln Ser Ser Gly Gly Asp Pro Glu Phe Val
            20                  25
```

<210> SEQ ID NO 112

<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Lys Gln Ile Ala Ser Lys Leu Arg Glu Gln Tyr Gly Asn Lys Thr Ile
1               5                   10                  15

Ile Phe Lys Pro Ser Ser Gly Gly Asp Pro Glu Phe Val
            20                  25
```

<210> SEQ ID NO 113
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Thr His Ser Phe Asn Cys Gly Gly Glu Phe Phe Tyr Cys Asp Ser Thr
1               5                   10                  15

Gln Leu Phe Asn Ser Thr Trp Phe Asn Ser Thr
            20                  25
```

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Thr His Ser Phe Asn Cys Gly Gly Glu Phe Phe Tyr Cys Asp Ser Thr
1               5                   10                  15

Gln Leu Phe Asn Ser Thr Trp Phe Asn Ser Thr
            20                  25
```

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Asn His Ser Phe Asn Cys Gly Gly Glu Phe Phe Tyr Cys Asp Ser Thr
1               5                   10                  15

Gln Leu Phe Asn Ser Thr Trp Phe Asn Ser Thr
            20                  25
```

<210> SEQ ID NO 116
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 117
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Ser Gly Asp Asp Thr Ser Trp His Phe Asp Pro Trp
            100                 105                 110

Gly Gln Gly Thr Leu Val Thr Val Ser Ser
        115                 120


<210> SEQ ID NO 118
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Gln Arg Ser Asp Phe Trp Asp Phe Asp Leu Trp Gly Arg Gly
            100                 105                 110

Thr Leu Val Thr Val Ser Ser
        115


<210> SEQ ID NO 119
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Ser Asp Phe Trp Asp Phe Asp Leu Trp Gly Arg Gly
            100                 105                 110

Thr Leu Val Thr Val Ser Ser
        115


<210> SEQ ID NO 120
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Cys Thr Gly Gly Val Ser Tyr Asn Trp Tyr Phe
            100                 105                 110

Asp Leu Trp Gly Arg Gly Thr Leu Val Thr Val Ser Ser
        115                 120                 125
```

<210> SEQ ID NO 121
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Lys Phe Tyr Thr Gly Gly Gln Gly Trp Tyr Phe Asp Leu
            100                 105                 110

Trp Gly Arg Gly Thr Leu Val Thr Val Ser Ser
        115                 120
```

<210> SEQ ID NO 122
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Lys Phe Ala Arg Gly Gly Gln Gly Trp Tyr Phe Asp Leu
            100                 105                 110

Trp Gly Arg Gly Thr Leu Val Thr Val Ser Ser
        115                 120
```

<210> SEQ ID NO 123
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Gly Gly Tyr Thr Gly Gly Gln Gly Trp Tyr Phe Asp Leu
100 105 110

Trp Gly Gln Gly Thr Leu Val Thr Val Ser Ser
115 120

<210> SEQ ID NO 124
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Met Gly Ala Ala Arg Glu Trp Asp Phe Gln Tyr Trp Gly Gln
100 105 110

Gly Thr Arg Val Leu Val Ser Ser
115 120

<210> SEQ ID NO 125
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

```
Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Met Arg Ser Gln Asp Arg Glu Trp Asp Phe Gln His Trp
            100                 105                 110

Gly Gln Gly Thr Leu Val Thr Val Ser Ser
        115                 120


<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 127
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Arg Gly Ser Cys Asp Tyr Cys Gly Asp Phe Pro Trp Gln His
            100                 105                 110

Trp Gly Gln Gly Thr Leu Val Thr Val Ser Ser
        115                 120


<210> SEQ ID NO 128
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Ser Ser Cys Pro His Cys Gly Asp Phe His Phe Asp
            100                 105                 110

Pro Trp Gly Gln Gly Thr Leu Val Thr Val Ser Ser
        115                 120


<210> SEQ ID NO 129
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Arg Arg Asp Ala Ser Trp Trp Leu Gln Phe Trp Gly
            100                 105                 110

Gln Gly Thr Leu Val Thr Val Ser Ser
        115                 120
```

<210> SEQ ID NO 130
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Lys Arg Gly Arg Ser Gly Trp Asp Phe Gln His Trp
            100                 105                 110

Gly Gln Gly Thr Leu Val Thr Val Ser Ser
        115                 120
```

<210> SEQ ID NO 131
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Lys Lys Arg Gly Asp Gly Phe Asn Leu Tyr Phe Asp Leu Trp
            100                 105                 110

Gly Arg Gly Thr Leu Val Thr Val Ser Ser
        115                 120
```

<210> SEQ ID NO 132
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gln Lys Phe Glu Ser Arg Tyr Thr Gly Gly Gln Gly Trp Tyr
            100                 105                 110

Phe Asp Leu Trp Gly Arg Gly Thr Leu Val Thr Val Ser Ser
        115                 120                 125
```

<210> SEQ ID NO 133
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 134
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Val Leu Glu Phe Phe Gly Pro
                85                  90                  95

Gly Thr Lys Val Glu Ile Lys
            100


<210> SEQ ID NO 135
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Phe Ile Gly Pro
                85                  90                  95

Gly Thr Lys Val Asp Ile Lys
            100


<210> SEQ ID NO 136
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Thr Phe Gly Gln
                85                  90                  95

Gly Thr Lys Leu Glu Ile Lys
            100


<210> SEQ ID NO 137
<211> LENGTH: 95
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 137

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 138
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Glu Phe Phe Gly Gln
                85                  90                  95

Gly Thr Lys Leu Glu Ile Lys
            100
```

<210> SEQ ID NO 139
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60
```

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro
85 90 95

<210> SEQ ID NO 140
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Glu Phe Phe Gly Gln
85 90 95

Gly Thr Lys Leu Glu Ile Lys
100

<210> SEQ ID NO 141
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Gln
85 90 95

Gly Thr Lys Val Glu Ile Lys
100

<210> SEQ ID NO 142
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

<210> SEQ ID NO 143
<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Leu Glu Phe Phe Gly
85 90 95

Gln Gly Thr Arg Leu Glu Ile Lys
100

<210> SEQ ID NO 144
<211> LENGTH: 104
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

```
Pro Glu Asp Phe Ala Val Tyr Tyr Cys Gln Gln Phe Glu Phe Phe Gly
                85                  90                  95

Gln Gly Thr Lys Leu Glu Ile Lys
            100


<210> SEQ ID NO 145
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Glu Phe Phe Gly
                85                  90                  95

Gln Gly Thr Lys Leu Glu Ile Lys
            100


<210> SEQ ID NO 146
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu


<210> SEQ ID NO 147
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 147

```
Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Glu Phe Phe
                85                  90                  95

Gly Gly Gly Thr Lys Val Phe Val Leu Gly
            100                 105
```

<210> SEQ ID NO 148
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Glu Phe Phe
                85                  90                  95

Gly Gly Gly Thr Lys Val Phe Val Leu Gly
            100                 105
```

<210> SEQ ID NO 149
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149

```
actggcctga ttctgacacg ggatggcgga atcagtaacg acaataccga aatt           54
```

<210> SEQ ID NO 150
<211> LENGTH: 18
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 150

Thr Gly Leu Ile Leu Thr Arg Asp Gly Gly Ile Ser Asn Asp Asn Thr
1               5                   10                  15

Glu Ile


<210> SEQ ID NO 151
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: a, c, t, g, unknown or other

<400> SEQUENCE: 151

actggcctga tcnnkacgcg ggatggcgga atcagtaacg acaataccga aatt           54


<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 152

Thr Gly Leu Ile Xaa Thr Arg Asp Gly Gly Ile Ser Asn Asp Asn Thr
1               5                   10                  15

Glu Ile


<210> SEQ ID NO 153
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: a, c, t, g, unknown or other

<400> SEQUENCE: 153

actggcctga ttctcnnkcg tgatggcgga atcagtaacg acaataccga aatt           54


<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
```

<400> SEQUENCE: 154

Thr Gly Leu Ile Leu Xaa Arg Asp Gly Gly Ile Ser Asn Asp Asn Thr
1               5                   10                  15

Glu Ile

<210> SEQ ID NO 155
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(20)
<223> OTHER INFORMATION: a, c, t, g, unknown or other

<400> SEQUENCE: 155
actggcctga ttctgaccnn kgacggcgga atcagtaacg acaataccga aatt 54

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Any amino acid

<400> SEQUENCE: 156

Thr Gly Leu Ile Leu Thr Xaa Asp Gly Gly Ile Ser Asn Asp Asn Thr
1               5                   10                  15

Glu Ile

<210> SEQ ID NO 157
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 157
actggcctga ttctgacacg tnnkggtgga atcagtaacg acaataccga aatt 54

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: Any amino acid

<400> SEQUENCE: 158

Thr Gly Leu Ile Leu Thr Arg Xaa Gly Gly Ile Ser Asn Asp Asn Thr
1 5 10 15

Glu Ile

<210> SEQ ID NO 159
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 159
actggcctga ttctgacacg ggacnnkggc atcagtaacg acaataccga aatt 54

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (9)..(9)
<223> OTHER INFORMATION: Any amino acid

<400> SEQUENCE: 160

Thr Gly Leu Ile Leu Thr Arg Asp Xaa Gly Ile Ser Asn Asp Asn Thr
1 5 10 15

Glu Ile

<210> SEQ ID NO 161
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 161
actggcctga ttctgacacg ggatggtnnk attagtaacg acaataccga aatt 54

<210> SEQ ID NO 162
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (10)..(10)
<223> OTHER INFORMATION: Any amino acid

<400> SEQUENCE: 162

Thr Gly Leu Ile Leu Thr Arg Asp Gly Xaa Ile Ser Asn Asp Asn Thr
1 5 10 15

Glu Ile

<210> SEQ ID NO 163
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (31)..(32)
<223> OTHER INFORMATION: a, c, t, g, unknown or other

<400> SEQUENCE: 163
actggcctga ttctgacacg ggatggcggt nnkagcaacg acaataccga aatt 54

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (11)..(11)
<223> OTHER INFORMATION: Any amino acid

<400> SEQUENCE: 164

Thr Gly Leu Ile Leu Thr Arg Asp Gly Gly Xaa Ser Asn Asp Asn Thr
1 5 10 15

Glu Ile

<210> SEQ ID NO 165
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 165
actggcctga ttctgacacg ggatggcgga atannkaatg acaataccga aatt 54

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (12)..(12)
<223> OTHER INFORMATION: Any amino acid -continued

<400> SEQUENCE: 166

Thr Gly Leu Ile Leu Thr Arg Asp Gly Gly Ile Xaa Asn Asp Asn Thr
1 5 10 15

Glu Ile

<210> SEQ ID NO 167
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 167
actggcctga ttctgacacg ggatggcgga atcagcnnkg ataataccga aatt 54

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (13)..(13)
<223> OTHER INFORMATION: Any amino acid

<400> SEQUENCE: 168

Thr Gly Leu Ile Leu Thr Arg Asp Gly Gly Ile Ser Xaa Asp Asn Thr
1 5 10 15

Glu Ile

<210> SEQ ID NO 169
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (40)..(41)
<223> OTHER INFORMATION: a, c, t, g, unknown or other

<400> SEQUENCE: 169
actggcctga ttctgacacg ggatggcgga atcagtaatn nkaacaccga aatt 54

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (14)..(14)
<223> OTHER INFORMATION: Any amino acid

<400> SEQUENCE: 170

Thr Gly Leu Ile Leu Thr Arg Asp Gly Gly Ile Ser Asn Xaa Asn Thr
1 5 10 15

Glu Ile

<210> SEQ ID NO 171
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (43)..(44)
<223> OTHER INFORMATION: a, c, t, g, unknown or other

<400> SEQUENCE: 171
actggcctga ttctgacacg ggatggcgga atcagtaacg atnnkactga aatt 54

<210> SEQ ID NO 172
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (15)..(15)
<223> OTHER INFORMATION: Any amino acid

<400> SEQUENCE: 172

Thr Gly Leu Ile Leu Thr Arg Asp Gly Gly Ile Ser Asn Asp Xaa Thr
1 5 10 15

Glu Ile

<210> SEQ ID NO 173
<211> LENGTH: 634
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Ala Glu Asn Leu Trp Val Thr Val Tyr Tyr Gly Val Pro Val Trp Lys
1 5 10 15

Asp Ala Glu Thr Thr Leu Phe Cys Ala Ser Asp Ala Lys Ala Tyr Glu
20 25 30

Thr Glu Lys His Asn Val Trp Ala Thr His Ala Cys Val Pro Thr Asp
35 40 45

Pro Asn Pro Gln Glu Ile His Leu Glu Asn Val Thr Glu Glu Phe Asn
50 55 60

Met Trp Lys Asn Asn Met Val Glu Gln Met His Thr Asp Ile Ile Ser
65 70 75 80

Leu Trp Asp Gln Ser Leu Lys Pro Cys Val Lys Leu Thr Pro Leu Cys
85 90 95

Val Thr Leu Gln Cys Thr Asn Val Thr Asn Asn Ile Thr Asp Asp Met
100 105 110

Arg Gly Glu Leu Lys Asn Cys Ser Pro Asn Met Thr Thr Glu Leu Arg
115 120 125

```
Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540
```

```
Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630


<210> SEQ ID NO 174
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Pro Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asp Phe Arg Asn Asn Ala Lys Asn Ile Leu Val
                245                 250                 255

Gln Phe Asn Thr Pro Val Gln Ile Asn Cys Thr Arg Pro Asn Asn Asn
            260                 265                 270
```

```
Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Tyr Gly Asn Asp Thr Thr Ile Arg Phe Ala Pro Ser Ser Gly Gly
                325                 330                 335

Asp Leu Glu Val Met Asn His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Val Arg Asp Gly Gly Tyr Thr Asn Ser Asn
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630
```

<210> SEQ ID NO 175
<211> LENGTH: 360
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 175

Val Trp Lys Asp Ala Glu Thr Thr Leu Phe Cys Ala Ser Asp Ala Lys
1 5 10 15

Ala Tyr Glu Thr Glu Lys His Asn Val Trp Ala Thr His Ala Cys Val
20 25 30

Pro Thr Asp Pro Asn Pro Gln Glu Ile His Leu Glu Asn Val Thr Glu
35 40 45

Glu Phe Asn Met Trp Lys Asn Asn Met Val Glu Gln Met His Thr Asp
50 55 60

Ile Ile Ser Leu Trp Asp Gln Ser Leu Lys Pro Cys Val Lys Leu Thr
65 70 75 80

Gly Gly Ser Ala Ile Thr Gln Ala Cys Pro Lys Val Ser Phe Glu Pro
85 90 95

Ile Pro Ile His Tyr Cys Ala Pro Ala Gly Phe Ala Ile Leu Lys Cys
100 105 110

Lys Asp Lys Lys Phe Asn Gly Thr Gly Pro Cys Pro Ser Val Ser Thr
115 120 125

Val Gln Cys Thr His Gly Ile Lys Pro Val Val Ser Thr Gln Leu Leu
130 135 140

Leu Asn Gly Ser Leu Ala Glu Glu Glu Val Met Ile Arg Ser Glu Asn
145 150 155 160

Ile Thr Asn Asn Ala Lys Asn Ile Leu Val Gln Phe Asn Thr Pro Val
165 170 175

Gln Ile Asn Cys Thr Arg Pro Asn Asn Gly Gly Ser Gly Ser Gly Gly
180 185 190

Asp Ile Arg Gln Ala His Cys Asn Val Ser Lys Ala Thr Trp Asn Glu
195 200 205

Thr Leu Gly Lys Val Val Lys Gln Leu Arg Lys His Phe Gly Asn Asn
210 215 220

Thr Ile Ile Arg Phe Ala Asn Ser Ser Gly Gly Asp Leu Glu Val Thr
225 230 235 240

Thr His Ser Phe Asn Cys Gly Gly Glu Phe Phe Tyr Cys Asn Thr Ser
245 250 255

Gly Leu Phe Asn Ser Thr Trp Ile Ser Asn Thr Ser Val Gln Gly Ser
260 265 270

Asn Ser Thr Gly Ser Asn Asp Ser Ile Thr Leu Pro Cys Arg Ile Lys
275 280 285

Gln Ile Ile Asn Met Trp Gln Arg Ile Gly Gln Ala Met Tyr Ala Pro
290 295 300

Pro Ile Gln Gly Val Ile Arg Cys Val Ser Asn Ile Thr Gly Leu Ile
305 310 315 320

Leu Thr Arg Asp Gly Gly Ser Thr Asn Ser Thr Thr Glu Thr Phe Arg
325 330 335

Pro Gly Gly Gly Asp Met Arg Asp Asn Trp Arg Ser Glu Leu Tyr Lys
340 345 350

Tyr Lys Val Val Lys Ile Glu Pro
355 360

<210> SEQ ID NO 176
<211> LENGTH: 360
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 176

Val Trp Lys Asp Ala Glu Thr Thr Leu Phe Cys Ala Ser Asp Ala Lys
1               5                   10                  15

Ala Tyr Glu Thr Glu Lys His Asn Val Trp Ala Thr His Ala Cys Val
            20                  25                  30

Pro Thr Asp Pro Asn Pro Gln Glu Ile His Leu Glu Asn Val Thr Glu
        35                  40                  45

Glu Phe Asn Met Trp Lys Asn Asn Met Val Glu Gln Met His Thr Asp
    50                  55                  60

Ile Ile Ser Leu Trp Asp Gln Ser Leu Lys Pro Cys Val Lys Leu Thr
65                  70                  75                  80

Gly Gly Ser Ala Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Thr Gly Pro Cys Pro Ser Val Ser Thr
        115                 120                 125

Val Gln Cys Thr His Gly Ile Lys Pro Val Val Ser Thr Gln Leu Leu
    130                 135                 140

Leu Asn Gly Ser Leu Ala Glu Glu Glu Val Met Ile Arg Ser Glu Asp
145                 150                 155                 160

Phe Arg Asn Asn Ala Lys Asn Ile Leu Val Gln Phe Asn Thr Pro Val
                165                 170                 175

Gln Ile Asn Cys Thr Arg Pro Asn Asn Gly Gly Ser Gly Ser Gly Gly
            180                 185                 190

Asp Ile Arg Gln Ala His Cys Asn Val Ser Lys Ala Thr Trp Asn Glu
        195                 200                 205

Thr Leu Gly Lys Val Val Lys Gln Leu Arg Lys His Tyr Gly Asn Asp
    210                 215                 220

Thr Thr Ile Arg Phe Ala Pro Ser Ser Gly Gly Asp Leu Glu Val Met
225                 230                 235                 240

Asn His Ser Phe Asn Cys Gly Gly Glu Phe Phe Tyr Cys Asn Thr Ser
                245                 250                 255

Gly Leu Phe Asn Ser Thr Trp Ile Ser Asn Thr Ser Val Gln Gly Ser
            260                 265                 270

Asn Ser Thr Gly Ser Asn Asp Ser Ile Thr Leu Pro Cys Arg Ile Lys
        275                 280                 285

Gln Ile Ile Asn Met Trp Gln Arg Ile Gly Gln Ala Met Tyr Ala Pro
    290                 295                 300

Pro Ile Gln Gly Val Ile Arg Cys Val Ser Asn Ile Thr Gly Leu Ile
305                 310                 315                 320

Leu Val Arg Asp Gly Gly Tyr Thr Asn Ser Asn Thr Glu Thr Phe Arg
                325                 330                 335

Pro Gly Gly Gly Asp Met Arg Asp Asn Trp Arg Ser Glu Leu Tyr Lys
            340                 345                 350

Tyr Lys Val Val Lys Ile Glu Pro
        355                 360

<210> SEQ ID NO 177
<211> LENGTH: 172
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 177

```
Gln Ile Ala Gly Thr Val Val Ser Thr Gln Leu Phe Leu Asn Gly Ser
1               5                   10                  15

Leu Ala Glu Glu Glu Val Val Ile Arg Ser Val Asp Phe Arg Asp Asn
            20                  25                  30

Ala Lys Ser Ile Cys Val Gln Leu Asn Thr Ser Val Glu Ile Asn Cys
        35                  40                  45

Thr Gly Ala Cys His Cys Asn Ile Ser Arg Ala Lys Trp Asn Asn Thr
    50                  55                  60

Leu Lys Gln Ile Ala Ser Lys Leu Arg Glu Gln Phe Gly Asn Arg Thr
65                  70                  75                  80

Ile Ile Phe Lys Gln Ser Ser Gly Gly Asp Pro Glu Phe Val Thr His
                85                  90                  95

Ser Phe Asn Cys Gly Gly Glu Phe Phe Tyr Cys Asp Ser Thr Gln Leu
            100                 105                 110

Phe Asn Ser Thr Trp Phe Asn Ser Thr Asp Thr Ile Thr Leu Pro Cys
        115                 120                 125

Arg Pro Ala Pro Pro Pro His Cys Ser Ser Asn Ile Thr Gly Leu Ile
    130                 135                 140

Leu Thr Arg Asp Gly Gly Val Ser Asn Asp Glu Thr Glu Ile Phe Arg
145                 150                 155                 160

Pro Ser Gly Gly Asp Met Arg Asp Ile Ala Arg Cys
                165                 170
```

<210> SEQ ID NO 178
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gln Ile Ala Gly Thr Val Val Ser Thr Gln Leu Phe Leu Asn Gly Ser
1               5                   10                  15

Leu Ala Glu Glu Glu Val Val Ile Arg Ser Glu Asp Trp Arg Asp Asn
            20                  25                  30

Ala Lys Ser Ile Cys Val Gln Leu Asn Thr Ser Val Glu Ile Asn Cys
        35                  40                  45

Thr Gly Ala Cys His Cys Asn Ile Ser Arg Ala Lys Trp Asn Asn Thr
    50                  55                  60

Leu Lys Gln Ile Ala Ser Lys Leu Arg Glu Gln Tyr Gly Asn Lys Thr
65                  70                  75                  80

Ile Ile Phe Lys Pro Ser Ser Gly Gly Asp Pro Glu Phe Val Asn His
                85                  90                  95

Ser Phe Asn Cys Gly Gly Glu Phe Phe Tyr Cys Asp Ser Thr Gln Leu
            100                 105                 110

Phe Asn Ser Thr Trp Phe Asn Ser Thr Asp Thr Ile Thr Leu Pro Cys
        115                 120                 125

Arg Pro Ala Pro Pro Pro His Cys Ser Ser Asn Ile Thr Gly Leu Ile
    130                 135                 140

Leu Thr Arg Gln Gly Gly Tyr Ser Asn Asp Asn Thr Val Ile Phe Arg
145                 150                 155                 160
```

```
Pro Ser Gly Gly Asp Trp Arg Asp Ile Ala Arg Cys
                165                 170


<210> SEQ ID NO 179
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Ser Gly Gly Ser Gly Gly Gly Val
                165                 170                 175

Trp Lys Asp Ala Glu Thr Thr Leu Phe Cys Ala Ser Asp Ala Lys Ala
            180                 185                 190

Tyr Glu Thr Glu Lys His Asn Val Trp Ala Thr His Ala Cys Val Pro
        195                 200                 205

Thr Asp Pro Asn Pro Gln Glu Ile His Leu Glu Asn Val Thr Glu Glu
    210                 215                 220

Phe Asn Met Trp Lys Asn Asn Met Val Glu Gln Met His Thr Asp Ile
225                 230                 235                 240

Ile Ser Leu Trp Asp Gln Ser Leu Lys Pro Cys Val Lys Leu Thr Gly
                245                 250                 255

Gly Ser Ala Ile Thr Gln Ala Cys Pro Lys Val Ser Phe Glu Pro Ile
            260                 265                 270

Pro Ile His Tyr Cys Ala Pro Ala Gly Phe Ala Ile Leu Lys Cys Lys
        275                 280                 285

Asp Lys Lys Phe Asn Gly Thr Gly Pro Cys Pro Ser Val Ser Thr Val
    290                 295                 300

Gln Cys Thr His Gly Ile Lys Pro Val Val Ser Thr Gln Leu Leu Leu
305                 310                 315                 320

Asn Gly Ser Leu Ala Glu Glu Glu Val Met Ile Arg Ser Glu Asp Phe
                325                 330                 335

Arg Asn Asn Ala Lys Asn Ile Leu Val Gln Phe Asn Thr Pro Val Gln
            340                 345                 350
```

```
Ile Asn Cys Thr Arg Pro Asn Asn Gly Gly Ser Gly Ser Gly Gly Asp
        355                 360                 365

Ile Arg Gln Ala His Cys Asn Val Ser Lys Ala Thr Trp Asn Glu Thr
    370                 375                 380

Leu Gly Lys Val Val Lys Gln Leu Arg Lys His Tyr Gly Asn Asp Thr
385                 390                 395                 400

Thr Ile Arg Phe Ala Pro Ser Ser Gly Gly Asp Leu Glu Val Met Asn
                405                 410                 415

His Ser Phe Asn Cys Gly Gly Glu Phe Phe Tyr Cys Asn Thr Ser Gly
            420                 425                 430

Leu Phe Asn Ser Thr Trp Ile Ser Asn Thr Ser Val Gln Gly Ser Asn
        435                 440                 445

Ser Thr Gly Ser Asn Asp Ser Ile Thr Leu Pro Cys Arg Ile Lys Gln
    450                 455                 460

Ile Ile Asn Met Trp Gln Arg Ile Gly Gln Ala Met Tyr Ala Pro Pro
465                 470                 475                 480

Ile Gln Gly Val Ile Arg Cys Val Ser Asn Ile Thr Gly Leu Ile Leu
                485                 490                 495

Val Arg Asp Gly Gly Tyr Thr Asn Ser Asn Thr Glu Thr Phe Arg Pro
            500                 505                 510

Gly Gly Gly Asp Met Arg Asp Asn Trp Arg Ser Glu Leu Tyr Lys Tyr
        515                 520                 525

Lys Val Val Lys Ile Glu Pro
    530                 535
```

<210> SEQ ID NO 180
<211> LENGTH: 154
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 181
<211> LENGTH: 360
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 181

```
Val Trp Lys Glu Ala Thr Thr Thr Leu Phe Cys Ala Ser Asp Ala Lys
1               5                   10                  15

Ala Tyr Asp Thr Glu Val His Asn Val Trp Ala Thr His Ala Cys Val
            20                  25                  30

Pro Thr Asp Pro Asn Pro Gln Glu Val Val Leu Val Asn Val Thr Glu
        35                  40                  45

Asn Phe Asn Trp Cys Lys Asn Asp Met Val Glu Gln Met His Glu Asp
    50                  55                  60

Ile Cys Ser Leu Trp Asp Gln Ser Leu Lys Pro Cys Val Lys Leu Thr
65                  70                  75                  80

Gly Gly Ser Val Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Asn Asn Lys Thr Phe Asn Gly Thr Gly Pro Cys Thr Asn Val Ser Thr
        115                 120                 125

Val Gln Cys Thr His Gly Ile Arg Pro Val Val Ser Ser Gln Leu Leu
    130                 135                 140

Leu Asn Gly Ser Leu Ala Glu Glu Glu Val Val Ile Arg Ser Cys Asn
145                 150                 155                 160

Phe Thr Asp Asn Ala Lys Thr Ile Ile Val Gln Leu Asn Thr Ser Val
                165                 170                 175

Glu Ile Asn Cys Thr Arg Pro Asn Asn Gly Gly Ser Gly Ser Gly Gly
            180                 185                 190

Asn Met Arg Gln Ala His Cys Asn Ile Ser Arg Ala Lys Trp Asn Asn
        195                 200                 205

Thr Leu Lys Gln Ile Ala Ser Lys Leu Arg Glu Gln Phe Gly Asn Asn
    210                 215                 220

Lys Thr Ile Ile Phe Lys Gln Ser Ser Gly Gly Asp Pro Glu Ile Val
225                 230                 235                 240

Thr His Trp Phe Asn Cys Gly Gly Glu Phe Phe Tyr Cys Asn Ser Thr
                245                 250                 255

Gln Leu Phe Asn Ser Thr Trp Phe Asn Ser Thr Trp Ser Thr Glu Gly
            260                 265                 270

Ser Asn Asn Thr Glu Gly Ser Asp Thr Ile Thr Leu Pro Cys Arg Ile
        275                 280                 285

Lys Gln Ile Ile Asn Met Trp Cys Lys Val Gly Lys Met Met Tyr Ala
    290                 295                 300

Pro Pro Ile Ser Gly Gln Ile Arg Cys Ser Ser Asn Ile Thr Gly Leu
305                 310                 315                 320

Leu Leu Thr Arg Asp Gly Gly Asn Ser Asn Asn Glu Ser Glu Ile Phe
                325                 330                 335

Arg Pro Gly Gly Gly Asp Met Arg Asp Asn Trp Arg Ser Glu Leu Tyr
            340                 345                 350

Lys Tyr Lys Val Val Lys Ile Glu
        355                 360
```

<210> SEQ ID NO 182
<211> LENGTH: 359
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Glu Trp Glu Asp Ala Thr Thr Lys Leu Tyr Cys Ala Ser Gln Ala Asp
1               5                   10                  15

Ala Ser Asp Glu Glu Val His Asn Val Trp Ala Thr Asn Ala Cys Val
            20                  25                  30

Pro Thr Asn Pro Glu Pro Asn Thr Thr Val Thr Val Asn Val Thr Val
        35                  40                  45

Thr Phe Asp Trp Cys Lys Asp Asp Met Val Ala Gln Met Asn Thr Asp
    50                  55                  60

Ile Cys Thr Leu Trp Lys Thr Ser Leu Asp Pro Cys Thr Lys Glu Asp
65                  70                  75                  80

Gly Gly Arg Val Ile Val Gln Ala Cys Pro Thr Val Arg Phe Lys Pro
                85                  90                  95

Val Pro Ile Arg Tyr Cys Ala Pro Pro Gly Tyr Ala Ile Leu Lys Cys
            100                 105                 110

Asn Asn Arg Ser Phe Asn Gly Thr Gly Pro Cys Thr Asn Val Ser Val
        115                 120                 125

Val Thr Cys Thr Asp Gly Ile His Pro Val Val Ser Ser Gln Leu Leu
    130                 135                 140

Leu Asn Gly Thr Leu Ala Asp Glu Lys Val Val Ile Arg Ser Cys Asn
145                 150                 155                 160

Phe Ser Asp Asn Ala Lys Thr Ile Ile Val Gln Leu Asn Thr Ser Val
                165                 170                 175

Glu Ile Asn Cys Thr Gly Pro Asn Asp Gly Gly Thr Gly Gly Gly Gly
            180                 185                 190

His Met Arg Gln Gly His Cys Asn Ile Thr Arg Ala Lys Trp Asn Gln
        195                 200                 205

Thr Leu Lys Gln Ile Ala Glu Lys Leu Arg Glu Gln Phe Gly Lys Asn
    210                 215                 220

Lys Thr Ile Ile Phe Arg Pro Ser Ser Gly Gly Asp Pro Glu Ile Val
225                 230                 235                 240

Thr His Trp Phe Asn Cys Gly Gly Lys Phe Phe Tyr Cys Asn Ser Thr
                245                 250                 255

Gln Leu Phe Asn Ser Thr Trp Phe Asn Ser Thr Trp Ser Thr Lys Gly
            260                 265                 270

Ser Asn Asn Thr Glu Gly Ser Asp Thr Ile Thr Leu Pro Cys Arg Ile
        275                 280                 285

Arg Ser Ile Thr Gly Met Val Cys Thr Val Gly Arg Met Ile Tyr Ala
    290                 295                 300

Pro Pro Val Glu Gly Val Ile Thr Cys Ser Ser Asn Ile Thr Gly Leu
305                 310                 315                 320

Leu Leu Thr Arg Asp Gly Gly Asn Asp Asn Asn Glu Ser Glu Ile Phe
                325                 330                 335

Arg Pro Gly Gly Gly Asp Met Arg Asp Asn Trp Arg Ser Glu Leu Tyr
            340                 345                 350

Lys Tyr Arg Val Val Arg Leu
        355
```

<210> SEQ ID NO 183
<211> LENGTH: 121
<212> TYPE: PRT
<213> ORGANISM: Mus sp.

<400> SEQUENCE: 183

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

Arg Gly Thr Pro Val Ile Val Ser Ser
115 120

<210> SEQ ID NO 184
<211> LENGTH: 121
<212> TYPE: PRT
<213> ORGANISM: Mus sp.

<400> SEQUENCE: 184

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 185
<211> LENGTH: 121
<212> TYPE: PRT
<213> ORGANISM: Mus sp.

<400> SEQUENCE: 185

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

```
Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 186
<211> LENGTH: 121
<212> TYPE: PRT
<213> ORGANISM: Mus sp.

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 187
<211> LENGTH: 121
<212> TYPE: PRT
<213> ORGANISM: Mus sp.

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110
```

```
Gln Gly Thr Leu Val Thr Val Ser Ser
        115                 120


<210> SEQ ID NO 188
<211> LENGTH: 121
<212> TYPE: PRT
<213> ORGANISM: Mus sp.

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 189
<211> LENGTH: 121
<212> TYPE: PRT
<213> ORGANISM: Mus sp.

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 190
<211> LENGTH: 121
<212> TYPE: PRT
<213> ORGANISM: Mus sp.

<400> SEQUENCE: 190

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 191
<211> LENGTH: 121
<212> TYPE: PRT
<213> ORGANISM: Mus sp.

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 192
<211> LENGTH: 121
<212> TYPE: PRT
<213> ORGANISM: Mus sp.

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 193
<211> LENGTH: 121
<212> TYPE: PRT
<213> ORGANISM: Mus sp.

<400> SEQUENCE: 193

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 194
<211> LENGTH: 121
<212> TYPE: PRT
<213> ORGANISM: Mus sp.

<400> SEQUENCE: 194

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 195
<211> LENGTH: 121
<212> TYPE: PRT
<213> ORGANISM: Mus sp.

<400> SEQUENCE: 195

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 196
<211> LENGTH: 121
<212> TYPE: PRT
<213> ORGANISM: Mus sp.

<400> SEQUENCE: 196

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 197
<211> LENGTH: 121
<212> TYPE: PRT
<213> ORGANISM: Mus sp.

<400> SEQUENCE: 197

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

-continued

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 198
<211> LENGTH: 121
<212> TYPE: PRT
<213> ORGANISM: Mus sp.

<400> SEQUENCE: 198

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 199
<211> LENGTH: 121
<212> TYPE: PRT
<213> ORGANISM: Mus sp.

<400> SEQUENCE: 199

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met Asn Trp Val Arg Gln Ala Pro Gly Gln Gly Leu Glu Trp Met
35 40 45

Gly Trp Leu Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Val Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 200
<211> LENGTH: 121

<212> TYPE: PRT
<213> ORGANISM: Mus sp.

<400> SEQUENCE: 200

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Met Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 201
<211> LENGTH: 121
<212> TYPE: PRT
<213> ORGANISM: Mus sp.

<400> SEQUENCE: 201

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 202
<211> LENGTH: 121
<212> TYPE: PRT
<213> ORGANISM: Mus sp.

<400> SEQUENCE: 202

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Phe Thr Gly Tyr
20 25 30

Tyr Met Asn Trp Val Arg Gln Ala Pro Gly Gln Gly Leu Glu Trp Met
35 40 45

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 203
<211> LENGTH: 121
<212> TYPE: PRT
<213> ORGANISM: Mus sp.

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 204
<211> LENGTH: 121
<212> TYPE: PRT
<213> ORGANISM: Mus sp.

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 205
<211> LENGTH: 121
<212> TYPE: PRT
<213> ORGANISM: Mus sp.

<400> SEQUENCE: 205

```
Gln Val Gln Leu Val Gln Ser Gly Ala Glu Val Lys Asn Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Phe Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 206
<211> LENGTH: 121
<212> TYPE: PRT
<213> ORGANISM: Mus sp.

<400> SEQUENCE: 206

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Asn
            20                  25                  30

Tyr Met Asn Trp Val Arg Gln Ala Pro Gly Gln Gly Leu Glu Trp Met
        35                  40                  45

Gly Trp Asn Asn Leu Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 207
<211> LENGTH: 121
<212> TYPE: PRT
<213> ORGANISM: Mus sp.

<400> SEQUENCE: 207

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

```
Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 208
<211> LENGTH: 121
<212> TYPE: PRT
<213> ORGANISM: Mus sp.

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 209
<211> LENGTH: 5
<212> TYPE: PRT
<213> ORGANISM: Mus sp.

<400> SEQUENCE: 209

Gln Gln Tyr Glu Phe
1               5


<210> SEQ ID NO 210
<211> LENGTH: 5
<212> TYPE: PRT
<213> ORGANISM: Mus sp.

<400> SEQUENCE: 210

Gln Gln Tyr Glu Phe
1               5


<210> SEQ ID NO 211
<211> LENGTH: 5
<212> TYPE: PRT
<213> ORGANISM: Mus sp.
```

<400> SEQUENCE: 211

Gln Gln Tyr Tyr Ser
1 5

<210> SEQ ID NO 212
<211> LENGTH: 5
<212> TYPE: PRT
<213> ORGANISM: Mus sp.

<400> SEQUENCE: 212

Gln Gln Phe Thr Thr
1 5

<210> SEQ ID NO 213
<211> LENGTH: 5
<212> TYPE: PRT
<213> ORGANISM: Mus sp.

<400> SEQUENCE: 213

Gln Gln Tyr Asn Ser
1 5

<210> SEQ ID NO 214
<211> LENGTH: 5
<212> TYPE: PRT
<213> ORGANISM: Mus sp.

<400> SEQUENCE: 214

Gln Gln Tyr Trp Thr
1 5

<210> SEQ ID NO 215
<211> LENGTH: 5
<212> TYPE: PRT
<213> ORGANISM: Mus sp.

<400> SEQUENCE: 215

Gln Gln Tyr Trp Thr
1 5

<210> SEQ ID NO 216
<211> LENGTH: 5
<212> TYPE: PRT
<213> ORGANISM: Mus sp.

<400> SEQUENCE: 216

Gln Gln Tyr Trp Thr
1 5

<210> SEQ ID NO 217
<211> LENGTH: 5
<212> TYPE: PRT
<213> ORGANISM: Mus sp.

<400> SEQUENCE: 217

Gln Gln Tyr Trp Thr
1 5

<210> SEQ ID NO 218
<211> LENGTH: 5
<212> TYPE: PRT
<213> ORGANISM: Mus sp.

<400> SEQUENCE: 218

Gln Gln Tyr Trp Thr
1 5

<210> SEQ ID NO 219
<211> LENGTH: 5
<212> TYPE: PRT
<213> ORGANISM: Mus sp.

<400> SEQUENCE: 219

Gln Gln Tyr Trp Thr
1 5

<210> SEQ ID NO 220
<211> LENGTH: 5
<212> TYPE: PRT
<213> ORGANISM: Mus sp.

<400> SEQUENCE: 220

Gln Gln Tyr Trp Thr
1 5

<210> SEQ ID NO 221
<211> LENGTH: 5
<212> TYPE: PRT
<213> ORGANISM: Mus sp.

<400> SEQUENCE: 221

Gln Gln Tyr Tyr Thr
1 5

<210> SEQ ID NO 222
<211> LENGTH: 5
<212> TYPE: PRT
<213> ORGANISM: Mus sp.

<400> SEQUENCE: 222

Gln Gln Tyr Tyr Thr
1 5

<210> SEQ ID NO 223
<211> LENGTH: 5
<212> TYPE: PRT
<213> ORGANISM: Mus sp.

<400> SEQUENCE: 223

Gln Gln Tyr Phe Thr
1 5

<210> SEQ ID NO 224
<211> LENGTH: 5
<212> TYPE: PRT
<213> ORGANISM: Mus sp.

<400> SEQUENCE: 224

Gln Gln Tyr Ala Thr
1 5

<210> SEQ ID NO 225
<211> LENGTH: 5
<212> TYPE: PRT
<213> ORGANISM: Mus sp.

<400> SEQUENCE: 225

Gln Gln Tyr His Thr
1 5

<210> SEQ ID NO 226
<211> LENGTH: 5
<212> TYPE: PRT
<213> ORGANISM: Mus sp.

<400> SEQUENCE: 226

Gln Gln Tyr Asn Thr
1 5

<210> SEQ ID NO 227
<211> LENGTH: 5
<212> TYPE: PRT
<213> ORGANISM: Mus sp.

<400> SEQUENCE: 227

Gln Gln Tyr Asn Thr
1 5

<210> SEQ ID NO 228
<211> LENGTH: 5
<212> TYPE: PRT
<213> ORGANISM: Mus sp.

<400> SEQUENCE: 228

Gln Gln Tyr Asn Ser
1 5

<210> SEQ ID NO 229
<211> LENGTH: 5
<212> TYPE: PRT
<213> ORGANISM: Mus sp.

<400> SEQUENCE: 229

Gln Gln Tyr Asn Ser
1 5

<210> SEQ ID NO 230
<211> LENGTH: 5
<212> TYPE: PRT
<213> ORGANISM: Mus sp.

<400> SEQUENCE: 230

Gln Gln Tyr Trp Thr
1 5

<210> SEQ ID NO 231
<211> LENGTH: 5
<212> TYPE: PRT
<213> ORGANISM: Mus sp.

<400> SEQUENCE: 231

Gln Gln Tyr Asp Thr
1 5

<210> SEQ ID NO 232
<211> LENGTH: 5
<212> TYPE: PRT
<213> ORGANISM: Mus sp.

<400> SEQUENCE: 232

Gln Gln Tyr Asp Ser
1               5

<210> SEQ ID NO 233
<211> LENGTH: 5
<212> TYPE: PRT
<213> ORGANISM: Mus sp.

<400> SEQUENCE: 233

Gln Gln Tyr Ser Thr
1               5

<210> SEQ ID NO 234
<211> LENGTH: 5
<212> TYPE: PRT
<213> ORGANISM: Mus sp.

<400> SEQUENCE: 234

Gln Gln Tyr Phe Thr
1               5

<210> SEQ ID NO 235
<211> LENGTH: 121
<212> TYPE: PRT
<213> ORGANISM: Mus sp.

<400> SEQUENCE: 235

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 236
<211> LENGTH: 121
<212> TYPE: PRT
<213> ORGANISM: Mus sp.

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 237
<211> LENGTH: 121
<212> TYPE: PRT
<213> ORGANISM: Mus sp.

<400> SEQUENCE: 237

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Thr Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 238
<211> LENGTH: 121
<212> TYPE: PRT
<213> ORGANISM: Mus sp.

<400> SEQUENCE: 238

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Leu Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Asp Arg Val Thr Met Thr Arg Asp Thr Ser Ile Ser Thr Ala Tyr
65 70 75 80

Met Asp Leu Ser Arg Leu Arg Ser Asp Asp Thr Ala Val Tyr Tyr Cys
85 90 95

Ala Arg Gly Lys Tyr Ser Asp Tyr Asn Trp Asp Phe Gln His Trp Gly
100 105 110

Gln Gly Thr Leu Val Thr Val Ser Ser
115 120

<210> SEQ ID NO 239

<211> LENGTH: 121
<212> TYPE: PRT
<213> ORGANISM: Mus sp.

<400> SEQUENCE: 239

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Ile Ser Asp Tyr Asn Trp Asp Phe Gln His Trp Gly
            100                 105                 110

Gln Gly Thr Leu Val Thr Val Ser Ser
        115                 120
```

<210> SEQ ID NO 240
<211> LENGTH: 121
<212> TYPE: PRT
<213> ORGANISM: Mus sp.

<400> SEQUENCE: 240

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 241
<211> LENGTH: 121
<212> TYPE: PRT
<213> ORGANISM: Mus sp.

<400> SEQUENCE: 241

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

Gly Trp Ile Asn Pro Asn Ser Gly Gly Thr Asn Tyr Ala Gln Lys Phe
    50              55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 242
<211> LENGTH: 121
<212> TYPE: PRT
<213> ORGANISM: Mus sp.

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 243
<211> LENGTH: 121
<212> TYPE: PRT
<213> ORGANISM: Mus sp.

<400> SEQUENCE: 243

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 244
<211> LENGTH: 121
<212> TYPE: PRT
<213> ORGANISM: Mus sp.

<400> SEQUENCE: 244

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 245
<211> LENGTH: 121
<212> TYPE: PRT
<213> ORGANISM: Mus sp.

<400> SEQUENCE: 245

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 246
<211> LENGTH: 121
<212> TYPE: PRT
<213> ORGANISM: Mus sp.

<400> SEQUENCE: 246

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 247
<211> LENGTH: 121
<212> TYPE: PRT
<213> ORGANISM: Mus sp.

<400> SEQUENCE: 247

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 248
<211> LENGTH: 121
<212> TYPE: PRT
<213> ORGANISM: Mus sp.

<400> SEQUENCE: 248

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Val Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

```
Gln Gly Thr Leu Val Thr Val Ser Ser
        115                 120


<210> SEQ ID NO 249
<211> LENGTH: 121
<212> TYPE: PRT
<213> ORGANISM: Mus sp.

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 250
<211> LENGTH: 121
<212> TYPE: PRT
<213> ORGANISM: Mus sp.

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 251
<211> LENGTH: 121
<212> TYPE: PRT
<213> ORGANISM: Mus sp.

<400> SEQUENCE: 251

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 252
<211> LENGTH: 121
<212> TYPE: PRT
<213> ORGANISM: Mus sp.

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 253
<211> LENGTH: 121
<212> TYPE: PRT
<213> ORGANISM: Mus sp.

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 254
<211> LENGTH: 121
<212> TYPE: PRT
<213> ORGANISM: Mus sp.

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 255
<211> LENGTH: 121
<212> TYPE: PRT
<213> ORGANISM: Mus sp.

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 256
<211> LENGTH: 121
<212> TYPE: PRT
<213> ORGANISM: Mus sp.
```

<400> SEQUENCE: 256

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 257
<211> LENGTH: 121
<212> TYPE: PRT
<213> ORGANISM: Mus sp.

<400> SEQUENCE: 257

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 258
<211> LENGTH: 121
<212> TYPE: PRT
<213> ORGANISM: Mus sp.

<400> SEQUENCE: 258

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

-continued

```
Gln Gly Arg Val Thr Met Thr Arg Asp Thr Ser Ile Ser Thr Val Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 259
<211> LENGTH: 121
<212> TYPE: PRT
<213> ORGANISM: Mus sp.

<400> SEQUENCE: 259

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 260
<211> LENGTH: 121
<212> TYPE: PRT
<213> ORGANISM: Mus sp.

<400> SEQUENCE: 260

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 261
<211> LENGTH: 121
```

<212> TYPE: PRT
<213> ORGANISM: Mus sp.

<400> SEQUENCE: 261

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 262
<211> LENGTH: 121
<212> TYPE: PRT
<213> ORGANISM: Mus sp.

<400> SEQUENCE: 262

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 263
<211> LENGTH: 121
<212> TYPE: PRT
<213> ORGANISM: Mus sp.

<400> SEQUENCE: 263

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 264
<211> LENGTH: 5
<212> TYPE: PRT
<213> ORGANISM: Mus sp.

<400> SEQUENCE: 264

Gln Gln Tyr Glu Phe
1               5


<210> SEQ ID NO 265
<211> LENGTH: 5
<212> TYPE: PRT
<213> ORGANISM: Mus sp.

<400> SEQUENCE: 265

Gln Gln Tyr Glu Phe
1               5


<210> SEQ ID NO 266
<211> LENGTH: 5
<212> TYPE: PRT
<213> ORGANISM: Mus sp.

<400> SEQUENCE: 266

Gln Gln Tyr Asp Ser
1               5


<210> SEQ ID NO 267
<211> LENGTH: 5
<212> TYPE: PRT
<213> ORGANISM: Mus sp.

<400> SEQUENCE: 267

Gln Gln Tyr His Ser
1               5


<210> SEQ ID NO 268
<211> LENGTH: 5
<212> TYPE: PRT
<213> ORGANISM: Mus sp.

<400> SEQUENCE: 268

Gln Gln Tyr His Ser
1               5


<210> SEQ ID NO 269
<211> LENGTH: 5
<212> TYPE: PRT
<213> ORGANISM: Mus sp.
```

<400> SEQUENCE: 269

Gln Gln Tyr Glu Thr
1 5

<210> SEQ ID NO 270
<211> LENGTH: 5
<212> TYPE: PRT
<213> ORGANISM: Mus sp.

<400> SEQUENCE: 270

Gln Gln Tyr Asn Ser
1 5

<210> SEQ ID NO 271
<211> LENGTH: 5
<212> TYPE: PRT
<213> ORGANISM: Mus sp.

<400> SEQUENCE: 271

Gln Gln Tyr Tyr Thr
1 5

<210> SEQ ID NO 272
<211> LENGTH: 5
<212> TYPE: PRT
<213> ORGANISM: Mus sp.

<400> SEQUENCE: 272

Gln Gln Tyr Tyr Thr
1 5

<210> SEQ ID NO 273
<211> LENGTH: 5
<212> TYPE: PRT
<213> ORGANISM: Mus sp.

<400> SEQUENCE: 273

Gln Gln Tyr Tyr Thr
1 5

<210> SEQ ID NO 274
<211> LENGTH: 5
<212> TYPE: PRT
<213> ORGANISM: Mus sp.

<400> SEQUENCE: 274

Gln Gln Tyr Trp Thr
1 5

<210> SEQ ID NO 275
<211> LENGTH: 5
<212> TYPE: PRT
<213> ORGANISM: Mus sp.

<400> SEQUENCE: 275

Gln Gln Tyr His Ser
1 5

<210> SEQ ID NO 276
<211> LENGTH: 5
<212> TYPE: PRT
<213> ORGANISM: Mus sp.

<400> SEQUENCE: 276

Gln Gln Tyr Tyr Thr
1 5

<210> SEQ ID NO 277
<211> LENGTH: 5
<212> TYPE: PRT
<213> ORGANISM: Mus sp.

<400> SEQUENCE: 277

Gln Gln Tyr Tyr Thr
1 5

<210> SEQ ID NO 278
<211> LENGTH: 5
<212> TYPE: PRT
<213> ORGANISM: Mus sp.

<400> SEQUENCE: 278

Gln Gln Tyr Tyr Ser
1 5

<210> SEQ ID NO 279
<211> LENGTH: 5
<212> TYPE: PRT
<213> ORGANISM: Mus sp.

<400> SEQUENCE: 279

Gln Gln Tyr Tyr Ser
1 5

<210> SEQ ID NO 280
<211> LENGTH: 5
<212> TYPE: PRT
<213> ORGANISM: Mus sp.

<400> SEQUENCE: 280

Gln Gln Tyr Trp Thr
1 5

<210> SEQ ID NO 281
<211> LENGTH: 5
<212> TYPE: PRT
<213> ORGANISM: Mus sp.

<400> SEQUENCE: 281

Gln Gln Tyr Trp Thr
1 5

<210> SEQ ID NO 282
<211> LENGTH: 5
<212> TYPE: PRT
<213> ORGANISM: Mus sp.

<400> SEQUENCE: 282

Gln Gln Tyr Trp Thr
1 5

<210> SEQ ID NO 283
<211> LENGTH: 5
<212> TYPE: PRT
<213> ORGANISM: Mus sp.

<400> SEQUENCE: 283

Gln Gln Tyr Tyr Thr
1 5

<210> SEQ ID NO 284
<211> LENGTH: 5
<212> TYPE: PRT
<213> ORGANISM: Mus sp.

<400> SEQUENCE: 284

Gln Gln Tyr Asn Thr
1 5

<210> SEQ ID NO 285
<211> LENGTH: 5
<212> TYPE: PRT
<213> ORGANISM: Mus sp.

<400> SEQUENCE: 285

Gln Gln Tyr Tyr Ser
1 5

<210> SEQ ID NO 286
<211> LENGTH: 5
<212> TYPE: PRT
<213> ORGANISM: Mus sp.

<400> SEQUENCE: 286

Gln Gln Tyr Leu Thr
1 5

<210> SEQ ID NO 287
<211> LENGTH: 5
<212> TYPE: PRT
<213> ORGANISM: Mus sp.

<400> SEQUENCE: 287

Gln Gln Tyr Phe Thr
1 5

<210> SEQ ID NO 288
<211> LENGTH: 5
<212> TYPE: PRT
<213> ORGANISM: Mus sp.

<400> SEQUENCE: 288

Gln Gln Tyr His Ser
1 5

<210> SEQ ID NO 289
<211> LENGTH: 5
<212> TYPE: PRT
<213> ORGANISM: Mus sp.

<400> SEQUENCE: 289

Gln Gln Tyr Trp Thr
1 5

<210> SEQ ID NO 290
<211> LENGTH: 5
<212> TYPE: PRT
<213> ORGANISM: Mus sp.

<400> SEQUENCE: 290

Gln Gln Tyr Tyr Thr
1 5

<210> SEQ ID NO 291
<211> LENGTH: 5
<212> TYPE: PRT
<213> ORGANISM: Mus sp.

<400> SEQUENCE: 291

Gln Gln Tyr Tyr Ser
1 5

<210> SEQ ID NO 292
<211> LENGTH: 5
<212> TYPE: PRT
<213> ORGANISM: Mus sp.

<400> SEQUENCE: 292

Gln Gln Tyr Asn Ser
1 5

<210> SEQ ID NO 293
<211> LENGTH: 121
<212> TYPE: PRT
<213> ORGANISM: Mus sp.

<400> SEQUENCE: 293

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

Arg Gly Thr Pro Val Ile Val Ser Ser
115 120

<210> SEQ ID NO 294
<211> LENGTH: 121
<212> TYPE: PRT
<213> ORGANISM: Mus sp.

<400> SEQUENCE: 294

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 295
<211> LENGTH: 121
<212> TYPE: PRT
<213> ORGANISM: Mus sp.

<400> SEQUENCE: 295

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 296
<211> LENGTH: 121
<212> TYPE: PRT
<213> ORGANISM: Mus sp.

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 297
```

<211> LENGTH: 121
<212> TYPE: PRT
<213> ORGANISM: Mus sp.

<400> SEQUENCE: 297

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 298
<211> LENGTH: 121
<212> TYPE: PRT
<213> ORGANISM: Mus sp.

<400> SEQUENCE: 298

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 299
<211> LENGTH: 121
<212> TYPE: PRT
<213> ORGANISM: Mus sp.

<400> SEQUENCE: 299

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 300
<211> LENGTH: 121
<212> TYPE: PRT
<213> ORGANISM: Mus sp.

<400> SEQUENCE: 300

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 301
<211> LENGTH: 121
<212> TYPE: PRT
<213> ORGANISM: Mus sp.

<400> SEQUENCE: 301

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 302
<211> LENGTH: 121
<212> TYPE: PRT
<213> ORGANISM: Mus sp.

<400> SEQUENCE: 302

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 303
<211> LENGTH: 121
<212> TYPE: PRT
<213> ORGANISM: Mus sp.

<400> SEQUENCE: 303

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 304
<211> LENGTH: 121
<212> TYPE: PRT
<213> ORGANISM: Mus sp.

<400> SEQUENCE: 304

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 305
<211> LENGTH: 121
<212> TYPE: PRT
<213> ORGANISM: Mus sp.

<400> SEQUENCE: 305

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 306
<211> LENGTH: 121
<212> TYPE: PRT
<213> ORGANISM: Mus sp.

<400> SEQUENCE: 306

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

-continued

```
Gln Gly Thr Leu Val Thr Val Ser Ser
        115                 120


<210> SEQ ID NO 307
<211> LENGTH: 121
<212> TYPE: PRT
<213> ORGANISM: Mus sp.

<400> SEQUENCE: 307

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 308
<211> LENGTH: 121
<212> TYPE: PRT
<213> ORGANISM: Mus sp.

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 309
<211> LENGTH: 121
<212> TYPE: PRT
<213> ORGANISM: Mus sp.

<400> SEQUENCE: 309

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 310
<211> LENGTH: 121
<212> TYPE: PRT
<213> ORGANISM: Mus sp.

<400> SEQUENCE: 310

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 311
<211> LENGTH: 121
<212> TYPE: PRT
<213> ORGANISM: Mus sp.

<400> SEQUENCE: 311

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 312
<211> LENGTH: 121
<212> TYPE: PRT
<213> ORGANISM: Mus sp.

<400> SEQUENCE: 312

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 313
<211> LENGTH: 121
<212> TYPE: PRT
<213> ORGANISM: Mus sp.

<400> SEQUENCE: 313

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 314
<211> LENGTH: 121
<212> TYPE: PRT
<213> ORGANISM: Mus sp.

<400> SEQUENCE: 314

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Gly Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 315
<211> LENGTH: 5
<212> TYPE: PRT
<213> ORGANISM: Mus sp.

<400> SEQUENCE: 315

Gln Gln Tyr Glu Phe
1 5

<210> SEQ ID NO 316
<211> LENGTH: 5
<212> TYPE: PRT
<213> ORGANISM: Mus sp.

<400> SEQUENCE: 316

Gln Gln Tyr Glu Phe
1 5

<210> SEQ ID NO 317
<211> LENGTH: 5
<212> TYPE: PRT
<213> ORGANISM: Mus sp.

<400> SEQUENCE: 317

Gln Gln Tyr Asp Ser
1 5

<210> SEQ ID NO 318
<211> LENGTH: 5
<212> TYPE: PRT
<213> ORGANISM: Mus sp.

<400> SEQUENCE: 318

Gln Gln Tyr Tyr Ser
1 5

<210> SEQ ID NO 319
<211> LENGTH: 5
<212> TYPE: PRT
<213> ORGANISM: Mus sp.

<400> SEQUENCE: 319

Gln Gln Tyr Tyr Ser
1 5

<210> SEQ ID NO 320
<211> LENGTH: 5
<212> TYPE: PRT
<213> ORGANISM: Mus sp.

<400> SEQUENCE: 320

Gln Gln Tyr Tyr Thr
1 5

<210> SEQ ID NO 321
<211> LENGTH: 5
<212> TYPE: PRT
<213> ORGANISM: Mus sp.

<400> SEQUENCE: 321

Gln Gln Tyr Tyr Ser
1 5

<210> SEQ ID NO 322
<211> LENGTH: 5
<212> TYPE: PRT
<213> ORGANISM: Mus sp.

<400> SEQUENCE: 322

Gln Gln Tyr Trp Thr
1 5

<210> SEQ ID NO 323
<211> LENGTH: 5
<212> TYPE: PRT
<213> ORGANISM: Mus sp.

<400> SEQUENCE: 323

Gln Gln Tyr Asn Thr
1 5

<210> SEQ ID NO 324
<211> LENGTH: 5
<212> TYPE: PRT
<213> ORGANISM: Mus sp.

<400> SEQUENCE: 324

Gln Gln Tyr Tyr Thr
1 5

<210> SEQ ID NO 325
<211> LENGTH: 5
<212> TYPE: PRT
<213> ORGANISM: Mus sp.

<400> SEQUENCE: 325

Cys Gln His Phe Trp
1 5

<210> SEQ ID NO 326
<211> LENGTH: 5
<212> TYPE: PRT
<213> ORGANISM: Mus sp.

<400> SEQUENCE: 326

Gln Gln Tyr Tyr Thr
1               5

<210> SEQ ID NO 327
<211> LENGTH: 5
<212> TYPE: PRT
<213> ORGANISM: Mus sp.

<400> SEQUENCE: 327

Gln Gln Tyr Asn Ser
1               5

<210> SEQ ID NO 328
<211> LENGTH: 5
<212> TYPE: PRT
<213> ORGANISM: Mus sp.

<400> SEQUENCE: 328

Gln Gln Tyr Asn Thr
1               5

<210> SEQ ID NO 329
<211> LENGTH: 5
<212> TYPE: PRT
<213> ORGANISM: Mus sp.

<400> SEQUENCE: 329

Gln Gln Tyr Glu Thr
1               5

<210> SEQ ID NO 330
<211> LENGTH: 5
<212> TYPE: PRT
<213> ORGANISM: Mus sp.

<400> SEQUENCE: 330

Gln Gln Tyr Trp Thr
1               5

<210> SEQ ID NO 331
<211> LENGTH: 5
<212> TYPE: PRT
<213> ORGANISM: Mus sp.

<400> SEQUENCE: 331

Gln Gln Tyr Trp Thr
1               5

<210> SEQ ID NO 332
<211> LENGTH: 5
<212> TYPE: PRT
<213> ORGANISM: Mus sp.

<400> SEQUENCE: 332

Gln Gln Tyr Tyr Thr
1               5

<210> SEQ ID NO 333
<211> LENGTH: 5
<212> TYPE: PRT
<213> ORGANISM: Mus sp.

<400> SEQUENCE: 333

Gln Gln Tyr Tyr Thr
1 5

<210> SEQ ID NO 334
<211> LENGTH: 5
<212> TYPE: PRT
<213> ORGANISM: Mus sp.

<400> SEQUENCE: 334

Gln Gln Tyr Tyr Thr
1 5

<210> SEQ ID NO 335
<211> LENGTH: 5
<212> TYPE: PRT
<213> ORGANISM: Mus sp.

<400> SEQUENCE: 335

Gln Gln Trp Ser Ser
1 5

<210> SEQ ID NO 336
<211> LENGTH: 5
<212> TYPE: PRT
<213> ORGANISM: Mus sp.

<400> SEQUENCE: 336

Gln Gln Tyr Glu Thr
1 5

<210> SEQ ID NO 337
<211> LENGTH: 121
<212> TYPE: PRT
<213> ORGANISM: Mus sp.

<400> SEQUENCE: 337

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

Arg Gly Thr Pro Val Ile Val Ser Ser
115 120

<210> SEQ ID NO 338
<211> LENGTH: 121
<212> TYPE: PRT
<213> ORGANISM: Mus sp.

<400> SEQUENCE: 338

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 339
<211> LENGTH: 121
<212> TYPE: PRT
<213> ORGANISM: Mus sp.

<400> SEQUENCE: 339

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly His Gly Leu Glu Trp Val
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Ser
65 70 75 80

Met Glu Leu Ser Arg Leu Arg Ser Asp Asp Thr Ala Val Tyr Tyr Cys
85 90 95

Ala Arg Gly Lys Asp Ser Asp Tyr Asn Trp Asp Phe Gln His Trp Gly
100 105 110

Gln Gly Thr Leu Val Thr Val Ser Ser
115 120

<210> SEQ ID NO 340
<211> LENGTH: 121
<212> TYPE: PRT
<213> ORGANISM: Mus sp.

<400> SEQUENCE: 340

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Asn
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Val Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 341
<211> LENGTH: 121
<212> TYPE: PRT
<213> ORGANISM: Mus sp.

<400> SEQUENCE: 341

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 342
<211> LENGTH: 121
<212> TYPE: PRT
<213> ORGANISM: Mus sp.

<400> SEQUENCE: 342

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 343

<211> LENGTH: 121
<212> TYPE: PRT
<213> ORGANISM: Mus sp.

<400> SEQUENCE: 343

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 344
<211> LENGTH: 121
<212> TYPE: PRT
<213> ORGANISM: Mus sp.

<400> SEQUENCE: 344

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 345
<211> LENGTH: 121
<212> TYPE: PRT
<213> ORGANISM: Mus sp.

<400> SEQUENCE: 345

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 346
<211> LENGTH: 121
<212> TYPE: PRT
<213> ORGANISM: Mus sp.

<400> SEQUENCE: 346

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 347
<211> LENGTH: 121
<212> TYPE: PRT
<213> ORGANISM: Mus sp.

<400> SEQUENCE: 347

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 348
<211> LENGTH: 121
<212> TYPE: PRT
<213> ORGANISM: Mus sp.

<400> SEQUENCE: 348

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Leu Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 349
<211> LENGTH: 121
<212> TYPE: PRT
<213> ORGANISM: Mus sp.

<400> SEQUENCE: 349

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 350
<211> LENGTH: 121
<212> TYPE: PRT
<213> ORGANISM: Mus sp.

<400> SEQUENCE: 350

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 351
<211> LENGTH: 121
<212> TYPE: PRT
<213> ORGANISM: Mus sp.

<400> SEQUENCE: 351

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Leu Asn Pro Asn Ser Gly Gly Thr Asn Tyr Ala Arg Lys Phe
50 55 60

Gln Asp Arg Val Thr Met Thr Arg Asp Thr Ser Ile Ser Thr Ser Tyr
65 70 75 80

Met Glu Leu Ser Arg Leu Arg Ser Asp Asp Thr Ala Val Tyr Tyr Cys
85 90 95

Ala Arg Gly Lys Ile Ser Asp Tyr Asn Trp Asp Phe Gln His Trp Gly
100 105 110

Gln Gly Thr Leu Val Thr Val Ser Ser
115 120

<210> SEQ ID NO 352
<211> LENGTH: 121
<212> TYPE: PRT
<213> ORGANISM: Mus sp.

<400> SEQUENCE: 352

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

```
Gln Gly Thr Leu Val Thr Val Ser Ser
        115                 120


<210> SEQ ID NO 353
<211> LENGTH: 121
<212> TYPE: PRT
<213> ORGANISM: Mus sp.

<400> SEQUENCE: 353

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 354
<211> LENGTH: 121
<212> TYPE: PRT
<213> ORGANISM: Mus sp.

<400> SEQUENCE: 354

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 355
<211> LENGTH: 121
<212> TYPE: PRT
<213> ORGANISM: Mus sp.

<400> SEQUENCE: 355

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 356
<211> LENGTH: 121
<212> TYPE: PRT
<213> ORGANISM: Mus sp.

<400> SEQUENCE: 356

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Pro Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 357
<211> LENGTH: 121
<212> TYPE: PRT
<213> ORGANISM: Mus sp.

<400> SEQUENCE: 357

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 358
<211> LENGTH: 121
<212> TYPE: PRT
<213> ORGANISM: Mus sp.

<400> SEQUENCE: 358

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 359
<211> LENGTH: 121
<212> TYPE: PRT
<213> ORGANISM: Mus sp.

<400> SEQUENCE: 359

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 360
<211> LENGTH: 121
<212> TYPE: PRT
<213> ORGANISM: Mus sp.
```

<400> SEQUENCE: 360

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 361
<211> LENGTH: 121
<212> TYPE: PRT
<213> ORGANISM: Mus sp.

<400> SEQUENCE: 361

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 362
<211> LENGTH: 121
<212> TYPE: PRT
<213> ORGANISM: Mus sp.

<400> SEQUENCE: 362

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 363
<211> LENGTH: 121
<212> TYPE: PRT
<213> ORGANISM: Mus sp.

<400> SEQUENCE: 363

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 364
<211> LENGTH: 121
<212> TYPE: PRT
<213> ORGANISM: Mus sp.

<400> SEQUENCE: 364

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 365
<211> LENGTH: 121

<212> TYPE: PRT
<213> ORGANISM: Mus sp.

<400> SEQUENCE: 365

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 366
<211> LENGTH: 121
<212> TYPE: PRT
<213> ORGANISM: Mus sp.

<400> SEQUENCE: 366

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 367
<211> LENGTH: 5
<212> TYPE: PRT
<213> ORGANISM: Mus sp.

<400> SEQUENCE: 367

Gln Gln Tyr Glu Phe
1 5

<210> SEQ ID NO 368
<211> LENGTH: 5
<212> TYPE: PRT
<213> ORGANISM: Mus sp.

<400> SEQUENCE: 368

Gln Gln Tyr Glu Phe
1 5

<210> SEQ ID NO 369
<211> LENGTH: 5
<212> TYPE: PRT
<213> ORGANISM: Mus sp.

<400> SEQUENCE: 369

Gln Gln Ser Ser Glu
1 5

<210> SEQ ID NO 370
<211> LENGTH: 5
<212> TYPE: PRT
<213> ORGANISM: Mus sp.

<400> SEQUENCE: 370

Gln Gln Ser Asn Glu
1 5

<210> SEQ ID NO 371
<211> LENGTH: 5
<212> TYPE: PRT
<213> ORGANISM: Mus sp.

<400> SEQUENCE: 371

Gln Gln Tyr His Ser
1 5

<210> SEQ ID NO 372
<211> LENGTH: 9
<212> TYPE: PRT
<213> ORGANISM: Mus sp.

<400> SEQUENCE: 372

Gln Gln His Tyr Ser Thr Pro Pro Thr
1 5

<210> SEQ ID NO 373
<211> LENGTH: 9
<212> TYPE: PRT
<213> ORGANISM: Mus sp.

<400> SEQUENCE: 373

Gln Gln His Tyr Ser Thr Pro Pro Thr
1 5

<210> SEQ ID NO 374
<211> LENGTH: 9
<212> TYPE: PRT
<213> ORGANISM: Mus sp.

<400> SEQUENCE: 374

Gln Gln His Tyr Ser Thr Pro Pro Thr
1 5

<210> SEQ ID NO 375
<211> LENGTH: 5
<212> TYPE: PRT
<213> ORGANISM: Mus sp.

<400> SEQUENCE: 375

Gln Gln Tyr Trp Thr
1 5

<210> SEQ ID NO 376
<211> LENGTH: 5
<212> TYPE: PRT
<213> ORGANISM: Mus sp.

<400> SEQUENCE: 376

Gln Gln Tyr Trp Thr
1 5

<210> SEQ ID NO 377
<211> LENGTH: 5
<212> TYPE: PRT
<213> ORGANISM: Mus sp.

<400> SEQUENCE: 377

Gln Gln Tyr Cys Ser
1 5

<210> SEQ ID NO 378
<211> LENGTH: 5
<212> TYPE: PRT
<213> ORGANISM: Mus sp.

<400> SEQUENCE: 378

Gln Gln Tyr Ser Thr
1 5

<210> SEQ ID NO 379
<211> LENGTH: 5
<212> TYPE: PRT
<213> ORGANISM: Mus sp.

<400> SEQUENCE: 379

Gln Gln Tyr Tyr Thr
1 5

<210> SEQ ID NO 380
<211> LENGTH: 5
<212> TYPE: PRT
<213> ORGANISM: Mus sp.

<400> SEQUENCE: 380

Gln Gln Tyr Tyr Thr
1 5

<210> SEQ ID NO 381
<211> LENGTH: 5
<212> TYPE: PRT
<213> ORGANISM: Mus sp.

<400> SEQUENCE: 381

Gln Gln Tyr Asp Ser
1 5

<210> SEQ ID NO 382
<211> LENGTH: 5
<212> TYPE: PRT
<213> ORGANISM: Mus sp.

<400> SEQUENCE: 382

Gln Gln Tyr Tyr Ser
1 5

<210> SEQ ID NO 383
<211> LENGTH: 5
<212> TYPE: PRT
<213> ORGANISM: Mus sp.

<400> SEQUENCE: 383

Gln Gln Tyr Tyr Thr
1 5

<210> SEQ ID NO 384
<211> LENGTH: 5
<212> TYPE: PRT
<213> ORGANISM: Mus sp.

<400> SEQUENCE: 384

Gln His Phe Trp Thr
1 5

<210> SEQ ID NO 385
<211> LENGTH: 5
<212> TYPE: PRT
<213> ORGANISM: Mus sp.

<400> SEQUENCE: 385

Gln Gln Tyr Asn Thr
1 5

<210> SEQ ID NO 386
<211> LENGTH: 5
<212> TYPE: PRT
<213> ORGANISM: Mus sp.

<400> SEQUENCE: 386

Gln Gln Tyr Phe Thr
1 5

<210> SEQ ID NO 387
<211> LENGTH: 5
<212> TYPE: PRT
<213> ORGANISM: Mus sp.

<400> SEQUENCE: 387

Gln Gln Tyr Ser Thr
1 5

<210> SEQ ID NO 388
<211> LENGTH: 5
<212> TYPE: PRT
<213> ORGANISM: Mus sp.

<400> SEQUENCE: 388

Gln Gln Tyr His Thr
1 5

<210> SEQ ID NO 389
<211> LENGTH: 5
<212> TYPE: PRT
<213> ORGANISM: Mus sp.

<400> SEQUENCE: 389

Gln Gln Tyr Asn Asn
1 5

<210> SEQ ID NO 390
<211> LENGTH: 5
<212> TYPE: PRT
<213> ORGANISM: Mus sp.

<400> SEQUENCE: 390

Gln Gln Tyr Tyr Ser
1 5

<210> SEQ ID NO 391
<211> LENGTH: 5
<212> TYPE: PRT
<213> ORGANISM: Mus sp.

<400> SEQUENCE: 391

Gln Asn Asp Leu Thr
1 5

<210> SEQ ID NO 392
<211> LENGTH: 5
<212> TYPE: PRT
<213> ORGANISM: Mus sp.

<400> SEQUENCE: 392

Gln Gln Tyr Trp Thr
1 5

<210> SEQ ID NO 393
<211> LENGTH: 5
<212> TYPE: PRT
<213> ORGANISM: Mus sp.

<400> SEQUENCE: 393

Gln Gln Tyr Trp Thr
1 5

<210> SEQ ID NO 394
<211> LENGTH: 5
<212> TYPE: PRT
<213> ORGANISM: Mus sp.

<400> SEQUENCE: 394

Gln Gln Tyr Trp Thr
1 5

<210> SEQ ID NO 395
<211> LENGTH: 5
<212> TYPE: PRT
<213> ORGANISM: Mus sp.

<400> SEQUENCE: 395

Gln Gln Tyr Phe Thr
1 5

<210> SEQ ID NO 396
<211> LENGTH: 5
<212> TYPE: PRT
<213> ORGANISM: Mus sp.

<400> SEQUENCE: 396

Gln Gln Tyr Tyr Ser
1               5

<210> SEQ ID NO 397
<211> LENGTH: 121
<212> TYPE: PRT
<213> ORGANISM: Mus sp.

<400> SEQUENCE: 397

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 398
<211> LENGTH: 121
<212> TYPE: PRT
<213> ORGANISM: Mus sp.

<400> SEQUENCE: 398

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 399
<211> LENGTH: 121
<212> TYPE: PRT
<213> ORGANISM: Mus sp.

<400> SEQUENCE: 399

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 400
<211> LENGTH: 121
<212> TYPE: PRT
<213> ORGANISM: Mus sp.

<400> SEQUENCE: 400

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 401
<211> LENGTH: 121
<212> TYPE: PRT
<213> ORGANISM: Mus sp.

<400> SEQUENCE: 401

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Leu Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 402
<211> LENGTH: 121
<212> TYPE: PRT
<213> ORGANISM: Mus sp.

<400> SEQUENCE: 402

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 403
<211> LENGTH: 121
<212> TYPE: PRT
<213> ORGANISM: Mus sp.

<400> SEQUENCE: 403

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 404
<211> LENGTH: 121

<212> TYPE: PRT
<213> ORGANISM: Mus sp.

<400> SEQUENCE: 404

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 405
<211> LENGTH: 121
<212> TYPE: PRT
<213> ORGANISM: Mus sp.

<400> SEQUENCE: 405

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 406
<211> LENGTH: 121
<212> TYPE: PRT
<213> ORGANISM: Mus sp.

<400> SEQUENCE: 406

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Tyr Met Asn Trp Val Arg Gln Ala Pro Gly Gln Gly Leu Glu Trp Met
        35                  40                  45
```

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Lys Asn His Asp Tyr Asn Trp Asp Phe Gln His Trp Gly
            100                 105                 110

Gln Gly Thr Leu Val Thr Val Ser Ser
        115                 120
```

<210> SEQ ID NO 407
<211> LENGTH: 121
<212> TYPE: PRT
<213> ORGANISM: Mus sp.

<400> SEQUENCE: 407

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Val Gln Lys Phe
    50                  55                  60

Gln Gly Arg Val Thr Met Thr Arg Asp Thr Ser Ile Ser Thr Ala Tyr
65                  70                  75                  80

Met Asp Leu Asn Ser Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 408
<211> LENGTH: 121
<212> TYPE: PRT
<213> ORGANISM: Mus sp.

<400> SEQUENCE: 408

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Gln
    50                  55                  60

Gln Gly Arg Val Thr Met Thr Arg Asp Thr Ser Ile Ser Thr Ala Tyr
65                  70                  75                  80

Met Glu Leu Arg Arg Leu Asn Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 409
<211> LENGTH: 121
<212> TYPE: PRT
<213> ORGANISM: Mus sp.

<400> SEQUENCE: 409

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met Asn Trp Val Arg Gln Ala Pro Gly Gln Gly Leu Glu Trp Met
35 40 45

Gly Trp Ile Asn Pro Asn Ser Gly Asp Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 410
<211> LENGTH: 121
<212> TYPE: PRT
<213> ORGANISM: Mus sp.

<400> SEQUENCE: 410

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Leu His Trp Val Arg Gln Ala Pro Gly Gln Gly Leu Glu Trp Met
35 40 45

Gly Trp Ile Asn Pro Asn Ser Ala Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Met Tyr Tyr Cys
85 90 95

Ala Arg Gly Lys Asn Ser Asp Tyr Asn Trp Ala Phe Gln His Trp Gly
100 105 110

Gln Gly Thr Leu Val Thr Val Ser Ser
115 120

<210> SEQ ID NO 411
<211> LENGTH: 121
<212> TYPE: PRT
<213> ORGANISM: Mus sp.

<400> SEQUENCE: 411

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Asn Gly Tyr
20 25 30

```
Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Lys Asn His Asp Tyr Asn Trp Asp Phe Gln His Trp Gly
            100                 105                 110

Gln Gly Thr Leu Val Thr Val Ser Ser
        115                 120


<210> SEQ ID NO 412
<211> LENGTH: 121
<212> TYPE: PRT
<213> ORGANISM: Mus sp.

<400> SEQUENCE: 412

Gln Val Gln Leu Val Gln Ser Gly Ala Glu Val Lys Lys Pro Gly Ala
1               5                   10                  15

Ser Val Lys Val Ser Cys Met Ala Ser Gly Tyr Thr Phe Thr Gly Tyr
            20                  25                  30

Tyr Val Asn Trp Val Arg Gln Ala Pro Gly Gln Gly Leu Glu Trp Met
        35                  40                  45

Gly Trp Ile Asn Pro Asn Ser Gly Gly Thr Asn Tyr Val Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Thr Ser Asp Tyr Asn Trp Asp Phe Gln His Trp Gly
            100                 105                 110

Gln Gly Thr Leu Val Thr Val Ser Ser
        115                 120


<210> SEQ ID NO 413
<211> LENGTH: 121
<212> TYPE: PRT
<213> ORGANISM: Mus sp.

<400> SEQUENCE: 413

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Val Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110
```

Gln Gly Thr Leu Val Thr Val Ser Ser
115 120

<210> SEQ ID NO 414
<211> LENGTH: 121
<212> TYPE: PRT
<213> ORGANISM: Mus sp.

<400> SEQUENCE: 414

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Asn
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 415
<211> LENGTH: 121
<212> TYPE: PRT
<213> ORGANISM: Mus sp.

<400> SEQUENCE: 415

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 416
<211> LENGTH: 121
<212> TYPE: PRT
<213> ORGANISM: Mus sp.

<400> SEQUENCE: 416

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Leu Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 417
<211> LENGTH: 121
<212> TYPE: PRT
<213> ORGANISM: Mus sp.

<400> SEQUENCE: 417

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 418
<211> LENGTH: 121
<212> TYPE: PRT
<213> ORGANISM: Mus sp.

<400> SEQUENCE: 418

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 419
<211> LENGTH: 121
<212> TYPE: PRT
<213> ORGANISM: Mus sp.

<400> SEQUENCE: 419

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 420
<211> LENGTH: 121
<212> TYPE: PRT
<213> ORGANISM: Mus sp.

<400> SEQUENCE: 420

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 421
<211> LENGTH: 121
<212> TYPE: PRT
<213> ORGANISM: Mus sp.
```

<400> SEQUENCE: 421

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 422
<211> LENGTH: 121
<212> TYPE: PRT
<213> ORGANISM: Mus sp.

<400> SEQUENCE: 422

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Ser Val Gln Lys Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 423
<211> LENGTH: 121
<212> TYPE: PRT
<213> ORGANISM: Mus sp.

<400> SEQUENCE: 423

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Gly Tyr
            20                  25                  30

Tyr Leu Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Thr Ser Asp Tyr Asn Trp Asp Phe Gln His Trp Gly
            100                 105                 110

Gln Gly Thr Leu Val Thr Val Ser Ser
        115                 120


<210> SEQ ID NO 424
<211> LENGTH: 121
<212> TYPE: PRT
<213> ORGANISM: Mus sp.

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 425
<211> LENGTH: 121
<212> TYPE: PRT
<213> ORGANISM: Mus sp.

<400> SEQUENCE: 425

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 426
<211> LENGTH: 121
```

<212> TYPE: PRT
<213> ORGANISM: Mus sp.

<400> SEQUENCE: 426

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Thr Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe His His Trp Gly
100 105 110

Gln Gly Thr Leu Val Thr Val Ser Ser
115 120

<210> SEQ ID NO 427
<211> LENGTH: 5
<212> TYPE: PRT
<213> ORGANISM: Mus sp.

<400> SEQUENCE: 427

Gln Gln Tyr Glu Phe
1 5

<210> SEQ ID NO 428
<211> LENGTH: 5
<212> TYPE: PRT
<213> ORGANISM: Mus sp.

<400> SEQUENCE: 428

Gln Gln Tyr Glu Phe
1 5

<210> SEQ ID NO 429
<211> LENGTH: 7
<212> TYPE: PRT
<213> ORGANISM: Mus sp.

<400> SEQUENCE: 429

Gln Gln Ser Asn Glu Asp Thr
1 5

<210> SEQ ID NO 430
<211> LENGTH: 5
<212> TYPE: PRT
<213> ORGANISM: Mus sp.

<400> SEQUENCE: 430

Gln Gln Tyr Asn Ser
1 5

<210> SEQ ID NO 431
<211> LENGTH: 5
<212> TYPE: PRT
<213> ORGANISM: Mus sp.

<400> SEQUENCE: 431

Gln Gln Tyr Ser Thr
1 5

<210> SEQ ID NO 432
<211> LENGTH: 5
<212> TYPE: PRT
<213> ORGANISM: Mus sp.

<400> SEQUENCE: 432

Gln Gln Tyr Tyr Thr
1 5

<210> SEQ ID NO 433
<211> LENGTH: 5
<212> TYPE: PRT
<213> ORGANISM: Mus sp.

<400> SEQUENCE: 433

Gln Gln Tyr Tyr Thr
1 5

<210> SEQ ID NO 434
<211> LENGTH: 5
<212> TYPE: PRT
<213> ORGANISM: Mus sp.

<400> SEQUENCE: 434

Gln Gln Tyr Tyr Thr
1 5

<210> SEQ ID NO 435
<211> LENGTH: 5
<212> TYPE: PRT
<213> ORGANISM: Mus sp.

<400> SEQUENCE: 435

Gln Gln Tyr Tyr Thr
1 5

<210> SEQ ID NO 436
<211> LENGTH: 8
<212> TYPE: PRT
<213> ORGANISM: Mus sp.

<400> SEQUENCE: 436

Leu Gln Tyr Asp Asn Leu Leu Thr
1 5

<210> SEQ ID NO 437
<211> LENGTH: 9
<212> TYPE: PRT
<213> ORGANISM: Mus sp.

<400> SEQUENCE: 437

Gln Gln Trp Ser Ser Lys Pro Leu Thr
1 5

<210> SEQ ID NO 438
<211> LENGTH: 5
<212> TYPE: PRT
<213> ORGANISM: Mus sp.

<400> SEQUENCE: 438

Gln Gln Tyr Asp Thr
1 5

<210> SEQ ID NO 439
<211> LENGTH: 5
<212> TYPE: PRT
<213> ORGANISM: Mus sp.

<400> SEQUENCE: 439

Gln Gln Tyr Asn Thr
1 5

<210> SEQ ID NO 440
<211> LENGTH: 5
<212> TYPE: PRT
<213> ORGANISM: Mus sp.

<400> SEQUENCE: 440

His Gln Tyr His Thr
1 5

<210> SEQ ID NO 441
<211> LENGTH: 5
<212> TYPE: PRT
<213> ORGANISM: Mus sp.

<400> SEQUENCE: 441

Gln Gln Tyr Asp Thr
1 5

<210> SEQ ID NO 442
<211> LENGTH: 5
<212> TYPE: PRT
<213> ORGANISM: Mus sp.

<400> SEQUENCE: 442

Gln Gln Tyr Asp Asn
1 5

<210> SEQ ID NO 443
<211> LENGTH: 5
<212> TYPE: PRT
<213> ORGANISM: Mus sp.

<400> SEQUENCE: 443

Gln Gln Tyr Asp Ser
1 5

<210> SEQ ID NO 444
<211> LENGTH: 5
<212> TYPE: PRT
<213> ORGANISM: Mus sp.

<400> SEQUENCE: 444

Gln Gln Tyr Asp Ser
1 5

<210> SEQ ID NO 445
<211> LENGTH: 5
<212> TYPE: PRT
<213> ORGANISM: Mus sp.

<400> SEQUENCE: 445

Gln Gln Tyr Asp Thr
1 5

<210> SEQ ID NO 446
<211> LENGTH: 5
<212> TYPE: PRT
<213> ORGANISM: Mus sp.

<400> SEQUENCE: 446

Gln Gln Tyr Asp Ser
1 5

<210> SEQ ID NO 447
<211> LENGTH: 5
<212> TYPE: PRT
<213> ORGANISM: Mus sp.

<400> SEQUENCE: 447

Gln Gln Tyr Asp Ser
1 5

<210> SEQ ID NO 448
<211> LENGTH: 5
<212> TYPE: PRT
<213> ORGANISM: Mus sp.

<400> SEQUENCE: 448

Gln Glu Tyr Asp Ser
1 5

<210> SEQ ID NO 449
<211> LENGTH: 5
<212> TYPE: PRT
<213> ORGANISM: Mus sp.

<400> SEQUENCE: 449

Gln Gln Ser Tyr Ser
1 5

<210> SEQ ID NO 450
<211> LENGTH: 5
<212> TYPE: PRT
<213> ORGANISM: Mus sp.

<400> SEQUENCE: 450

Gln Gln Tyr His Thr
1 5

<210> SEQ ID NO 451
<211> LENGTH: 5
<212> TYPE: PRT
<213> ORGANISM: Mus sp.

<400> SEQUENCE: 451

Gln Gln Tyr Asn Thr
1 5

<210> SEQ ID NO 452
<211> LENGTH: 5
<212> TYPE: PRT
<213> ORGANISM: Mus sp.

<400> SEQUENCE: 452

Gln Gln Tyr Asp Glu
1 5

<210> SEQ ID NO 453
<211> LENGTH: 5
<212> TYPE: PRT
<213> ORGANISM: Mus sp.

<400> SEQUENCE: 453

Gln Gln Tyr Asp Ser
1 5

<210> SEQ ID NO 454
<211> LENGTH: 5
<212> TYPE: PRT
<213> ORGANISM: Mus sp.

<400> SEQUENCE: 454

Arg Gln Tyr Tyr Thr
1 5

<210> SEQ ID NO 455
<211> LENGTH: 5
<212> TYPE: PRT
<213> ORGANISM: Mus sp.

<400> SEQUENCE: 455

Gln Gln Tyr Ser Thr
1 5

<210> SEQ ID NO 456
<211> LENGTH: 5
<212> TYPE: PRT
<213> ORGANISM: Mus sp.

<400> SEQUENCE: 456

Gln Gln Tyr Ser Ser
1 5

<210> SEQ ID NO 457
<211> LENGTH: 121
<212> TYPE: PRT
<213> ORGANISM: Mus sp.

<400> SEQUENCE: 457

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

```
Arg Gly Thr Pro Val Ile Val Ser Ser
        115                 120


<210> SEQ ID NO 458
<211> LENGTH: 121
<212> TYPE: PRT
<213> ORGANISM: Mus sp.

<400> SEQUENCE: 458

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 459
<211> LENGTH: 121
<212> TYPE: PRT
<213> ORGANISM: Mus sp.

<400> SEQUENCE: 459

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 460
<211> LENGTH: 121
<212> TYPE: PRT
<213> ORGANISM: Mus sp.

<400> SEQUENCE: 460

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Phe Ile Ser Thr Ala Tyr
65                  70                  75                  80

Met Glu Leu Ser Arg Leu Ile Ser Asp Asp Thr Ala Val Tyr Tyr Cys
                85                  90                  95

Ala Arg Gly Lys Asp Ser Asp Tyr Asn Trp Asp Phe Gln His Trp Gly
            100                 105                 110

Gln Gly Thr Leu Val Thr Val Ser Ser
        115                 120


<210> SEQ ID NO 461
<211> LENGTH: 121
<212> TYPE: PRT
<213> ORGANISM: Mus sp.

<400> SEQUENCE: 461

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu Asn Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 462
<211> LENGTH: 121
<212> TYPE: PRT
<213> ORGANISM: Mus sp.

<400> SEQUENCE: 462

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 463
<211> LENGTH: 121
<212> TYPE: PRT
<213> ORGANISM: Mus sp.

<400> SEQUENCE: 463

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 464
<211> LENGTH: 121
<212> TYPE: PRT
<213> ORGANISM: Mus sp.

<400> SEQUENCE: 464

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Phe Tyr Cys
                85                  90                  95

Ala Arg Gly Lys Asn Ser Asp Tyr Thr Trp Asp Phe Gln His Trp Gly
            100                 105                 110

Gln Gly Thr Leu Val Thr Val Ser Ser
        115                 120


<210> SEQ ID NO 465
<211> LENGTH: 121
<212> TYPE: PRT
<213> ORGANISM: Mus sp
```

<400> SEQUENCE: 465

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 466
<211> LENGTH: 121
<212> TYPE: PRT
<213> ORGANISM: Mus sp.

<400> SEQUENCE: 466

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asp Tyr Ala Gln Lys Phe
    50                  55                  60

Gln Gly Arg Val Thr Met Thr Arg Asp Thr Ser Ile Ser Thr Ala Phe
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 467
<211> LENGTH: 121
<212> TYPE: PRT
<213> ORGANISM: Mus sp.

<400> SEQUENCE: 467

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Val Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 468
<211> LENGTH: 121
<212> TYPE: PRT
<213> ORGANISM: Mus sp.

<400> SEQUENCE: 468

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Val Tyr Ala Gln Lys Phe
50 55 60

Gln Asp Arg Val Thr Met Thr Arg Asp Thr Ser Ile Thr Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 469
<211> LENGTH: 121
<212> TYPE: PRT
<213> ORGANISM: Mus sp.

<400> SEQUENCE: 469

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 470
<211> LENGTH: 121

<212> TYPE: PRT
<213> ORGANISM: Mus sp.

<400> SEQUENCE: 470

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 471
<211> LENGTH: 121
<212> TYPE: PRT
<213> ORGANISM: Mus sp.

<400> SEQUENCE: 471

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 472
<211> LENGTH: 121
<212> TYPE: PRT
<213> ORGANISM: Mus sp.

<400> SEQUENCE: 472

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

```
Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Trp Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 473
<211> LENGTH: 121
<212> TYPE: PRT
<213> ORGANISM: Mus sp.

<400> SEQUENCE: 473

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 474
<211> LENGTH: 121
<212> TYPE: PRT
<213> ORGANISM: Mus sp.

<400> SEQUENCE: 474

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 475
<211> LENGTH: 121
<212> TYPE: PRT
<213> ORGANISM: Mus sp.

<400> SEQUENCE: 475

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Val Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Asp Arg Val Thr Met Thr Arg Asp Thr Ser Ile Ser Thr Ala Tyr
65 70 75 80

Met Glu Leu Asn Arg Leu Thr Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 476
<211> LENGTH: 121
<212> TYPE: PRT
<213> ORGANISM: Mus sp.

<400> SEQUENCE: 476

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Leu Asn Ser Gly Gly Thr Asn Tyr Ala Gln Lys Phe
50 55 60

Gln Gly Arg Val Thr Met Thr Arg Asp Thr Ser Ile Ser Thr Ala Asn
65 70 75 80

Met Glu Leu Ser Trp Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 477
<211> LENGTH: 121
<212> TYPE: PRT
<213> ORGANISM: Mus sp.

<400> SEQUENCE: 477

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 478
<211> LENGTH: 121
<212> TYPE: PRT
<213> ORGANISM: Mus sp.

<400> SEQUENCE: 478

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Asn Arg Leu Thr Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 479
<211> LENGTH: 121
<212> TYPE: PRT
<213> ORGANISM: Mus sp.

<400> SEQUENCE: 479

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Leu Asn Pro Asn Ser Gly Gly Thr Asn Tyr Ala Gln Lys Phe
    50                  55                  60

Gln Gly Arg Val Thr Met Thr Arg Asp Thr Ser Phe Ser Thr Ala Tyr
65                  70                  75                  80

Met Glu Leu Ser Ser Leu Arg Ser Asp Asp Ser Ala Val Tyr Tyr Cys
                85                  90                  95

Ala Arg Gly Lys Thr Ser Asp Tyr Asn Trp Asp Phe Arg His Trp Gly
            100                 105                 110

Gln Gly Thr Leu Val Thr Val Ser Ser
        115                 120
```

<210> SEQ ID NO 480
<211> LENGTH: 121
<212> TYPE: PRT
<213> ORGANISM: Mus sp.

<400> SEQUENCE: 480

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Ala Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 481
<211> LENGTH: 121
<212> TYPE: PRT
<213> ORGANISM: Mus sp.

<400> SEQUENCE: 481

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 482
<211> LENGTH: 5
<212> TYPE: PRT
<213> ORGANISM: Mus sp.

<400> SEQUENCE: 482

Gln Gln Tyr Glu Phe
1 5

<210> SEQ ID NO 483
<211> LENGTH: 5

<212> TYPE: PRT
<213> ORGANISM: Mus sp.

<400> SEQUENCE: 483

Gln Gln Tyr Glu Phe
1               5

<210> SEQ ID NO 484
<211> LENGTH: 8
<212> TYPE: PRT
<213> ORGANISM: Mus sp.

<400> SEQUENCE: 484

Gln Gln Trp Ser Ser Tyr Pro Thr
1               5

<210> SEQ ID NO 485
<211> LENGTH: 5
<212> TYPE: PRT
<213> ORGANISM: Mus sp.

<400> SEQUENCE: 485

Gln Gln Tyr Glu Thr
1               5

<210> SEQ ID NO 486
<211> LENGTH: 5
<212> TYPE: PRT
<213> ORGANISM: Mus sp.

<400> SEQUENCE: 486

Gln Gln Tyr Glu Thr
1               5

<210> SEQ ID NO 487
<211> LENGTH: 5
<212> TYPE: PRT
<213> ORGANISM: Mus sp.

<400> SEQUENCE: 487

Gln Gln Tyr Asn Asn
1               5

<210> SEQ ID NO 488
<211> LENGTH: 5
<212> TYPE: PRT
<213> ORGANISM: Mus sp.

<400> SEQUENCE: 488

Gln Gln Tyr Tyr Arg
1               5

<210> SEQ ID NO 489
<211> LENGTH: 5
<212> TYPE: PRT
<213> ORGANISM: Mus sp.

<400> SEQUENCE: 489

Gln Gln Tyr Glu Ala
1               5

<210> SEQ ID NO 490
<211> LENGTH: 5
<212> TYPE: PRT
<213> ORGANISM: Mus sp.

<400> SEQUENCE: 490

Gln Gln Tyr Trp Thr
1 5

<210> SEQ ID NO 491
<211> LENGTH: 5
<212> TYPE: PRT
<213> ORGANISM: Mus sp.

<400> SEQUENCE: 491

Gln Gln Tyr Ser Ser
1 5

<210> SEQ ID NO 492
<211> LENGTH: 5
<212> TYPE: PRT
<213> ORGANISM: Mus sp.

<400> SEQUENCE: 492

Gln Gln Tyr Ser Thr
1 5

<210> SEQ ID NO 493
<211> LENGTH: 5
<212> TYPE: PRT
<213> ORGANISM: Mus sp.

<400> SEQUENCE: 493

Gln Gln Tyr Tyr Ser
1 5

<210> SEQ ID NO 494
<211> LENGTH: 5
<212> TYPE: PRT
<213> ORGANISM: Mus sp.

<400> SEQUENCE: 494

Gln Gln Tyr Phe Thr
1 5

<210> SEQ ID NO 495
<211> LENGTH: 5
<212> TYPE: PRT
<213> ORGANISM: Mus sp.

<400> SEQUENCE: 495

Gln Gln Tyr Phe Thr
1 5

<210> SEQ ID NO 496
<211> LENGTH: 5
<212> TYPE: PRT
<213> ORGANISM: Mus sp.

<400> SEQUENCE: 496

Gln Gln Tyr Tyr Ser
1 5

<210> SEQ ID NO 497
<211> LENGTH: 5
<212> TYPE: PRT
<213> ORGANISM: Mus sp.

<400> SEQUENCE: 497

Gln Gln Tyr Phe Thr
1 5

<210> SEQ ID NO 498
<211> LENGTH: 5
<212> TYPE: PRT
<213> ORGANISM: Mus sp.

<400> SEQUENCE: 498

Gln Gln Tyr Phe Ser
1 5

<210> SEQ ID NO 499
<211> LENGTH: 5
<212> TYPE: PRT
<213> ORGANISM: Mus sp.

<400> SEQUENCE: 499

Gln Gln Tyr Asp Thr
1 5

<210> SEQ ID NO 500
<211> LENGTH: 5
<212> TYPE: PRT
<213> ORGANISM: Mus sp.

<400> SEQUENCE: 500

Gln Gln Tyr His Ser
1 5

<210> SEQ ID NO 501
<211> LENGTH: 5
<212> TYPE: PRT
<213> ORGANISM: Mus sp.

<400> SEQUENCE: 501

Gln Gln Tyr Trp Thr
1 5

<210> SEQ ID NO 502
<211> LENGTH: 5
<212> TYPE: PRT
<213> ORGANISM: Mus sp.

<400> SEQUENCE: 502

Gln Gln Tyr Leu Thr
1 5

<210> SEQ ID NO 503
<211> LENGTH: 5
<212> TYPE: PRT
<213> ORGANISM: Mus sp.

<400> SEQUENCE: 503

Gln Gln Tyr His Ser
1 5

<210> SEQ ID NO 504
<211> LENGTH: 5
<212> TYPE: PRT
<213> ORGANISM: Mus sp.

<400> SEQUENCE: 504

Gln Gln Tyr Asp Ser
1 5

<210> SEQ ID NO 505
<211> LENGTH: 5
<212> TYPE: PRT
<213> ORGANISM: Mus sp.

<400> SEQUENCE: 505

Gln Gln Tyr Ser Ser
1 5

<210> SEQ ID NO 506
<211> LENGTH: 9
<212> TYPE: PRT
<213> ORGANISM: Mus sp.

<400> SEQUENCE: 506

Leu Gln Tyr Ala Ser Ser Pro Trp Thr
1 5

<210> SEQ ID NO 507
<211> LENGTH: 121
<212> TYPE: PRT
<213> ORGANISM: Mus sp.

<400> SEQUENCE: 507

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

Gly Trp Leu Lys Pro Arg Gly Gly Ala Val Asn Tyr Ala Arg Pro Leu
50 55 60

Gln Gly Arg Val Thr Met Thr Arg Asp Val Tyr Ser Asp Thr Ala Phe
65 70 75 80

Leu Glu Leu Arg Ser Leu Thr Val Asp Asp Thr Ala Val Tyr Phe Cys
85 90 95

Thr Arg Gly Lys Asn Cys Asp Tyr Asn Trp Asp Phe Glu His Trp Gly
100 105 110

Arg Gly Thr Pro Val Ile Val Ser Ser
115 120

<210> SEQ ID NO 508
<211> LENGTH: 121
<212> TYPE: PRT
<213> ORGANISM: Mus sp.

<400> SEQUENCE: 508

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 509
<211> LENGTH: 121
<212> TYPE: PRT
<213> ORGANISM: Mus sp.

<400> SEQUENCE: 509

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 510
<211> LENGTH: 121
<212> TYPE: PRT
<213> ORGANISM: Mus sp.

<400> SEQUENCE: 510

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met Asn Trp Val Arg Gln Gly Pro Gly Gln Gly Leu Glu Trp Met
35 40 45

Gly Trp Ile Asn Pro Asn Ser Gly Gly Thr Asn Tyr Ala Gln Gln Phe
50 55 60

Gln Gly Arg Val Thr Met Thr Arg Asp Thr Ser Ile Ser Thr Ala Tyr
65 70 75 80

Met Glu Leu Ser Arg Leu Thr Ser Asp Asp Thr Ala Val Tyr Tyr Cys
85 90 95

Ala Arg Gly Lys Asp Ser Asp Tyr Asn Trp Asp Phe His His Trp Gly
100 105 110

Gln Gly Thr Leu Val Thr Val Ser Ser
115 120

<210> SEQ ID NO 511

<211> LENGTH: 121
<212> TYPE: PRT
<213> ORGANISM: Mus sp.

<400> SEQUENCE: 511

Gln Val Gln Leu Val Gln Ser Gly Ala Glu Val Lys Lys Pro Gly Ala
1 5 10 15

Ser Val Arg Val Ser Cys Glu Ala Ser Gly Tyr Thr Phe Thr Gly Tyr
20 25 30

Tyr Ile Asn Trp Val Arg Gln Ala Pro Gly Gln Gly Leu Glu Trp Met
35 40 45

Gly Trp Leu Asn Pro Asn Ser Gly Gly Thr Asn Tyr Ala Gln Gln Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 512
<211> LENGTH: 121
<212> TYPE: PRT
<213> ORGANISM: Mus sp.

<400> SEQUENCE: 512

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 513
<211> LENGTH: 121
<212> TYPE: PRT
<213> ORGANISM: Mus sp.

<400> SEQUENCE: 513

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

-continued

```
Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 514
<211> LENGTH: 121
<212> TYPE: PRT
<213> ORGANISM: Mus sp.

<400> SEQUENCE: 514

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 515
<211> LENGTH: 121
<212> TYPE: PRT
<213> ORGANISM: Mus sp.

<400> SEQUENCE: 515

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 516
<211> LENGTH: 121
<212> TYPE: PRT
<213> ORGANISM: Mus sp.

<400> SEQUENCE: 516

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Phe Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Phe Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 517
<211> LENGTH: 121
<212> TYPE: PRT
<213> ORGANISM: Mus sp.

<400> SEQUENCE: 517

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 518
<211> LENGTH: 121
<212> TYPE: PRT
<213> ORGANISM: Mus sp.

<400> SEQUENCE: 518

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 519
<211> LENGTH: 121
<212> TYPE: PRT
<213> ORGANISM: Mus sp.

<400> SEQUENCE: 519

Gln Val Gln Leu Val Gln Ser Gly Thr Glu Val Lys Lys Pro Gly Ala
1 5 10 15

Ser Val Lys Val Ser Cys Lys Ala Ser Ala Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Arg Asn Ser Asp Tyr Asn Trp Asp Phe Gln His Trp Gly
100 105 110

Gln Gly Thr Leu Val Thr Val Ser Ser
115 120

<210> SEQ ID NO 520
<211> LENGTH: 121
<212> TYPE: PRT
<213> ORGANISM: Mus sp.

<400> SEQUENCE: 520

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
        115                 120

<210> SEQ ID NO 521
<211> LENGTH: 121
<212> TYPE: PRT
<213> ORGANISM: Mus sp.

<400> SEQUENCE: 521

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 522
<211> LENGTH: 121
<212> TYPE: PRT
<213> ORGANISM: Mus sp.

<400> SEQUENCE: 522

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 523
<211> LENGTH: 121
<212> TYPE: PRT
<213> ORGANISM: Mus sp.

<400> SEQUENCE: 523

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 524
<211> LENGTH: 121
<212> TYPE: PRT
<213> ORGANISM: Mus sp.

<400> SEQUENCE: 524

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 525
<211> LENGTH: 121
<212> TYPE: PRT
<213> ORGANISM: Mus sp.

<400> SEQUENCE: 525

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Arg Thr Ala Tyr
65                  70                  75                  80

Met Glu Leu Ser Arg Leu Arg Ser Asp Asp Thr Ala Val Arg Tyr Cys
                85                  90                  95
```

-continued

```
Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 526
<211> LENGTH: 5
<212> TYPE: PRT
<213> ORGANISM: Mus sp.

<400> SEQUENCE: 526

Gln Gln Tyr Glu Phe
1               5


<210> SEQ ID NO 527
<211> LENGTH: 5
<212> TYPE: PRT
<213> ORGANISM: Mus sp.

<400> SEQUENCE: 527

Gln Gln Tyr Glu Phe
1               5


<210> SEQ ID NO 528
<211> LENGTH: 5
<212> TYPE: PRT
<213> ORGANISM: Mus sp.

<400> SEQUENCE: 528

Gln His Phe Trp Thr
1               5


<210> SEQ ID NO 529
<211> LENGTH: 5
<212> TYPE: PRT
<213> ORGANISM: Mus sp.

<400> SEQUENCE: 529

Gln Gln Tyr Asp Met
1               5


<210> SEQ ID NO 530
<211> LENGTH: 5
<212> TYPE: PRT
<213> ORGANISM: Mus sp.

<400> SEQUENCE: 530

Gln Gln Tyr Asp Thr
1               5


<210> SEQ ID NO 531
<211> LENGTH: 5
<212> TYPE: PRT
<213> ORGANISM: Mus sp.

<400> SEQUENCE: 531

Gln Gln Tyr Asn Thr
1               5


<210> SEQ ID NO 532
<211> LENGTH: 5
<212> TYPE: PRT
<213> ORGANISM: Mus sp.
```

<400> SEQUENCE: 532

Gln Gln Tyr Asn Thr
1 5

<210> SEQ ID NO 533
<211> LENGTH: 5
<212> TYPE: PRT
<213> ORGANISM: Mus sp.

<400> SEQUENCE: 533

Gln Gln Tyr Tyr Ser
1 5

<210> SEQ ID NO 534
<211> LENGTH: 5
<212> TYPE: PRT
<213> ORGANISM: Mus sp.

<400> SEQUENCE: 534

Gln Gln Leu Tyr Thr
1 5

<210> SEQ ID NO 535
<211> LENGTH: 5
<212> TYPE: PRT
<213> ORGANISM: Mus sp.

<400> SEQUENCE: 535

Gln Gln Tyr Trp Thr
1 5

<210> SEQ ID NO 536
<211> LENGTH: 5
<212> TYPE: PRT
<213> ORGANISM: Mus sp.

<400> SEQUENCE: 536

Gln Gln Tyr Trp Thr
1 5

<210> SEQ ID NO 537
<211> LENGTH: 5
<212> TYPE: PRT
<213> ORGANISM: Mus sp.

<400> SEQUENCE: 537

Gln Gln Tyr Trp Thr
1 5

<210> SEQ ID NO 538
<211> LENGTH: 5
<212> TYPE: PRT
<213> ORGANISM: Mus sp.

<400> SEQUENCE: 538

Gln Gln Tyr Asp Ser
1 5

<210> SEQ ID NO 539
<211> LENGTH: 5
<212> TYPE: PRT
<213> ORGANISM: Mus sp.

<400> SEQUENCE: 539

Gln Gln Tyr Tyr Thr
1 5

<210> SEQ ID NO 540
<211> LENGTH: 5
<212> TYPE: PRT
<213> ORGANISM: Mus sp.

<400> SEQUENCE: 540

Glu Gln Tyr Asp Ser
1 5

<210> SEQ ID NO 541
<211> LENGTH: 5
<212> TYPE: PRT
<213> ORGANISM: Mus sp.

<400> SEQUENCE: 541

Gln Gln Tyr Ser Thr
1 5

<210> SEQ ID NO 542
<211> LENGTH: 5
<212> TYPE: PRT
<213> ORGANISM: Mus sp.

<400> SEQUENCE: 542

Gln Gln Tyr Tyr Lys
1 5

<210> SEQ ID NO 543
<211> LENGTH: 5
<212> TYPE: PRT
<213> ORGANISM: Mus sp.

<400> SEQUENCE: 543

Gln Gln Tyr Tyr Ser
1 5

<210> SEQ ID NO 544
<211> LENGTH: 5
<212> TYPE: PRT
<213> ORGANISM: Mus sp.

<400> SEQUENCE: 544

Gln Gln Tyr Ser Thr
1 5

<210> SEQ ID NO 545
<211> LENGTH: 121
<212> TYPE: PRT
<213> ORGANISM: Mus sp.

<400> SEQUENCE: 545

Gln Val Gln Leu Val Gln Ser Gly Gly Gln Met Lys Lys Pro Gly Glu
1 5 10 15

Ser Met Arg Ile Ser Cys Arg Ala Ser Gly Tyr Glu Phe Ile Asp Cys
20 25 30

Thr Leu Asn Trp Ile Arg Leu Ala Pro Gly Lys Arg Pro Glu Trp Met
35 40 45

```
Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120


<210> SEQ ID NO 546
<211> LENGTH: 121
<212> TYPE: PRT
<213> ORGANISM: Mus sp.

<400> SEQUENCE: 546

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 547
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110
```

Gln Gly Thr Leu Val Thr Val Ser Ser
        115                 120

<210> SEQ ID NO 548
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 549
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 550
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

```
Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 551
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 552
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

```
Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Ala Arg Val Thr Met Ala Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 553
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gln Val Gln Leu Val Gln Ser Gly Ala Glu Val Lys Lys Pro Gly Ala
1               5                   10                  15

Ser Val Lys Val Ser Cys Lys Pro Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 554
<211> LENGTH: 5
<212> TYPE: PRT
<213> ORGANISM: Mus sp.

<400> SEQUENCE: 554

Gln Gln Tyr Glu Phe
1               5


<210> SEQ ID NO 555
<211> LENGTH: 5
<212> TYPE: PRT
<213> ORGANISM: Mus sp.

<400> SEQUENCE: 555

Gln Gln Tyr Glu Phe
1               5
```

<210> SEQ ID NO 556
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 556

Gln Gln Tyr Trp Thr
1 5

<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 557

Gln Gln Asp Tyr Ser Ser Pro Tyr Thr
1 5

<210> SEQ ID NO 558
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 558

Gln Gln Tyr Asp Cys
1 5

<210> SEQ ID NO 559
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 559

Gln Gln Tyr Asn Thr
1 5

<210> SEQ ID NO 560
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 560

Gln Gln Tyr Asp Thr
1 5

<210> SEQ ID NO 561
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 561

Gln Gln Tyr Asp Ser
1 5

<210> SEQ ID NO 562
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Gln Gln Tyr Asp Ser
1 5

<210> SEQ ID NO 563
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 563

Cys Gln Gln Tyr Trp Thr
1 5

<210> SEQ ID NO 564
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 564

Cys Gln Gln Asp Tyr Ser Ser Pro Tyr Thr
1 5 10

<210> SEQ ID NO 565
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 565

Cys Gln Gln Tyr Asp Cys
1 5

<210> SEQ ID NO 566
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 566

Cys Gln Gln Tyr Asn Thr
1 5

<210> SEQ ID NO 567
<211> LENGTH: 6

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 567

Cys Gln Gln Tyr Asp Thr
1 5

<210> SEQ ID NO 568
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 568

Cys Gln Gln Tyr Asp Ser
1 5

<210> SEQ ID NO 569
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 569

Cys Gln Gln Tyr Asp Ser
1 5

<210> SEQ ID NO 570
<211> LENGTH: 121
<212> TYPE: PRT
<213> ORGANISM: Mus sp.

<400> SEQUENCE: 570

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 571
<211> LENGTH: 121
<212> TYPE: PRT
<213> ORGANISM: Mus sp.

<400> SEQUENCE: 571

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Phe Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 572
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120

<210> SEQ ID NO 573
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

-continued

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 574
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 574

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 575
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 575

Gln Val Gln Val Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Phe Ala Gln Lys Phe
50 55 60

Gln Gly Arg Val Thr Met Thr Arg Asp Thr Ser Ile Ser Thr Ala Tyr
65 70 75 80

```
Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 576
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Gly Lys Asn Ser Asp Tyr Asn Trp Asp Phe Gln His Trp Gly
            100                 105                 110

Gln Gly Thr Leu Val Thr Val Ser Ser
        115                 120


<210> SEQ ID NO 577
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Ala Arg Val Thr Met Ala Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Lys Asn Ser Asp Tyr Asn Trp Asp Phe Gln His Trp Gly
            100                 105                 110

Gln Gly Thr Leu Val Thr Val Ser Ser
        115                 120
```

<210> SEQ ID NO 578
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 578

Gln Val Gln Leu Val Gln Ser Gly Ala Glu Val Lys Lys Pro Gly Ala
1 5 10 15

Ser Val Lys Val Ser Cys Lys Pro Ser Gly Tyr Thr Phe Thr Gly Tyr
20 25 30

Tyr Met Asn Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Lys Asn Ser Asp Tyr Asn Trp Asp Phe Gln His Trp Gly
100 105 110

Gln Gly Thr Leu Val Thr Val Ser Ser
115 120

<210> SEQ ID NO 579
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 579

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro
100

<210> SEQ ID NO 580
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 580

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Trp Thr Phe Gly Gly Gly Thr Lys Leu Glu Ile Lys
100 105

<210> SEQ ID NO 581
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 581

Asp Ile Val Met Ser Gln Ser Pro Ser Ser Leu Ala Val Ser Val Gly
1 5 10 15

Glu Arg Val Thr Met Ser Cys Lys Ser Ser Gln Ser Leu Leu Tyr Ser
20 25 30

Thr Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Asp Cys Phe Gly Gly Gly Thr Lys Leu Glu Ile Lys
100 105

<210> SEQ ID NO 582
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 582

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Lys Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Asp Ser Phe Gly Ala Gly Thr Lys Leu Glu Leu Lys
100 105

<210> SEQ ID NO 583
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 583

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu His Ser
20 25 30

Ile Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Asp Thr Phe Gly Gly Gly Thr Lys Leu Glu Ile Lys
100 105

<210> SEQ ID NO 584
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 584

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro
85 90 95

<210> SEQ ID NO 585
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 585

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Thr Phe Gly Ala
                85                  90                  95

Gly Thr Lys Leu Glu Leu Lys
            100
```

<210> SEQ ID NO 586
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 586

```
Asp Ile Val Met Thr Gln Ser Gln Lys Phe Met Ser Thr Ser Ile Gly
1               5                   10                  15

Asp Arg Val Ser Val Thr Cys Lys Ala Ser Gln Asn Val Gly Thr Asn
            20                  25                  30

Val Ala Trp Tyr Gln His Lys Pro Gly Gln Ser Pro Lys Ala Leu Ile
        35                  40                  45

Tyr Ser Thr Ser Tyr Arg Phe Ser Gly Val Pro Asp Arg Phe Thr Gly
    50                  55                  60

Gly Gly Ser Gly Thr Asp Phe Thr Leu Thr Ile Thr Asn Val Gln Ser
65                  70                  75                  80

Glu Asp Leu Ala Lys Tyr Phe Cys Gln Gln Tyr Asp Thr Phe Gly Gly
                85                  90                  95

Gly Thr Lys Leu Glu Ile Lys
            100
```

<210> SEQ ID NO 587
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 587

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60
```

Ser Gly Tyr Gly Thr Asp Phe Thr Phe Thr Ile Ser Thr Val Gln Ala
65 70 75 80

Glu Asp Leu Ala Val Tyr Phe Cys Gln Gln Asp Tyr Ser Ser Pro
85 90 95

<210> SEQ ID NO 588
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 588

Ser Ile Val Met Thr Gln Thr Pro Lys Phe Leu Leu Val Ser Ala Gly
1 5 10 15

Asp Arg Val Thr Ile Thr Cys Lys Ala Ser Gln Ser Val Ser Asn Asp
20 25 30

Val Ala Trp Tyr Gln Gln Lys Pro Gly Gln Ser Pro Lys Leu Leu Ile
35 40 45

Tyr Tyr Ala Ser Asn Arg Tyr Thr Gly Val Pro Asp Arg Phe Thr Gly
50 55 60

Ser Gly Tyr Gly Thr Asp Phe Thr Phe Thr Ile Ser Thr Val Gln Ala
65 70 75 80

Glu Asp Leu Ala Val Tyr Phe Cys Gln Gln Asp Tyr Ser Ser Pro Tyr
85 90 95

Thr Phe Gly Gly Gly Thr Lys Leu Glu Ile Lys
100 105

<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 589

Cys Gln His Phe Trp Gly Thr Pro Trp Thr
1 5 10

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 590

Cys His Gln His Tyr Gly Thr Pro Thr
1 5

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 591

Cys Gly Gln Ser Tyr Ser Tyr Pro Leu Thr
1 5 10

<210> SEQ ID NO 592
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 592

Cys Ala Leu Trp Tyr Ser Thr His Phe Val
1 5 10

<210> SEQ ID NO 593
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 593

Cys Gln Gln Gly Ser Ser Ile Pro Thr
1 5

<210> SEQ ID NO 594
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 594

Cys Gln His Phe Trp Ser Thr Pro Trp Thr
1 5 10

<210> SEQ ID NO 595
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Any amino acid

<400> SEQUENCE: 595

Cys Leu Gln Tyr Xaa Ser Ser Pro Pro Thr
1 5 10

<210> SEQ ID NO 596
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 596

Cys Gln Gln Ser Asn Glu Asp Pro Tyr Thr
1 5 10

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 597

Cys Gln His Phe Trp Ser Thr Pro Arg Ala
1 5 10

<210> SEQ ID NO 598
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 598

Cys Gln His Phe Trp Ser Thr Pro Arg Ala
1 5 10

<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 599

Cys Ser Gln Ser Thr His Val Pro Tyr Thr
1 5 10

<210> SEQ ID NO 600
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 600

Cys Ser Gln Ser Thr His Val Pro Tyr Thr
1 5 10

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 601

Cys His Gln Tyr Ser Tyr Pro Leu Thr
1 5

<210> SEQ ID NO 602
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 602

Cys Gln His His Tyr Gly Thr Pro Tyr Thr
1 5 10

<210> SEQ ID NO 603
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 603

Cys Gln His Phe Trp Gly Thr Pro Tyr Thr
1 5 10

<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 604

Cys Gln His Phe Trp Gly Thr Pro Tyr Thr
1 5 10

<210> SEQ ID NO 605
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 605

Cys His Gln Tyr Leu Ser Tyr Thr
1 5

<210> SEQ ID NO 606
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 606

Cys Gln Asn Asp His Ser Tyr Pro Leu Thr
1 5 10

<210> SEQ ID NO 607
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 607

Cys Gln Asn Asp His Ser Tyr Pro Leu Thr
1 5 10

<210> SEQ ID NO 608
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 608

Cys Gln Asn Asp His Ser Tyr Pro Leu Thr
1 5 10

<210> SEQ ID NO 609
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 609

Cys Gln Asn Asp His Ser Tyr Pro Leu Thr
1 5 10

<210> SEQ ID NO 610
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 610

Cys Gln Asn Asp His Ser Tyr Pro Leu Thr
1 5 10

<210> SEQ ID NO 611
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 611

Cys Gln Asn Asp His Ser Tyr Pro Leu Thr
1 5 10

<210> SEQ ID NO 612
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 612

Cys Gln Asn Asp His Ser Tyr Pro Leu Thr
1 5 10

<210> SEQ ID NO 613
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 613

Cys Gln Asn Asp His Ser Tyr Pro Leu Thr
1 5 10

<210> SEQ ID NO 614
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 614

Cys Gln Asn Asp His Ser Tyr Pro Leu Thr
1 5 10

<210> SEQ ID NO 615
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 615

Cys Gln Gln Ser Asn Glu Asp Pro Tyr Thr
1 5 10

<210> SEQ ID NO 616
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 616

Cys Gln Lys Asn His Arg Tyr Pro Phe Thr
1 5 10

<210> SEQ ID NO 617
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 617

Cys Gln Gln Tyr Tyr Ser Tyr Pro Phe Thr
1 5 10

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 618

Cys Lys Gln Ser Tyr Asn Leu Tyr Thr
1 5

<210> SEQ ID NO 619
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 619

Cys Leu Gln Gly Ser His Val Pro Trp Thr
1 5 10

<210> SEQ ID NO 620
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 620

Cys Phe Gln Gly Ser His Val Pro Tyr Thr
1 5 10

<210> SEQ ID NO 621
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 621

Cys Ala Leu Trp Tyr Ser Asn His Trp Val
1 5 10

<210> SEQ ID NO 622
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 622

Cys Ala Leu Trp Tyr Ser Asn Leu Trp Val
1 5 10

<210> SEQ ID NO 623
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 623

Cys Ala Leu Trp Tyr Ser Asn His Leu Val
1 5 10

<210> SEQ ID NO 624
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 624

Cys Ala Leu Trp Tyr Ser Asn His Leu Val
1 5 10

<210> SEQ ID NO 625
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 625

Cys Ala Leu Trp Tyr Ser Thr His Tyr Val
1 5 10

<210> SEQ ID NO 626
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 626

Cys Ala Leu Trp Tyr Ser Thr His Tyr Val
1 5 10

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 627

Cys Ala Leu Trp Tyr Ser Thr His Tyr Val
1 5 10

<210> SEQ ID NO 628
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 628

Cys Ala Leu Trp Tyr Ser Thr His Tyr Val
1 5 10

<210> SEQ ID NO 629
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 629

Cys Ala Leu Trp Tyr Ser Thr His Tyr Val
1 5 10

<210> SEQ ID NO 630
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 630

Cys Ala Leu Trp Tyr Ser Thr His Tyr Val
1 5 10

<210> SEQ ID NO 631
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

Cys Lys Gln Ser Tyr Asn Leu Tyr Thr
1 5

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 632

Cys Lys Gln Ser Tyr Asn Leu Tyr Thr
1 5

<210> SEQ ID NO 633
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 633

Cys Gln Gln Tyr Asn Arg Phe Gly Ser Gly Thr
1 5 10

<210> SEQ ID NO 634
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 634

Cys Phe Gln Gly Ser His Val Pro Phe Thr
1 5 10

<210> SEQ ID NO 635
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 635

Cys Gln Gln Tyr His Thr
1 5

<210> SEQ ID NO 636
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 636

Cys Gln Gln Tyr Ser Ser Tyr Pro Thr
1 5

<210> SEQ ID NO 637
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 637

Cys Lys Gln Ala Tyr Asp Val Pro Pro Thr
1 5 10

<210> SEQ ID NO 638
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 638

Cys Gln Gln Ser Asn Glu Asp Pro Phe Thr
1 5 10

<210> SEQ ID NO 639
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 639

Cys Ala Leu Trp Tyr Ser Asn His Leu Val
1 5 10

<210> SEQ ID NO 640
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 640

Cys Gln Gln Trp Ser Ser Asn Pro Ile Thr
1 5 10

<210> SEQ ID NO 641
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 641

Cys Ala Leu Trp Tyr Ser Asn His Thr Phe Trp Val
1 5 10

<210> SEQ ID NO 642
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 642

Cys Gln Gln Tyr Asn Ser Tyr Pro Tyr Thr
1 5 10

<210> SEQ ID NO 643
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 643

Cys Ala Leu Trp Tyr Ser Thr His Tyr Val
1 5 10

<210> SEQ ID NO 644
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 644

Cys Gln Gln Asn Asn Glu Asp Leu Thr
1 5

<210> SEQ ID NO 645
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 645

Cys Ala Leu Trp Tyr Ser Asn Thr His Tyr Val
1 5 10

<210> SEQ ID NO 646
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 646

Cys Gln Gln Trp Ser Ser Tyr Pro Pro Thr
1 5 10

<210> SEQ ID NO 647
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 647

Cys Ala Leu Trp Tyr Ser Asn His Trp Val
1 5 10

<210> SEQ ID NO 648
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 648

Cys Ala Leu Trp Tyr Ser Asn His Trp Val
1 5 10

<210> SEQ ID NO 649
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 649

Cys Gln Xaa Gly His Xaa Phe Xaa Phe Thr
1 5 10

<210> SEQ ID NO 650
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 650

Cys Leu Gln His Trp Asn Tyr Pro Trp Thr
1 5 10

<210> SEQ ID NO 651
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 651

Cys Ser Gln Ser Thr His Val Pro Tyr Thr
1 5 10

<210> SEQ ID NO 652
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 652

Cys Leu Gln Tyr Glu Cys Val Phe Thr
1 5

<210> SEQ ID NO 653
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 653

Cys Gln Gln Ser Lys Glu Val Pro Tyr Thr
1 5 10

<210> SEQ ID NO 654
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 654

Cys Ala Leu Trp Tyr Ser Thr His Tyr Val
1 5 10

<210> SEQ ID NO 655
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 655

Cys Gln Gln Asn Ser Ile Ile Pro Arg Thr
1 5 10

<210> SEQ ID NO 656
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 656

Cys Gln Asn Asp His Ser Tyr Pro Leu Thr
1 5 10

<210> SEQ ID NO 657
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 657

Cys Gln Gln Tyr Asn Ser Tyr Pro Leu Thr
1 5 10

<210> SEQ ID NO 658
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 658

Cys Ala Leu Trp Tyr Ser Asn His Trp Val
1 5 10

<210> SEQ ID NO 659
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 659

Cys Gln Gln Ser Asn Glu Asp Pro Leu Thr
1 5 10

<210> SEQ ID NO 660
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 660

Cys Gln Gln Ser Asn Glu Asp Pro Leu Thr
1 5 10

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 661

Cys Lys Gln Ser Tyr Asn Leu Pro Thr
1 5

<210> SEQ ID NO 662
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 662

Cys Gln Asn Asp His Ser Tyr Pro Leu Thr
1 5 10

<210> SEQ ID NO 663
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 663

Cys Gln His His Tyr Gly Thr Pro Pro Thr
1 5 10

<210> SEQ ID NO 664
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 664

Cys Gln Gln His Tyr Ser Thr Pro Leu Thr
1 5 10

<210> SEQ ID NO 665
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 665

Cys Gln Gln His Tyr Ser Thr Pro Leu Thr
1 5 10

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 666

Cys Gln Gln Tyr Ser Ser Tyr Pro Thr
1 5

<210> SEQ ID NO 667
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 667

Cys Lys Gln Ser Tyr Asn Leu Trp Thr
1 5

<210> SEQ ID NO 668
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 668

Cys Gln Gln Trp Ser Ser Asn Pro Pro Met Gly Thr
1 5 10

<210> SEQ ID NO 669
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 669

Cys Gln Gln Arg Ser Ser Tyr Pro Leu Thr
1 5 10

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 670

Cys Leu Gln Tyr Asp Asn Leu Tyr Thr
1 5

<210> SEQ ID NO 671
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 671

Cys Gln His Phe Trp Gly Thr Pro Tyr Thr
1 5 10

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 672

Cys Leu Gln Tyr Asp Asn Leu Leu Thr
1 5

<210> SEQ ID NO 673
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 673

Cys Gln Gln Gly Asn Thr Leu Pro Tyr Thr
1 5 10

<210> SEQ ID NO 674
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Cys Gln Gln Ser Asn Glu Asp Pro Tyr Thr
1               5                   10

<210> SEQ ID NO 675
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Cys Ala Leu Trp Tyr Ser Asn His Leu Val
1               5                   10

<210> SEQ ID NO 676
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Cys Ala Leu Trp Tyr Ser Asn His Leu Val
1               5                   10

<210> SEQ ID NO 677
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Cys Ala Leu Trp Tyr Ser Asn His Leu Val
1               5                   10

<210> SEQ ID NO 678
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Cys Ala Leu Trp Tyr Ser Asn His Leu Val
1               5                   10

<210> SEQ ID NO 679
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Cys Ala Leu Trp Tyr Ser Asn His Trp Val
1 5 10

<210> SEQ ID NO 680
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 680

Cys Ala Leu Trp Tyr Ser Asn His Trp Val
1 5 10

<210> SEQ ID NO 681
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 681

Gln Xaa Xaa Xaa Xaa Xaa Trp Arg Xaa Xaa Xaa Xaa Ile Xaa Xaa Asn
1 5 10 15

<210> SEQ ID NO 682
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 682

Gln Xaa Xaa Val Xaa Xaa Xaa Arg Xaa Xaa Xaa Xaa Ile Xaa Xaa Asn
1 5 10 15

<210> SEQ ID NO 683
<211> LENGTH: 16

<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 683

Gln Xaa Xaa Val Xaa Xaa Xaa Arg Xaa Xaa Xaa Xaa Ile Xaa Xaa Asn
1 5 10 15

<210> SEQ ID NO 684
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 684

Gln Xaa Xaa Xaa Xaa Xaa Xaa Met Xaa Xaa Xaa Xaa Ile Xaa Xaa Asn
1 5 10 15

<210> SEQ ID NO 685
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 685

Gln Tyr Xaa Xaa Xaa Xaa Xaa Xaa Xaa Tyr Xaa Xaa Ile Xaa Xaa Asn
1 5 10 15

<210> SEQ ID NO 686
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 686

```
Gln Tyr Xaa Xaa Xaa Xaa Xaa Xaa Xaa Tyr Xaa Xaa Ile Xaa Xaa Asn
1               5                   10                  15
```

<210> SEQ ID NO 687
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 687

```
Gln Tyr Xaa Xaa Xaa Xaa Xaa Xaa Xaa Tyr Xaa Xaa Ile Xaa Xaa Asn
1               5                   10                  15
```

<210> SEQ ID NO 688
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 688

```
Gln Xaa Xaa Xaa Xaa Xaa Xaa Xaa Xaa Tyr Xaa Xaa Ile Xaa Xaa Asn
1               5                   10                  15
```

<210> SEQ ID NO 689
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 689

Gln Tyr Xaa Xaa Xaa Xaa Xaa Xaa Gln Tyr Xaa Xaa Ile Xaa Xaa Asn
1               5                   10                  15

<210> SEQ ID NO 690
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 690

Gln Tyr Xaa Xaa Ile Trp Xaa Xaa Xaa Tyr Xaa Ile Ile Xaa Xaa Asn
1               5                   10                  15

<210> SEQ ID NO 691
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 691

Gln Xaa Xaa Val Xaa Trp Trp Arg Xaa Tyr Xaa Xaa Ile Xaa Xaa Xaa
1 5 10 15

<210> SEQ ID NO 692
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 692

Gln Tyr Xaa Val Xaa Xaa Xaa Met Xaa Tyr Xaa Xaa Ile Xaa Xaa Xaa
1 5 10 15

<210> SEQ ID NO 693
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 693

Gln Xaa Xaa Xaa Xaa Xaa Xaa Xaa Xaa Xaa Xaa Xaa Ile Xaa Xaa Xaa
1 5 10 15

<210> SEQ ID NO 694
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(6)
<223> OTHER INFORMATION: Any amino acid
<220> FEATURE:

<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 694

Gln Xaa Xaa Xaa Xaa Xaa Trp Xaa Xaa Xaa Xaa Xaa Ile Xaa Xaa Asn
1               5                   10                  15

<210> SEQ ID NO 695
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 695

Gln Xaa Xaa Xaa Xaa Xaa Xaa Xaa Xaa Tyr Xaa Xaa Ile Xaa Xaa Asn
1               5                   10                  15

<210> SEQ ID NO 696
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 696

Gln Tyr Xaa Xaa Xaa Xaa Xaa Xaa Xaa Tyr Xaa Xaa Ile Ala Xaa Asn
1               5                   10                  15

<210> SEQ ID NO 697
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 697

Gln Tyr Xaa Xaa Xaa Xaa Xaa Xaa Xaa Xaa Xaa Xaa Ile Xaa Xaa Xaa
1 5 10 15

<210> SEQ ID NO 698
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 698

Gln Xaa Xaa Val Xaa Xaa Trp Xaa Xaa Xaa Xaa Xaa Ile Xaa Xaa Xaa
1 5 10 15

<210> SEQ ID NO 699
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 699

Cys Ala Arg Ile Tyr Ser Gly Tyr Asp Leu Trp Trp Phe Asp Pro Trp
1 5 10 15

<210> SEQ ID NO 700
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 700

Cys His Gln Phe Gly Thr Phe
1 5

<210> SEQ ID NO 701
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 701

Cys Ala Lys Ile Ser Gly Ser Tyr Ser Phe Asp Tyr Trp
1 5 10

<210> SEQ ID NO 702
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 702

Cys Gln Gln Tyr Tyr Ser Phe
1 5

<210> SEQ ID NO 703
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 703

Cys Ala Arg Met Tyr Asn Trp Asn Asp Val Trp Phe Asp Pro Trp
1 5 10 15

<210> SEQ ID NO 704
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 704

Cys Gln Gln Tyr Ser Thr Phe
1 5

<210> SEQ ID NO 705
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 705

Cys Ala Arg Ala Ser Arg Leu Gly Gly Tyr Phe Gln His Trp
1 5 10

<210> SEQ ID NO 706
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 706

Cys Gln His Gln Glu Thr Phe
1 5

<210> SEQ ID NO 707
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 707

Cys Ala Lys His His Ile Arg Gly Trp Phe Asp Pro Trp
1               5                   10

<210> SEQ ID NO 708
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Cys Gln His Tyr Asn Thr Phe
1               5

<210> SEQ ID NO 709
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Cys Ala Arg Val Asp Tyr Gly Asp Tyr Tyr Gly Ser Trp Tyr Phe Asp
1               5                   10                  15

Leu Trp

<210> SEQ ID NO 710
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Cys Gln Gln Tyr Gly Ser Phe
1               5

<210> SEQ ID NO 711
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Cys Ala Arg Ser Asp Gly Tyr Asn Leu Gly Trp Tyr Phe Asp Leu Trp
1               5                   10                  15

<210> SEQ ID NO 712
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Cys Gln Lys Phe Glu Thr Phe
1               5

<210> SEQ ID NO 713
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 713

Cys Ala Leu Ser Pro Tyr Tyr Asp Ser Ser Gly Tyr Phe Asp Trp
1 5 10 15

<210> SEQ ID NO 714
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 714

Cys Gln Gln Tyr Ala Leu Phe
1 5

<210> SEQ ID NO 715
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 715

Cys Ala Arg Asp Ser Asn Trp Trp Phe Asp Pro Trp
1 5 10

<210> SEQ ID NO 716
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 716

Cys Gln Gln Tyr Gly Thr Phe
1 5

<210> SEQ ID NO 717
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 717

Cys Ala Arg Arg Gln Tyr Cys Ser Gly Gly Ser Cys Leu Tyr Leu Phe
1 5 10 15

Asp Pro Trp

<210> SEQ ID NO 718
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 718

Cys Gln Gln Tyr Tyr Ser Phe
1 5

<210> SEQ ID NO 719
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 719

Cys Ala Ser Lys Val Ala Ala Ala Gly Thr Leu Ala Lys Asp Ala Phe
1 5 10 15

Asp Ile Trp

<210> SEQ ID NO 720
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 720

Cys Gln Gln Tyr Ile Thr Phe
1 5

<210> SEQ ID NO 721
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 721

Cys Ala Arg Ala Ala Ile Ala Ala Ala Tyr Phe Arg Asp Pro Trp
1 5 10 15

<210> SEQ ID NO 722
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 722

Cys Gln Ile Glu Tyr Thr Phe
1 5

<210> SEQ ID NO 723
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 723

Cys Ala Arg Arg Gly Leu Leu Gly Arg Gly Tyr Ser Gly Tyr Asp Arg
1 5 10 15

Met Gly Tyr Tyr Tyr Tyr Tyr Gly Met Asp Val Trp
20 25

<210> SEQ ID NO 724
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 724

Cys Met Gln Gly Asp Thr Phe
1 5

<210> SEQ ID NO 725
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 725

Cys Ala Arg Pro Thr Glu Tyr Ser Ser Ser Trp Tyr Trp Phe Asp Pro
1 5 10 15

Trp

<210> SEQ ID NO 726
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 726

Cys Gln Gln Tyr Asn Ser Phe
1 5

<210> SEQ ID NO 727
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 727

Cys Ala Arg Asp His Gln Gly His Ser Ser Ser Trp Ser Lys Arg Phe
1 5 10 15

Asp Tyr Trp

<210> SEQ ID NO 728
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 728

Cys Gln Gln Tyr Asp Leu Phe
1 5

<210> SEQ ID NO 729
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 729

```
Cys Ala Arg Val Ile Arg Ser Ser Ser Ser Trp Arg Tyr Asp Tyr Trp
1               5                   10                  15
```

<210> SEQ ID NO 730
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 730

```
Cys Gln Gln Tyr Glu Thr Phe
1               5
```

<210> SEQ ID NO 731
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 731

```
Cys Ala Arg Val Arg Tyr Gly Ser Trp Thr Gly Tyr Tyr Phe Asp Tyr
1               5                   10                  15

Trp
```

<210> SEQ ID NO 732
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 732

```
Cys Gln Gln Tyr Glu Thr Phe
1               5
```

<210> SEQ ID NO 733
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 733

```
Cys Ala Arg Val Pro Tyr Asp Phe Trp Ser Gly Tyr Tyr Val Leu Ser
1               5                   10                  15

His Phe Asp Tyr Trp
            20
```

<210> SEQ ID NO 734
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 734

Cys Gln Gln Tyr Glu Thr Phe
1 5

<210> SEQ ID NO 735
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 735

Cys Ala Arg Leu Val Gly Ala Thr Gly Thr Ser Glu Asp Tyr Trp
1 5 10 15

<210> SEQ ID NO 736
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 736

Cys Gln Gln Trp Gly Thr Phe
1 5

<210> SEQ ID NO 737
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 737

Cys Ala Arg Glu Gly Arg Gly Tyr Ser Thr Gly Ala Tyr Phe Asp Tyr
1 5 10 15

Trp

<210> SEQ ID NO 738
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 738

Cys Gln Gln Leu Asn Ser Phe
1 5

<210> SEQ ID NO 739
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 739

Cys Ala Arg Pro Pro Gly Pro Ala Val Ala Gly Arg Tyr Asn Trp Trp
1               5                   10                  15

Phe Asp Pro Trp
            20

<210> SEQ ID NO 740
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 740

Cys Gln Gln Tyr Gly Thr Phe
1               5

<210> SEQ ID NO 741
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 741

Cys Ala Arg Gly Ser Arg Ala Thr Trp Ile Gln Leu His Trp
1               5                   10

<210> SEQ ID NO 742
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 742

Cys Gln Gln Tyr Asn Thr Phe
1               5

<210> SEQ ID NO 743
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 743

Cys Ala Arg Val Gly Glu Gln Leu Val Leu Asn Asp Ala Phe Asp Ile
1               5                   10                  15

Trp

<210> SEQ ID NO 744
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 744

Cys Gln Gln Tyr Asn Lys Phe
1 5

<210> SEQ ID NO 745
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 745

Cys Ala Arg Asp Leu Thr Glu Val Thr Thr Pro Pro Pro Trp
1 5 10

<210> SEQ ID NO 746
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 746

Cys Gln Gln Tyr Asn Thr Phe
1 5

<210> SEQ ID NO 747
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 747

Cys Gln Gln Leu Ser Thr Phe
1 5

<210> SEQ ID NO 748
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 748

Cys Gln Gln Tyr Gly Ser Phe
1 5

<210> SEQ ID NO 749
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 749

Met Gln Ile Tyr Glu Gly Lys Leu Thr Ala Glu Gly Leu Arg Phe Gly
1 5 10 15

Ile Val Ala Ser Arg Phe Asn His Ala Leu Val Asp Arg Leu Val Glu
20 25 30

```
Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340
```

<210> SEQ ID NO 750
<211> LENGTH: 334
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 750

```
Met Gln Ile Tyr Glu Gly Lys Leu Thr Ala Glu Gly Leu Arg Phe Gly
1               5                   10                  15

Ile Val Ala Ser Arg Asn His Ala Leu Val Asp Arg Leu Val Glu Gly
            20                  25                  30

Ala Ile Asp Ala Ile Val Arg His Gly Gly Arg Glu Glu Asp Ile Thr
        35                  40                  45
```

Leu Val Arg Val Gly Ser Trp Glu Ile Pro Val Ala Ala Gly Glu Leu
50 55 60

Ala Arg Lys Glu Asp Ile Asp Ala Val Ile Ala Ile Gly Val Leu Arg
65 70 75 80

Gly Ala Thr Pro Phe Asp Tyr Ile Ala Ser Glu Val Ser Lys Gly Leu
85 90 95

Ala Asp Leu Ser Leu Glu Leu Arg Lys Pro Ile Thr Phe Gly Val Ile
100 105 110

Thr Ala Asp Thr Leu Glu Gln Ala Ile Glu Ala Gly Thr His Gly Asn
115 120 125

Lys Gly Trp Glu Ala Ala Leu Ala Ile Glu Met Ala Asn Leu Phe Lys
130 135 140

Ser Leu Arg Gly Gly Ser Gly Gly Ser Gly Gly Ser Gly Gly Ser Gly
145 150 155 160

Gly Gly Asp Thr Ile Thr Leu Pro Cys Arg Pro Ala Pro Pro Pro His
165 170 175

Cys Ser Ser Asn Ile Thr Gly Leu Ile Leu Thr Arg Gln Gly Gly Tyr
180 185 190

Ser Asn Asp Asn Thr Val Ile Phe Arg Pro Ser Gly Gly Asp Trp Arg
195 200 205

Asp Ile Ala Arg Cys Gln Ile Ala Gly Thr Val Val Ser Thr Gln Leu
210 215 220

Phe Leu Asn Gly Ser Leu Ala Glu Glu Glu Val Val Ile Arg Ser Glu
225 230 235 240

Asp Trp Arg Asp Asn Ala Lys Ser Ile Cys Val Gln Leu Asn Thr Ser
245 250 255

Val Glu Ile Asn Cys Thr Gly Ala Gly His Cys Asn Ile Ser Arg Ala
260 265 270

Lys Trp Asn Asn Thr Leu Lys Gln Ile Ala Ser Lys Leu Arg Glu Gln
275 280 285

Tyr Gly Asn Lys Thr Ile Ile Phe Lys Pro Ser Ser Gly Gly Asp Pro
290 295 300

Glu Phe Val Asn His Ser Phe Asn Cys Gly Gly Glu Phe Phe Tyr Cys
305 310 315 320

Asp Ser Thr Gln Leu Phe Asn Ser Thr Trp Phe Asn Ser Thr
325 330

<210> SEQ ID NO 751
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 751

Met Gln Ile Tyr Glu Gly Lys Leu Thr Ala Glu Gly Leu Arg Phe Gly
1 5 10 15

Ile Val Ala Ser Arg Ala Asn His Ala Leu Val Asp Arg Leu Val Glu
20 25 30

Gly Ala Ile Asp Ala Ile Val Arg His Gly Gly Arg Glu Glu Asp Ile
35 40 45

Thr Leu Val Arg Val Cys Gly Ser Trp Glu Ile Pro Val Ala Ala Gly
50 55 60

```
Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Gln Gly Gly Tyr Ser Asn Asp Asn Thr Val Ile Phe Arg
        195                 200                 205

Pro Ser Gly Gly Asp Trp Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Glu Asp Trp Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Tyr Gly Asn Lys Thr Ile Ile Phe Lys
    290                 295                 300

Pro Ser Ser Gly Gly Asp Pro Glu Phe Val Asn His Ser Phe Asn Cys
305                 310                 315                 320

Gly Gly Glu Phe Phe Tyr Cys Asp Ser Thr Gln Leu Phe Asn Ser Thr
                325                 330                 335

Trp Phe Asn Ser Thr
            340


<210> SEQ ID NO 752
<211> LENGTH: 14
<212> TYPE: PRT
<213> ORGANISM: Homo sapiens

<400> SEQUENCE: 752

Phe Gln His Trp Gly Gln Gly Thr Leu Val Thr Val Ser Ser
1               5                   10


<210> SEQ ID NO 753
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 753

Met Gln Ile Tyr Glu Gly Lys Leu Thr Ala Glu Gly Leu Arg Phe Gly
1               5                   10                  15
```

-continued

```
Ile Val Ala Ser Arg Ala Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Cys Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Cys Arg Gly Ala Thr Pro Ser Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Ala Ala
        115                 120                 125

Gly Thr Cys His Gly Asn Lys Gly Trp Glu Ala Ala Leu Cys Ala Ile
    130                 135                 140

Glu Met Ala Asn Leu Phe Lys Ser Leu Arg Gly Gly Ser Gly Gly Ser
145                 150                 155                 160

Gly Gly Ser Gly Gly Ser Gly Gly Gly Asp Thr Ile Thr Leu Pro Cys
                165                 170                 175

Arg Pro Ala Pro Pro Pro His Cys Ser Ser Asn Ile Thr Gly Leu Ile
            180                 185                 190

Leu Thr Arg Asp Gly Gly Val Ser Asn Asp Glu Thr Glu Ile Phe Arg
        195                 200                 205

Pro Ser Gly Gly Asp Met Arg Asp Ile Ala Arg Cys Gln Ile Ala Gly
    210                 215                 220

Thr Val Val Ser Thr Gln Leu Phe Leu Asn Gly Ser Leu Ala Glu Glu
225                 230                 235                 240

Glu Val Val Ile Arg Ser Val Asp Phe Arg Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Arg Thr Ile Ile Phe Lys
    290                 295                 300

Gln Ser Ser Gly Gly Asp Pro Glu Phe Val Thr His Ser Phe Asn Cys
305                 310                 315                 320

Gly Gly Glu Phe Phe Tyr Cys Asp Ser Thr
                325                 330
```

ENGINEERED OUTER DOMAIN (EOD) OF HIV GP120, MUTANTS AND USE THEREOF

RELATED APPLICATIONS AND INCORPORATION BY REFERENCE

This application is a continuation-in-part of International Patent Application Serial No. PCT/US2016/038162 filed Jun. 17, 2016 which published as PCT Publication No. WO 2016/205704 on Dec. 22, 2016, claims priority and benefit of U.S. provisional application Ser. No. 62/181,147 filed Jun. 17, 2015.

Reference is made to international patent application Ser. No. PCT/US2012/060062 filed Oct. 12, 2012 and published on Apr. 18, 2013 as WO2013/056122, and Ser. No. PCT/US2012/044,996 filed Jun. 29, 2012 and published on Jan. 3, 2013 as WO2013/003752. Reference is also made to applicants disclosure entitled "HIV-1 broadly neutralizing antibody precursor B cells revealed by germline-targeting immunogen" (Jardine et al., Science. 2016 Mar. 25; 351 (6280):1458-63. doi: 10.1126/science.aad9195).

The foregoing applications, and all documents cited therein ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT OF GOVERNMENT LICENSE RIGHTS

This invention was made with government support under grant numbers AI073148, AI081625, and AI100663 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 20, 2016, is named 43094_99_2037_SL.txt and is 564,266 bytes in size.

FIELD OF THE INVENTION

The invention relates to an engineered outer domain (eOD) of HIV gp120 and mutants thereof and methods of making and using the same.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally encoded membrane proteins (Abbas et al., Cellular and Molecular Immunology, 4th edition, W.B. Saunders Company, 2,000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2,000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Viruses have evolved a variety of mechanisms to escape antibody recognition, many of which involve features of the viral surface proteins, such as high variability, steric occlusion, and glycan coating. For HIV, the dense shield of glycans that decorate the viral Env protein was once believed to be refractory to antibody recognition, shielding conserved protein epitopes of important functional significance whose greater exposure would result in increased susceptibility to antibody neutralization.

The outer domain (OD) of human immunodeficiency virus (HIV)-1 gp120 represents an attractive, if difficult, target for a beneficial immune response to HIV infection. Unlike the entire gp120, the OD is structurally stable and contains the surfaces that interact with both the primary and secondary cellular receptors. The primary strain-specific neutralizing target, the V3 loop, lies within the OD, as do epitopes for two cross-reactive neutralizing monoclonal antibodies (mAbs), b12 and 2G12, and the contact sites for a number of inhibitory lectins. The OD is poorly immunogenic, at least in the context of complete gp120, but purposeful OD immunization can lead to a substantial antibody response.

An effective vaccine against HIV has not been generated despite its identification more than 30 years ago. An effective HIV vaccine most likely will need to elicit antibodies capable of neutralizing the majority of the diverse strains circulating in the population. A minority of HIV infected individuals eventually do develop such bnAbs, but generally only after years of protracted viral/antibody co-evolution (1, 2). Although they fail to control virus in the individuals themselves, passive transfer of recombinant forms of such bnAbs can prevent infection in animal models (3-8). Hence, there is an expectation that successful elicitation of bnAbs by vaccination prior to infection will be protective in humans, and developing such a bnAb-based vaccine is a major research goal.

The CD4 binding site (CD4bs) antibody VRC01 (9) and other VRC01-class bnAbs identified in at least seven different donors represent a response with distinguishing features that might be amenable to reproducible vaccine elicitation (10-15). In particular, VRC01-class bnAbs share a mode of binding that uses the immunoglobulin heavy (H) chain variable (V) gene segment VH1-2*02 to mimic CD4, in contrast to many antibodies that rely on the CDRH3 loop (10, 14, 16). The VH1-2*02 gene or suitable alternative alleles are present in ~96% of humans (17), and these genes are employed frequently, in ~3% of all human antibodies (18, 19), suggesting that the B cell precursors for a VRC01-class response are generally available for vaccine targeting.

However, several key challenges must be met to induce VRC01-class bnAbs. First, as is true for some but not all classes of HIV bnAbs, the predicted germline precursors of VRC01-class bnAbs lack detectable affinity for native HIV Envelope glycoproteins (Env) (10, 12, 17, 20-22). Therefore, "germline-targeting" immunogens capable of binding and activating VRC01-class precursor B cells in vitro were designed (17, 21). Whether these immunogens can activate precursors in vivo is an open question. Second, VRC01-class bnAbs carry light (L) chains with unusually short CDRL3s composed of 5 amino acid (aa) residues, typically within a CQQYEFF motif (SEQ ID NO: 62) (14, 16). The short CDRL3 length is required to avoid clashing with gp120 Env loop D and V5, and amino acids within this motif make specific interactions to stabilize the antibody and to contact gp120 (10, 14, 16). CDRL3s with this length occur in only 0.6-1% of human kappa antibodies (14, 16) and in 0.1% of mouse kappa antibodies, and the specific amino acid requirements will reduce the frequency of useful light chains further. Therefore, a germline-targeting immunogen must be capable of activating relatively rare VRC01-class precursors in the repertoire. Third, VRC01-class bnAbs, like most other HIV bnAbs, are heavily somatically mutated, as a result of chronic stimulation of B cells by successive HIV variants (9, 11, 12, 23). While engineering approaches can be used to develop less mutated bnAbs (24, 25), it is unknown whether vaccine induction can induce relatively high mutation levels. This may be achieved by a sequence of different immunogens that successively returns B cells to germinal centers to undergo repeated rounds of affinity maturation (1, 10, 11, 17, 21, 26-29). In this view, each immunogen in the sequence, while naturally inducing antibodies of increasing affinity to itself, must induce maturation in memory B cells that enables weak binding to the next immunogen in the sequence.

Thus, there is a need for germline precursor immunogens capable of activating relatively rare precursors on the pathway to producing bnAbs and boosting immunogens capable of enhancing affinity maturation.

Citation or identification of any document in this application is not an admission that such document is available as prior art to the present invention.

SUMMARY OF THE INVENTION

A major goal of HIV-1 vaccine research is the design of immunogens capable of inducing broadly neutralizing antibodies (bnAbs) that bind to the viral envelope glycoprotein (Env). Poor binding of Env to unmutated precursors of bnAbs, including those of the VRC01-class, appears to be a major problem for bnAb induction. Applicants have engineered novel OD immunogens, eOD-GT8 and eOD-GT10, that bind to VRC01-class bnAb precursors and that exhibit major improved characteristics over previously described OD immunogens.

Applicants immunized novel knock-in mice expressing germline-reverted VRC01 heavy chains with the OD immunogens and induced antibodies that showed characteristics of VRC01-class bnAbs, including a short light chain complementarity determining region 3 (CDRL3) and mutations that favored binding to near-native HIV-1 gp120 constructs. In contrast, native-like immunogens failed to activate VRC01-class precursors. The results show for the first time that rational epitope design can prime rare B cell precursors for affinity maturation to desired targets. Thus, Applicants have shown in an unprecedented way that germline precursors can be expanded by priming with novel engineered immunogens directed to the precursors and this results in the generation of mutations leading to broadly neutralizing antibodies recognizing HIV Env.

Another objective of the present invention is to provide for methods of determining germline precursors, engineering immunogens to expand specific precursors and priming with the engineered immunogens. Applicants show for the first time that a germline-targeting prime can activate VRC01-class precursors, and induce mutations that enable binding to more native-like boost immunogens, which themselves have no detectable affinity for the precursors.

Another objective of the present invention is to provide for a vaccination strategy comprising priming germline precursors with eOD immunogens. The vaccination strategy may also include boosting with HIV Env epitopes after priming of germline precursors.

Applicants employed deep mutational scanning and multi-target optimization to develop germline-targeting immunogens (eOD-GT8 and eOD-GT10) for diverse VRC01-class bnAbs. Applicants then used eOD-GT8 to isolate VRC01-class precursor naïve B cells from HIV-uninfected donors. Frequencies of true VRC01-class precursors, their structures, and their eOD-GT8 affinities support this immunogen as a candidate human vaccine prime. These methods can be applied to germline targeting for other classes of HIV bnAbs and for Abs to other pathogens.

In one aspect, the present invention provides for a non-naturally occurring protein comprising an engineered outer domain (eOD) with at least 90% homology or identity with SEQ ID NO: 10 (eOD-GT8) or 11 (eOD-GT10). The eOD may have at least 95% homology or identity with SEQ ID NO: 10 (eOD-GT8) or 11 (eOD-GT10). The present invention relates to proteins with 70, 75, 80, 85, 90, 91, 92, 93, 94 95, 96, 97 or 98, 99% similarity to eOD-GT8 or eOD-GT10.

In another aspect, the present invention provides for a non-naturally occurring protein comprising an engineered outer domain (eOD), wherein the protein comprises any one of SEQ ID NO: 10 to 40 or any combination thereof.

In another aspect, the present invention provides for a non-naturally occurring protein comprising an eOD variant comprising at least one mutation relative to eOD (=c1d1) in the eOD variants in this section listed below, in both eOD numbering (left column) and HxB2 numbering (right column), wherein the HxB2 numbering uniquely defines a position in any HIV Env sequence once it has been aligned to the HxB2 sequence, wherein the mutation is selected from the table consisting of:

| mut_count | eOD_numbering | HxB2_numbering |
|---|---|---|
| (a) mutations to go from eOD_VH1-2_v6.0 to eOD-GT8.1 | | |
| 1 | D27Q | D457Q |
| 2 | V30Y | V460Y |
| 3 | E34N | E464N |
| 4 | E36V | E466V |
| 5 | M45W | M475W |
| 6 | V78E | V275E |
| 7 | F80W | F277W |
| 8 | F127Y | F353Y |
| 9 | R131K | R357K |
| 10 | Q137P | Q363P |
| 11 | T147N | T373N |
| (b) mutations to go from eOD_VH1-2_v6.0 to eOD-GT10.8 | | |
| 1 | D27Q | D457Q |
| 2 | V30W | V460W |
| 3 | E34N | E464N |
| 4 | E36V | E466V |
| 5 | G42A | G472A |
| 6 | M45W | M475W |
| 7 | V78R | V275R |
| 8 | F80W | F277W |
| 9 | F127Y | F353Y |
| 10 | R131K | R357K |
| 11 | I133V | I359V |
| 12 | K136A | K362A |
| 13 | Q137P | Q363P |
| 14 | T147N | T373N |
| (c) mutations to go from eOD-GT8.1 to eOD-GT10.8 | | |
| 1 | Y30W | Y460W |
| 2 | G42A | G472A |
| 3 | E78R | E275R |

-continued

| mut_count | eOD_numbering | HxB2_numbering |
|---|---|---|
| 4 | I133V | I359V |
| 5 | K136A | K362A |

or any combination thereof.

In another aspect, the present invention provides for a non-naturally occurring protein capable of binding to VRC01-class antibodies comprising a HIV gp120-derived variant in which the position in the HIV Env reference strain HxB2 is given, the corresponding position in eOD is given, wherein at least one mutation is selected from the table consisting of:

| HxB2_Position | eOD_Position | AA |
|---|---|---|
| 455 | 25 | VAL |
| 457 | 27 | GLN |
| 460 | 30 | ARG |
| 460 | 30 | ASN |
| 460 | 30 | GLN |
| 460 | 30 | GLY |
| 460 | 30 | HIS |
| 460 | 30 | LEU |
| 460 | 30 | MET |
| 460 | 30 | PHE |
| 460 | 30 | PRO |
| 460 | 30 | TYR |
| 461 | 31 | MET |
| 461 | 31 | TRP |
| 462 | 32 | ASP |
| 462 | 32 | CYS |
| 462 | 32 | GLN |
| 462 | 32 | GLU |
| 462 | 32 | ILE |
| 462 | 32 | LEU |
| 462 | 32 | LYS |
| 462 | 32 | PHE |
| 462 | 32 | THR |
| 462 | 32 | TRP |
| 462 | 32 | TYR |
| 462 | 32 | VAL |
| 463 | 33 | GLU |
| 465 | 35 | ALA |
| 465 | 35 | GLN |
| 465 | 35 | MET |
| 465 | 35 | TRP |
| 466 | 36 | ALA |
| 466 | 36 | ILE |
| 466 | 36 | LEU |
| 466 | 36 | MET |
| 466 | 36 | PHE |
| 466 | 36 | TYR |
| 466 | 36 | VAL |
| 467 | 37 | VAL |
| 471 | 41 | ALA |
| 472 | 42 | ALA |
| 472 | 42 | TRP |
| 473 | 43 | ALA |
| 473 | 43 | ASP |
| 473 | 43 | GLN |
| 473 | 43 | GLU |
| 473 | 43 | HIS |
| 473 | 43 | MET |
| 473 | 43 | SER |
| 473 | 43 | TRP |
| 473 | 43 | TYR |
| 475 | 45 | ARG |
| 475 | 45 | ASP |
| 475 | 45 | GLN |
| 475 | 45 | GLU |
| 475 | 45 | GLY |
| 475 | 45 | HIS |
| 475 | 45 | ILE |
| 475 | 45 | LEU |
| 475 | 45 | MET |

-continued

| HxB2_Position | eOD_Position | AA |
|---|---|---|
| 475 | 45 | PHE |
| 475 | 45 | PRO |
| 475 | 45 | THR |
| 475 | 45 | TYR |
| 475 | 45 | VAL |
| 476 | 46 | ALA |
| 476 | 46 | ASP |
| 476 | 46 | GLN |
| 476 | 46 | GLU |
| 476 | 46 | THR |
| 476 | 46 | TYR |
| 478 | 48 | GLU |
| 478 | 48 | LEU |
| 478 | 48 | MET |
| 478 | 48 | TRP |
| 479 | 49 | ASP |
| 479 | 49 | GLU |
| 479 | 49 | TYR |
| 480 | 50 | ALA |
| 480 | 50 | ASN |
| 480 | 50 | ASP |
| 480 | 50 | GLN |
| 480 | 50 | GLU |
| 480 | 50 | HIS |
| 480 | 50 | LYS |
| 480 | 50 | MET |
| 480 | 50 | PHE |
| 480 | 50 | SER |
| 480 | 50 | THR |
| 480 | 50 | TYR |
| 480 | 50 | VAL |
| 275 | 78 | ALA |
| 275 | 78 | ARG |
| 275 | 78 | ASN |
| 275 | 78 | ASP |
| 275 | 78 | GLN |
| 275 | 78 | GLY |
| 275 | 78 | HIS |
| 275 | 78 | LYS |
| 275 | 78 | PRO |
| 275 | 78 | SER |
| 275 | 78 | THR |
| 275 | 78 | VAL |
| 277 | 80 | TRP |
| 278 | 81 | HIS |
| 278 | 81 | MET |
| 279 | 82 | ASN |
| 281 | 84 | SER |
| 352 | 126 | ARG |
| 352 | 126 | HIS |
| 352 | 126 | ILE |
| 352 | 126 | LYS |
| 352 | 126 | PRO |
| 352 | 126 | VAL |
| 353 | 127 | TYR |
| 355 | 129 | GLN |
| 355 | 129 | GLU |
| 355 | 129 | PRO |
| 360 | 133 | ALA |
| 360 | 133 | GLN |
| 360 | 133 | GLU |
| 360 | 133 | LYS |
| 360 | 133 | MET |
| 360 | 133 | SER |
| 360 | 133 | THR |
| 360 | 133 | TRP |
| 362 | 135 | ASP |
| 362 | 135 | GLU |
| 362 | 135 | SER |
| 363 | 136 | GLU |
| 363 | 136 | PRO |
| 365 | 138 | ASN |
| 369 | 142 | LEU |
| 369 | 142 | MET |
| 369 | 142 | TRP |
| 369 | 142 | TYR |
| 372 | 145 | ALA |

-continued

| HxB2_Position | eOD_Position | AA |
|---|---|---|
| 373 | 146 | ALA |
| 373 | 146 | ASN |
| 373 | 146 | HIS |
| 373 | 146 | MET |
| 373 | 146 | SER |

The gp120-derived molecule may be an eOD variant and the selected mutations may provide for favorable binding to at least three VRC01-class broadly neutralizing antibodies. The mutations selected may be from 1 to 10 of the mutations.

In another aspect, the present invention provides for a monomeric protein comprising an engineered outer domain (eOD), wherein the protein comprises any one of SEQ ID NO: 10 (eOD-GT8) or 11 (eOD-GT10). The protein may further comprise a tag for purification or biotinylation. The tag for purification may be a his tag. The tag for biotinylation may be an avi-tag. The protein may further comprise an additional cysteine, whereby the cysteine is configured for chemical conjugation. The present invention relates to eOD-GT8 and eOD-GT10 as monomeric proteins, with or without any standard tags for purification (e.g. histag) or biotinylation (e.g. avi-tag), or with an additional cysteine to be used for chemical conjugation purposes.

In another aspect, the present invention provides for a protein comprising SEQ ID NO: 10 (eOD-GT8) or 11 (eOD-GT10) fused to a multimerization motif. The protein may be a 3mer or 60mer.

In another aspect, the present invention provides for a protein comprising an eOD 60mer selected from the group consisting of SEQ ID NO: 2 (eOD-GT6), 10 (eOD-GT8) or 11 (eOD-GT10) fused to a lumazine synthase protein, wherein the lumazine synthase protein may comprise “d4”, “d41”, or “d44” disulfide bonds; and/or “m1”, “m2”, or “m3” mutations. The lumazine synthase protein may comprise “d4”, “d41”, or “d44” disulfide bonds. The lumazine synthase protein may comprise “m1”, “m2”, or “m3” mutations.

The present invention relates to eOD-GT8_3mer, eOD_GT10_3mer, eOD-GT8_60mer, eOD-GT10_60mer, as well as genetic fusions of eOD-GT8 or eOD-GT10 to any other multimerization motif.

The present invention relates to the “d4”, “d41”, and “d44” disulfide bonds in eOD-GT6_60mer, eOD-GT8_60mer, and eOD_GT10_60mer.

The present invention relates to the “m1”, “m2”, and “m3” mutations in the eOD-GT6_60mer, eOD-GT8_60mer, and eOD GT10_60mer, with or without the “d4”, “d41”, and “d44” disulfide bonds.

The invention also encompasses a protein having at least 90% homology or identity with the sequence of the protein of any one of the eOD mutants disclosed herein. The invention also encompasses a protein having at least 95% homology or identity with the sequence of the protein of any one of the eODs disclosed herein.

The invention also encompasses any nucleic acid encoding the protein of any one of the eODs disclosed herein. The invention also encompasses a nucleic acid having at least 90% or 95% homology or identity with the sequence of said nucleic acid.

In another aspect, the present invention provides for methods for eliciting an immune response which may comprise systemically administering to an animal in need thereof an effective amount of the protein of any one of the eODs disclosed herein. The animal may be a mammal, advantageously a human. The animal in need thereof may be at risk for HIV infection and an effective amount of the protein is administered prophylactically. Not being bound by a theory, activating germline precursor B cells with an eOD described herein may provide protection against infection with HIV similar to how broadly neutralizing antibodies prevent infection in animal models.

In certain embodiments, the method for eliciting an immune response may comprise priming with any one of the eODs disclosed herein followed by boosting with at least one boost protein, wherein the boost protein is an HIV immunogen. The priming protein may be a 60mer. The priming protein may be an eOD-GT8 or eOD-GT10 60mer. The 60mer may be selected from the group consisting of SEQ ID NOs: 12-21 and 23-31. The at least one boost protein may be selected from the group consisting of BG505 GT3 SOSIP, BG505 core-GT3 60mer, BG505 SOSIP N276D trimer, BG505 SOSIP N276D, and core-e-2CC N276D 60mer. The method may comprise at least one boost and the first boost may comprise BG505 GT3 SOSIP, BG505 core-GT3 60mer, or core-e-2CC N276D 60mer. In preferred embodiments, the first boost may comprise core-e-2CC N276D 60mer. The method may comprise more than one boost and any boost following the first boost may comprise BG505 SOSIP N276D trimer or BG505 SOSIP N276D. In certain embodiments, the second boost may comprise BG505 SOSIP N276D trimer or BG505 SOSIP N276D. In preferred embodiments, the second boost may comprise BG505 SOSIP N276D. The at least one boost protein may also be selected from the group consisting of BG505 GT3 SOSIP, BG505 core-GT3 60mer, BG505 SOSIP N276D trimer, BG505 SOSIP N276D, and core-e-2CC N276D 60mer or may be selected from the group consisting of SEQ ID NO:41 and SEQ ID NO: 43-54. The method may comprise at least one boost and the first boost comprises BG505 GT3 SOSIP, BG505 core-GT3 60mer, or core-e-2CC N276D 60mer. The first boost may comprise core-e-2CC N276D 60mer, SEQ ID NO: 44, or SEQ ID NO: 45. The 60mer may further comprise "d4", "d41", or "d44" disulfide bonds; and/or "m1", "m2", or "m3" mutations. The 60mer may comprise "d4", "d41", or "d44" disulfide bonds. The 60mer may comprise "m1", "m2", or "m3" mutations. The method may comprise more than one boost and any boost following the first boost may comprise a HIV SOSIP immunogen, whereby the boost comprises a native like immunogen. Any boost following the first boost may comprise an HIV SOSIP N276D trimer or HIV SOSIP N276D. Any boost following the first boost may comprise BG505 SOSIP N276D trimer or BG505 SOSIP N276D. The second boost may comprise BG505 SOSIP N276D trimer or BG505 SOSIP N276D. The second boost may comprise BG505 SOSIP N276D. Any boost following the second boost may comprise an HIV SOSIP immunogen that includes the N276 glycan. Any boost following the second boost may comprise BG505 SOSIP trimer or BG505 SOSIP. Not being bound by a theory, a vaccination strategy that includes priming with eOD-GT8 or eOD-GT10 60mer followed by a first boost with core-e-2CC N276D 60mer, and followed by a second boost with BG505 SOSIP N276D results in activation of rare precursor B cells and subsequent maturation on the pathway to produce broadly neutralizing antibodies against HIV. Not being bound by a theory, subsequent boosts with native like trimers, including trimers with the N276 glycan may be required to further mature the response to induce broadly neutralizing antibodies against HIV.

In another aspect, the present invention provides for novel boost immunogens that unexpectedly function in combination with the eOD immunogens of the present invention to elicit antibodies on the pathway to fully mature broadly neutralizing antibodies. The boost immunogens may be any non-naturally occurring protein comprising an HIV boosting molecule with at least 90% homology or identity with BG505 GT3 SOSIP, BG505 core-GT3 60mer, BG505 SOSIP N276D trimer, BG505 SOSIP N276D or core-e-2CC N276D 60mer.

In another aspect, the present invention provides for a knock-in mouse for testing immunogens capable of activating germline precursors of VRC01 class antibodies. The mouse may advantageously comprise a substitution of the VRC01 gH VDJ exon, wherein the CDRH3 comprises a mutation to remove an unpaired cysteine.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of", and "consists essentially of", have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

Figure 1A:
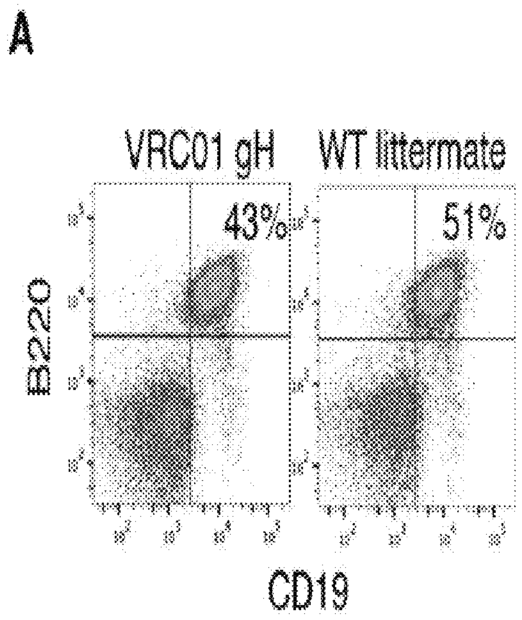
FIG. 1A-D depicts the generation of VRC01 gH mice and an outline of priming experiments. (A) Flow cytometry analysis of spleen cells showing B cell frequencies in VRC01 gH mice and WT littermates. (B) Next-generation sequencing of splenic cDNA from VRC01 gH mice revealed VH1-2*02 usage compared to mouse VH gene usage. (C)
Figure 1B:
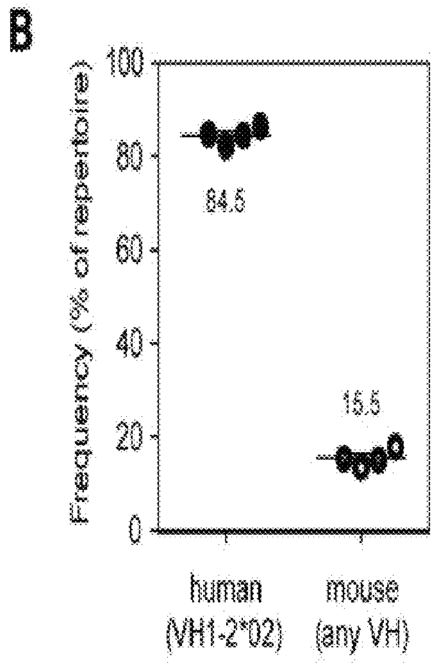

Summary of the time course for experiments and analysis. Mice were given a single prime of immunogen in adjuvant and then serum immune responses were evaluated at days 14, 28, and 42 post-immunization. Two of five mice per group were sacrificed for B cell sorting analysis at day 14, and the remaining three of five mice were sacrificed at day 42. In other animals, splenic B cells were collected at day 5, day 10, or day 31 for hybridoma generation. (D) Overview of the immunization groups listed by immunogen (eOD-GT8 60mer, eOD-GT8 3mer, eOD17 60mer, and BG505 SOSIP), multimeric state (nanoparticle or trimer), and adjuvant (Alum, Iscomatrix, and Ribi), along with the number of mice used to test each group. All groups were tested in both VRC01 gH and wild-type (WT) mice, except for BG505 SOSIP which was tested only in VRC01 gH mice. 5 mice per group were used for B cell sorting and/or ELISA, and an additional 13 VRC01 gH mice were employed for hybridoma generation after immunization with eOD-GT8 60mer (6 for Alum, 7 for Ribi).

Figure 1C:
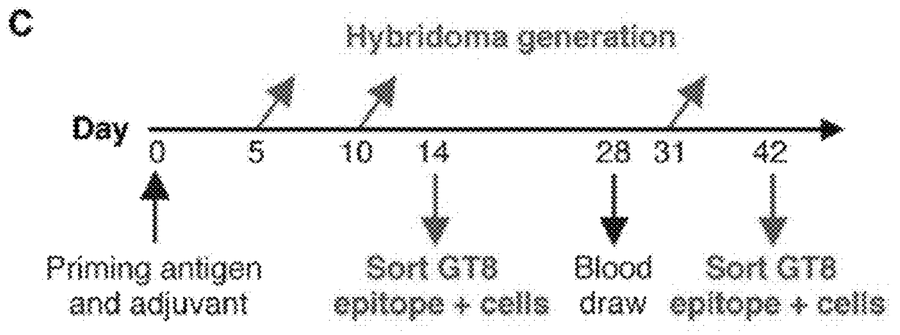
Figures 1D, 2A:
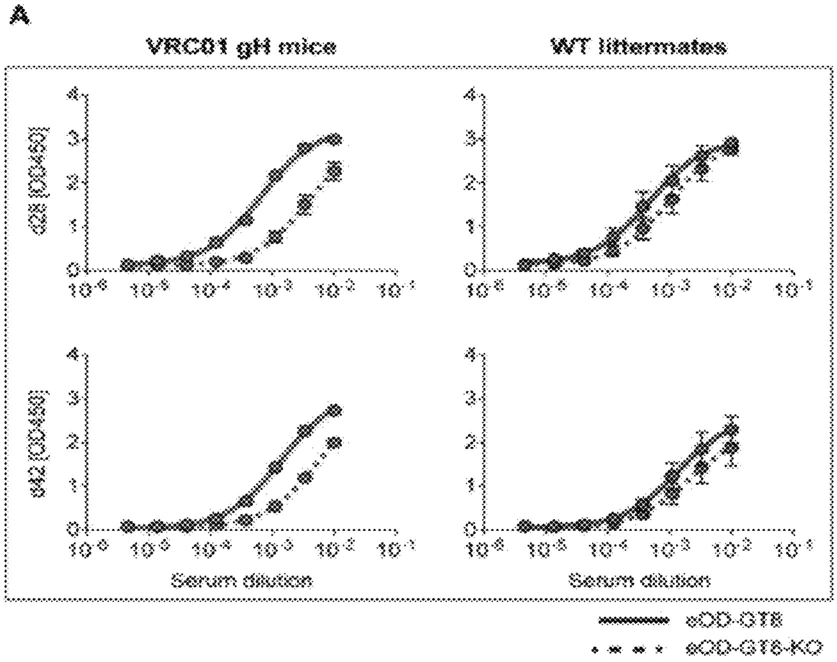
Figure 2B:
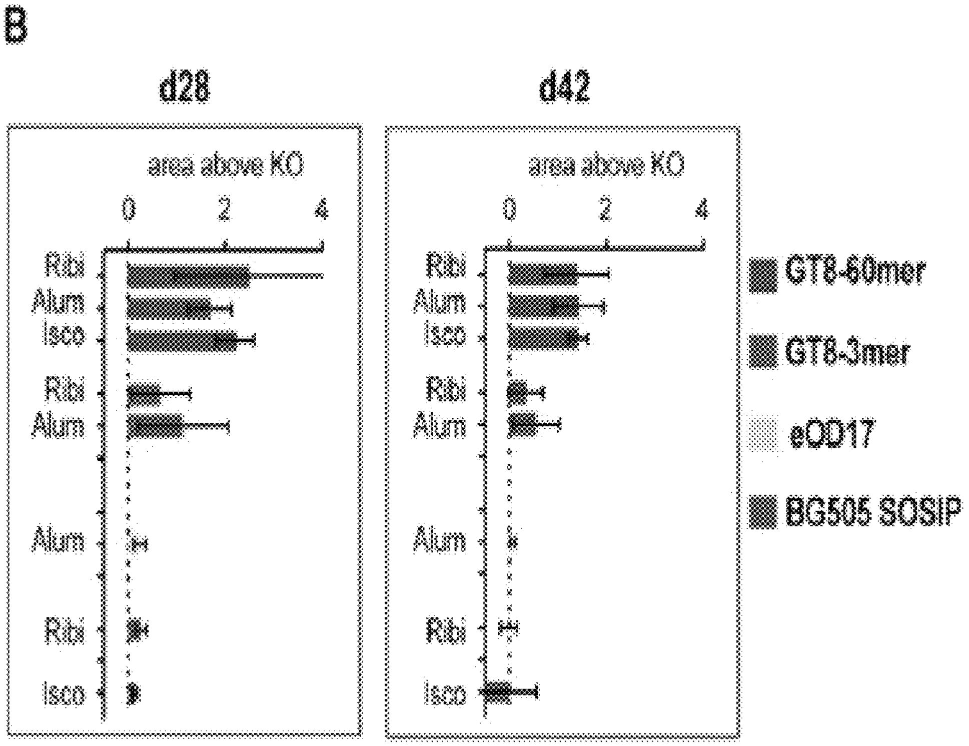
Figure 2C:
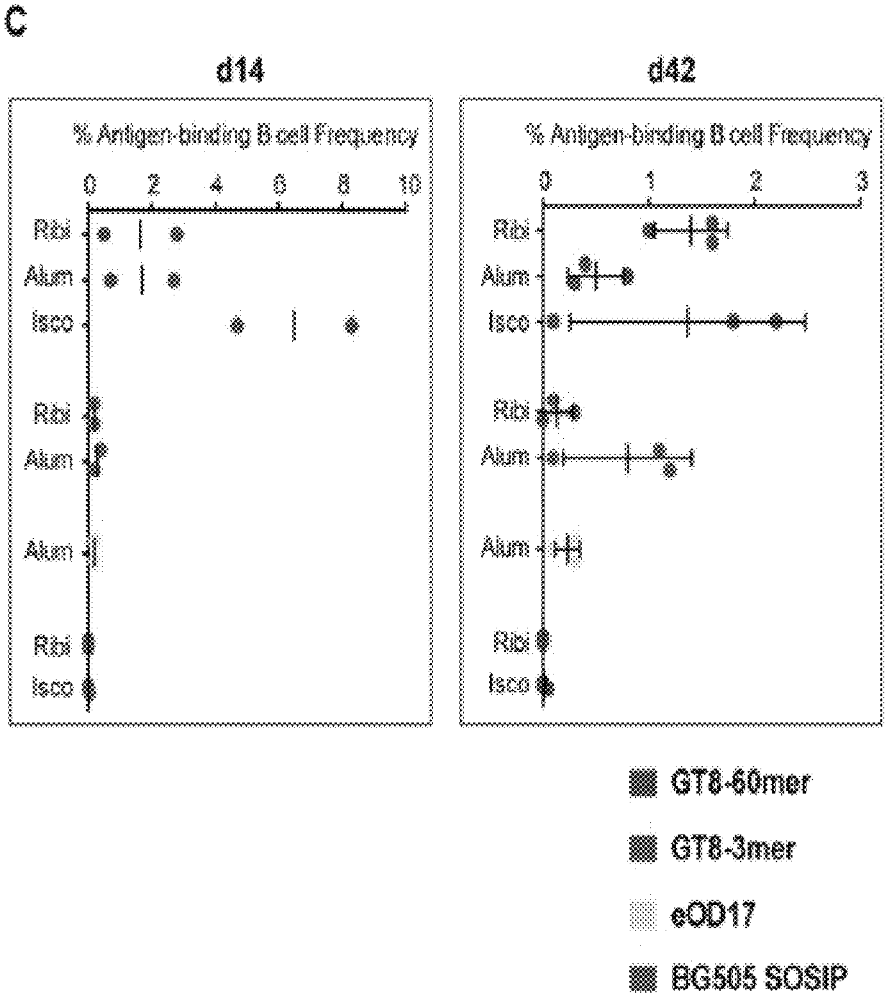

FIG. 2A-C depicts that serum and B cell analysis of antibody responses following priming immunization showed robust responses for the eOD-GT8 60mer. (A) Serum binding titers of VRC01 gH or WT littermate mice immunized with eOD-GT8-60mer nanoparticles in Ribi were measured by enzyme-linked immunosorbent assay (ELISA). Sera were titrated for binding to monomers of eOD-GT8 or eOD-GT8-KO. Plotted values represent the mean of OD450 measurements from 3 different mice for the indicated serum time point (day 28, top; day 42, bottom) at the listed dilutions. Error bars are standard error of the mean (SEM). (B) To determine differences in the level of specificity of antibody responses, the differences between the areas under the eOD-GT8 and eOD-GT8-KO ELISA binding curves were calculated for day 28 and 42 sera. Mean and standard deviation for 3 animals are shown. (C) Frequencies of epitope- or antigen-specific memory phenotype B cells sorted by flow cytometry for each immunization group. The frequency of eOD-GT8$^{(+)}$/eOD-GT8-KO$^{(-)}$ cells among all memory phenotype B cells is shown for all groups except for BG505 SOSIP, for which the frequency of BG505 SOSIP+ cells among all memory phenotype B cells is shown. Each point represents a mouse sacrificed at day 14 (left) or day 42 (right). Mean (day 14), or mean and standard deviation (day 42, N=3), are indicated by bars.

Figure 3:
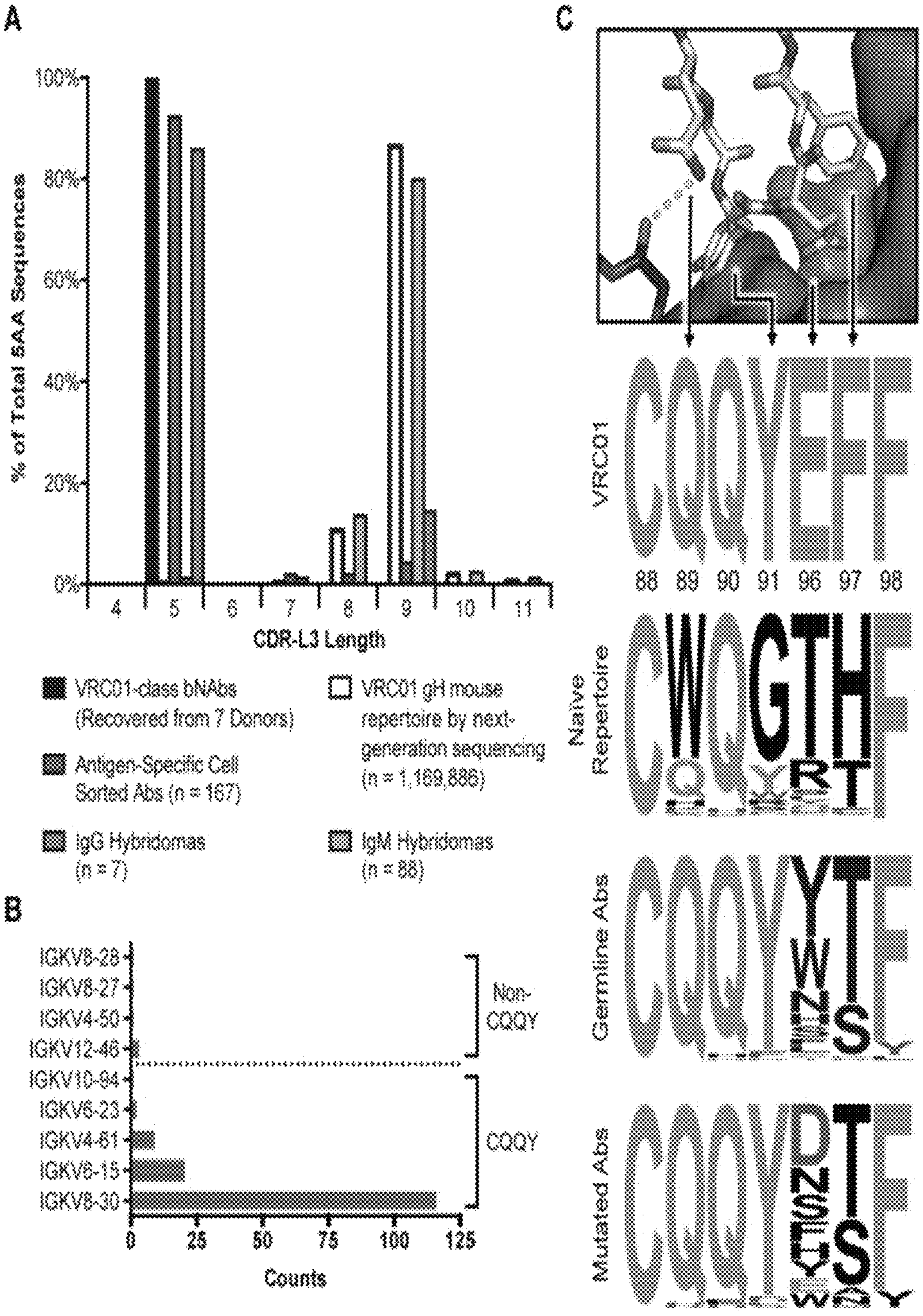

FIG. 3 depicts that priming with eOD-GT8 60mer selects for mouse light chains with VRC01-class features. (A) Mouse light chains from sorted antigen-specific IgG+ memory phenotype B cells (red) and from hybridomas (blue) as well as mouse light chains from IgM+ antigen-specific hybridomas (orange) were sequenced to identify CDRL3 lengths and mutations from germline mouse kappa chains. The distribution of CDRL3 lengths is shown in a histogram compared to known VRC01-class antibodies (black) and to the naïve (un-immunized) VRC01 gH mouse antibody repertoire (white). This analysis is based on all sequences using the VRC01 gH-chain from all mice immunized with eOD-GT8 60mers (from all hybridoma or sorting timepoints and all adjuvant groups listed in FIG. 1). (B) Gene usage is shown for all Vκ genes in antibodies using the VRC01 gH-chain and a 5aa CDRL3 recovered by sorting IgG+ eOD-GT8+/eOD-GT8-KO(−) memory phenotype B cells at day 14 or 42 from all mice immunized with eOD-GT8 60mers in all adjuvants (table 7). FIG. 3B discloses "CQQY" as SEQ ID NO: 65. (C) Comparison of the VRC01 CDRL3 sequence with sequences of 5 aa CDRL3s recovered from VRC01 gH mice. Sequences are depicted as sequence logos at the indicated positions, with the size of each letter corresponding to the prevalence of that residue at that position. The "VRC01" sequence logo shows the sequence of the VRC01 CDRL3; the "Naïve Repertoire" sequence logo represents all 1,653 sequences with 5 aa CDRL3 found by deep sequencing of 4 unimmunized VRC01 gH mice (these sequences amount to 0.14% of all 1,169,886 sequences from those mice); the "Unmutated Abs" and "Mutated Abs" sequence logos represent the sets of unmutated (N=84) or mutated (N=70) antibodies, respectively, using the human VH1-2*02 gene and a 5aa CDRL3, isolated from VRC01 gH mice at days 14 or 42 after immunization with eOD-GT8 60mer and Alum, Isco, or Ribi (the red bar at CDRL3 length=5 in FIG. 3A corresponds to these 154 sequences, and see table 7).

Figure 4:
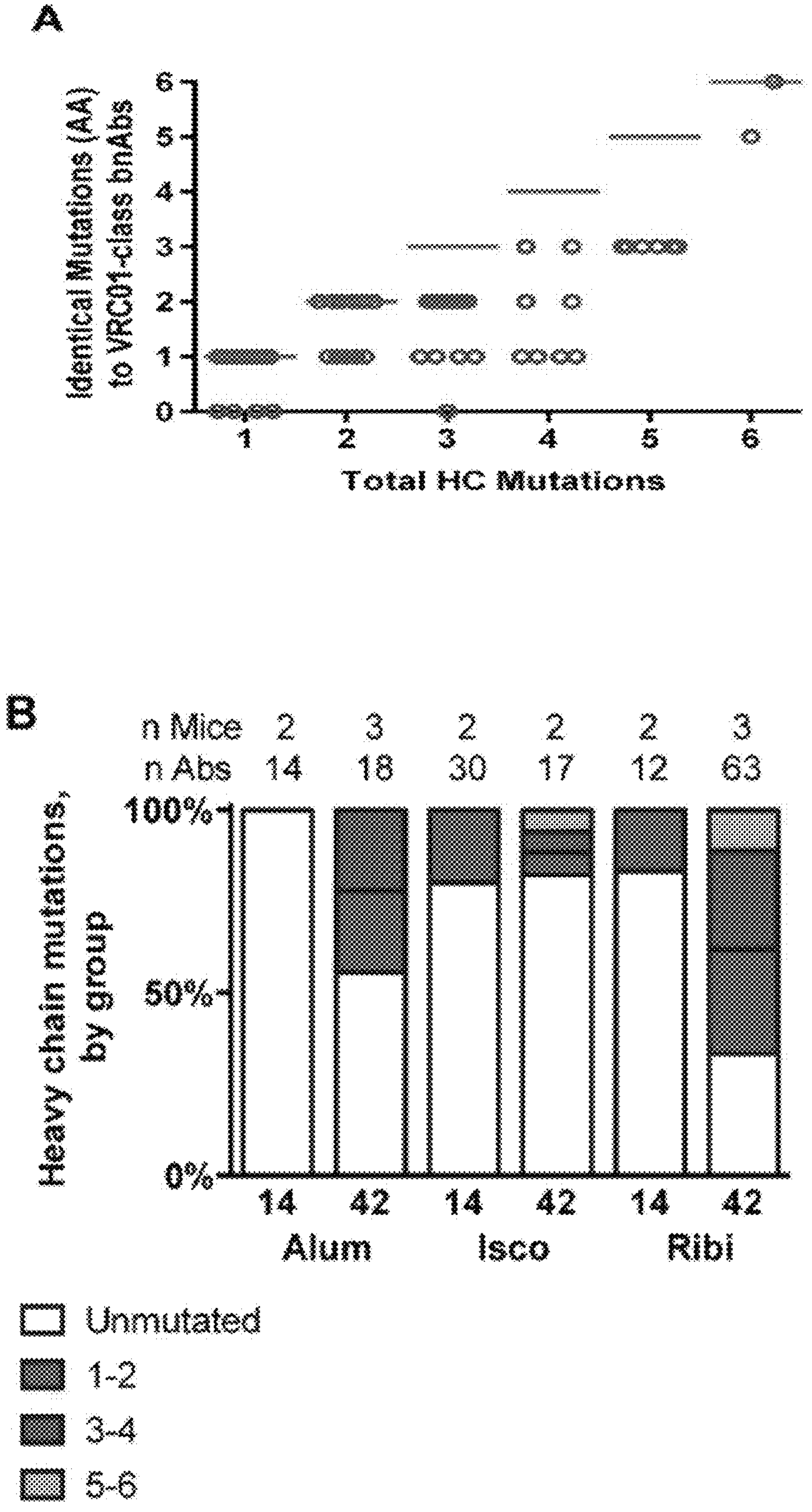

FIG. 4 depicts that priming with eOD-GT8 60mer selects for productive heavy chains mutations found in VRC01-class bnAbs. (A) A total of 61 mutated heavy chain sequences from day 14 and 42 eOD-GT8 60mer-immunized VRC01 gH-chain mice (table 7) were evaluated for the number of amino acids that match the mutations found in VRC01-class bnAbs (12a12, 3BNC60, PGV04, PGV20, VRC-CH31 and VRC01) compared to total heavy chain amino acid mutations from germline. Each circle represents a single heavy chain sequence that was isolated by antigen-specific memory phenotype B cell sorting. (B) The total number of amino acid mutations observed in the heavy chains of antibodies isolated by antigen-specific memory phenotype B cell sorting are listed by adjuvant (Alum, Isco, or Ribi) for spleen and lymph node samples harvested at 14 or 42 days post-priming immunization. Bar graphs are divided by unmutated (white) vs mutated (colored). The mutated bars are divided into Abs with 1-2 coding mutations (red), 3-4 coding mutations (blue) or 5-6 coding mutations (orange). The number of mice and the number of antibodies used to compute the frequencies in each bar are listed at the top of the graph.

FIG. 5 depicts that binding affinities of eOD-GT8 60mer elicited antibodies for eOD-GT8 and candidate boost immunogens. (A) eOD-GT8 dissociation constants measured by Surface Plasmon resonance (SPR) for 115 eOD-GT8 60mer-elicited antibodies isolated by antigen-specific B cell sorting (table 7). Antibodies were captured on the sensor chip and eOD-GT8 monomer was analyte. Data are shown for 42 antibodies from day 14 and 73 antibodies from day 42 following immunization of VRC01 gH mice with eOD-GT8 60mer. Each point is colored to indicate the type of adjuvant used (Alum, Iscomatrix, and Ribi) in the immunizations. The scale on the y-axis spans from the smallest dissociation constant (16 pM) measurable by the SPR instrument (as stated by the manufacturer) to the highest dissociation constant (10 μM) measurable based on the analyte concentration used in the experiment. (B) Dissociation constants measured by SPR between selected eOD-GT8 60mer-elicited antibodies and candidate boost immunogens. Among the 115 Abs in (A), the 29 antibodies with highest affinity for eOD-GT8 (KD<1 nM), along with 8 unmutated antibodies with lower affinity for eOD-GT8, were selected for binding to candidate boosting immunogens (HxB2 core-e 2CC N276D and core BG505 N276D) by SPR. High analyte concentration was used to determine KDs up to 100 μM. HxB2 core-e 2CC N276D 60mer nanoparticles were also assayed, with values presented as apparent affinity, due to the avidity between particles and IgG. Mutated antibodies are shown as green open squares while germline antibodies are shown as black open diamonds.

FIG. 6 depicts Human light chain CDRL3 length distributions for kappa (A.) and lambda (B.) chains. Histograms are based on 127,701 antibody sequences (81,910 of which had kappa light chains and 45,791 of which had lambda light chains) from three donors determined by DeKosky et al. (19).

FIG. 7 depicts Light chain CDRL3 length distributions in VRC01 gH mice, WT littermates, and humans, for kappa chains (A) and lambda chains (B). A. Next-generation sequencing (NGS) of spleen from 4 VRC01 gH mice and 4 WT littermate mice show similar kappa chain CDRL3 length distributions compared to sequences from PBMCs from 4 humans, with a peak in the distribution at a length of 9. B. NGS of spleen from 4 VRC01 gH mice and 4 C57B/6 WT littermate mice show similar lambda chain CDRL3 length distributions, indicating the repertoire is not biased by the knock-in VRC01 gH. The human lambda distribution is broader. The frequency of 5 aa CDRL3 is lower in mouse lambda chains compared to mouse kappa chains by a factor of ~8. CDRL3 lengths (amino acid) are shown based on percent frequency in the repertoire. Values plotted are mean and standard deviation for each sample (N=4 in all cases). The total number of sequences for each histogram was 1,169,886 (VRC01 gH kappa), 1,220,394 (WT kappa), and 799,458 (human kappa), 2,522,669 (VRC01 gH lambda), 1,800,093 (WT lambda), and 1,061,959 (human kappa).

FIG. 8 depicts the sequence of VRC01 gH. (A) Alignments of the VRC01 H chain to the closest human V, D, and J gene segments are shown, as determined by JoinSolver (31). Multiple DH and JH genes are shown in the order ranked by JoinSolver to reflect the uncertainty in those assignments. Highlighted in red is the region of the CDRH3 encoded by the D gene and N/P addition where the determination of the true germline sequence is particularly uncertain. Based on this analysis, Applicants selected IGHV1-02*02 and IGHJ1*01 as the V and J genes, respectively, for VRC01 gH. These choices are supported by recent analysis of the VRC01 lineage over 15 years of chronic infection in the VRC01 donor (30). FIG. 8A discloses SEQ ID NOS 66-82, respectively, in order of appearance. (B) Amino acid alignment of VRC01 and VRC01 gH. The CDRH3 for VRC01 gH used the same CDRH3 as VRC01, except that Applicants mutated an unpaired cysteine in the CDRH3 to serine to avoid potential solubility and B cell development problems (in VRC01 this cysteine in CDRH3 makes a disulfide bond with a cysteine that arose by affinity maturation in CDRH1, but germline reversion of the V gene, including the CDRH1, leaves the CDRH3 cysteine without a disulfide-bonding partner). FIG. 8B discloses SEQ ID NOS 83-85 and 752, respectively, in order of appearance.

Figure 9:
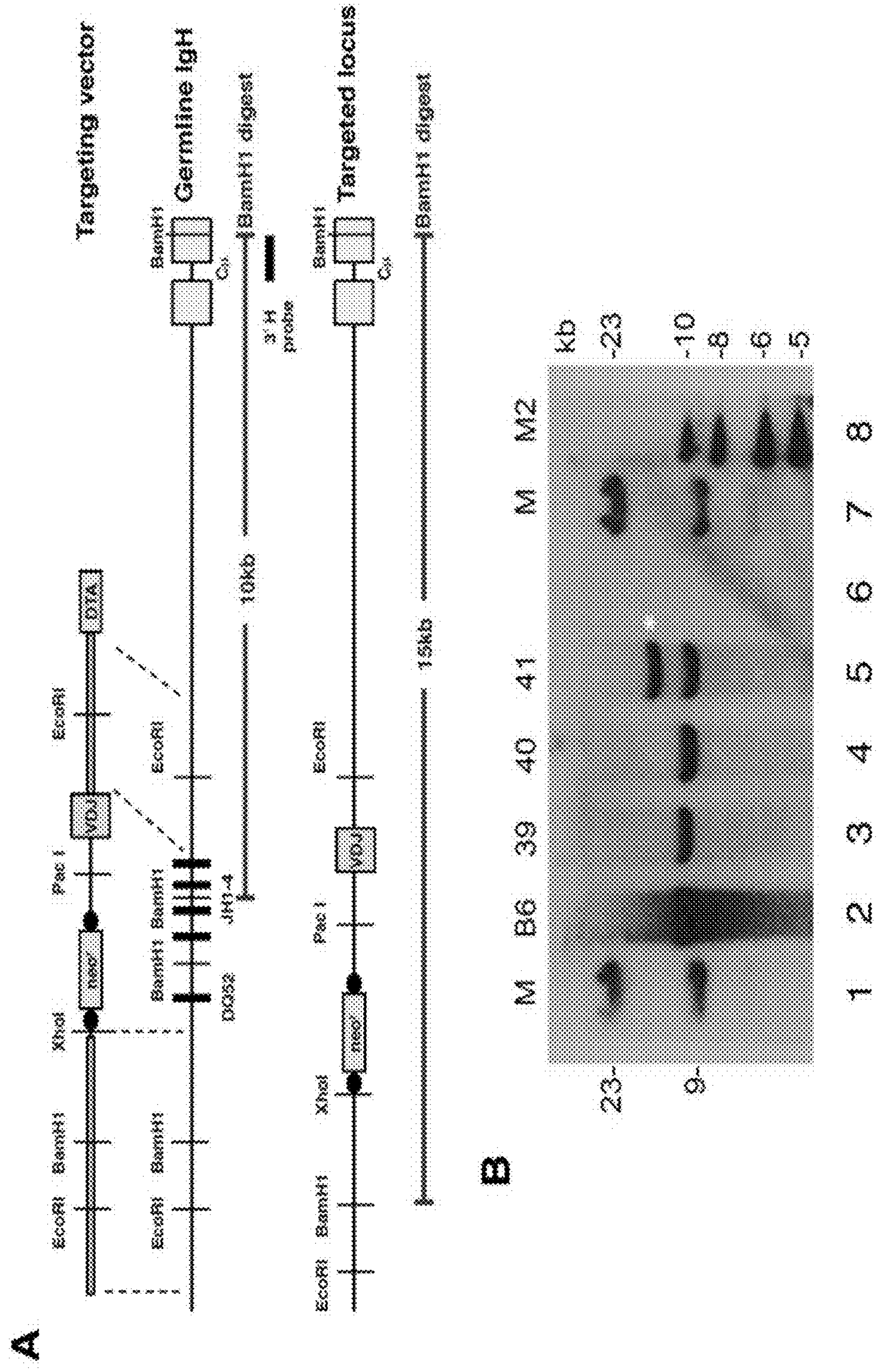

FIG. 9 depicts an approach for knock-in of VRC01 germline heavy chain (gH) gene. (A) Schematic of targeting strategy and analysis. Shown are partial restriction maps of the targeting vector, germline locus, and the predicted targeted allele before and after neomycin resistance gene ($neo^r$) removal by cre/lox recombination. Gray horizontal bars indicate arms of homology of the targeting vector. Dotted lines show areas of homology involved in recombination between the targeting vector and host locus to generate the knock-in allele. Note that targeting eliminates the host Jh locus and Dq52 gene and replaces it with the VRC01 gH variable gene, upstream elements and promoter, along with the neo gene which allows selection for the desired allele. Black circles represent loxP sites; white and lighter gray boxes indicate the elements of the inserted coding sequences including leader, intron and VDJ exon with upstream promoter elements not specifically shown. Blue boxes represent other coding sequences, including $neo^r$, diptheia toxin A (DTA), and Cm exons. The germline locus shows JH and nearby $D_{Q52}$ elements in black boxes. Horizontal black bar below the lower part of the figure indicates location of probe used in southern blot analysis. Blue lines indicate predicted fragments generated with BamH1 restriction enzyme. (B) Shown is southern blotting analysis of genomic DNA of individual ES cell clones tail DNA from C57Bl/6 (B6) mice of the indicated genotypes. Asterisk shows positive clone used in blastocyst injections for mouse production. Breeding to EIIa-cre transgenic mice was used to remove $neo^r$.

Figure 10A:
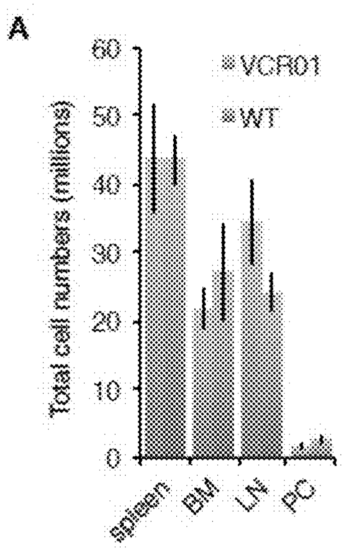
Figure 10B:
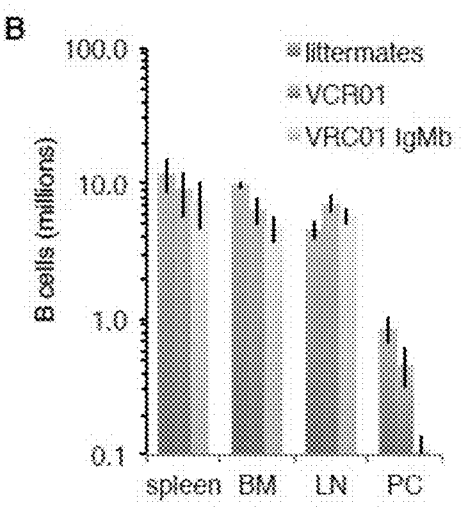
Figure 10C:
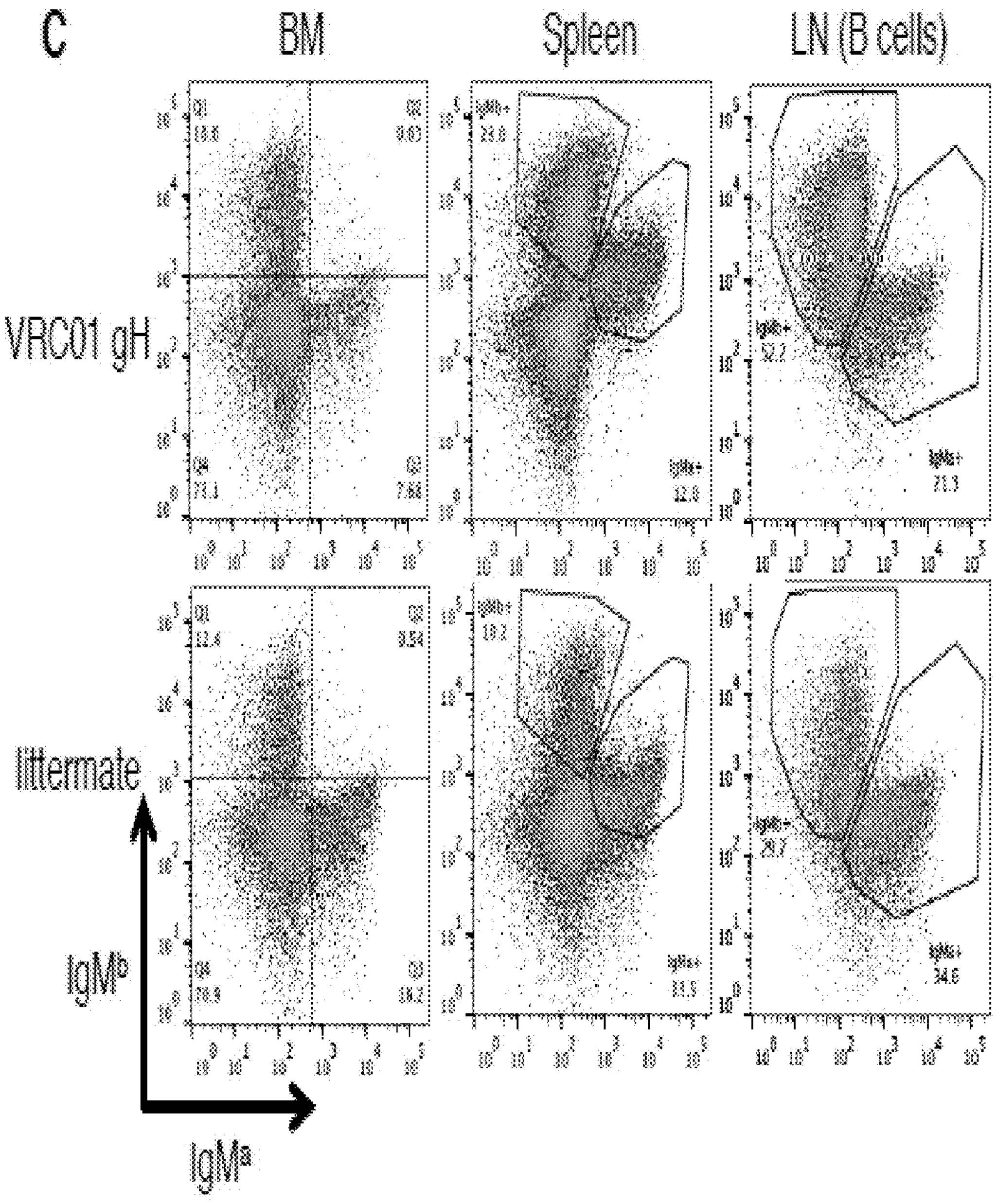

FIG. 10A-C depicts that VRC01 gH mice have significant numbers of B cells in secondary lymphoid tissues expressing the targeted allele. To track B cells carrying the knock-in allele, VRC01 gH mice, carrying a single knock-in locus, were bred one generation to mice carrying the "a" allelic haplotype of the Igh locus. In these mice, IgMa is carried only by cells expressing the endogenous allele whereas IgMb cells almost invariably express the VRC01 gH transgene. Controls were non-transgenic littermates from the same cross where expression of the two allele is expected to be ~50:50. Lymphoid tissue of the indicated mice were analyzed at 8 weeks of age for (A) total cell numbers, (B) B cells (CD19+B220+; marked blue), and cells carrying IgMb (green), which is the knock-in Hchain allele of surface IgM. Cells tested were from the following tissues: spleen, bone marrow (BM), lymph nodes (LN), peritoneal cavity (PC). As the knockin replaces the Jh cluster on the Ighb allele, in VRC01 gH mice virtually all B cells expressing IgMb use VRC01 gH. The allele usage frequency found here was consistent with the deep sequencing data shown in FIG. 1. (C) Examples of flow cytometry plots enumerating B cells carrying IgMa and IgMb. Dh regions can rearrange into the knock-in VDJ, leading usually to loss of function. This likely explains the presence of IgMa cells in the VRC01 gH mice. LN plots were from gated B220+ cells.

Figure 11:
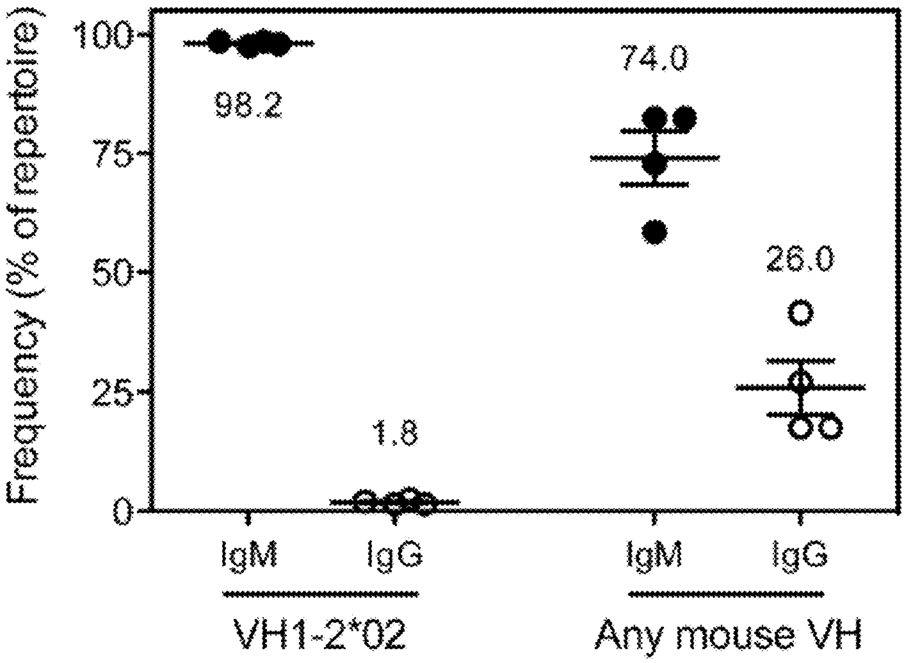

FIG. 11 depicts that the antibody repertoire of naïve VRV01 gH mice contains a high proportion of IgM. Next-generation sequencing of spleen from VRC01 gH mice show that, for the VH1-2*02 gene, 98.2% of sequences are IgM while 1.8% of sequences are IgG. Different primers were used to amplify IgG vs IgM, introducing some uncertainty into the comparison of absolute frequencies.

Figure 12:
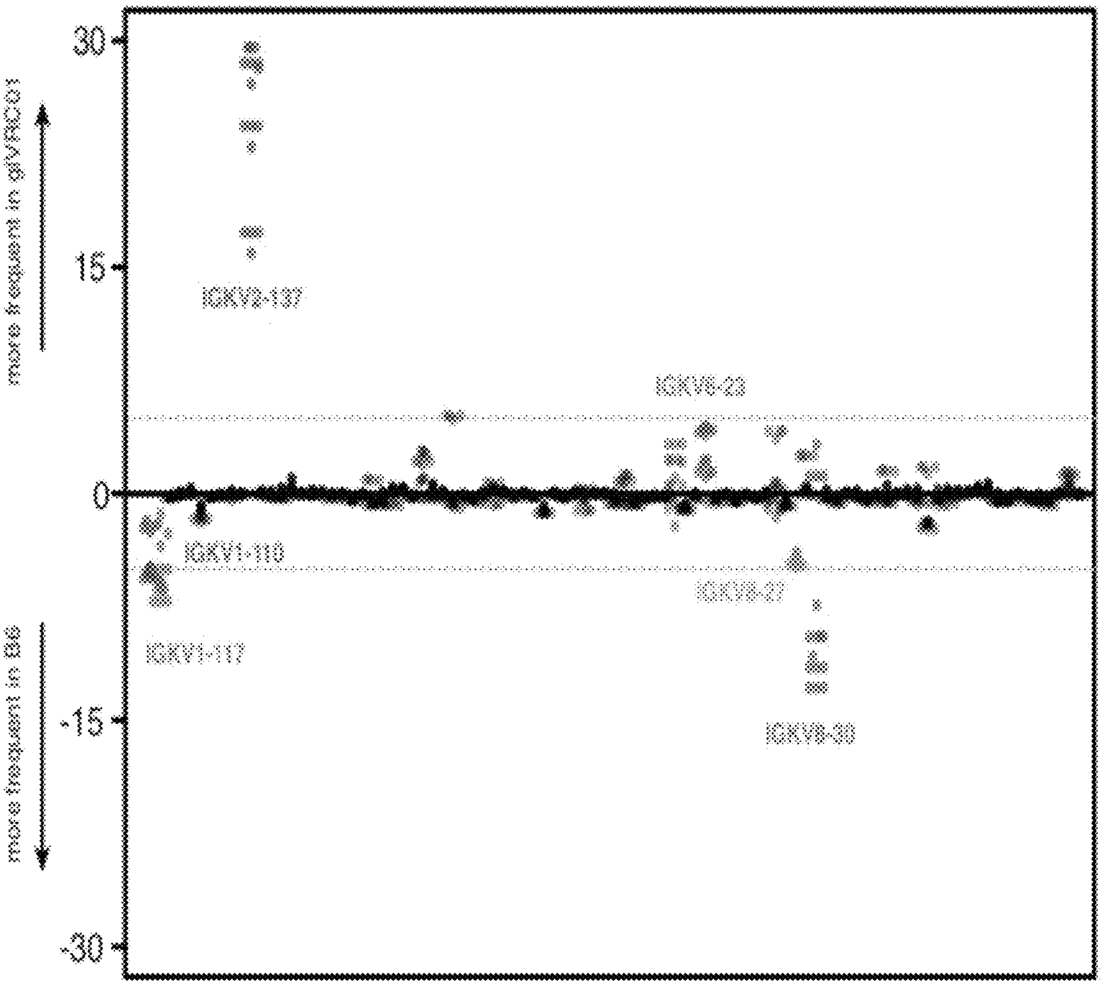

FIG. 12 depicts that the majority of Vκ genes are used similarly between VRC01 gH mice and littermate mice. Next-generation sequencing of spleen from VRC01 gH mice and littermate mice show largely the same Vκ gene usage. Vκ genes that show different frequencies are highlighted with color, with Vκ genes used more frequency by VRC01 gH mice shown above the center axis and Vκ genes used more frequency by littermate mice shown below the center axis.

Figure 13:
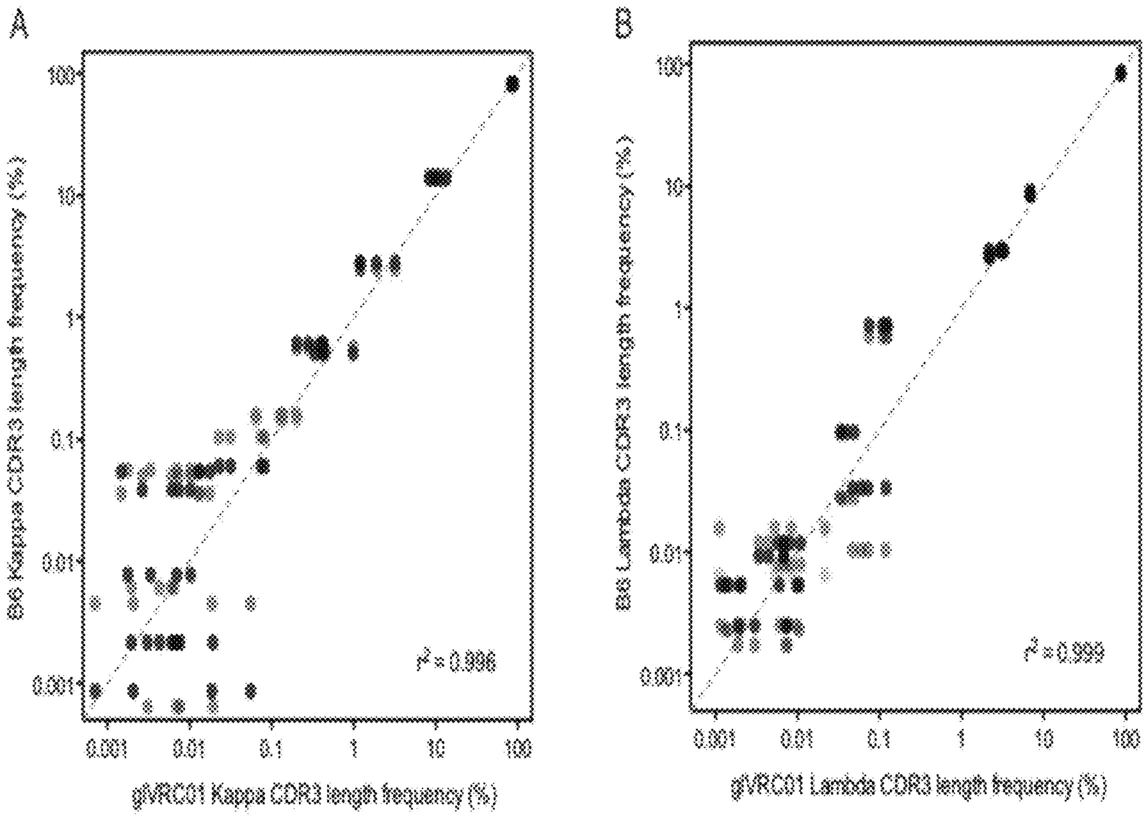

FIG. 13 depicts that VRC01 gH mice and littermates have similar CDRL3 length distributions for both kappa and lambda chains. Next-generation sequencing of spleen from VRC01 gH mice and littermate mice show highly similar CDRL3 length distributions for both (A) kappa and (B) lambda chains.

Figure 14:
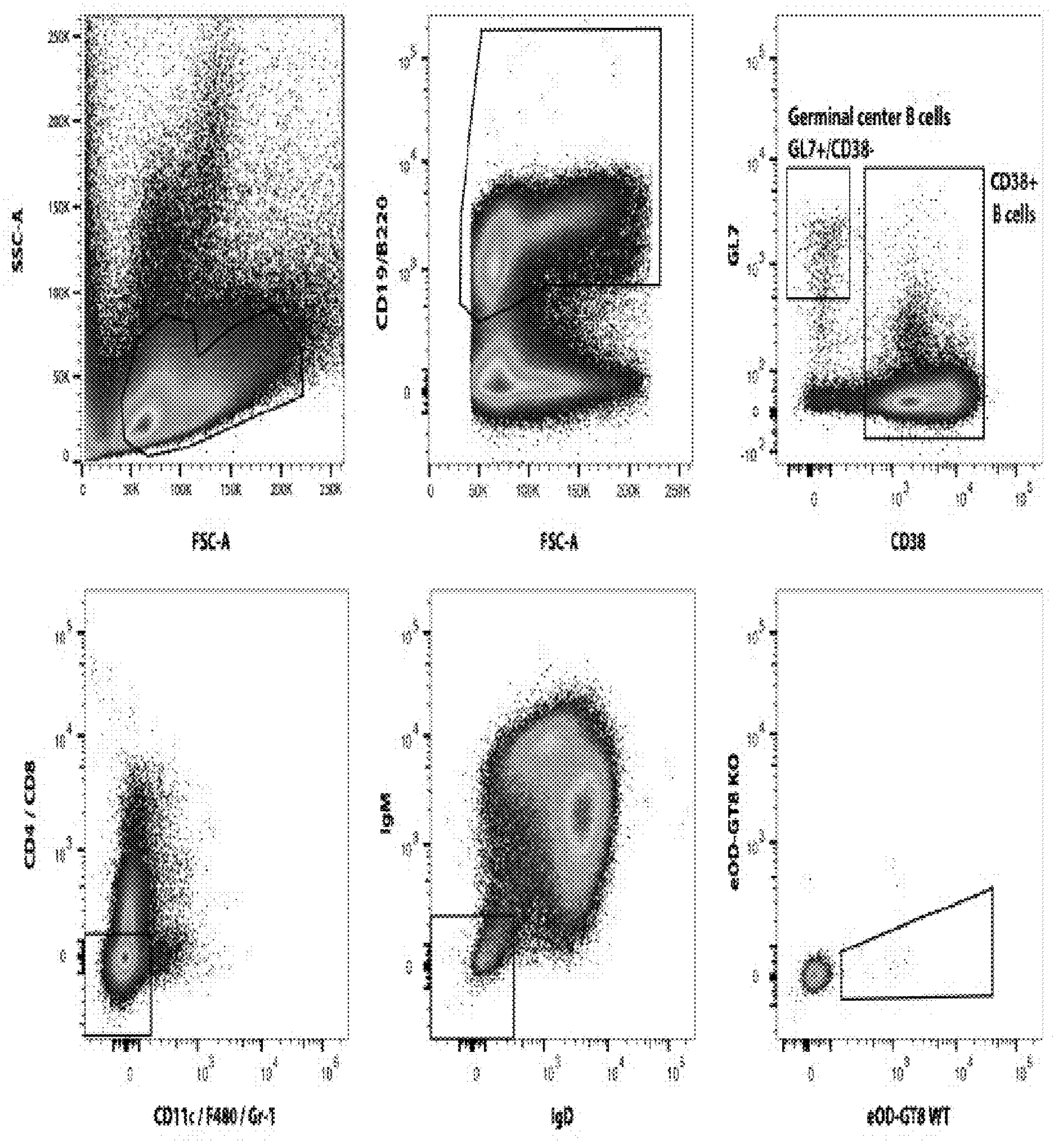

FIG. 14 depicts epitope-specific memory B cell sorting by flow cytometry. Example gating strategy for sorting of epitope specific memory phenotype B cells. B cells were selected for a CD19+/B220+/CD38+/CD4−/CD8−/IgM−/IgD−/eOD-GT8+/eOD-GT8 KO− events. Frequency of germinal center phenotype B cell events could also be distinguished using GL7 and CD38 markers (GL7+/CD38−).

Figure 15A:
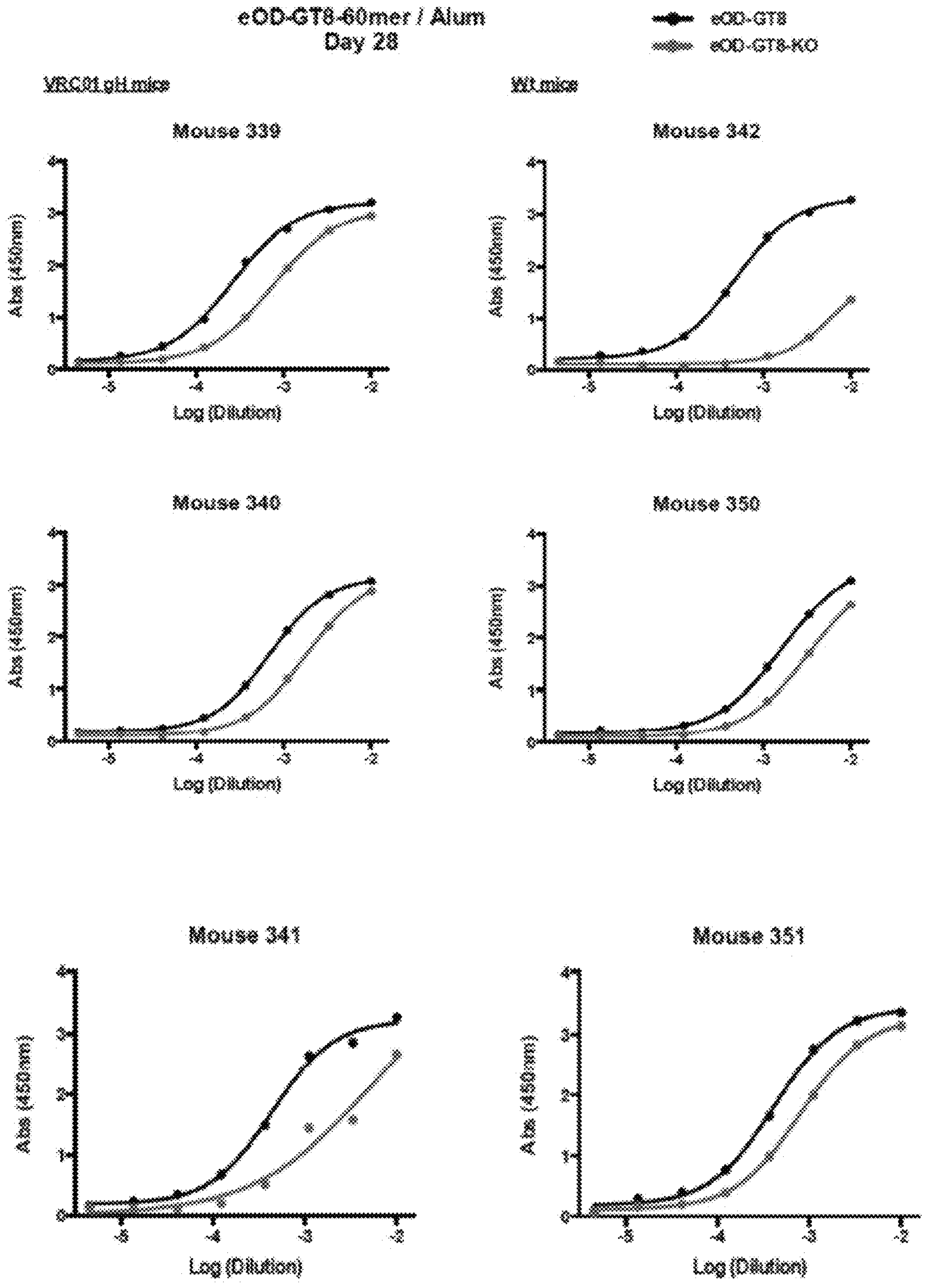
Figure 15B:
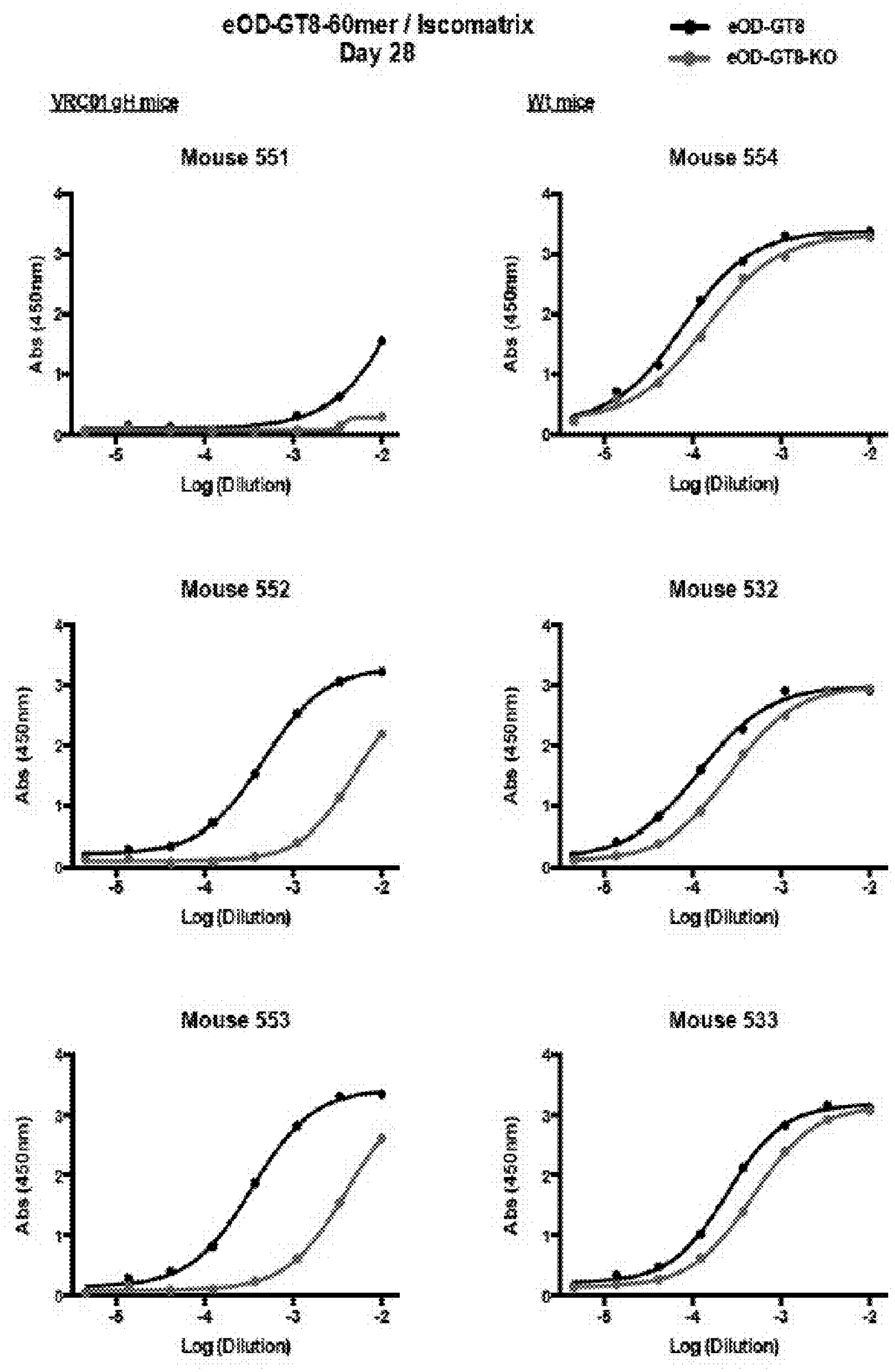
Figure 15C:
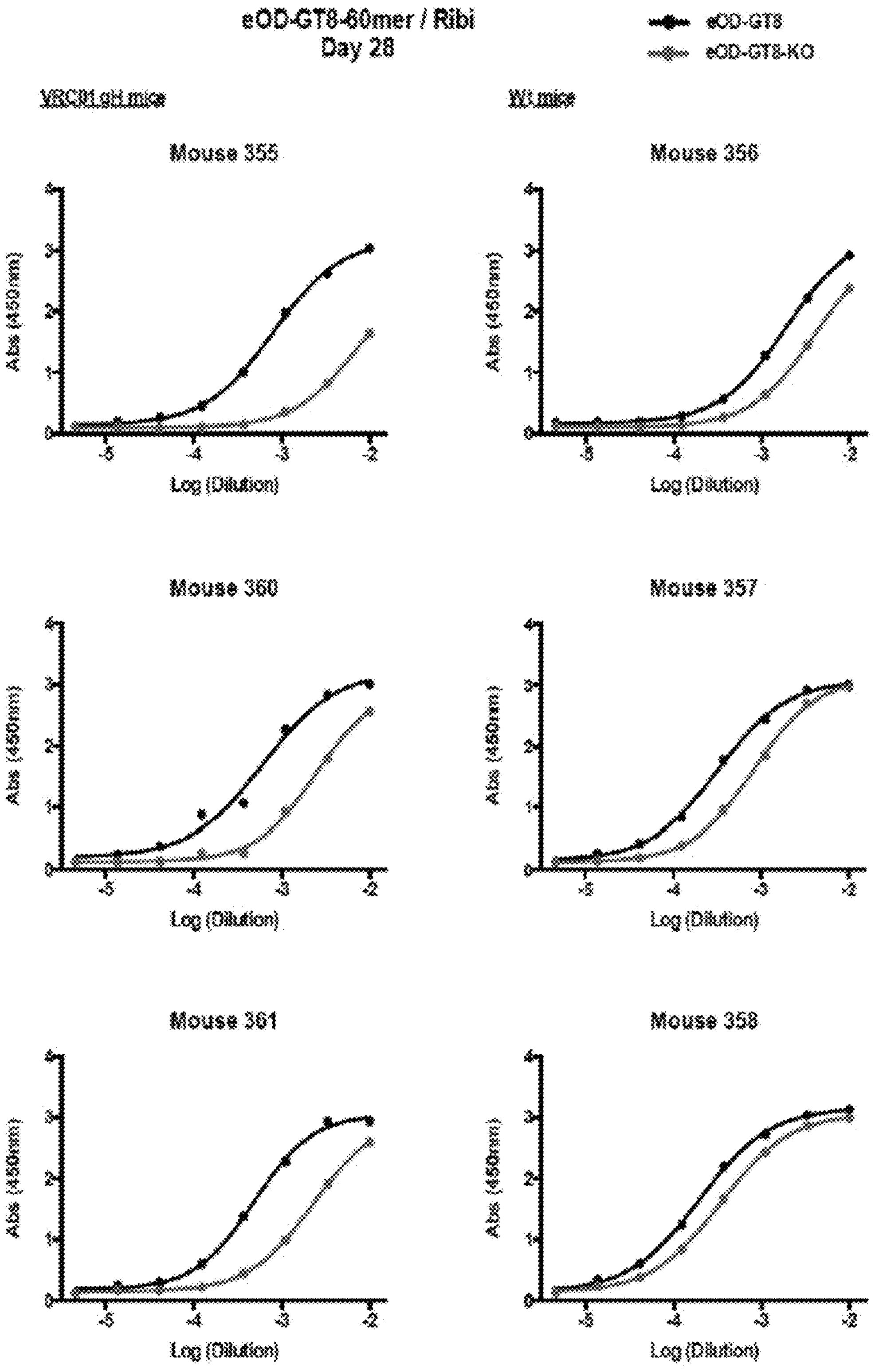
Figure 15D:
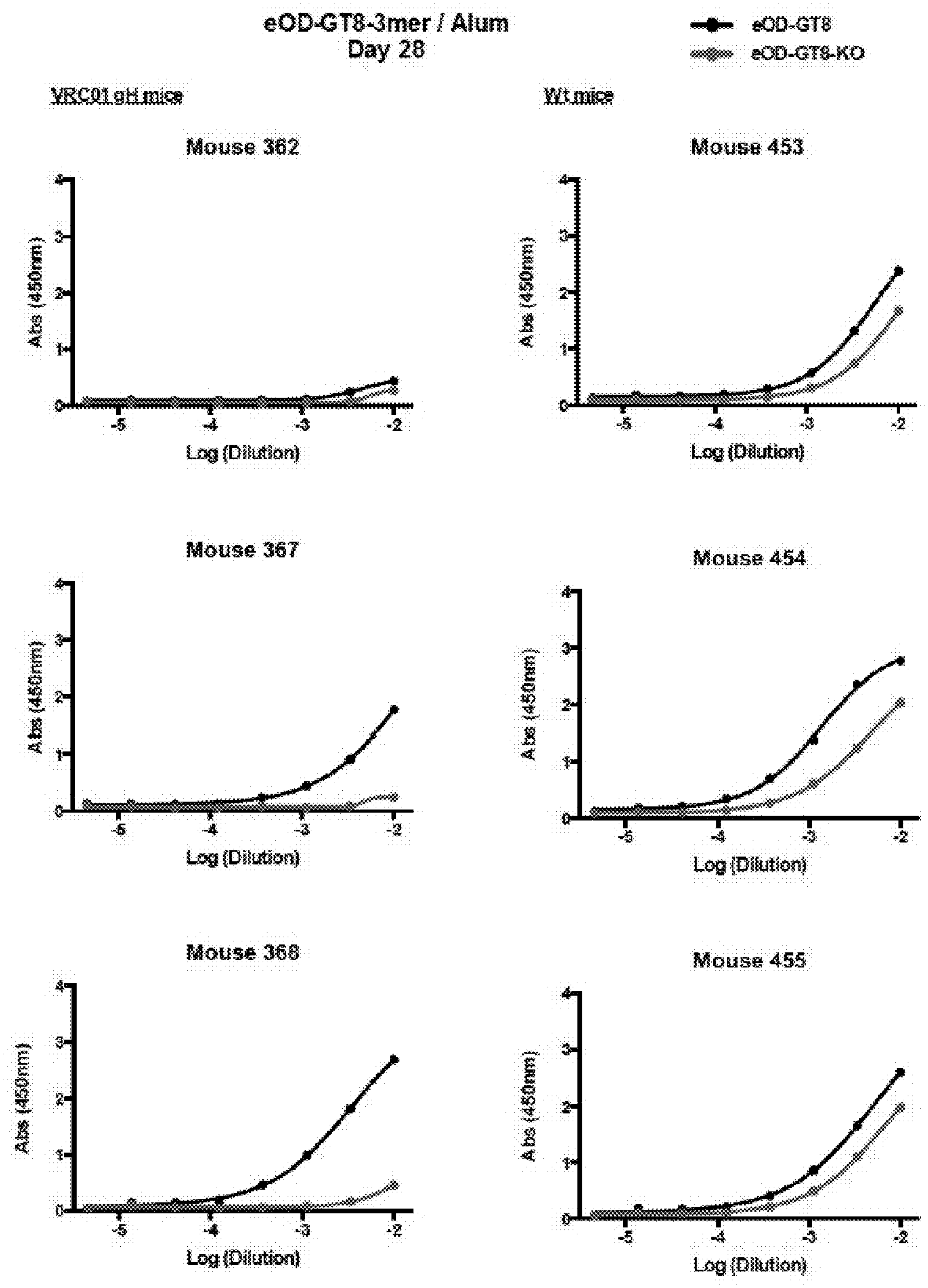
Figure 15E:
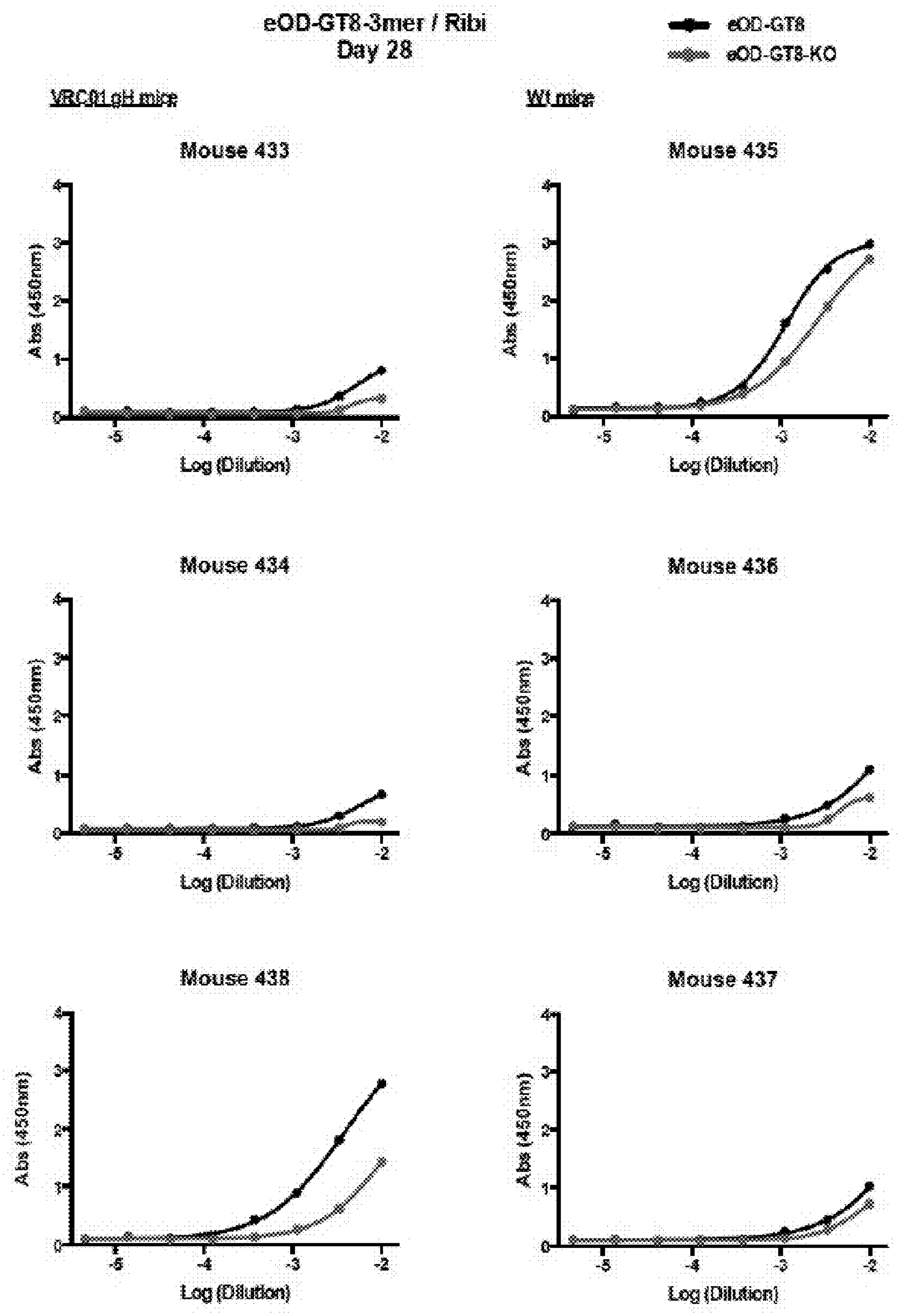
Figure 15F:
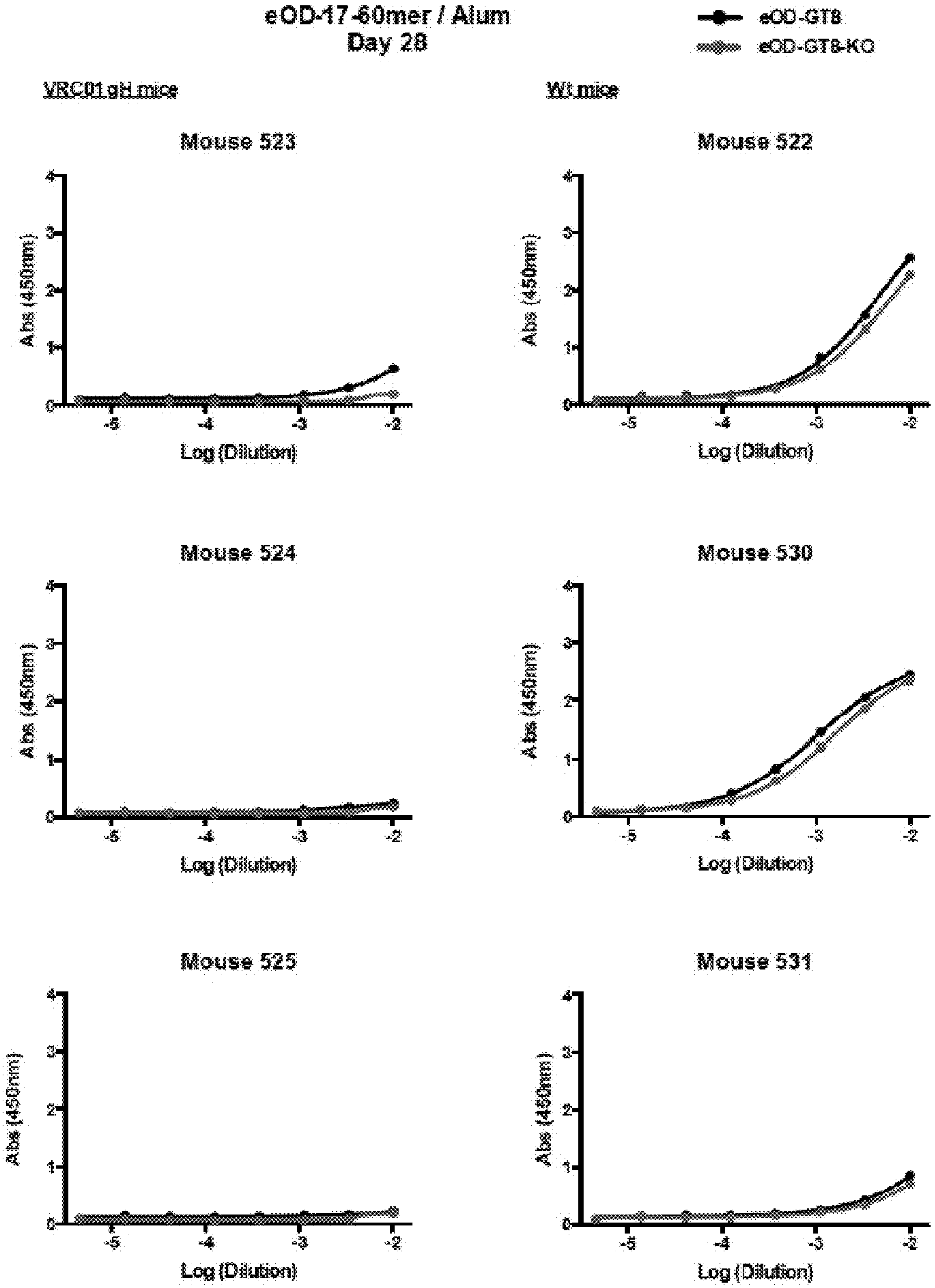
Figure 15G:
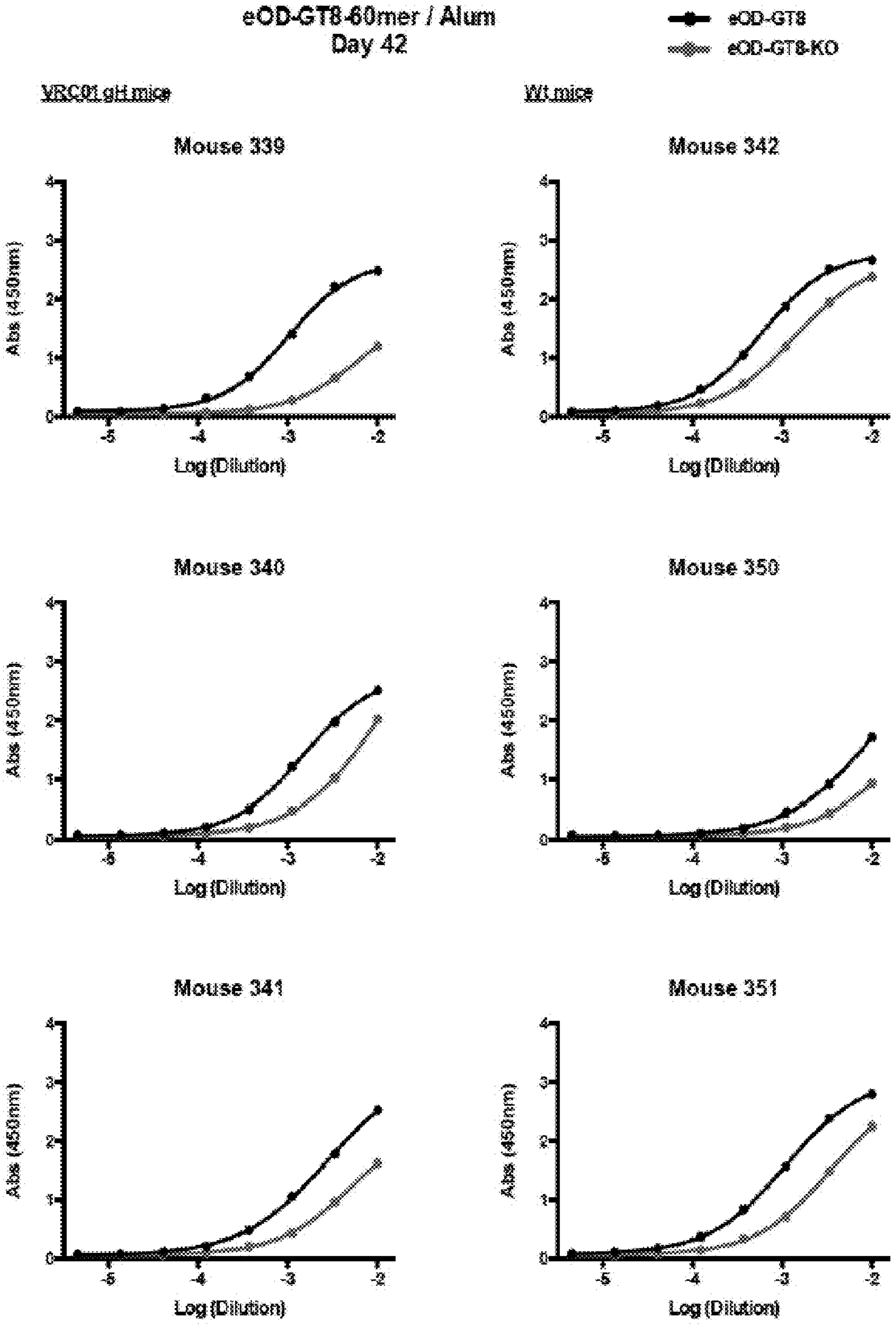
Figure 15H:
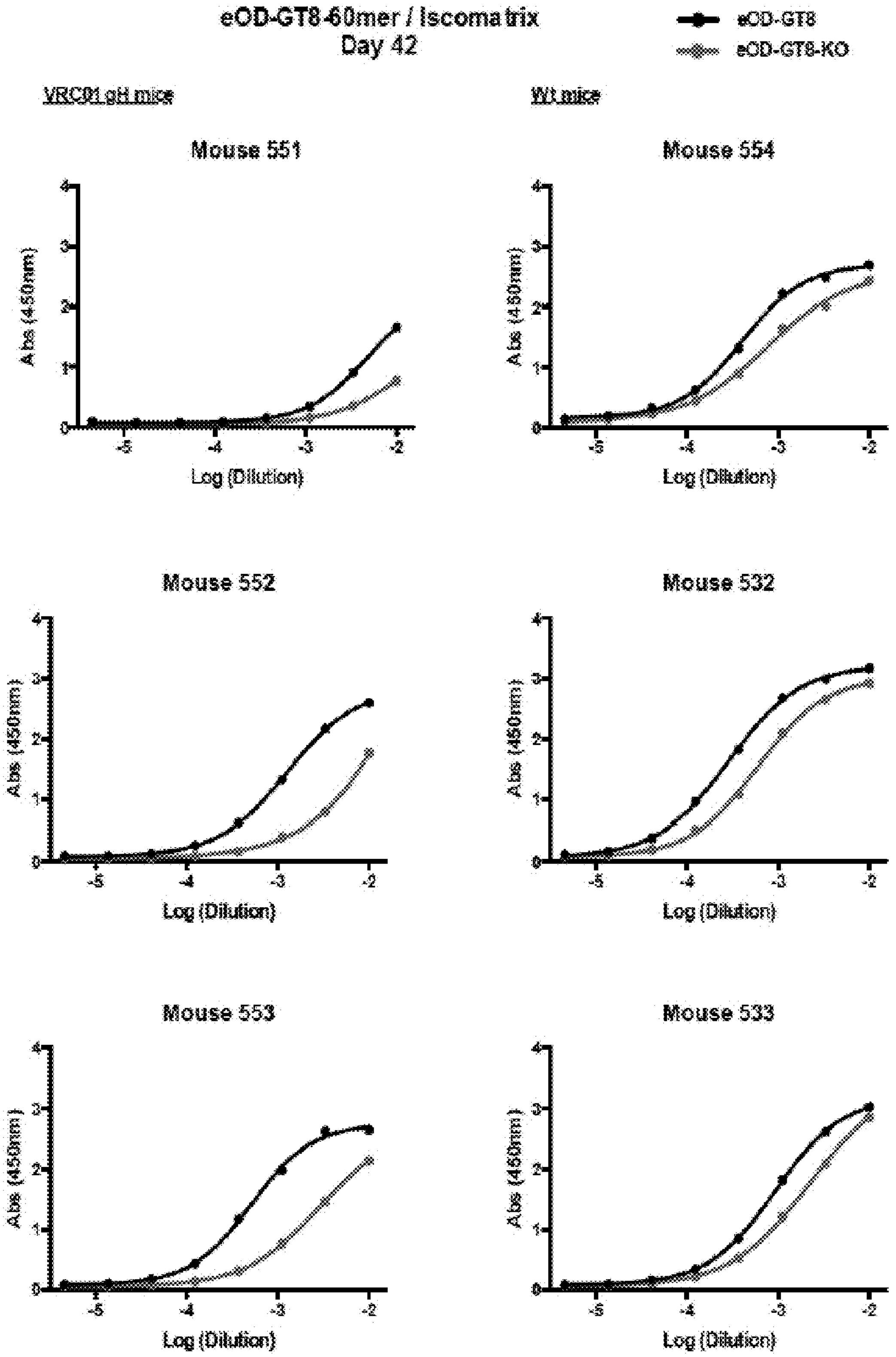
Figure 15I:
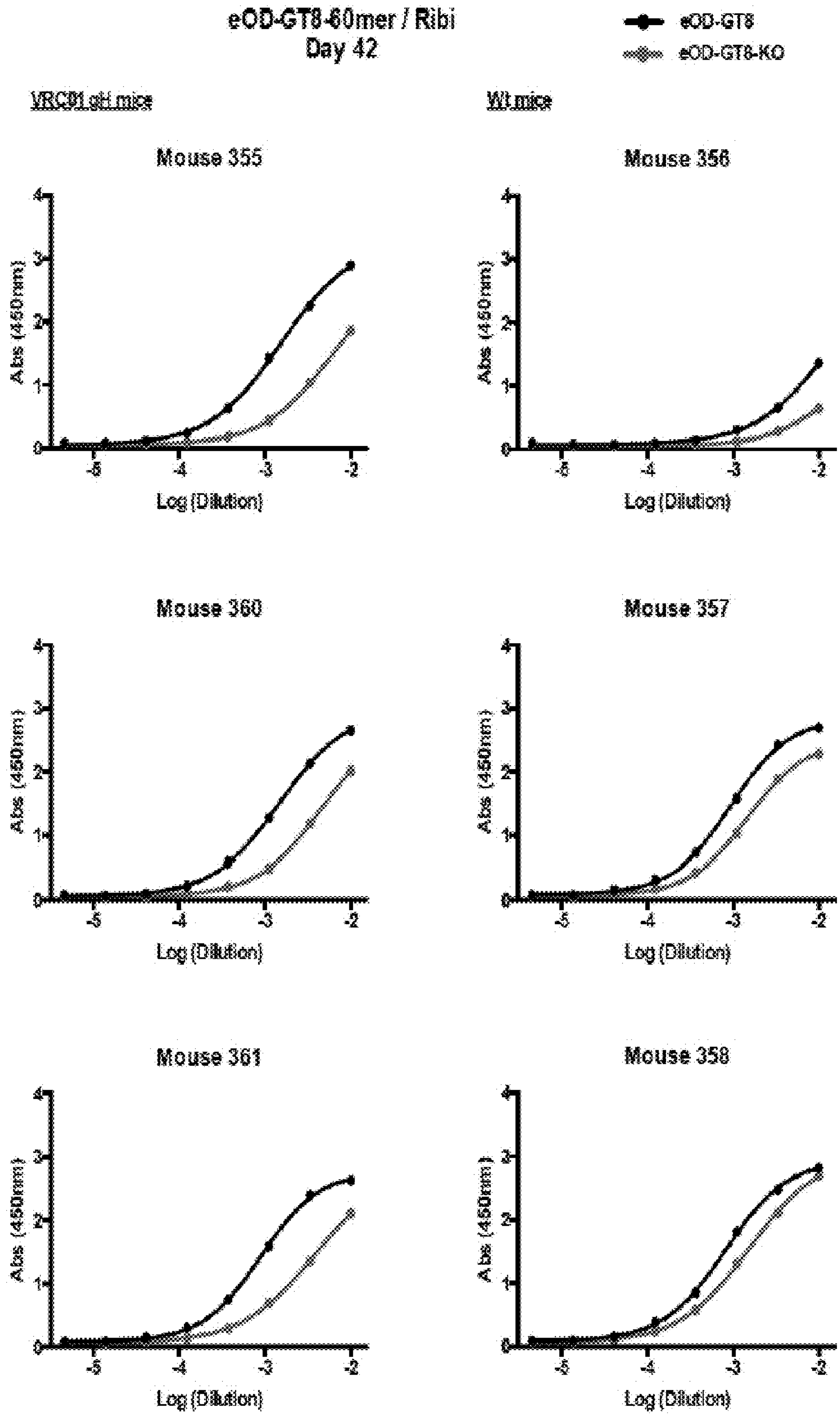
Figure 15J:
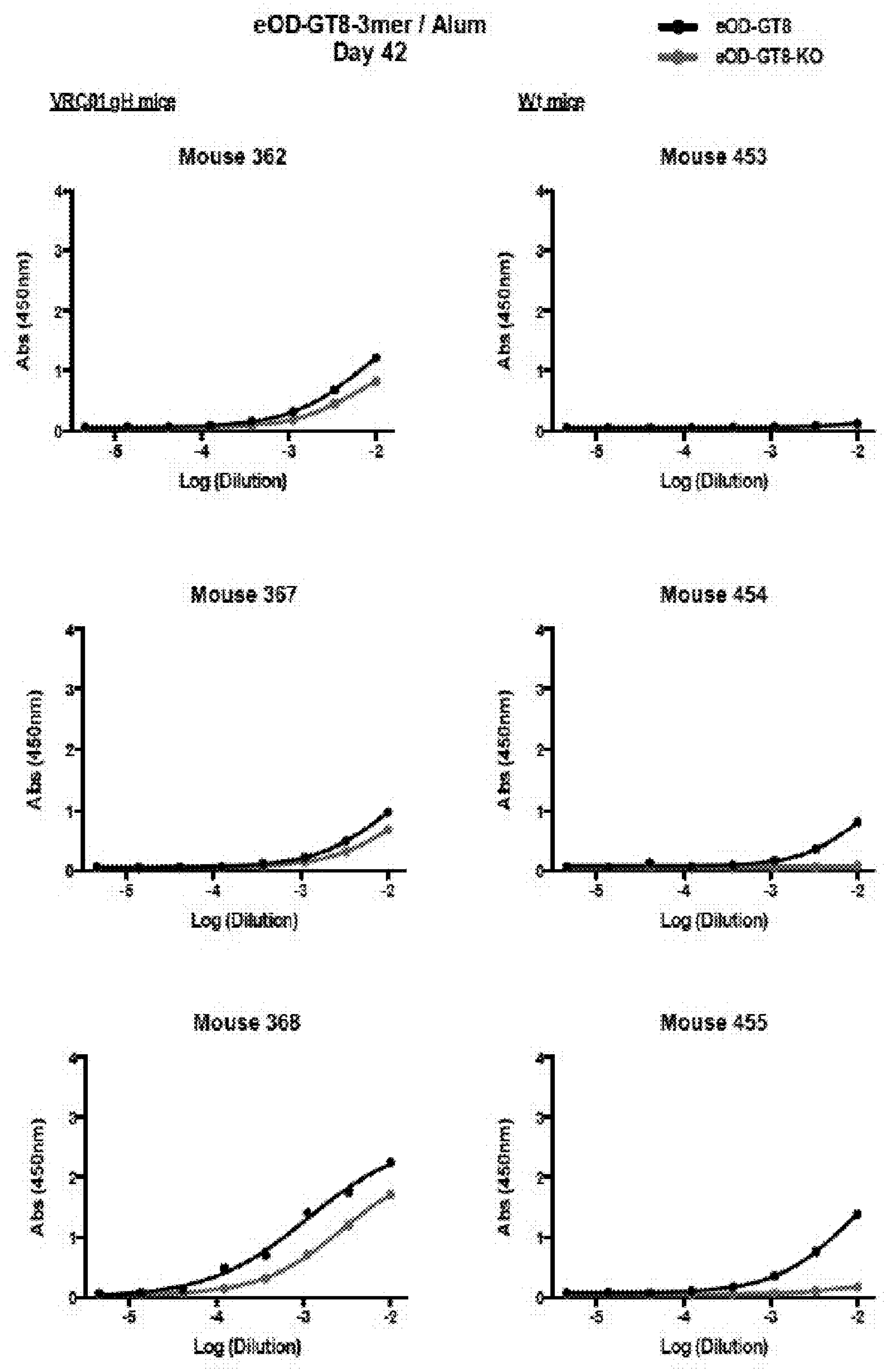
Figure 15K:
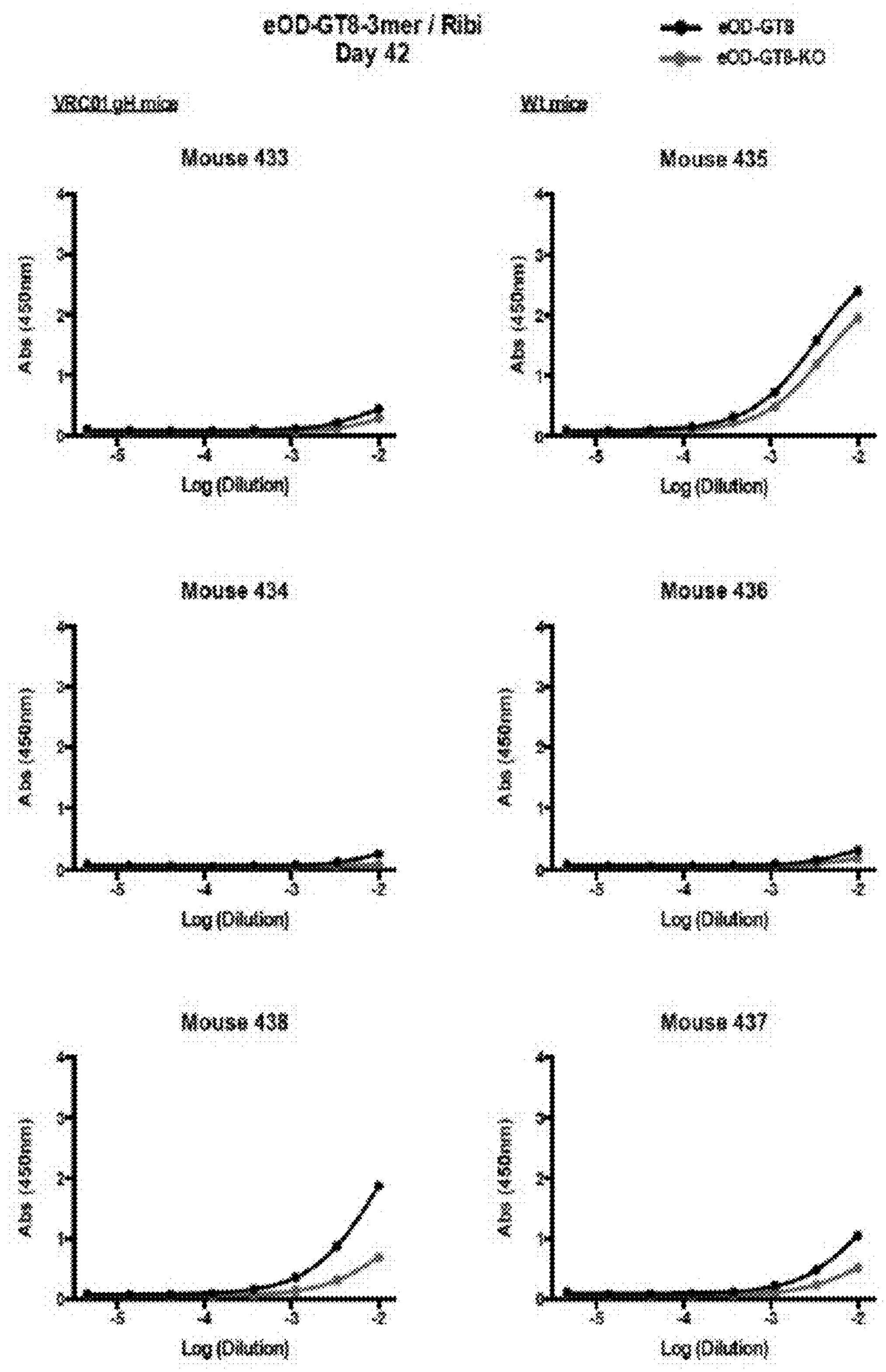
Figure 15L:
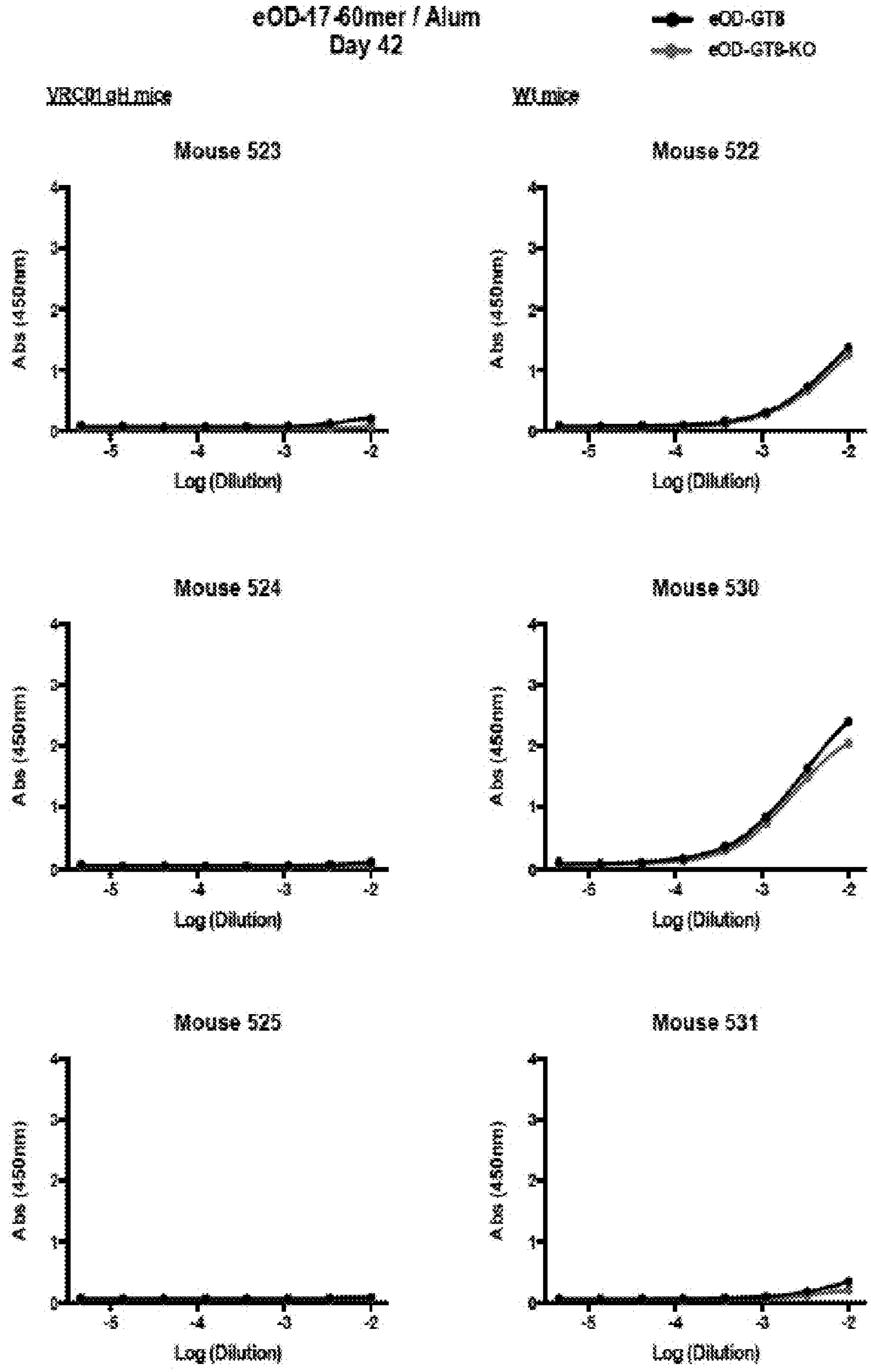
Figure 15M:
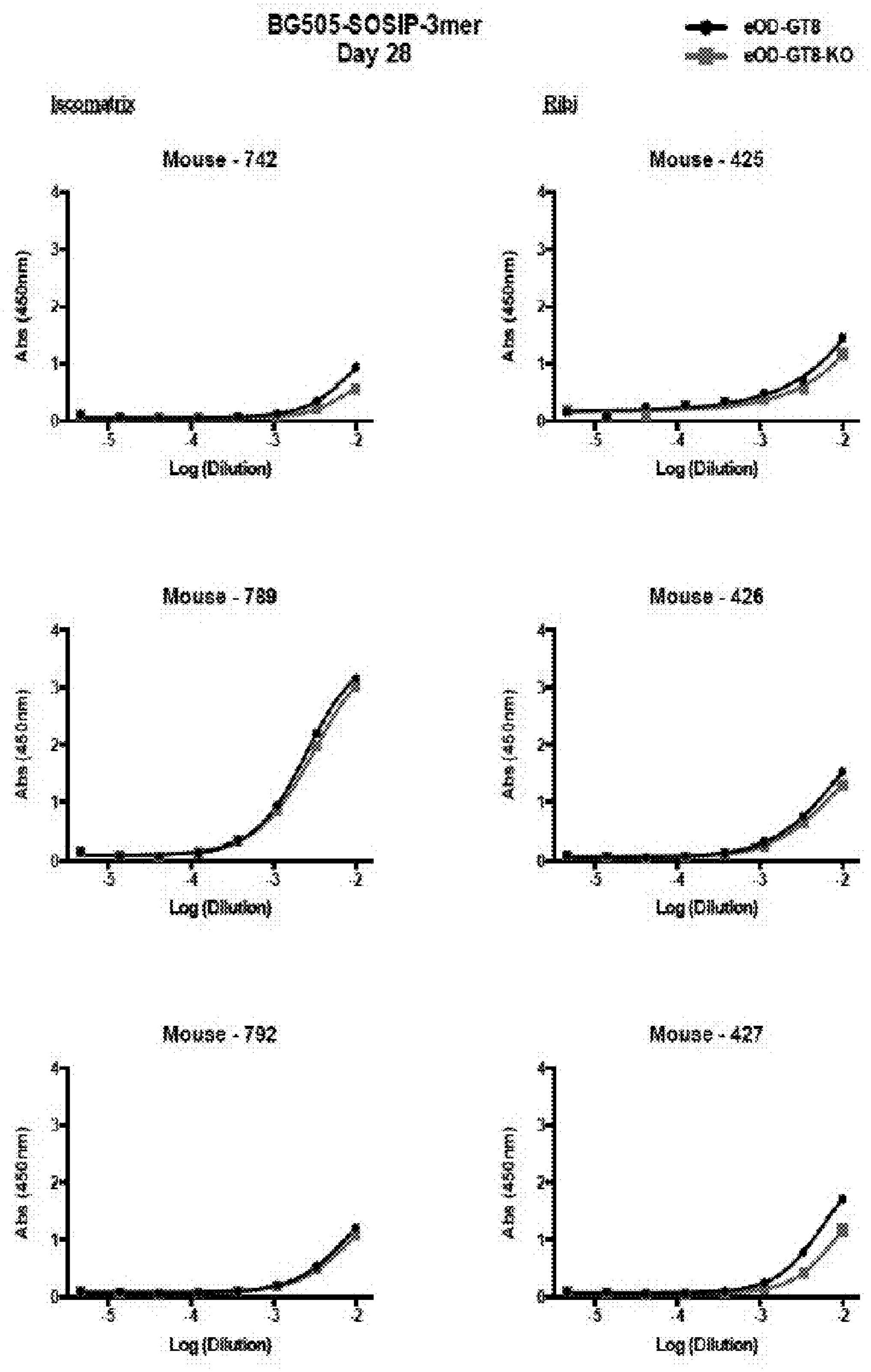
Figure 15N:
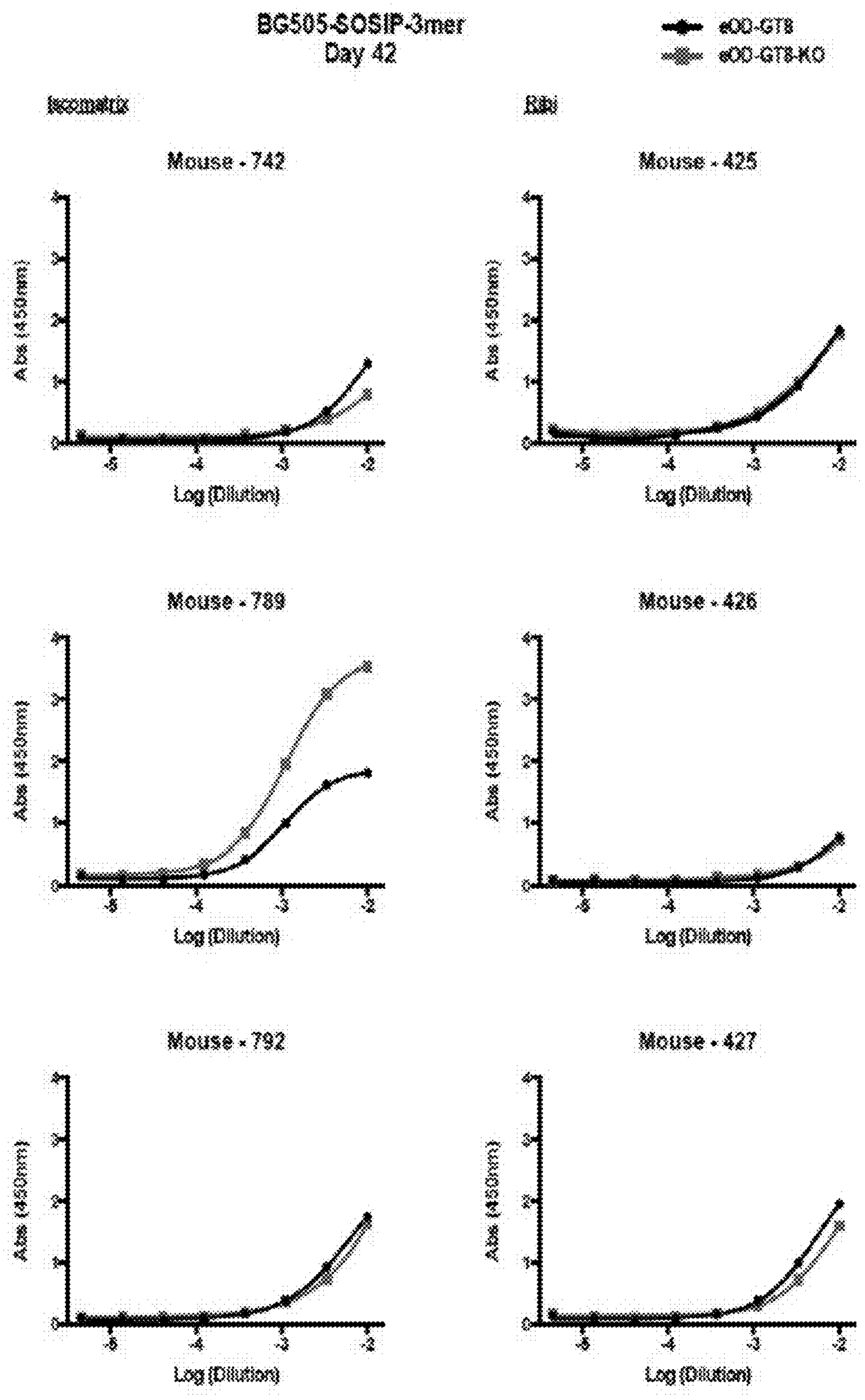
Figure 15O:
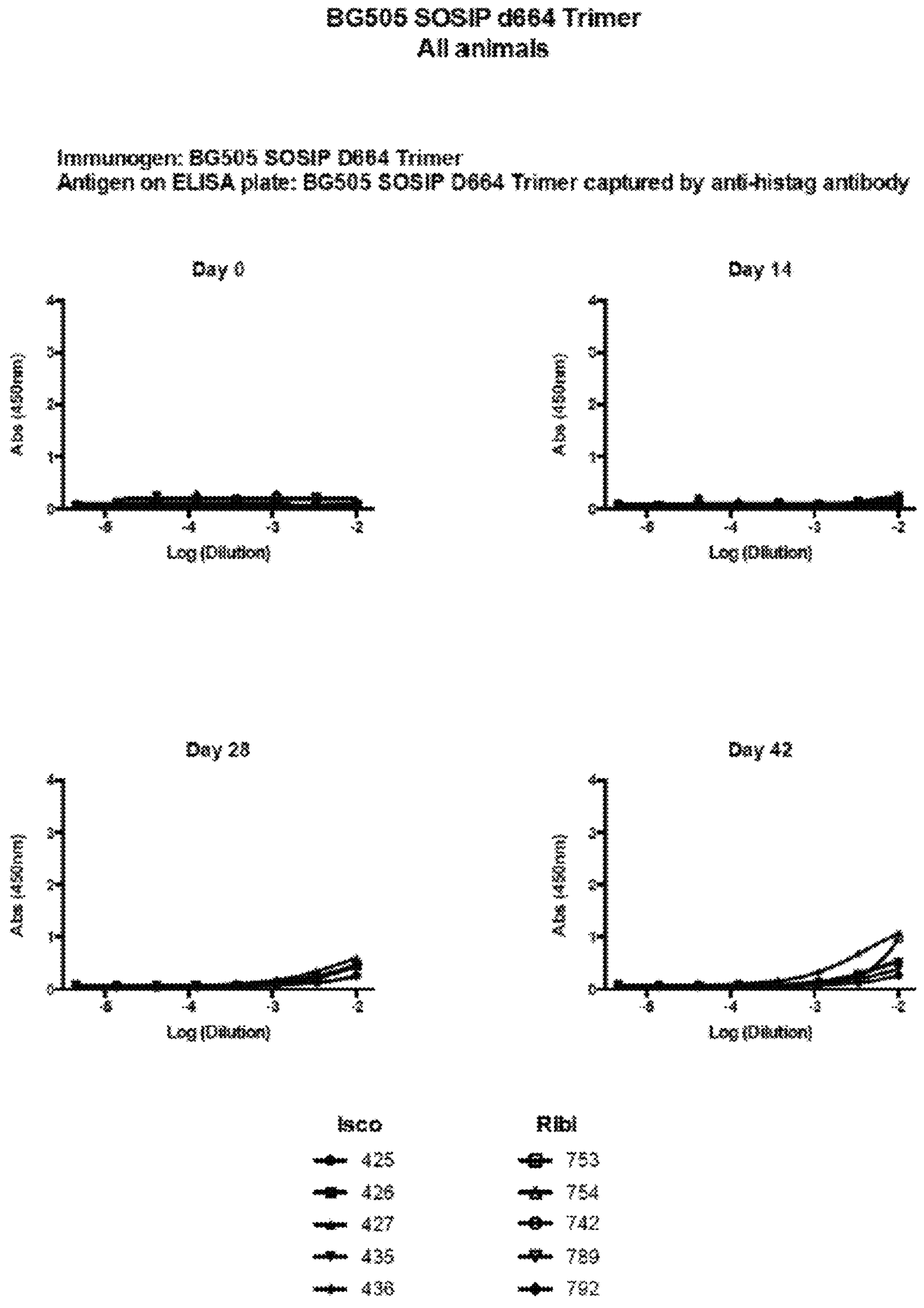

FIG. 15A-O depicts ELISA titrations of serum from immunized mice against eOD-GT8 and eOD-GT8-KO, and against BG505 SOSIP.

Figure 16:
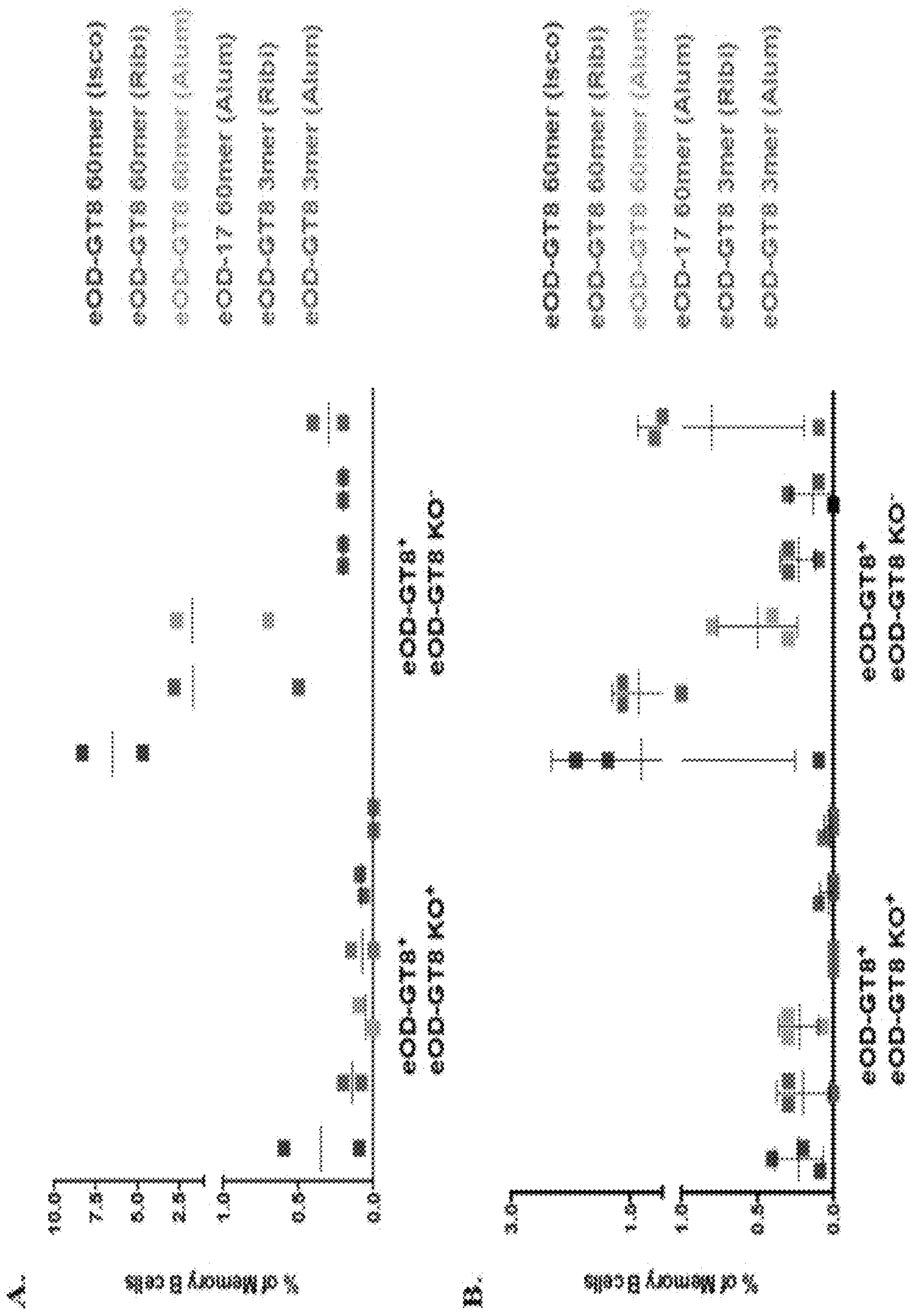

FIG. 16 depicts the frequencies of memory phenotype B cells at day 14. (A) and day 42 (B) that either bind eOD-GT8 but not eOD-GT8-KO (eOD-GT8+/eOD-GT8-KO$^{(-)}$) and hence are epitope specific (right), or that bind both eOD-GT8 and eOD-GT8-KO (eOD-GT8+/eOD-GT8-KO$^{(+)}$) and hence are not epitope specific (left). Data for different immunogen/adjuvant combination are shown. Bars represent mean (N=2) in (A); bars represent mean and standard deviation (N=3) in (B).

Figure 17:
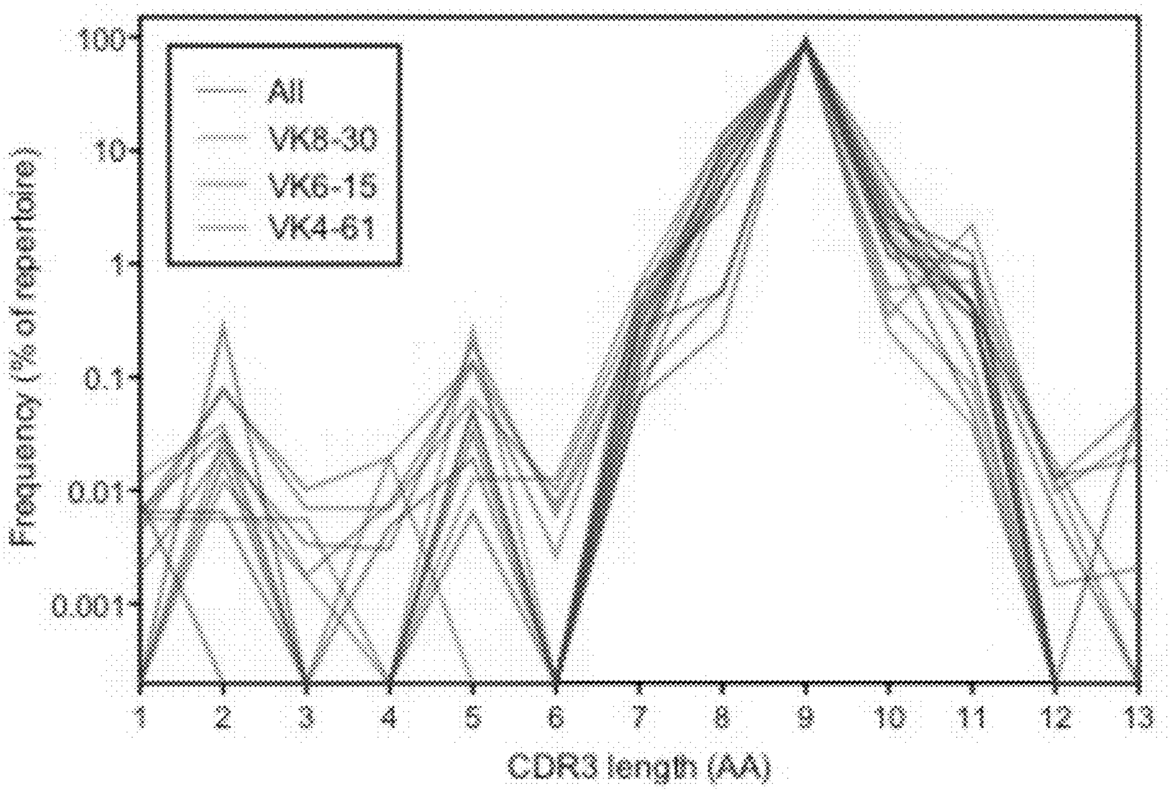

FIG. 17 depicts CDRL3 length distribution for selected Vκ genes from non-immunized mice. CDRL3 length distribution from non-immunized mice, for antibodies derived from the three Vk genes most common in eOD-GT8 60mer-induced Abs isolated by cell sorting. There is no apparent bias in 5 aa CDRL3s within these families.

Figure 18:
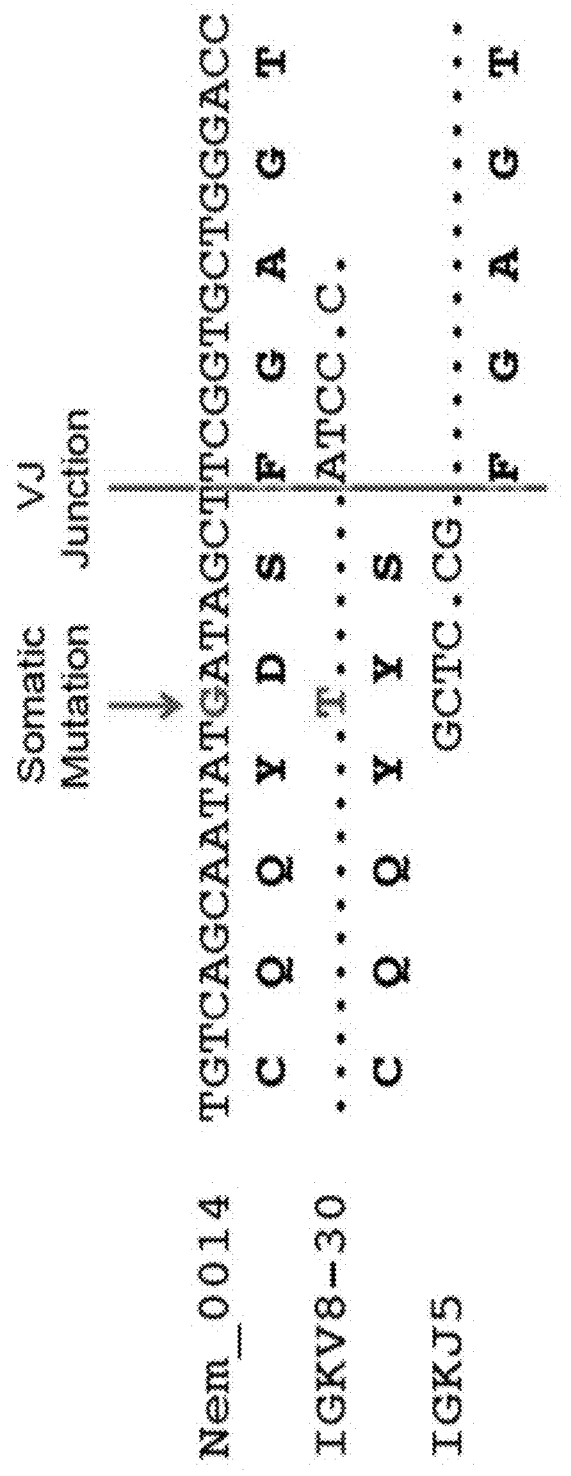

FIG. 18 depicts evidence for productive somatic mutation in the CDRL3 of an eOD-GT8 60mer induced Ab. Example of the T:G mutation found in the CDRL3 codons. The probable VJ junction is marked with a blue line, therefore, the D likely arose through somatic mutation. FIG. 18 discloses SEQ ID NOS 86-91, respectively, in order of appearance.

Figure 19:
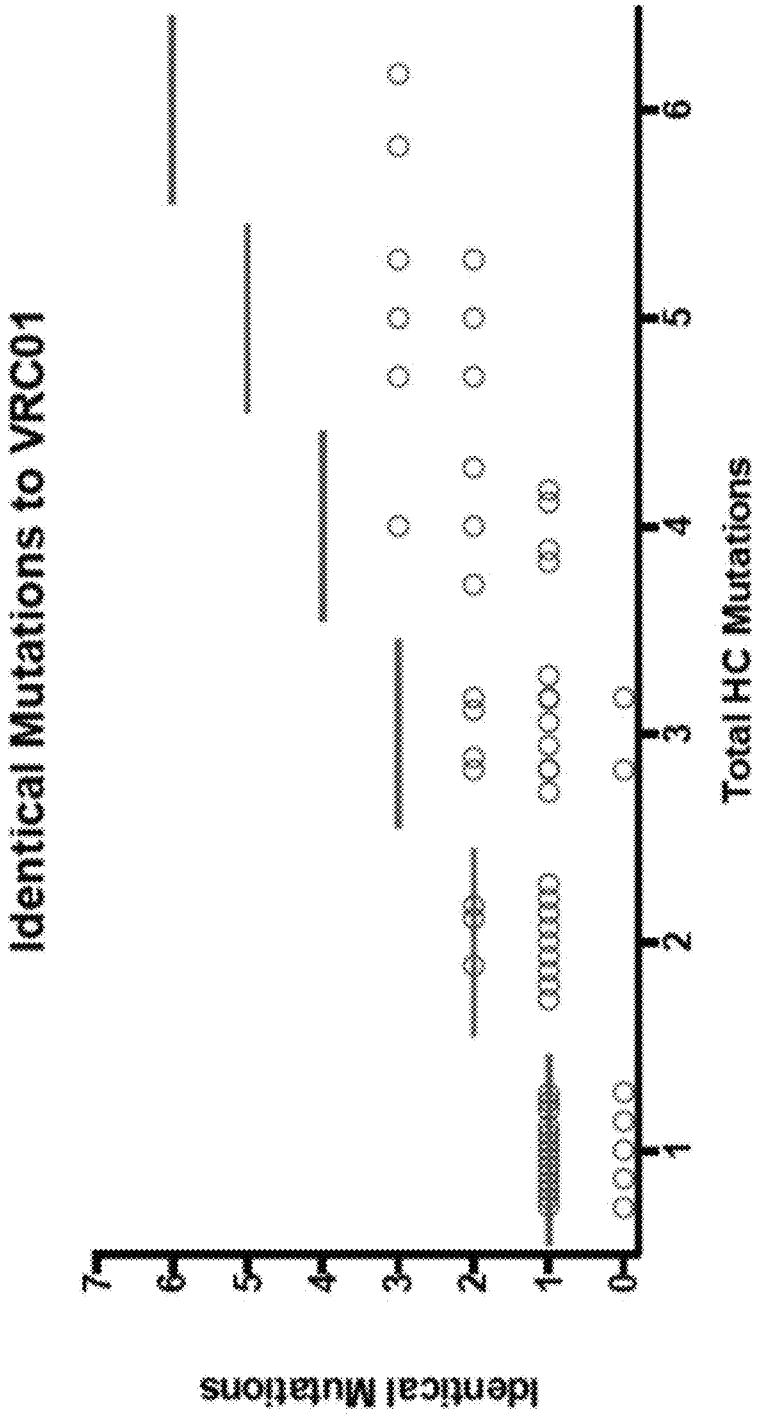

FIG. 19 depicts a plot of the number of VRC01-identical heavy chain mutations in eOD-GT8 60mer induced Abs versus the total number of mutations in those Abs. A total of 61 mutated heavy chain sequences were evaluated for the number of amino acids that match the mutations found in only VRC01 compared to total heavy chain amino acid mutations from gennline. Each circle represents a single heavy chain sequence that was isolated by antigen-specific sorting of memory phenotype B cells.

FIG. 20 depicts the visualization of the structural role of a His residue in germline VRC01, or an Asn residue in mature VRC01, at position 35 in the heavy chain. The H35N mutation commonly found in mutated Abs from the crystal structure of the cGL VRC01 and VRC01.

Figure 21:
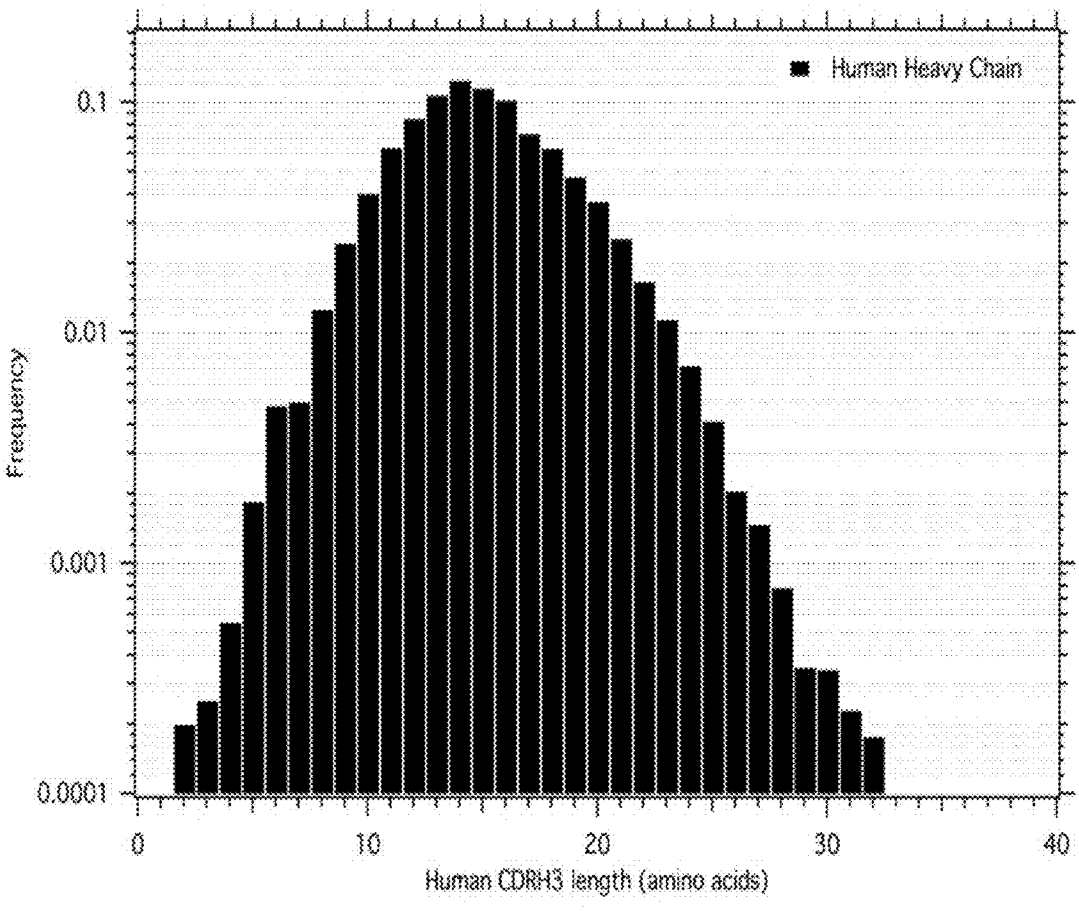

FIG. 21 depicts Human heavy chain CDRH3 length distribution, based on 127,701 antibody sequences from three donors determined by DeKosky et al. (19).

FIG. 22 depicts neutralization measurements of select eOD-GT8 60mer-induced antibodies. Antibodies demonstrating modest affinity to core-e-2CC HxB2 N276D (Nem_0072, Nem_0098, Nem_0103, Nem_0110, Nem_0164) and antibodies with lower affinity to the same protein (Nem_0109, Nem_0071, Nem_080) were tested for neutralization activity against isolates BG505 and HXB2 as well as the corresponding viruses with the glycan site at N276 removed by alanine mutagenesis (N276A).

Figure 23:
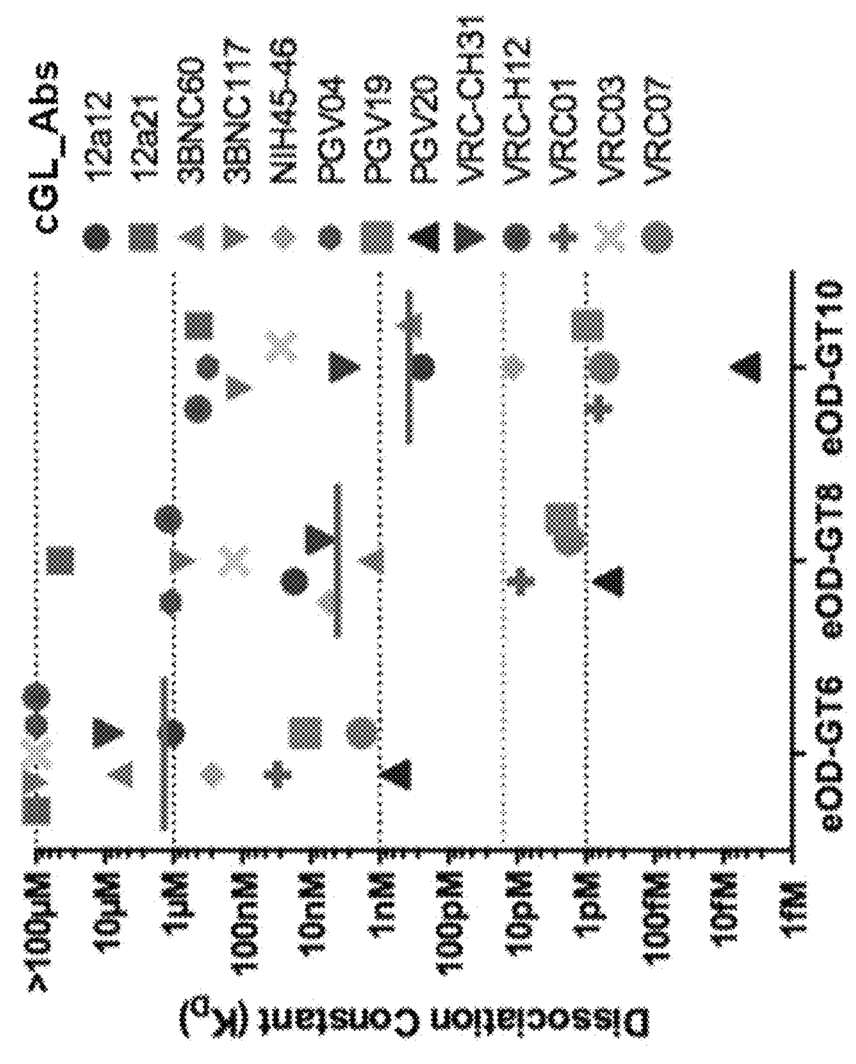

FIG. 23 depicts binding affinities for a large panel of calculated germline precursors of VRC01-class antibodies.

FIG. 24 depicts sorting naïve human B cells using an eOD-GT8 tetramer (avi-tagged and biotinylated eOD-GT8 mixed with a fluorescently-labelled streptavidin), an eOD-GT8_3mer, and an eOD-GT8-KO tetramer (similar tetramer as above but with mutations in the eOD-GT8 epitope to "knock-out" binding by germline VRC01-class antibodies). 19 VRC01-class precursors were isolated from 54 million B cells from 12 different human donors.

Figure 25:
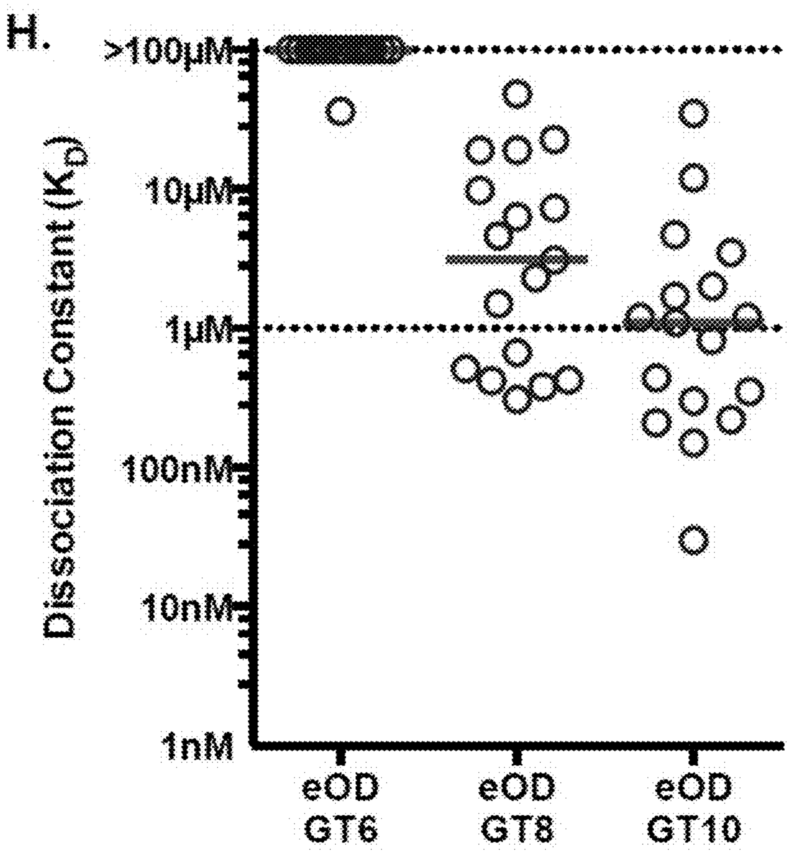

FIG. 25 depicts 19 bona fide VRC01-class precursor antibodies from that experiment were produced as soluble IgG and their binding was tested to eOD-GT6, eOD-GT8, and eOD-GT10; the results from that binding assessment show that while eOD-GT6 had measureable affinity for only one of 19 bona fide precursor antibodies, eOD-GT8 had measureable affinity for all 19 antibodies, with a mean affinity of ~2 μM, and eOD-GT10 also had measurable affinity for all 19 antibodies, with a slightly improved mean affinity of ~1 μM.

Figure 26:
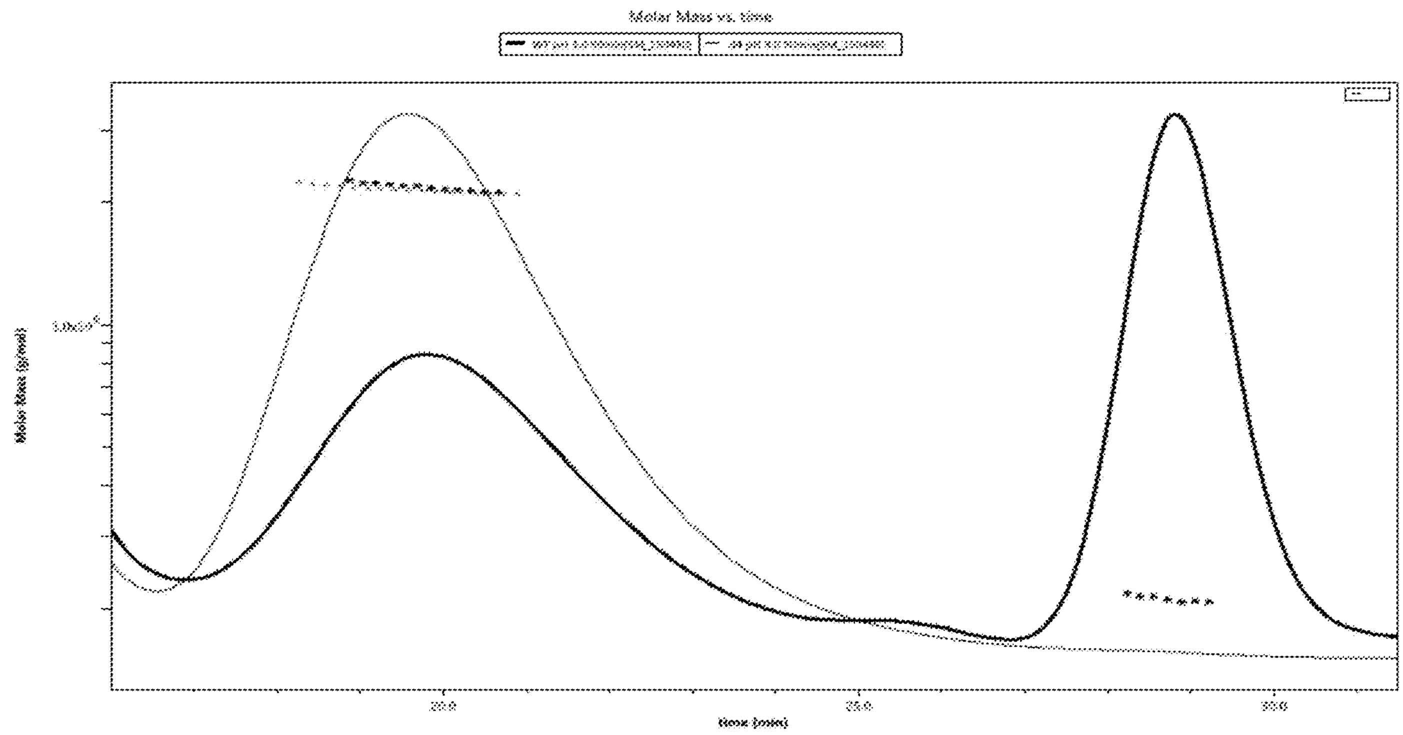

FIG. 26 depicts eOD-GT8-60mer (wild-type) and eOD-GT8-d4-60mer were incubated at pH 3 for 90 minutes and analyzed by SECMALS. Only eOD-GT8-60mer has a pentamer peak after 90 min @ pH 3.

FIG. 27 depicts the observed MW for pH 4-treated samples.

FIG. 28A-D depicts the development of eOD-GT8. (A) Model of germline-reverted VRC01 (gray surface) interacting with eOD-GT7 (cartoon) with the 58 positions subjected to deep mutational scanning shown as magenta, green and orange spheres representing the three mutagenized linear segments. Binding enrichments, the ratio of the frequency of a mutation in the top 10% binding population to the frequency of the same mutation in all cells displaying eOD-GT7, were computed for each mutation on eOD-GT7 for germline-reverted VRC01 and are shown as a heatmap on the right, in which blue indicates unfavorable mutations, red indicates favorable mutations and white indicates the amino-acid residue in eOD-GT7. (B) The combined binding enrichments from independent yeast display screens for 18 germline-reverted VRC01-class bnAbs are shown as a multi-dimensional heatmap in which the color scale from yellow to red indicates increasing favorable average enrichment and the symbol sizes reflect the breadth of enrichment, the number of germline-reverted Abs with enriched binding for each point mutation. If enriched, the eOD-GT7 amino-acid residue is indicated by crosses. (C) Sequence logos depicting amino acids at each of 16 positions in the combinatorial library (top), the sequences selected from the combinatorial library for improved binding to germline-reverted VRC01-class bnAbs (middle), and the final sequence of eOD-GT8 (bottom). (D) SPR dissociation constants measured for both germline-reverted and mature VRC01-class bnAbs against eOD-GT6 and eOD-GT8. Solid blue lines show geometric mean measured over all the data, using the value KD=100 μM for samples with KD>100 uM; dashed blue lines show geometric means computed for the 8 germline-reverted Abs or 12 bnAbs for which KDs<100 μM could be measured for both eOD-GT6 and eOD-GT8. The red dotted line signifies the limit of detection for the SPR instrument (16 μM); KDs below this value were measured by KinExa.

FIG. 29A-L depicts eOD-GT8-binding VRC01-class naïve B cells exist in healthy human donors. (A) eOD-GT8+ naïve CD19+IgG− B cells. (B) eOD-GT8+ B cell frequency (C) and eOD-GT8 KO(−) cells among eOD-GT8+ B cells in individual donors. (D) VH1-2 usage among eOD-GT8+/eOD-GT8 KO(−) sorted B cells (n=173) versus control B cells. VH1-2 (red) allele frequencies are indicated. (E) B cells expressing a 5-aa L-CDR3 among VH1-2+ B cells isolated by eOD-GT8 versus control B cells. (F) L-CDR3 sequence logos of VRC01-class bnAbs (top), VRC01-class naïve precursors (middle), and control B cells (bottom). (G) L-CDR1 lengths of 27 VRC01-class naïve B cells. (H) Light chain V gene usage of 27 VRC01-class naïve B cells. Known VRC01-class bnAb Vκ are red. (I) H-CDR3 lengths of VRC01-class naïve B cells versus control B cells. (J) Total B cells screened and VRC01-class naïve B cells found in 15 individuals. (K) Poisson distribution modeling of the number of VRC01-class naïve B cells. Vertical lines show the 2.5% and 97.5% quantiles. (L) SPR dissociation constants for eOD-GT6 or eOD-GT8 binding to VRC01-class or non-VRC01-class Abs derived from eOD-GT8-sorted human naïve B cells. Solid red lines indicate geometric mean.

Figure 30:
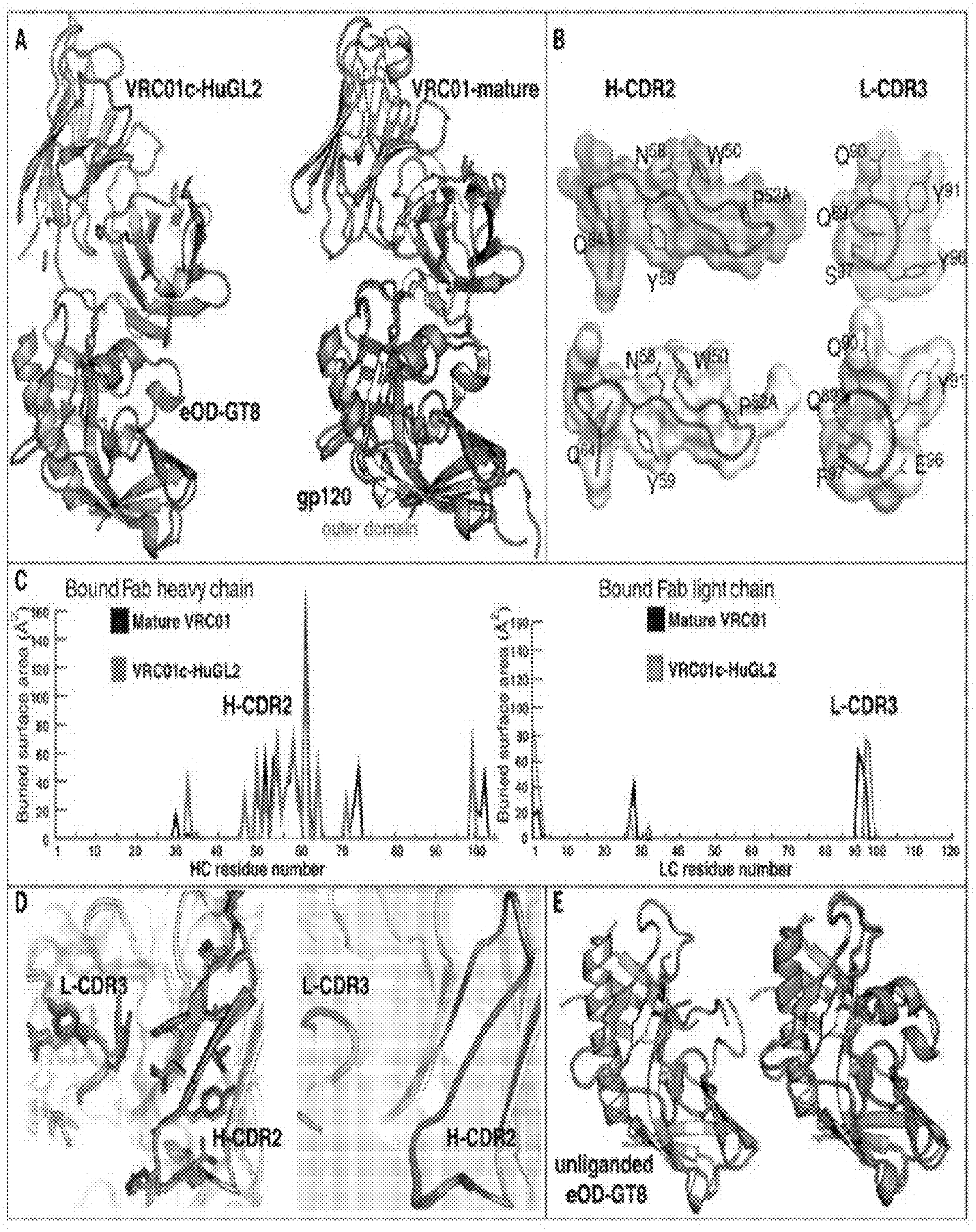

FIG. 30 depicts structural analysis of eOD-GT8 and human germline antibody VRC01c-HuGL2 complex. (A) Crystal structures of VRC01c-HuGL2+ eOD-GT8 (LC: blue, HC: salmon and eOD-GT8: orange) and of mature VRC01+gp120 (PDB ID: 3NGB in white) shown in the same orientation, showing eOD-GT8 superimposed on gp120, and showing only the antibody Fv regions for clarity. (B) Comparison of the H-CDR2 and L-CDR3 conformations from the structures in (A). (C) Comparison of buried surface areas for the VH and VL residues of VRC01c-HuGL2 and mature VRC01+gp120, in their bound forms. (D) Comparison of H-CDR2 and L-CDR3 conformations of unliganded and eOD-GT8-liganded VRC01c-HuGL2 Fab. All atoms of VH and VL were aligned. In the left image, H-CDR2 and L-CDR3 are shown as sticks; in the right image the CDRs are shown according to B-factors reporting local structural flexibility using a relative scale in which increasing wire thickness and warmness of color (blue to red) indicates increasing mobility. (E) Crystal structure of unliganded eOD-GT8 shown in cartoon and surface (left) and a superposition of unliganded and VRC01c-HuGL2-bound forms of eOD-GT8 (right; Cα RMSD=0.4 Å).

Figures 31A, 31B, 31C:
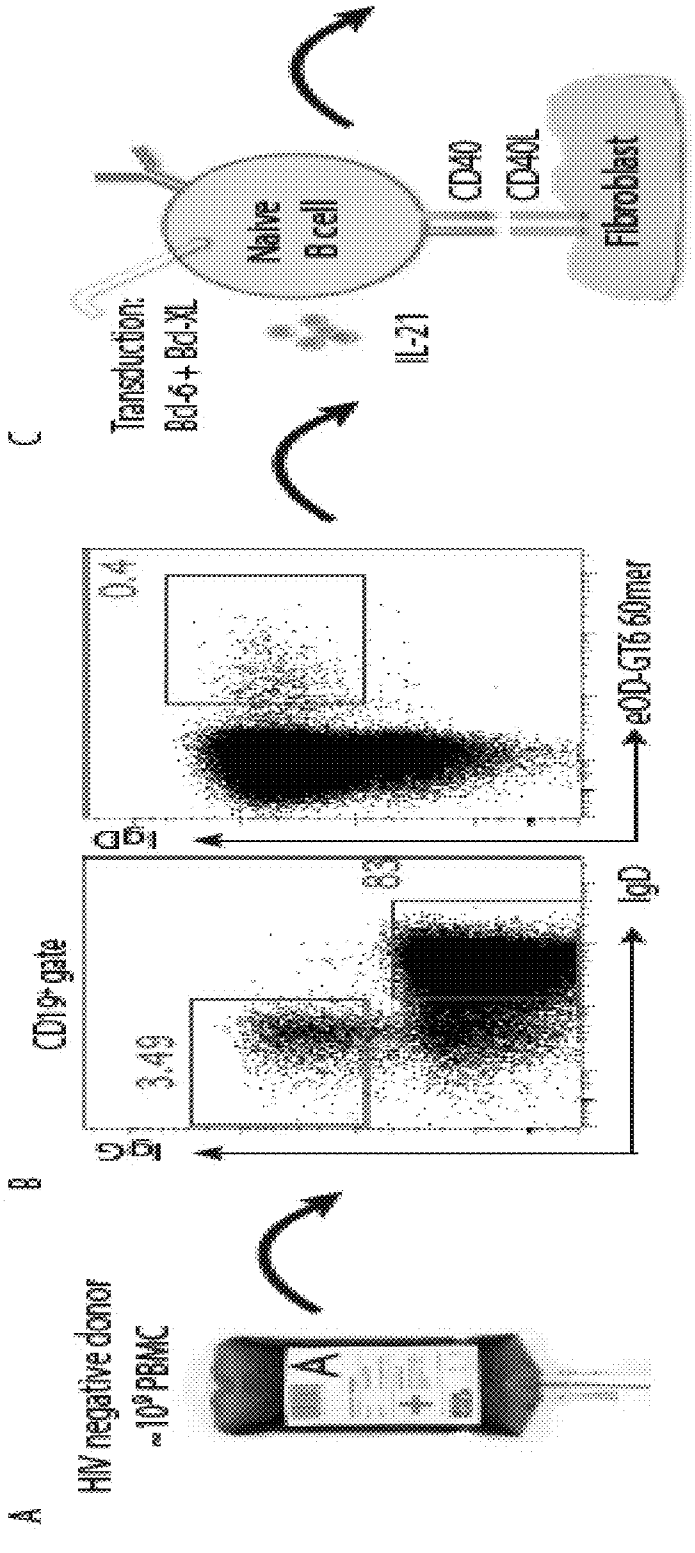
Figure 31F:
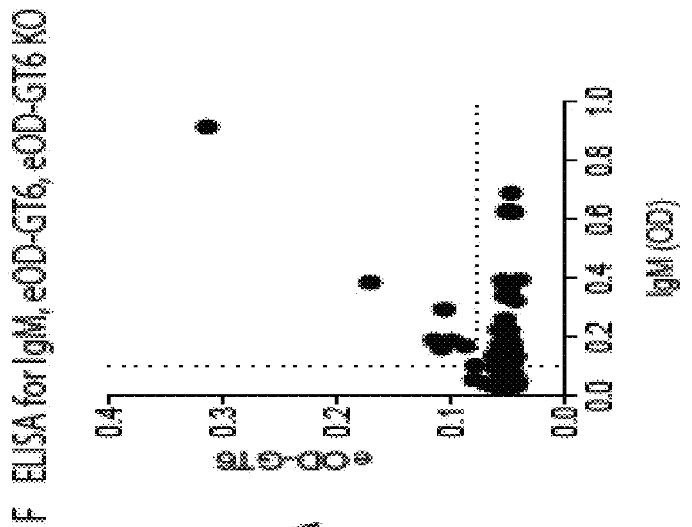
Figure 31E:
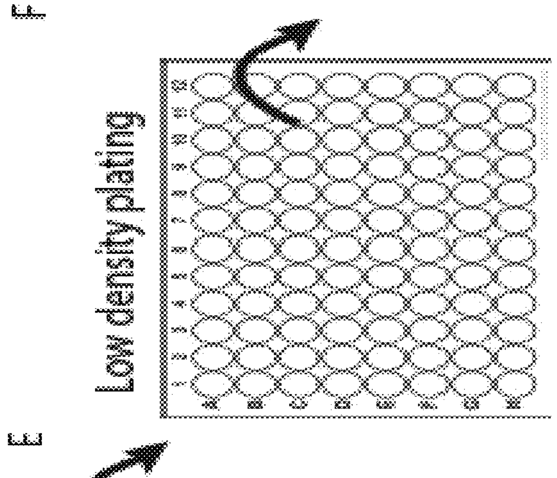
Figure 31D:
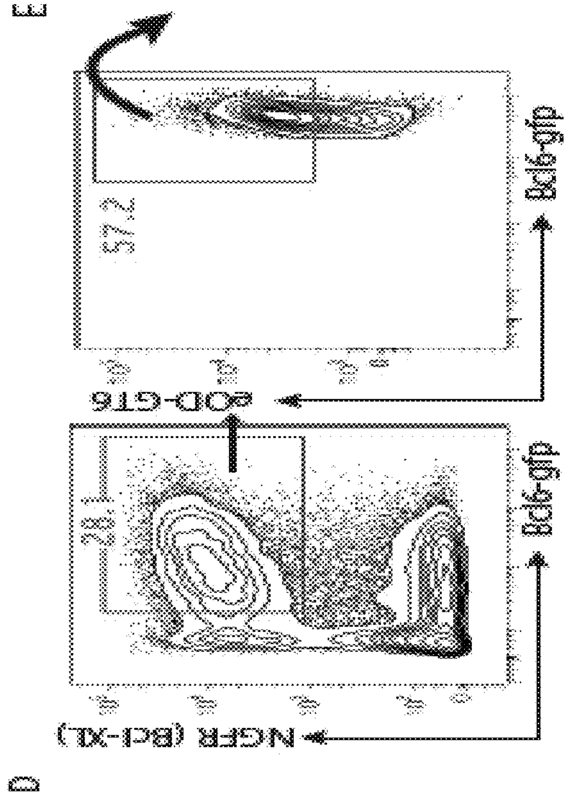
Figure 31H:
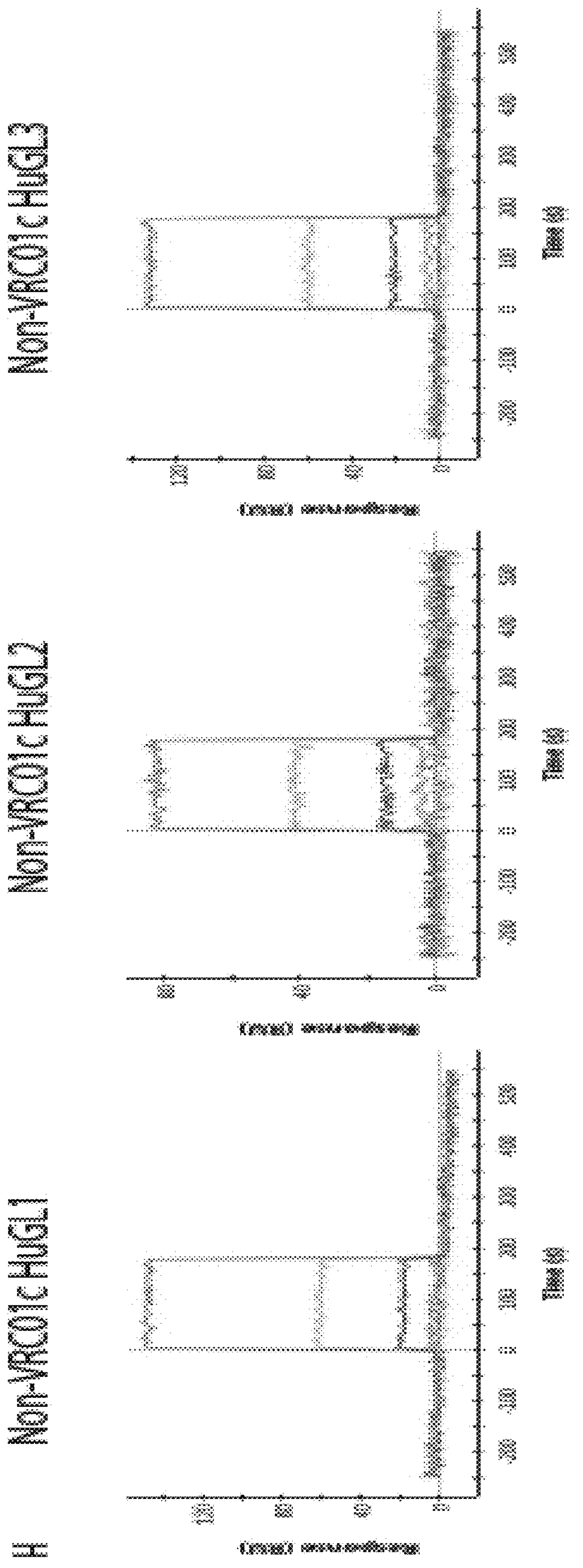
Figure 32B:
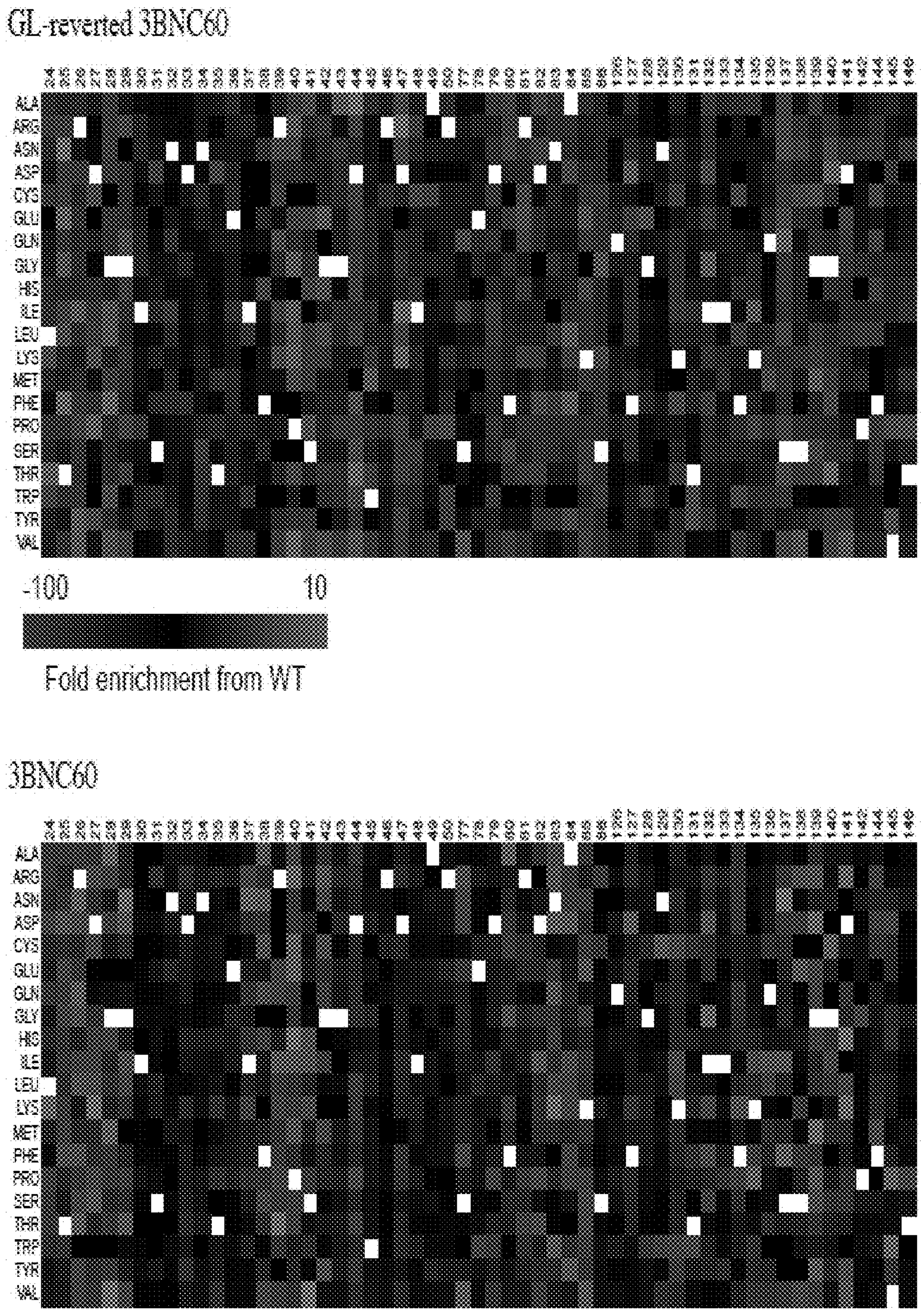
Figure 32C:
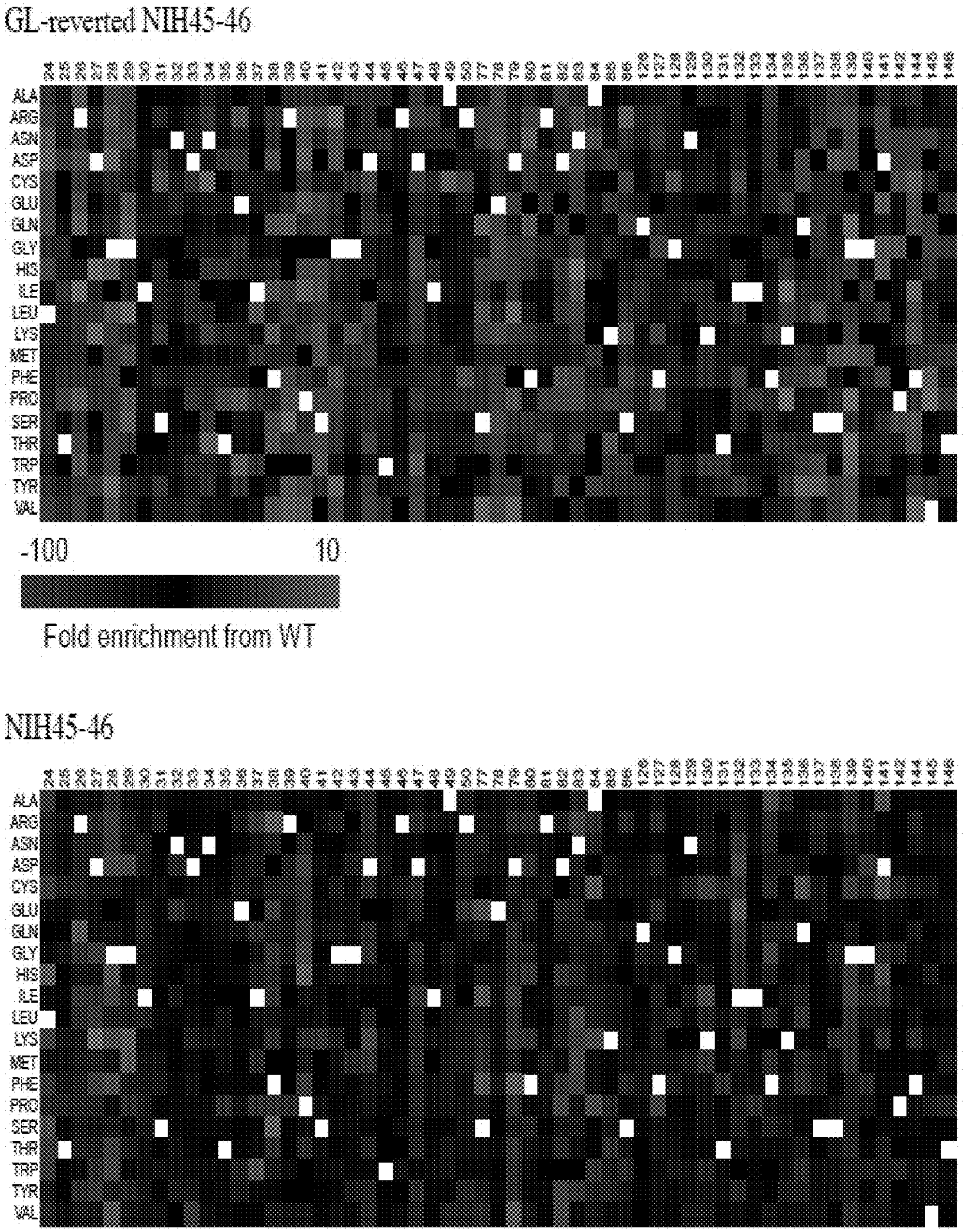
Figure 32D:
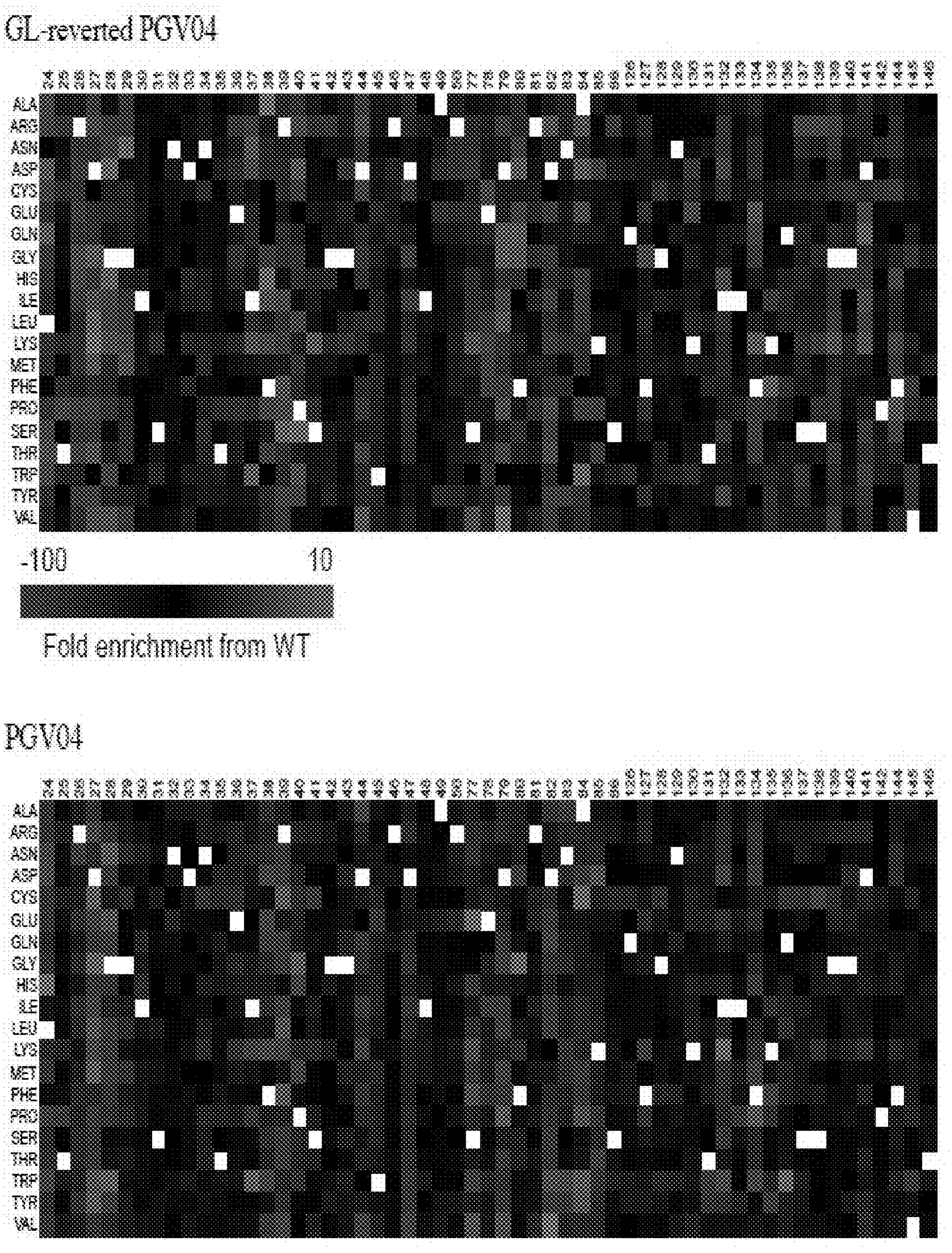
Figure 32F:
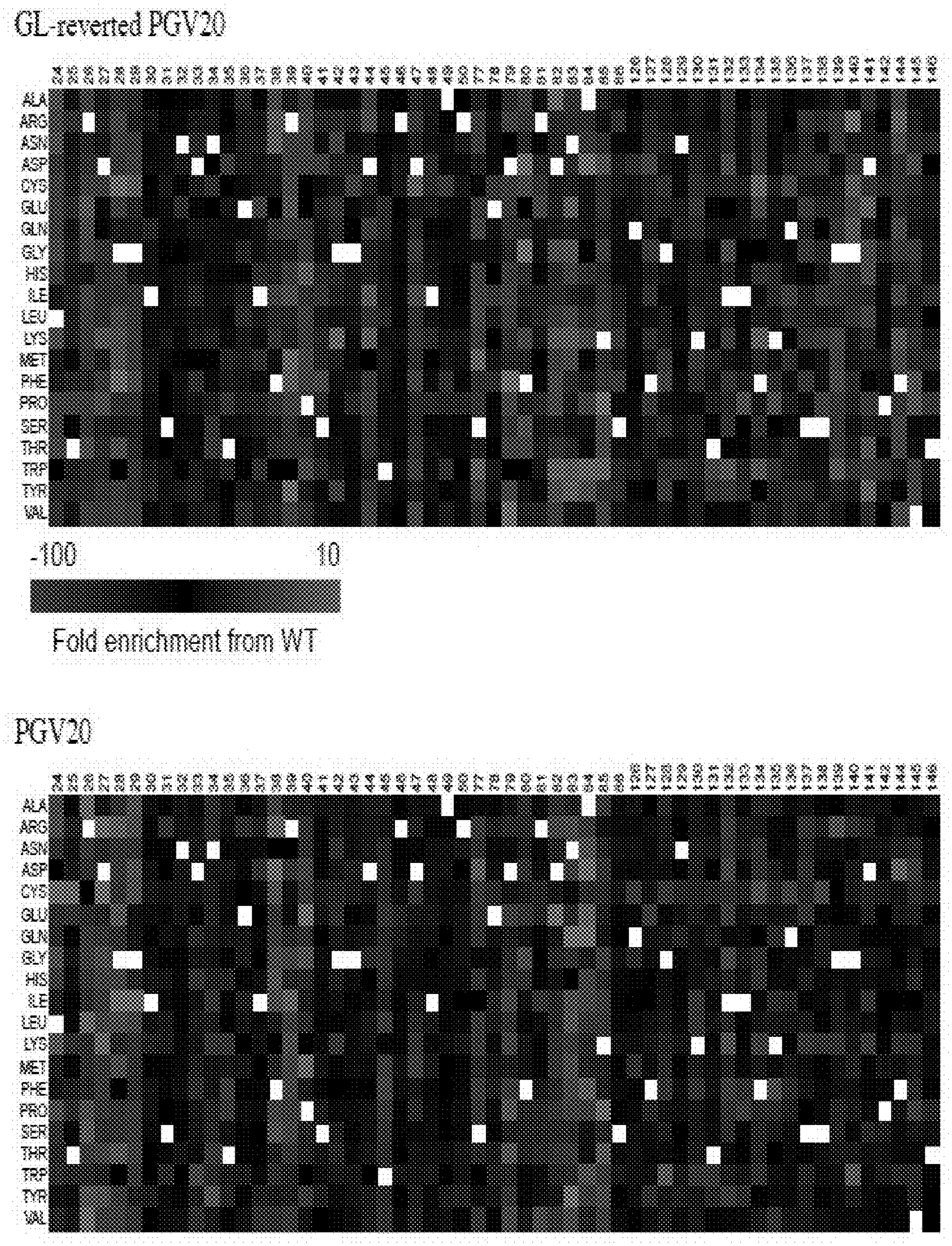
Figure 32G:
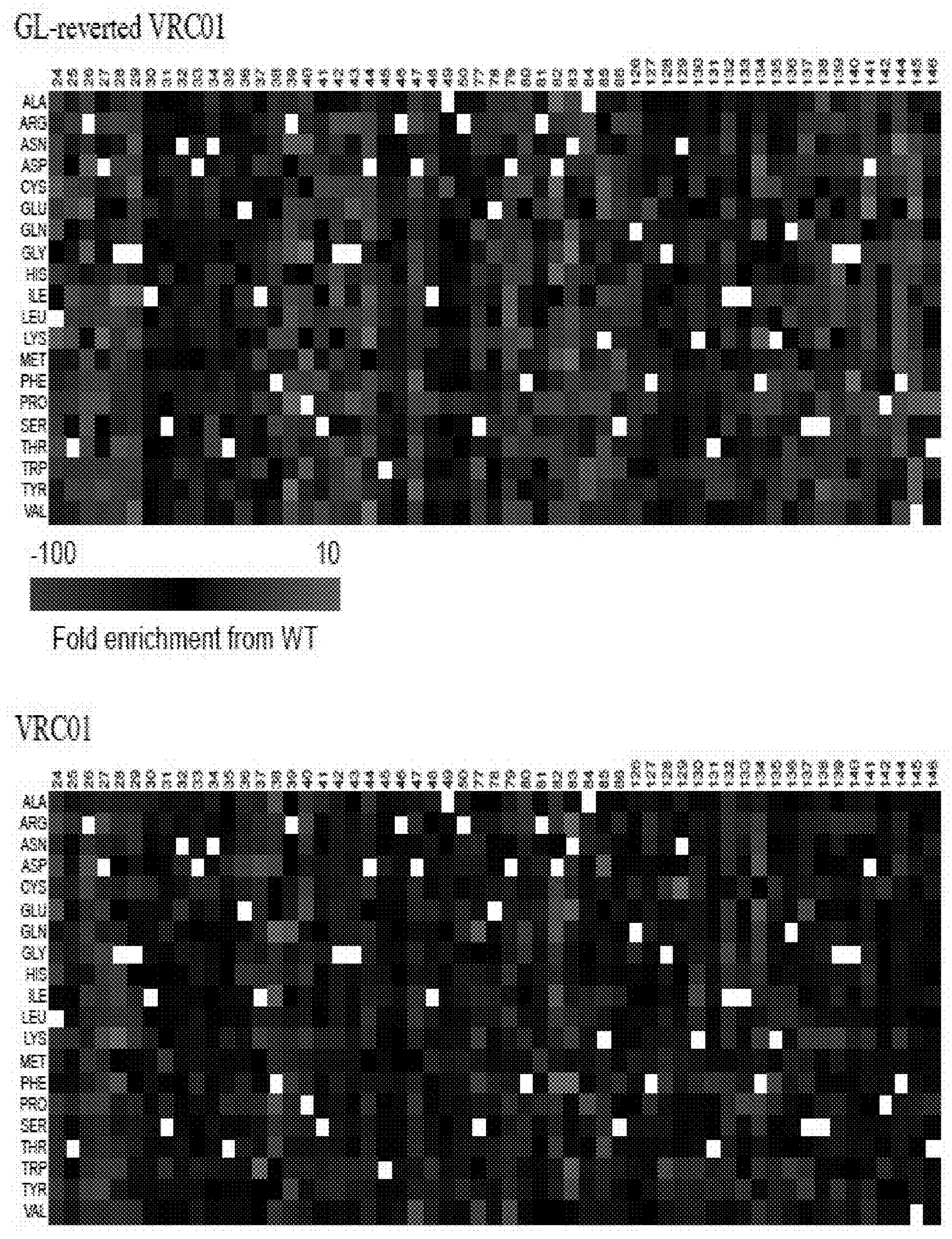

FIG. 31A-H depicts screening and isolation of eOD-GT6+ B cells using a two-stage, multiple validation methodology. (A-B) The first stage of screening utilized FACS. (A) CD19+ B cells were selected by magnetic beads from large numbers of PBMC from individual HIV seronegative donors. The total number of B cells was 9.5 million naïve B cells. (B) B cells were labeled with an eOD-GT6 probe and anti-CD19 and IgD. Anti-IgG, CD4, CD8, CD14, CD16, and LIVE/DEAD dye were used to exclude non-specific events. eOD-GT6 60mer+ IgD+ B cells were sorted. (C-F) The second phase of screening involved screening supernatants from single IgM producing B cells. (C) FACS probe-positive naïve B cells were activated in vitro and transduced with Bcl6 and Bcl-XL. Cells were cultured for 3-5 days on CD40L expressing L cells and IL-21. (D) Cells were rescreened for eOD-GT6 60mer specificity by FACS (and the surrogate marker ΔNGFR and GFP for transduced cells). (E) Then Bcl6+BclXL+ eOD-GT6+ cells were sorted at limiting dilution (1-4 cells per well) in 96 well plates with CD40L expressing L cells and IL-21. (F) Cells were grown for 12-14 days and supernatants were tested by multiple ELISAs to determine specificity for eOD-GT6 and not eOD-GT6 KO, and not exhibiting polyreactivity. (G) BCR sequences were determined. Four B cell clones were chosen for Ab synthesis; three showed detectable binding to eOD-GT6 monomer. FIG. 31G discloses SEQ ID NOS 92-97, respectively, in order of appearance. (H) Affinities were measured by fitting equilibrium titrations.

FIG. 32A-H depicts enrichment profiles of eOD-GT7 binding to germline reverted VRC01-class Abs and VRC01-class bnAbs.

Figure 33:

FIG. 33 depicts sequence logo diagrams of the 16 positions in the combinatorial sorts used to generate eOD-GT8. Shown are the results from 8 $GL_{Rev}$ Abs and 8 bnAbs, with a display only population as a control.

FIG. 34 depicts sequence alignment of eOD-GT6, eOD-GT7 and eOD-GT8, highlighting the mutations from eOD-GT6. FIG. 34 discloses SEQ ID NOS 98-115, respectively, in order of appearance.

Figure 35:
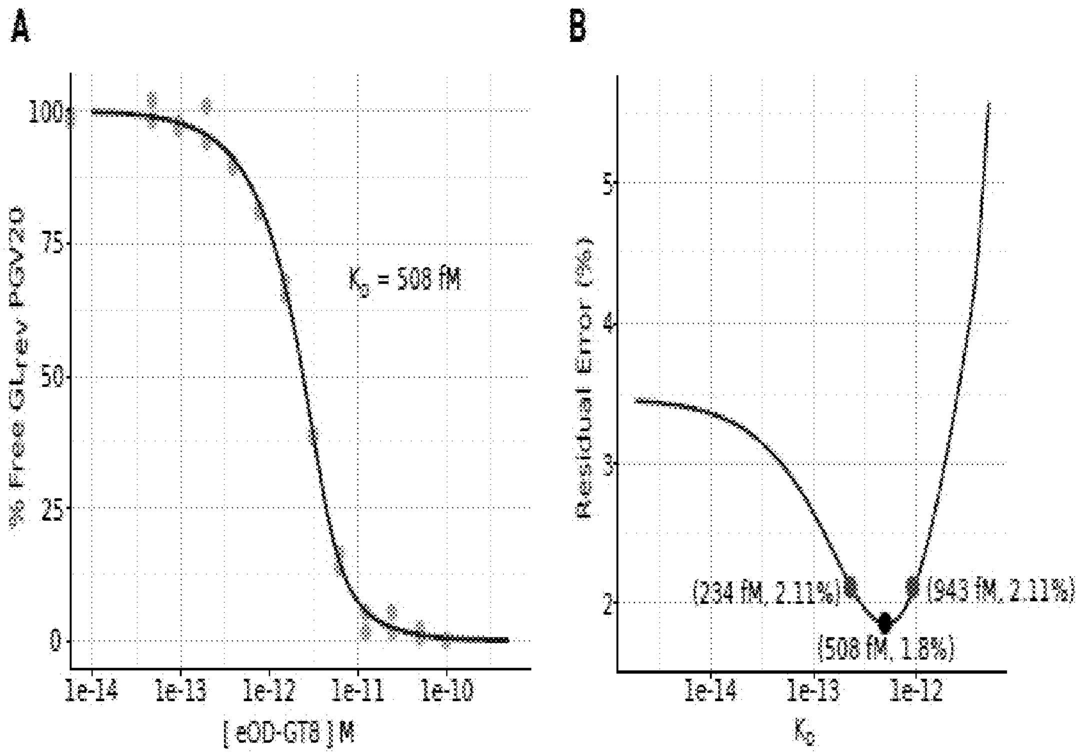

FIG. 35 depicts binding of $GL_{Rev}$ PGV20 to eOD-GT8 by KinExA. A. An equilibrium KinExA binding experiment. Titrations of eOD-GT8 into a solution of constant $GL_{Rev}$ PGV20 were equilibrated, then the percent free $GL_{Rev}$ PGV20 was measured by flowing the titrations over eOD-GT8 coated beads and detecting Abs left over on the beads. The data is fit to a 1:1 binding model. B. the residual error in the fit of the KD (shown as a black circle, 508 fM) and the 95% confidence interval for the KD (shown as red circles, 234 fM and 943 fM).

Figure 36:
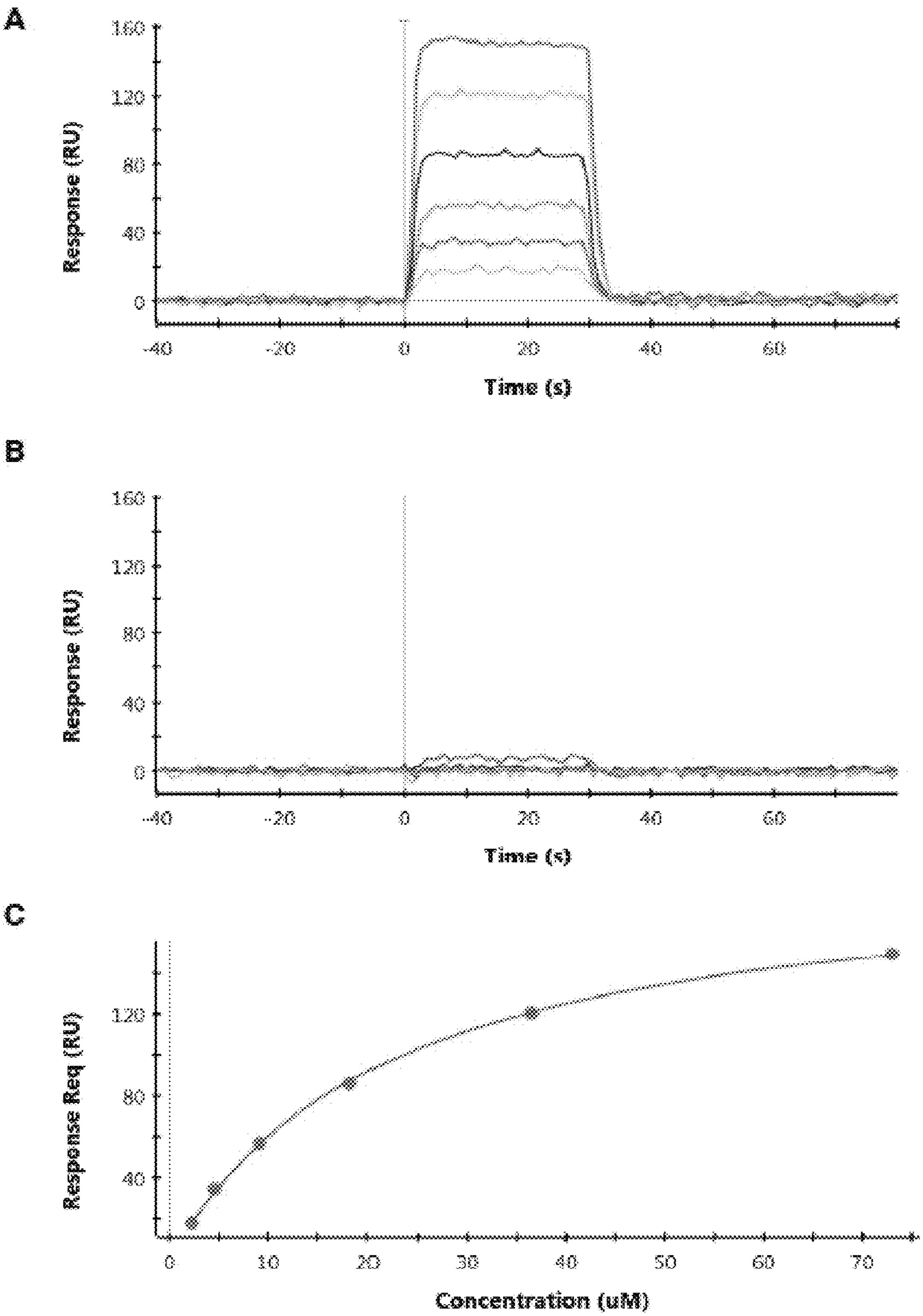

FIG. 36 depicts SPR sensorgrams and equilibrium titration data for VRC01c-HuGL1 binding to eOD-GT8 and eOD-GT8-KO. A. VRC01c-HuGL1 binding to eOD-GT8. B. VRC01c-HuGL1 binding to eOD-GT8-KO. C. Equilibrium titration for VRC01c-HuGL1 binding to eOD-GT8; the fit line corresponds to a KD of 22 μM.

Figure 37:
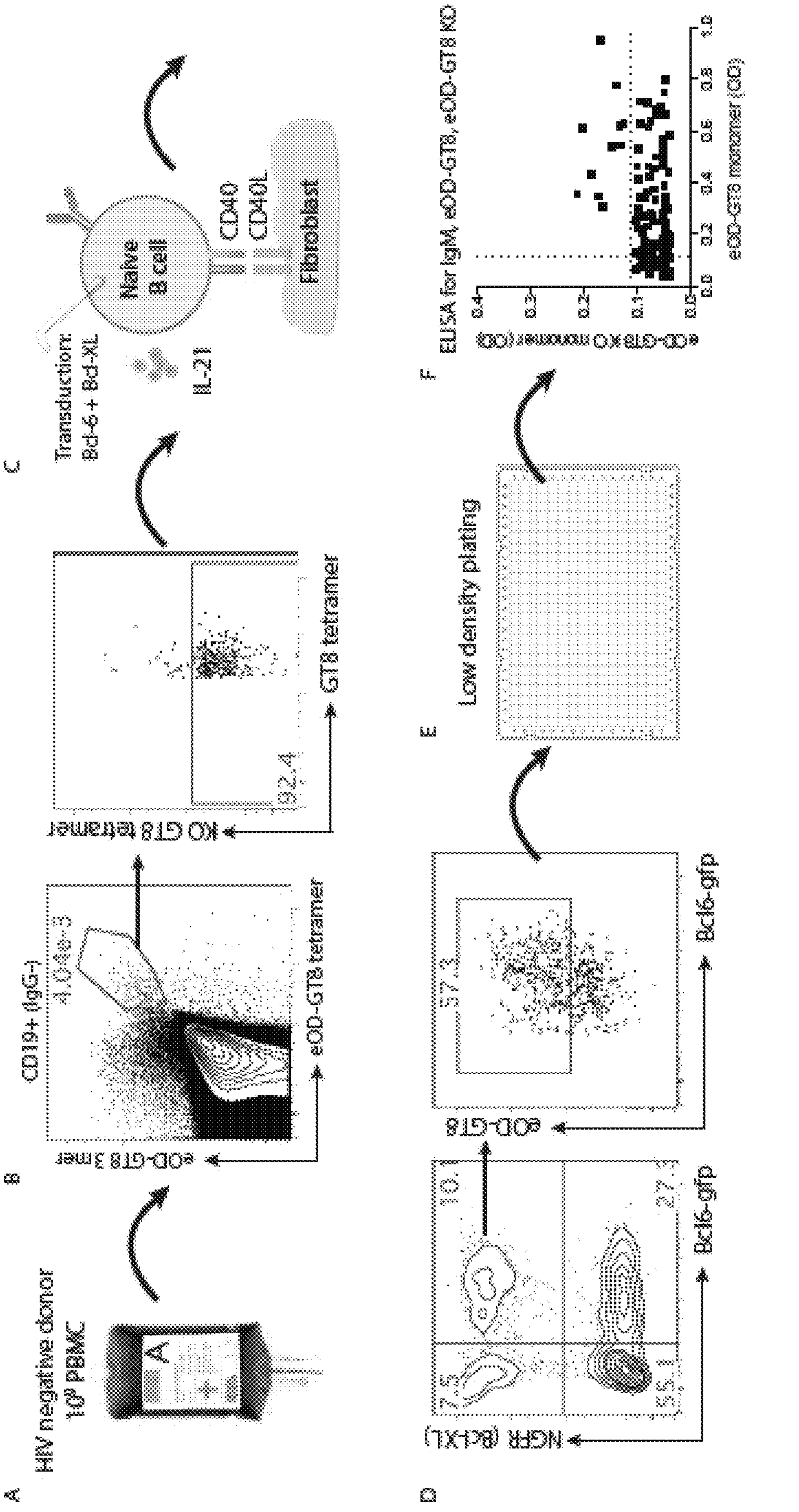

FIG. 37 depicts a schematic for the screening and isolation of eOD-GT8+ B cells using a two-stage, multiple validation methodology. (A-B) The first stage of screening utilized FACS. (A) $CD19^+$ B cells were selected by magnetic beads from large numbers of PBMC from individual HIV seronegative donors. The total number of B cells was 7 million naïve B cells. (B) B cells were labeled with eOD-GT8 probes and anti-CD19. Anti-IgG, CD4, CD8, CD14, CD16, and LIVE/DEAD dye were used to exclude non-specific events. eOD-GT8 3mer and eOD-GT8 tetramer double positive B cells were gated. Within that gated populations, binding to eOD-GT8 KO tetramer was assessed. eOD-GT8 3mer+ eOD-GT8 $tet^+$ eOD-GT8 KO− B cells were sorted. (C-F) The second phase of screening involved screening supernatants from single IgM secreting B cells. (C) FACS probe-positive naïve B cells were activated in vitro and transduced with Bcl6 and Bcl-XL. Cells were cultured for 3-5 days on CD40L expressing L cells and IL-21. (D) Cells were rescreened for eOD-GT8 specificity by FACS (eOD-GT8 3mer and the surrogate markers ΔNGFR and GFP for transduced cells). (E) Then Bcl6+ BclXL+ eOD-GT8+ cells were sorted at limiting dilution (1-4 cells per well) in 384 well plates with CD40L expressing L cells and IL-21. (F) Cells were grown for 12-14 days and supernatants were tested by multiple ELISAs to determine specificity for eOD-GT8 and not eOD-GT8 KO, and not exhibiting polyreactivity.

Figure 38:
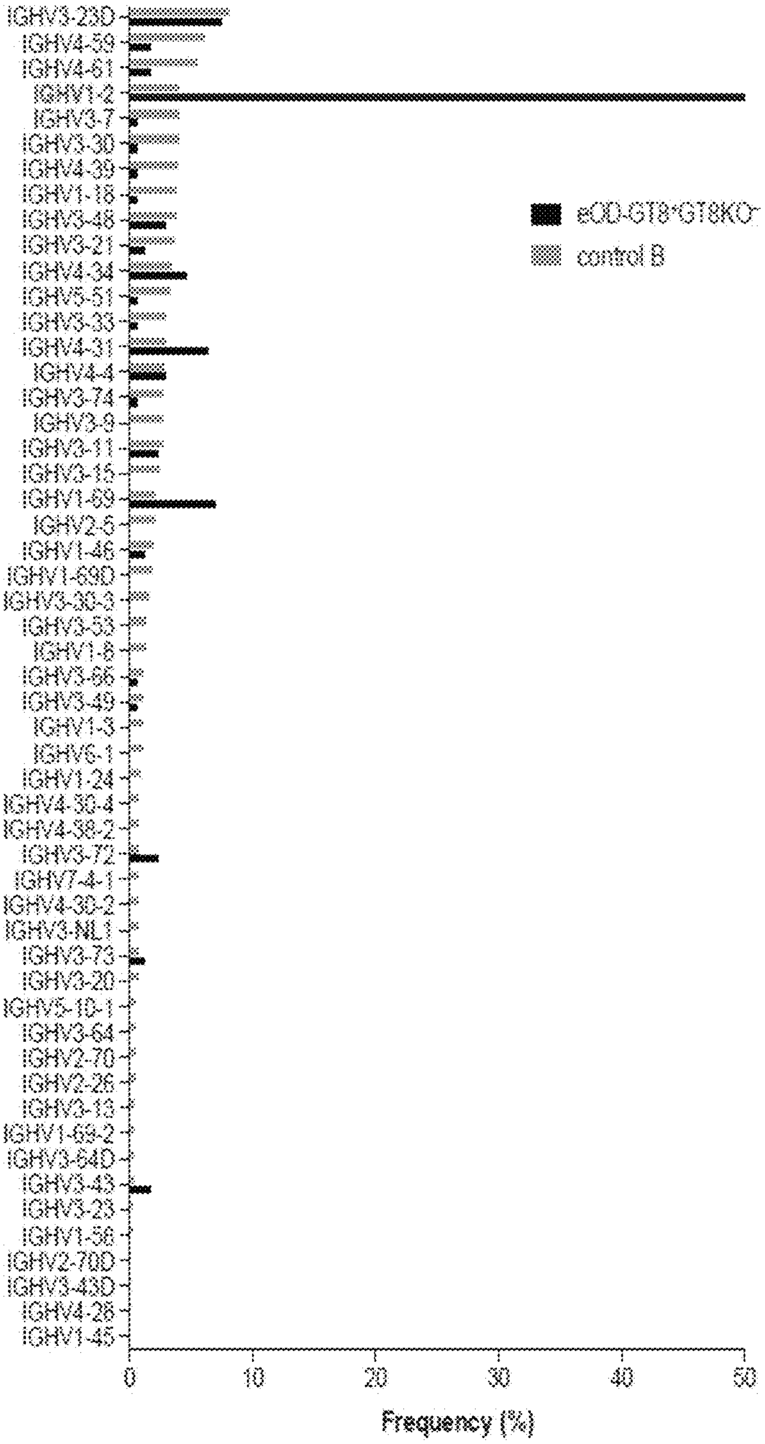

FIG. 38 depicts heavy chain variable gene usage among eOD-GT8 specific B cells. Frequency of heavy usage among 173 eOD-GT8 specific B cells (gray; VH1-2 highlighted in red) is compared to a control set of memory B cells (black). This is an alternate representative of the data shown in FIG. 2D, identifying each of the heavy chain variable gene families.

Figure 39:
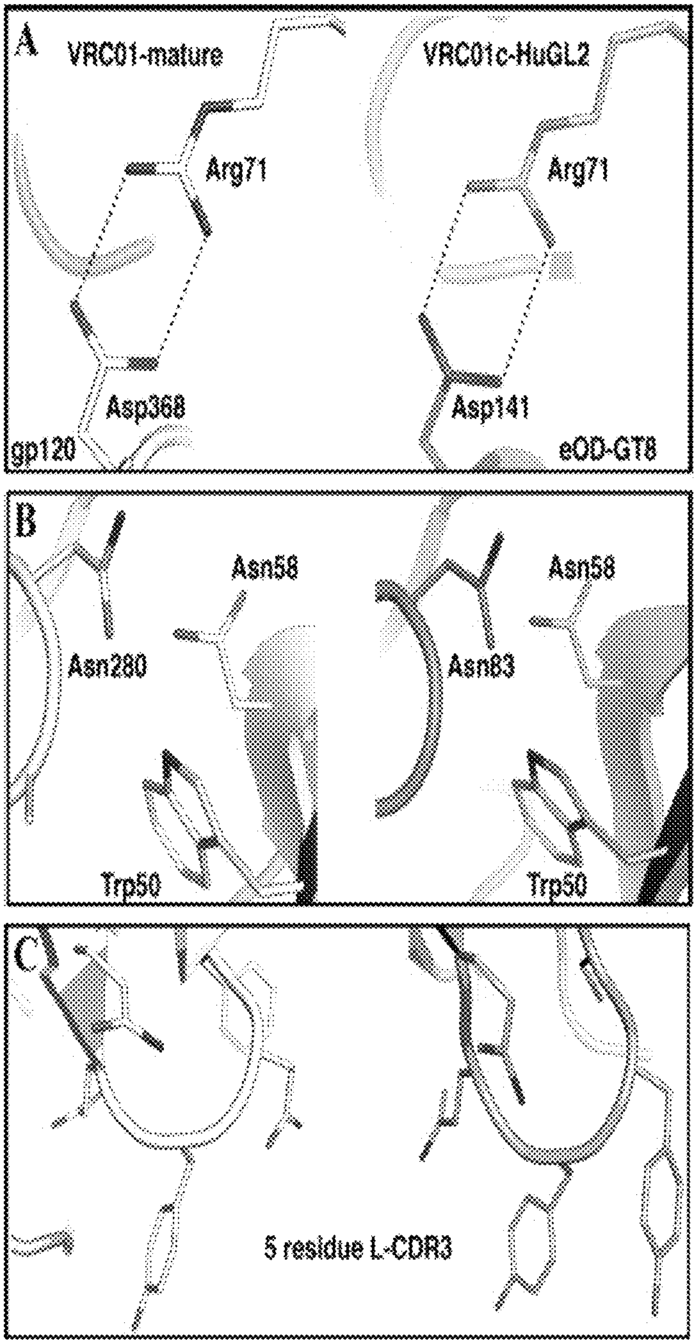

FIG. 39 depicts VRC01-class signatures present in VRC01c-HuGL2 Fab. The VRC01c-HuGL2 Fab features most of the common interactions observed in mature VRC01-class antibodies. This figure compares mature VRC01 antibody bound to gp120 (PDB id: 3NGB) and illustrates (A) the conserved conformation and hydrogen bond formed between the Arg71 of the heavy chain with the Asp368 on gp120 (Asp141 on eOD-GT8), (B) Conserved conformations of Asn58 and Trp50 on the antibody heavy chains that form hydrogen bonds with Arg456 and Asn 280 on gp120 (corresponding to Arg26 and Asn83 on eOD-GT8), respectively, and (C) The 5-residue L-CDR3.

Figure 40:
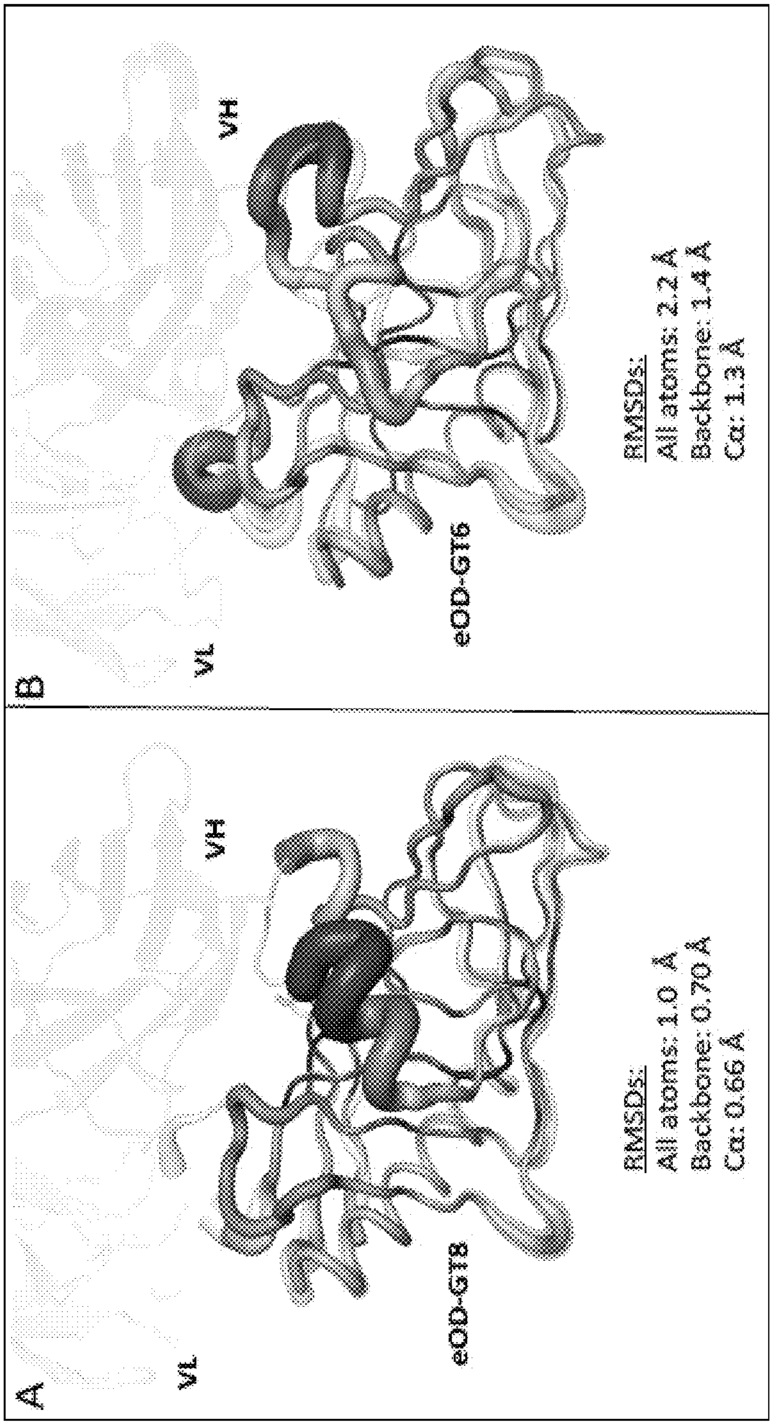

FIG. 40 depicts a comparison of the crystal structures of eOD-GT8 (panel A) and eODGT6 (panel B), unliganded and bound to VRC01-class Fab. (A) Superposition of eOD-GT8minglyc bound to HuGL2 (in grey) and unbound eODGT8minglyc (rainbow coloured). (B) Superposition of eOD-GT6 (in wheat) bound to the GL-VRC01 (grey) (PDB ID: 4JPK) and unbound eOD-GT6 (rainbow coloured) (PDB ID: 4JPJ). Flexibility in each structure (B-factor) is represented by different thickness and colors of the backbone. The thicker and redder the backbone, the more flexible it is. Conversely, the thinner and bluer the backbone, the less intrinsic flexibility. Corresponding RMSD values are depicted below the structures. RMSD values are based on alignment of the following eOD residue ranges, which are present in all four structures: 1–28+32–138+140–169. The unbound eOD-GT8 has smaller RMSD values to antibody-bound eOD-GT8 (panel A), when compared with unbound eOD-GT6 to antibody-bound eOD-GT6 (panel B). Mutations that led to eOD-GT8 from eOD-GT6 thus appear to further stabilize the Fab-bound state.

Figure 41:
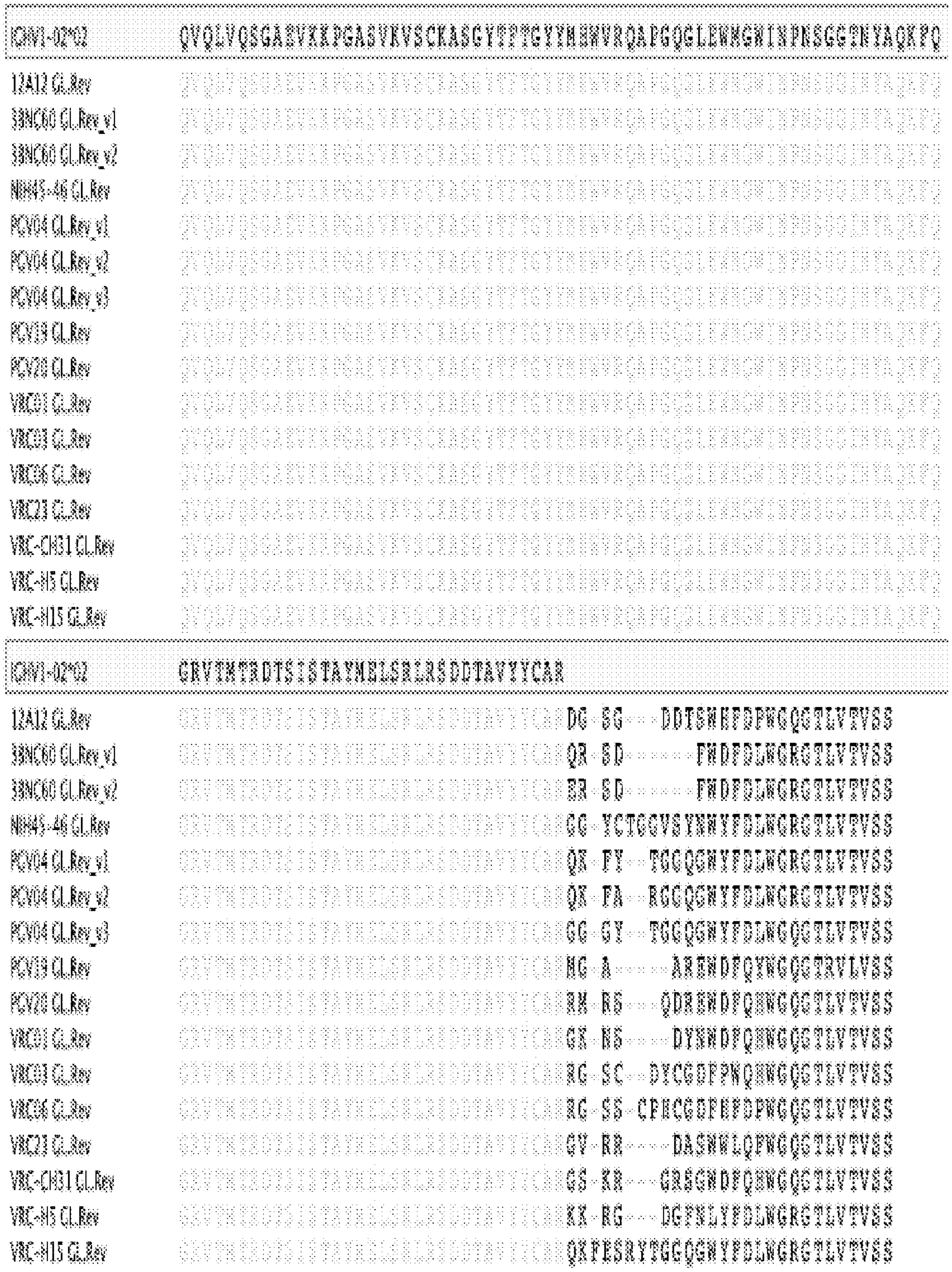

FIG. 41 depicts germline-reverted heavy chain sequences. The heavy chain sequences for the $GL_{Rev}$ Abs used in the development of eOD-GT7 and eOD-GT8 (see Table 15 for pairings). FIG. 41 discloses SEQ ID NOS 116-132, respectively, in order of appearance.

Figure 42:
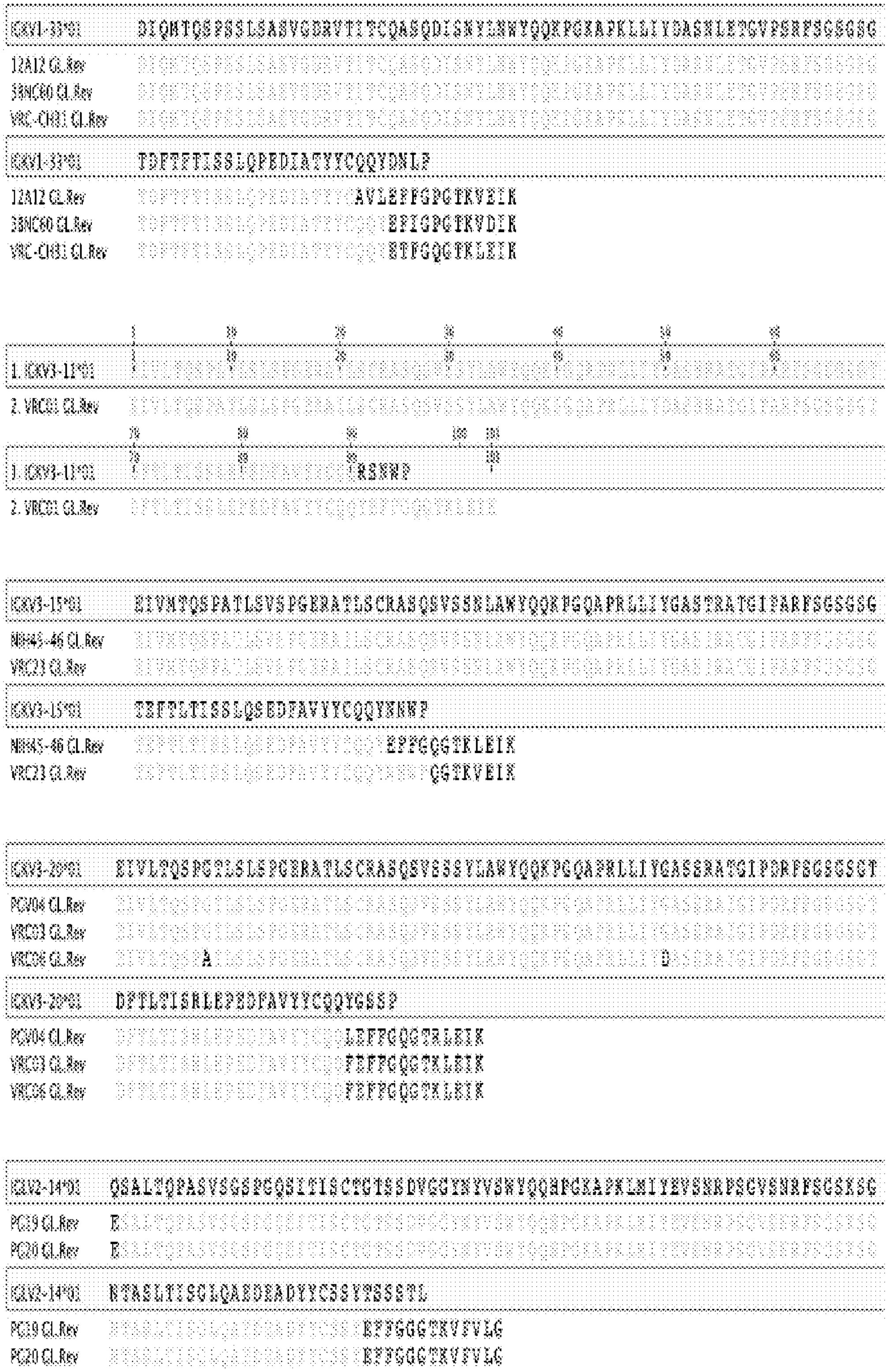

FIG. 42 depicts germline-reverted light chain sequences. The light chain sequences for the $GL_{Rev}$ Abs used in the development of eOD-GT7 and eOD-GT8 (see Table 15 for pairings). FIG. 42 discloses SEQ ID NOS 133-148, respectively, in order of appearance.

Figure 43:
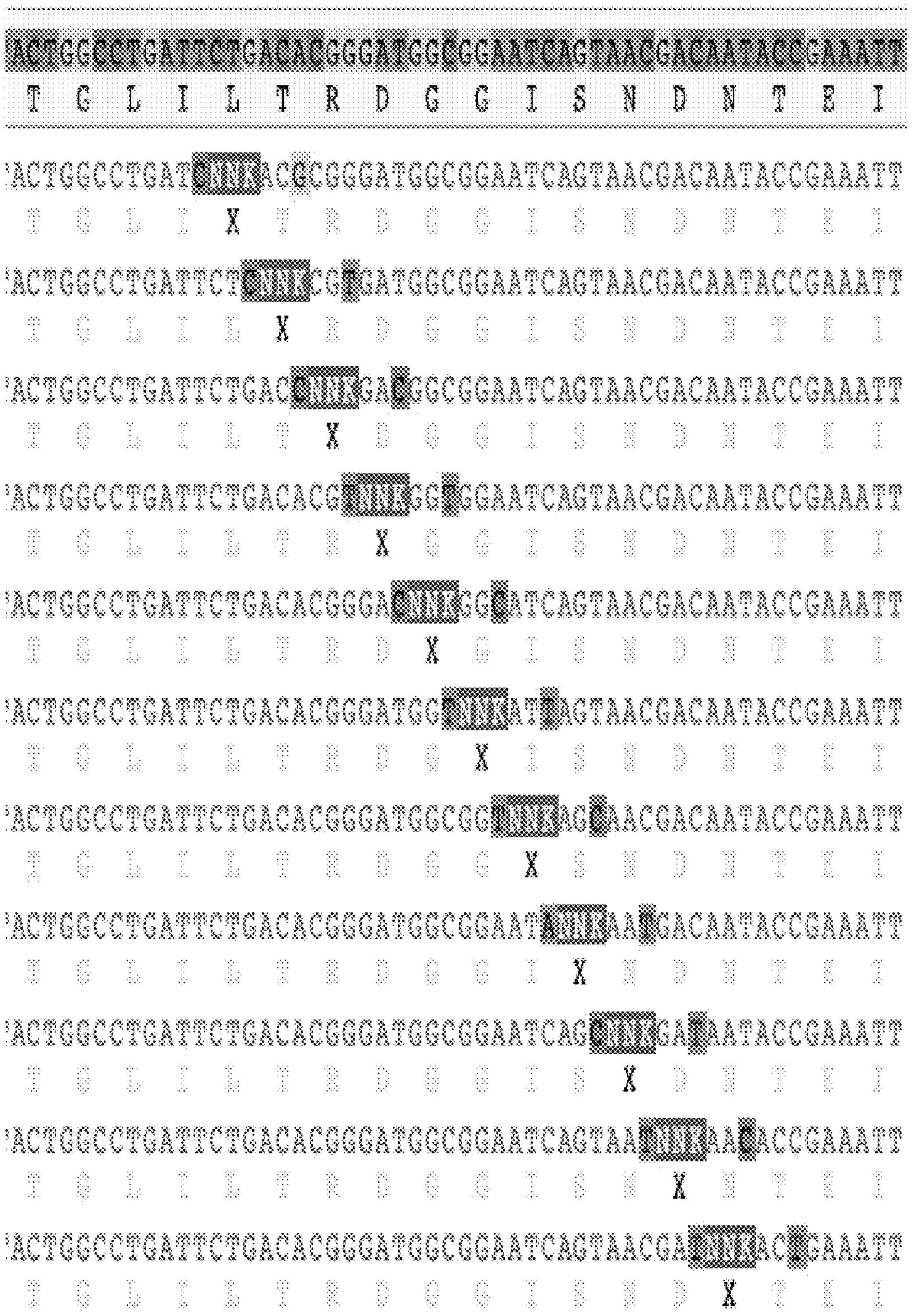
Figure 44B:
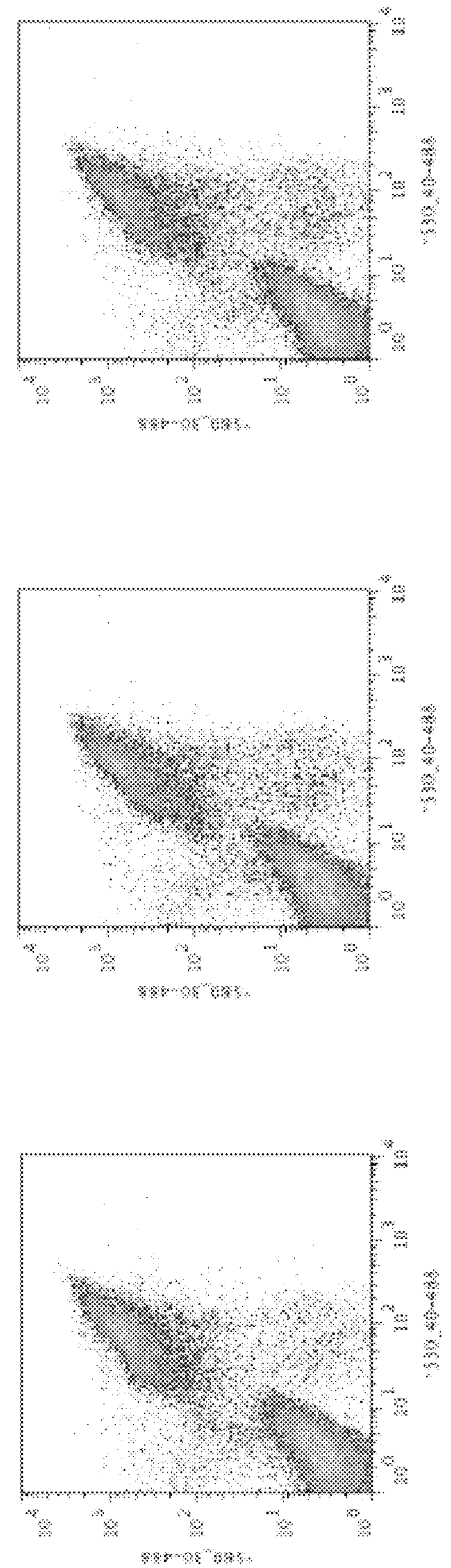
Figure 44D:
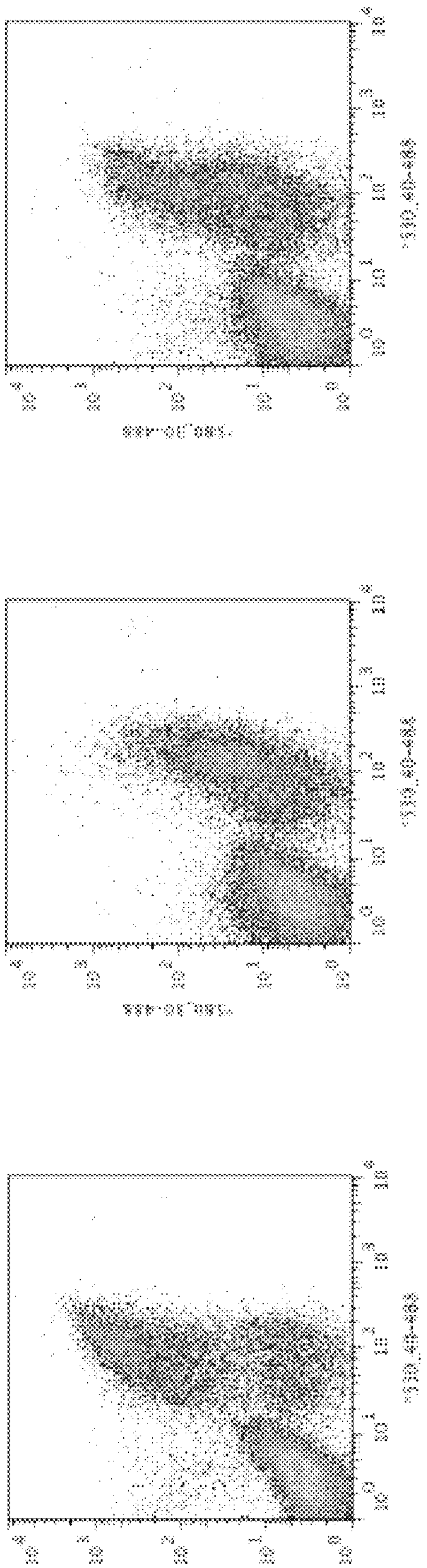
Figure 44E:
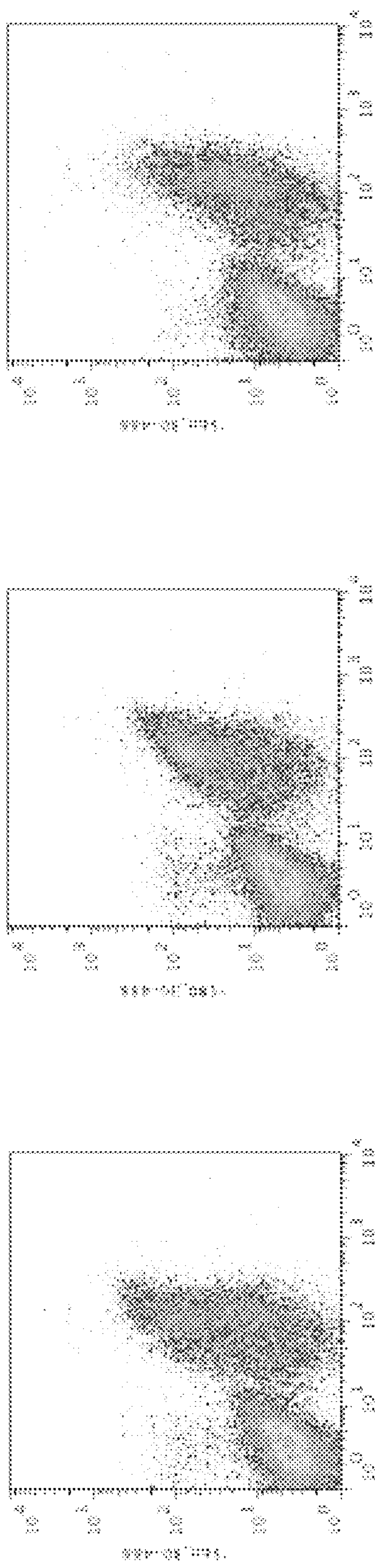
Figure 44F:
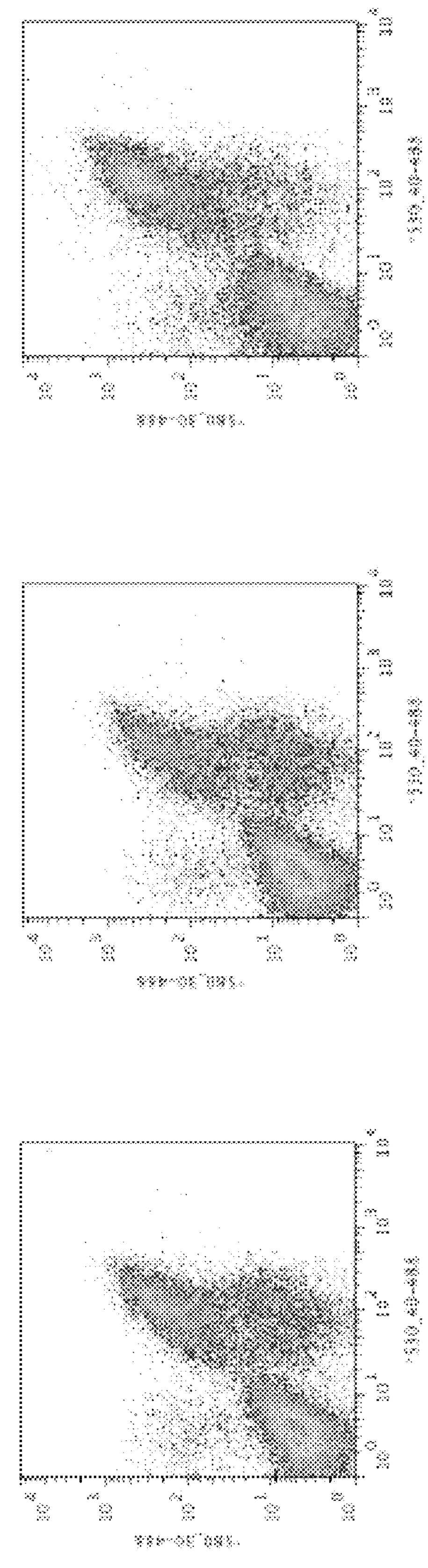
Figure 44H:
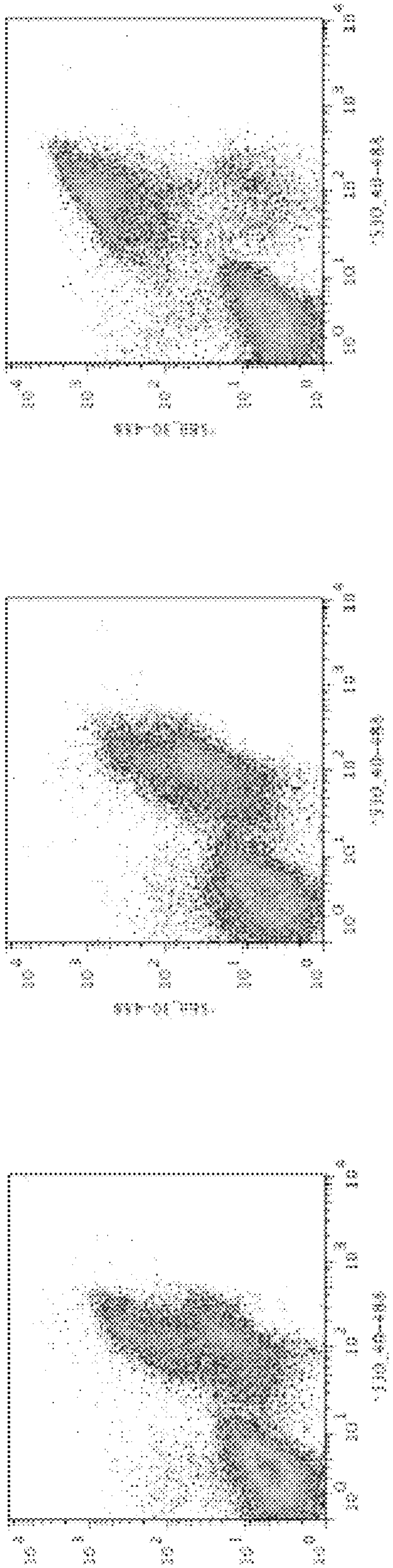
Figure 44I:
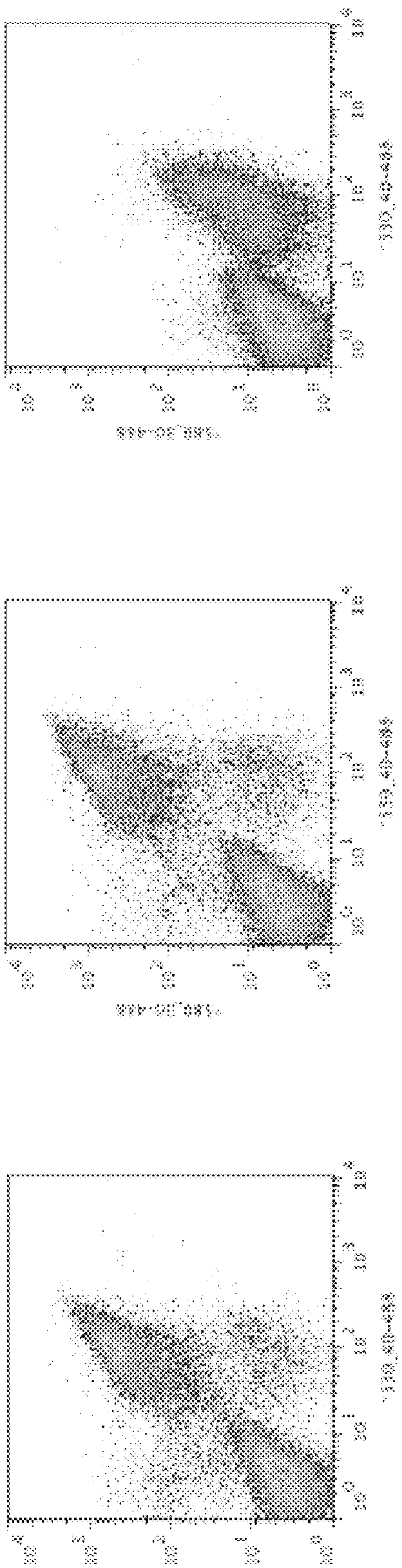
Figure 44J:
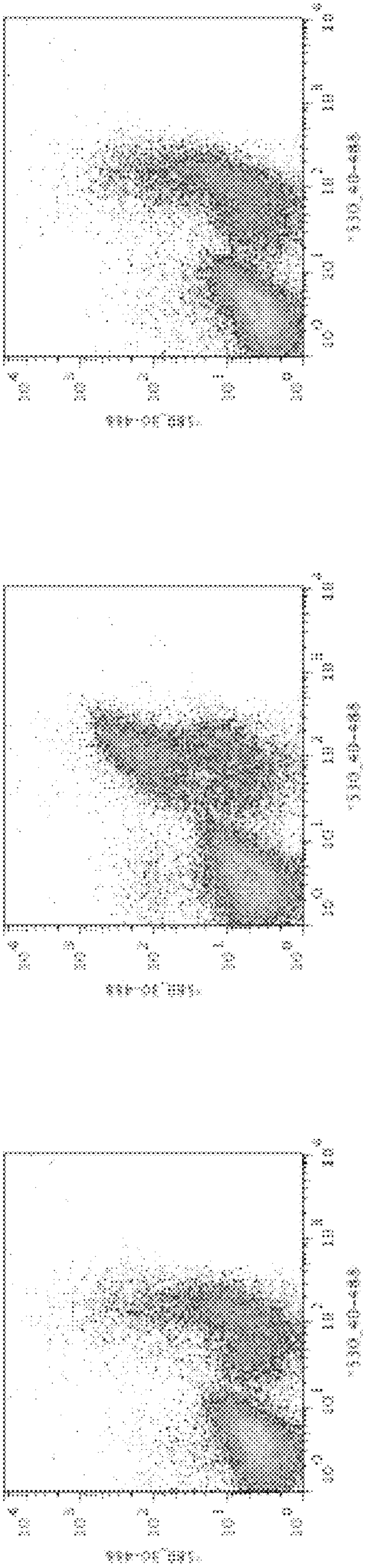

FIG. 43 depicts a graphical representation of the double-barcoded NNK scanning libraries. The base construct is at the top (yellow box) and the individual NNK libraries are aligned below. A silent codon change is flanking either side of the position being sampled to allow rapid and unambiguous identification by deep sequencing. FIG. 43 discloses SEQ ID NOS 149-172, respectively, in order of appearance.

FIG. 44A-K depicts FACS plots of eOD-GT7 NNK mutagenesis library binding to VRC01-class bnAbs and germline-reverted antibodies.

Figure 45:
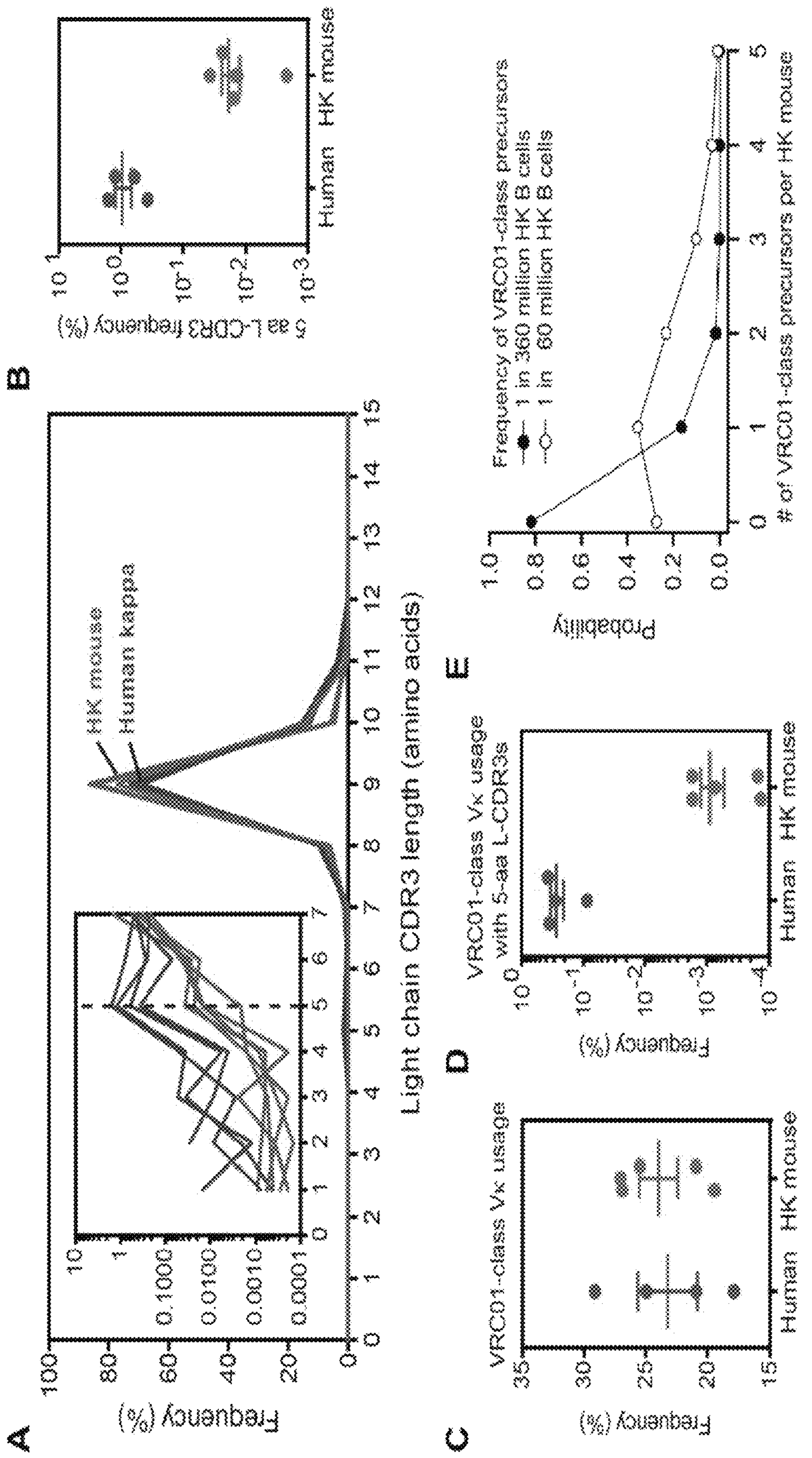

FIG. 45. depicts frequency analysis of VRC01-class light chains and precursors in Kymab HK mice. (A) Light chain L-CDR3 length distributions in humans and HK mice. (B) Frequencies of 5-amino acid L-CDR3s in humans and HK mice. (C) Frequencies of known VRC01-class bnAb light chain Vκ genes in humans and HK mice. (D) Frequencies of known VRC01-class bnAb Vκ genes with 5-amino acid L-CDR3s in humans and HK mice. (E) Modeled distributions of the number of VRC01-class precursors per HK mouse.

FIG. 46. depicts an outline of priming experiments and B cell sorting analysis of responses. (A) Overview of two immunization experiments in Kymab mice. (B) Frequencies of epitope-specific memory B cells at days 14 or 42 after priming under different conditions as shown in (A).

Figure 47:
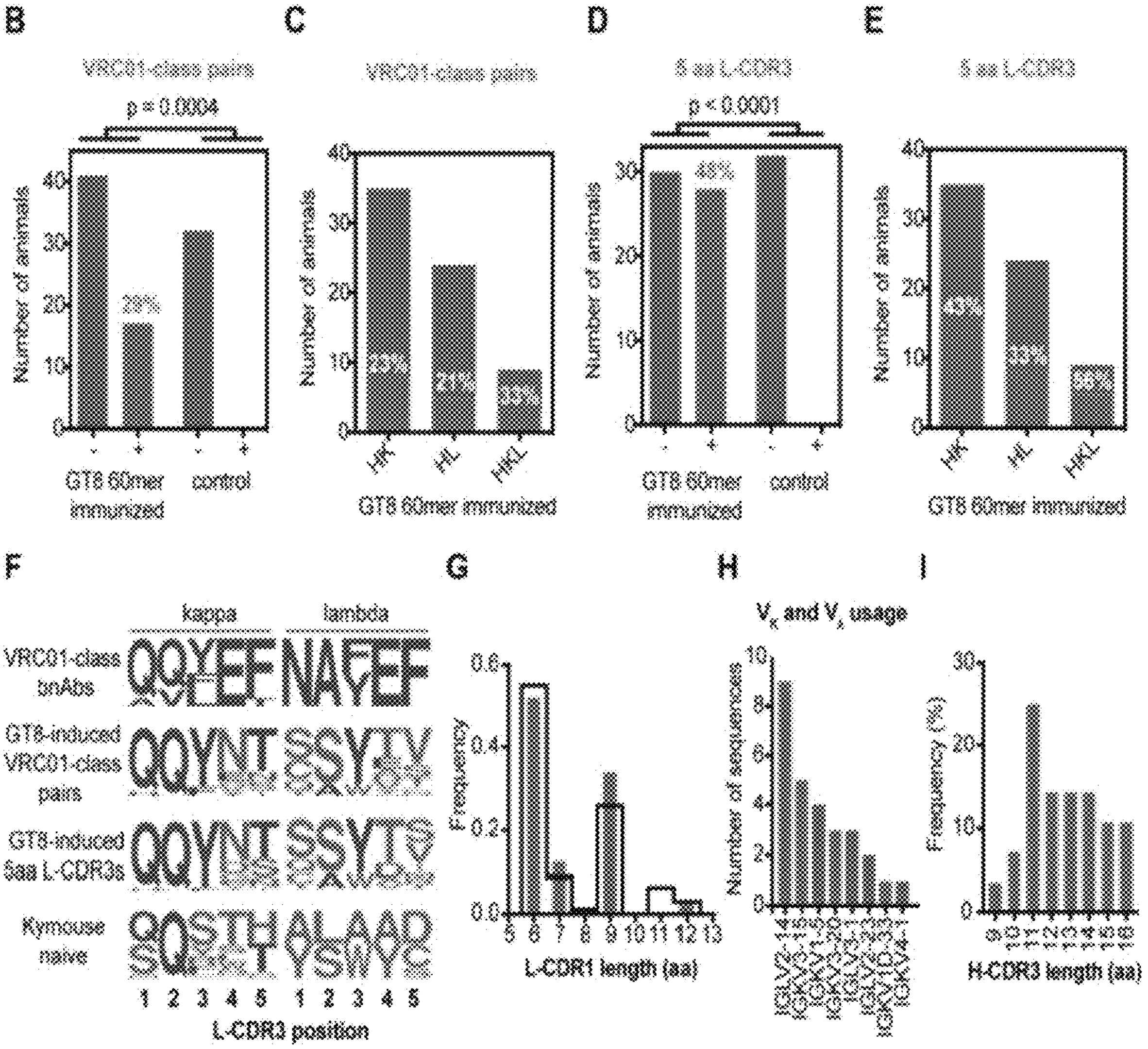

FIG. 47. depicts analysis of antibody sequences from epitope-specific memory B cells. (A) Summary of all sequence information obtained from experiments 1 and 2 in FIG. 46A. HCs, heavy chains; LCs, light chains; Pairs, pairs of heavy and light chains; $V_H$1-2 HCs, heavy chains using $V_H$1-2; 5 aa L-CDR3 LCs, light chains using a 5-amino acid L-CDR3; VH1-2 pairs, heavy-light pairs using $V_H$1-2; 5 aa L-CDR3 pairs, heavy-light pairs using a 5-amino acid L-CDR3; VRC01-class pairs, heavy-light pairs using $V_H$1-2 and a 5-amino acid L-CDR3. (B) Number of eOD-GT8 60mer-immunized or control mice from which at least one VRC01-class pair was isolated by B cell sorting (+) or from which no VRC01-class pairs were isolated (−). Data are aggregated from all animals and conditions in experiments 1 and 2 in FIG. 46A. (C) Number of eOD-GT8 60mer-immunized HK, HL, or HKL mice for which at least one VRC01-class pair was isolated by B cell sorting (red, with percentages listed in white) or from which no VRC01-class pairs were isolated (gray). (D) Number of eOD-GT8 60mer-immunized or control mice from which at least one 5-amino acid L-CDR3 light chain was isolated by B cell sorting (+) or from which no such light chains were isolated (−). Data are aggregated as in (B). (E) Number of eOD-GT8 60mer-immunized HK, HL, or HKL mice for which at least one 5-amino acid L-CDR3 light chain was isolated by B cell sorting (red, with percentages listed in white) or from which no such light chains were isolated (gray). (F) L-CDR3 sequence logos for VRC01-class bnAbs (top row), eOD-GT8 60mer-induced VRC01-class paired antibodies (second row), eOD-GT8 60mer-induced 5-amino acid L-CDR3s (third row), and naive kymab mice (bottom row), shown separately for kappa light chains (left column) and lambda light chains (right column). (G) L-CDR1 length distribution for eOD-GT8 60mer-induced VRC01-class antibodies (red) and all LCs in (A) (black). (H) Light chain Vκ and Vλ gene usage for eOD-GT8 60mer-induced VRC01-class antibodies. Red bars denote genes used by, or highly similar to those used by, known VRC01-class antibodies. (I) H-CDR3 length distribution for eOD-GT8 60mer-induced VRC01-class antibodies.

Figure 48:
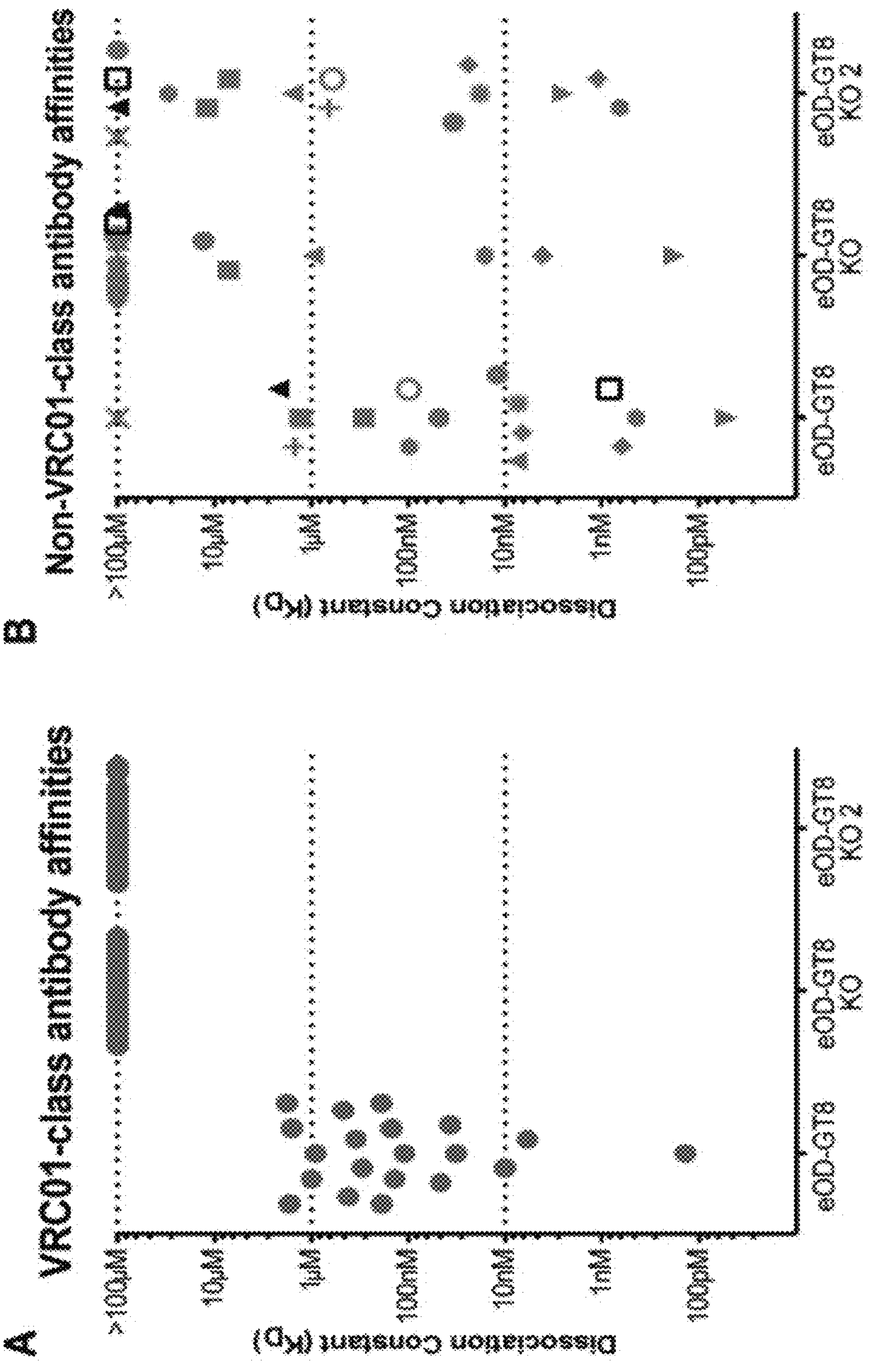

FIG. 48. depicts surface plasmon resonance (SPR)-determined dissociation constants for eOD-GT8 60mer-induced antibodies binding to eOD-GT8 and two epitope mutants. (A) VRC01-class antibodies. (B) Non-VRC01-class antibodies. Blue symbols represent antibodies binding eOD-GT8 KO, $V_H$1-2 antibodies are in black and the remaining are red.

FIG. 49A-E. depicts the design and characterization of BG505-GT3. (A) Design of boosting immunogens (BG505-GT3 and SOSIP N276D) presenting a CD4bs epitope that is increasingly more native-like than the priming immunogen eOD-GT8. (B) BG05 core-GT3 and SOSIP-GT3 were also designed to minimize off-target responses. (C) Large sequence segments, likely containing T-helper cell epitopes, are conserved between sequential immunogens. When using BG505 core-GT3 NP, the nanoparticle base is shared between the prime and first boost, while the BG505 inner domain and outer domain are shared between the first and second boost. When using BG505 SOSIP-GT3, a PADRE peptide is conserved between the prime and first boost. (D) Affinity of germline-reverted (GLrev) and mature VRC01-class antibodies for BG505-GT3. (E) Comparison of affinities of GLrev and mature antibodies reveals an affinity gradient toward mature VRC01-class bnAbs. No such affinity gradient is present with eOD-GT8. See also Figures S1, S2 and S3 and Tables S1 and S2.

Figure 50:
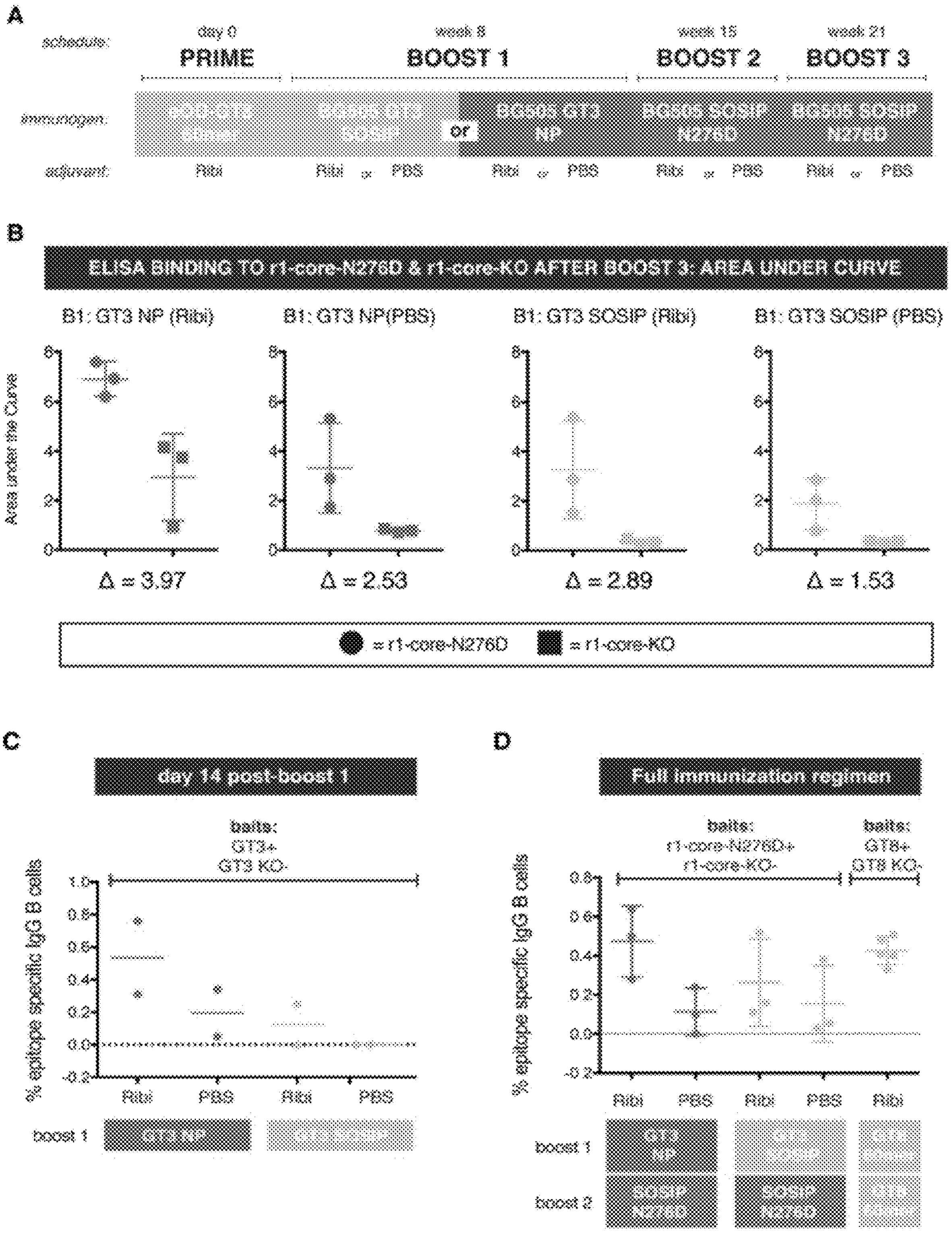

FIG. 50. depicts the immunization of VRC01-gH mice. (A) Immunization schedule for priming and boosting VRC01-gH mice. (B) ELISA binding of VRC01-gH mouse serum following boost 3. Binding to r1-core-N276D and r1-core-KO is represented as area under the curve, and the difference between binding to r1-core-N276D and r1-core-KO is shown beneath each plot. (C) Frequency of epitope-specific IgG memory B cells in VRC01-gH mice 14 days following boost 1, as measured by binding to GT3 and lack of binding to GT3-KO. (D) Frequency of epitope-specific IgG memory B cells after the full immunization regimen, measured by binding to r1-core-N276D and lack of binding to r1-core-KO (for animals boosted twice with GT3 and SOSIP N276S) or binding to GT8 and lack of binding to GT8-KO (for animals that were boosted twice with GT8). See also FIG. 57.

FIG. 51A-I. depicts the genetic maturation of immunogen-induced antibodies. (A) Paired heavy-light mAb sequences were grouped by mouse and the fraction of mAb sequences that were VRC01-like (VH1-2 heavy chain and a 5AA long LCDR3) was determined. The mice were then grouped by immunization regime and the VRC01-like frequency is plotted. Each bubble represents antibody sequences from a single mouse and the area of the bubble is proportional to the total number of mAb sequences recovered. For each immunization group, the frequency of nucleotide mutations (B) or amino acid mutations (C) was determined for each sequence. Each violin plot represents all sequences from all animals in each immunization group. For each sequence in each immunization group, the total number of amino acid mutations was calculated, as well as the number of amino acid mutations shared with one or more of a panel of VRC01-class sequences: VRC01, PGV04, PGV20, VRC-CH31, 3BNC60 and 12A12. Two-dimensional heatmaps were created for each immunization group, plotting the frequency of total amino acid mutations against VRC01-class mutations. The frequency of VRC01-class mutations obtained by random somatic hyper mutation (SHM) (black line) is shown on each plot, as well as the 95% confidence interval (grey shading). Each sequence from all animals receiving the complete immunization schedule (eOD-GT8 60mer, BG505 GT3, and SOSIP N276D) was aligned with GLRev VRC01 and all mutations were highlighted (D). Mutations shared with VRC01-class antibodies are highlighted in blue, and other mutations are indicated in black. Positions at which the antibody sequence was identical to GLRev VRC01 are colored light gray. (E) 150 sequences were randomly selected from a pool of 2,000 artificial antibody sequences that represent random SHM activity, aligned to GLRev VRC01, and mutations were highlighted as in (D). Paired VRC01-like sequences were combined by immunization group and the frequency of each light chain variable gene was calculated (F). Light chain V-genes that naturally encode a short (≤6AA) LCDR1 are indicated with asterisks. For each mouse in each immunization group, the frequency of light chains encoding a short (≤6AA) LCDR1 was computed from the total number of VRC01-like paired sequences (G). (H) Each bubble represents a single animal, and the area of the bubble is proportional to the total number of VRC01-like pairs. Light chain junction sequences from each paired VRC01-like mAb were used to generate WebLogo sequence plots for each immunization group (I). Increasing convergence on critical junctional residues found in the mature VRC01 light chain is highlighted.

Figure 52A:
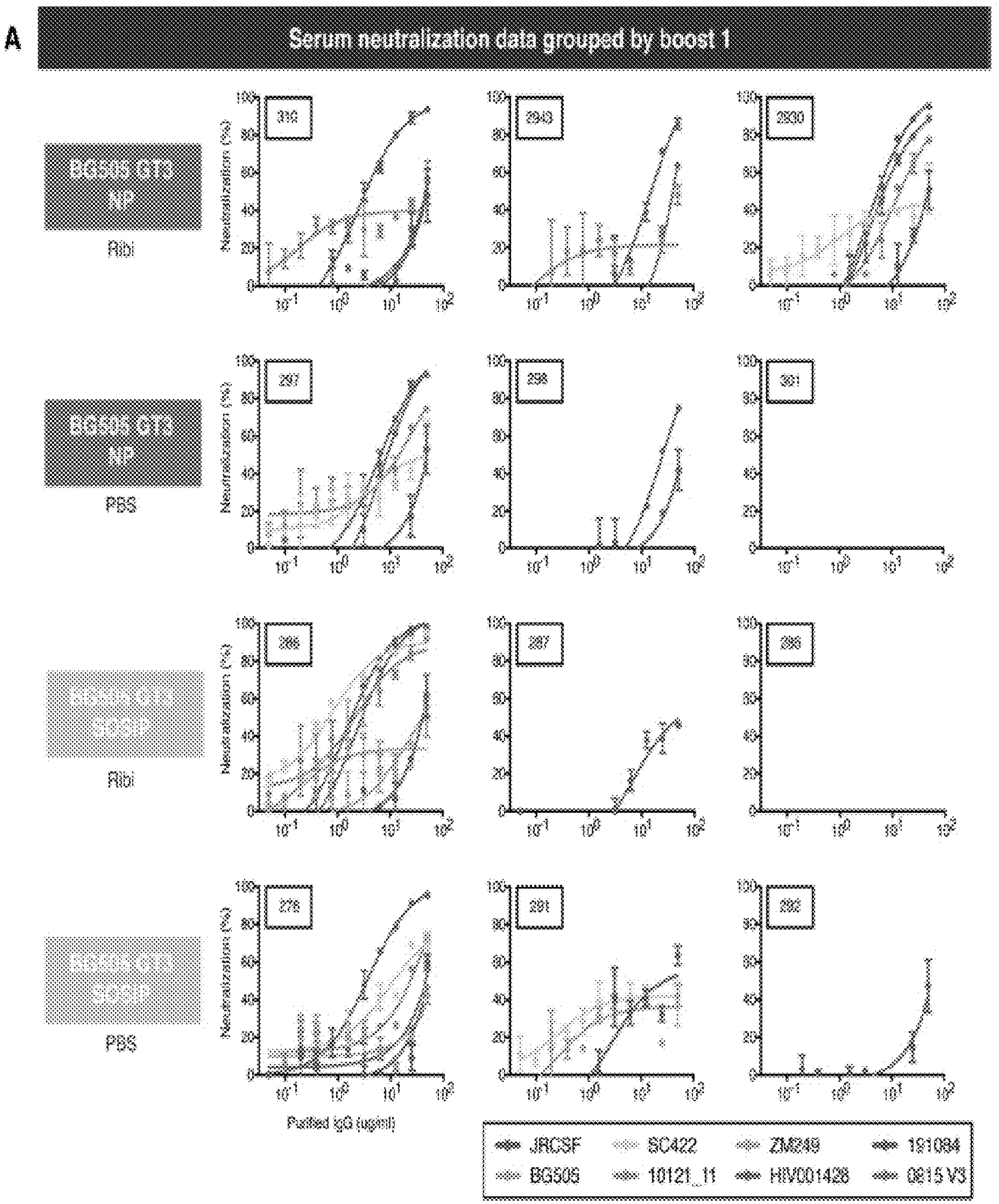
Figure 52B:
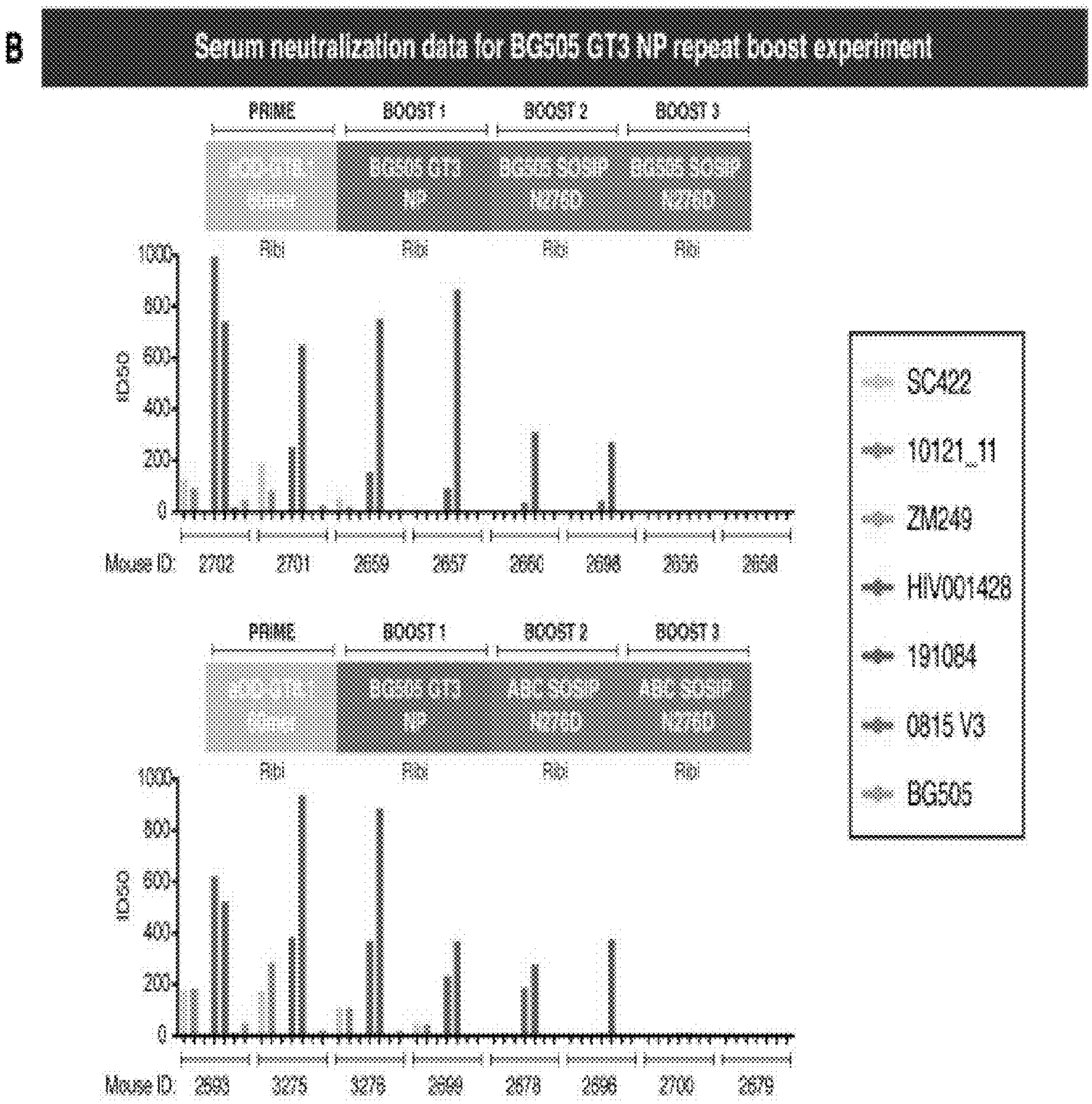

FIG. 52A-B. depicts the serology of immunized VRC01-gH mice. Neutralization curves of total IgG purified from sera of immunized mice. (A) Twelve mice were primed with eOD-GT8 60mer and boosted with either core-GT3 NP or GT3 SOSIP (adjuvanted with either Ribi or PBS) followed by an additional two boosts with BG505 SOSIP N276D (with either Ribi or PBS). The leftmost column describes the immunization regimen of the three plots immediately to the right. Each neutralization plot shows neutralization activity against an 8-virus panel of near-native (N276A) virus isolates. All total IgG concentrations are shown in mg/ml. (B) Sixteen additional VRC01 gH mice were primed with eOD-GT8 60mer and boosted with GT3 NP, followed by two boosts with either BG505 SOSIP N276D in Ribi (top) or ABC SOSIP N276D cocktail in Ribi (bottom). Purified serum IgG was screened against a 7-virus panel of near-native (N276A) virus isolates, and $IC_{50}$ values are plotted for each mouse, as reciprocal serum titers.

Figure 53A:
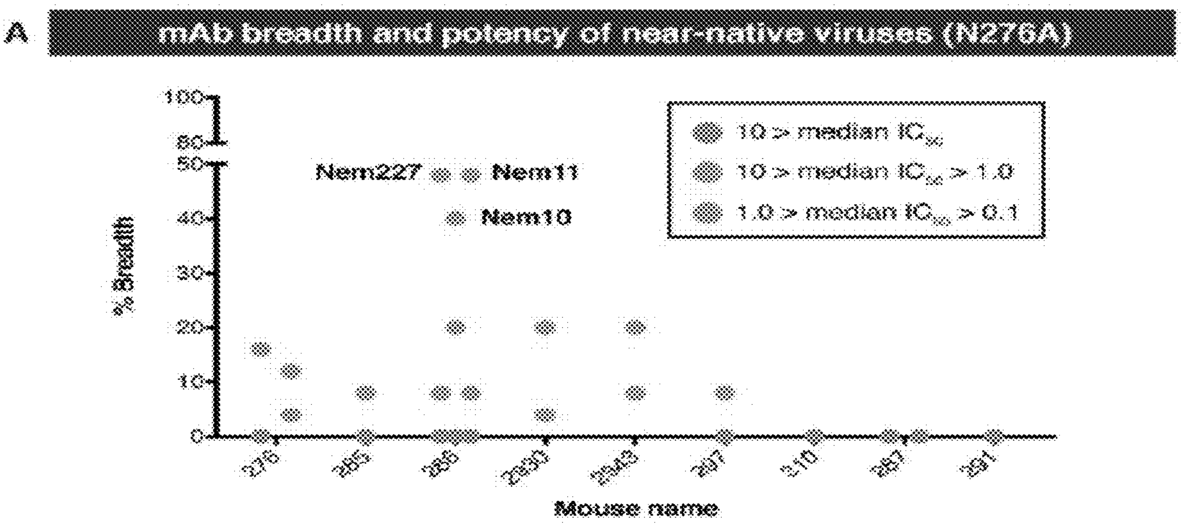
Figure 53B:
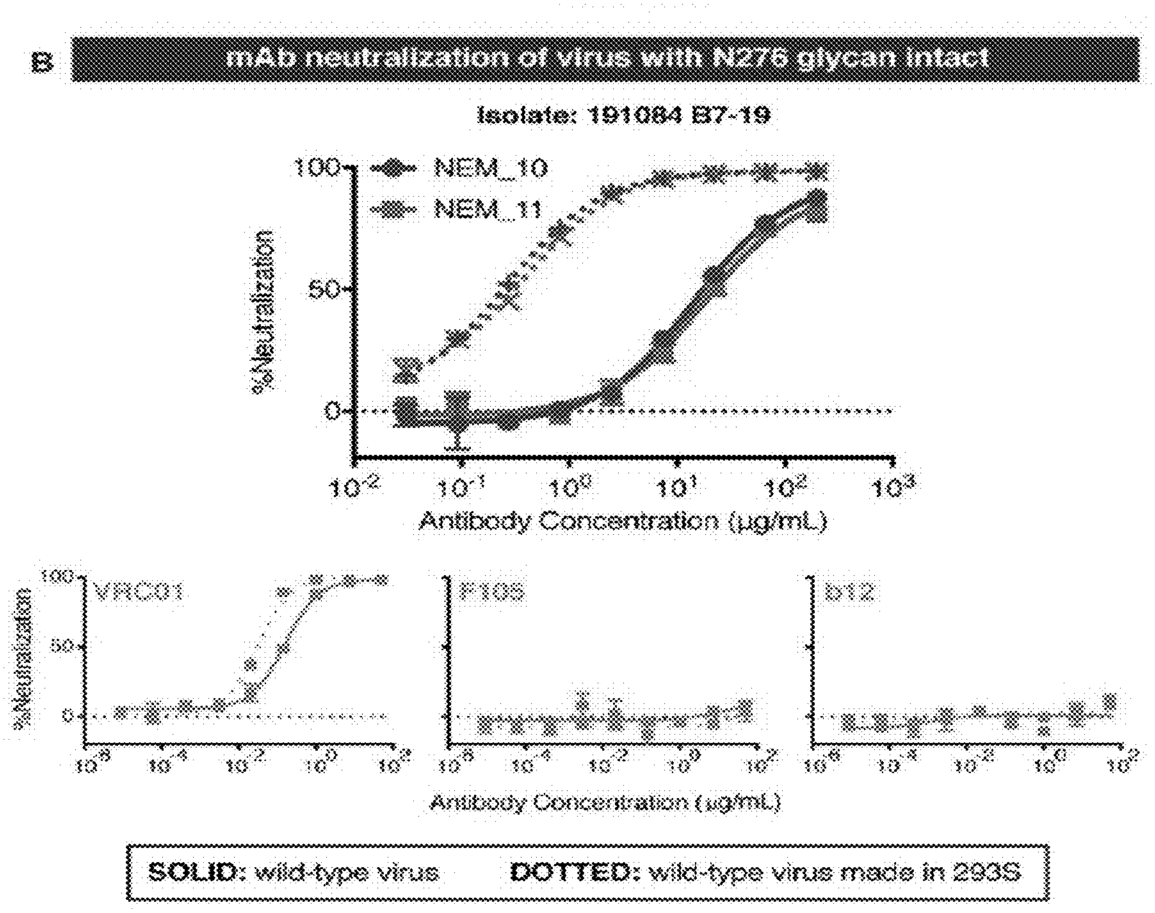
Figure 56A:
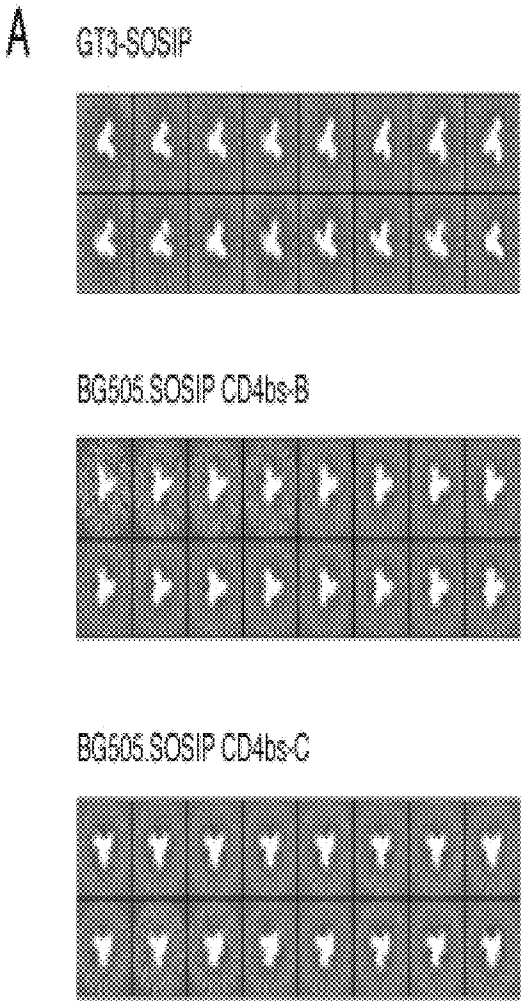
Figure 56B:
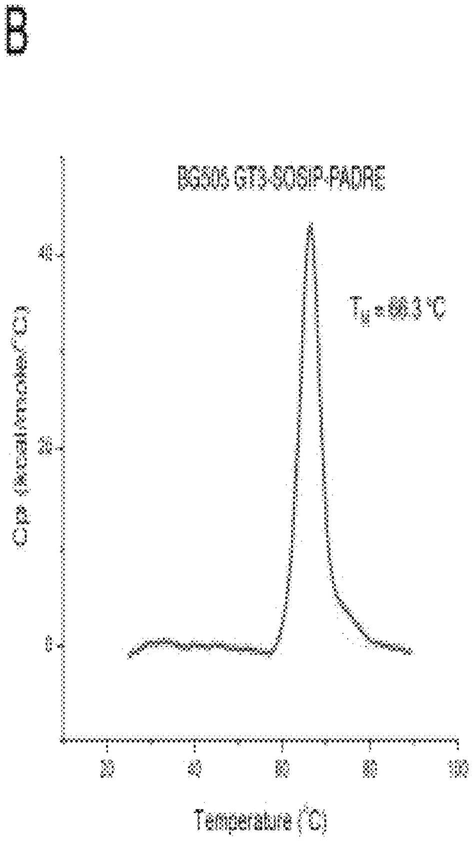
Figure 56C:
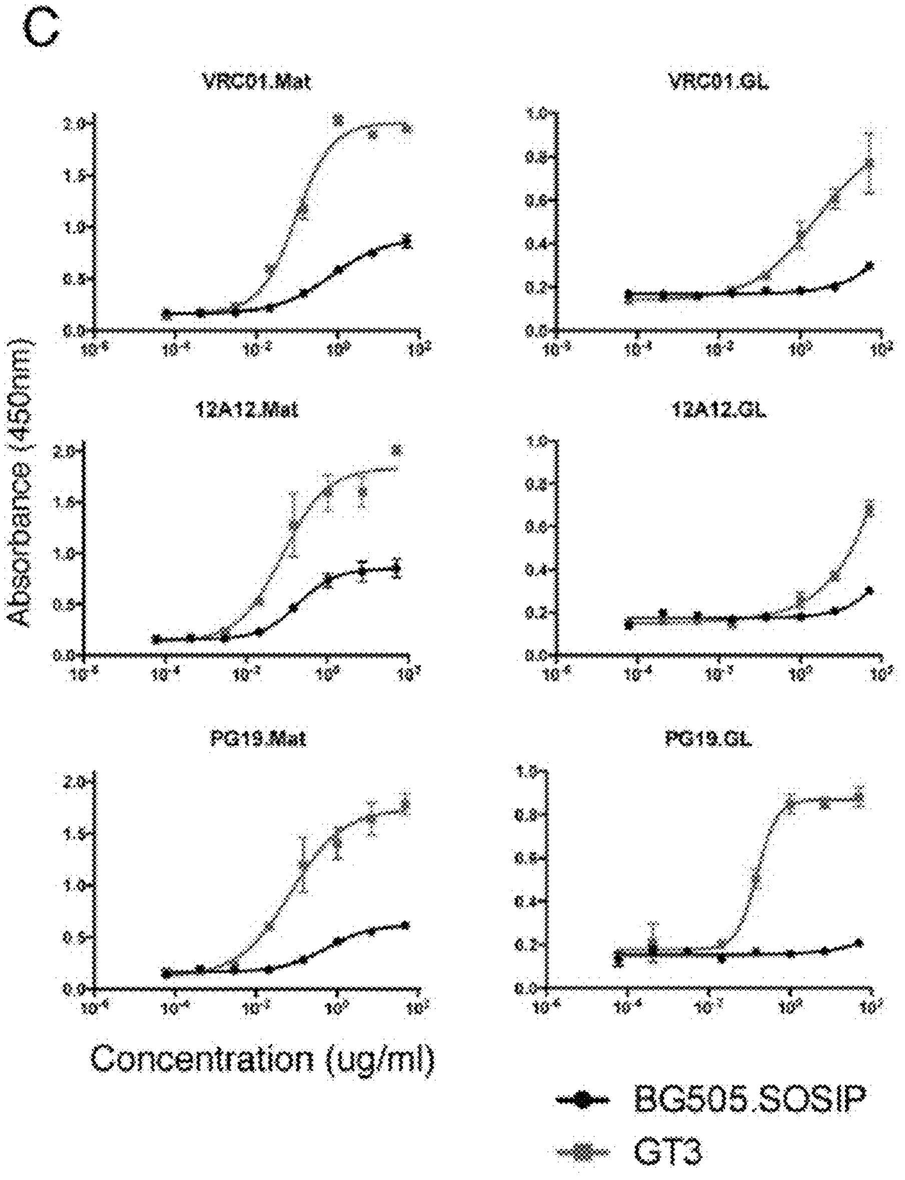
Figure 56D:
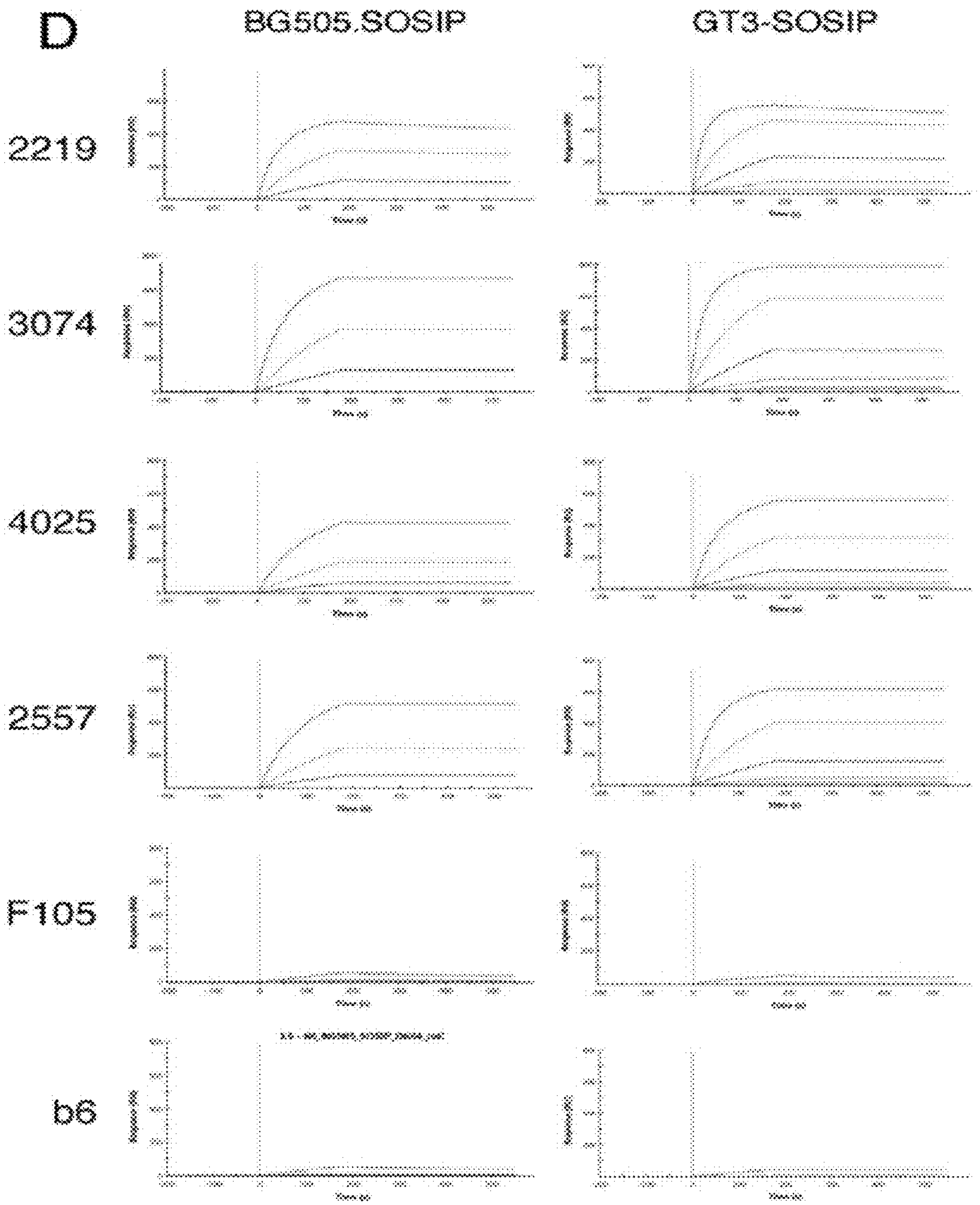

FIG. 53A-C. depicts the neutralization by mAbs from immunized mice. (A) Neutralization breadth and potency of mAbs isolated from several mice receiving the entire immunization program and screened on a 25-virus cross-clade panel of near-native (N276A) isolates. (B) Neutralization of two mAbs isolated from mouse 286. Both Nem10 (blue) and Nem11 (red) were able to neutralize wild-type 191801 B7-19 virus grown in 293S cells (dashed lines) or 293T cells (solid lines). In the bottom three panels, binding curves for mature VRC01 (grey), F105 (light blue) and b12 (orange) are shown for wild-type 191084 B7-19 grown in either 293S cells (dashed lines) or 293T cells (solid lines). (C) Comparison of the neutralization potency of VRC01, CD4 IgG2, b12 and two non-neutralizing CD4bs mAbs on wild-type virus (left panel) or N276A virus (right panel). Only VRC01 shows consistently higher potency against N276A virus. See also FIG. 58.

FIG. 54. Related to FIG. 49. depicts the development of boosting immunogen GT3.1. Sequence alignment of BG505 SOSIP.664, BG505 GT3.1 SOSIP, BG505 core, BG505 GT3.1 core, GT6, and GT8. Engineered mutations in GT3.1 are highlighted in magenta. FIG. 54 discloses SEQ ID NOS 173-178, respectively, in order of appearance.

FIG. 55. Related to FIG. 49. depicts the sequence and characterization of BG505 core-GT3.1 nanoparticles (NPs). (A) Sequence of BG505 core-GT3.1 60mer and 'naked' nanoparticle. In the BG505 core-GT3.1 60mer gene, BG505 core-GT3.1 (blue) is fused to the lumazine synthase gene (red) via a flexible linker (cyan) as shown. Sequence of the 'naked' nanoparticle base is also shown. FIG. 55A discloses SEQ ID NOS 179-180, respectively, in order of appearance. (B) SECMALS analysis of BG505 core-GT3.1 60mer (NPs). (C) ELISA binding of mature VRC01 (black) or GLRev VRC01 (red) to BG505 core-GT3.1 60mer (NPs).

FIG. 56A-D. Related to FIG. 49. depicts the characterization and structural analysis of BG505 GT3.1 SOSIP and ABC SOSIP trimers. (A) Negative-stain 2D class average images of the GT3.1 SOSIP, CD4bs-B SOSIP and CD4bs-C SOSIP are shown. (B) DSC thermogram of GT3.1 SOSIP (C) ELISA analysis of mature and GLRev VRC01-class abs binding to BG505 SOSIP and BG505 GT3.1 SOSIP (D) SPR sensograms of BG505 SOSIP and BG505 GT3.1 SOSIP as analytes and non-nAbs IgGs as ligands.

Figure 57:
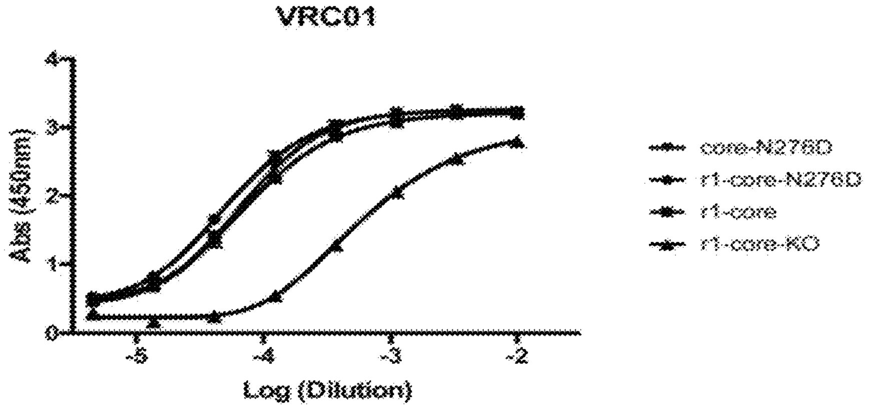

FIG. 57. Related to FIG. 50. depicts the sequence and antigenicity of the r1-core resurfaced core gp120. (A) Sequence alignment of r1-core with gp120core-e-2CC HxB2. The r1-core is derived from the core-e-2CC HxB2 protein Applicants previously described (Jardine et al., 2015) and is also known as gp120core-e-2CC_HxB2_r1. A total of 78 surface positions have been modified, out of 358 total residues. Mutations are classified in the third row of the alignment, with ":" denoting a conservative mutation; " " denoting a non-conservative mutation; and "." denoting a semi-conservative mutation. FIG. 57A discloses SEQ ID NOS 181-182, respectively, in order of appearance. (B) Dissociation constants for core-e-2CC HxB2, r1-core, and RSC3 (Wu et al., 2010) with VRC01-class bnAbs. (C) ELISA binding of mature VRC01 to core-N276D (core-e-2CC HxB2 with the N276D mutation; inverted triangles), r1-core-N276D (circles), r1-core (squares) and r1-core-KO (triangles). Starting concentration of mature VRC01 was 2 μg/ml.

Figure 58:
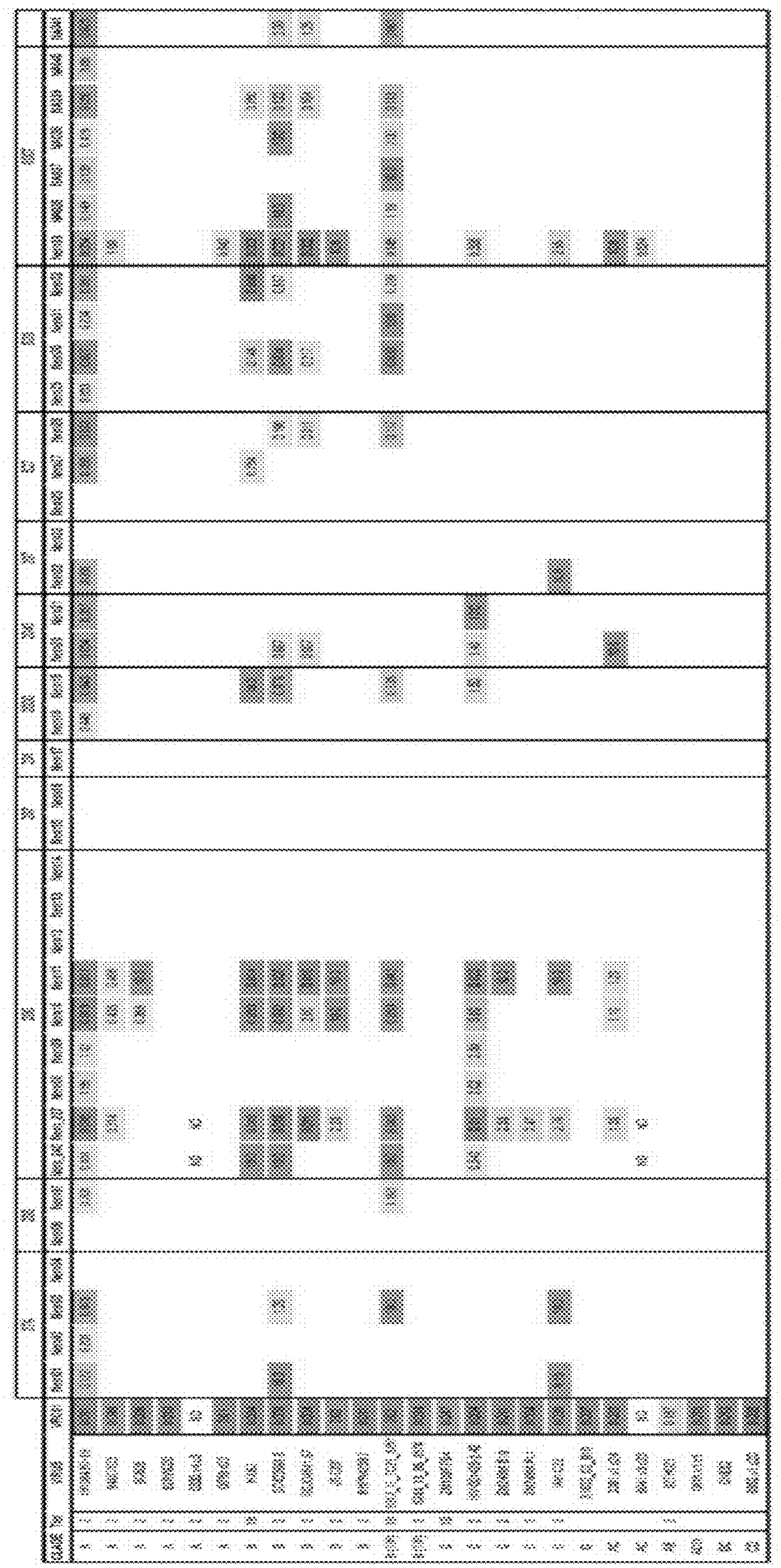

FIG. 58. Related to FIG. 53. depicts broad neutralization of near-native viruses by VRC01-gH mAbs. Neutralization of a 25-virus panel consisting of near-native (N276A) viruses. Antibodies are grouped by the mouse from which they were isolated. Neutralization by mature VRC01 is shown for comparison.

FIG. 59 depicts a summary of IgG B cells and is also referred to as Table 1.

FIG. 60A-G depicts antigen sorted IgG sequences and is also referred to as Table 2. FIG. 60A discloses the "VDJ" sequences as SEQ ID NOS 183-208 and the "CDRL3" sequences as SEQ ID NOS 209-234, all respectively, in order of appearance. FIG. 60B discloses the "VDJ"

sequences as SEQ ID NOS 235-263 and the "CDRL3" sequences as SEQ ID NOS 264-292, all respectively, in order of appearance. FIG. 60C discloses the "VDJ" sequences as SEQ ID NOS 293-314 and the "CDRL3" sequences as SEQ ID NOS 315-336, all respectively, in order of appearance. FIG. 60D discloses the "VDJ" sequences as SEQ ID NOS 337-366 and the "CDRL3" sequences as SEQ ID NOS 367-396, all respectively, in order of appearance. FIG. 60E discloses the "VDJ" sequences as SEQ ID NOS 397-426 and the "CDRL3" sequences as SEQ ID NOS 427-456, all respectively, in order of appearance. FIG. 60F discloses the "VDJ" sequences as SEQ ID NOS 457-481 and the "CDRL3" sequences as SEQ ID NOS 482-506, all respectively, in order of appearance. FIG. 60G discloses the "VDJ" sequences as SEQ ID NOS 507-525 and the "CDRL3" sequences as SEQ ID NOS 526-544, all respectively, in order of appearance.

FIG. 61 depicts hybridoma IgG sequences and is also referred to as Table 3. Figure discloses the "VDJ" sequences as SEQ ID NOS 545-553 and the "CDRL3" sequences as SEQ ID NOS 554-562, respectively, in order of appearance.

FIG. 62 depicts properties of VRC01 gH hybridomas raised by eOD-GT8 60mer and is also referred to as Table 4.

FIG. 63 depicts sequences and sequence analysis of VRC01 gH IgG hybridomas raised by eOD-GT8 60mer and is also referred to as Table 5. FIG. 63 discloses SEQ ID NOS 563-588, respectively, in order of appearance.

FIG. 64A-B depicts L-chain sequence analysis of IgM hybridomas positive for binding to GT8-60mer and is also referred to as Table 6. FIG. 64A discloses SEQ ID NOS 589-628, respectively, in order of appearance. FIG. 64B discloses SEQ ID NOS 629-680, respectively, in order of appearance.

FIG. 65 depicts a summary of the numbers of complete H/L paired antibody sequences recovered by B cell sorting from VRC01 gH mice immunized with eOD-GT8 60-mers and is also referred to as Table 7.

FIG. 66A-D depicts a summary of SPR results for eOD-GT8 60mer-induced Abs isolated by cell sorting and is also referred to as Table 8.

FIG. 67 depicts consensus sequences from NNK library of eOD-GT7 sorted with $GL_{rev}$ VRC01-class Abs and is also referred to as Table 9. FIG. 67 discloses SEQ ID NOS 681-698, respectively, in order of appearance.

FIG. 68A-C depicts SPR binding to germline-reverted and VRC01-class bnAbs and is also referred to as Table 10.

FIG. 69A-B depicts a summary of isolated VRC01-class germline Abs and is also referred to as Table 11. FIG. 69A discloses SEQ ID NOS 699-722, respectively, in order of appearance. FIG. 69B discloses SEQ ID NOS 723-748, respectively, in order of appearance.

FIG. 70 depicts SPR binding to isolated human GL Abs and is also referred to as Table 12.

FIG. 71 depicts X-ray data collection and refinement statistics and is also referred to as Table 13.

FIG. 72 depicts the per-residue buried surface area (BSA) and interactions of VRC01 bound to gp120 and VRC01c-HuGL2 bound to eOD-GT8. This figure is also referred to as Table 14.

FIG. 73 depicts a list of VRC01-class bnAbs and $GL_{REV}$ Abs. This figure is also referred to as Table 15.

Figure 74C:
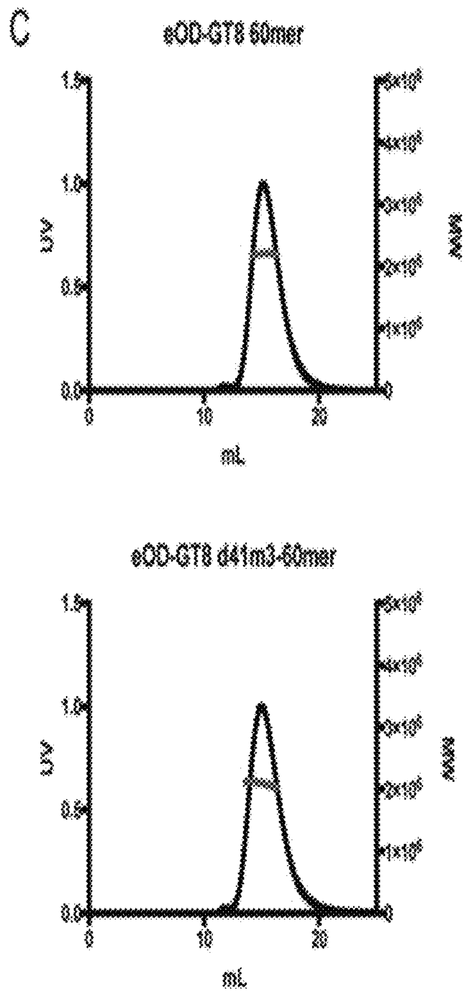
Figure 74D:
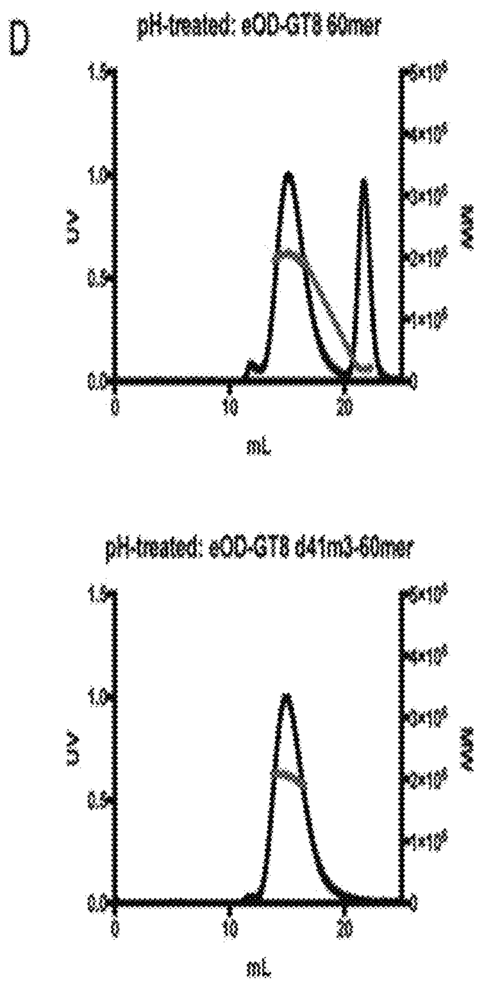
Figure 75:
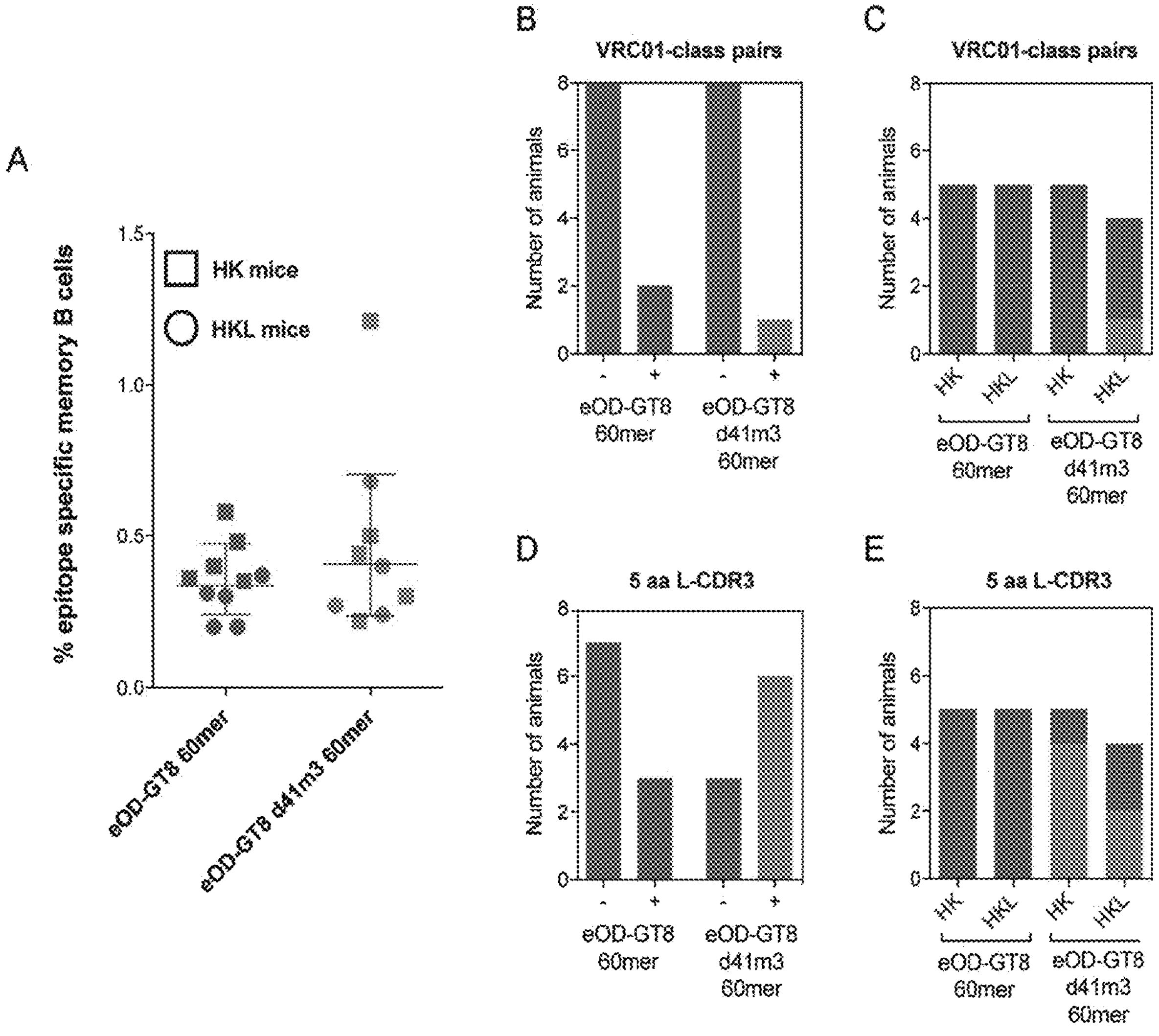

FIG. 74A-D. depicts a design of eOD-GT8 d41m3 60mer. (A) Alignment of eOD-GT8 60mer and eOD-GT8 d41m3-60mer with 4 additional stabilizing mutations (P54C, I82C, K131C, S142C) and 3 active site mutations (F22A, H88S, R127A). FIG. 74A discloses SEQ ID NOS 749-751, respectively, in order of appearance. (B) Denaturing and reducing SDS-PAGE. Lane 1: Novex Sharp Molecular Weight Marker, Lane 2: eOD-GT8 60mer, Lane 3: eOD-GT8 d41m3-60mer (C) SEC trace for eOD-GT8 60mer and eOD-GT8 d41m3-60mer at pH 7 in black. Molecular weight calculated across the peak in blue. D) SEC trace for eOD-GT8 60mer and eOD-GT8 d41m3-60mer at pH 4 in black. Molecular weight calculated across the peak in blue. eOD-GT8 60mer falls apart into pentamers at low pH. eOD-GT8 d41m3-60mer remains fully intact FIG. 75 depicts the immunogenicity of eOD-GT8 d41m3 60mer in Kymab mice. (A) Epitope-specific (eOD-GT8+/eOD-GT8-KO−) memory B cell frequencies from HK (squares) and HKL (circles) mice immunized with eOD-GT8 60mer (red) or eOD-GT8 d41m3 60mer (blue). (B) Number of animals that elicited VRC01-class pairs in either eOD-GT8 60mer or eOD-GT8 d41m3 60mer immunized mice. HK and HKL mice are combined into a single group. (C) Number of animals that elicited VRC01-class pairs in either eOD-GT8 60mer or eOD-GT8 d41m3 60mer immunized mice. Groups are separated by HK and HKL mice. (D) Number of animals that elicited 5 aa L-CDR3s in either eOD-GT8 60mer or eOD-GT8 d41m3 60mer immunized mice. HK and HKL mice are combined into a single group. (E) Number of animals that elicited 5 aa L-CDR3s in either eOD-GT8 60mer or eOD-GT8 d41m3 60mer immunized mice. Groups are separated by HK and HKL mice.

Figure 76:
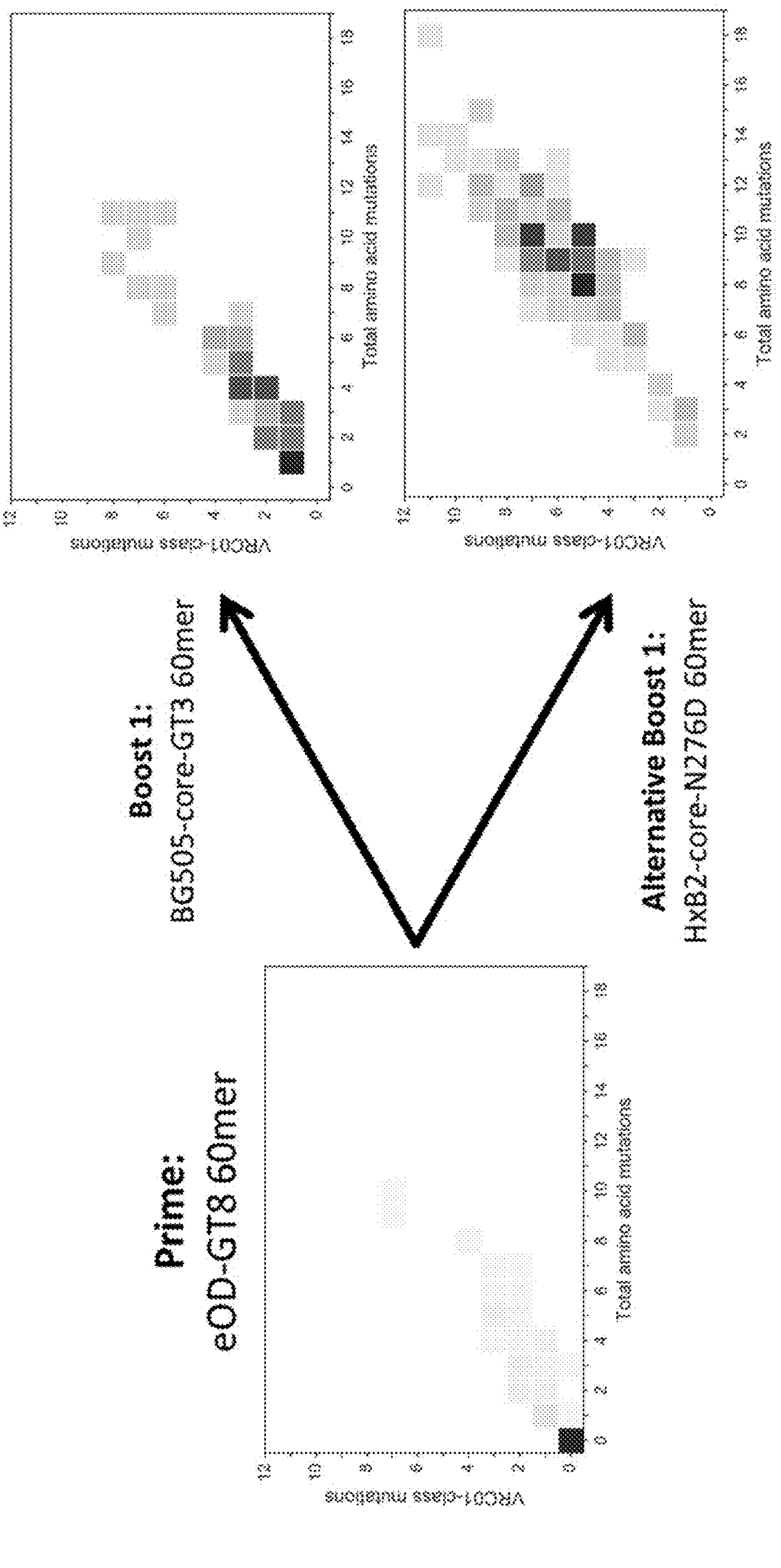

FIG. 76. depicts an improved first boost. Shown are two-dimensional histograms indicating the frequency of vaccine-induced antibodies with heavy chains having the total number of amino acid mutations indicated on the x-axis and the number of VRC01-class mutations on the y-axis. Data shown are for antibodies recovered by B cell sorting after the prime only, or after the prime plus either of two boosts (BG505-core-GT3 60mer boost or HxB2-core-N276D 60mer (core-e-2CC N276D) boost).

Figure 77:
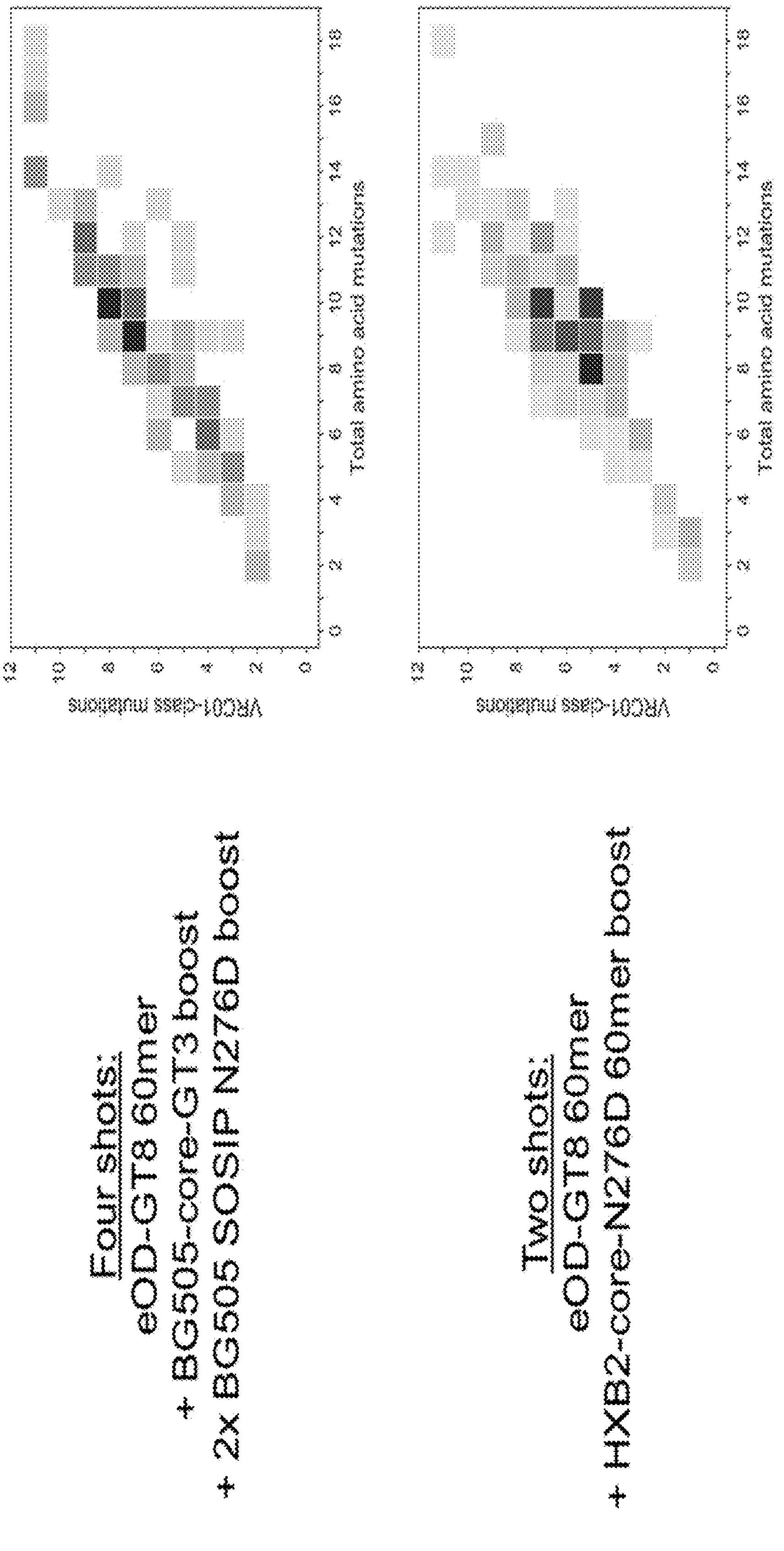

FIG. 77. depicts results of a two shot and four shot immunization protocol.

FIG. 78. depicts that a two shot protocol using the native-like boost elicits cross-reactive neutralization of N276A viruses. Data shown are neutralization titers on N276A viruses for monoclonal antibodies isolated from VRC01 gH mice immunized with the two-shot regimen indicated.

FIG. 79 depicts a reductionist vaccine strategy to induce VRC01-class bnAbs. The strategy has four main objectives for affinity maturation to be achieved by a sequence of four types of immunogens. Incremental progress can be assessed by using neutralization assays against panels of mutant viruses, as well as analysis of antibody sequences from antigen-specific B cells. Thus, using this strategy, each step can be optimized individually. One strategy is indicated; variant strategies, for example incorporating cocktails of Env, can be readily envisaged.

DETAILED DESCRIPTION OF THE INVENTION

The invention pertains to the identification, design, synthesis and isolation of mutant eOD proteins disclosed herein as well as nucleic acids encoding the same. The present invention also relates to homologues, derivatives and variants of the sequences of the mutant eOD proteins and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant eOD proteins and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention still further relates to nucleic acid sequences expressing the mutant eOD proteins disclosed herein, or homologues, variants or derivatives thereof. One of skill in the art will know, recognize and understand techniques used to create such. Additionally, one of skill in the art will be able to incorporate such a nucleic acid sequence into an appropriate vector, allowing for production of the amino acid sequence of mutant proteins and nucleic acids encoding the same or a homologue, variant or derivative thereof.

The invention also pertains to the identification, design, synthesis and isolation of mutant HIV boost proteins disclosed herein as well as nucleic acids encoding the same. The present invention also relates to homologues, derivatives and variants of the sequences of the mutant HIV boost proteins and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant HIV boost proteins and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention also pertains to the use of the eOD mutants and boost proteins in a novel vaccination strategy that includes sequential prime boost steps. Applicants have discovered for the first time a vaccination strategy that includes priming germline precursors with a mutant eOD protein followed by boosts with engineered HIV immunogens.

In certain embodiments, soluble trimer design involves actively promoting the natural gp120-gp41 cleavage event while also introducing specific stabilizing mutations. In preferred embodiments, the Env includes an engineered disulfide bond that covalently links the two subunits and an Ile-to-Pro change at residue 559 (SOSIP) that helps maintain the gp41 ectodomain moieties in the pre-fusion form (Binley J M, et al., 2000, J Virol 74:627-643; and Sanders R W, et al., 2002, J Virol 76:8875-8889). An ectodomain is the domain of a membrane protein that extends into the extracellular space. In addition, the truncation of the gp41 ectodomain at residue 664 eliminates a hydrophobic region that tends to cause trimer aggregation (Khayat R, et al., 2013, J Virol 87:9865-9872; and Klasse P J, et al., 2013, J Virol 87:9873-9885). The resulting trimers are designated SOSIP.664 gp140s. The paradigm of this particular trimer design is based on the BG505 subtype A pediatric founder virus (Wu X, et al., 2006, J Virol 80:835-844; Hoffenberg S, et al., 2013, J Virol 87:5372-5383; and Sanders R W, et al., 2013, PLoS Pathog 9:e1003618). The BG505 SOSIP.664 trimers have antigenic properties and morphologies that mimic those of native Env complexes and were the trimers used for determination of high-resolution X-ray crystallography and cryo-electron microscopy (cryo-EM) Env structures (Sanders R W and Moore J P, 2014, Nature 514:437-438; Sanders R W, et al., 2013, PLoS Pathog 9:e1003618; Julien J P, et al., 2013, Science 342:1477-1483; Lyumkis D, et al., 2013, Science 342:1484-1490; and Pancera M, et al., 2014, Nature 514:455-461).

Additional stabilizing mutations may also be used for the present invention. SOSIP gp140 proteins based on the subtype A HIV-1 strain KNH1144 form particularly homogenous trimers compared to a prototypic strain (JR-FL, subtype B). U.S. Pat. No. 7,939,083 describes the determinants of this enhanced stability, which are located in the N-terminal region of KNH11144 gp41, and when substituted into heterologous Env sequences (e.g., JR-FL) they have a similarly beneficial effect on trimer stability. These stabilized trimers retain the epitopes for several neutralizing antibodies and related agents (e.g., CD4-IgG2, b12, 2G12, 2F5 and 4E10).

Where used herein and unless specifically indicated otherwise, the following terms are intended to have the following meanings in addition to any broader (or narrower) meanings the terms might enjoy in the art:

The term “isolated” or “non-naturally occurring” is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art may readily determine appropriate levels of purity according to the use to which the peptide is to be put. The term “isolating” when used as a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

The proteins and compounds of the invention need not be isolated in the sense defined above, however.

The term “pharmaceutical composition” is used herein to define a solid or liquid composition in a form, concentration and level of purity suitable for administration to a patient (e.g. a human patient) upon which administration it may elicit the desired physiological changes. The terms “immunogenic composition” and “immunological composition” and “immunogenic or immunological composition” cover any composition that elicits an immune response against the targeted pathogen, HIV. Terms such as “vaccinal composition” and “vaccine” and “vaccine composition” cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response, which may, but need not, be a protective immune response. An immunogenic or immunological composition may be used in the treatment of individuals infected with the pathogen, e.g., to stimulate an immune response against the pathogen, such as by stimulating antibodies against the pathogen. Thus, an immunogenic or immunological composition may be a pharmaceutical composition. Furthermore, when the text speaks of "immunogen, antigen or epitope", an immunogen may be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc, of an antibody that binds to the compound or an immunogen, antigen or epitope that binds to the antibody; for instance, an anti-HIV antibody or an HIV immunogen, antigen or epitope.

A "conservative amino acid change" is one in which the amino acid residue is replaced with an amino acid residue having a similar side chain. Families of amino acid residues having similar side chains have been defined in the art. These families include amino acids with basic side chains (e.g. lysine, arginine and histidine), acidic side chains (e.g. aspartic acid and glutamic acid), non-charged amino acids or polar side chains (e.g. glycine, asparagine, glutamine, serine, threonine, tyrosine and cysteine), non-polar side chains (e.g. alanine, valine, leucine, isoleucine, proline, phenylalanine, methionine and tryptophan), beta-branched side chains (e.g. threonine, valine and isoleucine), and aromatic side chains (e.g. tyrosine, phenylalanine, tryptophan and histidine).

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

(a) Fab, the fragment which contains a monovalent antigen-binding fragment of an antibody molecule may be produced by digestion of whole antibody with the enzyme papain to yield an intact light chain and a portion of one heavy chain;

(b) Fab', the fragment of an antibody molecule may be obtained by treating whole antibody with pepsin, followed by reduction, to yield an intact light chain and a portion of the heavy chain; two Fab' fragments are obtained per antibody molecule;

(c) $F(ab')_2$, the fragment of the antibody that may be obtained by treating whole antibody with the enzyme pepsin without subsequent reduction; $F(ab')_2$ is a dimer of two Fab' fragments held together by two disulfide bonds;

(d) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988); and E. A. Greenfield ed., Antibodies A Laboratory Manual, 2nd edition (2013) which are incorporated herein by reference). Fabs, Fv and scFV may also be made recombinantly, i.e. expressed as Fab, Fv or scFV rather than cleaving an intact IgG.

A "neutralizing antibody" may inhibit the entry of HIV-1 virus for example SF162 and/or JR-CSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" may comprise a portion of an intact antibody, preferably the antigen binding or variable region of the intact antibody. Examples of antibody fragments include Fab, Fab', $F(ab')_2$, scFV and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the sequences of the invention, such as the mutant eOD proteins, may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989) and "Molecular Cloning: A Laboratory Manual" fourth edition (Green and Sambrook 2012).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies or proteins of the present invention may be used in accordance with the present invention. In certain embodiments, the antibodies of the present invention may be used in vitro (such as using cell-free expression systems) and/or in cultured cells grown in vitro in order to produce the encoded HIV-antibodies, which may then be used for various applications such as in the production of proteinaceous vaccines. For such applications, any vector that allows expression of the antibodies in vitro and/or in cultured cells may be used.

For applications where it is desired that the antibodies or proteins be expressed in vivo, for example when the transgenes of the invention are used in DNA or DNA-containing vaccines, any vector that allows for the expression of the antibodies or proteins of the present invention and is safe for use in vivo may be used. In preferred embodiments the vectors used are safe for use in humans, mammals and/or laboratory animals.

For the antibodies or proteins of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The vectors used in accordance with the present invention should typically be chosen such that they contain a suitable gene regulatory region, such as a promoter or enhancer, such that the antibodies or proteins of the invention may be expressed.

For example, when the aim is to express the antibodies or proteins of the invention in vitro, or in cultured cells, or in any prokaryotic or eukaryotic system for the purpose of producing the protein(s) encoded by that antibody, then any suitable vector may be used depending on the application. For example, plasmids, viral vectors, bacterial vectors, protozoal vectors, insect vectors, baculovirus expression vectors, yeast vectors, mammalian cell vectors, and the like, may be used. Suitable vectors may be selected by the skilled artisan taking into consideration the characteristics of the vector and the requirements for expressing the antibodies or proteins under the identified circumstances.

In an advantageous embodiment, IgG1 and Fab expression vectors may be utilized to reconstitute heavy and light chain constant regions if heavy and light chain genes of the antibodies of the present invention are cloned.

When the aim is to express the antibodies or proteins of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies or proteins of the invention in a laboratory animal, such as for pre-clinical testing of the HIV-1 immunogenic compositions and vaccines of the invention. In other embodiments, it will be desirable to express the antibodies or proteins of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors.

The nucleotide sequences and vectors of the invention may be delivered to cells, for example if the aim is to express the HIV-1 antigens in cells in order to produce and isolate the expressed proteins, such as from cells grown in culture. For expressing the antibodies or proteins in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies or proteins may be carried out in any suitable type of host cells, such as bacterial cells, yeast, insect cells, and mammalian cells. The antibodies or proteins of the invention may also be expressed using including in vitro transcription/translation systems. All of such methods are well known by those skilled in the art, and one of skill in the art would readily be able to select a suitable method depending on the nature of the nucleotide sequences, vectors, and cell types used.

The terms "eOD" or "c1d1" are used interchangeably and refer to the following sequence (see e.g., to international patent application Ser. No. PCT/US2012/060,062).

eOD (SEQ ID NO: 1)

DTITLPCRPAPPPHCSSNITGLILTRDGGNSNNESEIFRPGGGDMRDIAR

CQIAGTVVSTQLLLNGSLAEEEVVIRSVNFTDNAKSICVQLNTSVEINCT

GAGHCNISRAKWNNTLKQIASKLREQFGNNKTIIFKQSSGGDPEIVTHSF

NCGGEFFYCNSTQLFNSTWFNSTWS

The terms "eOD_VH1-2_v6.0" and "eOD-GT6" refer to the following sequence ("#" indicates a deletion relative to eOD (c1d1).) (see, e.g., to international patent application Serial No. PCT/US2012/060062 filed Oct. 12, 2012).

eOD_VH1-2_v6.0

(SEQ ID NO: 2)

DTITLPCRPAPPPHCSSNITGLILTRDGGVSNDETEIFRPSGGDMRDIAR

CQIAGTVVSTQLFLNGSLAEEEVVIRSVDFRDNAKSICVQLNTSVEINCT

GAGHCNISRAKWNNTLKQIASKLREQFGN#RTIIFKQSSGGDPEFVTHSF

NCGGEFFYCDSTQLFNSTWFNST##

A synthetic mutant eOD may be chemically synthesized in whole or part using techniques that are well-known in the art (see, e.g., Kochendoerfer, G. G., 2001). Additionally, homologs and derivatives of the polypeptide may be also be synthesized.

Alternatively, methods which are well known to those skilled in the art may be used to construct expression vectors containing nucleic acid molecules that encode the polypeptide or homologs or derivatives thereof under appropriate transcriptional/translational control signals, for expression. These methods include in vitro recombinant DNA techniques, synthetic techniques and in vivo recombination/genetic recombination. See, for example, the techniques described in Maniatis et al., 1989.

In one embodiment, to enhance immunogenicity, multimeric forms of eOD may be generated. Not being bound by a theory, these should provide the ability to stimulate B cells using multivalent avidity, and in addition the larger particulate forms should mimic a virus-like symmetric presentation of epitopes, reduce immune responses to regions buried in the multimer, and enhance in vivo trafficking of eODs to lymph nodes. Trimers, tetramers, and octamers of eOD may be formed by engineering genetic fusions of eOD to coiled-coil motifs that form trimers (PDBID: 1GCN) and tetramers (PDBID: 1GCL and PDBID: 2B22). Larger virus-like particles of eOD may be formed by engineering fusions to proteins that assemble into 24mers (protein name: 03-33, PDBID:3VCD), 60mers (protein name: Lumazine Synthase from Aquafex Aeolicus, PDBID: 1HQK), and 180mers (protein name:PfV, PDBID: 2E0Z).

In certain embodiments, linkers are used. The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins. However, in certain embodiments, the constituent amino acids of a spacer may be selected to influence some property of the molecule such as the folding, net charge, or hydrophobicity of the molecule.

Suitable linkers for use in an embodiment of the present invention are well known to those of skill in the art. Preferred peptide linker sequences adopt a flexible extended conformation and do not exhibit a propensity for developing an ordered secondary structure that could interact with the functional domains. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Still other amino acid sequences that may be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180.

Linkers may be used to fuse multimerization domains to eOD variants. The linkers (shown in bold) here are used as examples but a diverse arrays of linkers could be employed. In many examples below a flexible GlySer linker is used, such as GGSGGSGG (SEQ ID NO: 3) or GGSGGSGGSGGSGGG (SEQ ID NO: 4), but a wide variety of types of flexible linkers could be used instead. In some examples below a known T-helper epitope, Tetanus toxoid p2 peptide, QYIKANSKFIGITEL (SEQ ID NO: 5), is employed as a linker. In other embodiments, Tetanus toxoid p2 peptide includes GS and SG flanking the peptide, such as GSQYIKANSKFIGITELSG (SEQ ID NO: 6). A variety of other T-helper epitopes could be used instead or in addition.

In certain embodiments, a tag a may be appended to the N-terminus or C-terminus of any of the 3mer, 4mer, or 8mer sequences. The tag may be, but is not limited to a his-tag, such as HHHHHH (SEQ ID NO: 7) or HHHHHHGSG (SEQ ID NO: 8) or GTKHHHHHH (SEQ ID NO: 9).

In certain embodiments, variants of eOD proteins as described herein may be developed or produced as in Jardine et al., (Science. 2016 Mar. 25; 351(6280):1458-63. doi: 10.1126/science.aad9195).

It is noted that therapeutics described herein may be a chemical compound, a composition which may comprise a polypeptide of the present invention and/or antibody elicited by such a chemical compound and/or portion thereof or a pharmaceutically acceptable salt or a composition which may comprise a polypeptide of the invention, and may be administered alone or as an active ingredient in combination with pharmaceutically acceptable carriers, diluents, and vehicles, as well as other active ingredients.

The compounds or compositions may be administered orally, subcutaneously or parenterally including intravenous, intraarterial, intramuscular, intraperitoneally, and intranasal administration as well as intrathecal and infusion techniques.

It is noted that humans are treated generally longer than the mice or other experimental animals which treatment has a length proportional to the length of the disease process and drug effectiveness. The doses may be single doses or multiple doses over a period of several days, but single doses are preferred. Thus, one may scale up from animal experiments, e.g., rats, mice, and the like, to humans, by techniques from this disclosure and documents cited herein and the knowledge in the art, without undue experimentation.

The treatment generally has a length proportional to the length of the disease process and drug effectiveness and the patient being treated.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier may be a solvent or dispersing medium containing, for example, water, ethanol, polyol (for example, glycerol, propylene glycol, liquid polyethylene glycol, and the like), suitable mixtures thereof, and vegetable oils.

Proper fluidity may be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, may be added. Prevention of the action of microorganisms may be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form may be brought about by the use of agents delaying absorption, for example, aluminum monostearate and gelatin. According to the present invention, however, any vehicle, diluent, or additive used would have to be compatible with the compounds.

Sterile injectable solutions may be prepared by incorporating the compounds utilized in practicing the present invention in the required amount of the appropriate solvent with various amounts of the other ingredients, as desired.

A pharmacological formulation of the present invention, e.g., which may comprise a therapeutic compound or polypeptide of the present invention, may be administered to the patient in an injectable formulation containing any compatible carrier, such as various vehicles, adjuvants, additives, and diluents; or the compounds utilized in the present invention may be administered parenterally to the patient in the form of slow-release subcutaneous implants or targeted delivery systems such as monoclonal antibodies, iontophoretic, polymer matrices, liposomes, and microspheres.

A pharmacological formulation of the compound and composition which may comprise a polypeptide utilized in the present invention may be administered orally to the patient. Conventional methods such as administering the compounds in tablets, suspensions, solutions, emulsions, capsules, powders, syrups and the like are usable. Known techniques, which deliver the compound orally or intravenously and retain the biological activity, are preferred.

In one embodiment, a formulation of the present invention may be administered initially, and thereafter maintained by further administration. For instance, a formulation of the invention may be administered in one type of composition and thereafter further administered in a different or the same type of composition. For example, a formulation of the invention may be administered by intravenous injection to bring blood levels to a suitable level. The patient's levels are then maintained by an oral dosage form, although other forms of administration, dependent upon the patient's condition, may be used. In the instance of a vaccine composition, the vaccine may be administered as a single dose, or the vaccine may incorporate set booster doses. For example, booster doses may comprise variants in order to provide protection against multiple clades of HIV.

The quantity to be administered will vary for the patient being treated and whether the administration is for treatment or prevention and will vary from a few micrograms to a few milligrams for an average 70 kg patient, e.g., 5 micrograms to 5 milligrams such as 500 micrograms, or about 100 ng/kg of body weight to 100 mg/kg of body weight per administration and preferably will be from 10 pg/kg to 10 mg/kg per administration. Typically, however, the antigen is present in an amount on, the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations may be ascertained without undue experimentation. For instance, dosages may be readily ascertained by those skilled in the art from this disclosure and the knowledge in the art. Thus, the skilled artisan may readily determine the amount of compound and optional additives, vehicles, and/or carrier in compositions and to be administered in methods of the invention. Typically, an adjuvant or additive is commonly used as 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Such determinations do not require undue experimentation from the knowledge of the skilled artisan, this disclosure and the documents cited herein. And, the time for sequential administrations may be ascertained without undue experimentation.

Examples of compositions which may comprise a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions may also be lyophilized. The compositions may contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention may be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers may preferably dispense a metered dose or, a dose having a particular particle size.

Compositions of the invention may contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5,000 cps, since above that range they become more difficult to administer. However, above that range, the compositions may approach solid or gelatin forms, which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, may be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions may be isotonic, i.e., it may have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative may be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems may be readily avoided by reference to standard texts or by simple experiments (not involving undue experimentation), from this disclosure and the documents cited herein.

It is generally envisaged that compounds and compositions of the invention will be administered by injection, as such compounds are to elicit anti-HIV antibodies, and the skilled artisan may, from this disclosure and the knowledge in the art, formulate compounds and compositions identified by herein methods for administration by injection and administer such compounds and compositions by injection.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions may be administered in dosages and by techniques well known to those skilled in the medical arts taking into consideration such factors as the age, sex, weight, and condition of the particular patient, and the composition form used for administration (e.g., solid vs. liquid). Dosages for humans or other mammals may be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

Applicants have advantageously provided for a framework for priming a broadly neutralizing antibody response and have provided novel engineered OD immugens capable of priming VRC01 class broadly neutralizing antibodies. Moreover, Applicants have provided a framework for the development of germline targeting immunogens to activate germline precursors on the pathway to any neutralizing antibody in a subject.

Applicants advantageously established a platform for screening immunogens capable of activating germline precursors necessary for developing mature neutralizing antibodies by providing for knock-in mouse models that express the germline precursors.

The emerging field of vaccine reverse engineering begins with neutralizing antibodies isolated from natural infection, and attempts to design vaccines that will “re-elicit” antibodies with similar specificities and protective functions. Structural vaccinology, another emerging field that partially overlaps with vaccine reverse engineering, attempts to create immunogens that are optimal faithful structural mimics of pathogen epitopes. Here, Applicants have gone beyond the boundaries of those disciplines. Applicants have engineered novel vaccine antigens that directly target the germline precursors of known HIV broadly-neutralizing antibodies. Germline to mature gradient immunogens may be used to activate appropriate germline B cells and guide somatic mutation and clonal expansion toward the development of VRC01-like Abs. The present invention advantageously provides the key step in development of such a vaccine.

The approach described herein is a novel extension of vaccine reverse engineering. However, the approach greatly departs from traditional structural vaccinology because Applicants are explicitly making mutations in the target epitope, hence Applicants are violating the usual goal of precise structural mimicry.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

VRC01 gH Knock-in Mice

The true germline precursor is not known for VRC01 or other VRC01-class bnAbs (30). In the knock-in mouse, Applicants approximated the true heavy chain precursor with a VRC01 germline-reverted heavy chain (VRC01 gH) composed of the VH1-2*02 and IGHJ1*01 genes assigned by JoinSolver (31) and supported by recent longitudinal analysis of the VRC01 lineage (30), along with the CDRH3 from VRC01 with a single mutation to remove an unpaired cysteine (FIG. 8). While the use of the VRC01 CDRH3 in VRC01 gH (necessary because the germline D gene and V-D and D-J junctions cannot be inferred with confidence) is likely a departure from the (unknown) true germline precursor, the VRC01 CDRH3 plays a relatively minor role in epitope recognition, accounting for only 13.7% of the area buried on the heavy chain in the VRC01 interaction with gp120 (10) or 10.2% of the area buried on germline-reverted VRC01 in its interaction with eOD-GT6 (17). Furthermore, the CDRH3 in VRC01 is disulfide-bonded to an affinity-matured cysteine in CDRH1, which may serve to stabilize the antibody conformation and increase affinity for gp120, but this disulfide is not included in VRC01 gH. Thus, use of this CDRH3 is unlikely to strongly bias the VRC01 gH mouse toward favorable interactions with gp120- or eOD-based immunogens, and Applicants believe the VRC01 gH sequence is a reasonable approximation for the true germline, for the purpose of evaluating germline-targeting immunogens.

Testing for the ability to stimulate VRC01-class precursor B cells could not be carried out directly in wild-type mice or other small animals, as none are known to have a VH gene with sufficient similarity to the human VH1-02 germline gene (16, 17). To overcome this limitation, Applicants engineered mice to express a VRC01 gH-chain exon under the control of a mouse VH promoter, introduced by gene targeting into the Igh locus (FIG. 9). This targeting to the physiological locus allows normal regulation of H-chain expression, antibody class switching and somatic mutation. These VRC01 gH mice have similar frequencies of CD19+/B220+ B cells as wild-type littermates (siblings of knock-in mice that lack the knock-in gene by random chance in breeding male heterozygous knock-in mice with wild-type females) (FIG. 1A). By next-generation sequencing, the VRC01 gH-chain gene was expressed by ~80% of B cells (FIG. 1B, FIGS. 10-11), and was paired with random mouse L-chains generated in the course of normal B cell development (FIG. 12). The L-chains have similar V gene usage and CDRL3 length distributions as those of wild type littermates (FIG. 13). Thus, VRC01 gH mice carry germline-reverted bnAb precursor B cells at a frequency appropriate for testing of germline-targeting VRC01-class immunogens, including eOD-GT8 60mer.

Example 2

Analysis of Antibody Responses to Different Priming Immunogens

VRC01 gH mice were immunized with a single injection of eOD-GT8 60mer, a self-assembling nanoparticle composed of an engineered outer domain from HIV gp120 fused to a lumazine synthase protein. To assess if VRC01-like germline precursors were indeed primed, Applicants followed antibody responses and sequenced antibody genes of eOD-GT8-reactive B cells that were captured as hybridomas or by cell sorting of eOD-GT8-binding IgG B cells (FIG. 1C, FIG. 14). To investigate the effect of multimeric state, Applicants compared responses to 60 subunit nanoparticles (eOD-GT8-60mers) and trimers (eOD-GT8-3mers). To probe for adjuvant effects, antigens were delivered in three different adjuvants: alum, Iscomatrix (“Isco”, 40 nm diameter cage-like structures composed of phosopholipids, cholesterol, and saponin that traffic to lymph nodes and can heighten both antibody and T cell responses but contain no known Toll-like receptor (TLR) agonist activity (32)), or Sigma Adjuvant system ("Ribi", an oil-in-water emulsion containing synthetic trehalose dicorynomycolate and the TLR4 agonist Monophosphoryl Lipid A). The alum and Ribi immunizations given by intraperitoneal injection, and the Isco immunizations were delivered subcutaneously per the manufacturer's recommendations (FIG. 1D). To evaluate if immunogens bearing an unmodified CD4bs could activate VRC01-like precursors, Applicants tested responses to both the native-like trimer BG505 SOSIP.664 (33-36) and also to eOD17-60mers, nanoparticles presenting a native-like and non-germline-targeting CD4bs on an eOD protein similar to eOD-Base (17) with all glycosylation sites intact.

eOD-GT8-60mer challenge elicited a CD4bs response in VRC01 gH mice, as their immune serum IgG bound more strongly to eOD-GT8 than to eOD-GT8-KO, a mutant designed to block germline VRC01 binding (D368R, N279A and mutations to restore the N276 glycosylation site) (FIG. 2A, FIG. 15). The IgG response of WT mice, in contrast, was mainly to non-CD4bs epitopes. eOD-GT8 immunogens given in all three adjuvants supported a serum IgG response to CD4bs, though eOD-GT8-60mers were stronger than eOD-GT8-3mers as assessed by an ELISA area-under-the-curve analysis (i.e., area under the eOD-GT8 reactivity curve minus area under the eOD-GT8-KO curve; FIG. 2B) and by frequencies of $IgG^+$ memory phenotype B cells that bound eOD-GT8 but not eOD-GT8-KO (eOD-GT8(+)/eOD-GT8-$KO^{(-)}$) identified by cell sorting (FIG. 2C). eOD-GT8 60mers induced lower frequencies of (non-CD4bs) $IgG^+$ memory phenotype B cells that bound both eOD-GT8 and eOD-GT8-KO (eOD-GT8(+)/eOD-GT8-KO $^{(+)}$), suggestive of an epitope-specific response (FIG. 16). Both BG505 SOSIP.664 trimer and eOD17-60mers elicited weak responses by ELISA and antigen-specific B cell frequencies (FIG. 2B, C).

Example 3

Selection of Light Chain Partners by the Priming Immunogen

Priming of the VRC01-class response was revealed in the sequencing data from sorted B cells and hybridomas. B cell sorting recovered 177 IgG heavy/light paired sequences from day 14 and 42, 167 of which utilized the VRC01 knock-in H-chain (some were unmutated and others had mutations in either or both of the H or L-chains, as discussed below), and 95 (IgG or IgM) hybridomas were recovered, all of which used the knock-in H-chain. Among IgG B cells, this H-chain was paired with K L-chain partners of highly restricted CDRL3 length and Vκ-gene usage (FIG. 3). 92% (154/167) of eOD-GT8(+)/eOD-GT8-$KO^{(-)}$ sorted IgG B cells using the VRC01 gH had L-chains with CDRL3 length of 5 aa (FIG. 3A, table 1-2), whereas only ~0.1% of naive (non-immunized) VRC01 gH B cells or wild-type mouse B cells had a K L-chain CDRL3 length of 5 aa (FIG. 7). None of the 10 sorted B cells that utilized an endogenous mouse VH gene contained a 5 aa CDRL3. Among IgG hybridomas, which were captured as early as day 5 of the response, 6 of 7 hybridomas carried a K L-chain with a 5 aa CDRL3, each isolated from a different mouse (table 3-6). In contrast, among 88 IgM hybridomas recovered following eOD-GT8 60mer immunization (for which eOD-GT8 affinity was weaker than 100 μM for all but two according to SPR), only one had this CDRL3 signature; this suggests that the initial selection for the unusual CDRL3 length occurred upon class switching. Priming was reproducible, as IgG B cells with 5 aa CDRL3s were isolated from 20 of 22 mice immunized with eOD-GT8 60mer (14 of 15 mice analyzed by sorting and 6 of 7 mice that produced IgG hybridomas) (table 1). eOD-GT8-binding IgGs preferentially used Vκ genes with a QQY motif at the start of CDRL3 common to mature VRC01-class bnAbs (CQQYEFF (SEQ ID NO: 62)) (FIG. 3B, C; FIG. 17). In contrast, IgM hybridomas used a broad distribution of Vκ and Vλs (table 6), again indicating selection at the class-switch stage. In summary, eOD-GT8-60mer immunization successfully recruited VRC01-like precursors into the T cell-dependent response and promoted the selective IgG class switching of cells carrying desirable L-chain features.

Example 4

Somatic Mutation Patterns

A bnAb priming immunogen must not only expand precursor numbers, but also promote somatic mutations that allow binding to boosting antigens with closer similarity to HIV Env. Applicants found many somatic mutations among IgG memory phenotype B cells responding to eOD-GT8 60mers and containing a 5aa CDRL3, including some L-chain mutations shared with mature VRC01-class antibodies (FIG. 3C). On the L-chain, many sequences isolated at day 42 of the response to eOD-GT8-60mer/Ribi achieved a D or E in the VRC01 CQQYEF (SEQ ID NO: 62) sequence motif. 16 of 47 analyzed IgG memory phenotype B cells had a T-to-G nucleotide mutation in their 5 aa CDRL3s to introduce a D at position 4 (FIG. 18), and several cells had an E at that position.

As the VRC01 gH-chain sequence was known, H-chain mutations were readily identified and could be compared directly to mature VRC01 to identify favorable mutations. To focus exclusively on VRC01-class antibodies, the heavy chain analysis only included the VH region of Abs that derived from the VRC01 gH-chain and contained a 5aa CDRL3. Nearly all VRC01-class Abs from day 14 were unmutated. By day 42, however, 53 of 98 VRC01-class Abs contained at least one coding mutation from the starting heavy chain sequence (table 7). Among all VRC01-class Abs from day 14 and day 42 with at least one coding mutation on the heavy chain, 55 of 61 contained at least one mutation that is identical to VRC01 (FIG. 19), and ≥50% of the mutations in 49 of 61 such Abs were identical to those in one of 6 VRC01-class bnAbs (12a21, 3BNC60, PGV04, PGV20, VRC-CH31, or VRC01) (FIG. 4A, table 7). In one case, all 6 coding mutations were identical to mutations found in VRC01-class bnAbs. One particular mutation (H35N) was found in >80% of B cells that had at least one mutation, including cells from 12 different mice and all adjuvant groups (table 2), and including both sorted IgG cells and hybridomas. Examination of the eOD-GT6/GL-VRC01 complex structure (PDBID:4jpk) and the gp120/VRC01 complex structure (PDBID:3ngb) revealed that the H35N mutation enables a favorable hydrogen bonding interaction with an asparagine on CDRH3 (FIG. 20). Applicants also noted differences in mutation levels in different adjuvant groups-among the day 42 sequences, the percentages of Abs with at least one heavy chain coding mutation were 44% (8/18) for alum-immunized mice, 19% (3/16) for Isco-immunized mice, and 67% (42/63) for Ribi-immunized mice (FIG. 4B). Overall, the strong selection of mutations is suggestive of a VRC01-class response, with many mutations identical to those in VRC01-class bnAbs that may help primed cells become cross-reactive to more native-like gp120 molecules. Thus, priming with the eOD-GT8 60mer selected antibody features predicted to improve binding to the CD4bs of Env.

Example 5

Antibody Affinity for the Germline-Targeting Prime and Candidate Boost Immunogens T cell-dependent immune responses promote somatic hypermutation (SHM) and selection for B cells with improved affinity for immunogen, but an additional requirement for an effective bnAb HIV priming immunogen is to promote enhanced affinity for the presumed HIV boosting antigen(s). To assess this aspect of the efficacy of eOD-GT8 60mer priming, Applicants expressed 115 H/L paired sequences that utilized the VRC01 knock-in H-chain and contained a 5aa CDRL3 from eOD-GT8(+)/eOD-GT8-KO$^{(-)}$ IgG memory phenotype sorted B cells (table 7), and Applicants then evaluated their binding to eOD-GT8, eOD-GT8-KO and to candidate boosting antigens by SPR. Of the 115 Abs, 72 contained no H- or L-chain mutations from germline. These unmutated Abs bound eOD-GT8 with a median $K_D$ of 32 nM (FIG. 5A-B, table 8). Few mutations were required to promote high affinity—most Abs with >3 coding mutations had an affinity too high to measure accurately ($K_D$<16 μM, FIG. 5A). Confirming epitope-specificity, antibodies for which Applicants could measure a $K_D$ for eOD-GT8 showed reduced affinity for eOD-GT8-KO by factors of 36 to 200. Applicants observed intriguing differences among adjuvant groups, with Ribi-immunized mice producing both more Abs (recoverable by sorting) and higher affinity Abs compared to Alum or Isco.

The eOD-GT8 60mer was designed both to prime germline VRC01-class precursors and to select for mutations that confer cross-reactivity to more native-like gp120 (17). To test if the latter was effective, Applicants selected the 29 Abs that bound eOD-GT8 with subnanomolar affinity as well as 8 unmutated variants (with average $K_D$s for eOD-GT8) and screened them for binding to more native-like gp120 constructs in both monomer and 60mer form. The Abs with more than 3 coding mutations not only had improved affinity for eOD-GT8 but in many cases showed affinity for core-e-2CC HxB2 N276D, a conformationally stabilized core gp120 monomer with a near-native CD4bs from strain HxB2 that combines the loop and termini trimming of the "coreE" design (10, 14) with the disulfides and space-fill mutations of the "2CC" design (37) but also lacks the N276 glycan. In total, 23 of 29 Abs that bound with high affinity to eOD-GT8 showed detectable binding to core-e-2CC HxB2 N276D ($K_D$<100 μM), while none of unmutated Abs did (FIG. 5B, table 8). 60mer nanoparticles of core-e-2CC HxB2 N276D bound to 24 of 29 mutated Abs more strongly than to the monomer by a factor of ~100 due to avidity, but the 60mers also showed no binding to the unmutated Abs. Applicants conclude that priming with eOD-GT8 60mers promotes clonal expansion and facilitates recognition of molecules presenting a near native CD4bs.

Example 6

Discussion: The Priming Problem

A vital goal of rational vaccine design is to understand how to prime naturally subdominant antibody responses in a reproducible manner. Germline-targeting offers one potential strategy to achieve this goal. Here, Applicants have demonstrated using a germline-reverted VRC01 H-chain knock-in mouse model that a germline-targeting immunogen (eOD-GT8 60mer) can activate relatively rare VRC01-class precursors, select productive mutations, and create a pool of memory phenotype B cells that are likely to be susceptible to boosting by more native-like immunogens. In contrast, Applicants found that immunogens bearing a native-like CD4 binding site, including both the eOD17-60mer and the well-ordered BG505 SOSIP.D664 trimer, failed to achieve these goals. These results illustrate the value of an engineered priming immunogen to initiate the development of bnAb lineages by vaccination.

The data in the VRC01 gH mouse model described here have strong potential relevance to human vaccination. Given that: (i) VH1-2*02 is expressed in ~80% of B cells in this mouse compared to ~3% of human B cells (18, 19); (ii) the frequency of 5aa CDRL3 L chains is 0.1% in VRC01 gH B cells compared to 0.6-1% in humans (FIG. 6-7) (16), and (iii) the CDRH3 requirements are modest for VRC01-class bnAbs (10, 14, 16, 38) and appear to be minimal for VRC01-class precursors, perhaps requiring a length of 11-18 (75% of human Abs (FIG. 21)), it is possible that VRC01-class precursors are less frequent in humans compared to the VRC01 gH mouse by a factor of only ~5 (=80/3×0.1/0.6×1/0.75). Even if this estimate is off by an order of magnitude or two due to unknown factors, it is also true that humans have orders of magnitude more B cells than mice, hence more potential targets. Therefore, Applicants believe that this study provides strong support for the idea of human clinical testing of the eOD-GT8 60mer, to assess whether this germline-targeting prime can perform similarly in diverse humans. Moreover, the differences observed with different adjuvants in this mouse model—in serum titers, B cell frequencies, selection of favorable mutations and generation of high affinity Abs—indicate that testing different adjuvants should be considered in the design of human clinical experiments probing activation of specific classes of precursor B cells.

Having demonstrated that eOD-GT8 60mer immunization initiates a VRC01-class response in this mouse model, several additional developments are likely needed to induce broad neutralizing activity. The eOD-GT8 60mer contains a modified CD4bs to confer germline-reactivity and as such is probably not capable of selecting all of the heavy and light chain mutations required for bnAb activity against the native CD4bs. Indeed, no neutralizing activity was detected for any of the 8 eOD-GT8 60mer-induced Abs (all with high affinity [$K_D$<1 nM] for eOD-GT8 and low affinity [1 μM<$K_D$<100

μM] for core-e-2CC HxB2 N276D) that Applicants tested against a panel of four viruses from clades A and B that included both wild-type and N276A mutant viruses with increased sensitivity to VRC01-class bnAbs (FIG. 22). One design feature of eOD-GT8 is that it lacks the N276 glycan-removal of this glycan is a requirement for germline-reactivity (17, 21). However, the N276 glycosylation site is conserved in 94.5% of HIV strains, according to analysis of 3,796 sequences from the Los Alamos HIV database (www.hiv.lanl.gov/). Induction of broad neutralization will likely require one or more boosting immunogens bearing a glycan at N276 so as to select mutations to accommodate that glycan (17). On the H chain of VRC01-class bnAbs, mutations in the CDR2, CDR1, FW1 and FW3 are likely required for maximum potency and breadth (24, 39), and native-like Env immunogens will probably be needed to select for these. In sum, boosting with a sequence of increasingly native-like antigens, and potentially including cocktails of different antigens within each boost to mimic the antigenic diversity of the CD4bs, will likely be needed to select the mutations required for VRC01-class bnAb activity. The mouse model presented here, as well as other newly developed VRC01-class knock-in mouse models (40), should aid us to test this notion and can be used to identify the antigens and boosting strategies that work best. Of note, Applicants demonstrated here that a single immunization with the eOD-GT8 60mer induces VRC01-class antibodies with modest affinity for the core-e-2CC HxB2 N276D monomer and 60mer, so these molecules represent promising candidates for the first boost. Applicants are thus mapping the first steps in a sequential strategy for the rational induction of bnAbs against HIV.

Example 7

Development of Germline-Targeting OD Immunogens

Applicants report the invention of two proteins (eOD-GT8 and eOD-GT10) that are major improvements on eOD-GT6, also known as eOD_VH1-2_v6.0. All of these molecules are intended as germline-targeting immunogens to activate germline precursors of VRC01-class antibodies. Compared to eOD-GT6, eOD-GT8 and eOD-GT10 have greatly improved binding affinities for a large panel of calculated germline precursors of VRC01-class antibodies (FIG. 23). This enables significantly better performance as germline-targeting immunogens.

As an important test of performance, eOD-GT8 has been employed as sorting bait to isolate bona fide VRC01-class germline precursors from naive human B cells, whereas eOD-GT6 tested in the same capacity was unable to isolate VRC01-class germline precursors. Sorting naive human B cells using an eOD-GT8 tetramer (avi-tagged and biotinylated eOD-GT8 mixed with a fluorescently-labelled streptavidin), an eOD-GT8_3mer, and an eOD-GT8-KO tetramer (similar tetramer as above but with mutations in the eOD-GT8 epitope to "knock-out" binding by germline VRC01-class antibodies), 19 VRC01-class precursors were isolated from 54 million B cells from 12 different human donors (FIG. 24). The 19 bona fide VRC01-class precursor antibodies from that experiment were produced as soluble IgG and their binding was tested to eOD-GT6, eOD-GT8, and eOD-GT10; the results from that binding assessment show that while eOD-GT6 had measureable affinity for only one of 19 bona fide precursor antibodies, eOD-GT8 had measureable affinity for all 19 antibodies, with a mean affinity of ~2 μM, and eOD-GT10 also had measurable affinity for all 19 antibodies, with a slightly improved mean affinity of ~1 μM (FIG. 25).

eOD-GT8, in multimeric form as a trimer (eOD-GT8_3mer) or as a 60mer nanoparticle (eOD-GT8_60mer) has also been tested as an immunogen in VRC01 gH mice. The results showed that the eOD-GT8_60mer in particular was capable of activating VRC01-class germline precursors, selecting favorable VRC01-like mutations, and generating memory B cells with modest affinity for candidate boost immunogens (see Examples 1-6).

Applicants also report the invention of stabilizing mutations in the lumazine synthase scaffold protein used to form 60mer nanoparticles with eOD-GT6, eOD-GT8 or eOD-GT10. Applicants have designed novel disulfide bonds that greatly stabilize the nanoparticles against low pH treatment. For particles produced in mammalian cell culture for use in humans, it is desirable to be able to incubate nanoparticles at low pH (pH 3 or 4) for at least 30 minutes in order to eliminate any contaminating viruses or other microorganisms from the cell culture. The original eOD-GT8_60mer cannot withstand this treatment, as it falls apart into pentamers (FIG. 26). The eOD-GT8_60mer particles with additional disulfides (either "d4" or "d41" or "d44") can be incubated for up to 90 minutes at low pH without loss of structure according to size exclusion chromatography coupled inline with multi-angle light scattering (SEC-MALS) (FIGS. 26 and 27).

Finally, Applicants report the invention of including mutations to eliminate lumazine synthase activity into these stabilized 60mers without loss of structure or stability. The lumazine synthase active site includes three key residues: F22, H88, and R127. Applicants have produced and tested eOD-GT8_60mers with a single mutation (R127A, called "m1"), a double mutation (H88S+R127A, called "m2") and a triple mutation (F22A+H88S+R127A, called "m3") in these residues, and Applicants have found that all of the particles maintain structure by SECMALS.

The following list of mutations describe converting eOD_VH1-2_v6.0 to eOD-GT8.1 (eOD-GT6 is also known as eOD_VH1-2_v6.0 (see, e.g., international patent application Serial No. PCT/US2012/060,062 filed Oct. 12, 2012)):

| mut_count | eOD_numbering | HxB2_numbering |
|---|---|---|
| 1 | D27Q | D457Q |
| 2 | V30Y | V460Y |
| 3 | E34N | E464N |
| 4 | E36V | E466V |
| 5 | M45W | M475W |
| 6 | V78E | V275E |
| 7 | F80W | F277W |
| 8 | F127Y | F353Y |
| 9 | R131K | R357K |
| 10 | Q137P | Q363P |
| 11 | T147N | T373N |

The following list of mutations describe converting eOD_VH1-2_v6.0 to eOD-GT10.8:

| mut_count | eOD_numbering | HxB2_numbering |
|---|---|---|
| 1 | D27Q | D457Q |
| 2 | V30W | V460W |
| 3 | E34N | E464N |
| 4 | E36V | E466V |
| 5 | G42A | G472A |
| 6 | M45W | M475W |
| 7 | V78R | V275R |
| 8 | F80W | F277W |
| 9 | F127Y | F353Y |
| 10 | R131K | R357K |
| 11 | I133V | I359V |
| 12 | K136A | K362A |
| 13 | Q137P | Q363P |
| 14 | T147N | T373N |

The following list of mutations describe converting eOD-GT8.1 to eOD-GT10.8:

| mut_count | eOD_numbering | HxB2_numbering |
|---|---|---|
| 1 | Y30W | Y460W |
| 2 | G42A | G472A |
| 3 | E78R | E275R |
| 4 | I133V | I359V |
| 5 | K136A | K362A |

The sequences of the eOD variants of the present invention are described below and the mutations from eOD-GT6 are shown in bold:

eOD-GT8 (also known as "eOD-GT8.1")

(SEQ ID NO: 10)

DTITLPCRPAPPPHCSSNITGLILTRQGGYSNDNTVIFRPSGGDWRDIAR

CQIAGTVVSTQLFLNGSLAEEEVVIRSEDWRDNAKSICVQLNTSVEINCT

GAGHCNISRAKWNNTLKQIASKLREQYGNKTIIFKPSSGGDPEFVNHSFN

CGGEFFYCDSTQLFNSTWFNST eOD-GT10 (also known as "eOD_GT10.8")

(SEQ ID NO: 11)

DTITLPCRPAPPPHCSSNITGLILTRQGGWSNDNTVIFRPSAGDWRDIAR

CQIAGTVVSTQLFLNGSLAEEEVVIRSRDWRDNAKSICVQLNTSVEINCT

GAGHCNISRAKWNNTLKQIASKLREQYGNKTVIFAPSSGGDPEFVNHSFN

CGGEFFYCDSTQLFNSTWFNST

Applicants also developed the multimers for eOD-GT6, eOD-GT8 and eOD-GT10. Exemplary multimers are shown below. One skilled in the art can also generate multimers for any eOD variant.

eOD-GT8 trimer, eOD-GT8_GCN4_mC (also known as "eOD-GT8_3mer")

(SEQ ID NO: 12)

DTITLPCRPAPPPHCSSNITGLILTRQGGYSNDNTVIFRPSGGDWRDIARCQIAGTVVSTQLFL

NGSLAEEEVVIRSEDWRDNAKSICVQLNTSVEINCTGAGHCNISRAKWNNTLKQIASKLREQYG

NKTIIFKPSSGGDPEFVNHSFNCGGEFFYCDSTQLFNSTWFNSTGSGGSGGSGGSGGSGRMKQI

EDKIEEILSKIYHIENEIARIKKLIGERGTKHHHHHH** eOD-GT8_d4_60mer (SEQ ID NO: 13)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d41_60mer (SEQ ID NO: 14)

MQIYEGKLTAEGLRFGIVASRFNHALVDRLVEGAIDAIVRHGGREEDITLVRVCGSWEIPVAAG

ELARKEDIDAVIAIGVLCRGATPHFDYIASEVSKGLADLSLELRKPITFGVITADTLEQAIERA

GTCHGNKGWEAALCAIEMANLFKSLRGGSGGSGGSGGSGGGDTITLPCRPAPPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d44_60mer (SEQ ID NO: 15)

MQIYCGKLTAEGLRFGIVASRFNHALVDRLVEGAIDAIVRHGGREEDITLVCVPGSWEIPVAAG

ELARKEDIDAVIAIGVLCRGATPHFDYIASEVSKGLADLSLELRKPITFGVITADTLEQAIERA

-continued

GTCHGNKGWEAALSAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d4_m1_60mer (d41 + R127A)
(SEQ ID NO: 16)
MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d4_m2_60mer (d41 + H88S + R127A)
(SEQ ID NO: 17)
MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d4_m3_60mer (d41 + F22A + H88S + R127A)
(SEQ ID NO: 18)
MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d41_m1_60mer (d41 + R127A)
(SEQ ID NO: 19)
MQIYEGKLTAEGLRFGIVASRFNHALVDRLVEGAIDAIVRHGGREEDITLVRVCGSWEIPVAAG

ELARKEDIDAVIAIGVLCRGATPHFDYIASEVSKGLADLSLELRKPITFGVITADTLEQAIEAA

GTCHGNKGWEAALCAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT8_d41_m2_60mer (d41 + H88S + R127A)
(SEQ ID NO: 20)
MQIYEGKLTAEGLRFGIVASRFNHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST**

-continued eOD-GT8_d41_m3_60mer (d41 + F22A + H88S + R127A)

(SEQ ID NO: 21)

MQIYEGKLTAEGLRFGIVASRANHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT10 trimer, eOD-GT10_GCN4_mC (also known as "eOD-GT10_3mer")

(SEQ ID NO: 22)

DTITLPCRPAPPPHCSSNITGLILTRQGGWSNDNTVIFRPSAGDWRDIARCQIAGTVVSTQLFL

NGSLAEEEVVIRSRDWRDNAKSICVQLNTSVEINCTGAGHCNISRAKWNNTLKQIASKLREQYG

NKTVIFAPSSGGDPEFVNHSFNCGGEFFYCDSTQLFNSTWFNSTGSGGSGGSGGSGGSGRMKQI

EDKIEEILSKIYHIENEIARIKKLIGERGTKHHHHHH** eOD-GT10_d4_60mer (SEQ ID NO: 23)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT10_d41_60mer (SEQ ID NO: 24)

MQIYEGKLTAEGLRFGIVASRFNHALVDRLVEGAIDAIVRHGGREEDITLVRVCGSWEIPVAAG

ELARKEDIDAVIAIGVLCRGATPHFDYIASEVSKGLADLSLELRKPITFGVITADTLEQAIERA

GTCHGNKGWEAALCAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT10_d44_60mer (SEQ ID NO: 25)

MQIYCGKLTAEGLRFGIVASRFNHALVDRLVEGAIDAIVRHGGREEDITLVCVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVENCTGAGHCNISRAKWNNTLKQIASKLREQYGNKTVIFAPSSGGDPEFVNHSFNC

GGEFFYCDSTQLFNSTWFNST** eOD-GT10_d4_m1_60mer (d41 + R127A)

(SEQ ID NO: 26)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST**

-continued eOD-GT10_d4_m2_60mer (d41 + H88S + R127A)

(SEQ ID NO: 27)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT10_d4_m3_60mer (d41 + F22A + H88S + R127A)

(SEQ ID NO: 28)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT10_d41_m1_60mer (d41 + R127A)

(SEQ ID NO: 29)

MQIYEGKLTAEGLRFGIVASRFNHALVDRLVEGAIDAIVRHGGREEDITLVRVCGSWEIPVAAG

ELARKEDIDAVIAIGVLCRGATPHFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRQGGYSNDNTVIFRPSGGDWRDIARCQIAGTVVSTQLFLNGSLAEEEVVIRSEDWRDNAKSI

CVQLNTSVEINCTGAGHCNISRAKWNNTLKQIASKLREQYGNKTIIFKPSSGGDPEFVNHSFNC

GGEFFYCDSTQLFNSTWFNST** eOD-GT10_d41_m2_60mer (d41 + H88S + R127A)

(SEQ ID NO: 30)

MQIYEGKLTAEGLRFGIVASRFNHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT10_d41_m3_60mer (d41 + F22A + H88S + R127A)

(SEQ ID NO: 31)

MQIYEGKLTAEGLRFGIVASRANHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRQGGWSNDNTVIFRPSAGDWRDIARCQIAGTVVSTQLFLNGSLAEEEVVIRSRDWRDNAKSI

CVQLNTSVEINCTGAGHCNISRAKWNNTLKQIASKLREQYGNKTVIFAPSSGGDPEFVNHSFNC

GGEFFYCDSTQLFNSTWFNST** eOD-GT6_d4_60mer (SEQ ID NO: 32)

MQIYEGKLTAEGLRFGIVASRFNHALVDRLVEGAIDAIVRHGGREEDITLVRVPGSWEIPVAAG

ELARKEDIDAVIAIGVLCRGATPHFDYIASEVSKGLADLSLELRKPITFGVITADTLEQAIERA

GTCHGNKGWEAALSAIEMANLFKSLRGGSGGSGGSGGSGGGDTITLPCRPAPPPHCSSNITGLI

LTRDGGVSNDETEIFRPSGGDMRDIARCQIAGTVVSTQLFLNGSLAEEEVVIRSVDFRDNAKSI

-continued

CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d41_60mer
(SEQ ID NO: 33)
MQIYEGKLTAEGLRFGIVASRFNHALVDRLVEGAIDAIVRHGGREEDITLVRVCGSWEIPVAAG
ELARKEDIDAVIAIGVLCRGATPHFDYIASEVSKGLADLSLELRKPITFGVITADTLEQAIERA
GTCHGNKGWEAALCAIEMANLFKSLRGGSGGSGGSGGSGGGDTITLPCRPAPPPHCSSNITGLI
LTRDGGVSNDETEIFRPSGGDMRDIARCQIAGTVVSTQLFLNGSLAEEEVVIRSVDFRDNAKSI
CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d44_60mer
(SEQ ID NO: 34)
MQIYCGKLTAEGLRFGIVASRFNHALVDRLVEGAIDAIVRHGGREEDITLVCVPGSWEIPVAAG
ELARKEDIDAVIAIGVLCRGATPHFDYIASEVSKGLADLSLELRKPITFGVITADTLEQAIERA
GTCHGNKGWEAALSAIEMANLFKSLRGGSGGSGGSGGSGGGDTITLPCRPAPPPHCSSNITGLI
LTRDGGVSNDETEIFRPSGGDMRDIARCQIAGTVVSTQLFLNGSLAEEEVVIRSVDFRDNAKSI
CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d4_m1_60mer (d41 + R127A)
(SEQ ID NO: 35)
MQIYEGKLTAEGLRFGIVASRFNHALVDRLVEGAIDAIVRHGGREEDITLVRVPGSWEIPVAAG
ELARKEDIDAVIAIGVLCRGATPHFDYIASEVSKGLADLSLELRKPITFGVITADTLEQAIERA
GTCHGNKGWEAALSAIEMANLFKSLRGGSGGSGGSGGSGGGDTITLPCRPAPPPHCSSNITGLI
LTRDGGVSNDETEIFRPSGGDMRDIARCQIAGTVVSTQLFLNGSLAEEEVVIRSVDFRDNAKSI
CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d4_m2_60mer (d41 + H88S + R127A)
(SEQ ID NO: 36)
MQIYEGKLTAEGLRFGIVASRFNHALVDRLVEGAIDAIVRHGGREEDITLVRVPGSWEIPVAAG
ELARKEDIDAVIAIGVLCRGATPHFDYIASEVSKGLADLSLELRKPITFGVITADTLEQAIERA
GTCHGNKGWEAALSAIEMANLFKSLRGGSGGSGGSGGSGGGDTITLPCRPAPPPHCSSNITGLI
LTRDGGVSNDETEIFRPSGGDMRDIARCQIAGTVVSTQLFLNGSLAEEEVVIRSVDFRDNAKSI
CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d4_m3_60mer (d41 + F22A + H88S + R127A)
(SEQ ID NO: 37)
MQIYEGKLTAEGLRFGIVASRFNHALVDRLVEGAIDAIVRHGGREEDITLVRVPGSWEIPVAAG
ELARKEDIDAVIAIGVLCRGATPHFDYIASEVSKGLADLSLELRKPITFGVITADTLEQAIERA
GTCHGNKGWEAALSAIEMANLFKSLRGGSGGSGGSGGSGGGDTITLPCRPAPPPHCSSNITGLI
LTRDGGVSNDETEIFRPSGGDMRDIARCQIAGTVVSTQLFLNGSLAEEEVVIRSVDFRDNAKSI
CVQLNTSVEINCTGAGHCNISRAKWNNTLKQIASKLREQFGN#RTIIFKQSSGGDPEFVTHSFN
CGGEFFYCDSTQLFNSTWFNST** eOD-GT6_d41_m1_60mer (d41 + R127A)
(SEQ ID NO: 38)
MQIYEGKLTAEGLRFGIVASRFNHALVDRLVEGAIDAIVRHGGREEDITLVRVCGSWEIPVAAG
ELARKEDIDAVIAIGVLCRGATPHFDYIASEVSKGLADLSLELRKPITFGVITADTLEQAIEAA
GTCHGNKGWEAALCAIEMANLFKSLRGGSGGSGGSGGSGGGDTITLPCRPAPPPHCSSNITGLI -continued

LTRDGGVSNDETEIFRPSGGDMRDIARCQIAGTVVSTQLFLNGSLAEEEVVIRSVDFRDNAKSI

CVQLNTSVEINCTGAGHCNISRAKWNNTLKQIASKLREQFGN#RTIIFKQSSGGDPEFVTHSFN

CGGEFFYCDSTQLFNSTWFNST** eOD-GT6_d41_m2_60mer (d41 + H88S + R127A)

(SEQ ID NO: 39)

MQIYEGKLTAEGLRFGIVASRFNHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRDGGVSNDETEIFRPSGGDMRDIARCQIAGTVVSTQLFLNGSLAEEEVVIRSVDFRDNAKSI

CVQLNTSVEINCTGAGHCNISRAKWNNTLKQIASKLREQFGN#RTIIFKQSSGGDPEFVTHSFN

CGGEFFYCDSTQLFNSTWFNST** eOD-GT6_d41_m3_60mer (d41 + F22A + H88S + R127A)

(SEQ ID NO: 40)

MQIYEGKLTAEGLRFGIVASRANHALVDRLVEGAIDAIVRHGGREEDITLVRVCGSWEIPVAAG

ELARKEDIDAVIAIGVLCRGATPSFDYIASEVSKGLADLSLELRKPITFGVITADTLEQAIEAA

GTCHGNKGWEAALCAIEMANLFKSLRGGSGGSGGSGGSGGGDTITLPCRPAPPPHCSSNITGLI

LTRDGGVSNDETEIFRPSGGDMRDIARCQIAGTVVSTQLFLNGSLAEEEVVIRSVDFRDNAKSI

CVQLNTSVEINCTGAGHCNISRAKWNNTLKQIASKLREQFGN#RTIIFKQSSGGDPEFVTHSFN

CGGEFFYCDSTQLFNSTWFNST**

Described below are a series of mutations on the disclosed inventions that were discovered by a protein engineering method involving directed evolution, next generation sequencing and bioinformatics, as described herein. The mutations were selected for the ability to bind to at least three VRC01-class broadly neutralizing antibodies. The binding of each mutation was measured on the surface of yeast cells and reported as a log ratio of the binding population and the unsorted population. These mutations were tested on yeast in the context of eOD-GT8 or an earlier variant of eOD-GT8. The present invention relates to eOD, eOD-GT6, eOD-GT8 or eOD-GT10 variants encoding 1 to 10 of the listed amino acid substitutions, wherein said protein still functions as a germline-targeting CD4bs immunogen. Further, the invention relates to placing 1 to 10 of the listed amino acid substitutions on any other gp120-derived molecule for the purpose of germline-targeting for VRC01-class antibody elicitation.

It should be noted that these sequence variants are purely amino acid sequences and any nucleotide sequence coding for this sequence are encompassed in the present invention.

What follows is a list of all such mutations, in which the position in the HIV Env reference strain HxB2 is given, the corresponding position in eOD is given, and the amino acid that was selected for favorable binding to at least three VRC01-class broadly neutralizing antibodies is given.

| HxB2 | eOD | AA |
|---|---|---|
| 455 | 25 | VAL |
| 457 | 27 | GLN |
| 460 | 30 | ARG |
| 460 | 30 | ASN |
| 460 | 30 | GLN |
| 460 | 30 | GLY |
| 460 | 30 | HIS |
| 460 | 30 | LEU |

-continued

| HxB2 | eOD | AA |
|---|---|---|
| 460 | 30 | MET |
| 460 | 30 | PHE |
| 460 | 30 | PRO |
| 460 | 30 | TYR |
| 461 | 31 | MET |
| 461 | 31 | TRP |
| 462 | 32 | ASP |
| 462 | 32 | CYS |
| 462 | 32 | GLN |
| 462 | 32 | GLU |
| 462 | 32 | ILE |
| 462 | 32 | LEU |
| 462 | 32 | LYS |
| 462 | 32 | PHE |
| 462 | 32 | THR |
| 462 | 32 | TRP |
| 462 | 32 | TYR |
| 462 | 32 | VAL |
| 463 | 33 | GLU |
| 465 | 35 | ALA |
| 465 | 35 | GLN |
| 465 | 35 | MET |
| 465 | 35 | TRP |
| 466 | 36 | ALA |
| 466 | 36 | ILE |
| 466 | 36 | LEU |
| 466 | 36 | MET |
| 466 | 36 | PHE |
| 466 | 36 | TYR |
| 466 | 36 | VAL |
| 467 | 37 | VAL |
| 471 | 41 | ALA |
| 472 | 42 | ALA |
| 472 | 42 | TRP |
| 473 | 43 | ALA |
| 473 | 43 | ASP |
| 473 | 43 | GLN |
| 473 | 43 | GLU |
| 473 | 43 | HIS |
| 473 | 43 | MET |

-continued

| HxB2 | eOD | AA |
|---|---|---|
| 473 | 43 | SER |
| 473 | 43 | TRP |
| 473 | 43 | TYR |
| 475 | 45 | ARG |
| 475 | 45 | ASP |
| 475 | 45 | GLN |
| 475 | 45 | GLU |
| 475 | 45 | GLY |
| 475 | 45 | HIS |
| 475 | 45 | ILE |
| 475 | 45 | LEU |
| 475 | 45 | MET |
| 475 | 45 | PHE |
| 475 | 45 | PRO |
| 475 | 45 | THR |
| 475 | 45 | TYR |
| 475 | 45 | VAL |
| 476 | 46 | ALA |
| 476 | 46 | ASP |
| 476 | 46 | GLN |
| 476 | 46 | GLU |
| 476 | 46 | THR |
| 476 | 46 | TYR |
| 478 | 48 | GLU |
| 478 | 48 | LEU |
| 478 | 48 | MET |
| 478 | 48 | TRP |
| 479 | 49 | ASP |
| 479 | 49 | GLU |
| 479 | 49 | TYR |
| 480 | 50 | ALA |
| 480 | 50 | ASN |
| 480 | 50 | ASP |
| 480 | 50 | GLN |
| 480 | 50 | GLU |
| 480 | 50 | HIS |
| 480 | 50 | LYS |
| 480 | 50 | MET |
| 480 | 50 | PHE |
| 480 | 50 | SER |
| 480 | 50 | THR |
| 480 | 50 | TYR |
| 480 | 50 | VAL |
| 275 | 78 | ALA |
| 275 | 78 | ARG |
| 275 | 78 | ASN |
| 275 | 78 | ASP |
| 275 | 78 | GLN |
| 275 | 78 | GLY |
| 275 | 78 | HIS |
| 275 | 78 | LYS |
| 275 | 78 | PRO |
| 275 | 78 | SER |
| 275 | 78 | THR |
| 275 | 78 | VAL |
| 277 | 80 | TRP |
| 278 | 81 | HIS |
| 278 | 81 | MET |
| 279 | 82 | ASN |
| 281 | 84 | SER |
| 352 | 126 | ARG |
| 352 | 126 | HIS |
| 352 | 126 | ILE |
| 352 | 126 | LYS |
| 352 | 126 | PRO |
| 352 | 126 | VAL |
| 353 | 127 | TYR |
| 355 | 129 | GLN |
| 355 | 129 | GLU |
| 355 | 129 | PRO |
| 360 | 133 | ALA |
| 360 | 133 | GLN |
| 360 | 133 | GLU |
| 360 | 133 | LYS |
| 360 | 133 | MET |
| 360 | 133 | SER |
| 360 | 133 | THR |

-continued

| HxB2 | eOD | AA |
|---|---|---|
| 360 | 133 | TRP |
| 362 | 135 | ASP |
| 362 | 135 | GLU |
| 362 | 135 | SER |
| 363 | 136 | GLU |
| 363 | 136 | PRO |
| 365 | 138 | ASN |
| 369 | 142 | LEU |
| 369 | 142 | MET |
| 369 | 142 | TRP |
| 369 | 142 | TYR |
| 372 | 145 | ALA |
| 373 | 146 | ALA |
| 373 | 146 | ASN |
| 373 | 146 | HIS |
| 373 | 146 | MET |
| 373 | 146 | SER |

Example 8

Generating Germline-Targeting Immunogens

When Applicants employed the VRC01-class germline-targeting immunogen eOD-GT6 (17) as bait to screen human naïve B cells using a two phase multiple-validation methodology (and FIG. 31), Applicants failed to isolate VRC01-class B cells. Applicants did, however, isolate non-VRC01-class naïve B cells with Ab affinities as low as 120 μM for eOD-GT6 (FIG. 31). Applicants therefore set out to develop an improved variant of eOD-GT6 with higher affinity and breadth for germline-reverted VRC01-class Abs, hypothesizing that such improvements might translate into improved affinity for diverse true VRC01-class precursor Abs.

To improve on eOD-GT6, Applicants utilized yeast display library screening coupled with next generation sequencing (55). Applicants screened a library of every point mutation at the 58 eOD:Ab interface positions on eOD-GT7, a slightly improved version of eOD-GT6, against each of 29 VRC01-class Abs (18 germline-reverted and 11 mature bnAbs). By measuring binding enrichments for each mutation and antibody (FIG. 28A and FIG. 32), Applicants identified 12 positions in eOD-GT7 at which one or more mutations were favorable (at least 2-fold enriched) for binding to the majority (at least 10 of 18) of germline-reverted bnAbs and another 4 positions at which one or more mutations were at least 1.25-fold enriched for binding to the vast majority (at least 17 of 18) of germline-reverted bnAbs (FIG. 28B). To identify combinations of mutations predicted to confer the greatest binding cross-reactivity, Applicants then created a library encompassing all combinations of a filtered set of the favorable mutations at those 16 positions (FIG. 28C). Filtering was done to limit library size, to exclude mutations detrimental to binding the majority of mature bnAbs, to reduce hydrophobic exposure, to exclude unpaired cysteines, and to minimize non-conservative changes to epitope components. Upon screening this combinatorial library against the panel of 29 VRC01-class Abs, Applicants identified a sequence, eOD-GT8, predicted to have optimal breadth against the entire panel (FIG. 28C, FIGS. 33-34 and table 9).

Compared to eOD-GT6, eOD-GT8 demonstrated superior affinity and breadth of binding to germline-reverted Abs (FIG. 28D and table 10). eOD-GT8 bound to all germline-reverted Abs in the panel, whereas eOD-GT6 bound to only 8 of 14 Abs with $K_D$s<100 μM. For those eight germline-reverted Abs, eOD-GT8 had a 2,100-fold higher geometric mean affinity compared to eOD-GT6. eOD-GT8 also had 3-fold improved affinity for VRC01-class bnAbs. The tightest eOD-GT8 binding detected was for germline-reverted PGV20, with a $K_D$ of 508 fM (234-943 fM 95% CI) (FIG. 28D, FIG. 35), a 5,900 fold improvement over eOD-GT6 ($K_D$=3 nM) and a 33 million fold improvement over the original eOD construct, eOD Base ($K_D$=17 μM (17)), a remarkable affinity improvement for a protein-protein interface.

To examine whether VRC01-class precursors targeted by eOD-GT8 exist in humans, Applicants performed epitope-specific B cell sorting from a pool of peripheral blood mononuclear cells (PBMCs) from healthy, HIV-seronegative donors. Epitope-specific B cells bound tetramers of eOD-GT8 but not tetramers of eOD-GT8-KO, a variant of eOD-GT8 with mutations abrogating binding by VRC01-class germline-reverted Abs. After sequencing immunoglobulin genes from single sorted cells, Applicants searched for VRC01-class antibody sequences—i.e. those with a heavy chain that utilized VH1-2 alleles *02, *03 or *04 and a light chain with a 5-amino acid (aa) CDR3 (16,17). After sorting 2.4 million $IgM^{(+)}/IgG^{(-)}/CD19^{(+)}$ B cells pooled from 9 donors, Applicants recovered a single $GT8^{(+)}$/GT8-$KO^{(-)}$ Ab that qualified as a VRC01-class precursor. This Ab, VRC01c-HuGL1, bound to eOD-GT8 with a $K_D$ of 22 μM and had no detectable affinity for eOD-GT8-KO (FIG. 36).

Figures 29A, 29B, 29C, 29D:
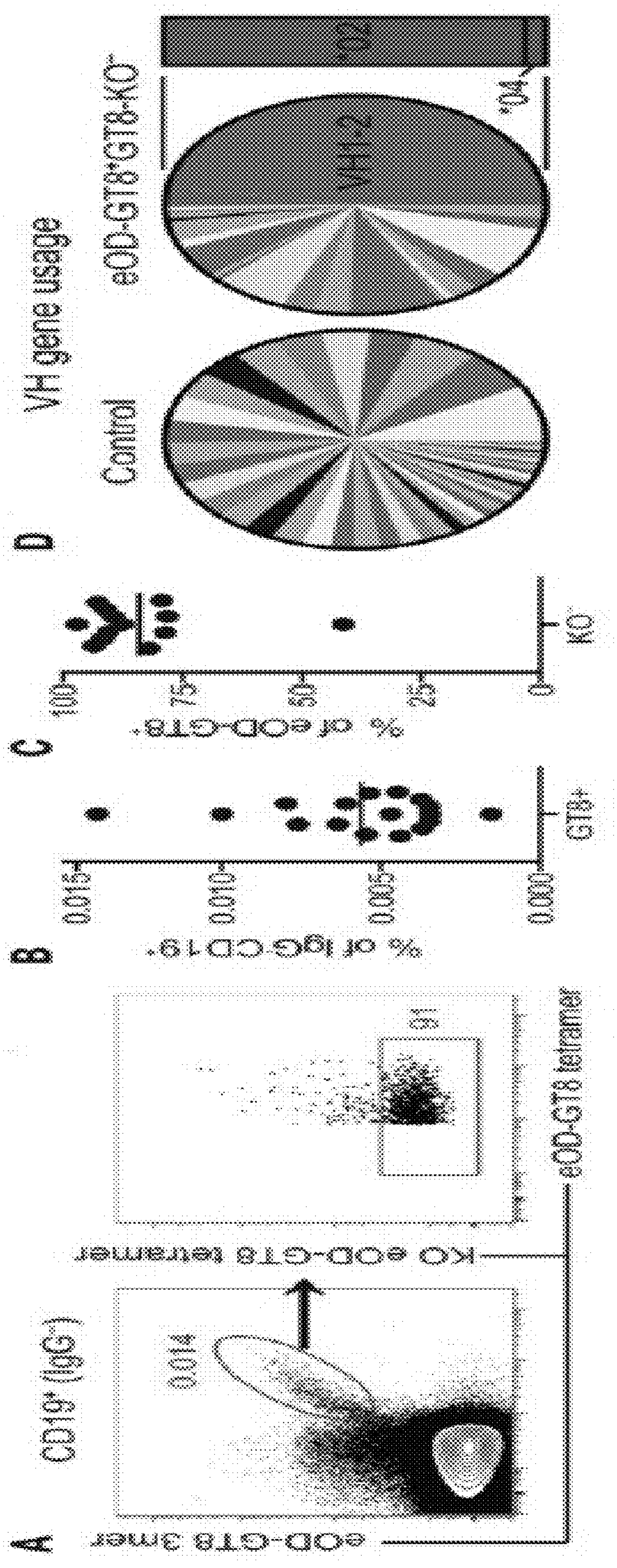

To assess both the percentage of people who possess VRC01-class germline precursor B cells and the frequency of VRC01-class germline precursor B cells within a given donor, Applicants screened naïve B cells from 15 healthy, HIV-seronegative donors individually rather than pooled. For 7 of 15 samples, Applicants used the two phase multiple-validation methodology that first assesses specificity by probe binding in flow cytometry and then confirms specificity and lack of polyreactivity by single cell secreted IgM (FIG. 37); for 8 subsequent donors, Applicants relied on sorting specificity alone. To improve cell sorting sensitivity, B cells were required to simultaneously bind two eOD-GT8 probes multimerized differently (trimer, 'tri'; and streptavidin tetramers, 'SA') and not bind eOD-GT8-KO-SA (FIG. 29A and FIG. 37). For the 15 donors, the mean frequency of eOD-$GT8^{(tri+/SA+)}$ B cells among 61.6 million naïve B cells sorted was 0.0056% (FIG. 29B). Strikingly, a vast majority (84%±14%) of these eOD-$GT8^{(tri+/SA+)}$ B cells did not bind eOD-GT8-KO-SA (FIG. 29C), suggesting that naïve B cell reactivity to eOD-GT8 is highly focused to the CD4 binding site (CD4bs). Several design features of eOD-GT8 are likely responsible for this immunofocusing, including the relatively small size of eOD-GT8 (175 aa) and its compact structure (no exposed loops except Loop D and V5 within the CD4bs), as well as the glycan shielding by ten glycans covering much of the eOD-GT8 surface outside the CD4bs.

Figures 29E, 29F, 29G, 29H, 29I:
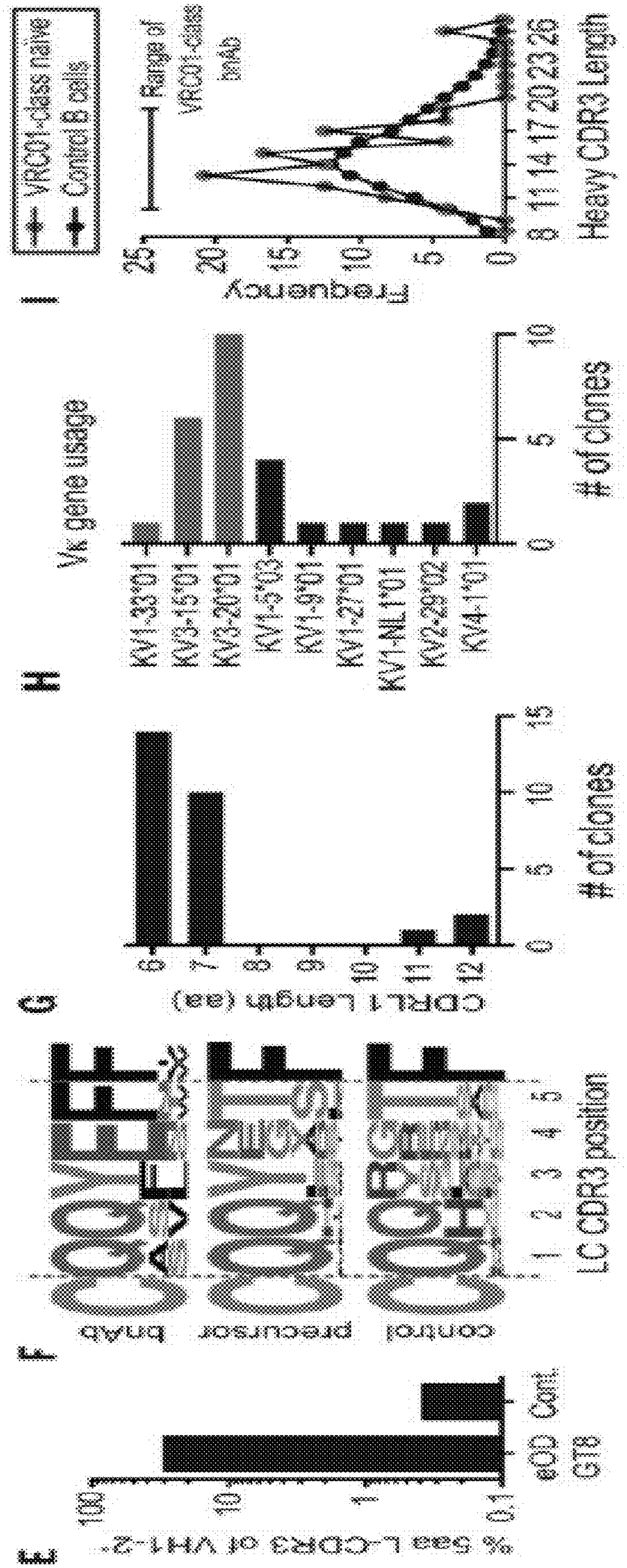

Paired heavy and kappa light chain sequences were recovered from 173 eOD-$GT8^{(tri+/SA+)}$/eOD-GT8-$KO^{(-)}$ B cells. All sequences were essentially germline, confirming the naïve B cell sorts. Half (50%) of these B cells were VH1-2, whereas only 4% of control B cells from reference (19) were VH1-2 ($X^2$=29.9, p<0.0001; FIG. 29D and FIG. 38). Among these 87 VH1-$2^+$ B cells, 26 had a light chain CDR3 (L-CDR3) length of 5 aa, an 85-fold enrichment compared to control B cells ($X^2$=32.6, p<0.0001; FIG. 29E). Twenty-five of the 26 used the VH1-2*02 allele and one used VH1-2*04 (table 11), thus 15% (=26/173) of $GT8^{(tri+/SA+)}$/eOD-GT8-$KO^{(-)}$ B cells were VRC01-class. In total, Applicants identified 27 independent VRC01-class naïve B cells, including VRC01c-HuGL1.

In addition to the VH1-2 alleles and critical 5-aa L-CDR3, VRC01-class bnAbs possess several additional defining features, including a consensus L-CDR3 of QQYEF (SEQ ID NO: 63). The majority of VRC01-class precursors Applicants isolated contained a QQYxx partial VRC01-class consensus motif, significantly enriched compared to control B cells (67% vs 11%; $\chi^2$=8.2, p<0.0001; FIG. 29F). Furthermore, 11% contained a QQYEx (SEQ ID NO: 64) L-CDR3 motif (vs 1.5% of control B cells), one mutation away from a perfect mature VRC01-class L-CDR3 (FIG. 29F). In addition, the L-CDR1 loop is under strong selective pressure during VRC01-class bnAb affinity maturation to minimize clashes with gp120 (10, 14). VRC01-class bnAb L-CDR1 loops generally become very short (2-6 aa) through deletion, or retain a germline length of 6 aa and add flexible glycines (14). Of the 27 VRC01-class precursors isolated by eOD-GT8, 23 used $V_k$ genes containing L-CDR1 loops of 6-7 aa (FIG. 29G), thus confirming potential to develop into VRC01-class bnAbs. Indeed, 17 of the VRC01-class naïve B cells had $V_k$ genes utilized in known VRC01-class bnAbs (FIG. 29H). At least 24 of the VRC01-class precursors had H-CDR3 lengths of 10-19 aa (FIG. 29I), consistent with known VRC01-class bnAb lengths of 10-19 aa. Two of the isolated VRC01-class precursors had incomplete H-CDR3 sequences preventing determination of H-CDR3 length. Thus, not only are the eOD-GT8 isolated naïve B cells highly enriched for VRC01-class core characteristics of VH1-02 and a 5-aa L-CDR3, they possess further refined sequence attributes of VRC01-class bnAbs.

Combining data from the 15 donors analyzed individually, the overall frequency of recovered VRC01-class precursors was 1 in 2.4 million naïve B cells (FIG. 29J), consistent with both the first pooled sort and a previous bioinformatically estimated range (14). The observed counts were consistent with a Poisson distribution with constant frequency of 1 in 2.4 million (FIG. 29K), suggesting that VRC01-class precursors occur at a consistent rate among 96% of humans possessing the necessary VH1-2 alleles (17). Adults have an estimated $10^{10}$-$10^{11}$ B cells, and lymph nodes each have ~50 million B cells, of which ~65-75% are naïve B cells (56). Thus, the results indicate that VRC01-class precursor B cells are relatively common in humans: at least 2,700 to 31,000 eOD-GT8-reactive VRC01-class naïve B cells are likely present in nearly all potential human vaccines, with ~15 such B cells in each lymph node, at any given time. The frequency of 1 in 2.4 million is an underestimate of the true frequency among naïve B cells, because not all B cells counted by the sorter as eOD-GT8tri+/SA+/eOD-GT8-KO− were sorted into a well (cell sorter loss), paired heavy chain and light chain (HC and LC) sequences were recovered from fewer than half of eOD-GT8tri+/SA+/eOD-GT8-KO− B cells sorted into wells [a result of the inherent limitations of single-cell polymerase chain reaction (PCR)], and B cells bearing lambda light chains were not analyzed. By correcting for cell sorter and PCR losses, the frequency of VRC01-class naïve B cell precursors is calculated as 1 in 400,000 naïve B cells. VRC01-class precursors may also exist in the memory B cell population in healthy humans, but their frequency remains to be measured.

The $K_D$s of 24 isolated VRC01-class precursors for monovalent eOD-GT8 ranged from 57 μM to 125 nM, with a geometric mean $K_D$ of 3.4 μM (FIG. 29L and table 12), 590-fold weaker than germline-reverted VRC01-class Abs (geometric mean $K_D$=5.8 nM for the panel), most likely due to the naïve CDR3 loops in the former as opposed to the affinity-matured CDR3 loops on the latter. The VRC01-class naïve B cell affinities are in the range expected to allow a multivalent eOD-GT8 immunogen, such as eOD-GT8 60mer (17, 54), to activate B cells and initiate germinal centers (57, 58). The data also suggest that eOD-GT8 has promise to produce VRC01-class memory even given competition from non-VRC01-class B cells, as eOD-GT8 exhibited a high degree of CD4bs immunofocusing (FIG. 29C), and VRC01-class precursors had an affinity advantage (≥3-fold) over non-VRC01-class CD4bs epitope-binding precursors (FIG. 29L). The frequencies and eOD-GT8 affinities of bona fide VRC01-class precursors isolated here warrant human immunization studies with eOD-GT8 60mer nanoparticles.

Only 2 of 20 tested VRC01-class precursors had detectable affinity for eOD-GT6 (FIG. 29L). Equilibrium binding $K_D$s were 36 μM and 69 μM, and these Abs had two of the highest affinities for eOD-GT8 at 506 nM and 258 nM, respectively (table 12). These data, combined with the failure of eOD-GT6 probe B cell screens to isolate VRC01-class precursors, suggest that the engineered breadth and affinity improvements in eOD-GT8 represent a major advance toward practical utility in human vaccination.

Applicants sought to confirm that the isolated VRC01-class precursors engage the CD4bs in the same structural binding mode as VRC01-class bnAbs (10, 11, 14, 38, 59) and germline-reverted VRC01 (17). Applicants solved the crystal structure of isolated precursor VRC01c-HuGL2 (eOD-GT8 affinity=368 nM) in complex with eOD-GT8 in two crystal forms (I222, 2.16 Å and C2, 2.44 Å, table 13). Comparison of this structure with the complex of core-gp120 bound to VRC01 (PDB ID: 3NGB (6)) shows the same binding mode (FIG. 30A), including specific H-CDR2 and L-CDR3 conformations (FIG. 30B) (60) that together account for over 67.2% of the Fv domain buried surface area (FIG. 30C and table 14). When interface residues of eOD-GT8 and core-gp120 are aligned, $V_H$ and $V_L$ of VRC01c-HuGL2 and VRC01 have high similarity (Cα RMSD 0.7 Å, FIG. 30A and FIG. 39). These structural observations confirm VRC01c-HuGL2 as a bonafide VRC01-class precursor and support the conclusion that all of the eOD-GT8-specific naïve B cells using VH1-2 and a 5-aa L-CDR3 are bona fide VRC01-class precursors. Comparison of the eOD-GT8/VRC01c-HuGL2 structure with a 1.82 Å unliganded VRC01c-HuGL2 structure shows that the important H-CDR2 and L-CDR3 loops are pre-configured in the unbound state and do not require any conformational changes for engagement with gp120 CD4bs (FIG. 30D), heightening the appeal of VRC01-class germline-targeting. A 2.9 Å unliganded structure of eOD-GT8 (FIG. 30E and FIG. 40) demonstrates mimicry of the VRC01-class antibody-bound conformation, thus helping to explain the increased affinity of eOD-GT8 for true VRC01-class bnAb precursors. Applicants conclude that mutations that led to the design of eOD-GT8 from eOD-GT6 further stabilize the antibody-bound state, based on a higher similarity between the VRC01c-HuGL2-bound and unliganded eOD-GT8 (all-atom rmsd=0.98 Å, alignment of 1206 atoms) vs GL-VRC01-bound (PDBID: 4JPK) and unliganded (PDBID: 4JPJ) eOD-GT6 (all-atom rmsd=3.0 Å, alignment of 1343 atoms) (FIG. 40).

The interaction of the naïve human B cell repertoire with vaccine antigens has not been characterized previously. Given the vast immunoglobulin sequence space, direct probing of the human naïve B cell repertoire was a critical test of the physiologically relevant binding potential of the germline-targeting immunogen. The antibody sequence features, binding affinities, and high structural similarity of the eOD-GT8-specific naïve B cell-derived antibodies to VRC01 all demonstrate the power of germline-targeting design when combined with human B cell probing. Similar methods, including both protein design and human B cell probing methods, could be employed to improve and evaluate germline-targeting immunogens for other classes of HIV bnAbs and for Abs against other pathogens. These methods may be particularly important to develop and test germline-targeting approaches for bnAbs that rely heavily on HCDR3 and hence may have lower precursor frequencies.

Example 9

Priming HIV-1 Broadly Neutralizing Antibody Precursors in Human Ig Loci Transgenic Mice.

Applicants tested the ability of the VRC01-class bnAb germline-targeting immunogen eOD-GT8 60mer to activate appropriate precursors in Kymab mice transgenic for human immunoglobulin loci. Repertoire analysis indicated an average frequency of at most ~1 VRC01-class precursor per mouse, and Applicants found that at least 29% of singly-immunized mice produced a VRC01-class memory response, suggesting that priming generally succeeded when at least one precursor was present. The results demonstrate the feasibility of using germline targeting to prime specific and exceedingly rare bnAb precursor B cells within a complex human-like repertoire.

To better model the conditions for initiation of a VRC01 class bnAb response in humans, Applicants investigated immunization with eOD-GT8 60mer in Kymab mice transgenic for the human antibody germline gene repertoire (E. C. Lee et al., Complete humanization of the mouse immunoglobulin loci enables efficient therapeutic antibody discovery. Nature biotechnology 32, 356-363 (2014)), HK mice, with human heavy and kappa light chains, HL mice, with human heavy and lambda light chains, and HKL mice with human heavy and both kappa and lambda chains, were employed.

To determine the level of difficulty for VRC01-class bnAb priming in Kymab mice, Applicants sought to determine the frequency in those mice of VRC01-class precursors defined as using VH1-2*02, *03, or *04 and a 5 amino acid L-CDR3. Using B cell sorting methods, Applicants previously found eOD-GT8-specific VRC01-class precursors at a frequency of 1 in 2.4 million among human naïve B cells expressing kappa light chains (J. G. Jardine et al., HIV-1 broadly neutralizing antibody precursor B cells revealed by germline-targeting immunogen. Science 351, 1458-1463 (2016)). Using similar methods to probe a total of approximately ~300 million B cells from the spleens and lymph nodes of HK and HL mice (N=3 each), Applicants were unable to isolate any VRC01-class B cells (not shown), suggesting that the frequency of such B cells was considerably lower than in humans. The frequency of the $V_H$1-2*02, *03, or *04 alleles among HK B cells was previously measured as 0.9% (E. C. Lee et al., Among human VH1-2 alleles, Kymab mice only contain VH1-2*04. This was misreported as *02 in Lee et al.), lower than the frequency in humans (2.8%) (R. Arnaout et al., Plos One 6, (2011); and B. J. DeKosky et al., Nature medicine 21, 86-91 (2015)) by a factor of only ~3. Therefore, to explain the reduced frequency of VRC01-class B cells in Kymab mice, Applicants analyzed the light chain gene usage and CDR3 length distribution from 5 HK mice by next-generation sequencing (NGS). The kappa LCDR3 length distribution was broadly similar to that of humans (FIG. 45A), but the frequency of 5-amino acid L-CDR3s was lower in HK mice (0.018±0.012%) than in humans (0.95±0.56%) by a factor of approximately 50 (FIG. 45B). The cumulative frequency of Vκ genes used by known VRC01-class bnAbs (IGVK3-20 and IGVK1-33 (T. Zhou et al., Immunity 39, 245-258 (2013)) was 24% in HK mice, consistent with a previous measurement (E. C. Lee et al.) and nearly identical to the 23% measured in humans (FIG. 45C). However, the frequency of 5-amino acid L-CDR3s associated with known VRC01-class kappa chains was reduced by a factor of approximately 300 in HK mice (0.00089±0.00079%) compared to humans (0.27±0.13%) (FIG. 45D). The reason for the particularly low frequency of 5-amino acid L-CDR3s among VRC01-class kappa chains in HK mice is unclear, but it may be due to different selection pressures in the different host environments of Kymab mice and humans. Whatever the cause, the NGS data together with VH1-2 allele frequencies indicate that VRC01-class precursors in HK mice are less frequent than in humans by a factor of 150 to 900.

Though Applicants previously detected eOD-GT8-specific VRC01-class precursors at a frequency of 1 in 2.4 million naïve human kappa-chain B cells, by correcting for cell sorter and PCR losses Applicants estimated the true frequency as 1 in 400,000 (J. G. Jardine et al., 2016). Based on this number and the calculations above, Applicants conclude that the frequency of precursors in HK mice is probably no higher than 1 in 60 million (=150×400,000) B cells and might be as low as 1 in 360 million (=900×400,000) B cells. The spleens of HK and HL mice (7-18 weeks of age) contain 50 million B220+ B cells, of which ~60% are mature B cells that are thought prepared to respond to antigen (E. C. Lee et al.). Allowing for half that number again in the lymph nodes and periphery, Applicants estimate that each mouse contains approximately 75 million B cells, of which 45 million are mature. Thus Applicants expect a very low average frequency of at most 1.3 (≈75/60) eOD-GT8-specific VRC01-class precursors per HK mouse. Modeling the precursor frequency with a Poisson distribution predicts that at least 27% of the HK mice will have zero precursors, at most 35% will have one precursor, fewer than 23% will have two precursors, and fewer than 15% will have will have either 3 or 4 precursors (FIG. 45E). Thus priming VRC01-class responses in HK mice appears to be substantially more difficult than in humans, as the precursor frequency is lower (by a factor of 150 to 900) and the total number of precursors is lower (by 3,000 to 30,000 precursors (J. G. Jardine et al., 2016). Indeed, in the >27% of HK mice that are expected to lack any VRC01-class precursors (FIG. 45E), priming this response is obviously impossible. Similar frequency analysis in one HL mouse and two HKL mice reached similar conclusions that were only slightly more favorable for VRC01-class priming.

Despite the low frequency of VRC01 class precursors in the Kymab mice, Applicants conducted immunization experiments to determine if eOD-GT8 60mer could prime these precursors. Our first experiment (FIG. 46A), conducted in both HK and HL mice (28 mice each), evaluated differences in antigen dose (20 μg versus 4 μg), adjuvant formulation and route (Iscomatrix/sub-cutaneous compared to the Sigma Adjuvant system also known as "Ribi"/intraperitoneal), and time point of sacrifice and antibody repertoire analysis (14 days compared to 42 days post-immunization). Unimmunized mice and mice immunized with 20 μg of the non-germline-targeting eOD-17 60mer in Iscomatrix adjuvant were included as controls. Serum ELISA binding to eOD-GT8 and eOD-GT8 KO, a mutant designed to eliminate binding of germline VRC01-class antibodies (J. G. Jardine et al., Priming a broadly neutralizing antibody response to HIV-1 using a germline-targeting immunogen. Science 349, 156-161 (2015)), showed robust responses to eOD-GT8 and somewhat lower responses to eOD-GT8 KO, indicating an epitope-specific response. Spleens and lymph nodes from culled mice were processed, stained, and single cell sorted for IgM−/IgD− memory B cells that bound to eOD-GT8 tetramers but not to eOD-GT8 KO tetramers (J. G. Jardine et al., 2016). Applicants found that only eOD-GT8 60mer-immunized mice showed evidence of epitope specific (eOD-GT8+/eOD-GT8 KO−) memory B cells (FIG. 46B). A control sort of eOD-17 60mer-immunized samples using eOD17/eOD17-KO probes identified memory B cells reactive with eOD-17 but not eOD-GT8.

To evaluate the reproducibility of eliciting eOD-GT8-specific responses in Kymab mice and to include an additional native-like trimer control, Applicants performed a second experiment with eOD-GT8 60mer, eOD-17 60mer, and the native-like trimer, BG505 SOSIP (R. W. Sanders et al., PLoS Pathog 9, e1003618 (2013); J. P. Julien et al., Science 342, 1477-1483 (2013); D. Lyumkis et al., Science 342, 1484-1490 (2013); M. Pancera et al., Nature 514, 455-461 (2014); and Y. Do Kwon et al., Nat Struct Mol Biol 22, 522-531 (2015)). Half the mice were HK and half were HKL (FIG. 46A). The memory B cell frequencies (FIG. 46C) largely recapitulated the findings from the first experiment (FIG. 46B).

To determine whether or not the epitope-specific memory B cells generated by eOD-GT8 60mer immunization contained VRC01-class memory B cells with a $V_H$1-2 heavy chain and 5-amino acid L-CDR3, RNA from single memory B cells was reverse transcribed and IgG variable genes were amplified and sequenced by NGS. The two experiments yielded a total of 13,847 wells from which at least a heavy or light chain sequence could be determined (10,343 such wells for eOD-GT8 60mer-immunized mice, 2933 for control immunized mice, 330 for unimmunized mice), and of these, 3,259 wells contained a heavy and light chain pair that could be sequenced (2,614 sequenced pairs for eOD-GT8 60mer-immunized mice, 548 pairs for control immunized mice and 60 pairs for unimmunized mice) (FIG. 47A). From these sequences, Applicants identified 33 VRC01-class heavy-light paired memory responses among 29% (17 of 58) of eOD-GT8 60mer-immunized mice (aggregating across different doses, adjuvants, timepoints, types of mice and the two experiments) (FIG. 47B). In contrast, Applicants detected no VRC01-class responses from 32 control immunized or unimmunized mice. eOD-GT8 60mer induced VRC01-class responses at approximately similar frequencies in HK, HL, and HKL mice (FIG. 47C). Whereas only 25% (37/146) of paired sequences using $V_H$1-2*02 heavy chains contained L-CDR3s of 5-amino acids, 89% (33/37) of paired sequences using a 5-amino acid L-CDR3 also included a $V_H$1-2*02 heavy chain, suggesting that the identification of 5-amino acid CDRL3s in memory B cells may serve as a reasonable proxy for VRC01-like responses. Therefore, Applicants also examined the frequency of 5-amino acid L-CDR3s among all paired and unpaired light chain sequences. Applicants identified 70 light chains with 5-amino acid L-CDR3s from 48% (28 of 58) of eOD-GT8 60mer-immunized mice, whereas Applicants found no 5-amino acid L-CDR3 responses in control mice (FIG. 47D). eOD-GT8 60mer induced memory B cells with 5-amino acid L-CDR3s at substantial frequencies in all three types of mice (FIG. 47E). All combinations of dose, adjuvant and timepoint produced VRC01-class responses and 5-amino acid L-CDR3 responses, though the 20 μg dose with Iscomatrix was best at day 42. Given the very low expected frequency of VRC01-class precursors, these results indicate that VRC01-class priming by eOD-GT8 60mer was highly efficient and may have succeeded in all or most mice in which at least one precursor was present.

The VRC01-class antibodies induced by eOD-GT8 60mer shared other characteristic features of VRC01-class bnAbs in addition to the $V_H$1-2 alleles and 5-amino acid L-CDR3. The L-CDR3 loop is a key site of affinity maturation in VRC01-class bnAbs (T. Zhou et al. 2013), and the 33 VRC01-class antibodies showed clear signs of L-CDR3 sequence selection toward the bnAb consensus sequence motifs in both kappa and lambda chains (FIG. 3F). In addition, 32 of 33 VRC01-class pairs induced by eOD-GT8 60mer had L-CDR1 lengths matching those of the germline $V_L$ genes of known VRC01-class bnAbs (FIG. 47G), indicating potential for VRC01-class-like L-CDR1 refinement during maturation (T. Zhou et al. 2013). Further supporting bnAb potential, 18 of these 33 antibodies used known VRC01-class $V_L$ genes or highly similar genes (FIG. 47H), and the H-CDR3 lengths among these 33 VRC01-class pairs (9 to 16 amino acids) were similar to those of known VRC01-class bnAbs (10 to 19 amino acids) (FIG. 47I).

Consistent with a VRC01-class binding mode, all 20 VRC01-class antibodies that Applicants expressed bound to eOD-GT8 but had no detectable affinity for either of two different eOD-GT8 mutants (eOD-GT8 KO and eOD-GT8 KO2) designed to abrogate binding of germline VRC01-class antibodies (FIG. 48A). These VRC01-class antibodies had geomean affinity for eOD-GT8 of 134×[1.0±9.9] nM, higher than the eOD-GT8 affinities of VRC01-class antibodies isolated from naïve human B cells by a factor of 25, possibly due to maturation of the immunogen-induced antibodies.

As might be expected from the low VRC01-class precursor frequency in the Kymab mice, VRC01-class antibodies constituted a small minority (1%=33/3259) of the antibodies cloned from eOD-GT8+/eOD-GT8 KO memory B cells of eOD-GT8 60mer-immunized mice. Mutation levels were similar in the VRC01-class antibodies (HC: 0.8±1.1%; LC:1.5±1.1%) and non-VRC01-class antibodies. For binding assessment, Applicants produced protein for 16 of the most highly mutated (HC: 1.5±1.0%; LC:2.3±1.2%) non-VRC01-class antibody sequences from different lineages. All but one antibody had detectable affinity for eOD-GT8, and six had affinity for eOD-GT8 KO despite the negative selection of their corresponding B cells against this probe during sorting (FIG. 48B). Two of the non-VRC01-class antibodies had $V_H$1-2 heavy chains paired with light chains containing 6- or 8-amino acid L-CDR3s; neither of these bound to eOD-GT8 KO or eOD-GT8 KO2 (FIG. 48B), suggesting that either or both might be employing a VRC01-like binding mode, but these antibodies could also use a more typical “loop-binder” mode relying on their H-CDR3s. Among the epitope-specific antibodies that lacked affinity for eOD-GT8 KO, affinities for eOD-GT8 were similar for VRC01-class (geomean=134×[1.0±9.9] nM) and non-VRC01-class antibodies (geomean=65×[1.0±16.6] nM) (FIG. 48B). Thus, despite the higher frequency non-VRC01-class precursors initiating approximately 100 times more CD4 binding site-directed maturation trajectories compared to VRC01-class precursors (3259 versus 33), eOD-GT8 60mer primed VRC01-class responses to similar mutation and affinity levels as non-VRC01-class responses.

Germline-targeting has great promise as a rational strategy to initiate the induction of pre-defined bnAbs targeting relatively conserved epitopes on HIV or other pathogens that have eluded vaccine development. Owing to significant differences in human antibody germline genes compared to standard animal models, evaluation of germline-targeting immunogens (and boosting schemes intended to guide bnAb maturation) requires testing in humans or in animal models engineered to produced human inferred-germline antibodies (P. Dosenovic et al., Cell 161, 1505-1515 (2015); J. G. Jardine et al., 2015; and D. R. Burton et al., Cell Host Microbe 12, 396-407 (2012)). Knock-in mice transgenic for a single inferred-germline human heavy or light chain or paired antibody, and adoptive transfer of B cells from knock-in mice to wild-type mice, provide important model systems (P. Dosenovic et al., Cell 161, 1505-1515 (2015); and J. G. Jardine et al., 2015). However, the ability of these models to predict human responses may be limited at least because they generally over-represent the frequency of the targeted bnAb germline B cells, lack the full diversity of the targeted bnAb class and lack clonal competition from human antibodies. Applicants tested the eOD-GT8 60mer VRC01-class germline-targeting immunogen in more stringent and human-like models that ameliorate the above problems, Kymab mice transgenic for highly complex human antibody repertoires. Although Applicants found that Kymab mice significantly under-represent the frequency of VRC01-class bnAb germline B cells compared to humans, and combining that factor with the small size of mice led us to estimate an average of at most only 1.3 precursors per mouse, the eOD-GT8 60mer still proved capable of priming. This study illustrates both the benefits and challenges of using human immunoglobulin loci transgenic mice for vaccine testing. The seemingly high targeting efficiency of eOD-GT8 60mer in this mouse model encourages testing in humans in which conditions for VRC01-class bnAb priming (significantly higher precursor frequency and total number of precursors), are more favorable. The results here should also encourage germline-targeting efforts for other bnAb specificities that may have lower precursor frequencies in humans compared to VRC01-class precursors and raise the question of whether germline-targeting to precursors with expected average frequencies as low as 1 per human (1 precursor per $10^{10}$-$10^{11}$ B cells) might be practical.

Example 10

Tailored Immunogens Direct Affinity Maturation Toward HIV Neutralizing Antibodies Applicants developed boosting immunogens designed to guide the genetic and functional maturation of previously primed VRC01-class precursors. Boosting a transgenic mouse model expressing germline VRC01 heavy chains produced broad neutralization of near-native isolates (N276A) and weak neutralization of fully native HIV. Functional and genetic characteristics indicate that the boosted mAbs are consistent with partially mature VRC01-class antibodies and place them on a maturation trajectory that leads toward mature VRC01-class bnAbs. The results show how reductionist sequential immunization can guide maturation of HIV bnAb responses.

Applicants demonstrated herein that eOD-GT8 60mer immunization primes relatively rare VRC01-class precursors in a transgenic mouse model expressing the VRC01 germline-reverted heavy chain (VRC01 gH) (Jardine et al., 2015). In this heterozygous knock-in mouse model, ~85% of the B cells express the VRC01 gH chain paired with diverse mouse light chains, while ~15% of the B cells express diverse mouse heavy and light chains. Owing largely to the low frequency of mouse light chains with a 5AA CDR3 loop (~0.1%), the frequency of VRC01-class precursors in the VRC01 gH mouse is estimated to be only ~5-fold higher than in humans. Furthermore, in contrast to homozygous knock-in mice, the VRC01 gH mouse imposes substantial competition from diverse mouse B cell specificities, competition that is reduced by a factor of only seven relative to a normal mouse. Despite these challenges, Applicants found that a single immunization of eOD-GT8 60mer in the VRC01 gH mouse resulted in activation of B cells encoding antibodies with VRC01-class genetic features, induction of specific somatic mutations shared with mature VRC01-class bnAbs, and production of a pool of mutated VRC01-class memory B cells with at least weak affinity for potential boost immunogens. As expected, although a subset of GT8-specific monoclonal antibodies (mAbs) isolated from memory-phenotype B cells in immunized VRC01 gH mice showed weak cross-reactivity to near-native Env, none of the mAbs acquired neutralizing activity (Jardine et al., 2015). The VRC01 gH mouse is thus an attractive model to evaluate boosting strategies to induce VRC01-class bnAbs following an eOD-GT8 60mer prime, and the results in this mouse should have potential relevance to human vaccination.

Based on previous structure-function studies of VRC01-class bnAbs (Diskin et al., 2013 J Exp Med 66, 213-817; 2011 Science 334, 1289-1293; Georgiev et al., 2014 J Immunol 192, 1302515-1106; Lyumkis et al., 2013 Science 342, 1484-1490; West et al., 2012 Proc Natl Acad Sci USA 109, E2083-E2090; Zhou et al., 2010 Science 329, 811-817; 2013 Immunity 39, 245-258) as well as the development and analysis of minimally mutated VRC01-class bnAbs, Applicants have formulated a working concept sequential immunization strategy for how to induce VRC01-class bnAbs. The strategy proposes a sequence of four types of immunogens, each of which has specific objectives for affinity maturation: (i) germline-targeting nanoparticles, to activate VRC01-class germline precursors and select sufficient VRC01-class mutations for low-affinity recognition of N276 (−) Env lacking the N276 glycosylation site; (ii) native-like trimers lacking the N276 glycosylation site, to select mutations that enable neutralization of N276(−) viruses; (iii) native-like trimers, including the N276 glycosylation site, produced in GnTI$^{-/-}$ cells to ensure that glycans are small (predominantly MansGlcNAc$_2$), for selection of light chain CDR1 mutations and/or deletions to accommodate the base of the N276 glycan and to allow neutralization of viruses passaged in GnTI$^{-/-}$ cells; (iv) native-like trimers bearing native glycans, for selection of light chain FW3 mutations to accommodate the distal portions of the N276 glycan and to allow neutralization of viruses bearing native glycans and characteristic of those circulating in the population.

In the present work, Applicants focused on the first two steps of this strategy. Applicants hypothesized that the eOD-GT8 60mer prime might fail to generate memory B cells capable of being activated by native-like trimers lacking the N276 glycosylation site. Supporting this hypothesis, mAbs induced by eOD-GT8 60mer in the VRC01 gH mouse showed affinity for a core gp120 lacking the N276 glycosylation site (Jardine et al., 2015) but showed no detectable affinity for native-like trimers lacking N276 or other CD4bs glycans (not shown). Thus Applicants sought to develop immunogens that could serve as a bridge between the eOD-GT8 60mer prime and near-native N276(−) trimers.

Applicants report the development and testing of two such boosting immunogens, BG505 core-GT3 nanoparticle (NP) and BG505 SOSIP-GT3 trimer. Applicants show that sequential immunization schemes employing these bridging boost immunogens drove the maturation of eOD-GT8 60mer primed B cells toward VRC01-class bnAbs and induced broad neutralization of near-native (N276A) viruses, and weak neutralization of a fully native virus, in VRC01 gH mice. The results demonstrate that reductionist sequential immunization can initiate and guide maturation of pre-defined neutralizing antibody specificities. Furthermore, the findings provide a foundation on which to develop a vaccine to induce VRC01-class bnAbs.

Example 11

Figure 49A:
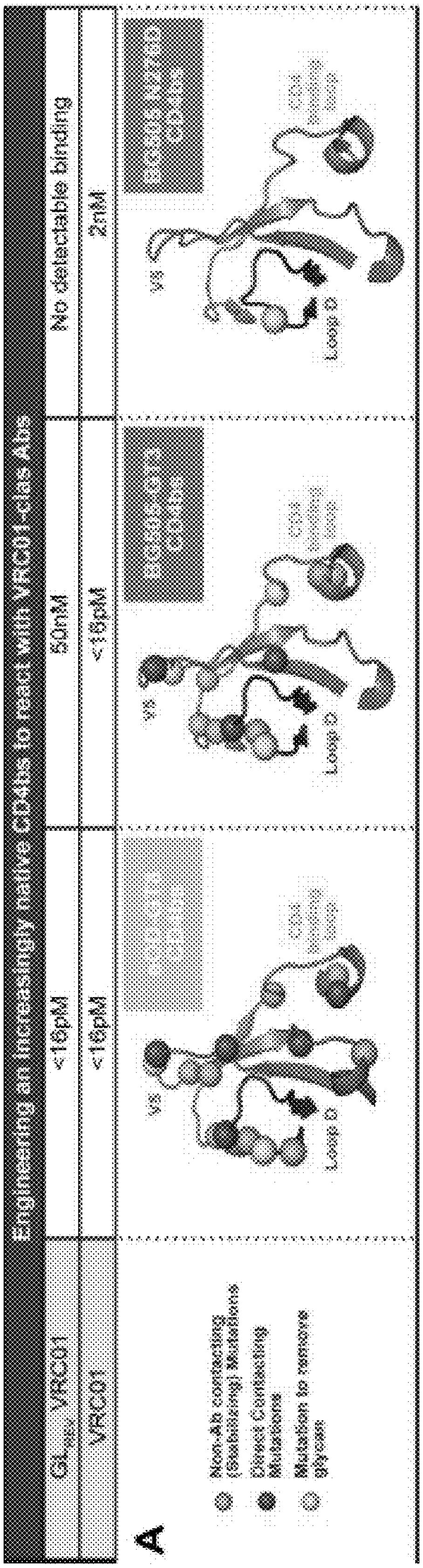
Figure 49B:
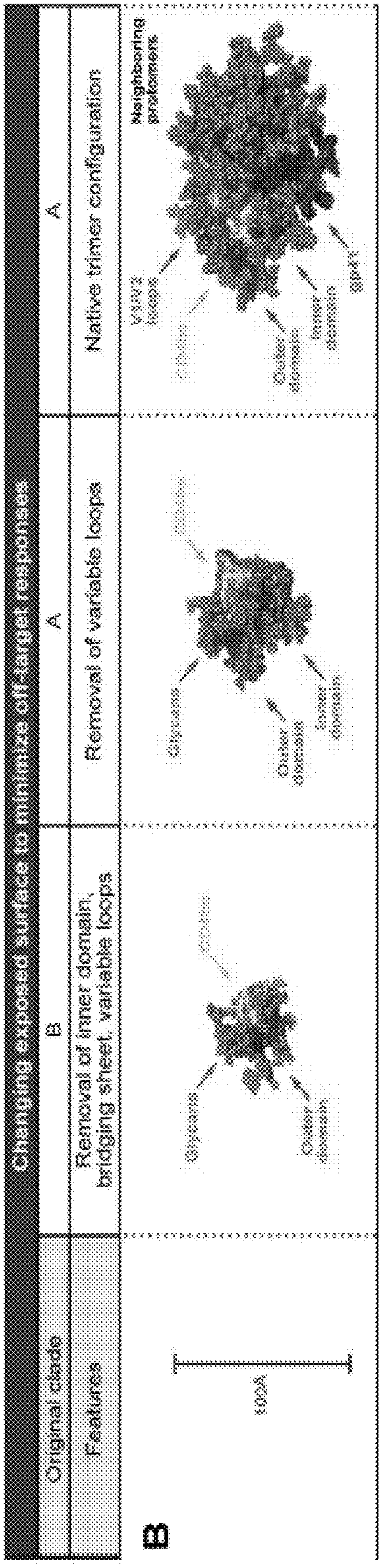
Figure 49C:
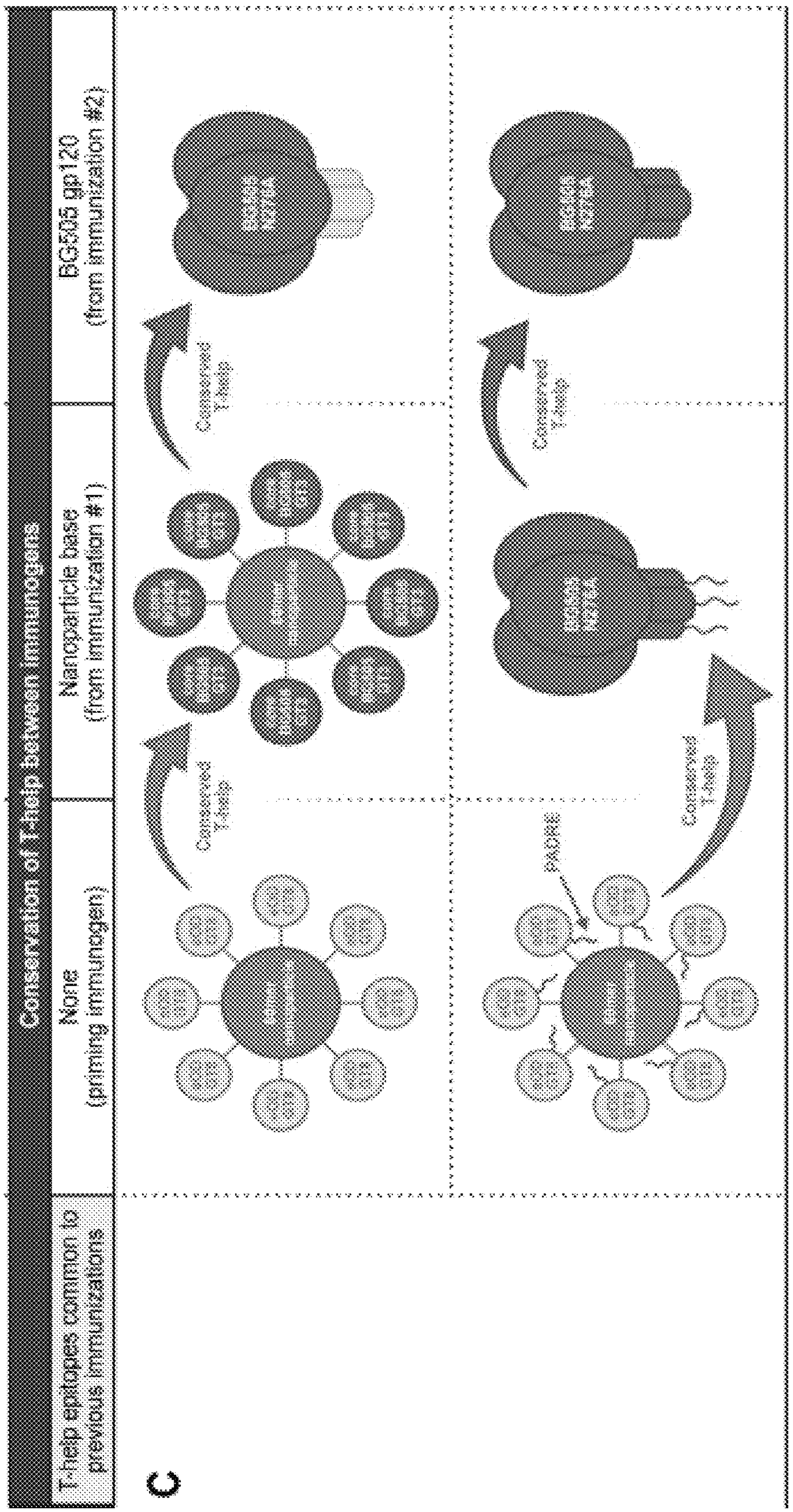

Engineering a Boosting Immunogen to Follow eOD-GT8 60 Mer Priming of VRC01-Class Abs Applicants sought to develop a boost immunogen to activate eOD-GT8 60mer-induced memory B cells, cause the formation of new germinal centers and select for a pool of more highly mutated memory B cells that could subsequently be boosted by native-like N276(−) trimers. To achieve this goal, Applicants designed ‘bridging’ molecules which, while still germline-targeted, display a more native CD4bs epitope in order to drive maturation toward mature VRC01-class bnAbs. Applicants allowed fewer overall mutations than in eOD-GT8 while retaining native VRC01-class contact residues as frequently as possible. Engineered mutations at non-contact positions were selected to improve affinity for GLrev Abs via conformational stabilization or removal of occluding glycans (FIG. 49A). Two design platforms were chosen: core gp120 and SOSIP native-like trimer. The core gp120 platform was selected as an intermediate presentation of the CD4bs, in terms of epitope completeness and steric restriction, between the minimal eOD and the native-like trimer; use of core gp120 would also minimize boosting of off-target responses, as core gp120 shares little exposed, non-glycosylated surface with eOD or the native-like trimer beyond the CD4bs epitope (FIG. 49B). The SOSIP trimer platform was used to test the effect of including more native-like epitope and steric access restrictions in this bridging boost immunogen. The BG505 strain was selected for both core gp120 and SOSIP platforms, primarily for the purpose of conserving T-help with the subsequent boost of BG505 SOSIP N276D (FIG. 49C), although changing to BG505 from the HXB2 strain used as the base strain for eOD-GT8 was also considered potentially advantageous for minimizing off-target responses (FIG. 49B). To conserve T-help with the eOD-GT8 60mer prime, Applicants displayed the core-gp120 on the same nanoparticle (Lumazine synthase) as eOD-GT8 (Jardine et al., 2013 Science 340, 711-716; 2015), thus using the underlying nanoparticle for conserved T-help. For the trimer platform, Applicants added an exogenous T-help epitope (PADRE) (Alexander et al., 1998 Immunol Res 18, 79-92; 1994 Immunity 1, 751-761) to the C-terminus of both the eOD-GT8 60mer prime and the SOSIP boost (FIG. 49C).

Figure 49E:
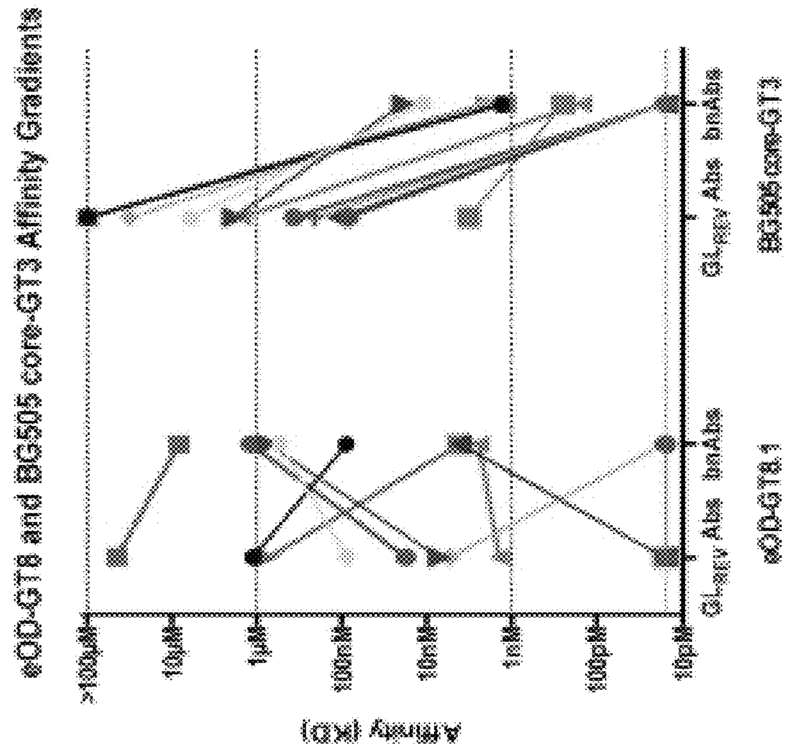
Figure 49D:
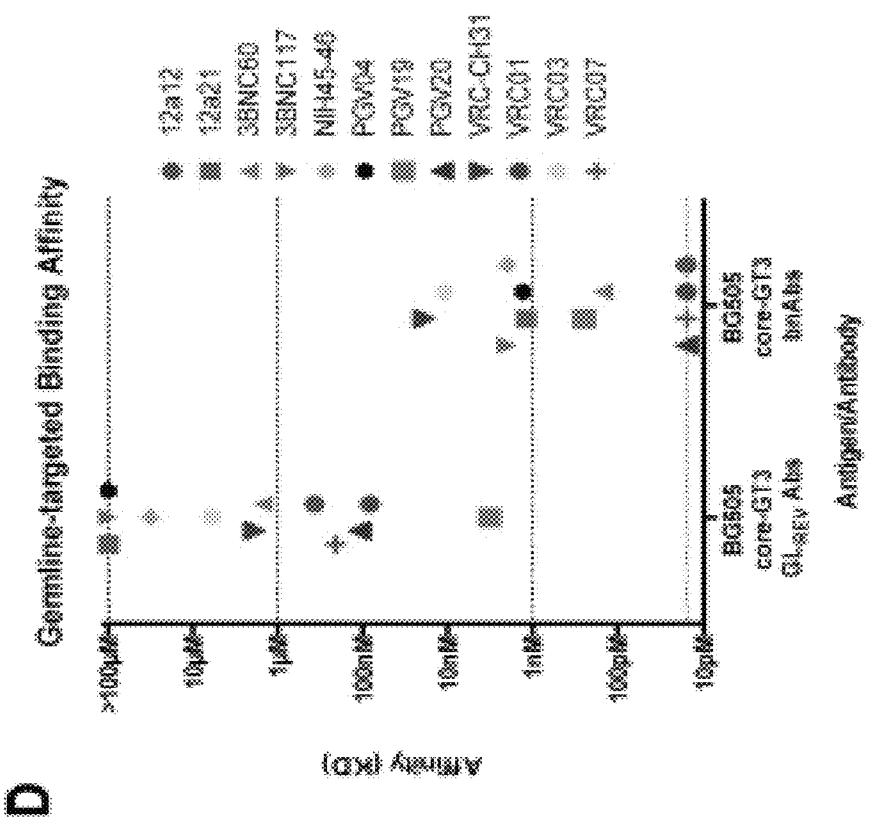

Protein engineering was initially carried out by yeast display directed evolution on the core gp120 platform. Applicants generated combinatorial libraries of core BG505 gp120 containing mutations that Applicants had previously noted in the development of core BaL-GT1 and eOD-GT8 (Jardine et al., 2013; 2016). These libraries were displayed on the surface of yeast and screened for binding to a panel of GLrev VRC01-class mAbs. After three rounds of optimization, a variant referred to as BG505 core-GT3 was developed (FIG. 54). This construct showed modest affinity for GLrev VRC01-class Abs (FIG. 49D). Unlike eOD-GT8, which displays similar affinity for both GLrev and mature VRC01-class mAbs, BG505 core-GT3 bound VRC01-class bnAbs with >1,000-fold higher affinity than their GLrev counterparts. Thus, in accordance with the design goal, the BG505 core-GT3 immunogen displayed a strong affinity gradient for mature bnAbs over GLrev Abs and was therefore promising as a boost to select productive somatic hypermutation (FIG. 49E). Applicants produced nanoparticles of BG505 core-GT3 by genetic fusion to lumazine synthase, as previously reported for eOD-GT6 and eOD-GT8 (Jardine et al., 2013; 2015). However, to accommodate the larger core-gp120, nanoparticles included ~20 mol % "naked" lumazine synthase. Thus Applicants estimate that there were approximately 48 copies of core-GT3 displayed on the nanoparticles. BG505 core-GT3 nanoparticles (NPs) displayed approximately the expected molecular weight in solution, according to SECMALS analysis, and maintained antigenicity for GLrev VRC01-class Abs (FIG. 55).

To generate a native-like trimer variant of GT3 with more native-like epitope features and CD4bs steric access restrictions, Applicants transferred the BG505 core-GT3 mutations onto BG505.D664 SOSIP and added a C-terminal PADRE epitope (as noted above), resulting in BG505 SOSIP-GT3-PADRE, from now on referred to as BG505 SOSIP-GT3 (FIG. 54). Overall, BG505 SOSIP-GT3 was trimeric by SECMALS and showed an antigenic profile similar to BG505 SOSIP.D664, with the added ability to bind VRC01-class GLrev Abs and with a similar VRC01-class affinity gradient as for BG505 core-GT3 (FIG. 56). The melting temperatures of BG505-SOSIP-GT3 (66.3° C.) and BG505 SOSIP.D664 (66.7° C.), were similar. By negative stain EM analysis, BG505 SOSIP-GT3 was indistinguishable from BG505 SOSIP.D664 (FIG. 56).

Thus, to develop a sequential immunization scheme with considerations of gradual epitope change toward native, T-help conservation, and minimizing the boosting of off-target responses, two boost candidates were designed to follow the eOD-GT8 60mer and precede the BG505 SOSIP N276D native-like trimer.

Example 12

Prime and Boosting of VRC01-gH Mice

To quantify the ability of BG505 core-GT3 NP and BG505 SOSIP-GT3 to recall VRC01-class precursor B cells primed with eOD-GT8 60mer, Applicants sequentially immunized a previously described transgenic mouse model expressing the human VRC01 germline heavy chain and a full complement of mouse light chains (VRC01 gH) with eOD-GT8 60mer, BG505 core-GT3 NP, and BG505 SOSIP N276D trimer according to the immunization schedule described in FIG. 50A. Twenty VRC01 gH mice were primed with eOD-GT8 60mer prime followed by either BG505 core-GT3 NP or BG505 SOSIP-GT3 boost. Eight mice were sacrificed following the initial boost, while twelve mice (6 boosted with core-GT3 NP and 6 boosted with SOSIP-GT3) received two additional boosting immunizations of BG505 SOSIP N276D.

For a serological probe, Applicants developed a resurfaced HXB2 core gp120 (r1-core-N276D) with superior VRC01-class antigenicity compared to RSC3 (Wu et al., 2010 Science 333, 1593-1602) that was originally designed based on the antibody b12 (FIG. 57). The resurfacing of this protein should minimize the reactivity of antibodies induced by the immunization protocol except for those antibodies directed to the VRC01-class epitope. A VRC01-class epitope knockout variant (r1-core-KO) with substantially depressed affinities for VRC01-class bnAbs was also engineered, by adding the mutations D368R and N279A in the CD4bs (Li et al., 2007 Nat Med 13, 1032-1034; 2011 J Virol 85, 8954-8967).

Following the third boost, Applicants evaluated serum antibody binding to r1-core-N276D and r1-core-KO (FIG. 50B). Areas under the curve (AUC) were calculated for each serum sample and the difference in AUC between r1-core-N276D and r1-core-KO are shown in FIG. 50B. The greatest differential was observed for BG505 core-GT3 NP delivered with Ribi adjuvant. Similar epitope-specific serums responses were seen in mice boosted with BG505 core-GT3 NP without adjuvant and BG505 SOSIP-GT3 delivered in Ribi adjuvant. In contrast, BG505 SOSIP-GT3 delivered without adjuvant produced relatively modest responses and the smallest delta between r1-core-N276D and r1-core-KO.

These differences in serum antibody responses were mirrored in the frequencies of epitope-specific memory B cells. Splenocytes and lymph nodes from immunized animals were harvested and stained for IgG memory B cells. Single cells were then antigen-sorted by flow cytometry using the baits listed in FIG. 50C-D. When comparing IgG memory B cell frequencies following the first boost, BG505 core-GT3 NP delivered in Ribi adjuvant showed the highest frequency of epitope-specific memory B cells (FIG. 50C). Consistent with this result, the group that received BG505 core-GT3 NP in Ribi showed the highest frequency of epitope-specific memory B cells upon completion of the full boosting schedule (FIG. 50D).

Example 13

Selection of Productive Mutations with Boosting

Figure 51A:
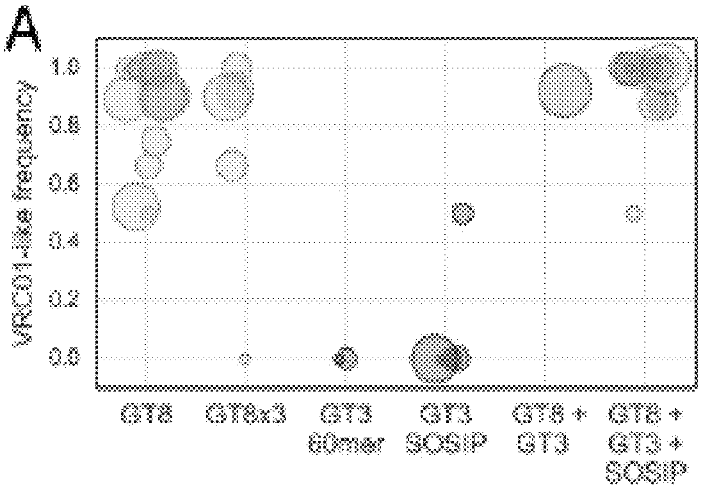
Figure 51B:
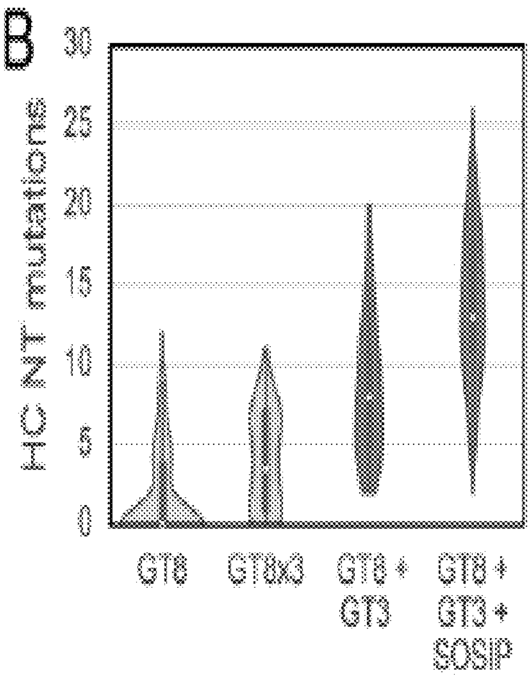
Figure 51C:
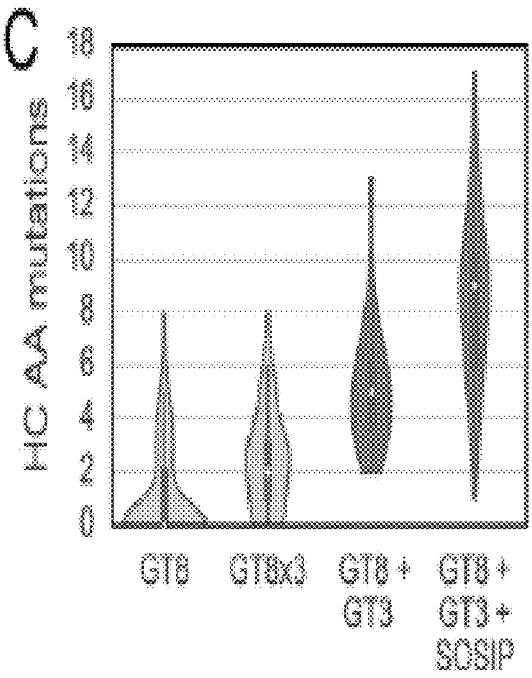

To determine whether consecutive boosting with tailored immunogens selects for productive mutations, Applicants divided the immunized VRC01 gH mice into two test groups: i) mice that received only the eOD-GT8 60mer prime and a single boost of BG505 GT3 (either SOSIP or NP), and ii) mice that received the complete immunization protocol outlined in FIG. 50A (with either GT3 SOSIP or NP as the initial boost). Applicants also analyzed four control groups of VRC01-gH mice that received the following regimens: i) a single immunization of eOD-GT8 60mer, ii) three successive immunizations of eOD-GT8 60mer, iii) a single priming immunization of BG505 core-GT3 NP, and iv) a single priming immunization of BG505 SOSIP-GT3. Overall, Applicants recovered 681 heavy chain sequences, 753 light chain sequences and 430 paired heavy-light chain sequences. In animals primed with eOD-GT8 60mer, the majority of paired sequences were VRC01-like (defined as using VH1-2 and encoding a 5AA LCDR3) (FIG. 51A). In contrast, only one of seven mice primed with BG505-GT3 (either SOSIP or NP) generated VRC01-like antibodies, demonstrating the necessity of a high-affinity germline-targeting prime (FIG. 51A). Although single or multiple immunizations with eOD-GT8 60mer alone failed to induce substantial somatic hypermutation (SHM), heterologous boosting resulted in significantly mutated antibody sequences, with the most mutated heavy chain sequence containing 17 amino acid mutations (17.3%) and a mean amino acid mutation frequency of 8.6% in mice that were primed with eOD-GT8 60mer and boosted with BG505 GT3 and twice with BG505 SOSIP N276A (FIG. 51B-C).

Figure 51D:
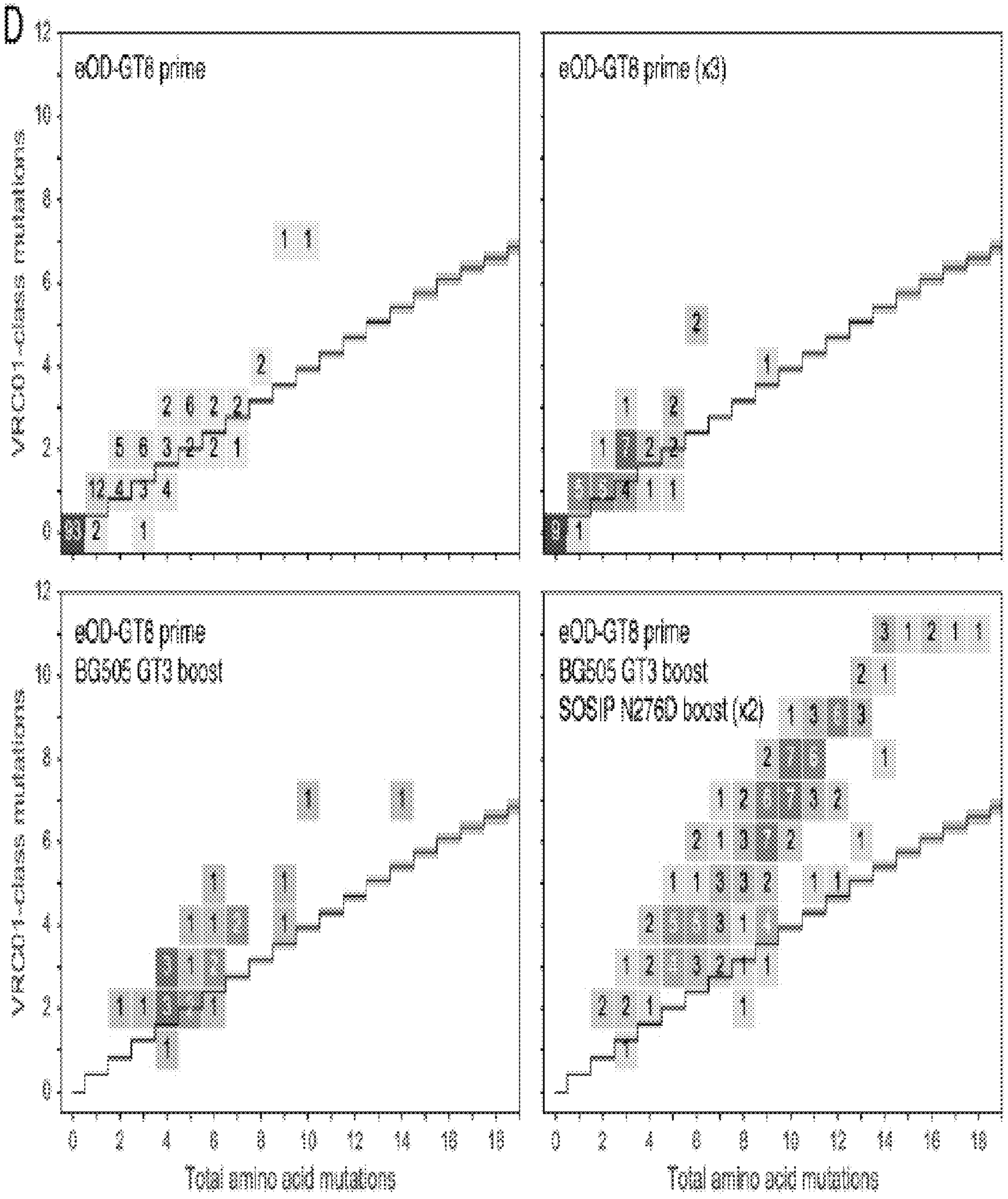
Figure 51E:
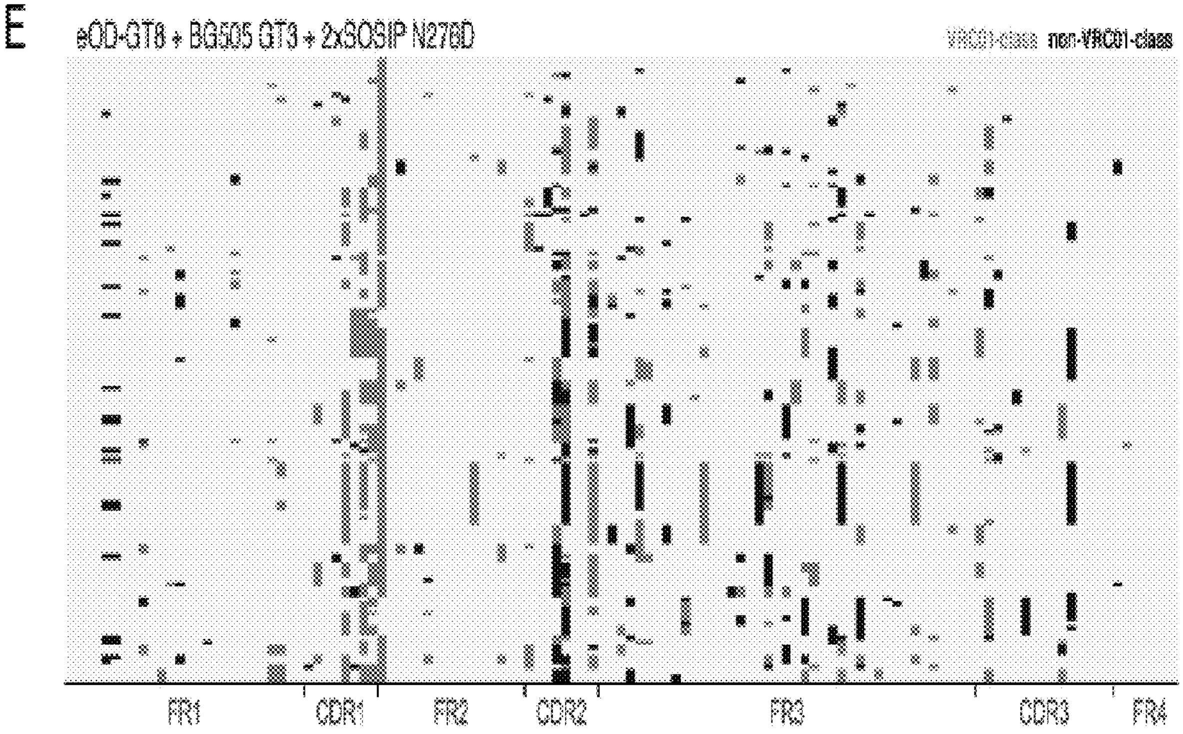
Figure 51F:
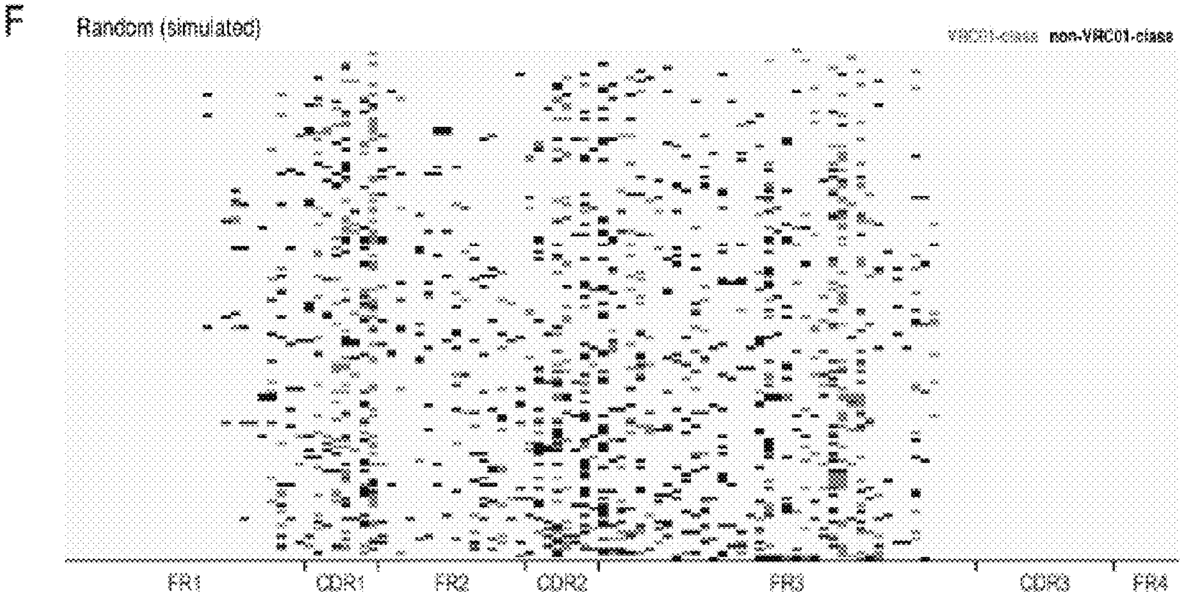
Figure 51G:
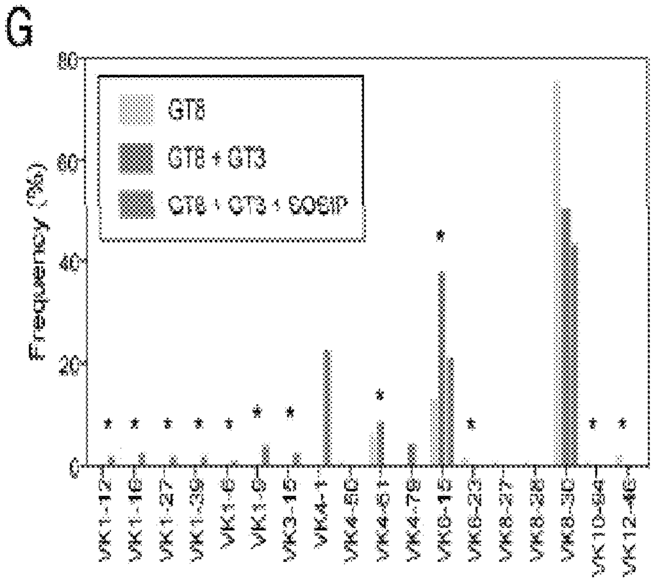

Applicants next examined whether vaccine-induced SHM was guiding the targeted VRC01 precursors toward mature VRC01. For each sequence, Applicants determined the total number of amino acid mutations as well as the number of amino acid mutations shared with a panel of VRC01-class mAbs (VRC01, PGV04, PGV20, VRC-CH31, 3BNC60 and 12A12) (Jardine et al., 2015) (FIG. 51D). In order to compare the observed frequency of shared VRC01-class mutations to the frequency expected by random SHM, Applicants performed extremely deep antibody repertoire sequencing on two healthy HIV-naïve individuals and used that information to compute the frequency of randomly incorporated VRC01-class mutations in human VH1-2 antibody sequences (FIG. 51D). In animals given a single or triple immunization of eOD-GT8 60mer alone, the frequency of VRC01-class mutations was similar to that expected by chance. This finding is anticipated, since eOD-GT8 has similar affinity for GLrev and mature VRC01-class antibodies and likely places minimal selective pressure on the incorporation of VRC01-class mutations. In animals boosted with more native-like immunogens, however, VRC01-class mutations were selected much more frequently than would be expected by chance: 126 of 130 VRC01-like heavy-light chain paired antibody sequences from animals boosted with GT3 and SOSIP N276A (2×) incorporated VRC01-class mutations at a frequency higher than the calculated 95% confidence interval of random SHM. Additionally, the stepwise increase in SHM after each boost and the general failure of GT3 to prime VRC01-class responses in this mouse model, suggest efficient recall of previously stimulated responses rather than recruitment of primarily naïve B cells upon each boost.

Figure 51H:
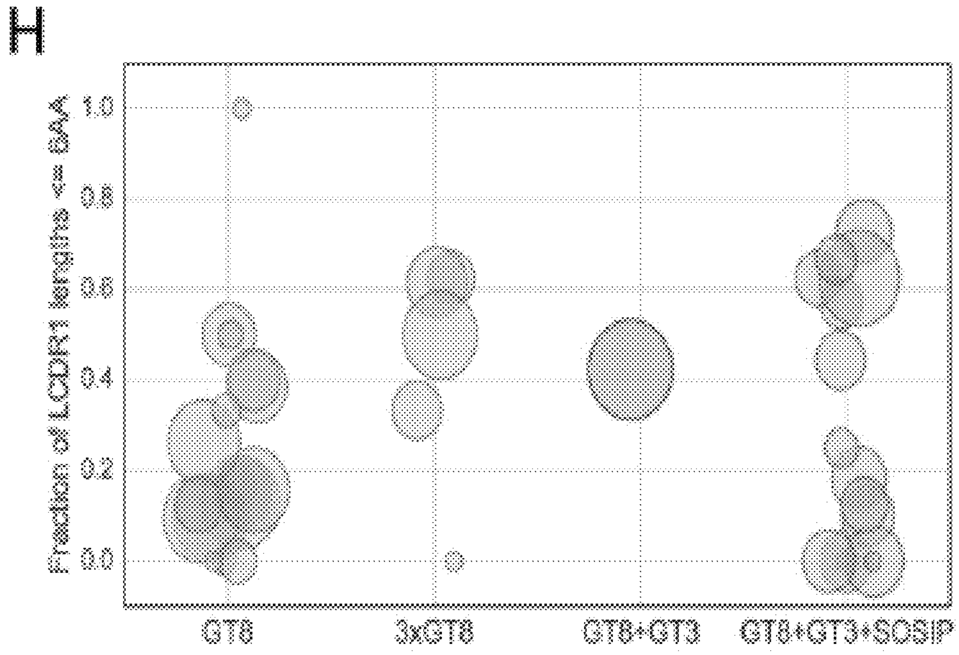
Figure 51I:

Applicants also interrogated vaccine-elicited light chains for evidence of maturation toward mature VRC01. This analysis is less straightforward than with heavy chains, since the elicited light chains are derived from mouse germline genes that would not be expected to follow the same maturation pathway as human VRC01-class light chains. Instead, Applicants were particularly interested in two critical features: the distribution of LCDR1 lengths and sequence convergence in the LCDR3. All VRC01-class antibodies encode short LCDR1 loops, produced either by SHM-associated deletions or by utilizing a germline variable gene with a naturally occurring short (≤6AA) LCDR1 (West et al., 2012; Zhou et al., 2013). Because indels are quite rare (Briney et al., 2012 Genes Immun. 13, 523-529) and likely will be difficult to elicit consistently by vaccination, Applicants were keenly interested in the ability of the boosting immunogens to select antibodies encoding naturally occurring short LCDR1s. Mice at all stages of the immunization program had VRC01-like antibodies encoding 6AA LCDR1s (FIG. 51G), accomplished through the use of a variety of light chain germline genes that naturally encode short LCDR1 loops (FIG. 51H). Applicants also noted strong sequence convergence of immunogen-elicited antibodies on a critical glutamate residue (Glu96) found in the LCDR3 of VRC01 and most other VRC01-class bnAbs (FIG. 51I) (West et al., 2012; Zhou et al., 2015 Cell 161, 1280-1292). While Glu96 was present only rarely in light chains recovered from GT8-primed mice (3%), the frequency increased upon successive boosts, and every antibody recovered from mice primed with GT8 and boosted with GT3 and SOSIP N276D (2×) contained the critical LCDR3 glutamate. Therefore, mirroring the data obtained from heavy chain sequences, the boosting immunogens successfully recalled primed VRC01-like precursors and drove the incorporation of specific genetic features that direct VRC01-class precursor light chains toward mature VRC01-class bnAbs.

Example 14

Broad Serum Neutralization of N276A Viruses

Following immunization, purified serum IgG from each of the twelve mice receiving the entire immunization schedule was screened on an 8-virus cross-clade indicator panel of near native (N276A) HIV isolates (FIG. 52A). Ten of the twelve mice demonstrated neutralization of at least one heterologous near-native isolate, and seven of the mice developed cross-clade neutralization. Five of six mice boosted with BG505 core-GT3 60mer developed cross-clade neutralization compared to three of six mice boosted with BG505 SOSIP-GT3. Interestingly, although all boosting immunogens were derived from BG505, only two mice acquired detectable neutralizing activity against BG505 N276D. Although 5/6 animals boosted with BG505 GT3 NP developed cross-clade neutralization compared to only 2/6 animals immunized with BG505 SOSIP-GT3, the two animals that exhibited the broadest neutralization were both boosted with BG505 SOSIP-GT3.

To verify the results of the first immunization experiment, Applicants performed a repeat immunization with an additional sixteen VRC01-gH mice, divided into two groups. All mice in the repeat experiment were primed with eOD-GT8 60mer and boosted with BG505 core-GT3 NP according to the immunization schedule detailed in FIG. 52B. One group of eight mice received BG505 SOSIP N276D for the final two boosts, while the other group received a cocktail of SOSIP N276D isolates, one each from clades A, B and C (ABC SOSIP N276D; FIG. 56, Table 17). Applicants did not observe any difference between the two groups of mice with respect to serum neutralization, with 6 mice in each group developing cross-clade neutralization on a 7-virus panel of near-native isolates (identical to the 8-virus panel used in the first round of immunizations, but without JRCSF) (FIG. 52B). Only three mice in each group developed neutralizing activity against BG505 N276A, suggesting that using a single isolate for the final two boosts did not focus the immune response on the immunizing isolate. This is also in agreement with the first immunizations, as three of the six BG505 N276A-boosted mice that displayed neutralizing activity developed heterologous neutralization without acquiring detectable autologous neutralizing activity.

Example 15 mAbs from Immunized Mice Broadly Neutralize Near-Native Viruses

Applicants expressed 40 mAbs from eight VRC01 gH mice that were primed with GT8 and boosted with GT3 and SOSIP and tested them for neutralizing activity on the 7-virus N276A virus panel described earlier (FIG. 52B). Generally, neutralization breadth of mAbs from each mouse correlated with the breadth of serum neutralization, although one mouse (285) that showed no detectable serum neutralization produced a single mAb with moderate neutralization activity. Antibodies from several mice showed broad neutralization on the 7-virus near-native panel, and mAbs from mouse 286 neutralized select isolates with potency comparable to mature VRC01 (FIG. 58). The mAbs were then screened on a larger 25-virus panel of N276A isolates (FIG.

53A). The broadest antibodies all came from a single mouse that also had the broadest serum neutralization (286, first boosted by SOSIP-GT3). Three mAbs from this mouse (Nem227, Nem10 and Nem11) were surprisingly broad and potent, neutralizing up to 48% of the viruses on the 25-virus panel with a median $IC_{50}$ of less than 1 ug/ml.

Because Nem_10 and Nem_11 neutralized 191084 B7-19 N276A with a potency comparable to mature VRC01, Applicants tested the ability of these two mAbs to neutralize the fully native version of 191084 B7-19. Both antibodies were able to neutralize wild-type virus grown in 293S cells, albeit with lower potency (FIG. 53B), suggesting that the mAbs can accommodate the N276 glycan and other CD4bs glycans when they are of reduced size. Critically, both antibodies also showed weak neutralizing activity against fully native virus grown in 293T cells, which in comparison to the high potency against 293T-grown N276A virus suggests that the antibodies are capable of accommodating the N276 glycan to some degree but at some energy cost to binding that precludes high affinity interaction. It is important to note that enhanced potency against virus isolates lacking the N276 glycan site is consistent with a VRC01-like response. Mature VRC01 is substantially more potent against isolates lacking the N276 glycan site, but removal of the N276 glycan site does not make tier 2 viruses more susceptible to the non-VRC01-class bnAb b12 or non-neutralizing antibodies that target the CD4 binding site (FIG. 53C). In summary, an immunization program consisting of an eOD-GT8 60mer prime followed by boosts with BG505 GT3 (NP or SOSIP) and SOSIP N276D has elicited antibodies with broad neutralization on a panel of near-native, tier-2 virus isolates, moderate neutralization of one wild-type virus grown in 293 S cells and weak neutralization of one fully native virus.

Example 16

Discussion

VRC01-class bnAbs are prototypical examples of the neutralizing anti-HIV response that an optimal vaccine would elicit: they are broadly and potently neutralizing; multiple VRC01-class bnAbs have been shown protective against infection in animal models; and VRC01-class naïve B cell precursors are likely to be present at a reasonable frequency in a large fraction of the population thus offering targets to initiate vaccine elicitation. However, induction of such responses remains a massive challenge in part because VRC01-class bnAbs display exceptionally high levels of somatic mutation and GLrev versions of these antibodies have no detectable affinity for all native-like HIV Env molecules tested thus far. A multi-step reductionist vaccine strategy has the potential to address both of these issues: an engineered germline-targeting prime can activate VRC01-class precursors and generate boostable VRC01-class memory B cells, and successive heterologous boosts with increasingly native-like immunogens can produce additive rounds of somatic mutation and gradually refine the ability of maturing antibodies to recognize native HIV Env. Development of minimally mutated variants of VRC01-class antibodies that retain broad and potent neutralizing activity has further raised expectation that a VRC01-like antibody response is achievable by vaccination (Georgiev et al., 2014.

Applicants have reported a germline-targeting immunogen, eOD-GT8 60mer, capable of activating germline precursors of VRC01-class bnAbs. Because eOD-GT8 60mer requires a highly engineered CD4bs epitope to effectively activate VRC01-class precursors, antibodies elicited by priming with eOD-GT8 60mer do not show any detectable affinity for native HIV Env. Therefore, the lack of intermediate immunogens to bridge the gap between the engineered CD4bs in eOD-GT8 60mer and the native CD4bs in native-like trimers like BG505 SOSIP has remained an obstacle to the elicitation of neutralizing VRC01-class antibody responses. Here, Applicants report the development of core-GT3 and SOSIP-GT3, vaccine components designed to shepherd primed VRC01-class precursors toward intermediate VRC01-class function. Boosting VRC01-gH mice with BG505-GT3 (NP or SOSIP) and SOSIP N276D resulted in the elicitation of highly mutated antibodies with a significant fraction of the mutations shared with mature VRC01-class bnAbs. Enrichment of VRC01-class mutations in heavy chains following immunization, and convergence of light chain CDR3 residues toward the sequence of mature VRC01, indicate that boosting with BG505-GT3 and SOSIP N276D establishes strong selective pressure on specific VRC01-class mutations and places these antibodies on a maturation trajectory consistent with partially mature VRC01-class antibodies.

Although boosted VRC01 gH mice showed broad neutralization on a panel of N276A viruses, neutralization of fully native virus containing the N276 glycan site was limited to a single heterologous isolate and was substantially less potent. While the weak neutralization of fully native HIV indicates that there is still significant work to be done before Applicants are able to elicit a truly functional broadly neutralizing response, these data strongly suggest that the elicited responses are VRC01-class antibodies of intermediate maturity. Mature VRC01, in contrast to non-neutralizing mAbs that target the CD4bs, neutralizes N276A viruses much more potently than fully native viruses, so the limited activity of the elicited mAbs against fully native viruses containing the N276 glycan site may simply be a normal feature of partially mature VRC01-class antibodies (Kong et al., 2016 J Virol 79, 10108-10125). Indeed, the observed preference for N276A is not completely unexpected, as neither the prime nor any of the boosting immunogens contain the N276 glycan site. In mature VRC01-class bnAbs, the N276 glycan is accommodated by use of a short LCDR1 loop, either naturally encoded or generated through SHM-mediated LCDR1 deletions (West et al., 2012; Zhou et al., 2013). Encouragingly, Applicants observed a significant fraction of elicited mAbs using light chain variable genes that encode an LCDR1 length matching the naturally encoded short LCDR1s in mature VRC01-class bnAbs.

The relatively low VRC01-class precursor frequency and substantial competition from other clones in the VRC01 gH mouse pose a relatively high bar for elicitation of VRC01-class responses. Thus, the ability to recall VRC01-class precursors and drive maturation toward mature VRC01- class function validates the reductionist sequential immunization strategy and represents a significant milestone in HIV vaccine development.

TABLE 16

Related to FIG. 49. Purpose of GT3 mutations.

| Mutation in GT3 | Purpose | Mutation in GT6? | Mutation in GT8? |
|---|---|---|---|
| N276D | eliminate 276 glycan | Y | Y |
| I277F | stabilize loop D for VRC01-class binding | Y | Y |
| T278R | stabilize loop D; possible VRC01-class contact | Y | Y |
| F353Y | improve packing behind loop D | N | Y |
| N356D | eliminate glycosylation site introduced by I358T | N | N |
| I358T | improve packing on beta sheet; not VRC01 contact | Y | Y |
| N363P | eliminate 363 glycan in BG505 but uncommon in HIV | N[#] | Y |
| T372M | stabilize CD4-binding loop? | N | N |
| T373N | add glycosylation site to 373 | N | Y |
| T455V | eliminate partially buried and unsatisfied hydroxyl? possible contact | N | N |
| S460Y | stabilize V5? possible VRC01-class contact | N | Y |
| T464N | eliminate the one V5 glycan in BG505 | N* | N* |

[#]GT6 lacks a glycan at 363 though it does not use P at that position.
*All V5 glycans have been removed from GT6 and GT8, by other mutations.

eOD-GT8 60mer, however, an alternative boost with HxB2-core-N276D 60mer provided an improved maturation. Maturation is determined by the accumulation of VRC01-class mutations in recovered antibodies. FIG. 77 shows that a two shot protocol using the native-like boost induces similar heavy chain maturation as the four shot GT3-based protocol. FIG. 78 shows that a two shot protocol using the native-like boost elicits cross-reactive neutralization of N276A viruses. Data shown are neutralization titers on N276A viruses for monoclonal antibodies isolated from VRC01 gH mice immunized with the two-shot regimen indicated. Thus, Applicants have shown improvements of the GT3-based protocols and have established for the first time the effectiveness of priming germline precursors followed by more native-like boosts. FIG. 79 depicts a reductionist vaccine strategy to induce VRC01-class bnAbs. The strategy has four main objectives for affinity maturation to be achieved by a sequence of four types of immunogens. Incremental progress can be assessed by using neutralization assays against panels of mutant viruses, as well as analysis of antibody sequences from antigen-specific B cells. Thus, using this strategy, each step can be optimized individually. One strategy is indicated; variant strategies, for example incorporating cocktails of Env, can be readily envisaged.

The sequences of boost immunogens of the present invention are described below:

BG505 core-GT3 60mer and core-e-2CC HXB2 N276D 60mer are produced by co-transfection of 80/20% with naked lumazine synthase. Sequences of the two genes co-transfected to produce BG505 core-GT3.1 nanoparticles

TABLE 17

Related to FIG. 49. Antigenic profile of GT3 SOSIP and native-like trimers
Table of monovalent binding affinities as measured by SPR using Fabs as analytes and BG505 SOSIP, BG505 GT3 SOSIP, CD4bs-B SOSIP and CD4bs-C SOSIP as ligands.

| | Dissociation constant Kd (nM) | | | | | | | | | | | | |
|---|---|---|---|---|---|---|---|---|---|---|---|---|---|
| | Mat-VRC01 | GL-VRC01 | Mat-12A12 | GL-12A12 | Mat-CH31 | GL-CH31 | Mat-3BNC60 | Mat-PGV04 | PGT145[a] | PGT151 | PGT121 | PGT128 | 35O22 |
| BG505 SOSIP | 122 | NB | 59 | NB | 137 | NB | 62 | 197 | 18 | 25* | 29 | 12 | 276 |
| BG505 N276D-SOSIP[b] | 41 | — | 9 | — | 69 | — | 11 | 67 | — | 234 | 26 | 12 | 30 |
| GT3 SOSIP | 27* | 290 | 19* | 1500 | 38* | 2400* | 23* | 70* | 11 | 39* | 40 | 20 | 411 |
| CD4bs-B N276D-SOSIP[b] | 43 | — | 12 | — | 811 | — | 33 | 165 | 81 | 263 | 19 | 11 | 37 |
| CD4bs-C N276D-SOSIP[b] | 170 | — | 212 | — | 3200 | — | 10000 | 17000 | 54 | 214 | 20 | 10 | 25 |

*complex kinetics poor fit to simple 1-to-1 binding model
[a]binding determined using IgG
[b]made in HEK 293S (-GnTI) cells
NB: no binding detected at ≥4 μM Example 17

Improving the First Boost with More Native-Like Immunogens

FIG. 76 shows that BG505-core-GT3 60mer effectively allows maturation of VRC01 antibodies after priming with (NPs). Nanoparticles are produced by co-transfection of 80% BG505 core-GT3.1 60mer and 20% LumSyn_lhqk_naked (red). In the BG505 core-GT3.1 60mer gene, BG505 core-GT3.1 (blue) is fused to the lumazine synthase gene (red) via a flexible linker (cyan) as shown. Multiple linker lengths and co-transfection ratios were evaluated.

BG505 core-GT3.1 60mer
(SEQ ID NO: 41)
MQIYEGKLTAEGLRFGIVASRFNHALVDRLVEGAIDAIVRHGGREEDITLVRVPGSWEIPVAAG
ELARKEDIDAVIAIGVLIRGATPHFDYIASEVSKGLADLSLELRKPITFGVITADTLEQAIERA
GTKHGNKGWEAALSAIEMANLFKSLRGGSGGSGGSGGSGGSGGSGGGVWKDAETTLFCASDAKA
YETEKHNVWATHACVPTDPNPQEIHLENVTEEFNMWKNNMVEQMHTDIISLWDQSLKPCVKLTG
GSAITQACPKVSFEPIPIHYCAPAGFAILKCKDKKFNGTGPCPSVSTVQCTHGIKPVVSTQLLL
NGSLAEEEVMIRSEDFRNNAKNILVQFNTPVQINCTRPNNGGSGSGGDIRQAHCNVSKATWNET
LGKVVKQLRKHYGNDTTIRFAPSSGGDLEVMNHSFNCGGEFFYCNTSGLFNSTWISNTSVQGSN
STGSNDSITLPCRIKQIINMWQRIGQAMYAPPIQGVIRCVSNITGLILVRDGGYTNSNTETFRP
GGGDMRDNWRSELYKYKVVKIEP LumSyn_1hqk_naked
(SEQ ID NO: 42)
MQIYEGKLTAEGLRFGIVASRFNHALVDRLVEGAIDAIVRHGGREEDITLVRVPGSWEIPVAAG
ELARKEDIDAVIAIGVLIRGATPHFDYIASEVSKGLADLSLELRKPITFGVITADTLEQAIERA
GTKHGNKGWEAALSAIEMANLFKSLR gp120core-e-2CC_HxB2
(SEQ ID NO: 43)
VWKEATTTLFCASDAKAYDTEVHNVWATHACVPTDPNPQEVVLVNVTENFNWCKNDMVEQMHED
ICSLWDQSLKPCVKLTGGSVITQACPKVSFEPIPIHYCAPAGFAILKCNNKTFNGTGPCTNVST
VQCTHGIRPVVSSQLLLNGSLAEEEVVIRSCNFTDNAKTIIVQLNTSVEINCTRPNNGGSGSGG
NMRQAHCNISRAKWNNTLKQIASKLREQFGNNKTIIFKQSSGGDPEIVTHWFNCGGEFFYCNST
QLFNSTWFNSTWSTEGSNNTEGSDTITLPCRIKQIINMWCKVGKMMYAPPISGQIRCSSNITGL
LLTRDGGNSNNESEIFRPGGGDMRDNWRSELYKYKVVKIE gp120core-e-2CC_HxB2_N276D_60mer
(SEQ ID NO: 44)
MQIYEGKLTAEGLRFGIVASRFNHALVDRLVEGAIDAIVRHGGREEDITLVRVPGSWEIPVAAG
ELARKEDIDAVIAIGVLIRGATPHFDYIASEVSKGLADLSLELRKPITFGVITADTLEQAIERA
GTKHGNKGWEAALSAIEMANLFKSLRGGSGGSGGSGGSGGSGGSGGGVWKEATTTLFCASDAKA
YDTEVHNVWATHACVPTDPNPQEVVLVNVTENFNWCKNDMVEQMHEDICSLWDQSLKPCVKLTG
GSVITQACPKVSFEPIPIHYCAPAGFAILKCNNKTFNGTGPCTNVSTVQCTHGIRPVVSSQLLL
NGSLAEEEVVIRSCDFTDNAKTIIVQLNTSVEINCTRPNNGGSGSGGNMRQAHCNISRAKWNNT
LKQIASKLREQFGNNKTIIFKQSSGGDPEIVTHWFNCGGEFFYCNSTQLFNSTWFNSTWSTEGS
NNTEGSDTITLPCRIKQIINMWCKVGKMMYAPPISGQIRCSSNITGLLLTRDGGNSNNESEIFR
PGGGDMRDNWRSELYKYKVVKIE** gp120core-e-2CC_HxB2_N276D_d41m3_60mer
(SEQ ID NO: 45)
MQIYEGKLTAEGLRFGIVASRANHALVDRLVEGAIDAIVRHGGREEDITLVRVCGSWEIPVAAG
ELARKEDIDAVIAIGVLCRGATPSFDYIASEVSKGLADLSLELRKPITFGVITADTLEQAIEAA
GTCHGNKGWEAALCAIEMANLFKSLRGGSGGSGGSGGSGGSGGSGGGVWKEATTTLFCASDAKA
YDTEVHNVWATHACVPTDPNPQEVVLVNVTENFNWCKNDMVEQMHEDICSLWDQSLKPCVKLTG
GSVITQACPKVSFEPIPIHYCAPAGFAILKCNNKTFNGTGPCTNVSTVQCTHGIRPVVSSQLLL
NGSLAEEEVVIRSCDFTDNAKTIIVQLNTSVEINCTRPNNGGSGSGGNMRQAHCNISRAKWNNT
LKQIASKLREQFGNNKTIIFKQSSGGDPEIVTHWFNCGGEFFYCNSTQLFNSTWFNSTWSTEGS
NNTEGSDTITLPCRIKQIINMWCKVGKMMYAPPISGQIRCSSNITGLLLTRDGGNSNNESEIFR
PGGGDMRDNWRSELYKYKVVKIE**

-continued

BG505_SOSIP_D664_N276D
(SEQ ID NO: 46)
AENLWVTVYYGVPVWKDAETTLFCASDAKAYETEKHNVWATHACVPTDPNPQEIHLENVTEEFN
MWKNNMVEQMHTDIISLWDQSLKPCVKLTPLCVTLQCTNVTNNITDDMRGELKNCSFNMTTELR
DKKQKVYSLFYRLDVVQINENQGNRSNNSNKEYRLINCNTSAITQACPKVSFEPIPIHYCAPAG
FAILKCKDKKFNGTGPCPSVSTVQCTHGIKPVVSTQLLLNGSLAEEEVMIRSEDITNNAKNILV
QFNTPVQINCTRPNNNTRKSIRIGPGQAFYATGDIIGDIRQAHCNVSKATWNETLGKVVKQLRK
HFGNNTIIRFANSSGGDLEVTTHSFNCGGEFFYCNTSGLFNSTWISNTSVQGSNSTGSNDSITL
PCRIKQIINMWQRIGQAMYAPPIQGVIRCVSNITGLILTRDGGSTNSTTETFRPGGGDMRDNWR
SELYKYKVVKIEPLGVAPTRCKRRVVGRRRRRRAVGIGAVFLGFLGAAGSTMGAASMTLTVQAR
NLLSGIVQQQSNLLRAPEAQQHLLKLTVWGIKQLQARVLAVERYLRDQQLLGIWGCSGKLICCT
NVPWNSSWSNRNLSEIWDNMTWLQWDKEISNYTQIIYGLLEESQNQQEKNEQDLLALD

BG505_core-GT3.1
(SEQ ID NO: 47)
VWKDAETTLFCASDAKAYETEKHNVWATHACVPTDPNPQEIHLENVTEEFNMWKNNMVEQMHTD
IISLWDQSLKPCVKLTGGSAITQACPKVSFEPIPIHYCAPAGFAILKCKDKKFNGTGPCPSVST
VQCTHGIKPVVSTQLLLNGSLAEEEVMIRSEDFRNNAKNILVQFNTPVQINCTRPNNGGSGSGG
DIRQAHCNVSKATWNETLGKVVKQLRKHYGNDTTIRFAPSSGGDLEVMNHSFNCGGEFFYCNTS
GLFNSTWISNTSVQGSNSTGSNDSITLPCRIKQIINMWQRIGQAMYAPPIQGVIRCVSNITGLI
LVRDGGYTNSNTETFRPGGGDMRDNWRSELYKYKVVKIEP BG505_core-GT3.1_60mer
(SEQ ID NO: 48)
MQIYEGKLTAEGLRFGIVASRFNHALVDRLVEGAIDAIVRHGGREEDITLVRVPGSWEIPVAAG
ELARKEDIDAVIAIGVLIRGATPHFDYIASEVSKGLADLSLELRKPITFGVITADTLEQAIERA
GTKHGNKGWEAALSAIEMANLFKSLRGGSGGSGGSGGSGGSGGSGGGVWKDAETTLFCASDAKA
YETEKHNVWATHACVPTDPNPQEIHLENVTEEFNMWKNNMVEQMHTDIISLWDQSLKPCVKLTG
GSAITQACPKVSFEPIPIHYCAPAGFAILKCKDKKFNGTGPCPSVSTVQCTHGIKPVVSTQLLL
NGSLAEEEVMIRSEDFRNNAKNILVQFNTPVQINCTRPNNGGSGSGGDIRQAHCNVSKATWNET
LGKVVKQLRKHYGNDTTIRFAPSSGGDLEVMNHSFNCGGEFFYCNTSGLFNSTWISNTSVQGSN
STGSNDSITLPCRIKQIINMWQRIGQAMYAPPIQGVIRCVSNITGLILVRDGGYTNSNTETFRP
GGGDMRDNWRSELYKYKVVKIEP**

BG505_SOSIP-GT3.1
(SEQ ID NO: 49)
AENLWVTVYYGVPVWKDAETTLFCASDAKAYETEKHNVWATHACVPTDPNPQEIHLENVTEEFN
MWKNNMVEQMHTDIISLWDQSLKPCVKLTPLCVTLQCTNVTNNITDDMRGELKNCSFNMTTELR
DKKQKVYSLFYRLDVVQINENQGNRSNNSNKEYRLINCNTSAITQACPKVSFEPIPIHYCAPAG
FAILKCKDKKFNGTGPCPSVSTVQCTHGIKPVVSTQLLLNGSLAEEEVMIRSEDFRNNAKNILV
QFNTPVQINCTRPNNNTRKSIRIGPGQAFYATGDIIGDIRQAHCNVSKATWNETLGKVVKQLRK
HYGNDTTIRFAPSSGGDLEVMNHSFNCGGEFFYCNTSGLFNSTWISNTSVQGSNSTGSNDSITL
PCRIKQIINMWQRIGQAMYAPPIQGVIRCVSNITGLILVRDGGYTNSNTETFRPGGGDMRDNWR
SELYKYKVVKIEPLGVAPTRCKRRVVGRRRRRRAVGIGAVFLGFLGAAGSTMGAASMTLTVQAR
NLLSGIVQQQSNLLRAPEAQQHLLKLTVWGIKQLQARVLAVERYLRDQQLLGIWGCSGKLICCT
NVPWNSSWSNRNLSEIWDNMTWLQWDKEISNYTQIIYGLLEESQNQQEKNEQDLLALD

-continued

BG505_SOSIP-GT3.1_PADRE (SEQ ID NO: 50)

AENLWVTVYYGVPVWKDAETTLFCASDAKAYETEKHNVWATHACVPTDPNPQEIHLENVTEEFN

MWKNNMVEQMHTDIISLWDQSLKPCVKLTPLCVTLQCTNVTNNITDDMRGELKNCSFNMTTELR

DKKQKVYSLFYRLDVVQINENQGNRSNNSNKEYRLINCNTSAITQACPKVSFEPIPIHYCAPAG

FAILKCKDKKFNGTGPCPSVSTVQCTHGIKPVVSTQLLLNGSLAEEEVMIRSEDFRNNAKNILV

QFNTPVQINCTRPNNNTRKSIRIGPGQAFYATGDIIGDIRQAHCNVSKATWNETLGKVVKQLRK

HYGNDTTIRFAPSSGGDLEVMNHSFNCGGEFFYCNTSGLFNSTWISNTSVQGSNSTGSNDSITL

PCRIKQIINMWQRIGQAMYAPPIQGVIRCVSNITGLILVRDGGYTNSNTETFRPGGGDMRDNWR

SELYKYKVVKIEPLGVAPTRCKRRVVGRRRRRRAVGIGAVFLGFLGAAGSTMGAASMTLTVQAR

NLLSGIVQQQSNLLRAPEAQQHLLKLTVWGIKQLQARVLAVERYLRDQQLLGIWGCSGKLICCT

NVPWNSSWSNRNLSEIWDNMTWLQWDKEISNYTQIIYGLLEESQNQQEKNEQDLLALDGTKHHH

HHHGSAFKVAAWTLKAAA**

BG505_core-GT3.3_mC (SEQ ID NO: 51)

VWKDAETTLFCASDAKAYETEKHNVWATHACVPTDPNPQEIHLENVTEEFNMWKNNMVEQMHTD

IISLWDQSLKPCVKLTGGSAITQACPKVSFEPIPIHYCAPAGFAILKCKDKKFNGTGPCPSVST

VQCTHGIKPVVSTQLLLNGSLAEEEVMIRSEDFRNNAKNILVQFNTPVQINCTRPNNGGSGSGG

DIRQAHCNVSKATWNETLGKVVKQLRKHYGDDTTIRFAPSSGGDLEVATHSFNCGGEFFYCNTS

GLFNSTWISNTSVQGSNSTGSNDSITLPCRIKQIINMWQRIGQAMYAPPIQGVIRCVSNITGLI

LVRDGGYTNSNTETFRPGGGDMRDNWRSELYKYKVVKIEP

BG505_core_VRC01-GT3.3_60mer (SEQ ID NO: 52)

MQIYEGKLTAEGLRFGIVASRFNHALVDRLVEGAIDAIVRHGGREEDITLVRVPGSWEIPVAAG

ELARKEDIDAVIAIGVLIRGATPHFDYIASEVSKGLADLSLELRKPITFGVITADTLEQAIERA

GTKHGNKGWEAALSAIEMANLFKSLRGGSGGSGGSGGSGGSGGSGGSGGGVWKDAETTLFCASDAKA

YETEKHNVWATHACVPTDPNPQEIHLENVTEEFNMWKNNMVEQMHTDIISLWDQSLKPCVKLTG

GSAITQACPKVSFEPIPIHYCAPAGFAILKCKDKKFNGTGPCPSVSTVQCTHGIKPVVSTQLLL

NGSLAEEEVMIRSEDFRNNAKNILVQFNTPVQINCTRPNNGGSGSGGDIRQAHCNVSKATWNET

LGKVVKQLRKHYGNDTTIRFAPSSGGDLEVATHSFNCGGEFFYCNTSGLFNSTWISNTSVQGSN

STGSNDSITLPCRIKQIINMWQRIGQAMYAPPIQGVIRCVSNITGLILVRDGGYTNSNTETFRP

GGGDMRDNWRSELYKYKVVKIEP**

BG505_SOSIP-GT3.3_PADRE (SEQ ID NO: 53)

AENLWVTVYYGVPVWKDAETTLFCASDAKAYETEKHNVWATHACVPTDPNPQEIHLENVTEEFN

MWKNNMVEQMHTDIISLWDQSLKPCVKLTPLCVTLQCTNVTNNITDDMRGELKNCSFNMTTELR

DKKQKVYSLFYRLDVVQINENQGNRSNNSNKEYRLINCNTSAITQACPKVSFEPIPIHYCAPAG

FAILKCKDKKFNGTGPCPSVSTVQCTHGIKPVVSTQLLLNGSLAEEEVMIRSEDFRNNAKNILV

QFNTPVQINCTRPNNNTRKSIRIGPGQAFYATGDIIGDIRQAHCNVSKATWNETLGKVVKQLRK

HYGNDTTIRFAPSSGGDLEVATHSFNCGGEFFYCNTSGLFNSTWISNTSVQGSNSTGSNDSITL

PCRIKQIINMWQRIGQAMYAPPIQGVIRCVSNITGLILVRDGGYTNSNTETFRPGGGDMRDNWR

SELYKYKVVKIEPLGVAPTRCKRRVVGRRRRRRAVGIGAVFLGFLGAAGSTMGAASMTLTVQAR

NLLSGIVQQQSNLLRAPEAQQHLLKLTVWGIKQLQARVLAVERYLRDQQLLGIWGCSGKLICCT

-continued

NVPWNSSWSNRNLSEIWDNMTWLQWDKEISNYTQIIYGLLEESQNQQEKNEQDLLALDGTKHHH

HHHGSAFKVAAWTLKAAA**

BG505_SOSIP_D664

(SEQ ID NO: 54)

AENLWVTVYYGVPVWKDAETTLFCASDAKAYETEKHNVWATHACVPTDPNPQEIHLENVTEEFN

MWKNNMVEQMHTDIISLWDQSLKPCVKLTPLCVTLQCTNVTNNITDDMRGELKNCSFNMTTELR

DKKQKVYSLFYRLDVVQINENQGNRSNNSNKEYRLINCNTSAITQACPKVSFEPIPIHYCAPAG

FAILKCKDKKFNGTGPCPSVSTVQCTHGIKPVVSTQLLLNGSLAEEEVMIRSENITNNAKNILV

QFNTPVQINCTRPNNNTRKSIRIGPGQAFYATGDIIGDIRQAHCNVSKATWNETLGKVVKQLRK

HFGNNTIIRFANSSGGDLEVTTHSFNCGGEFFYCNTSGLFNSTWISNTSVQGSNSTGSNDSITL

PCRIKQIINMWQRIGQAMYAPPIQGVIRCVSNITGLILTRDGGSTNSTTETFRPGGGDMRDNWR

SELYKYKVVKIEPLGVAPTRCKRRVVGRRRRRRAVGIGAVFLGFLGAAGSTMGAASMTLTVQAR

NLLSGIVQQQSNLLRAPEAQQHLLKLTVWGIKQLQARVLAVERYLRDQQLLGIWGCSGKLICCT

NVPWNSSWSNRNLSEIWDNMTWLQWDKEISNYTQIIYGLLEESQNQQEKNEQDLLALD

Note that any sequence that does not end in "" (meaning double stop codon) may end in GTKHHHHHH (SEQ ID NO: 9) (linker+his-tag followed by double stop). Applicants have determined that the immunogens core-GT3.3 and SOSIP-GT3.3 have slightly better binding profiles compared to 3.1.

Boost immunogens may be modified for stability by making any of the "d4", "d41", or "d44" disulfide bonds; and/or "m1", "m2", or "m3" mutations described herein. In preferred embodiments Materials And Methods Study Design for Priming a Broadly Neutralizing Antibody Response to HIV-1 Using a Germline-Targeting Immunogen.

The overall objectives of this study were: (a) to develop a knock-in mouse model for the germline-reverted heavy chain of the HIV broadly neutralizing antibody VRC01 (VRC01 gH mouse model); and (b) to test germline-targeting and native-like immunogens in this mouse model. Specifically, Applicants sought to test the immunogens for their ability to induce immune responses, activate VRC01-class precursors using the VRC01 gH-chain and a short (5aa) CDRL3, select favorable VRC01-like mutations, and produce memory antibodies with affinity for candidate boost immunogens. To make these assessments, Applicants employed ELISA to evaluate polyclonal serum responses, antigenspecific B cell sorting and subsequent antibody cloning to evaluate sequences of induced antibodies, antibody expression and purification and SPR to evaluate antibody binding affinities to various immunogens, and neutralization assays to assess whether elicited antibodies had the capacity to neutralize HIV. Applicants also employed next-generation sequencing and B cell sorting to assess the naive VRC01 gH repertoire. Randomization: VRC01 gH and wild-type littermates of similar ages were assigned to the same immunogens. Blinding: the studies were not blinded. Replication: the main experiment that focused on analysis by ELISA and B cell sorting included 14 groups of 5 mice each (FIG. 1D), and this experiment was conducted once; this experiment did include internal controls by using wild-type littermate mice and it did also have some redundancy in that several immunogens were tested in more than one adjuvant; additional experiments for hybridoma generation were conducted in 13 additional animals for two of the experimental groups (FIG. 1D).

Knock-in Mouse Generation.

Generation of VRC01 gH mice was carried out essentially as described (41), by substituting the VRC01 gH VDJ exon in the targeting construct by overlap PCR. Briefly, linearized targeting construct DNA was introduced into C57Bl/6-derived embryonic stem cells and selected in media supplemented with G418. Cells that insert the gene non specifically carry the DTA gene, which is toxic and cells lacking the neomycin resistance gene are counterselected. Positive clones were identified initially by a PCR strategy and confirmed by southern blot analysis as indicated in FIG. 9.

Polymerase chain reaction conditions were as follows. Reactions were carried out with Q5 Hot start Master mix (NEB) according to the instructions of the manufacturer, using primers at a final concentration of 0.25 mM and ~200 ng genomic DNA template. Reaction conditions were 98° C. 45 sec (1 cycle), followed by 98° C. 15 sec, 67° C. 30 sec, 72° C. 1 min (35 cycles) then 72° C. 10 min. Primers used were as follows:

(SEQ ID NO: 55)

gv3_13: GTG CAG TCT GGG GCT GAG GTG AG (SEQ ID NO: 56)

gv3_3123: AGC ACT CAG AGA AGC CCA CCC ATC T

The sequence used for VRC01 gH encodes the following predicted mature protein V region:

(SEQ ID NO: 57)

QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCARGK

NCDYNWDFQHWGQGTLVTVSS

The upstream promoter, leader and intron elements were from VHJ558.85.191. Targeting, embryonic stem cell screening and mouse generation were as described (41).

Generation and Screening of B Cell Hybridomas from VRC01 gH Mice.

Hybridomas were prepared by fusion of spleen or lymph node cells with sp2/0 cell line and selected in HAT medium (42). Fusions done on days 5 and 10 were carried out directly, whereas those done on day 31 were from mice boosted 3d previously with GT8-60mer in saline. Supernatants were screened for GT8 binding using ELISA assay with GT8-60mer applied to 96-well microtiter plates, followed by blocking with 1% BSA and application of undiluted culture supernatants. Antibody binding was developed with HRP coupled-antibodies (BD Biosciences) specific to the relevant mouse isotypes, followed by incubation with chromogenic substrate (Millipore). Analysis of hybridoma V gene sequences was carried out using a 5' RACE approach as described (43, 44).

Serum Binding Titers by ELISA.

eOD ELISAs were performed as described previously (2) with minor modifications. Microlon 96-well plates (Corning) were coated overnight with antigen (eOD-GT8, eOD-GT8 KO, eOD-17, eOD-17 KO) at 2 μg/mL in PBS (25 l/well). After washing and blocking with 1% FBS+5% skim milk+0.2% Tween20 for 1 h at RT, serially diluted serum in PBS+1% FBS+0.2% Tween20 were then added for 2 h at RT. Plates were then washed and alkaline phosphatase-labeled goat-anti-mouse immunoglobulin G (IgG) (Jackson Immunoresearch, Suffolk, England) was added for 1 h at a 1:2,000 dilution in PBS+1% FBS+0.2% Tween20 at RT. After washing, absorption was measured at 450 nm.

BG505 SOSIP ELISA.

Microlon 96-well plates (Corning) were coated overnight with anti-HIS epitope tag antibody (Thermo Scientific) at a concentration of 2 μg/mL in PBS (25 μL per well). After washing (PBS+0.2% Tween20) and blocking (5% skim milk in PBS with 1% FBS and 0.2% Tween20), 25 μL of C-terminally HIS-tagged SOSIP trimers were added to each well and incubated for 2 hours. Serially diluted serum in PBS/1% FBS+0.2% Tween20 were then added for 2 h at RT. Plates were then washed and alkaline phosphatase-labeled goat-anti-mouse immunoglobulin G (IgG) (Jackson Immunoresearch, Suffolk, England) was added for 1 h at a 1:2,000 dilution in PBS+1% FBS+0.2% Tween20 at RT. After washing, absorption was measured at 450 nm.

Single-Cell Sorting by Flow Cytometry.

Mice spleen and lymph node samples were processed for single B cell sorting based on previously described methods (Wu et al Science 2013, Tiller at al 2008, Sok et al PNAS 2014). In brief, mice spleen were stained with primary fluorophore-conjugated antibodies to murine CD4, CD8, F4/80, CD11c, Gr-1, CD19, B220, IgD, IgM, CD38, and GL7 markers. Memory B cells were selected for the phenotype CD19+, B220+, CD4−, CD8−, F4/80−, CD11c−, Gr-1−, IgM−, IgD−, while CD38 and GL7 markers were monitored to measure germinal center B cell frequencies (CD38-, GL7+). For antigen-specific staining, 50 nM of biotinylated AviTag eOD-GT8 monomer and its CD4bs KO variant (eOD-GT8-KO) were coupled to Streptavidin-AF488 and Streptavidin-PE (Life Technologoies) in equimolar ratios, respectively. Similarly, eOD17 immunized mice were sorted using 50 nM of biotinylated AviTag eOD17 monomer and its CD4bs KO variant (eOD17-KO), while BG505 SOSIP immunized mice were sorted with 50 nM of biotinylated AviTag BG505 SOSIP trimer (45). B cells of interest were single-cell sorted into 96 well plates containing lysis buffer on a BD FACSAria III sorter and immediately stored at −80° C. (9, 45, 46).

Single B-Cell RT-PCR, Gene Amplification, and Cloning.

Reverse transcription and subsequent PCR amplification of heavy and light chain variable genes were performed using SuperScript III (Life Technologies) according to published protocols (9, 45, 46). All PCR reactions were performed in 25 μl volume with 2.5 μl of cDNA transcript using HotStar Taq DNA polymerase master mix (Qiagen) and mixtures of previously described primers (47) that were supplemented with a human VH1-2 primer (CAGGTGCAGCTGGTGCAGTCTGG (SEQ ID NO: 58)). Second round nested-PCR reactions were performed using Phusion proof reading polymerase (NEB). PCR products were then directly cloned into respective human Igγ1, Igκ and Igλ pFuse expression vectors via Gibson assembly (5). Multiple clones for each heavy and light chain pair were sequenced using Sanger sequencing and corrected for PCR errors before further analysis and expression.

Antibody Production.

Heavy and light chain plasmids were co-transfected (1:1 ratio) in 293 FreeStyle cells using 293fectin (Invitrogen) according to the manufacturer's protocol, and antibody supernatants were harvested four to five days following transfection. Supernatants were further purified using protein A Sepharose (GE Healthcare) and dialysed overnight into PBS (0.01 M sodium phosphate, pH 7.4, 0.137 M sodium chloride).

Antibodies were also expressed in the pFUSEss human IgG1 vector (Invitrogen). Heavy- and light-chain plasmids were cotransfected (1:1 ratio) in 293 FreeStyle cells using 293fectin (Invitrogen). Transfections were performed according to the manufacturer's protocol, and antibody supernatants were harvested 4-5 days after transfection. Antibody supernatants were purified over Protein A Sepharose 4 Fast Flow (GE healthcare) columns, eluted with 0.1 M citric acid (pH 3.0), and dialyzed against phosphate-buffered saline.

Protein Production and Purification.

eOD monomers and 60mers were produced and purified as described previously (17). BG505 SOSIP D664 gp140 trimers (33-36) were produced in mammalian cells (HEK-293F) by co-transfection of the trimer gene and furin protease, at a trimer to furin ratio of 2:1. The pre-transfected cells were maintained in 293 Freestyle media (Life Technologies) in a humidified 37° C. $CO^2$ incubator (8%), rotating at 135 rpm at a density of ~$2.4\times10^6$ cells/ml. The genes were transfected using 293fectin (Invitrogen) and harvested 4-5 days later. The cells were centrifuged at 4,000 rpm for 15 min, filtered using 0.2 m filter (Millipore) and a protease inhibitor was added at ratio of 1 ml per liter of supernant (Protease Arrest, GBiosciences). The supernants were purified by nickel affinity purification using His-Trap columns (GE), starting with a wash buffer (20 mM Imidizole, 500 mM NaCl, 20 mM Na2HPO4) and mixing with elution buffer (500 mM Imidizole, 500 mM NaCl, 20 mM Na2HPO4) using a linear gradient. The trimers were then purified by semi-analytical size exclusion chromatography on a S200Increase 10-300 column (GE) in HBS (10 mM HEPES, 150 mM NaCl). The trimer fractions were pooled, concentrated to 1 mg/ml by using Ultracel 30K centrifugal spin concentrators (Millipore) and measuring concentration on a NanoDrop 2000c Spectrophotometer using the absorption signal at 280 nm, frozen in thin-walled PCR tubes using liquid nitrogen, and then stored at −80° C. BG505 SOSIP trimers produced by this in-house process have been thawed and analyzed by SECMALS, SPR, differential scanning calorimetry, and electron microscopy and have been found to possess the native-like antigenic profile, thermal stability and closed trimeric structure that have been reported by others for BG505 SOSIP purified by an antibody-affinity column followed by SEC (33-36) (data not shown).

eOD-GT8 and BG505 GT3 monomers and NPs were produced and purified as described herein (Jardine et al., 2015). BG505 SOSIP D664 and BG505-GT3 SOSIP gp140 trimers were produced in mammalian cells (HEK-293F) by co-transfection of the trimer gene and furin protease, at a trimer to furin ratio of 2:1. The pre-transfected cells were maintained in 293 Freestyle media (Life Technologies) in a humidified 37C C02 incubator (8%), rotating at 135 rpm at a density of ~$2.4\times10^6$ cells/ml. The genes were transfected using 293fectin (Invitrogen) and harvested 4-5 days later. The cells were centrifuged at 4,000 rpm for 15 min, filtered using 0.2 m filter (Millipore) and a protease inhibitor was added at ratio of 1 ml per liter of supernant (Protease Arrest, GBiosciences). The supernants were purified by nickel affinity purification using His-Trap columns (GE), starting with a wash buffer (20 mM Imidizole, 500 mM NaCl, 20 mM Na2HPO4) and mixing with elution buffer (500 mM Imidizole, 500 mM NaCl, 20 mM Na2HPO4) using a linear gradient. The trimers were then purified by semi-analytical size exclusion chromatography on a S200Increase 10-300 column (GE) in HBS (10 mM HEPES, 150 mM NaCl). The trimer fractions were pooled, concentrated to 1 mg/ml by using Ultracel 30K centrifugal spin concentrators (Millipore) and measuring concentration on a NanoDrop 2000c Spectrophotometer using the absorption signal at 280 nm, frozen in thin-walled PCR tubes using liquid nitrogen, and then stored at −80° C. BG505 SOSIP trimers produced by this in-house process have been thawed and analyzed by SECMALS, SPR, differential scanning calorimetry, and electron microscopy and have been found to possess the native-like antigenic profile, thermal stability and closed trimeric structure that have been reported by others for BG505 SOSIP purified by an antibody-affinity column followed by SEC (Julien et al., 2013; Lyumkis et al., 2013; Pancera et al., 2014; Sanders et al., 2013).

The thermostable self-assembling lumazine synthase 60mer (PDB ID: 1HQK), previously described for displaying eOD-GT6 (Jardine:2013hba) and eOD-GT8 (Jardine: 2015hd), was adapted to display stabilized extended HIV gp120 core (gp120core-e) antigens from different strains. Initial expression tests with gp120core-e fused to the 1 hqk sequence (gp120core-e-lhqk) via various length linkers failed to produce fully-assembled particles despite high expression levels of the subunits. Applicants then tested co-transfection with a plasmid encoding only the base subunit of lumazine synthase to insert spacers into the 60mer thereby reducing the crowding on the surface. Of all gp120core-e-lhqk/base lhqk plasmid DNA combinations tested (95/5, 90/10, 85/15, 80/20, 66/33, 50/50, 33/60), an 80% gp120core-e-lhqk and 20% base lhqk mixture produced the highest proportion of assembled 60mers.

Surface Plasmon Resonance (SPR).

Applicants measured kinetics and affinities of antibody-antigen interactions on a ProteOn XPR36 (Bio-Rad) using GLC Sensor Chip (Bio-Rad) and 1×HBS-EP+ pH 7.4 running buffer (20× stock from Teknova, Cat. No H8022) supplemented with BSA at 1 mg/ml. Applicants followed the Human Antibody Capture Kit instructions (Cat. No BR-1008-39 from GE) to prepare chip surfaces for ligand capture. In a typical experiment, about 6000 RU of capture antibody was amine-coupled in all 6 flow cells of the GLC Chip. Regeneration was accomplished using 3 M Magnesium Chloride with 180 seconds contact time and injected four times per each cycle. Raw sensograms were analyzed using ProteOn Manager software (Bio-Rad), including interspot and column double referencing, and either Equilibrium fits or Kinetic fits with Langmuir model, or both, were employed when applicable. Analyte concentrations were measured on a NanoDrop 2000c Spectrophotometer using Absorption signal at 280 nm.

Pseudovirus Production and Neutralization Assays.

Pseudoviruses were generated by transfection of 293T cells with an HIV-1 Env expressing plasmid and an Env-deficient genomic backbone plasmid (pSG3ΔEnv), as described previously (48). Pseudoviruses were harvested 72 hrs post-transfection for use in neutralization assays. Neutralizing activity was assessed using a single round of replication pseudovirus assay and TZM-B1 target cells, as described previously (48). Briefly, TZM-b1 cells were seeded in a 96-well flat bottom plate. To this plate was added pseudovirus, which was preincubated with serial dilutions of antibody for 1 hr at 37° C. Luciferase reporter gene expression was quantified 72 hrs after infection upon lysis and addition of Bright-Glo™ Luciferase substrate (Promega). To determine IC50 values, dose-response curves were fit by nonlinear regression.

Pseudoviruses were also produced with plasmids encoding Env were co-transfected with an Env-deficient genomic backbone plasmid (pSG3ΔEnv) in a 1:2 ratio with the transfection reagent Fugene 6 (Promega). Pseudoviruses were harvested 72 hours post transfection for use in neutralization assays. Neutralizing activity was assessed using a single round of replication pseudovirus assay and TZM-b1 target cells, as described previously (Li et al., 2005; Walker et al., 2011).

Processing of DeKosky/Georgiou Paired Antibody Sequences.

Raw sequence data from DeKosky et al. (19) was downloaded from the Short Read Archive (SRA) and, because SRA files are generated by concatenating paired Illumina reads into a single file, each SRA file was split into two 'read' files corresponding to the paired sequencing reads. In each pair of read files, paired reads were assigned the same sequence ID to enable reconstitution of native heavy/light pairs. Quality and length trimming was performed on each read file using Sickle (49) (with options -q 25 and -l 200) such that the 3' end of each read was trimmed until a 25-base sliding window contained an average sequence quality of 25 and trimmed reads of less than 200 bases were discarded. Germline V(D)J gene assignment and junction identification was performed with an in-house BLASTn-based pipeline and resulting assignments were stored in a MongoDB database. Heavy chain junctions were clustered at 96% sequence identity to collapse duplicate sequencing reads and centroid sequences were calculated for each cluster with at least 2 heavy chain junctions. For each centroid heavy chain sequence, the sequence ID was used to retrieve the appropriate paired light chain sequence. Length distributions for heavy, kappa light, and lambda light chains were measured using IMGT (50) conventions.

Healthy Human Subjects.

Peripheral blood was obtained from healthy adult donors following informed consent, under a protocol (IRB #12-5951) approved by the Scripps Institutional Review Board. Peripheral blood mononuclear cells (PBMCs) were isolated from the whole blood of four healthy donors by gradient centrifugation (Histopaque-1077; Sigma-Aldrich).

NGS Sample Preparation.

Total RNA was isolated from PBMCs (human subjects) or splenocytes (mouse subjects) (RNeasy; Qiagen). Approximately 5% of each total RNA sample was separately subjected to template-switching reverse transcription (SMARTer RACE kit; Clonetech) using the manufacturer's protocol, except that an alternate template-switching primer was used (TS-Illumina: AAGCAGTGGTATCAACGCAGAGTAGACGTGTGCTCTTCCGATCTrGrGrGrGrG, where rG=riboguanosine (SEQ ID NO: 59)). 2.5 uL of each RT product was used in a 50 uL touch-down PCR reaction (Advantage2 Polymerase; Clonetech), with the following cycling conditions: 94° C. for 1 min; 5 cycles of 94° C. for 30 sec, 72° C. for 2 min; 5 cycles of 94° C. for 30 sec, 70C for 30 sec, 72° C. for 2 minutes; 25 cycles of 94° C. for 30 sec, 68C for 30 sec, 72° C. for 2 min; 72° C. for 5 min. PCR products were purified using 0.7 volumes of SPRI beads (SPRIselect; Beckman Coulter Genomics) using the manufacturer's standard protocol and eluted in 50 uL of water. 2 uL of each purified PCR product was used in a 50 uL indexing PCR reaction (HotStarTaq Plus; Qiagen) with the following cycling conditions: 95C for 5 min; 15 cycles of 95C for 30 sec, 58C for 30 sec, 72° C. for 2 min; 72° C. for 10 min. Indexing PCR products were again purified using 0.7 volumes of SPRI beads and eluted in 50 uL of water. Each purified product was quantified by fluorometry (Qubit; Life Technologies), products were pooled at approximately equimolar concentrations, and the pool was re-quantified (Qubit).

Next-Generation Antibody Sequencing.

Amplicons were loaded onto a MiSeq sequencer (MiSeq v3 Reagent Kit, 600-cycles; Illumina) with a target loading concentration of 40 pM. To ensure that full-length 5'RACE products were sequenced (including the leader and 5' UTR region), Applicants modified the run setup such that the first read was 350 bp, followed by a second read of 300 bp. Paired sequencing reads were merged with PANDAseq (51) and sequences were annotated with in-house antibody analysis software based on BLASTn, using human and mouse germline V(D)J databases from IMGT (52). Following annotation, sequences were loaded into a MongoDB database for querying and additional analysis.

Overall Strategy for Improvement of eOD-GT6.

eOD-GT6 was originally developed through an iterative process of computational design and yeast display screening of directed and random mutagenesis libraries (17), but Applicants suspected that four aspects of this work may have limited the breadth of eOD-GT6 reactivity. First, the libraries screened to generate eOD-GT6 addressed a relatively small number of mutations and positions located at the binding interface (61 computationally predicted mutations and 3 mutations identified by error prone PCR across 21 positions). Second, the libraries sampled a limited number of amino acids at each position. Third, the libraries were screened against a small set of germline-reverted and mature VRC01-class Abs available at the time (eOD-GT6 developed occurred during the early stages of VRC01-class bnAb discoveries). Fourth, Applicants attempted to minimize the number of mutations from the initial eOD construct (eOD-Base) that contained a wild-type CD4-binding site epitope except for lacking the 276 and 463 glycans. To improve on the eOD-GT6 affinities for germline-reverted VRC01-class Abs, Applicants removed these four limitations. Applicants expanded the library positions to include all 58 positions on eOD within 8 Å of germline-reverted VRC01 according to the crystal structure of eOD-GT6 bound to germline reverted VRC01 (PDBID: 4jpk, FIG. 28A). At each of those positions, Applicants constructed libraries that sampled all 20 amino acids. Applicants expanded the antibody screening panel to include 18 germline reverted VRC01-class Abs and 11 VRC01-class bnAbs (table 15 and FIG. 41-42). Finally, Applicants eliminated the design goal of minimizing the number of mutations from the initial eOD construct.

Development of eOD-GT7.

To optimize the output of yeast display screening of deep mutational scanning libraries against a large panel of germline-reverted VRC01-class Abs, Applicants first attempted to develop a construct (eOD-GT7) with at least low detectable affinity for diverse germline-reverted ($GL_{Rev}$) VRC01-class Abs on the surface of yeast. Applicants used this construct as a starting point to improve the effectiveness of deep mutational scanning and to identify mutations with individually small effects. To develop eOD-GT7, a round of yeast display screening was done using 11 mature VRC01-class antibodies and 17 $GL_{Rev}$ VRC01-class antibodies, in some cases including several variants with differences in the CDR3 loops and/or different light chain V genes. An additional 4 $GL_{Rev}$ antibodies were generated using reverted heavy chain sequences isolated from the deep sequencing of donor 74 as well as using PGV04 variants that contained partially reverted CDRH3 sequences (11), totaling 21 antibodies containing germline-reverted VH and VL genes (table 15). The yeast cell surface display library to make eOD-GT7 was generated from the sort data collected in all optimization up through eOD-GT6. Any mutation that had been observed to either be neutral or beneficial for binding to $GL_{Rev}$ VRC01 was resampled, allowing all possible combinations. The eOD-GT7 library was sorted twice against $GL_{Rev}$ VRC01 at 1 μM IgG concentration, resulting in a population of clones all of which had detectable affinity for $GL_{Rev}$ VRC01 IgG on the surface of yeast. The library was sorted in parallel against each of the $GL_{Rev}$ Abs and mature VRC01-class bnAbs at various concentrations (32 parallel sorts). All but one VRC01-class bnAb sort showed significant numbers of clones with high affinity in the first sort, therefore the bnAb sorts were only conducted once. After 3 additional sorts with high concentrations of different $GL_{Rev}$ antibodies, 14 of 21 libraries enriched for clones that successfully bound their GLRev Ab. Those libraries were then grown until stationary phase was reached (OD600~10) at which point they were miniprepped (Zymoprep™ Yeast Plasmid Miniprep II, Zymo Research) and the resulting DNA was PCR amplified to recover the genes encoding the eOD variants. For each sorted library, the eOD region containing all of the resampled positions was amplified and indexed using universal tag PCR (the gene-specific primers were eOD_fwd: CCCATTGCTCTTCCAACATT (SEQ ID NO: 60) and eOD_rev: CAATAGAAAAACTCACCACCACA (SEQ ID NO: 61)) and sequenced on an Illumina MiSeq using a paired-end 250 bp kit. A total of 3,849,908 sequencing reads were obtained. Paired-end reads were merged using PANDAseq, merged reads were trimmed to remove primer sequences and low-quality bases, and the resampled positions were translated. Bioinformatic analysis on the next generation sequencing data from the eOD-GT7 library was utilized to extract the mutations that enhance affinity for GLRev VRC01-class antibodies. The number of total possible unique sequences, or the theoretical library size, was 16,384. Within the reads, specific sequences that occurred most frequently in the sorted libraries and less frequently in the display only library were assumed to have improved affinity for the antibodies used to sort. To calculate relative frequencies, Applicants computed the ratio of the frequency each sequence was found in the $GL_{Rev}$ sorted libraries over the frequency the same sequence was found in the display only library, and Applicants computed a similar ratio for the bnAb sorted libraries. If no enrichment occurred (the "null expectation"), then each of the 16,384 sequences would be seen 2 times in the unsorted library (36,164 reads), 9 times in the bnAb sorted library (146,334 reads), and 9 times in the GLRev sorted library (145,551 reads). The most common sequence seen in the $GL_{Rev}$ sorted library was found in 5,305 reads, ~590 times more than the null expectation. The four most common sequences selected in the $GL_{Rev}$ libraries only differed in the last two positions, where arginine and lysine were seen equally. Of the 20 most frequent sequences in the bnAb library, the closest one to the most frequent $GL_{Rev}$ sequence was found 203 times, which was 23 times more than the null expectation. This sequence had lysine in the last two positions. Therefore, Applicants hypothesized that a reasonable consensus sequence which would maintain binding to both $GL_{Rev}$ and mature antibodies would be the most enriched $GL_{Rev}$ selected sequence with inclusion of lysine at the last two positions. The resulting antigen, eOD-GT7, contained 9 mutations from the starting eOD construct (eOD-Base (17)), compared to the 7 present in eOD-GT6 (FIG. 34). The eOD-GT7 protein was produced as a recombinant protein, and binding to antibodies was evaluated by SPR (table 10). An average binding improvement of only a factor of 3 was achieved, and binding to several $GL_{Rev}$ Abs could not be detected at a concentration of 100 μM, but the rest bound with sufficient affinity to be detected using yeast surface display, therefore eOD-GT7 served as a good starting point for deep mutational scanning (see below).

Development of eOD-GT8.

Figure 28A:
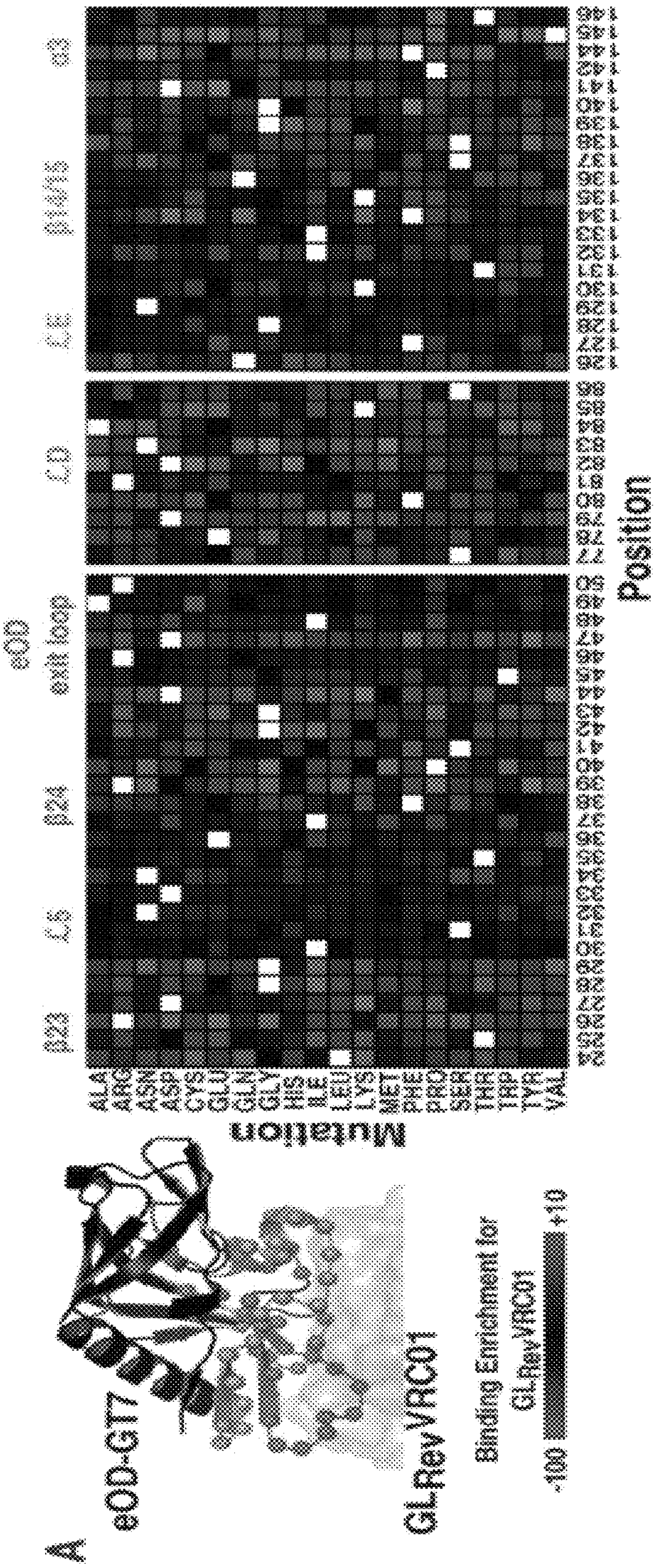
Figure 28B:
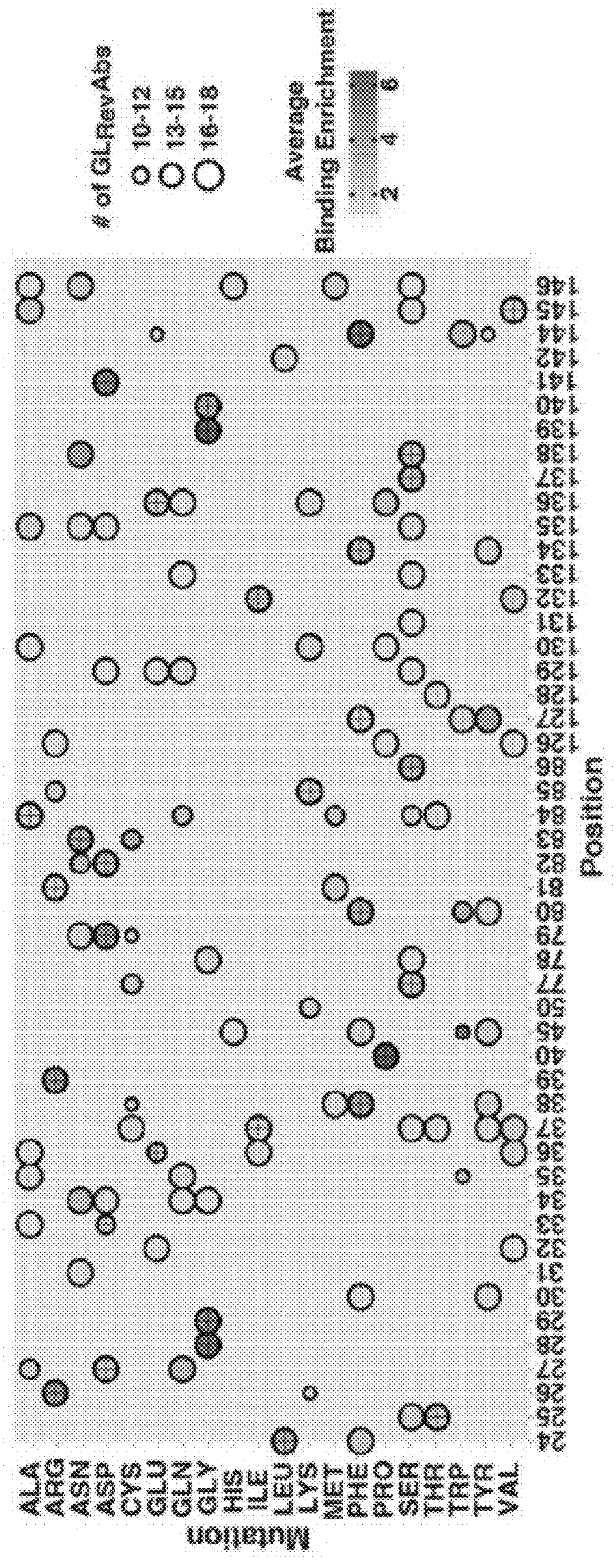
Figure 28D:
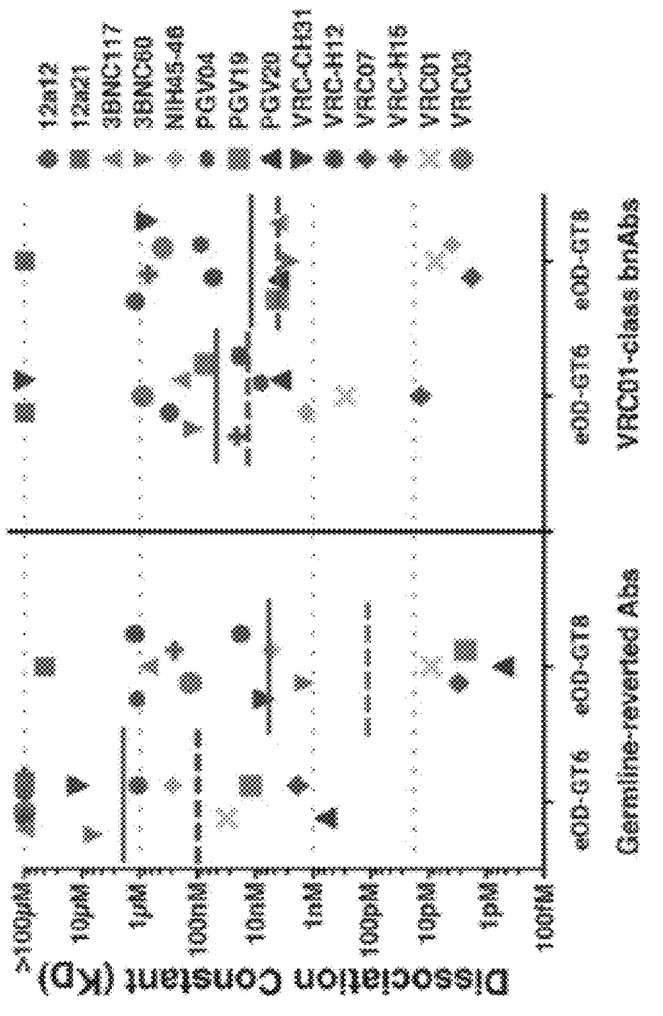
Figure 28C:
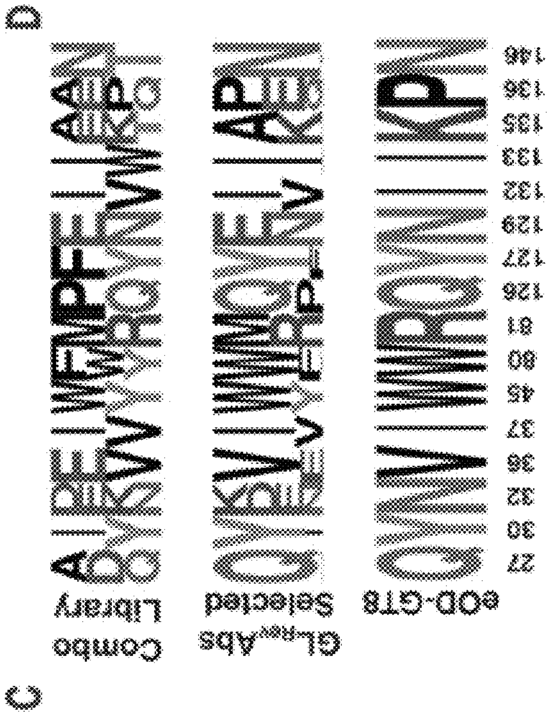

The 58 amino acids within 8 Å of the GL-reverted VRC01 antibody present in the crystal structure (PDBID: 4JPK) were included in a new set of 58 libraries (FIG. 28A). For each of the libraries a single position was varied by replacing the codon encoding the eOD-GT7 amino acid with the degenerate codon "NNK", which encodes all 20 amino acids. A silent "barcode" mutation was made on either side of the degenerate codon to unambiguously identify the site of interest in the next generation sequencing data (FIG. 43). In the cases of methionine or tryptophan a single codon was used to encode those amino acids, so the silent mutation was shifted to a neighboring codon or omitted. The barcoded NNK scanning libraries were constructed using overlap extension PCR with primers containing the degenerate codon 'NNK', flanked by silent mutations on either side (Integrated DNA Technologies). Briefly, the base eOD-GT7 parental DNA was used as a template for PCR to generate two fragments, overlapping by ~25 nucleotides (predicted $T_M$>65° C.). One fragment was a truncated variant of eOD-GT7, the other fragment was generated with a primer where a codon in the eOD-GT7 base was replaced with an "NNK" position, flanked by the closest possible silent mutation on either side. These two fragments were then joined with overlapping PCR to generate full length eOD-GT7 containing a single degenerate position. This process was repeated for each position included in the library, pooled and transformed into EBY100 as previously described (17). The pooled eODGT7 single site mutagenesis library was transformed into yeast, induced and sorted against 32 antibodies-11 VRC01-class bnAbs and 21 $GL_{Rev}$ VRC01-class antibodies. The cells were sorted once, collecting the top 10% of binders at an antibody concentration that was less than saturating, collecting 50,000 cells. Three of the libraries labeled with $GL_{Rev}$ Abs did not bind with sufficiently high affinity to produce a useful dataset; thus Applicants ended up with a total of 29 Ab sorts-11 VRC01-class bnAbs and 18 $GL_{Rev}$ VRC01-class antibodies. Plots of the binding versus display populations for each Ab are shown in FIG. 44. The sorted cells were grown overnight and treated as before. For each sorted library, DNA was amplified and indexed using universal tag PCR and sequenced on an Illumina MiSeq using a paired-end 250 bp kit. A total of 14,212,503 sequencing reads were obtained. Since each amplicon was less than 250 bp in size, paired-end reads provided full forward and reverse coverage of each sequence, which allows for correction of sequencing errors. Paired-end reads were merged using PANDAseq, merged reads were trimmed to remove primer sequences and low-quality bases, and each resampled region was translated. The next generation sequencing datasets for the sorted NNK libraries were analyzed to find amino acid biases at the 58 positions due to improved binding of eOD-GT7 to CD4bs antibodies. The unselected library had 216,663 raw reads. The selected libraries had on average 292,690 raw reads. The raw reads were filtered to exclude reads with insufficient length, stop codons, or any number of barcode mutations other than two. Each sequence could only encode a single point mutation, so the sequences were counted according to the position and the type of amino acid. The binding enrichment of a given amino acid at a given position was then computed for each dataset (FIG. 28B and FIG. 32). Using the binding enrichment data, Applicants constructed a combinatorial library that allowed a combinations of a filtered set of favorable mutations at 16 positions on the eOD-GT7 base construct (FIG. 28C). Filtering was done to limit library size, to exclude mutations detrimental to the majority of mature bnAbs, to reduce hydrophobic exposure, to exclude unpaired cysteines, and to minimize non-conservative changes to epitope components. This library was assembled with overlapping ultramers containing degenerate codons at the library positions encoding the desired mutations to sample. The theoretical size of this library was $1.1\times10^6$, and approximately $2\times10^8$ clones were achieved from the transformation, providing >100 fold coverage of the theoretical library size. The initial sort was done by labeling with 100 nM concentrations of bnAb and $GL_{Rev}$ Abs: VRC01, PGV04_H1/L1, 12a12, PGV20, 3BNC60, VRC-CH31. Sort gates were drawn generously to select all clones that bound, creating an initial population of eOD GT7-based variants that contained combinations of mutations that were compatible with antibody binding. The library was sorted 4 times against 32 antibodies at non-saturating antibody concentrations to enrich the highest affinity binders (the $GL_{Rev}$ Abs used for these sorts are listed in table 9). The resulting libraries were grown, miniprepped and deep sequenced, as described above. The final design of eOD-GT8 sequences was accomplished by bioinformatic analysis of the next generation sequencing datasets. The highest stringency sorts were used for the analysis because they were the most converged. To obtain quality reads with minimal sequencing errors, Applicants filtered sequences for those that contained allowed amino acid diversity at the 16 positions and were observed a minimum of 3 times in the sequencing dataset. A sequence logo diagram for each $GL_{Rev}$ Ab sort shows the amino acid frequencies at each position (FIG. 33). Next, Applicants searched for sequence motifs in each $GL_{Rev}$ dataset that contained amino acids seen in at least 90% of the reads, which should have the highest affinity for the sorted antibody. For example, in the $GL_{Rev}$ VRC01 dataset, position 27 was glutamine and position 133 was isoleucine in more than 90% of the reads, making a sequence motif of 'Q . . . I . . . ', where a dot is any amino acid (Table 9). The consensus sequence of these sequence motifs was used as the base design for eOD-GT8. This base design and two variants of eOD-GT8 were expressed and tested for binding to a panel of matched VRC01-class $GL_{Rev}$ Abs and bnAbs (12a12, 3BNC60, NIH4546, PGV04, PGV19, PGV20, VRC01, VRC03, VRC-CH31). The variants tested were the mutants Q27/457D, which reconstituted a salt bridge highly conserved on HIV gp120 at position 27 in eOD residue numbering and 457 in HxB2 gp120 residue numbering, and Q27/457D+N146/373T, which reconstituted the salt bridge and eliminated a new glycosylation site present in the consensus eOD-GT8 but generally absent in HIV gp120 at eOD position 146 and HxB2 position 373. The base design had superior $GL_{Rev}$ affinities and only slightly reduced bnAb affinities, so the base design was retained.

Biophysical Characterization: KinExa.

Equilibrium binding affinity for NIH45-46 binding to eOD-GT6 and $GL_{Rev}$ PGV19, $GL_{Rev}$ PGV20, $GL_{Rev}$ VRC01, $GL_{Rev}$ VRC07, NIH45-45, VRC01 and VRC07 binding to eOD-GT8 was determined by a solution kinetic exclusion assay using a KinExA™ 3200 instrument (Sapidyne, Boise, Id.). eOD-GT8 was cross-linked to NHS-activated Sepharose 4 Fast Flow beads (GE) as a capture reagent. Alexa Fluor 647-conjugated AffiniPure Goat Anti-Human IgG (Jackson ImmunoResearch) was used at 500 ng/ml to label $GL_{Rev}$ PGV20. The measurements were taken at room temperature. eOD-GT8 was serially diluted into a constant concentration of antibody (1.33 μM for KD controlled experiment and 133 μM for antibody controlled experiment). Samples were equilibrated for three days. All the data points were measured in duplicates and analyzed with the KinExA Pro software (Version 4.0.12).

eOD-GT6- and eOD-GT8-Specific Naïve B Cell Isolation Methodology Overview.

A stringent two-stage, multiple-validation methodology was employed to combat the predicted rarity of eOD-GT6 and eOD-GT8 specific naïve B cells and limit the number of false positive results inherent in analyzing potential low affinity interactions (FIG. 31 eOD-GT6, FIG. 37 eOD-GT8). The first screening stage was cell sorting, the second stage was single cell culture of the sorted probe+ IgM+ B cells. For a cell to be considered antigen-specific at the end of the screening process, multiple specificity criteria were required to be achieved at each stage, described in the sections below, which correspond to the progression of steps shown in FIGS. 31 and 37.

B Cell Isolation and Purification.

LRS (leukoreduction) tubes were obtained from the San Diego Blood Bank. Greater than one billion PBMC were regularly recovered by Histopaque-1077 (Sigma) density gradient separation. B cells were isolated by positive selection using CD19 microbeads (Miltenyi Biotec).

B Cell Probe Generation.

eOD-GT6 60mers were generated and directly labeled with an Alexa 647 protein labeling kit (Life Technologies), and purified via the included purification resin. Avi-tagged eOD-GT8 and eOD-GT8 KO monomers were biotinylated and purified. Biotinylated monomers were individually premixed with fluorescently labeled streptavidin to form eOD-GT8 Alexa488 tetramers and eOD-GT8 KO phycoerythrin tetramers. eOD-GT8 GCN-3mers were generated, directly labeled with an Alexa 647 protein labeling kit (Life Technologies), and purified via the included purification resin. Fluorochromes and multimerization methods were carefully chosen to avoid false positives due to isolation of B cells specific for non eOD-GT8 epitopes present on the probes, such as epitopes present on biotin, streptavidin, GCN, and the fluorochromes. The positive probes were labeled with small Alexa Fluor molecules, which likely provide fewer potential epitopes for B cell recognition than larger fluorescent proteins. Different multimerization methods were used for the two positive probes to avoid isolating B cells specific for multimerization domains (streptavidin, biotin, and GCN).

B Cell Sorting.

eOD-GT6 probes B cell sorts: Cells were incubated with an eOD-GT6 Alexa 647 probe for 30 mins at 4° C. Without washing, anti-CD19 (HIB19; BD Biosciences) and anti-IgD (IA6-2), as well as anti-IgG (G18-145), CD8, CD14, CD16, and Live/Dead (eBioscience) for exclusion, were added for an additional 30 mins. A BD FACS Aria was used for all cell sorting. Cells were sorted at a flow rate of ~5,000 events/second using an 85 m nozzle. Sorting stringency was set to the strictest setting (single cell) to obtain one and only one cell per well. The high stringency sorting settings increases the ‘abort’ rate of accurately counted events that are not sorted into wells. Representative flow cytometry is shown in FIG. 31 and FIG. 37.

eOD-GT8 probes B cell sorts: Cells were incubated with eOD-GT8 probes (eOD-GT8 biotin-streptavidin Alexa 488, eOD-GT8 GCN-3mer Alexa647, and eOD-GT8 KO biotin-streptavidin PE) for 30 mins at 4° C. Then further staining was done as described above. Representative flow cytometry is shown in FIG. 29A and FIG. 37. The total number of B cells screened for each donor is shown in FIG. 29J (range 0.5 to 14.4 million naïve B cells per donor).

Single-Cell Sorting by Flow Cytometry.

Mice spleen and lymph node samples were processed for single B cell sorting based on previously described methods (Sok et al., 2014; Tiller et al., 2008; Wu et al., 2011), with slight modifications that are fully detailed herein.

B Cell Transduction and Culture.

Schematic is shown in FIG. 37. Sorted probe-positive B cells were activated on mouse fibroblasts expressing human CD40L (CD40L+ L cells) with 100 ng/ml rmIL-21 (Pepro Tech) for 36 hrs at 37° C. Cells were mixed with LZRS vectors expressing Bcl6-GFP and Bcl-XL-ΔNGFR on RetroNectin (1 μg/ml, Clontech) coated 96-well plates (61). Plates were centrifuged at 300×g for 90 min at 37° C. and placed in the incubator for 5 additional hours. B cells were then washed and re-plated on CD40L+ L cells with 100 ng/ml rmIL-21. Three to five days later, cells were re-sorted after staining for eOD-GT8 3mer Alexa 647 and ΔNGFR (BDbioscience). eODGT8+ Bcl6+ Bcl-$XL^+$ B cells were sorted near limiting dilution at 2-4 cells per well on a 384-well plate on CD40L+ L cells with 100 ng/ml rmIL-21 to generate B cells lines. Cells were grown on CD40L+ L cells with 100 ng/ml rmIL-21 in RPMI 1640 medium (Life Technologies)+10% FBS (Omega Scientific)+1% Penicillin-Streptomycin (Gibco)+1% GlutaMAX (Gibco). Cells were split as needed.

ELISA Screening for eOD-GT8 Specificity.

Culture supernatants were tested for IgM antibodies by ELISA. No IgG antibodies were detected by ELISA. Antigen-specificity was checked by coating 1 μg of antigen on MaxiSorp (Thermo Scientific) plates overnight. Plates were then washed, incubated with supernatant for 2 hrs at room temperature, washed, incubated with a monoclonal mouse anti-human IgM Fc antibody conjugated to HRP (Hybridoma Reagents Laboratory), washed, and developed with TMB substrate (Thermo Scientific). PBS+0.05% Tween was used for all washes. Monomeric eOD-GT8 was used to confirm eOD-GT8 specificity as opposed to specificity to other epitopes present on the multimeric fluorescent eOD-GT8 probes. Monomeric eOD-GT8 KO was used to determine CD4bs epitope specificity. eOD-GT8 60mer and eOD-GT8 KO 60mer were used to determine the specificity of potentially specific clones displaying lower affinity that were not revealed by the monomer ELISA. Detection of lower affinity clones was expected as the eODGT8 probe multimer-BCR interaction on cells in the FACS-based screening is multivalent and may be expected to capture lower affinity events than the secreted IgM-eOD GT8 monomer interaction of the ELISA. Phycoerythrin (PE) and Keyhole limpet hemocyanin (KLH) were used to check for polyreactivity and no VRC01-class naïve B cells were found to be polyreactive.

B Cell Lysis, RT, PCR, and Sequence Analysis.

For transduced B cells clones, 100-1,000 cells were lysed in 20-50 μl lysis buffer (1 ml water, 10 μl 1 M Trizma Hydrochloride (Sigma), 12.5 μl murine RNAse Inhibitor (New England BioLabs). In some experiments, single B cells were sorted directly into 10-20 μl lysis buffer. Lysed cells were immediately frozen on dry ice then moved to −80° C. for storage. First-strand cDNA synthesize was done using SuperScript II RT (Invitrogen) as stated in the instructions. Nested PCR protocol was modified from Tiller et al. (46). For the Heavy Chain reactions, pooled primers were used at 25 nM. Fifty cycle PCR reactions were used (polymerase activation 98° C. for 30 sec; denaturation, 98° C. for 15 sec; annealing, 62° C. for 20 sec; extension, 72° C. for 35 sec). For the Kappa Light Chain reaction, pooled primers were used at 250 nM and only 25 cycle PCR reactions were used. Phusion Taq polymerase (ThermoFisher, F530L) was used at 0.5 units/reaction for all reactions. Primers used from Tiller et al. (46). PCR products were run out on 2% agarose E-gels (Life Technologies). Reactions with 300-400 bp products were sequenced in both directions. Sequencher 5.0 was used to align sequences. IMGT/V-QUEST was used for VDJ assignments.

Heavy chain PCR reactions were performed first. Only wells with a 300-400 basepair product from the HC PCR were then subjected to kappa light chain PCR reactions. Lambda light chain PCR was not done. In total, single cell PCR reactions were performed on 1123 eOD-GT8 isolated B cells. 306 (27%) wells produced readable, unique HC sequences. Of these 306 wells with HC sequences, 173 (57%) produced readable kappa sequences. This data set of 173 naïve B cells with paired HC and LC sequences was used for the analysis of the frequency of VH1-2+ naïve B cells among all eOD-GT8-specific naïve B cells (FIG. 29). The frequency of VH1-2+ B cells among all successful HC PCR sequences (135 of 306, 44%) was similar to the % of VH1-2+ B cells among B cells for which both HC and LC sequences were determined (87 of 173, 50%).

Additional eOD-GT8 Screening.

For eOD-GT8 specific naïve B cell screening, seven donors (donors #1-7) were analyzed using the two stage, multiple-validation methodology. The screening experiments with donors #1-7 indicated that further refinements to flow cytometric gating may be adequate to isolate naïve B cells specific for eOD-GT8. An additional 8 donors (donors #8-15) were then screened by FACS sorting eOD-GT8$^{(tr+/SA+)}$ eOD-GT8-KO naïve B cells and directly proceeding to B cell receptor PCR and sequencing.

Antibody Synthesis.

All eOD-GT8-specific naïve B cell sequences were synthesized as IgG Abs, as previously described (17).

Epitope-Specific Naïve B Cell Frequency Calculations.

Using the screening methodology detailed above and schematized in FIG. 31 and FIG. 37, in total, paired HC/LC sequences were determined for 173 eOD-GT8 specific naïve B cells. 50% (87 of 173; FIG. 29D) were VH1-2+ and of these 30% (26 of 87) were VRC01-class naïve B cells (VH1-2 paired with a 5aa L-CDR3). The frequency calculation of 1 in 2.4 million was obtained by dividing the number of VRC01-class naïve B cell precursors recovered by the total number of naïve B cells screened across all donors (26 of 61.6 million; FIG. 29J).

This calculated frequency is likely to be an underestimate of the true frequency of VRC01-class naïve B cell precursors, because not all B cells counted as eOD-GT8$^{(tri+/SA+)/eOD-GT8-KO(-)}$ actually made it into a well to allow RT-PCR, and paired HC and LC sequences were recovered from only a proportion of eOD-GT$_8^{(tri+/SA+)/eOD-GT8-KO(-)}$ B cells in wells due to inherent limitations of single-cell PCR. Applicants evaluated these losses by analyzing the data from donors #8-15 (N=8 donors, 48.8 million B cells) from which eOD-GT$_8^{(tri+/SA+)/eOD-GT8-KO(-)}$ B cells were sorted directly for PCR. To compute the cell sorter loss due to the high stringency sorting conditions, Applicants noted that only 1123 GT8$^{(tri+/SA+)/eOD-GT8-KO(-)}$ B cells were collected out of a theoretical maximum of 1985 (calculated by summing the frequency eOD-GT8$^{(tri+/SA+)/eOD-GT8-KO(-)}$ B cells for each individual donor multiplied by the total number of B cells sorted for that donor). Thus cell sorting losses reduced the number of cells sorted into wells by a factor of 1.7. To compute the PCR losses, Applicants calculated the fraction of wells with a successful heavy chain PCR for each donor (on average this fraction was 27%). Correcting only for PCR losses for each individual donor, the frequency of VRC01-class naïve B cell precursors was calculated to be 1 in 700,000 naïve B cells. Correcting also for the cell sorting losses, the frequency of VRC01-class naïve B cell precursors was estimated as 1 in 400,000 naïve B cells.

Poisson Modeling of the Number of Sorted VRC01-Class Naïve B Cells.

If Applicants assume that all donors in FIG. 29J have VRC01-class precursors at a fixed frequency of 1 in 2.4 million, then the probability distribution of the number of VRC01-class precursors in any number of B cells will follow a Poisson distribution, due to the Law of Rare Events. Applicants first tested the Poisson model for goodness of fit to the data in FIG. 29J using a Chi-squared test. That test failed to reject the null hypothesis (p-value=0.47) that the observed counts are from a Poisson distribution, thus providing evidence that the data are consistent with a Poisson distribution. Applicants next simulated the precursor count data by constructing 15 binomial (more general form of Poisson) distributions, each one representing the distribution of the precursor counts for one of the 15 samples in the study, then randomly drawing 10,000 precursor count values from each binomial distribution, and finally computing the mean precursor count and empirical 95% confidence interval for each of the 15 samples. The 95% confidence intervals from those simulations suggest that all experimentally observed counts are consistent with a Poisson distribution with constant frequency of 1 in 2.4 million (FIG. 29K). In the same simulation study, Applicants counted the empirical distribution of the number of samples with zero counts of VRC01-class precursors and found that the experimentally observed number of zeros, 4, was also consistent with the same Poisson distribution.

Crystallization and Structure Determination of eOD-GT8.

For crystallization of eOD-GT8, it was necessary to use a resurfaced construct where N-linked glycosylation sites (NXT/S) are mutated to alanine residues (AXT/S), as previously described (17). A minimal glycan (mglyc) construct possessing three N-linked glycosylation sites (N18, N65 and N146, eOD numbering; 448, 262 and 373, gp120 numbering, respectively) was designed and transfected in labadapted suspension 293S (GnT I−/−) cells. The $His_{6x}$-tagged glycoprotein ("$His6_x$" disclosed as SEQ ID NO: 7) was isolated from the supernatant and purified using a HisTrap nickel column (GE Healthcare). Affinity-purified eOD-GT8-mglyc was then treated with EndoH (NEB) (17) and subsequently purified to size homogeneity using a Superdex 200 gel filtration column (GE Healthcare). Deglycosylated eOD-GT8mglyc entered crystallization trials at a concentration of ~5 mg/mL and experiments were set-up using the Rigaku CrystalMation robotic system at the Joint Center for Structural Genomics (www.jcsg.org). Crystal hits were obtained at 20° C. in a solution containing 2% (v/v) PEG 400, 2 M ammonium sulfate and 0.1 M HEPES, pH 7.5. Crystals were cryo-protected in the mother liquor supplemented with 20% glycerol before being flash-frozen in liquid nitrogen.

Recombinant VRC01c-HuGL Fabs were produced by co-transfecting the heavy (Fab) and light chains in FreeStyle™ 293F (Invitrogen) suspension cultures. These cultures were purified by Kappa Select (GE Healthcare) affinity chromatography followed by MonoS cation exchange chromatography (Sigma) in sodium acetate. The VRC01c-HuGL2 Fab purified sample was then concentrated to ~7 mg/ml and subjected to crystallization trials using the automated Rigaku CrystalMation robotic system at the Joint Center for Structural Genomics (www.jcsg.org). The apo VRC01c-HuGL2 Fab crystallized at 20° C. in a solution containing 0.2 M lithium sulfate and 20% (w/v) PEG3350 and the crystals were cryo-protected in the mother liquor with an additional 25% glycerol before flash freezing in liquid nitrogen.

The complex of the VRC01c-HuGL2+ eOD-GT8-mglyc was obtained by incubating the purified Fab with a molar excess of eOD-GT8-mglyc (both purified separately as described herein). After incubation, this complex was treated with EndoH (NEB), followed by purification over Superdex 200 size exclusion chromatography (GE Healthcare). The purified deglycosylated complex was concentrated to ~10 mg/ml. The VRC01c-HuGL2+ eOD-GT8mglyc complex was subjected to crystallization trials using the automated Rigaku CrystalMation robotic system at the Joint Center for Structural Genomics (www.jcsg.org). Crystals that diffracted to 2.4 Å were obtained at 20° C. in a solution of 0.2 M potassium dihydrogen phosphate, 20% (w/v) PEG3350 and those formed in a solution containing 0.1 M citric acid (pH 4.0), 20% (w/v) PEG6000 with an overall pH 5.0 of the solution diffracted to 2.16 Å resolution. The crystals in the mother liquor were cryo-protected in 25% glycerol followed by fast plunging in liquid nitrogen.

X-Ray Data Collection, Data Processing and Structure Determination of eOD-GT8.

Flash-cooled crystals of EndoH-treated eOD-GT8-mglyc were subjected to high energy X-ray radiation at the Stanford Synchrotron Radiation Lightsource (SSRL). Data processing was performed using XDS (62). The data was found to have severe anisotropy when analyzed using the UCLA MBI—Diffraction Anisotropy Server (services.mbi.ucla.edu/anisoscale/anisoscale_xds/) (63). To correct for anisotropy, XDS scaling output files were truncated by the server at 3.0 Å, 2.7 Å and 2.9 Å along the a, b and c axes, respectively. Statistics for the anisotropy-corrected data are reported in table 13. Molecular replacement was performed using Phaser (32) with the 2.5 Å-resolution eOD-GT6mglyc structure as a search model (PDB ID: 4JPJ). Refinements were carried out in PHENIX (65) and model building was performed using Coot (34). Secondary structure was determined using STRIDE (67). Structure validation was achieved using Molprobity (68) and refinement statistics are reported in table 13.

Diffraction data for VRC01c-HuGL2 Fab and the deglycosylated complex of VRC01c-HuGL2+ eOD-GT8-mglyc were collected at SSRL BL-12-2. Data processing was performed using HKL2000 (69). Molecular replacement for the apo-VRC01c-HuGL2 Fab and the VRC01c-HuGL2+ eOD-GT8-mglyc complexes were performed using VRC01GL Fab (PDB ID: 4JPK) and apo-VRC01c-HuGL2 (table 13) determined at 1.8 Å resolution and eOD-GT6 (PDB ID: 4JPK) at 2.4 Å and 2.16 Å, respectively, as search models in Phaser (64). The structures were refined in PHENIX (65) and model building was done in Coot (66). Molprobity was used for structure validation. The refinement statistics are as reported in table 13.

Single B-cell RT-PCR, gene amplification, and cloning.

Reverse transcription and subsequent PCR amplification of heavy and light chain variable genes were performed using SuperScript III (Life Technologies) according to published protocols (Sok et al., 2014; Tiller et al., 2008; Wu et al., 2011).

Single-Cell Sorting by Flow Cytometry.

Mice spleen and lymph node samples were processed for single B cell sorting based on previously described methods (Sok et al., 2014; Tiller et al., 2008; Wu et al., 2011). In brief, mouse spleens were stained with primary fluorophore-conjugated antibodies to murine CD4, CD8, F4/80, CD11c, Gr-1, CD19, B220, IgD, IgM, CD38, and GL7 markers. Memory B cells were selected for the phenotype CD19+, B220+, CD4−, CD8−, F4/80−, CD11c−, Gr-1−, IgM−, IgD−, while CD38 and GL7 markers were monitored to measure germinal center B cell frequencies (CD38-, GL7+). For antigen-specific staining, 50 nM of biotinylated AviTag r1-core-N276D monomer and its CD4bs KO variant (r1-core-KO) were coupled to Streptavidin-AF488 and Streptavidin-PE (Life Technologoies) in equimolar ratios, respectively. B cells of interest were single-cell sorted into 96 well plates containing lysis buffer on a BD FACSAria Fusion sorter and immediately stored at −80° C. (Sok et al., 2014; Tiller et al., 2008; Wu et al., 2011).

Single B-Cell RT-PCR, Gene Amplification, and Cloning.

Reverse transcription and subsequent PCR amplification of heavy and light chain variable genes were performed using SuperScript III (Life Technologies) according to published protocols (Sok et al., 2014; Tiller et al., 2008; Wu et al., 2011). All PCR reactions were performed in 25 μl volume with 2.5 μl of cDNA transcript using HotStar Taq DNA polymerase master mix (Qiagen) and mixtures of previously described primers (Tiller et al., 2008) that were supplemented with a human VH1-2 primer (Jardine et al., 2015). Second round nested-PCR reactions were performed using Phusion proof reading polymerase (NEB). A third round of PCR was performed using primers with barcodes specific to the plate number and well location as well as adapters appropriate for sequencing on an Illumina MiSeq. This reaction was performed in a 25-μL volume with HotStar Taq DNA polymerase master mix (Qiagen). Amplified IgG heavy- and light-chain variable regions were sequenced on an Illumina MiSeq (600-base v3 reagent kit; Illumina) and reads corresponding to the same plate/well location were combined into consensus sequences. Germline assignment and sequence annotation of the consensus sequences was performed with Ab Star (www.github.com/briney/abstar).

Antibody Production.

Heavy- and light-chain plasmids were cotransfected (1:1 ratio) in 293 FreeStyle cells using 293fectin (Invitrogen). Transfections were performed according to the manufacturer's protocol, and antibody supernatants were harvested 4-5 days after transfection. Antibody supernatants were purified over Protein A Sepharose 4 Fast Flow (GE healthcare) columns, eluted with 0.1 M citric acid (pH 3.0), and dialyzed against phosphate-buffered saline.

Surface Plasmon Resonance (SPR).

Applicants measured kinetics and affinities of antibody-antigen interactions on a ProteOn XPR36 (Bio-Rad) using GLC Sensor Chip (Bio-Rad) and 1×HBS-EP+pH 7.4 running buffer (20× stock from Teknova, Cat. No H8022) supplemented with BSA at 1 mg/ml. Applicants followed the Human Antibody Capture Kit instructions (Cat. No BR-1008-39 from GE) to prepare chip surfaces for ligand capture. In a typical experiment, about 6000 RU of capture antibody was amine-coupled in all 6 flow cells of the GLC Chip. Regeneration was accomplished using 3 M Magnesium Chloride with 180 seconds contact time and injected four times per each cycle. Raw sensograms were analyzed using ProteOn Manager software (Bio-Rad), including interspot and column double referencing, and either Equilibrium fits or Kinetic fits with Langmuir model, or both, were employed when applicable. Analyte concentrations were measured on a NanoDrop 2000c Spectrophotometer using Absorption signal at 280 nm.

ELISA Assays.

Ninety-six-well ELISA plates were coated overnight at 4° C. with 50 uL PBS containing 100 ng of antigen per well. The wells were washed four times with PBS containing 0.05% Tween 20 and blocked with 3% BSA at room temperature for 1 h. Serial dilutions of sera were then added to the wells, and the plates were incubated at room temperature for 1 hour. After washing four times, goat anti-mouse IgG F(ab')2 conjugated to alkaline phosphatase (Pierce), diluted 1:1,000 in PBS containing 1% BSA and 0.025% Tween 20, was added to the wells. The plate was incubated at room temperature for 1 h, washed four times, and the plate was developed by adding 50 uL of alkaline phosphatase substrate (Sigma) to 5 mL alkaline phosphatase staining buffer (pH 9.8), according to the manufacturer's instructions. The optical density at 405 nm was read on a microplate reader (Molecular Devices). ELISA protocol for mAbs was as follows. ELISA plates were coated overnight at 4° C. with 25 μl of 4 μg/ml anti-His (Epitope TagAntibody His.H8, MA1-21315). The wells were washed 5 times with PBST (PBS with 0.2% Tween 20) and blocked with 5% milk at RT for 1 hr. The wells were washed 5 times with PBST. mAb were diluted to 10 μg/mL in 0.1% milk PBST then added to the plates and incubated at RT for 1 hr. After washing 5 times in PBST, goat anti-human HRP (Jackson) was diluted 1:5,000 in 0.1% milk PBST, then 25 μL was added to each well and the plate was incubated at RT for 1 hr. After washing 5 times in PBST, the plate was developed by adding 50 μL TMB ELISA solution (Thermofisher) and then adding 50 μL sulfuric acid stop solution after 10 min. The optical density at 450 nm was read on a microplate reader (Molecular Devices).

Envelope Mutations.

Mutations were introduced by site-directed mutagenesis using the QuikChange site-directed mutagenesis kit (Stratagene) and mutants were verified by Sanger DNA sequencing.

Pseudovirus Production and Neutralization Assays.

To produce pseudoviruses, plasmids encoding Env were co-transfected with an Env-deficient genomic backbone plasmid (pSG3ΔEnv) in a 1:2 ratio with the transfection reagent Fugene 6 (Promega). Pseudoviruses were harvested 72 hours post transfection for use in neutralization assays. Neutralizing activity was assessed using a single round of replication pseudovirus assay and TZM-b1 target cells, as described previously (Li et al., 2005; Walker et al., 2011). Briefly, TZM-b1 cells were seeded in a 96-well flat bottom plate at a concentration of 20,000 cells/well. The serially diluted virus/antibody mixture, which was pre-incubated for 1 hr, was then added to the cells and luminescence was quantified 48 hrs following infection via lysis and addition of Bright-Glo™ Luciferase substrate (Promega). To determine IC50 values, serial dilutions of mAbs were incubated with virus and the dose-response curves were fitted using nonlinear regression.

Antibody NGS on HIV-Negative Donors.

Leukopaks were obtained from two heathy, HIV-negative individuals (AllCells) and peripheral blood mononuclear cells (PBMCs) were isolated by gradient centrifugation. PBMCs from each donor were separated into aliquots of 500m cells and total RNA was extracted separately from each PBMC aliquot (RNeasy Maxi Kit, Qiagen). In quadruplicate, 10 uL of each RNA aliquot was separately amplified in 100 uL RT-PCR reactions (OneStep RT-PCR Kit, Qiagen) using previously reported primers (Briney et al., 2012) and with the following cycling conditions: 55° C. for 30 minutes; 94° C. for 5 minutes; 25 cycles of 94° C. for 30 seconds, 55° C. for 30 seconds, 72° C. for 2 minutes; 72° C. for 7 minutes. RT-PCR reactions were purified using 0.8 volumes of SPRIselect magnetic beads (Beckman-Coulter Genomics) and replicate RT-PCR reactions were eluted together in 50 ul of water. In duplicate reactions for each pooled RT-PCR sample, Illumina sequencing adapters and sample-specific indexes were added during a second round of PCR using 2 uL of purified RT-PCR product in 100 uL of total reaction volume (HotStarTaq Plus; Qiagen) and using the following thermal cycling program: 94° C. for 5 minutes; 10 cycles of 94° C. for 30 seconds, 55° C. for 30 seconds, 72° C. for 2 minutes; 72° C. for 7 minutes. Indexed PCR products were purified using 75 uL of SPRIselect beads and eluted in 50 uL of water. Samples from each donor were quantified using fluorometry (Qubit; Life Technologies), pooled at approximately equimolar concentrations and each sample pool was requantified. The end result was two pools of samples, each pool corresponding to a single subject and consisting of 18-20 separately barcoded samples that represent the amplification product of approximately 500 million PBMCs. Sequencing was then performed on an Illumina HiSeq (HiSeq Rapid SBS Kit v2, 500 cycles).

Processing of NGS Sequence Data.

Using the AbStar analysis pipeline (www.github.com/briney/abstar), raw sequencing reads were quality trimmed with Sickle (www.github.com/najoshi/sickle), adapters were removed with cutadapt (Martin, 2011), and paired reads were merged with PANDAseq (Masella et al., 2012). Germline gene assignment and sequence annotation was performed with AbStar and output was deposited into a MongoDB database. For each sample, which represents the antibody sequences derived from approximately 500m PBMCs, a non-redundant database of amino acid sequence was created, including only heavy chain sequences encoded by IGHV1-2. Because each PBMC aliquot was processed separately, redundant copies across samples represents independent occurrences of the same sequence and these redundancies were retained.

Synthetic Generation of Randomly Mutated VH1-2 Heavy Chain Sequences.

Separately for each subject, each IGHV1-2 heavy chain sequence was aligned to the AbStar-assigned germline allele of IGHV1-2 and the position and mutated residue of each mutation were noted. These mutations were then used to generate synthetically mutated antibody sequences based on the conditional probability of actually occurring somatic mutations. For example, if the first synthetic mutation was an Alanine at position 24 (24A), the probability distribution for the subsequent synthetic mutation was computed using NGS sequences that contain a naturally occurring 24A mutation. If the second mutation was 36F, then the probability distribution for the third synthetic mutation would be computed from NGS sequences with both 24A and 36F. Of note, prior mutations were excluded from the conditional probability distribution. This ensures that, for example, the 24A mutation will not happen a second time in the same sequence.

Design of CD4bs Native-Like Trimer Cocktail.

A five member CD4bs cocktail was engineered on gp120-core by analyzing the sequence diversity of HIV strains at VRC01-class epitope positions, which includes the V5 loop. Each member of the cocktail incorporates mutations from a single strain, and these five strains were chosen to best mimic the diversity of HIV at VRC01-class epitope positions. Applicants next created a native-like trimer cocktail (ABC) by transferring the mutations from the gp120-core cocktail and adding new mutations found proximal to the PGV04 VRC01-class bnAbs in the trimer structure (PDB id: 3J5 M) as well as inclusion of the V2 loop. Three of the five trimers formed native-like structures and antigenic profiles and were used as boosting immunogens in the VRC01-gH mice.

Negative-Stain Electron Microscopy.

BG505-based SOSIP trimers were analyzed by negative stain EM by adapting a previously published protocol (de Taeye et al., 2016).

Differential Scanning Calorimetry.

MicroCal VP-Capillary differential scanning calorimeter (Malvern Instruments) was used for DSC measurements. The protein samples were diluted into hepes buffer to a final concentration of 0.25 mg/ml. The experiment scanned from 20° C. to 90° C. at a scan rate of 90° C./h. Data was analyzed by buffer correction, normalization, and baseline subtraction (Origin 7.0).

60 mer Methods.

The thermostable self-assembling lumazine sythase 60mer (PDB ID: 1HQK), described for displaying eOD-GT6 and eOD-GT8, was adapted to display stabilized extended HIV gp120 core (gp120core-e) antigens from different strains. Initial expression tests with gp120core-e fused to the lhqk sequence (gp120core-e-lhqk) via various length linkers failed to produce fully-assembled particles despite high expression levels of the subunits. Applicants then tested co-transfection with a plasmid encoding only the base subunit of lumazine synthase to insert spacers into the 60mer thereby reducing the crowding on the surface. Of all gp120core-e-lhqk/base-lhqk plasmid DNA combinations tested (95/5, 90/10, 85/15, 80/20, 66/33, 50/50, 33/60), an 80% gp120core-e-lhqk and 20% base lhqk mixture produced the highest proportion of assembled 60mers.

The invention is further described by the following numbered paragraphs:

1. A non-naturally occurring protein comprising an engineered outer domain (eOD) with at least 90% homology or identity with SEQ ID NO: 10 (eOD-GT8) or 11 (eOD-GT10).

2. The protein according to claim 1, wherein the eOD has at least 95% homology or identity with SEQ ID NO: 10 (eOD-GT8) or 11 (eOD-GT10).

3. A non-naturally occurring protein comprising an engineered outer domain (eOD), wherein the protein comprises any one of SEQ ID NO: 10 to 40 or any combination thereof.

4. A non-naturally occurring protein comprising an eOD variant comprising at least one mutation relative to eOD (=c1d1) in the eOD variants in this section listed below, in both eOD numbering (left column) and HxB2 numbering (right column), wherein the HxB2 numbering uniquely defines a position in any HIV Env sequence once it has been aligned to the HxB2 sequence, wherein the mutation is selected from the table consisting of:

| mut_count | eOD_numbering | HxB2_numbering |
|---|---|---|
| (a) mutations to go from eOD_VH1-2_v6.0 to eOD-GT8.1 | | |
| 1 | D27Q | D457Q |
| 2 | V30Y | V460Y |
| 3 | E34N | E464N |
| 4 | E36V | E466V |
| 5 | M45W | M475W |
| 6 | V78E | V275E |
| 7 | F80W | F277W |
| 8 | F127Y | F353Y |
| 9 | R131K | R357K |
| 10 | Q137P | Q363P |
| 11 | T147N | T373N |
| (b) mutations to go from eOD_VH1-2_v6.0 to eOD-GT10.8 | | |
| 1 | D27Q | D457Q |
| 2 | V30W | V460W |
| 3 | E34N | E464N |
| 4 | E36V | E466V |
| 5 | G42A | G472A |
| 6 | M45W | M475W |
| 7 | V78R | V275R |
| 8 | F80W | F277W |
| 9 | F127Y | F353Y |
| 10 | R131K | R357K |
| 11 | I133V | I359V |
| 12 | K136A | K362A |
| 13 | Q137P | Q363P |
| 14 | T147N | T373N |
| (c) mutations to go from eOD-GT8.1 to eOD-GT10.8 | | |
| 1 | Y30W | Y460W |
| 2 | G42A | G472A |
| 3 | E78R | E275R |
| 4 | I133V | I359V |
| 5 | K136A | K362A |
| | or any combination thereof. | |

5. A non-naturally occurring protein capable of binding to VRC01-class antibodies comprising a HIV gp120-derived variant in which the position in the HIV Env reference strain HxB2 is given, the corresponding position in eOD is given, wherein at least one mutation is selected from the table consisting of:

| HxB2_Position | eOD_Position | AA |
|---|---|---|
| 455 | 25 | VAL |
| 457 | 27 | GLN |

-continued

| HxB2_Position | eOD_Position | AA |
|---|---|---|
| 460 | 30 | ARG |
| 460 | 30 | ASN |
| 460 | 30 | GLN |
| 460 | 30 | GLY |
| 460 | 30 | HIS |
| 460 | 30 | LEU |
| 460 | 30 | MET |
| 460 | 30 | PHE |
| 460 | 30 | PRO |
| 460 | 30 | TYR |
| 461 | 31 | MET |
| 461 | 31 | TRP |
| 462 | 32 | ASP |
| 462 | 32 | CYS |
| 462 | 32 | GLN |
| 462 | 32 | GLU |
| 462 | 32 | ILE |
| 462 | 32 | LEU |
| 462 | 32 | LYS |
| 462 | 32 | PHE |
| 462 | 32 | THR |
| 462 | 32 | TRP |
| 462 | 32 | TYR |
| 462 | 32 | VAL |
| 463 | 33 | GLU |
| 465 | 35 | ALA |
| 465 | 35 | GLN |
| 465 | 35 | MET |
| 465 | 35 | TRP |
| 466 | 36 | ALA |
| 466 | 36 | ILE |
| 466 | 36 | LEU |
| 466 | 36 | MET |
| 466 | 36 | PHE |
| 466 | 36 | TYR |
| 466 | 36 | VAL |
| 467 | 37 | VAL |
| 471 | 41 | ALA |
| 472 | 42 | ALA |
| 472 | 42 | TRP |
| 473 | 43 | ALA |
| 473 | 43 | ASP |
| 473 | 43 | GLN |
| 473 | 43 | GLU |
| 473 | 43 | HIS |
| 473 | 43 | MET |
| 473 | 43 | SER |
| 473 | 43 | TRP |
| 473 | 43 | TYR |
| 475 | 45 | ARG |
| 475 | 45 | ASP |
| 475 | 45 | GLN |
| 475 | 45 | GLU |
| 475 | 45 | GLY |
| 475 | 45 | HIS |
| 475 | 45 | ILE |
| 475 | 45 | LEU |
| 475 | 45 | MET |
| 475 | 45 | PHE |
| 475 | 45 | PRO |
| 475 | 45 | THR |
| 475 | 45 | TYR |
| 475 | 45 | VAL |
| 476 | 46 | ALA |
| 476 | 46 | ASP |
| 476 | 46 | GLN |
| 476 | 46 | GLU |
| 476 | 46 | THR |
| 476 | 46 | TYR |
| 478 | 48 | GLU |
| 478 | 48 | LEU |
| 478 | 48 | MET |
| 478 | 48 | TRP |
| 479 | 49 | ASP |
| 479 | 49 | GLU |
| 479 | 49 | TYR |
| 480 | 50 | ALA |

-continued

| HxB2_Position | eOD_Position | AA |
|---|---|---|
| 480 | 50 | ASN |
| 480 | 50 | ASP |
| 480 | 50 | GLN |
| 480 | 50 | GLU |
| 480 | 50 | HIS |
| 480 | 50 | LYS |
| 480 | 50 | MET |
| 480 | 50 | PHE |
| 480 | 50 | SER |
| 480 | 50 | THR |
| 480 | 50 | TYR |
| 480 | 50 | VAL |
| 275 | 78 | ALA |
| 275 | 78 | ARG |
| 275 | 78 | ASN |
| 275 | 78 | ASP |
| 275 | 78 | GLN |
| 275 | 78 | GLY |
| 275 | 78 | HIS |
| 275 | 78 | LYS |
| 275 | 78 | PRO |
| 275 | 78 | SER |
| 275 | 78 | THR |
| 275 | 78 | VAL |
| 277 | 80 | TRP |
| 278 | 81 | HIS |
| 278 | 81 | MET |
| 279 | 82 | ASN |
| 281 | 84 | SER |
| 352 | 126 | ARG |
| 352 | 126 | HIS |
| 352 | 126 | ILE |
| 352 | 126 | LYS |
| 352 | 126 | PRO |
| 352 | 126 | VAL |
| 353 | 127 | TYR |
| 355 | 129 | GLN |
| 355 | 129 | GLU |
| 355 | 129 | PRO |
| 360 | 133 | ALA |
| 360 | 133 | GLN |
| 360 | 133 | GLU |
| 360 | 133 | LYS |
| 360 | 133 | MET |
| 360 | 133 | SER |
| 360 | 133 | THR |
| 360 | 133 | TRP |
| 362 | 135 | ASP |
| 362 | 135 | GLU |
| 362 | 135 | SER |
| 363 | 136 | GLU |
| 363 | 136 | PRO |
| 365 | 138 | ASN |
| 369 | 142 | LEU |
| 369 | 142 | MET |
| 369 | 142 | TRP |
| 369 | 142 | TYR |
| 372 | 145 | ALA |
| 373 | 146 | ALA |
| 373 | 146 | ASN |
| 373 | 146 | HIS |
| 373 | 146 | MET |
| 373 | 146 | SER |

6. The non-naturally occurring protein according to claim 5, wherein the gp120-derived molecule is an eOD variant and wherein the selected mutations provide for binding to at least three VRC01-class broadly neutralizing antibodies.

7. The non-naturally occurring protein according to claim 5 or 6, wherein 1 to 10 mutations are selected.

8. A non-naturally occurring protein comprising a monomeric engineered outer domain (eOD), wherein the protein comprises any one of SEQ ID NO: 10 (eOD-GT8) or 11 (eOD-GT10).

9. The protein according to claim 8, further comprising a tag for purification or biotinylation.

10. The protein according to claim 9, wherein the tag for purification is a his tag.

11. The protein according to claim 9, wherein the tag for biotinylation is an avi-tag.

12. The protein according to claim 8, further comprising an additional cysteine, whereby the cysteine is configured for chemical conjugation.

13. A non-naturally occurring protein comprising SEQ ID NO: 10 (eOD-GT8) or 11 (eOD-GT10) fused to a multimerization motif.

14. The protein according to claim 13, wherein the protein is a 3mer or 60mer.

15. A non-naturally occurring protein comprising an eOD 60mer selected from the group consisting of SEQ ID NO: 2 (eOD-GT6), 10 (eOD-GT8) and 11 (eOD-GT10) fused to a lumazine synthase protein, wherein the lumazine synthase protein further comprises "d4", "d41", or "d44" disulfide bonds; and/or "m1", "m2", or "m3" mutations.

16. The protein according to claim 15, wherein the lumazine synthase protein comprises "d4", "d41", or "d44" disulfide bonds.

17. The protein according to claim 15, wherein the lumazine synthase protein comprises "m1", "m2", or "m3" mutations.

18. A nucleic acid encoding the protein of any one of claims 1 to 17.

19. A nucleic acid having at least 90% homology or identity with the sequence of the nucleic acid of claim 18.

20. A nucleic acid having at least 95% homology or identity with the sequence of the nucleic acid of claim 18.

21. A method for eliciting an immune response comprising systemically administering to an animal in need thereof an effective amount of the protein of any one of claims 1-17.

22. The method according to claim 21, wherein the method for eliciting an immune response further comprises priming with a protein of any one of claims 1-17 followed by boosting with at least one boost protein, wherein the boost protein is an HIV immunogen.

23. The method according to claim 22, wherein the priming protein is a 60mer.

24. The method according to claim 23, wherein the priming protein is an eOD-GT8 or eOD-GT10 60mer.

25. The method according to claim 24, wherein the 60mer is selected from the group consisting of SEQ ID NO: 12-21 and SEQ ID NO: 23-31.

26. The method according to any of claims 22 to 25, wherein the at least one boost protein is selected from the group consisting of BG505 GT3 SOSIP, BG505 core-GT3 60mer, BG505 SOSIP N276D trimer, BG505 SOSIP N276D, and core-e-2CC N276D 60mer or is selected from the group consisting of SEQ ID NO:41 and SEQ ID NO: 43-54.

27. The method according to claim 26, wherein the method comprises at least one boost and the first boost comprises BG505 GT3 SOSIP, BG505 core-GT3 60mer, or core-e-2CC N276D 60mer.

28. The method according to claim 27, wherein the first boost comprises core-e-2CC N276D 60mer, SEQ ID NO: 44, or SEQ ID NO: 45.

29. The method according to any of claims 23 to 28, wherein the 60mer further comprises "d4", "d41", or "d44" disulfide bonds; and/or "m1", "m2", or "m3" mutations.

30. The method according to claim 29, wherein the 60mer comprises "d4", "d41", or "d44" disulfide bonds.

31. The method according to claim 29, wherein the 60mer comprises "m1", "m2", or "m3" mutations.

32. The method according to any of claims 26 to 31, wherein the method comprises more than one boost and any boost following the first boost comprises a HIV SOSIP immunogen, whereby the boost comprises a native like immunogen.

33. The method according to claim 32, wherein any boost following the first boost comprises an HIV SOSIP N276D trimer or HIV SOSIP N276D.

34. The method according to claim 33, wherein any boost following the first boost comprises BG505 SOSIP N276D trimer or BG505 SOSIP N276D.

35. The method according to claim 34, wherein the second boost comprises BG505 SOSIP N276D trimer or BG505 SOSIP N276D.

36. The method according to claim 35, wherein the second boost comprises BG505 SOSIP N276D.

37. The method according to claims 35 or 36, wherein any boost following the second boost comprises an HIV SOSIP immunogen that includes the N276 glycan.

38. The method according to claim 37, wherein any boost following the second boost comprises BG505 SOSIP trimer or BG505 SOSIP.

39. The method according to any of claims 21 to 38, wherein the animal in need thereof is at risk for HIV infection and an effective amount of the protein is administered prophylactically.

40. The method of claim 21, wherein the animal is a mammal.

41. The method of claim 21, wherein the mammal is a human.

42. A knock-in mouse for testing immunogens capable of activating germline precursors of VRC01 class antibodies, said mouse comprising a substitution of the VRC01 gH VDJ exon, wherein the CDRH3 comprises a mutation to remove an unpaired cysteine.

43. A non-naturally occurring protein comprising an HIV boosting molecule with at least 90% homology or identity with BG505 GT3 SOSIP, BG505 core-GT3 60mer, BG505 SOSIP N276D trimer, BG505 SOSIP N276D, core-e-2CC N276D 60mer, SEQ ID NO:41 or SEQ ID NO: 43-54.

REFERENCES

1. Liao H X, et al. Co-evolution of a broadly neutralizing HIV-1 antibody and founder virus. Nature. 2013; 496: 469-476.
2. Doria-Rose N A, et al. Developmental pathway for potent V1V2-directed HIV-neutralizing antibodies. Nature. 2014; 509:55-62.
3. Gauduin M C, et al. Passive immunization with a human monoclonal antibody protects hu-PBL-SCID mice against challenge by primary isolates of HIV-1. Nature medicine. 1997; 3:1389-1393.
4. Mascola J R, et al. Protection of macaques against vaginal transmission of a pathogenic HIV-1/SIV chimeric virus by passive infusion of neutralizing antibodies. Nature medicine. 2000; 6:207-210.
5. Parren P W, et al. Antibody protects macaques against vaginal challenge with a pathogenic R5 simian/human immunodeficiency virus at serum levels giving complete neutralization in vitro. Journal of virology. 2001; 75:8340-8347.
6. Moldt B, et al. Highly potent HIV-specific antibody neutralization in vitro translates into effective protection against mucosal SHIV challenge in vivo. Proceedings of the National Academy of Sciences of the United States of America. 2012; 109:18921-18925.

7. Pietzsch J, et al. A mouse model for HIV-1 entry. Proceedings of the National Academy of Sciences of the United States of America. 2012; 109:15859-15864.
8. Shingai M, et al. Passive transfer of modest titers of potent and broadly neutralizing anti-HIV monoclonal antibodies block SHIV infection in macaques. The Journal of experimental medicine. 2014; 211:2061-2074.
9. Wu X, et al. Rational design of envelope identifies broadly neutralizing human monoclonal antibodies to HIV-1. Science. 2010; 329:856-861.
10. Zhou T, et al. Structural basis for broad and potent neutralization of HIV-1 by antibody VRC01. Science. 2010; 329:811-817.
11. Wu X, et al. Focused evolution of HIV-1 neutralizing antibodies revealed by structures and deep sequencing. Science. 2011; 333:1593-1602.
12. Scheid J F, et al. Sequence and structural convergence of broad and potent HIV antibodies that mimic CD4 binding. Science. 2011; 333:1633-1637.
13. Bonsignori M, et al. Two distinct broadly neutralizing antibody specificities of different clonal lineages in a single HIV-1-infected donor: implications for vaccine design. Journal of virology. 2012; 86:4688-4692.
14. Zhou T, et al. Multidonor analysis reveals structural elements, genetic determinants, and maturation pathway for HIV-1 neutralization by VRC01-class antibodies. Immunity. 2013; 39:245-258.
15. Georgiev I S, et al. Delineating antibody recognition in polyclonal sera from patterns of HIV-1 isolate neutralization. Science. 2013; 340:751-756.
16. West A P, Jr, Diskin R, Nussenzweig M C, Bjorkman P J. Structural basis for germ-line gene usage of a potent class of antibodies targeting the CD4-binding site of HIV-1 gp120. Proceedings of the National Academy of Sciences of the United States of America. 2012; 109: E2083-2090.
17. Jardine J, et al. Rational HIV immunogen design to target specific germline B cell receptors. Science. 2013; 340:711-716.
18. Arnaout R, et al. High-resolution description of antibody heavy-chain repertoires in humans. Plos One. 2011; 6.
19. DeKosky B J, et al. In-depth determination and analysis of the human paired heavy- and light-chain antibody repertoire. Nature medicine. 2015; 21:86-91.
20. Hoot S, et al. Recombinant HIV envelope proteins fail to engage germline versions of anti-CD4bs bNAbs. PLoS pathogens. 2013; 9:e1003106.
21. McGuire A T, et al. Engineering HIV envelope protein to activate germline B cell receptors of broadly neutralizing anti-CD4 binding site antibodies. The Journal of experimental medicine. 2013; 210:655-663.
22. Xiao X, et al. Germline-like predecessors of broadly neutralizing antibodies lack measurable binding to HIV-1 envelope glycoproteins: implications for evasion of immune responses and design of vaccine immunogens. Biochemical and biophysical research communications. 2009; 390:404-409.
23. Mascola J R, Haynes B F. HIV-1 neutralizing antibodies: understanding nature's pathways. Immunological reviews. 2013; 254:225-244.
24. Georgiev I S, et al. Antibodies VRC01 and 10E8 neutralize HIV-1 with high breadth and potency even with Ig-framework regions substantially reverted to germline. Journal of immunology. 2014; 192:1100-1106.
25. Sok D, et al. The effects of somatic hypermutation on neutralization and binding in the PGT121 family of broadly neutralizing HIV antibodies. PLoS pathogens. 2013; 9:e1003754.
26. Xiao X, Chen W, Feng Y, Dimitrov D S. Maturation Pathways of Cross-Reactive HIV-1 Neutralizing Antibodies. Viruses. 2009; 1:802-817.
27. Dimitrov D S. Therapeutic antibodies, vaccines and antibodyomes. mAbs. 2010; 2:347-356.
28. Haynes B F, Kelsoe G, Harrison S C, Kepler T B. B-cell-lineage immunogen design in vaccine development with HIV-1 as a case study. Nature biotechnology. 2012; 30:423-433.
29. Klein F, et al. Antibodies in HIV-1 vaccine development and therapy. Science. 2013; 341:1199-1204.
30. Wu X, et al. Maturation and Diversity of the VRC01-Antibody Lineage over 15 Years of Chronic HIV-1 Infection. Cell. 2015; 161:470-485.
31. Souto-Carneiro M M, Longo N S, Russ D E, Sun H W, Lipsky P E. Characterization of the human Ig heavy chain antigen binding complementarity determining region 3 using a newly developed software algorithm, JOINSOLVER. Journal of immunology. 2004; 172:6790-6802.
32. Morelli A B, et al. ISCOMATRIX: a novel adjuvant for use in prophylactic and therapeutic vaccines against infectious diseases. J Med Microbiol. 2012; 61:935-943.
33. Sanders R W, et al. A next-generation cleaved, soluble HIV-1 Env trimer, BG505 SOSIP.664 gp140, expresses multiple epitopes for broadly neutralizing but not non-neutralizing antibodies. PLoS pathogens. 2013; 9:e1003618.
34. Julien J P, et al. Crystal structure of a soluble cleaved HIV-1 envelope trimer. Science. 2013; 342:1477-1483.
35. Lyumkis D, et al. Cryo-EM structure of a fully glycosylated soluble cleaved HIV-1 envelope trimer. Science. 2013; 342:1484-1490.
36. Pancera M, et al. Structure and immune recognition of trimeric pre-fusion HIV-1 Env. Nature. 2014; 514:455-461.
37. Dey B, et al. Structure-based stabilization of HIV-1 gp120 enhances humoral immune responses to the induced co-receptor binding site. PLoS pathogens. 2009; 5:e1,000445.
38. Diskin R, et al. Increasing the potency and breadth of an HIV antibody by using structure-based rational design. Science. 2011; 334:1289-1293.
39. Klein F, et al. Somatic mutations of the immunoglobulin framework are generally required for broad and potent HIV-1 neutralization. Cell. 2013; 153:126-138.
40. Dosenovic P, et al. Immunization for HIV-1 Broadly Neutralizing Antibodies in Human Ig Knockin Mice. Cell. 2015 in_press.
41. Ota T, et al. B Cells from Knock-in Mice Expressing Broadly Neutralizing HIV Antibody b12 Carry an Innocuous B Cell Receptor Responsive to HIV Vaccine Candidates. Journal of immunology. 2013
42. Shulman M, Wilde C D, Kohler G. A better cell line for making hybridomas secreting specific antibodies. Nature. 1978; 276:269-270.
43. Aoki-Ota M, Torkamani A, Ota T, Schork N, Nemazee D. Skewed primary igkappa repertoire and v-j joining in C57BL/6 mice: implications for recombination accessibility and receptor editing. Journal of immunology. 2012; 188:2305-2315.
44. Ota M, et al. Regulation of the B cell receptor repertoire and self-reactivity by BAFF. Journal of immunology. 2010; 185:4128-4136.

45. Sok D, et al. Recombinant HIV envelope trimer selects for quaternary-dependent antibodies targeting the trimer apex. Proceedings of the National Academy of Sciences of the United States of America. 2014; 111:17624-17629.
46. Tiller T, et al. Efficient generation of monoclonal antibodies from single human B cells by single cell RT-PCR and expression vector cloning. J Immunol Methods. 2008; 329:112-124.
47. Tiller T, Busse C E, Wardemann H. Cloning and expression of murine Ig genes from single B cells. J Immunol Methods. 2009; 350:183-193.
48. Li M, et al. Human immunodeficiency virus type 1 env clones from acute and early subtype B infections for standardized assessments of vaccine-elicited neutralizing antibodies. Journal of virology. 2005; 79:10108-10125.
49. Joshi N, Fass J. Sickle: A sliding-window, adaptive, quality-based trimming tool for FastQ files (Version 1.33) [Software] 2011 Available at https://github.com/najoshi/sickle.
50. Brochet X, Lefranc M P, Giudicelli V. IMGT/V-QUEST: the highly customized and integrated system for IG and TR standardized V-J and V-D-J sequence analysis. Nucleic Acids Res. 2008; 36:W503-508.
51. Masella A P, Bartram A K, Truszkowski J M, Brown D G, Neufeld J D. PANDAseq: paired-end assembler for illumina sequences. BMC Bioinformatics. 2012; 13:31.
52. Lefranc M P, et al. IMGT, the international ImMunoGeneTics information system. Nucleic Acids Res. 2009; 37:D1006-1012.
53. Burton D R, Mascola J R. Antibody responses to envelope glycoproteins in HIV-1 infection. Nat Immunol. 2015; 16:571-576.
54. Jardine J G, et al. Priming a broadly neutralizing antibody response to HIV-1 using a germline-targeting immunogen. Science. 2015; 349:156-161.
55. Whitehead T A, et al. Optimization of affinity, specificity and function of designed influenza inhibitors using deep sequencing. Nature biotechnology. 2012; 30:543-548.
56. Morbach H, Eichhorn E M, Liese J G, Girschick H J. Reference values for B cell subpopulations from infancy to adulthood. Clin Exp Immunol. 2010; 162:271-279.
57. Shih T A, Meffre E, Roederer M, Nussenzweig M C. Role of BCR affinity in T cell dependent antibody responses in vivo. Nat Immunol. 2002; 3:570-575.
58. Dal Porto J M, Haberman A M, Kelsoe G, Shlomchik M J. Very low affinity B cells form germinal centers, become memory B cells, and participate in secondary immune responses when higher affinity competition is reduced. The Journal of experimental medicine. 2002; 195:1215-1221.
59. Diskin R, et al. Restricting HIV-1 pathways for escape using rationally designed anti-HIV-1 antibodies. The Journal of experimental medicine. 2013; 210:1235-1249.
60. Zhou T, et al. Structural Repertoire of HIV-1-Neutralizing Antibodies Targeting the CD4 Supersite in 14 Donors. Cell. 2015; 161:1280-1292.
61. Kwakkenbos M J, et al. Generation of stable monoclonal antibody-producing B cell receptor-positive human memory B cells by genetic programming. Nature medicine. 2010; 16:123-128.
62. Kabsch W. Xds. Acta Crystallogr D Biol Crystallogr. 2010; 66:125-132.
63. Strong M, et al. Toward the structural genomics of complexes: crystal structure of a PE/PPE protein complex from *Mycobacterium tuberculosis*. Proceedings of the National Academy of Sciences of the United States of America. 2006; 103:8060-8065.
64. McCoy A J, et al. Phaser crystallographic software. J Appl Crystallogr. 2007; 40:658-674.
65. Adams P D, et al. PHENIX: a comprehensive Python-based system for macromolecular structure solution. Acta Crystallogr D Biol Crystallogr. 2010; 66:213-221.
66. Emsley P, Cowtan K. Coot: model-building tools for molecular graphics. Acta Crystallogr D Biol Crystallogr. 2004; 60:2126-2132.
67. Heinig M, Frishman D. STRIDE: a web server for secondary structure assignment from known atomic coordinates of proteins. Nucleic Acids Res. 2004; 32:W500-502.
68. Chen V B, et al. MolProbity: all-atom structure validation for macromolecular crystallography. Acta Crystallogr D Biol Crystallogr. 2010; 66:12-21.
69. Otwinowski Z, Minor W. Processing of x-ray diffraction data collected in oscillation mode. Methods in Enzymology. 1997; 276:307-326.
70. Krissinel E, Henrick K. Inference of macromolecular assemblies from crystalline state. J Mol Biol. 2007; 372:774-797.
71. Li Y, et al. HIV-1 neutralizing antibodies display dual recognition of the primary and coreceptor binding sites and preferential binding to fully cleaved envelope glycoproteins. Journal of virology. 2012; 86:11231-11241.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A non-naturally occurring protein comprising a monomeric engineered outer domain (eOD), wherein the protein comprises SEQ ID NO: 10 (eOD-GT8).

2. The protein according to claim 1, further comprising a tag for purification or biotinylation.

3. The protein according to claim 2, wherein the tag for purification is a his tag.

4. The protein according to claim 2, wherein the tag for biotinylation is an avi-tag.

5. The protein according to claim 1, further comprising an additional cysteine, whereby the cysteine is configured for chemical conjugation.

* * * * *